(12) United States Patent
Chou et al.

(10) Patent No.: US 12,077,537 B2
(45) Date of Patent: Sep. 3, 2024

(54) CAPSID INHIBITORS FOR THE TREATMENT OF HIV

(71) Applicant: Gilead Sciences, Inc., Foster City, CA (US)

(72) Inventors: Chienhung Chou, Dublin, CA (US); Scott E. Lazerwith, San Francisco, CA (US); John O. Link, San Francisco, CA (US); Scott D. Schroeder, Union City, CA (US); Winston C. Tse, Redwood City, CA (US); Jennifer R. Zhang, Union City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 18/110,126

(22) Filed: Feb. 15, 2023

(65) Prior Publication Data
US 2023/0312567 A1   Oct. 5, 2023

Related U.S. Application Data

(63) Continuation of application No. 17/357,376, filed on Jun. 24, 2021, now Pat. No. 11,680,064.

(60) Provisional application No. 63/044,086, filed on Jun. 25, 2020.

(51) Int. Cl.
| | |
|---|---|
| C07D 513/06 | (2006.01) |
| A61K 31/4365 | (2006.01) |
| A61K 31/437 | (2006.01) |
| A61K 45/06 | (2006.01) |
| C07D 403/12 | (2006.01) |
| C07D 471/04 | (2006.01) |
| C07D 471/06 | (2006.01) |
| C07D 498/04 | (2006.01) |
| C07D 513/04 | (2006.01) |
| C07D 519/00 | (2006.01) |

(52) U.S. Cl.
CPC .......... *C07D 471/04* (2013.01); *A61K 45/06* (2013.01); *C07D 403/12* (2013.01); *C07D 498/04* (2013.01); *C07D 513/04* (2013.01); *C07D 519/00* (2013.01)

(58) Field of Classification Search
CPC .. C07D 513/06; C07D 471/06; C07D 235/04; A61K 31/4365; A61K 31/437; A61K 31/4184; A61P 31/18
USPC ......... 546/114, 112, 118; 514/301, 300, 303, 514/394
See application file for complete search history.

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,816,570 A | 3/1989 | Farquhar |
| 4,902,514 A | 2/1990 | Barclay et al. |
| 4,968,788 A | 11/1990 | Farquhar |
| 4,992,445 A | 2/1991 | Lawter et al. |
| 5,001,139 A | 3/1991 | Lawter et al. |
| 5,023,252 A | 6/1991 | Hseih |
| 5,616,345 A | 4/1997 | Geoghegan et al. |
| 5,663,159 A | 9/1997 | Starrett, Jr. et al. |
| 5,792,756 A | 8/1998 | Starrett, Jr. et al. |
| 5,922,695 A | 7/1999 | Arimilli et al. |
| 5,935,946 A | 8/1999 | Munger, Jr. et al. |
| 5,977,089 A | 11/1999 | Arimilli et al. |
| 7,390,791 B2 | 6/2008 | Becker et al. |
| 7,803,788 B2 | 9/2010 | Becker et al. |
| 8,263,627 B2 | 9/2012 | Barrow et al. |
| 8,748,412 B2 | 6/2014 | Liao et al. |
| 8,754,065 B2 | 6/2014 | Liu et al. |
| 8,835,488 B2 | 9/2014 | Yamashita et al. |
| 9,012,441 B2 | 4/2015 | Bondy et al. |
| 9,050,344 B2 | 6/2015 | Brizgys et al. |
| 9,216,996 B2 | 12/2015 | Jin et al. |
| 9,220,710 B2 | 12/2015 | Bondy et al. |
| 9,540,343 B2 | 1/2017 | Bondy et al. |
| 9,670,205 B2 | 6/2017 | Aktoudianakis et al. |
| 9,730,936 B2 | 8/2017 | Baszcynski et al. |
| 9,789,089 B2 | 10/2017 | Bondy et al. |
| 9,873,680 B2 | 1/2018 | Brizgys et al. |
| 9,944,619 B2 | 4/2018 | Bondy et al. |
| 9,951,043 B2 | 4/2018 | Brizgys et al. |
| 10,071,985 B2 | 9/2018 | Graupe et al. |
| 10,294,234 B2 | 5/2019 | Bacon et al. |
| 10,370,342 B2 | 8/2019 | Chin et al. |
| 10,370,358 B2 | 8/2019 | Bondy et al. |
| 10,640,499 B2 | 5/2020 | Chin et al. |

(Continued)

FOREIGN PATENT DOCUMENTS

| | | |
|---|---|---|
| CN | 101910133 | 12/2010 |
| WO | WO 1991019721 | 12/1991 |

(Continued)

OTHER PUBLICATIONS

[No Author Listed], "2-[9-(Difluoromethyl)-5,5-difluoro-7,8-diazatricylo[4.4.0.02,4]nona-1(6),8-dien-7-yl]acetic acid," PubChem CID 71186949, Mar. 21, 2013, 18 pages.

(Continued)

*Primary Examiner* — Charanjit Aulakh

(74) *Attorney, Agent, or Firm* — Fish & Richardson P.C.

(57) ABSTRACT

The present disclosure relates generally to certain compounds, pharmaceutical compositions comprising said compounds, and methods of making and using said compounds and pharmaceutical compositions. The compounds and compositions disclosed herein may be used for the treatment or prevention of a Retroviridae viral infection, including an infection caused by the HIV virus.

8 Claims, No Drawings

(56) References Cited

U.S. PATENT DOCUMENTS

| | | |
|---|---|---|
| 10,654,827 B2 | 5/2020 | Graupe et al. |
| 10,696,657 B2 | 6/2020 | Vandehey |
| 10,836,746 B2 | 11/2020 | Brizgys et al. |
| 10,849,892 B2 | 12/2020 | Houston et al. |
| 11,034,668 B2 | 6/2021 | Bondy et al. |
| 11,078,208 B1 | 8/2021 | Bacon et al. |
| 11,117,886 B2 | 9/2021 | Vandehey et al. |
| 11,680,064 B2 | 6/2023 | Chou et al. |
| 11,753,399 B2 | 9/2023 | Brizgy et al. |
| 11,787,825 B2 | 10/2023 | Farand et al. |
| 11,807,625 B2 | 11/2023 | Bekerman et al. |
| 11,845,739 B2 | 12/2023 | Shi |
| 11,944,611 B2 | 4/2024 | Bauer et al. |
| 2005/0282805 A1 | 12/2005 | Hangeland et al. |
| 2007/0083045 A1 | 4/2007 | Di Francesco et al. |
| 2008/0234251 A1 | 9/2008 | Doherty et al. |
| 2008/0306050 A1 | 12/2008 | Doherty et al. |
| 2010/0029585 A1 | 2/2010 | Dietsch et al. |
| 2010/0129306 A1 | 5/2010 | Julien et al. |
| 2010/0143301 A1 | 6/2010 | Desai et al. |
| 2010/0189796 A1 | 7/2010 | Stokbroekx |
| 2010/0249176 A1 | 9/2010 | Barrow et al. |
| 2011/0092485 A1 | 4/2011 | Burgess et al. |
| 2011/0118235 A1 | 5/2011 | Burgess et al. |
| 2012/0045761 A1 | 2/2012 | Jagannath et al. |
| 2012/0082658 A1 | 4/2012 | Hershberg |
| 2012/0219615 A1 | 8/2012 | Coukos et al. |
| 2013/0165489 A1 | 6/2013 | Cocklin et al. |
| 2013/0251673 A1 | 9/2013 | Flores et al. |
| 2014/0045849 A1 | 2/2014 | McGowan et al. |
| 2014/0066432 A1 | 3/2014 | Burgess et al. |
| 2014/0073642 A1 | 3/2014 | Embrechts et al. |
| 2014/0088085 A1 | 3/2014 | Burgess et al. |
| 2014/0142085 A1 | 5/2014 | Bondy et al. |
| 2014/0221346 A1 | 8/2014 | Halcomb et al. |
| 2014/0221347 A1 | 8/2014 | Brizgys et al. |
| 2014/0221356 A1 | 8/2014 | Jin et al. |
| 2014/0221378 A1 | 8/2014 | Miyazaki et al. |
| 2014/0221380 A1 | 8/2014 | Miyazaki et al. |
| 2014/0221417 A1 | 8/2014 | Halcomb et al. |
| 2014/0221421 A1 | 8/2014 | Bondy et al. |
| 2014/0275167 A1 | 9/2014 | Hartman |
| 2014/0296266 A1 | 10/2014 | Hu et al. |
| 2014/0303164 A1 | 10/2014 | Brizgys et al. |
| 2014/0350031 A1 | 11/2014 | McGowan et al. |
| 2015/0104511 A1 | 4/2015 | Malhotra et al. |
| 2016/0067224 A1 | 3/2016 | Bondy et al. |
| 2016/0083368 A1 | 3/2016 | Brizgys et al. |
| 2016/0108030 A1 | 4/2016 | Brizgys et al. |
| 2016/0250215 A1 | 9/2016 | Baszcynski et al. |
| 2016/0289229 A1 | 10/2016 | Aktoudianakis et al. |
| 2016/0368881 A1 | 12/2016 | Bondy et al. |
| 2017/0137405 A1 | 5/2017 | Bondy et al. |
| 2018/0051005 A1 | 2/2018 | Graupe et al. |
| 2018/0194746 A1 | 7/2018 | Bondy et al. |
| 2018/0258097 A1 | 9/2018 | Bacon et al. |
| 2018/0273508 A1 | 9/2018 | Brizgys et al. |
| 2018/0370950 A1 | 12/2018 | Grape et al. |
| 2019/0083478 A1 | 3/2019 | Houston et al. |
| 2019/0084963 A1 | 3/2019 | Shi |
| 2019/0300505 A1 | 10/2019 | Allan et al. |
| 2019/0345136 A1 | 11/2019 | Brizgys et al. |
| 2019/0375726 A1 | 12/2019 | Bondy et al. |
| 2020/0038389 A1 | 2/2020 | Bauer |
| 2020/0262815 A1 | 8/2020 | Graupe et al. |
| 2020/0369647 A1 | 11/2020 | Allan et al. |
| 2020/0397772 A1 | 12/2020 | Houston et al. |
| 2021/0009555 A1 | 1/2021 | Brizgys et al. |
| 2021/0188815 A1 | 6/2021 | Bekerman et al. |
| 2022/0009904 A1 | 1/2022 | Allan et al. |
| 2022/0249460 A1 | 8/2022 | Houston et al. |
| 2022/0251069 A1 | 8/2022 | Shi |
| 2022/0267302 A1 | 8/2022 | Brizgys et al. |
| 2023/0038823 A1 | 2/2023 | Chou et al. |
| 2023/0203069 A1 | 6/2023 | Nair et al. |
| 2024/0051941 A1 | 2/2024 | Bekerman et al. |
| 2024/0067629 A1 | 2/2024 | Brizgys et al. |
| 2024/0101533 A1 | 3/2024 | Allan et al. |

FOREIGN PATENT DOCUMENTS

| | | |
|---|---|---|
| WO | WO 2003002530 | 1/2003 |
| WO | WO 2003002553 | 1/2003 |
| WO | WO 2004050643 | 6/2004 |
| WO | WO 2004071448 | 8/2004 |
| WO | WO 2004096286 | 11/2004 |
| WO | WO 2005087725 | 9/2005 |
| WO | WO 2005123680 | 12/2005 |
| WO | WO 2006015261 | 2/2006 |
| WO | WO 2006110157 | 10/2006 |
| WO | WO 2007070826 | 8/2007 |
| WO | WO 2008013622 | 1/2008 |
| WO | WO 2008118849 | 10/2008 |
| WO | WO 2009005677 | 1/2009 |
| WO | WO 2009010804 | 1/2009 |
| WO | WO 2009062285 | 5/2009 |
| WO | WO 2009114677 | 9/2009 |
| WO | WO 2010130034 | 11/2010 |
| WO | WO 2011059887 | 5/2011 |
| WO | WO 2011143772 | 11/2011 |
| WO | WO 2012003497 | 1/2012 |
| WO | WO 2012003498 | 1/2012 |
| WO | WO 2012065062 | 5/2012 |
| WO | WO 2012145728 | 10/2012 |
| WO | WO 2013006738 | 1/2013 |
| WO | WO 2013006792 | 1/2013 |
| WO | WO 2013091096 | 6/2013 |
| WO | WO 2013159064 | 10/2013 |
| WO | WO 2014016358 | 1/2014 |
| WO | WO 2014023813 | 2/2014 |
| WO | WO 2014028931 | 2/2014 |
| WO | WO 2014056953 | 4/2014 |
| WO | WO 2014076221 | 5/2014 |
| WO | WO 2014100323 | 6/2014 |
| WO | WO 2014110297 | 7/2014 |
| WO | WO 2014110298 | 7/2014 |
| WO | WO 2014110323 | 7/2014 |
| WO | WO 2014128189 | 8/2014 |
| WO | WO 2014128213 | 8/2014 |
| WO | WO 2014134566 | 9/2014 |
| WO | WO 2015008097 | 1/2015 |
| WO | WO 2015061518 | 4/2015 |
| WO | WO 2015130966 | 9/2015 |
| WO | WO 2016033243 | 3/2016 |
| WO | WO 2016040084 | 3/2016 |
| WO | WO 2016172424 | 10/2016 |
| WO | WO 2016172425 | 10/2016 |
| WO | WO 2017007689 | 1/2017 |
| WO | WO 2018035359 | 2/2018 |
| WO | WO 2018145021 | 8/2018 |
| WO | WO 2018203235 | 11/2018 |
| WO | WO 2019035904 | 2/2019 |
| WO | WO 2019035973 | 2/2019 |
| WO | WO 2020018459 | 1/2020 |

OTHER PUBLICATIONS

[No Author Listed], "3-Methyl-3-methylsulfonylbut-1-yne," PubChem CID 14241469, Feb. 9, 2002, 16 pages.

[No Author Listed], CAS registry No. 1620056-83-8, Aug. 6, 2014, 1 page.

Bastin et al., "Salt Selection and Optimisation Procedures for Pharmaceutical New Chemical Entities," Organic Process Research & Development, Jul. 2000, 4(5): 427-435.

Benzaria et al., "Synthesis, In Vitro Antiviral Evaluation, and Stability Studies of Bis( S-Acyl-2-Thioethyl) Ester Derivatives of 9-[2-(Phosphonomethoxy)Ethyl]adenine (PMEA) as Potential PMEA Prodrugs with Improved Oral Bioavailability," J. Med. Chem., Dec. 1996, 39(25):4958-4965.

Berge et al., "Pharmaceutical Salts," J. Pharma. Sci., 1977, 66(1): 1-19.

Bhattacharya et al., Structural Basis of HIV-1 Capsid Recognition by PF74 and CPSF6, PNAS, 2014, 111(52):18625-18630.

(56) References Cited

OTHER PUBLICATIONS

Blair et al., "HIV Capsid is a Tractable Target for Small Molecule Therapeutic Intervention," PLoS Pathog., 2010, 6(12): e1001220, 10 pages.
Briggs et al., "Structural Organization of Authentic, Mature HIV-1 Virions and Cores," The EMBO Journal, 2003, 22(7): 1707-1715.
Brittain, "Polymorphism in pharmaceutical solids," Marcel Dekker, Inc., 1999, 235-238.
Brown et al., "Highly Enantioselective Cu-Catalyzed Conjugate Additions of Dialkylzinc Reagents to Unsaturated Furanones and Pyranones: Preparation of Air-Stable and Catalytically Active Cu-Peptide," Angew. Chem. Int. Ed. Engl., 2005, 44(33):5306-5310.
Bundgaard, "Design and Application of Prodrugs," Chapter 5 in A Textbook of Drug Design and Development, Krogsgaard-Larsen, P. et al. eds., Harwood Academic Publishers, Chur, Switzerland, 1991, pp. 113-191.
Campbell et al., "HIV-1 Capsid: The Multifaceted Key Player in HIV-1 Infection," Nat Rev Microbial., 2015, 13(8): 471-483.
Carnes et al., "Inhibitors of the HIV-1 Capsid, A Target of Opportunity," Curr. Opin. HIV AIDS, 2018, 13(4):359-365.
Chin et al., "Direct Visualization of HIV-1 Replication Intermediates Shows That Capsid and CPSF6 Modulate HIV-1 Intra-Nuclear Invasion and Integration", Cell Repotis, 2015, 13:1717-1731.
Cos et al., "Structure-Activity Relationship and Classification of Flavonoids as Inhibitors of Xanthine Oxidase and Su peroxide Scavengers," J. Natl. Prod., 1998, 61:71-76.
Cossy et al., "Ring Opening of Cyclopropylketones Induced by Photochemical Electron Transfer," Tetrahedron, Oct. 1995, 51 (43):11751-11764.
Curreli et al., "Virtual Screening Based Identification of Novel Small-molecule Inhibitors Targeted to the HIV-1 Capsid," Bioorganic & Medicinal Chemistry, 2011, 19:77-90.
De Lombaert et al., "N-Phosphonomethyl Dipeptides and Their Phosphonate Prodrugs, A New Generation of Neutral Endopeptidase (NEP, EC 3.4.24.11) Inhibitors," J. Med. Chem., Feb. 1994, 37(4):498-511.
Fader et al., "Optimization of a 1,5 dihydrobenzo[b][1,4]diazepine-2,4-dione Series of HIV Capsid Assembly Inhibitors 2: Structure-Activity Relationships (SAR) of the C3-Phenyl Moiety," Bioorganic & Medicinal Chemistry Letters, 2013, 23(11):3396-3400.
Farquhar et al., "Biologically Reversible Phosphate-Protective Groups," J. Pharm. Sci., Mar. 1983, 72(3):324-325.
Fields, "Methods for Removing the Fmnoc Group," Methods in Molecular Biology, 1994, 35:17-27.
Fontes Ferreira da Cunha et al., "4D-QSAR Models of HOE/BAY-793 Analogues as HIV-1 Protease Inhibitors," QSAR & Combinatorial Science, 2005, 24(2): 240-253.
Forshey et al., "Fonnation of a Human Immunodeficiency Virus Type 1 Core of Optimal Stability is Crucial for Viral Replication," J. Virology, 2002, 76(11) p. 5667-5677.
Foster, "Deuterium Isotope Effects in Studies of Drug Metabolism," Trends Pharmacol. Sci., 1984, 5(12):524-527.
Ganser et al., "Assembly and Analysis of Conical Models for the HIV-1 Core," Science, 1999, 283: 80-82.
Ganser-Pornillos et al., "Structure of Full-Length HIV-1 CA: A Model for the Mature Capsid Lattice," Cell, 2007, 131(1):70-9, 29 pages.
Hagmann, "The many roles for fluorine in medicinal chemistry," J. Med. Chem., 2008, 51(15):4359-4369.
Hammer et al., "Antiretroviral Treatment of Adult HIV Infection. 2008 Recommendations of the International AIDS Society: USA Panel," JAMA, Aug. 2008, 300(5):555-570.
Hanack et al., "cis- und trans bicyclo [3.1.0] hexano-(2)," Chemische Berichte, 1964, 97(6):1669-1672, XP055573746 (with English translation).
Hodgson et al. "Intramolecular Cyclopropanation of Unsaturated Terminal Epoxides," J. Am. Chem. Soc., 2004, 126(28):8664-8665.
Hodgson et al., "Intramolecular Cyclopropanation of Unsaturated Terminal Epoxides and Chlorohydrins," J. Am. Chem. Soc., 2007, 129(14):4456-4462.
Hung et al., "Large-Scale Functional Purification of Recombinant HIV-1 Capsid," PLOS One, 2013, 8(3):e58035, 11 pages.
Ishiyama et al., "Palladium(0)-Catalyzed Cross-Coupling Reaction of Alkoxydiboron with Haloarenes: A Direct Procedure for Arylboronic Esters," J. Org. Chem., 1995, 60(23):7508-7510.
Jarvis et al., "Conquering HIV's capsid", C&EN Chicago, Jul. 2017, 95(31): 23-25.
Jeong, "Synthesis of Tetrasubstituted Pyrazones and Pyrazone N-Oxides," Tetrahedron Letters, 2010, 51 (6):974-976.
Jin et al., "SAR and Molecular Mechanism Study of Novel Acylhydrazone Compounds Targeting HIV-1 CA," Bioorganic & Medicinal Chemistry, 2010, 18: 2135-2140.
Jouvenet et al., "Plasma Membrane is the Site of Productive HIV-1 Particle Assembly," PLoS Biol., 2006, 4(12):e435, 15 pages.
Kashima et al., "New Peptide Synthesis Using the Ozonolysate of 2-(1-Phthalimido)alkyl-5-Phenyloxazoles," J. Heterocyclic Chem., 1991, 28: 1241-1244.
Kelly et al., "Structure of the Antiviral Assembly Inhibitor CAP-I Complex with the HIV-1 CA Protein," Journal of Molecular Biology, 2007, 373(2):355-66.
Khamnei et al., "Neighboring Group Catalysis in the Design of Nucleotide Prodrugs," J. Med. Chem., 1996, 39(20):4109-4115.
Kim et al., "Discovery of a New HIV-1 Inhibitor Scaffold and Synthesis of Potential Prodrugs of Indazoles," Bioorganic & Medicinal Chemistry Letters, 2013, 23(10): 2888-2892.
Kocienski, "Carbonyl Protecting Groups," Chapter 5 in Protecting Groups, Thieme Publishing Group: New York, NY, May 1994, pp. 155-184.
Kocienski, "Carboxyl Protecting Groups," Chapter 4 in Protecting Groups, Thieme Publishing Group: New York, NY, May 1994, pp. 118-154.
Kocienski, "Diol Protecting Groups," Chapter 3 in Protecting Groups, Thieme Publishing Group: New York, NY, May 1994, pp. 95-117.
Kocienski, "Hydroxyl Protecting Groups," Chapter 2 in Protecting Groups, Thieme Publishing Group: New York, NY, May 1994, pp. 21-94.
Kocienski, "Protecting Groups: An Overview," Chapter 1 in Protecting Groups, Thieme Publishing Group: New York, NY, May 1994, pp. 1-20.
Lad et al., "Functional Label-Free Assays for Characterizing the in Vitro Mechanism of Action of Small Molecule Modulators of Capsid Assembly" Biochemistry, 2015, 54: 2240-2248.
Lamorte et al., "Discovery of Novel Small-Molecule HIV-1 Replication Inhibitors That Stabilize Capsid Complexes" Antimicrobial Agents and Chemotherapy, 2015, 57(10): 4622-4631.
Lazerwith et al., "New Antiretrovirals for HIV and Antivirals for HBV," in Comprehensive Medicinal Chemistry, 3rd Edition, 2017, pp. 1-36.
Lee et al., "Flexible Use of Nuclear Import Pathways by HIV-1," Cell Host & Microbe, 2010, 7:221-233.
Lemke et al., "Distinct Effects of Two HIV-1 Capsid Assembly Inhibitor Families That Bind the Same Site Within the N-Terminal Domain of the Viral CA Protein," J. Virol., Jun. 2012, 86(12):6643-6655.
Macmillan et al., "Evaluation of alternative solvent in common amide coupling reactions: replacement of dicloromethane and N,N-dimethlformamide," Green Chem, 2013, 15: 596-600.
Magiorakos et al., "Multidrug-resistant, extensively drug-resistant and pandrug-resistant bacteria: an international expert proposal for interim standard definitions for acquired resistance," Clinical Microbiology and Infection, Mar. 2012, 18(3): 268-281.
Matreyek et al., "Nucleoporin NUP153 Phenylalanine-Glycine Motifs Engage a Common Binding Pocket within the HIV-1 Capsid Protein to Mediate Lentiviral Infectivity" PLOS Pathogens, 2013, 9(10): e1003693. 21 pages.
Mitchell et al., "Bioreversible Protection for the Phospho Group: Bioactivation of the Di(4-Acyloxybenzyl) and Mono(4-acyloxybenzyl) Phosphoesters of Methylphosphonate and Phosphonoacetate," J. Chem. Soc. Perkin Trans. 1, 1992, pp. 2345-2353.
Miyaura et al., "Palladium-Catalyzed Cross-Coupling Reactions of Oganoboron Compounds," Chem Rev, 1995, 95:2457-2483.

(56) References Cited

OTHER PUBLICATIONS

Molina et al., "On-Demand Preexposure Prophylaxis in Men at High Risk for HIV-1 Infection", The New England Journal of Medicine, Dec. 2015, 353:2237-2246.
Montalbetti et al., "Amide bond formation and peptide coupling," Tetrahedon, 2005, 61:10827-10852.
Morissette et al., "High-throughput crystallization: polymorphs, salts, co-crystals and solvates of pharmaceutical solids," Advanced Drug Delivery Reviews, Feb. 2004, 56(3):275-300.
Nicolaou et al., "Palladium-Catalyzed Cross-Coupling Reactions in Total Synthesis," Angew Chem Int Ed, 2005, 44:4442-4489.
Ovais et al. "Synthesis, antiproliferative and anti-inflammatory activities of some novel 6-aryl-2-(p-(methanesulfonyl)phenyl)-4,5-dihydropyridazi-3(2H)-ones," European Journal of Medicinal Chemistry, 2013, 67:352-358.
Owen et al., "Strengths, weaknesses, opportunities and challenges for long acting injectable therapies: Insights for applications in HIV therapy," Advances Drug Delivery Reviews, 2016, 103:144-156.
Palella et al., "Declining morbidity and mortality among patients with advanced human immunodeficiency virus infection," N Engl. J Med., 1998, 338:853-860.
Palombo et al., "Prodrug and conjugate drug delivery strategies for improving HIV/ADS therapy," Journal of drug delivery science and technology, Jan. 2009, 19(1): 31 pages.
Patel et al., "Poloxamers: a pharmaceutical excipients with therapeutic behaviors," International Journal of PharmTech Research, 2009, 1(2):299-303.
Pornillos et al., "Atomic level modeling of the HIV capsid," Nature, Jan. 2011, 469(7330):424-427.
Pornillos et al., "X-ray Structures of the Hexameric Building Block of the HIV Capsid" Cell, 2009, 137(7): 1282-1292.
Powers et al., "Synthesis of Methyl-, Fluoro-, and Chloro-substituted 6-Hydroxyisoindolin-1-1-Ones," Tetrahedron Letters, 2009, 50(12):1267-1269.
Price et al., "CPSF6 Defines a Conserved Capsid Interface That Modulates HIV-1 Replication," PLOS Pathogens, 2012, 8(8):e1002896, 14 pages.
Puech et al., "Intracellular Delivery of Nucleoside Monophosphates Through a Reductase-Mediated Activation Process," Antiviral Res., Oct. 1993, 22(2-3):155-174.
Pungpo et al., "Computer-aided molecular design of highly potent HIV-1 RT inhibitors: 3D QSAR and molecular docking studies of efavirenz derivatives," SAR and QSAR in Environmental Research, 2006, 17(4):353-370.
Registry (STN) [online], Mar. 22, 2010 [date of retrieval: Nov. 12, 2018], CAS registry No. 1213065-84-9.
Registry (STN) [online], Mar. 23, 2010 [date of retrieval: Nov. 12, 2018], CAS registry No. 1213495-28-3.
Registry (STN)[online], Nov. 15, 1991, STN Registry No. 137349-29-2, 1 page.
Rihn et al., "Extreme Genetic Fragility of the HIV-1 Capsid," PLOS One, 2013, 9(6): e1003461, 25 pages.
Shi et al., "Small-Molecule Inhibition of Human Immunodeficiency Virus Type 1 Capsid Destabilization," Journal of Virology, 2011, 85(1): 542-549.
Siddiqui et al., "The Presence of Substituents on the Aryl Moiety of the Aryl Phosphoramidate Derivative of d4T Enhances Anti-HIV Efficacy in Cell Culture: A Structure-Activity Relationship," J. Med. Chem., 1999, 42:393-399.
Silverman, "The Organic Chemistry of Drug Design and Drug Action," Elsevier, 2004, pp. 121-169.
Silvestri et al., "Novel Indolyl Aryl Sulfones Active against HIV-1 Carrying NNRTI Resistance Mutations: Synthesis and SAR Studies," Journal of Medical Chemistry, 2003, 46(12): 2482-2493.
Smith et al., "Evolutionary Dynamics of Complex Networks of HIV Drug-Resistant Strains: The Case of San Francisco," Science, 2010, 327(5966):697-701.
Sticht et al., "A peptide inhibitor of HIV-1 assembly in vitro," Nature Structural & Molecular Biology, 2005, 12(8): 671-677.
SUBLOCADE Product Label, issued: Nov. 2017, 43 pages.
Taiwo, "Understanding Transmitted HIV Resistance Through the Experience in the USA," International Journal of Infectious Diseases, 2009, 13(5):552-559.
Talele, "The 'Cyclopropyl Fragment' is a Versatile Player that Frequently Appears in Preclinical/Clinical Drug Molecules," Journal of Medicinal Chemistry, 2016, 59(19):8712-8756.
Tanaka et al., "One-Pot Synthesis of Metalated Pyridines from Two Acetylenes, a Nitrile, and a Titanium(II) Alkoxide," J. Am. Chem. Soc., 2005, 127(21):7774-7780.
Tang et al., "Antiviral Inhibition of the HIV-1 Capsid Protein," J. Mol. Biol., 2003, 327: 1013-1020.
Thenin-Houssier et al., "HIV-1 capsid inhibitors as antiretroviral agents," Curr. HIV Res., 2016, 14(3):270-282.
Tse et al., "Discovery of Novel Potent HIV Capsid Inhibitors with Long-Acting Potential," Abstract for Oral Presentation at the Conference on Retroviruses and Opportunistic Infections (CROI), Seattle, WA, 2017, 18 pages.
Tsiang et al., "A Trimer of Dimers is the Basic Building Block for Human Immunodeficiency Virus-1 Capsid Assembly," Biochemistry, 2012, 51: 4416-4428.
Wong et al., "SPR Assay Development to Characterize Caps id Inhibitors Binding & MOA," Poster Presented at the Developments in Protein Interaction (DiPIA), La Jolla, CA, 2014, 1 page.
Wu et al., "Selective Inhibitors of Tumor Progression Loci-2(Tp12) Kinase with Potent Inhibition of TNF-Alpha Production in Human Whole Blood," Bioorg. Med. Chem. Lett., 2009, 19(13):3485-3488.
Xianghui et al., "In Silico Virtual Screening," Biotechnology in the Post-Genome Era, 2003, 16 pages.
Yadav et al., "Co-crystals: a novel approach to modify physicochemical properties of active pharmaceutical ingredients," Indian J. Pharm. Sci., 2009, 71(4):359-370.
Yale, "The trifluoromethyl group in medicinal chemistry," J. Med. Chem., 1958, 1(2):121-133.
Yang et al., "Design, synthesis and anti-HIV-1 evaluation of hydrazide-based peptidomimetics as selective gelatinase inhibitors," Bioorganic & Medicinal Chemistry, May 2016, 24(9):2125-2136.
Yant et al., "An Improved PF74 Analog Inhibits Multiple HIV Capsid Functions Independently of Host Cyclophilin A and CPSF6," Poster Presented at the Conference on Retroviruses and Opportunistic Infections (CROI), Boston, Massachusetts, 2014, 1 page.
Yant et al., "PF74 Inhibits Multiple HIV Capsid Functions Independently of Host Cyclophilin A and CPSF6," Abstract for Poster Presented at the Conference on Retroviruses and Opportunistic Infections (CROI), Boston, Massachusetts, 2014, 1 page.
Zheng et al. "GS-6207: A Novel, Potent and Selective First-In-Class Inhibitor of HIV-1 Capsid Function Displays Nonclinical Pharmacokinetics Supporting Long-Acting Potential," Poster Presented at ID Week 2018, San Francisco, CA, 1 page.
Zhou et al. "HIV-1 Resistance to the Capsid-Targeting Inhibitor PF74 Results in Altered Dependence on Host Factors Required for Virus Nuclear Entry," Journal of Virology, 2015, 89(17): 9068-9079.
PCT International Search Report and Written Opinion in International Application No. PCT/US2021/038915, dated Sep. 24, 2021, 11 pages.
Taiwanese Office Action in TW Appln. No. 110123105, dated Apr. 12, 2022, 7 pages (with English translation).
Taiwanese Office Action in TW Appln. No. 110123105, dated Nov. 14, 2022, 8 pages (with English translation).
Australian Office Action in AU Appln. No. 2021296607, dated Jul. 13, 2023, 3 pages.
European Office Action in EP Appln. No. 21743003.2, dated Nov. 29, 2023, 5 pages.
Indian Office Action in IN Appln. No. 202317003791, dated Nov. 30, 2023, 5 pages.
Japanese Office Action in JP Appln. No. 2022-579945, dated Dec. 13, 2023, 15 pages (with English translation).
Taiwanese Office Acton in TW Appln. No. 110123105, dated Aug. 28, 2023, 4 pages (with English translation).
Taiwanese Office Acton in TW Appln. No. 110123105, dated Jan. 15, 2024, 5 pages (with English translation).

CAPSID INHIBITORS FOR THE TREATMENT OF HIV

CROSS REFERENCE TO RELATED APPLICATIONS

This application is a continuation of U.S. Ser. No. 17/357,376, filed Jun. 24, 2021, which claims priority to U.S. Provisional Application No. 63/044,086, filed Jun. 25, 2020, which is incorporated by reference herein in its entirety for all purposes.

FIELD

This disclosure relates generally to novel compounds, pharmaceutical compositions comprising said compounds, and methods of making and using said compounds and pharmaceutical compositions. In some embodiments, the novel compounds provided herein may be used in the treatment of a Retroviridae viral infection including an infection caused by the HIV virus.

BACKGROUND

Positive-single stranded RNA viruses comprising the Retroviridae family include those of the subfamily Orthoretrovirinae and genera Alpharetrovirus, Betaretrovirus, Gammaretrovirus, Deltaretrovirus, Epsilonretrovirus, Lentivirus, and Spumavirus which cause many human and animal diseases. Among the Lentivirus, HIV-1 infection in humans leads to depletion of T helper cells and immune dysfunction, producing immunodeficiency and vulnerability to opportunistic infections. Treating HIV-1 infections with highly active antiretroviral therapies (HAART) has proven to be effective at reducing viral load and significantly delaying disease progression (Hammer, S. M., et al.; *JAMA* 2008, 300: 555-570). However, these treatments could lead to the emergence of HIV strains that are resistant to current therapies (Taiwo, B., *International Journal of Infectious Diseases* 2009, 13:552-559; Smith, R. J., et al., *Science* 2010, 327: 697-701). Therefore, there is a pressing need to discover new antiretroviral agents that are active against emerging drug-resistant HIV variants. There is a need for compounds that are potent and stable and exhibit improved pharmacokinetic and/or pharmacodynamic profiles for the treatment of a Retroviridae viral infection including an infection caused by the HIV virus.

SUMMARY

In one aspect, provided herein is a compound of Formula I,

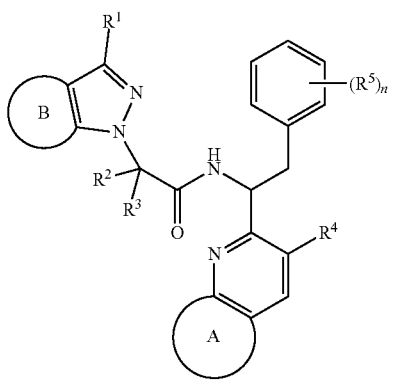

Formula I or a pharmaceutically acceptable salt thereof,
wherein
$R^2$ and $R^3$ are each independently H or $C_{1-3}$ alkyl;
each $R^5$ is halogen which may be the same or different;
$R^1$ is H, —CN, halogen, $C_{1-8}$ alkyl, $C_{3-7}$ monocyclic cycloalkyl, —C(O)NR$^6$R$^6$, —NR$^6$R$^6$, —NR$^7$C(O)R$^8$, or —C(O)R$^8$, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy;
Ring B, together with the two carbons to which it is attached, forms a $C_{3-7}$ monocyclic cycloalkyl, 5-9 membered fused or bridged bicyclic cycloalkyl, 3-4 membered monocyclic heterocyclyl, 5-7 membered monocyclic heterocyclyl, or 5-9 membered fused or bridged bicyclic heterocyclyl,
wherein the $C_{3-7}$ monocyclic cycloalkyl, 5-9 membered fused or bridged bicyclic cycloalkyl, 3-7 membered monocyclic heterocyclyl, and 5-9 membered fused or bridged bicyclic heterocyclyl are each optionally substituted with 1-5 $R^{16}$ groups
wherein the 3-4 membered monocyclic heterocyclyl has 1-2 ring heteroatoms independently selected from N, O, and S, and
wherein the 5-7 membered monocyclic heterocyclyl and 5-9 membered fused or bridged bicyclic heterocyclyl each have 1-3 ring heteroatoms independently selected from N, O, and S;
each $R^{16}$ is independently oxo, —OH, halogen, —CN, $C_{1-8}$alkyl, $C_{1-4}$ alkoxy, $C_{3-7}$ monocyclic cycloalkyl, —C(O)NR$^6$R$^6$, —NR$^6$R$^6$, —NR$^6$C(O)R$^8$, or —C(O)R$^8$, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy;
$R^4$ is a phenyl, 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, or 9-12 membered fused tricyclic heteroaryl,
wherein the phenyl, 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, and 9-12 membered fused tricyclic heteroaryl are each optionally substituted with 1-3 $R^{4a}$ groups, and
wherein the 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, and 9-12 membered fused tricyclic heteroaryl each have 1-3 ring heteroatoms independently selected from N, O, and S;
each $R^{4a}$ is independently oxo, —OH, halogen, —CN, $C_{1-8}$ alkyl, $C_{1-8}$ alkoxy, —NR$^6$R$^6$, —NR$^7$S(O)$_2$R$^9$, —NR$^7$S(O)$_2$NR$^6$R$^6$, —NR$^7$C(O)R$^8$, —NR$^7$C(O)R$^{10}$NR$^6$R$^6$, —NR$^7$C(O)NR$^6$R$^6$, or —C(O)NR$^6$R$^6$, wherein the $C_{1-8}$ alkyl is optionally substituted with 1-3 groups independently selected from —OH, halogen, —CN, and $C_{1-4}$ alkoxy, or two $R^{4a}$ of the 1-3 $R^{4a}$ groups are attached to the same carbon and the two $R^{4a}$, together with the carbon to which they are attached, form a $C_{3-7}$ monocyclic cycloalkyl;

each $R^6$ is independently H, $C_{1-8}$ alkyl, $C_{3-7}$ monocyclic cycloalkyl, or 4-6 membered monocyclic heterocyclyl having 1-3 ring heteroatoms independently selected from N, O, and S,
- wherein the $C_{1-8}$ alkyl is optionally substituted with 1-3 groups independently selected from —OH, halogen, —CN, and $C_{1-4}$ alkoxy, and
- wherein the $C_{3-7}$ monocyclic cycloalkyl and 4-6 membered monocyclic heterocyclyl having 1-3 ring heteroatoms independently selected from N, O, and S are each optionally substituted with 1-3 groups independently selected from —OH, halogen, —CN, $C_{1-4}$ alkyl, and $C_{1-4}$ alkoxy; or
- both $R^6$, together with the nitrogen to which they are attached, form a 4-6 membered monocyclic heterocyclyl having 1-3 ring heteroatoms independently selected from N, O, and S;

each $R^7$ is independently H or $C_{1-8}$ alkyl which may be the same or different, wherein the $C_{1-8}$ alkyl is optionally substituted with 1-3 groups independently selected from —OH, halogen, —CN, and $C_{1-4}$ alkoxy;

each $R^8$ is independently —OH, $C_{1-8}$ alkyl, $C_{1-8}$ alkoxy, $C_{3-7}$ monocyclic cycloalkyl, 4-6 membered monocyclic heterocyclyl, or 4-6 membered monocyclic heteroaryl,
- wherein the $C_{1-8}$ alkyl and $C_{1-8}$ alkoxy are each optionally substituted with 1-3 groups independently selected from —OH, halogen, —CN, and $C_{1-4}$ alkoxy,
- wherein the $C_{3-7}$ monocyclic cycloalkyl, 4-6 membered monocyclic heterocyclyl, and 4-6 membered monocyclic heteroaryl are each optionally substituted with 1-3 groups independently selected from —OH, halogen, —CN, $C_{1-4}$ alkyl, and $C_{1-4}$ alkoxy, and
- wherein the 4-6 membered monocyclic heterocyclyl and 4-6 membered monocyclic heteroaryl each have 1-3 ring heteroatoms independently selected from N, O, and S;

each $R^9$ is independently $C_{1-8}$ alkyl, $C_{3-7}$ monocyclic cycloalkyl, 4-6 membered monocyclic heterocyclyl, or 5-6 membered monocyclic heteroaryl,
- wherein the $C_{1-8}$ alkyl is optionally substituted with 1-3 groups independently selected from —OH, halogen, —CN, and $C_{1-4}$ alkoxy,
- wherein the $C_{3-7}$ monocyclic cycloalkyl, 4-6 membered monocyclic heterocyclyl, and 5-6 membered monocyclic heteroaryl are each optionally substituted with 1-3 groups independently selected from —OH, halogen, —CN, $C_{1-4}$ alkyl, and $C_{1-4}$ alkoxy, and
- wherein the 4-6 membered monocyclic heterocyclyl and 5-6 membered monocyclic heteroaryl each have 1-3 ring heteroatoms independently selected from N, O, and S;

each $R^{10}$ is $C_{1-4}$ alkylene, which may be the same or different;

Ring A, together with the two carbons to which it is attached, forms a 5-6 membered monocyclic heterocyclyl or 5-6 membered monocyclic heteroaryl, wherein the 5-6 membered monocyclic heterocyclyl and 5-6 membered monocyclic heteroaryl are each substituted with one Z group and each have 1-3 ring heteroatoms independently selected from N, O, and S;

Z is
i) oxo,
ii) —OH,
iii) —CN,
iv) $C_{1-8}$ alkyl, wherein the $C_{1-5}$ alkyl is substituted with one group selected from —OH and $C_{1-4}$ alkoxy, and wherein the $C_{1-8}$ alkyl is optionally further substituted with 1-2 groups independently selected from —OH, halogen, and —CN,
v) $C_{6-8}$ alkyl, wherein the $C_{6-8}$ alkyl is optionally substituted with 1-3 groups independently selected from —OH, halogen, —CN, and $C_{1-4}$ alkoxy,
vi) —$Z^1$-$Z^2$—$Z^3$—$Z^4$,
- wherein $Z^1$ is $C_{2-6}$ alkynylene optionally substituted with 1-3 groups independently selected from —OH, halogen, —CN, and $C_{1-4}$ alkoxy,
- wherein $Z^2$ and $Z^3$ are each independently $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, or 7-10 membered spirocyclic heterocyclylene, wherein the $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene each have 1-3 ring heteroatoms independently selected from N, O, and S, and
- wherein $Z^4$ is a $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S, vii) $C_{3-7}$ monocyclic cycloalkyl optionally substituted with 1-3 groups independently selected from —OH, halogen, —CN, $C_{1-4}$ alkyl, and $C_{1-4}$ alkoxy, viii) —S($C_{1-8}$ alkyl), wherein the $C_{1-8}$ alkyl is optionally substituted with 1-3 groups independently selected from —OH, halogen, —CN, and $C_{1-4}$ alkoxy, ix) —NR$^{11}$R$^{12}$, wherein one of R$^{11}$ and R$^{12}$ is H or $C_{1-8}$ alkyl and the other of R$^{11}$ and R$^{12}$ is $C_{1-8}$ alkyl, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein each $C_{1-8}$ alkyl is substituted with 1-3 R$^{17}$ groups, wherein the $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S, x) $C_{6-10}$ monocyclic or fused bicyclic aryl optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, —NR$^6$R$^6$, 4-6 membered monocyclic heterocyclyl, and 5-6 membered monocyclic heteroaryl, wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, and —NR$^6$R$^6$, and wherein the 4-6 membered monocyclic heterocyclyl and 5-6 membered monocyclic heteroaryl each have 1-3 ring heteroatoms independently selected from N, O, and S, xi) 4-6 membered monocyclic heterocyclyl having 1-3 ring heteroatoms independently selected from N, O, and S and optionally substituted with 1-3 R$^{13}$ groups, xii) 8-10 membered fused or bridged bicyclic heterocyclyl having 1-3 ring heteroatoms independently selected from N, O, and S and optionally substituted with 1-3 R$^{13}$ groups, xiii) 5-6 membered monocyclic heteroaryl having 1-3 ring heteroatoms independently selected from N, O, and S and optionally substituted with 1-3 R$^{13}$ groups, xiv) 8-10 membered fused bicyclic heteroaryl having 1-3 ring heteroatoms independently selected from N, O, and S and optionally substituted with 1-3 R$^{13}$ groups, or xv) 7-10 membered spirocyclic heterocyclyl having 1-3 ring heteroatoms independently selected from N, O, and S and optionally substituted with 1-3 R$^{13}$ groups;

each R$^{17}$ is independently —OH, halogen, —CN, $C_{1-4}$ alkoxy, —NR$^6$R$^6$, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl, wherein the $C_{1-4}$ alkoxy, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S;

each R$^{13}$ is independently oxo, —OH, halogen, —CN, $C_{1-4}$ alkyl, $C_{1-4}$ alkoxy, —NR$^6$R$^6$, —C(O)R$^{10}$NR$^6$R$^6$, —C(O)NR$^6$R$^6$, —C(O)R$^8$, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 R$^{14}$ groups, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S;

each R$^{14}$ is independently halogen, $C_{1-4}$ alkyl, —C(O)R$^8$, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{1-4}$ alkyl is optionally substituted with 1-3 groups independently selected from —OH, halogen, CN, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with $C_{1-3}$ alkyl, wherein the $C_{1-3}$ alkyl is optionally substituted with —OR$^{10}$Si(R$^{15}$)$_3$;

wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S;

each R$^{15}$ is independently $C_{1-3}$ alkyl, which may be the same or different; and n is 0, 1, 2, or 3.

In one aspect, provided herein are pharmaceutical compositions comprising a compound provided herein, or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (i.e., one, two, three, four; one or two; one to three; or one to four) additional therapeutic agents, or a pharmaceutically acceptable salt thereof. In some embodiments, the pharmaceutical compositions further comprise a therapeutically effective amount of the one or more (i.e., one, two, three, or four; one or two; one to three; or one to four) additional therapeutic agents, or a pharmaceutically acceptable salt thereof.

In one aspect, the present disclosure provides methods of treating or preventing a human immunodeficiency virus (HIV) infection in a subject in need thereof, comprising administering to the subject a therapeutically effective amount of a compound provided herein (i.e., a compound of Formula I, Ia, II, or IIa), or a pharmaceutically acceptable salt thereof, or a pharmaceutical composition provided herein.

DETAILED DESCRIPTION

I. Definitions

The description below is made with the understanding that the present disclosure is to be considered as an exemplification of the claimed subject matter, and is not intended to limit the appended claims to the specific embodiments illustrated. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth.

As used in the present disclosure, the following words, phrases and symbols are generally intended to have the meanings as set forth below, except to the extent that the context in which they are used indicates otherwise.

A dash ("-") that is not between two letters or symbols is used to indicate a point of attachment for a substituent. For example, —CONH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named. A solid line coming out of the center of a ring indicates that the point of attachment for a substituent on the ring can be at any ring atom. For example, R$^a$ in the below structure can be attached to any of the five carbon ring atoms or R$^a$ can replace the hydrogen attached to the nitrogen ring atom:

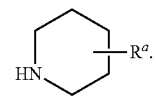

The prefix "$C_{u-v}$" indicates that the following group has from u to v carbon atoms. For example, "$C_{1-6}$ alkyl" indicates that the alkyl group has from 1 to 6 carbon atoms. Likewise, the term "x-y membered" rings, wherein x and y are numerical ranges, such as "3 to 12-membered heterocyclyl", refers to a ring containing x-y atoms (i.e., 3-12), of which up to 80% may be heteroatoms, such as N, O, S, P, and the remaining atoms are carbon.

Also, certain commonly used alternative chemical names may or may not be used. For example, a divalent group such as a divalent "alkyl" group, a divalent "aryl" group, etc., may also be referred to as an "alkylene" group or an "alkylenyl" group, or alkylyl group, an "arylene" group or an "arylenyl" group, or arylyl group, respectively.

"A compound disclosed herein" or "a compound of the present disclosure" or "a compound provided herein" or "a compound described herein" refers to the compounds of Formula I, II, IIa, III, IV, and/or V. Also included are the specific compounds of Examples 1 to 195.

Reference to "about" a value or parameter herein includes (and describes) embodiments that are directed to that value or parameter per se. In certain embodiments, the term "about" includes the indicated amount±10%. In other embodiments, the term "about" includes the indicated amount±5%. In certain other embodiments, the term "about" includes the indicated amount±1%. Also, the term "about X" includes description of "X".

"Alkyl" refers to an unbranched or branched saturated hydrocarbon chain. As used herein, alkyl has 1 to 20 carbon atoms (i.e., $C_{1-20}$ alkyl), 1 to 12 carbon atoms (i.e., $C_{1-12}$ alkyl), 1 to 8 carbon atoms (i.e., $C_{1-8}$ alkyl), 1 to 6 carbon atoms (i.e., $C_{1-6}$ alkyl), 1 to 4 carbon atoms (i.e., $C_{1-4}$ alkyl), 1 to 3 carbon atoms (i.e., $C_{1-3}$ alkyl), or 1 to 2 carbon atoms (i.e., $C_{1-2}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH (CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an aliphatic group containing at least one carbon-carbon double bond and having from 2 to 20 carbon atoms (i.e., C$_{2-20}$ alkenyl), 2 to 8 carbon atoms (i.e., C$_{2-8}$ alkenyl), 2 to 6 carbon atoms (i.e., C$_{2-6}$ alkenyl), or 2 to 4 carbon atoms (i.e., C$_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., C$_{2-20}$ alkynyl), 2 to 8 carbon atoms (i.e., C$_{2-8}$ alkynyl), 2 to 6 carbon atoms (i.e., C$_{2-6}$ alkynyl), or 2 to 4 carbon atoms (i.e., C$_{2-4}$ alkynyl). The term "alkynyl" also includes those groups having one triple bond and one double bond.

"Alkylene" refers to a divalent and unbranched saturated hydrocarbon chain. As used herein, alkylene has 1 to 20 carbon atoms (i.e., C$_{1-20}$ alkylene), 1 to 12 carbon atoms (i.e., C$_{1-12}$ alkylene), 1 to 8 carbon atoms (i.e., C$_{1-8}$ alkylene), 1 to 6 carbon atoms (i.e., C$_{1-6}$ alkylene), 1 to 4 carbon atoms (i.e., C$_{1-4}$ alkylene), 1 to 3 carbon atoms (i.e., C$_{1-3}$ alkylene), or 1 to 2 carbon atoms (i.e., C$_{1-2}$ alkylene). Examples of alkylene groups include methylene, ethylene, propylene, butylene, pentylene, and hexylene. In some embodiments, an alkylene is optionally substituted with an alkyl group. Examples of substituted alkylene groups include —CH(CH$_3$)CH$_2$—, —CH$_2$CH(CH$_3$)—, —CH$_2$CH(CH$_2$CH$_3$)—, —CH$_2$C(CH$_3$)$_2$—, —C(CH$_3$)$_2$CH$_2$—, —CH(CH$_3$)CH(CH$_3$)—, —CH$_2$C(CH$_2$CH$_3$)(CH$_3$)—, and —CH$_2$C(CH$_2$CH$_3$)$_2$.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy. "Haloalkoxy" refers to an alkoxy group as defined above, wherein one or more hydrogen atoms are replaced by a halogen.

"Acyl" refers to a group —C(=O)R, wherein R is hydrogen, alkyl, cycloalkyl, heterocyclyl, aryl, heteroalkyl, or heteroaryl; each of which may be optionally substituted, as defined herein. Examples of acyl include formyl, acetyl, cylcohexylcarbonyl, cyclohexylmethyl-carbonyl, and benzoyl.

"Amido" refers to both a "C-amido" group which refers to the group —C(=O)NR$^y$R$^z$ and an "N-amido" group which refers to the group —NR$^y$C(=O)R$^z$, wherein R$^y$ and R$^z$ are independently selected from the group consisting of hydrogen, alkyl, aryl, haloalkyl, heteroaryl, cycloalkyl, or heterocyclyl; each of which may be optionally substituted.

"Amino" refers to the group —NR$^y$R$^z$ wherein R$^y$ and R$^z$ are independently selected from the group consisting of hydrogen, alkyl, haloalkyl, aryl, heteroaryl, cycloalkyl, or heterocyclyl; each of which may be optionally substituted.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., C$_{6-20}$ aryl), 6 to 12 carbon ring atoms (i.e., C$_{6-12}$ aryl), or 6 to 10 carbon ring atoms (i.e., C$_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl ring, the resulting ring system is heteroaryl.

"Cyano" or "carbonitrile" refers to the group —CN.

"Cycloalkyl" refers to a saturated or partially saturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., C$_{3-20}$ cycloalkyl), 3 to 12 ring carbon atoms (i.e., C$_{3-12}$ cycloalkyl), 3 to 10 ring carbon atoms (i.e., C$_{3-10}$ cycloalkyl), 3 to 8 ring carbon atoms (i.e., C$_{3-8}$ cycloalkyl), or 3 to 6 ring carbon atoms (i.e., C$_{3-6}$ cycloalkyl). Examples of cycloalkyl groups include cyclopropyl, cyclobutyl, cyclopentyl, and cyclohexyl.

"Bridged" refers to a ring fusion wherein non-adjacent atoms on a ring are joined by a divalent substituent, such as an alkylenyl group, an alkylenyl group containing one or two heteroatoms, or a single heteroatom. Quinuclidinyl and admantanyl are examples of bridged ring systems.

The term "fused" refers to a ring which is bound to an adjacent ring.

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkylene" refers to a divalent and unbranched saturated hydrocarbon chain having one, two, or three heteroatoms selected from NH, O, or S. As used herein, a heteroalkylene has 1 to 20 carbon atoms and one, two, or three heteroatoms selected from NH, O, and S (i.e., C$_{1-20}$ heteroalkylene); 1 to 8 carbon atoms and one, two, or three heteroatoms selected from NH, O, and S (i.e., C$_{1-8}$ heteroalkylene); 1 to 6 carbon atoms and one, two, or three heteroatoms selected from NH, O, and S S (i.e., C$_{1-6}$ heteroalkylene); 1 to 4 carbon atoms and one, two, or three heteroatoms selected from NH, O, and S (i.e., C$_{1-4}$ heteroalkylene); 1 to 3 carbon atoms and one, two, or three heteroatoms selected from NH, O, and S (i.e., C$_{1-3}$ heteroalkylene); or 1 to 2 carbon atoms and one, two, or three heteroatoms selected from NH, O, and S (i.e., C$_{1-3}$ heteroalkylene). For example, —CH$_2$O— is a C$_1$ heteroalkylene and —CH$_2$SCH$_2$— is a C$_2$ heteroalkylene. Examples of heteroalkylene groups include —CH$_2$CH$_2$OCH$_2$—, —CH$_2$SCH$_2$OCH$_2$—, —CH$_2$O—, and —CH$_2$NHCH$_2$—. In some embodiments, a heteroalkylene is optionally substituted with an alkyl group. Examples of substituted heteroalkylene groups include —CH(CH$_3$)N(CH$_3$)CH$_2$—, —CH$_2$OCH(CH$_3$)—, —CH$_2$CH(CH$_2$CH$_3$)S—, —CH$_2$NHC(CH$_3$)$_2$—, —C(CH$_3$)$_2$SCH$_2$—, —CH(CH$_3$)N(CH$_3$)CH(CH$_3$)O—, —CH$_2$SC(CH$_2$CH$_3$)(CH$_3$)—, and —CH$_2$C(CH$_2$CH$_3$)$_2$NH—.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 carbon ring atoms (i.e., C$_{1-20}$ heteroaryl), 3 to 12 carbon ring atoms (i.e., C$_{3-12}$ heteroaryl), or 3 to 8 carbon ring atoms (i.e., C$_{3-8}$ heteroaryl); and 1 to 5 ring heteroatoms, 1 to 4 ring heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Heteroaryl does not encompass or overlap with aryl as defined above.

"Heterocyclyl" or "heterocyclic ring" or "heterocycle" refers to a non-aromatic cyclic alkyl group, with one or more ring heteroatoms independently selected from nitrogen, oxygen and sulfur. As used herein, "heterocyclyl" or "heterocyclic ring" or "heterocycle" refer to rings that are saturated or partially saturated unless otherwise indicated, e.g., in some embodiments "heterocyclyl" or "heterocyclic ring" or "heterocycle" refers to rings that are partially saturated where specified. The term "heterocyclyl" or "heterocyclic ring" or "heterocycle" includes heterocycloalkenyl groups (i.e., the heterocyclyl group having at least one double bond). A heterocyclyl may be a single ring or multiple rings wherein the multiple rings may be fused, bridged, or spiro. As used herein, heterocyclyl has 2 to 20 carbon ring atoms (i.e., $C_{2-20}$ heterocyclyl), 2 to 12 carbon ring atoms (i.e., $C_{2-12}$ heterocyclyl), 2 to 10 carbon ring atoms (i.e., $C_{2-10}$ heterocyclyl), 2 to 8 carbon ring atoms (i.e., $C_{2-8}$ heterocyclyl), 3 to 12 carbon ring atoms (i.e., $C_{3-12}$ heterocyclyl), 3 to 8 carbon ring atoms (i.e., $C_{3-8}$ heterocyclyl), or 3 to 6 carbon ring atoms (i.e., $C_{3-6}$ heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. Examples of heterocyclyl groups include pyrrolidinyl, piperidinyl, piperazinyl, oxetanyl, dioxolanyl, azetidinyl, and morpholinyl. As used herein, the term "bridged-heterocyclyl" refers to a four- to ten-membered cyclic moiety connected at two non-adjacent atoms of the heterocyclyl with one or more (e.g., 1 or 2) four- to ten-membered cyclic moiety having at least one heteroatom where each heteroatom is independently selected from nitrogen, oxygen, and sulfur. As used herein, "bridged-heterocyclyl" includes bicyclic and tricyclic ring systems. Also as used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. As used herein, the terms "heterocycle", "heterocyclyl", and "heterocyclic ring" are used interchangeably. In some embodiments, a heterocyclyl is substituted with an oxo group.

"Hydroxy" or "hydroxyl" refers to the group —OH.

"Oxo" refers to the group (=O) or (O).

"Sulfonyl" refers to the group —S(O)$_2$R$^e$, where R$^e$ is alkyl, haloalkyl, heterocyclyl, cycloalkyl, heteroaryl, or aryl. Examples of sulfonyl are methylsulfonyl, ethylsulfonyl, phenylsulfonyl, and toluenesulfonyl.

As used herein, "2-oxa-6-azaspiro[3.3]heptane" has the structure:

As used herein, "2,5-diazabicyclo[2.2.1]heptane" has the structure:

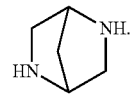

As used herein, "2,6-diazaspiro[3.3]heptane" has the structure:

As used herein, "1,6-diazaspiro[3.3]heptane" has the structure:

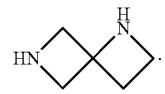

As used herein, "2,7-diazaspiro[3.5]nonane" has the structure:

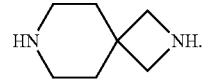

As used herein, "1-oxa-3,8-diazaspiro[4.5]decane" has the structure:

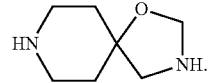

As used herein, "5,6,7,8-tetrahydro-[1,2,4]triazolo[4,3-a]pyrazine" has the structure:

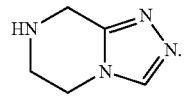

As used herein, "2,3-dihydrobenzo[b][1,4]dioxine" has the structure:

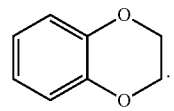

As used herein, "1H-benzo[d]imidazole" has the structure:

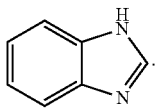

Whenever the graphical representation of a group terminates in a singly bonded nitrogen atom, that group represents an —NH group unless otherwise indicated. Similarly, unless otherwise expressed, hydrogen atom(s) are implied and deemed present where necessary in view of the knowledge of one of skill in the art to complete valency or provide stability.

The terms "optional" or "optionally" mean that the subsequently described event or circumstance may or may not occur, and that the description includes instances where said event or circumstance occurs and instances in which it does not. Also, the term "optionally substituted" means that any one or more hydrogen atoms on the designated atom or group may or may not be replaced by a moiety other than hydrogen.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. For example, the term "substituted aryl" includes, but is not limited to, "alkylaryl." Unless specified otherwise, where a group is described as optionally substituted, any substituents of the group are themselves unsubstituted.

In some embodiments, a substituted cycloalkyl, a substituted heterocyclyl, a substituted aryl, and/or a substituted heteroaryl includes a cycloalkyl, a heterocyclyl, an aryl, and/or a heteroaryl that has a substituent on the ring atom to which the cycloalkyl, heterocyclyl, aryl, and/or heteroaryl is attached to the rest of the compound. For example, in the below moiety, the cyclopropyl is substituted with a methyl group:

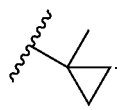

The compounds of the embodiments disclosed herein, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

"Enantiomers" are a pair of stereoisomers that are non-superimposable mirror images of each other. A 1:1 mixture of a pair of enantiomers is a "racemic" mixture. A mixture of enantiomers at a ratio other than 1:1 is a "scalemic" mixture.

"Diastereoisomers" are stereoisomers that have at least two asymmetric atoms, but which are not mirror-images of each other.

A "tautomer" refers to a proton shift from one atom of a molecule to another atom of the same molecule. The present disclosure includes tautomers of any compounds provided herein.

Some of the compounds provided herein exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

A "solvate" is formed by the interaction of a solvent and a compound. Solvates of salts of the compounds provided herein are also provided. Hydrates of the compounds provided herein are also provided.

Any formula or structure provided herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P $^{35}$S $^{36}$Cl and $^{125}$I. Various isotopically labeled compounds of the present disclosure, for example those into which radioactive isotopes such as $^2$H, $^3$H, $^{13}$C and $^{14}$C are incorporated, are also provided herein. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The present disclosure also includes compounds of Formula I, II, or IIa, in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I, II, or IIa, when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the present disclosure may have improved DMPK (drug metabolism and pharmacokinetics) properties, relating to absorption, distribution, metabolism and excretion (ADME). Substitution with heavier isotopes such as deuterium may afford certain therapeutic advantages resulting from greater metabolic stability, for example, increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I, II, or IIa.

The concentration of such a heavier isotope, specifically deuterium, may be defined by an isotopic enrichment factor. In the compounds of this disclosure, any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure, any atom specifically designated as a deuterium (D) is meant to represent deuterium.

In many cases, the compounds of this disclosure are capable of forming acid and/or base salts by virtue of the presence of amino and/or carboxyl groups or groups similar thereto.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, and the like. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Treatment" or "treating" is an approach for obtaining beneficial or desired results including clinical results. Beneficial or desired clinical results may include one or more of the following: a) inhibiting the disease or condition (i.e., decreasing one or more symptoms resulting from the disease or condition, and/or diminishing the extent of the disease or condition); b) slowing or arresting the development of one or more clinical symptoms associated with the disease or condition (i.e., stabilizing the disease or condition, preventing or delaying the worsening or progression of the disease or condition, and/or preventing or delaying the spread (i.e., metastasis) of the disease or condition); and/or c) relieving the disease, that is, causing the regression of clinical symptoms (i.e., ameliorating the disease state, providing partial or total remission of the disease or condition, enhancing effect of another medication, delaying the progression of the disease, increasing the quality of life, and/or prolonging survival).

"Prevention" or "preventing" means any treatment of a disease or condition that causes the clinical symptoms of the disease or condition not to develop. Compounds may, in some embodiments, be administered to a subject (including a human) who is at risk or has a family history of the disease or condition.

"Subject" refers to an animal, such as a mammal (including a human), that has been or will be the object of treatment, observation or experiment. The methods described herein may be useful in human therapy and/or veterinary applications. In some embodiments, the subject is a mammal. In one embodiment, the subject is a human.

The term "therapeutically effective amount" or "effective amount" of a compound described herein or pharmaceutically acceptable salts, isomer, or a mixture thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a disease or condition responsive to activation of protein kinase C (PKC). The therapeutically effective amount may vary depending on the subject, and the disease or condition being treated, the weight and age of the subject, the severity of the disease or condition, and the manner of administering, which can readily be determined by one of ordinary skill in the art.

II. Compounds

In one aspect, provided herein is a compound of Formula I,

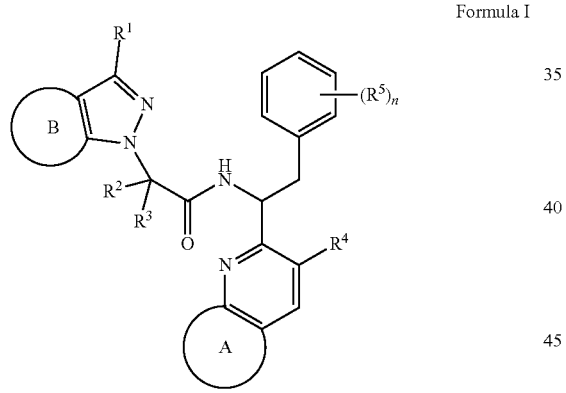

Formula I or a pharmaceutically acceptable salt thereof, wherein $R^2$ and $R^3$ are each independently H or $C_{1-3}$ alkyl;

each $R^5$ is halogen which may be the same or different;

$R^1$ is H, —CN, halogen, $C_{1-8}$ alkyl, $C_{3-7}$ monocyclic cycloalkyl, —C(O)NR$^6$R$^6$, —NR$^6$R$^6$, —NR$^7$C(O)R$^8$, or —C(O)R$^8$, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy;

Ring B, together with the two carbons to which it is attached, forms a $C_{3-7}$ monocyclic cycloalkyl, 5-9 membered fused or bridged bicyclic cycloalkyl, 3-4 membered monocyclic heterocyclyl, 5-7 membered monocyclic heterocyclyl, or 5-9 membered fused or bridged bicyclic heterocyclyl, wherein the $C_{3-7}$ monocyclic cycloalkyl, 5-9 membered fused or bridged bicyclic cycloalkyl, 3-7 membered monocyclic heterocyclyl, and 5-9 membered fused or bridged bicyclic heterocyclyl are each optionally substituted with 1-5 $R^{16}$ groups, wherein the 3-4 membered monocyclic heterocyclyl has 1-2 ring heteroatoms independently selected from N, O, and S, and wherein the 5-7 membered monocyclic heterocyclyl and 5-9 membered fused or bridged bicyclic heterocyclyl each have 1-3 ring heteroatoms independently selected from N, O, and S;

each $R^{16}$ is independently oxo, —OH, halogen, —CN, $C_{1-8}$ alkyl, $C_{1-4}$ alkoxy, $C_{3-7}$ monocyclic cycloalkyl, —C(O)NR$^6$R$^6$, —NR$^6$R$^6$, —NR$^6$C(O)R$^8$, or —C(O)R$^8$, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy;

$R^4$ is a phenyl, 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, or 9-12 membered fused tricyclic heteroaryl, wherein the phenyl, 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, and 9-12 membered fused tricyclic heteroaryl are each optionally substituted with 1-3 $R^{4a}$ groups, and wherein the 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, and 9-12 membered fused tricyclic heteroaryl each have 1-3 ring heteroatoms independently selected from N, O, and S;

each $R^{4a}$ is independently oxo, —OH, halogen, —CN, $C_{1-8}$ alkyl, $C_{1-8}$ alkoxy, —NR$^6$R$^6$, —NR$^7$S(O)$_2$R$^9$, —NR$^7$S(O)$_2$NR$^6$R$^6$, —NR$^7$C(O)R$^8$, —NR$^7$C(O)R$^{10}$NR$^6$R$^6$, —NR$^7$C(O)NR$^6$R$^6$, or —C(O)NR$^6$R$^6$, wherein the $C_{1-8}$ alkyl is optionally substituted with 1-3 groups independently selected from —OH, halogen, —CN, and $C_{1-4}$ alkoxy, or two $R^{4a}$ of the 1-3 $R^{4a}$ groups are attached to the same carbon and the two $R^{4a}$, together with the carbon to which they are attached, form a $C_{3-7}$ monocyclic cycloalkyl;

each $R^6$ is independently H, $C_{1-8}$ alkyl, $C_{3-7}$ monocyclic cycloalkyl, or 4-6 membered monocyclic heterocyclyl having 1-3 ring heteroatoms independently selected from N, O, and S, wherein the $C_{1-8}$ alkyl is optionally substituted with 1-3 groups independently selected from —OH, halogen, —CN, and $C_{1-4}$ alkoxy, and wherein the $C_{3-7}$ monocyclic cycloalkyl and 4-6 membered monocyclic heterocyclyl having 1-3 ring heteroatoms independently selected from N, O, and S are each optionally substituted with 1-3 groups independently selected from —OH, halogen, —CN, $C_{1-4}$ alkyl, and $C_{1-4}$ alkoxy; or both $R^6$, together with the nitrogen to which they are attached, form a 4-6 membered monocyclic heterocyclyl having 1-3 ring heteroatoms independently selected from N, O, and S;

each $R^7$ is independently H or $C_{1-8}$ alkyl which may be the same or different, wherein the $C_{1-8}$ alkyl is optionally substituted with 1-3 groups independently selected from —OH, halogen, —CN, and $C_{1-4}$ alkoxy;

each $R^8$ is independently —OH, $C_{1-8}$ alkyl, $C_{1-8}$ alkoxy, $C_{3-7}$ monocyclic cycloalkyl, 4-6 membered monocyclic heterocyclyl, or 4-6 membered monocyclic heteroaryl,
  wherein the $C_{1-8}$ alkyl and $C_{1-8}$ alkoxy are each optionally substituted with 1-3 groups independently selected from —OH, halogen, —CN, and $C_{1-4}$ alkoxy,
  wherein the $C_{3-7}$ monocyclic cycloalkyl, 4-6 membered monocyclic heterocyclyl, and 4-6 membered monocyclic heteroaryl are each optionally substituted with 1-3 groups independently selected from —OH, halogen, —CN, $C_{1-4}$ alkyl, and $C_{1-4}$ alkoxy, and
  wherein the 4-6 membered monocyclic heterocyclyl and 4-6 membered monocyclic heteroaryl each have 1-3 ring heteroatoms independently selected from N, O, and S;

each $R^9$ is independently $C_{1-8}$ alkyl, $C_{3-7}$ monocyclic cycloalkyl, 4-6 membered monocyclic heterocyclyl, or 5-6 membered monocyclic heteroaryl,
  wherein the $C_{1-8}$ alkyl is optionally substituted with 1-3 groups independently selected from —OH, halogen, —CN, and $C_{1-4}$ alkoxy,
  wherein the $C_{3-7}$ monocyclic cycloalkyl, 4-6 membered monocyclic heterocyclyl, and 5-6 membered monocyclic heteroaryl are each optionally substituted with 1-3 groups independently selected from —OH, halogen, —CN, $C_{1-4}$ alkyl, and $C_{1-4}$ alkoxy, and
  wherein the 4-6 membered monocyclic heterocyclyl and 5-6 membered monocyclic heteroaryl each have 1-3 ring heteroatoms independently selected from N, O, and S;

each $R^{10}$ is $C_{1-4}$ alkylene, which may be the same or different;

Ring A, together with the two carbons to which it is attached, forms a 5-6 membered monocyclic heterocyclyl or 5-6 membered monocyclic heteroaryl, wherein the 5-6 membered monocyclic heterocyclyl and 5-6 membered monocyclic heteroaryl are each substituted with one Z group and each have 1-3 ring heteroatoms independently selected from N, O, and S;

Z is
  i) oxo,
  ii) —OH,
  iii) —CN,
  iv) $C_{1-5}$ alkyl, wherein the $C_{1-8}$ alkyl is substituted with one group selected from —OH and $C_{1-4}$ alkoxy, and wherein the $C_{1-5}$ alkyl is optionally further substituted with 1-2 groups independently selected from —OH, halogen, and —CN,
  v) $C_{6-8}$ alkyl, wherein the $C_{6-8}$ alkyl is optionally substituted with 1-3 groups independently selected from —OH, halogen, —CN, and $C_{1-4}$ alkoxy,
  vi) —$Z^1$-$Z^2$—$Z^3$—$Z^4$,
    wherein $Z^1$ is $C_{2-6}$ alkynylene optionally substituted with 1-3 groups independently selected from —OH, halogen, —CN, and $C_{1-4}$ alkoxy,
    wherein $Z^2$ and $Z^3$ are each independently $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, or 7-10 membered spirocyclic heterocyclylene,
      wherein the $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene each have 1-3 ring heteroatoms independently selected from N, O, and S, and
    wherein $Z^4$ is a $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S,
  vii) $C_{3-7}$ monocyclic cycloalkyl optionally substituted with 1-3 groups independently selected from —OH, halogen, —CN, $C_{1-4}$ alkyl, and $C_{1-4}$ alkoxy,
  viii) —S($C_{1-8}$ alkyl), wherein the $C_{1-8}$ alkyl is optionally substituted with 1-3 groups independently selected from —OH, halogen, —CN, and $C_{1-4}$ alkoxy,
  ix) —N$R^{11}R^{12}$, wherein one of $R^{11}$ and $R^{12}$ is H or $C_{1-8}$ alkyl and the other of $R^{11}$ and $R^{12}$ is $C_{1-8}$ alkyl, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein each $C_{1-8}$ alkyl is substituted with 1-3 $R^{17}$ groups, wherein the $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S, x) $C_{6-10}$ monocyclic or fused bicyclic aryl optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, —NR$^6$R$^6$, 4-6 membered monocyclic heterocyclyl, and 5-6 membered monocyclic heteroaryl, wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, and —NR$^6$R$^6$, and wherein the 4-6 membered monocyclic heterocyclyl and 5-6 membered monocyclic heteroaryl each have 1-3 ring heteroatoms independently selected from N, O, and S, xi) 4-6 membered monocyclic heterocyclyl having 1-3 ring heteroatoms independently selected from N, O, and S and optionally substituted with 1-3 $R^{13}$ groups, xii) 8-10 membered fused or bridged bicyclic heterocyclyl having 1-3 ring heteroatoms independently selected from N, O, and S and optionally substituted with 1-3 $R^{13}$ groups, xiii) 5-6 membered monocyclic heteroaryl having 1-3 ring heteroatoms independently selected from N, O, and S and optionally substituted with 1-3 $R^{13}$ groups, xiv) 8-10 membered fused bicyclic heteroaryl having 1-3 ring heteroatoms independently selected from N, O, and S and optionally substituted with 1-3 $R^{13}$ groups, or xv) 7-10 membered spirocyclic heterocyclyl having 1-3 ring heteroatoms independently selected from N, O, and S and optionally substituted with 1-3 $R^{13}$ groups;

each $R^{17}$ is independently —OH, halogen, —CN, $C_{1-4}$ alkoxy, —NR$^6$R$^6$, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl, wherein the $C_{1-4}$ alkoxy, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S;

each $R^{13}$ is independently oxo, —OH, halogen, —CN, $C_{1-4}$ alkyl, $C_{1-4}$ alkoxy, —NR$^6$R$^6$, —C(O)R$^{10}$NR$^6$R$^6$, —C(O)NR$^6$R$^6$, —C(O)R$^8$, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 $R^{14}$ groups, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S;

each $R^{14}$ is independently halogen, $C_{1-4}$ alkyl, —C(O)R$^8$, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{1-4}$ alkyl is optionally substituted with 1-3 groups independently selected from —OH, halogen, CN, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with $C_{1-3}$ alkyl, wherein the $C_{1-3}$ alkyl is optionally substituted with —OR$^{10}$Si(R$^{15}$)$_3$;

wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S;

each $R^{15}$ is independently $C_{1-3}$ alkyl, which may be the same or different; and n is 0, 1, 2, or 3.

In some embodiments, the compound of Formula I is of Formula Ia:

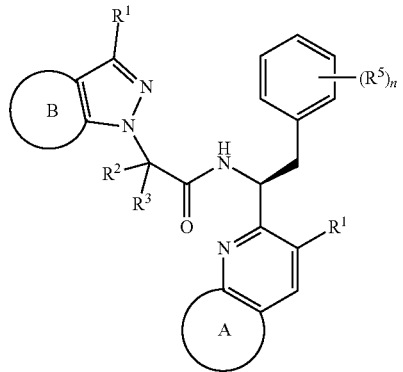

Formula Ia or a pharmaceutically acceptable salt thereof.

In some embodiments of the compound of Formula I or Ia, or a pharmaceutically acceptable salt thereof, $R^2$ and $R^3$ are each independently H or $C_{1-3}$ alkyl;

each $R^5$ is halogen which may be the same or different;

$R^1$ is H, —CN, halogen, $C_{1-8}$ alkyl, or $C_{3-7}$ monocyclic cycloalkyl, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy;

Ring B, together with the two carbons to which it is attached, forms a $C_{3-7}$ monocyclic cycloalkyl or 5-9 membered fused or bridged bicyclic cycloalkyl, wherein the $C_{3-7}$ monocyclic cycloalkyl and 5-9 membered fused or bridged bicyclic cycloalkyl are each optionally substituted with 1-5 $R^{16a}$ groups;

each $R^{16a}$ is independently —OH, halogen, —CN, $C_{1-8}$ alkyl, $C_{1-4}$ alkoxy, and $C_{3-7}$ monocyclic cycloalkyl, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy;

$R^4$ is a phenyl, 8-10 membered fused or bridged bicyclic heterocyclyl, 8-10 membered fused bicyclic heteroaryl, or 9-12 membered fused or bridged tricyclic heterocyclyl,
  wherein the phenyl, 8-10 membered fused or bridged bicyclic heterocyclyl, 8-10 membered fused bicyclic heteroaryl, and 9-12 membered fused or bridged tricyclic heterocyclyl are each optionally substituted with 1-3 $R^{4a}$ groups, and
  wherein the 8-10 membered fused or bridged bicyclic heterocyclyl, 8-10 membered fused bicyclic heteroaryl, and 9-12 membered fused or bridged tricyclic heterocyclyl each have 1-3 ring heteroatoms independently selected from N, O, and S;

each $R^{4a}$ is independently oxo, —OH, halogen, —CN, $C_{1-8}$ alkyl, $C_{1-8}$ alkoxy, —$NR^6R^6$, —$NR^7S(O)_2R^9$, or —$C(O)NR^6R^6$, wherein the $C_{1-8}$ alkyl is optionally substituted with 1-3 groups independently selected from —OH, halogen, —CN, and $C_{1-4}$ alkoxy, or two $R^{4a}$ of the 1-3 $R^{4a}$ groups are attached to the same carbon and the two $R^{4a}$, together with the carbon to which they are attached, form a $C_{3-7}$ monocyclic cycloalkyl;

each $R^6$ is independently H, $C_{1-8}$ alkyl, or $C_{3-7}$ monocyclic cycloalkyl,
  wherein the $C_{1-8}$ alkyl is optionally substituted with 1-3 groups independently selected from —OH, halogen, —CN, and $C_{1-4}$ alkoxy, and
  wherein the $C_{3-7}$ monocyclic cycloalkyl is optionally substituted with 1-3 groups independently selected from —OH, halogen, —CN, $C_{1-4}$ alkyl, and $C_{1-4}$ alkoxy;

each $R^7$ is independently H or $C_{1-8}$ alkyl which may be the same or different, wherein the $C_{1-8}$ alkyl is optionally substituted with 1-3 groups independently selected from —OH, halogen, —CN, and $C_{1-4}$ alkoxy;

each $R^8$ is independently —OH, $C_{1-8}$ alkyl, or $C_{1-8}$ alkoxy;

each $R^9$ is independently $C_{1-8}$ alkyl or $C_{3-7}$ monocyclic cycloalkyl,
  wherein the $C_{1-8}$ alkyl is optionally substituted with 1-3 groups independently selected from —OH, halogen, —CN, and $C_{1-4}$ alkoxy, and
  wherein the $C_{3-7}$ monocyclic cycloalkyl is optionally substituted with 1-3 groups independently selected from —OH, halogen, —CN, $C_{1-4}$ alkyl, and $C_{1-4}$ alkoxy;

each $R^{10}$ is $C_{1-4}$ alkylene, which may be the same or different;

Ring A, together with the two carbons to which it is attached, forms a 5-6 membered monocyclic heterocyclyl or 5-6 membered monocyclic heteroaryl, wherein the 5-6 membered monocyclic heterocyclyl and 5-6 membered monocyclic heteroaryl are each substituted with one Z group and each have 1-3 ring heteroatoms independently selected from N, O, and S;

Z is
  i) oxo,
  ii) —OH,
  iii) —CN,
  iv) $C_{1-5}$ alkyl, wherein the $C_{1-5}$ alkyl is substituted with one group selected from —OH and $C_{1-4}$ alkoxy, and wherein the $C_{1-5}$ alkyl is optionally further substituted with 1-2 groups independently selected from —OH, halogen, and —CN,
  v) $C_{6-8}$ alkyl, wherein the $C_{6-8}$ alkyl is optionally substituted with 1-3 groups independently selected from —OH, halogen, —CN, and $C_{1-4}$ alkoxy,
  vi) —$Z^1$-$Z^2$—$Z^3$—$Z^4$,
    wherein $Z^1$ is $C_{2-6}$ alkynylene optionally substituted with 1-3 groups independently selected from —OH, halogen, —CN, and $C_{1-4}$ alkoxy,
    wherein $Z^2$ is a $C_{6-10}$ monocyclic or fused bicyclic arylene, 4-6 membered monocyclic heterocyclylene, or 5-6 membered monocyclic heteroarylene, wherein the $C_{6-10}$ monocyclic or fused bicyclic arylene, 4-6 membered monocyclic heterocyclylene, and 5-6 membered monocyclic heteroarylene, are each optionally substituted with 1-3 groups independently selected from —OH, halogen, —CN, $C_{1-4}$ alkyl, $C_{1-4}$ alkoxy, and —$C(O)R^8$, and wherein the 4-6 membered monocyclic heterocyclylene and 5-6 membered monocyclic heteroarylene each have 1-3 ring heteroatoms independently selected from N, O, and S,
    wherein $Z^3$ is a 5-6 membered monocyclic heterocyclylene or 5-6 membered monocyclic heteroarylene,
      wherein the 5-6 membered monocyclic heterocyclylene and 5-6 membered monocyclic heteroarylene are each optionally substituted with 1-3 groups independently selected from —OH, halogen, —CN, $C_{1-4}$ alkyl, $C_{1-4}$ alkoxy, and —C(O)R$^8$, and wherein the 5-6 membered monocyclic heterocylene and 5-6 membered monocyclic heteroarylene each have 1-3 ring heteroatoms independently selected from N, O, and S, and wherein $Z^4$ is a 5-6 membered monocyclic heterocyclyl or 5-6 membered monocyclic heteroaryl, wherein the 5-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, and —C(O)R$^8$, and wherein the 5-6 membered monocyclic heterocyclyl and 5-6 membered monocyclic heteroaryl each have 1-3 ring heteroatoms independently selected from N, O, and S, vii) $C_{3-7}$ monocyclic cycloalkyl optionally substituted with 1-3 groups independently selected from —OH, halogen, —CN, $C_{1-4}$ alkyl, and $C_{1-4}$ alkoxy, viii) —S($C_{1-4}$ alkyl), wherein the $C_{1-4}$ alkyl is optionally substituted with 1-3 groups independently selected from —OH, halogen, —CN, and $C_{1-4}$ alkoxy, ix) —NR$^{11}$R$^{12}$, wherein one of R$^{11}$ and R$^{12}$ is H or $C_{1-8}$ alkyl and the other of R$^{11}$ and R$^{12}$ is $C_{1-8}$ alkyl, $C_{3-7}$ monocyclic cycloalkyl, 4-6 membered monocyclic heterocyclyl, or 5-6 membered monocyclic heteroaryl, wherein each $C_{1-8}$ alkyl is substituted with 1-3 R$^{17a}$ groups;

wherein the $C_{3-7}$ monocyclic cycloalkyl, 4-6 membered monocyclic heterocyclyl, and 5-6 membered monocyclic heteroaryl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl and 5-6 membered monocyclic heteroaryl each have 1-3 ring heteroatoms independently selected from N, O, and S, x) $C_{6-10}$ monocyclic or fused bicyclic aryl optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, —NR$^6$R$^6$, 4-6 membered monocyclic heterocyclyl, and 5-6 membered monocyclic heteroaryl, wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, and —NR$^6$R$^6$, and wherein the 4-6 membered monocyclic heterocyclyl and 5-6 membered monocyclic heteroaryl each have 1-3 ring heteroatoms independently selected from N, O, and S, xi) 4-6 membered monocyclic heterocyclyl having 1-3 ring heteroatoms independently selected from N, O, and S and optionally substituted with 1-3 R$^{13}$ groups, xii) 8-10 membered fused or bridged bicyclic heterocyclyl having 1-3 ring heteroatoms independently selected from N, O, and S and optionally substituted with 1-3 R$^{13}$ groups, xiii) 5-6 membered monocyclic heteroaryl having 1-3 ring heteroatoms independently selected from N, O, and S and optionally substituted with 1-3 R$^{13}$ groups, xiv) 8-10 membered fused bicyclic heteroaryl optionally substituted with 1-3 R$^{13}$ groups, or xv) 7-10 membered spirocyclic heterocyclyl having 1-3 ring heteroatoms independently selected from N, O, and S and optionally substituted with 1-3 R$^{13}$ groups;

each R$^{17a}$ is independently —OH, halogen, —CN, $C_{1-4}$ alkoxy, —NR$^6$R$^6$, $C_{3-7}$ monocyclic cycloalkyl, 4-6 membered monocyclic heterocyclyl, and 5-6 membered monocyclic heteroaryl, wherein the $C_{1-4}$ alkoxy, $C_{3-7}$ monocyclic cycloalkyl, 4-6 membered monocyclic heterocyclyl, and 5-6 membered monocyclic heteroaryl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl and 5-6 membered monocyclic heteroaryl each have 1-3 ring heteroatoms independently selected from N, O, and S;

each R$^{13}$ is independently oxo, —OH, halogen, —CN, $C_{1-4}$ alkyl, $C_{1-4}$ alkoxy, —NR$^6$R$^6$, —C(O)R$^{10}$NR$^6$R$^6$, —C(O)NR$^6$R$^6$, —C(O)R$^8$, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, or 8-10 membered fused bicyclic heteroaryl, wherein the $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, and 8-10 membered fused bicyclic heteroaryl are each optionally substituted with 1-3 R$^{14}$ groups, and wherein the 4-6 membered monocyclic heterocyclyl, 5-6 membered monocyclic heteroaryl, 8-10 membered fused or bridged bicyclic heterocyclyl, and 8-10 membered fused bicyclic heteroaryl each have 1-3 ring heteroatoms independently selected from N, O, and S;

each R$^{14}$ is independently halogen, $C_{1-4}$ alkyl, —C(O)R$^8$, or 5-6 membered monocyclic heteroaryl having 1-3 ring heteroatoms independently selected from N, O, and S, wherein the $C_{1-4}$ alkyl is optionally substituted with 1-3 groups independently selected from —OH, halogen, CN, and $C_{1-4}$ alkoxy, and wherein the 5-6 membered monocyclic heteroaryl having 1-3 ring heteroatoms independently selected from N, O, and S is optionally substituted with $C_{1-3}$ alkyl, wherein the $C_{1-3}$ alkyl is optionally substituted with —OR$^{10}$Si(R$^{15}$)$_3$;

each R$^{15}$ is independently $C_{1-3}$ alkyl, which may be the same or different; and n is 0, 1, 2, or 3.

In some embodiments of the compound of Formula I or Ia, or a pharmaceutically acceptable salt thereof, n is 0, 1, 2, or 3. In some embodiments of the compound of Formula I or Ia, or a pharmaceutically acceptable salt thereof, n is 0. In some embodiments of the compound of Formula I or Ia, or a pharmaceutically acceptable salt thereof, n is 1. In some embodiments of the compound of Formula I or Ia, or a pharmaceutically acceptable salt thereof, n is 2. In some embodiments of the compound of Formula I or Ia, or a pharmaceutically acceptable salt thereof, n is 3.

In some embodiments, the compound of Formula I is of Formula II:

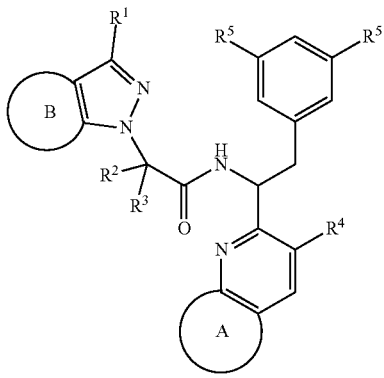

Formula II or a pharmaceutically acceptable salt thereof.

In some embodiments, the compound of Formula I, Ia, or II is of Formula IIa:

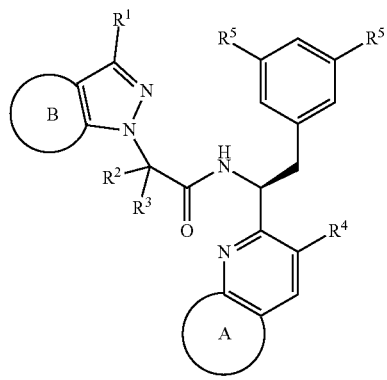

Formula IIa or a pharmaceutically acceptable salt thereof.

In some embodiments of the compound of Formula I, Ia, II, or IIa, or a pharmaceutically acceptable salt thereof, $R^2$ and $R^3$ are each independently H or $C_{1-3}$ alkyl. In some embodiments of the compound of Formula I, Ia, II, or IIa, or a pharmaceutically acceptable salt thereof, one of $R^2$ and $R^3$ is H and the other of $R^2$ and $R^3$ is $C_{1-3}$ alkyl. In some embodiments of the compound of Formula I, Ia, II, or IIa, or a pharmaceutically acceptable salt thereof, one of $R^2$ and $R^3$ is H and the other of $R^2$ and $R^3$ is methyl. In some embodiments of the compound of Formula I, Ia, II, or IIa, or a pharmaceutically acceptable salt thereof, one of $R^2$ and $R^3$ is H and the other of $R^2$ and $R^3$ is ethyl. In some embodiments of the compound of Formula I, Ia, II, or IIa, or a pharmaceutically acceptable salt thereof, one of $R^2$ and $R^3$ is H and the other of $R^2$ and $R^3$ is propyl. In some embodiments of the compound of Formula I, Ia, II, or IIa, or a pharmaceutically acceptable salt thereof, one of $R^2$ and $R^3$ is H and the other of $R^2$ and $R^3$ is isopropyl. In some embodiments of the compound of Formula I, Ia, II, or IIa, or a pharmaceutically acceptable salt thereof, both $R^2$ and $R^3$ are H. In some embodiments of the compound of Formula I, Ia, II, or IIa, or a pharmaceutically acceptable salt thereof, $R^2$ and $R^3$ are each independently methyl, ethyl, propyl, or isopropyl.

In some embodiments of the compound of Formula I, Ia, II, or IIa, or a pharmaceutically acceptable salt thereof, each $R^5$ is halogen which may be the same or different. In some embodiments of the compound of Formula I, Ia, II, or IIa, or a pharmaceutically acceptable salt thereof, each $R^5$ is independently chloro, fluoro, bromo, or iodo. In some embodiments of the compound of Formula I, Ia, II, or IIa, or a pharmaceutically acceptable salt thereof, each $R^5$ is independently chloro, fluoro, or bromo. In some embodiments of the compound of Formula I, Ia, II, or IIa, or a pharmaceutically acceptable salt thereof, one or more $R^5$ is fluoro. In some embodiments of the compound of Formula I, Ia, II, or IIa, or a pharmaceutically acceptable salt thereof, two $R^5$ are fluoro. In some embodiments of the compound of Formula I, Ia, II, or IIa, or a pharmaceutically acceptable salt thereof, each $R^5$ is fluoro.

In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, 5-9 membered fused or bridged bicyclic cycloalkyl, 3-4 membered monocyclic heterocyclyl, 5-7 membered monocyclic heterocyclyl, or 5-9 membered fused or bridged bicyclic heterocyclyl,
wherein the $C_{3-7}$ monocyclic cycloalkyl, 5-9 membered fused or bridged bicyclic cycloalkyl, 3-7 membered monocyclic heterocyclyl, and 5-9 membered fused or bridged bicyclic heterocyclyl are each optionally substituted with 1-5 $R^{16}$ groups
wherein the 3-4 membered monocyclic heterocyclyl has 1-2 ring heteroatoms independently selected from N, O, and S, and
wherein the 5-7 membered monocyclic heterocyclyl and 5-9 membered fused or bridged bicyclic heterocyclyl each have 1-3 ring heteroatoms independently selected from N, O, and S.

In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl or 5-9 membered fused or bridged bicyclic cycloalkyl,
wherein the $C_{3-7}$ monocyclic cycloalkyl and the 5-9 membered fused or bridged bicyclic cycloalkyl are each optionally substituted with 1-5 $R^{16a}$ groups.

In some embodiments of the compound of Formula I, Ia, II, or IIa, or a pharmaceutically acceptable salt thereof, Ring B, together with the two carbons to which it is attached, forms a cyclohexyl or 6-7 membered fused or bridged bicyclic cycloalkyl, wherein the cyclohexyl and 6-7 membered fused or bridged bicyclic cycloalkyl are each optionally substituted with 1-5 halogens.

In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is optionally substituted with 1-5 $R^{16}$ groups. In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is optionally substituted with 1-5 $R^{16a}$ groups.

In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is substituted with 1-5 $R^{16}$ groups. In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is substituted with 1-5 $R^{16a}$ groups. In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is substituted with 1-5 groups independently selected from —OH, halogen, —CN, and $C_{1-8}$ alkyl. In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is substituted with 1-5 halogens. In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl, wherein the $C_{3-7}$ monocyclic cycloalkyl is substituted with 1-5 fluoro. In some embodiments of the compound of Formula I, Ia, II, or IIa, or a pharmaceutically acceptable salt thereof, Ring B, together with the two carbons to which it is attached, forms a cyclopentyl, wherein the cyclopentyl is substituted with 1-5 fluoro.

In some embodiments of the compound of Formula I, Ia, II, or IIa, or a pharmaceutically acceptable salt thereof, Ring B, together with the two carbons to which it is attached, forms a $C_{3-7}$ monocyclic cycloalkyl. In some embodiments of the compound of Formula I, Ia, II, or IIa, or a pharmaceutically acceptable salt thereof, Ring B, together with the two carbons to which it is attached, forms a cyclopentyl or cyclohexyl.

In some embodiments of the compound of Formula I, Ia, II, or IIa, or a pharmaceutically acceptable salt thereof, Ring B, together with the two carbons to which it is attached, forms a cyclohexyl, wherein the cyclohexyl is optionally substituted with 1-5 halogens. In some embodiments of the compound of Formula I, Ia, II, or IIa, or a pharmaceutically acceptable salt thereof, Ring B, together with the two carbons to which it is attached, forms a cyclohexyl, wherein the cyclohexyl is substituted with 1-5 halogens. In some embodiments of the compound of Formula I, Ia, II, or IIa, or a pharmaceutically acceptable salt thereof, Ring B, together with the two carbons to which it is attached, forms a cyclohexyl, wherein the cyclohexyl is substituted with 1-4 halogens. In some embodiments of the compound of Formula I, Ia, II, or IIa, or a pharmaceutically acceptable salt thereof, Ring B, together with the two carbons to which it is attached, forms a cyclohexyl, wherein the cyclohexyl is substituted with 1-5 fluoro.

In some embodiments of the compound of Formula I, Ia, II, or IIa, or a pharmaceutically acceptable salt thereof, Ring B, together with the two carbons to which it is attached, forms a 5-9 membered fused or bridged bicyclic cycloalkyl, wherein the 5-9 membered fused or bridged bicyclic cycloalkyl is optionally substituted with 1-5 $R^{16}$ groups. In some embodiments of the compound of Formula I, Ia, II, or IIa, or a pharmaceutically acceptable salt thereof, Ring B, together with the two carbons to which it is attached, forms a 5-9 membered fused or bridged bicyclic cycloalkyl, wherein the 5-9 membered fused or bridged bicyclic cycloalkyl is optionally substituted with 1-5 $R^{16a}$ groups.

In some embodiments of the compound of Formula I, Ia, II, or IIa, or a pharmaceutically acceptable salt thereof, Ring B, together with the two carbons to which it is attached, forms a 5-9 membered fused or bridged bicyclic cycloalkyl, wherein the 5-9 membered fused or bridged bicyclic cycloalkyl is substituted with 1-5 groups independently selected from —OH, halogen, —CN, and $C_{1-8}$ alkyl. In some embodiments of the compound of Formula I, Ia, II, or IIa, or a pharmaceutically acceptable salt thereof, Ring B, together with the two carbons to which it is attached, forms a 5-9 membered fused or bridged bicyclic cycloalkyl, wherein the 5-9 membered fused or bridged bicyclic cycloalkyl is substituted with 1-5 halogens. In some embodiments of the compound of Formula I, Ia, II, or IIa, or a pharmaceutically acceptable salt thereof, Ring B, together with the two carbons to which it is attached, forms a 5-9 membered fused or bridged bicyclic cycloalkyl, wherein the 5-9 membered fused or bridged bicyclic cycloalkyl is substituted with 1-4 halogens. In some embodiments of the compound of Formula I, Ia, II, or IIa, or a pharmaceutically acceptable salt thereof, Ring B, together with the two carbons to which it is attached, forms a 5-9 membered fused or bridged bicyclic cycloalkyl, wherein the 5-9 membered fused or bridged bicyclic cycloalkyl is substituted with 1-5 fluoro. In some embodiments of the compound of Formula I, Ia, II, or IIa, or a pharmaceutically acceptable salt thereof, Ring B, together with the two carbons to which it is attached, forms a 6-8 membered fused or bridged bicyclic cycloalkyl, wherein the 6-8 membered fused or bridged bicyclic cycloalkyl is substituted with 1-5 fluoro. In some embodiments of the compound of Formula I, Ia, II, or IIa, or a pharmaceutically acceptable salt thereof, Ring B, together with the two carbons to which it is attached, forms a 6-membered fused or bridged bicyclic cycloalkyl, wherein the 6-membered fused or bridged bicyclic cycloalkyl is substituted with 1-5 fluoro. In some embodiments of the compound of Formula I, Ia, II, or IIa, or a pharmaceutically acceptable salt thereof, Ring B, together with the two carbons to which it is attached, forms a 7-membered fused or bridged bicyclic cycloalkyl, wherein the 7-membered fused or bridged bicyclic cycloalkyl is substituted with 1-5 fluoro.

In some embodiments of the compound of Formula I, Ia, II, or IIa, or a pharmaceutically acceptable salt thereof, Ring B, together with the two carbons to which it is attached, forms a 6-7 membered fused or bridged bicyclic cycloalkyl, wherein the 6-7 membered fused or bridged bicyclic cycloalkyl is optionally substituted with 1-5 halogens. In some embodiments of the compound of Formula I, Ia, II, or IIa, or a pharmaceutically acceptable salt thereof, Ring B, together with the two carbons to which it is attached, forms a 6-7 membered fused or bridged bicyclic cycloalkyl, wherein the 6-7 membered fused or bridged bicyclic cycloalkyl is substituted with 1-5 halogens. In some embodiments of the compound of Formula I, Ia, II, or IIa, or a pharmaceutically acceptable salt thereof, Ring B, together with the two carbons to which it is attached, forms a 6-7 membered fused or bridged bicyclic cycloalkyl, wherein the 6-7 membered fused or bridged bicyclic cycloalkyl is substituted with 1-4 halogens. In some embodiments of the compound of Formula I, Ia, II, or IIa, or a pharmaceutically acceptable salt thereof, Ring B, together with the two carbons to which it is attached, forms a 6-7 membered fused or bridged bicyclic cycloalkyl, wherein the 6-7 membered fused or bridged bicyclic cycloalkyl is substituted with 1-3 halogens. In some embodiments of the compound of Formula I, Ia, II, or IIa, or a pharmaceutically acceptable salt thereof, Ring B, together with the two carbons to which it is attached, forms a 6-7 membered fused or bridged bicyclic cycloalkyl, wherein the 6-7 membered fused or bridged bicyclic cycloalkyl is substituted with 1-3 fluoro.

In some embodiments of the compound of Formula I, Ia, II, or IIa, or a pharmaceutically acceptable salt thereof, Ring B, together with the two carbons to which it is attached, forms a 3-4 membered monocyclic heterocyclyl, wherein the 3-4 membered monocyclic heterocyclyl has 1-2 ring heteroatoms independently selected from N, O, and S and is optionally substituted with 1-5 $R^{16}$ groups. In some embodiments of the compound of Formula I, Ia, II, or IIa, or a pharmaceutically acceptable salt thereof, Ring B, together with the two carbons to which it is attached, forms a 3-4 membered monocyclic heterocyclyl, wherein the 3-4 membered monocyclic heterocyclyl has 1-2 ring heteroatoms independently selected from N, O, and S and is optionally substituted with 1-5 $R^{16a}$ groups.

In some embodiments of the compound of Formula I, Ia, II, or IIa, or a pharmaceutically acceptable salt thereof, Ring B, together with the two carbons to which it is attached, forms a 3-4 membered monocyclic heterocyclyl, wherein the 3-4 membered monocyclic heterocyclyl has 1-2 ring heteroatoms independently selected from N, O, and S and is substituted with 1-5 $R^{16}$ groups. In some embodiments of the compound of Formula I, Ia, II, or IIa, or a pharmaceutically acceptable salt thereof, Ring B, together with the two carbons to which it is attached, forms a 3-4 membered monocyclic heterocyclyl, wherein the 3-4 membered monocyclic heterocyclyl has 1-2 ring heteroatoms independently selected from N, O, and S and is substituted with 1-5 $R^{16a}$ groups. In some embodiments of the compound of Formula I, Ia, II, or IIa, or a pharmaceutically acceptable salt thereof, Ring B, together with the two carbons to which it is attached, forms a 3-4 membered monocyclic heterocyclyl having 1-2 ring heteroatoms independently selected from N, O, and S.

In some embodiments of the compound of Formula I, Ia, II, or IIa, or a pharmaceutically acceptable salt thereof, Ring B, together with the two carbons to which it is attached, forms a 5-7 membered monocyclic heterocyclyl, wherein the 5-7 membered monocyclic heterocyclyl has 1-3 ring heteroatoms independently selected from N, O, and S and is optionally substituted with 1-5 $R^{16}$ groups. In some embodiments of the compound of Formula I, Ia, II, or IIa, or a pharmaceutically acceptable salt thereof, Ring B, together with the two carbons to which it is attached, forms a 5-7 membered monocyclic heterocyclyl, wherein the 5-7 membered monocyclic heterocyclyl has 1-3 ring heteroatoms independently selected from N, O, and S and is optionally substituted with 1-5 $R^{16a}$ groups.

In some embodiments of the compound of Formula I, Ia, II, or IIa, or a pharmaceutically acceptable salt thereof, Ring B, together with the two carbons to which it is attached, forms a 5-7 membered monocyclic heterocyclyl, wherein the 5-7 membered monocyclic heterocyclyl has 1-3 ring heteroatoms independently selected from N, O, and S and is substituted with 1-5 $R^{16}$ groups. In some embodiments of the compound of Formula I, Ia, II, or IIa, or a pharmaceutically acceptable salt thereof, Ring B, together with the two carbons to which it is attached, forms a 5-7 membered monocyclic heterocyclyl, wherein the 5-7 membered monocyclic heterocyclyl has 1-3 ring heteroatoms independently selected from N, O, and S and is substituted with 1-5 $R^{16a}$ groups. In some embodiments of the compound of Formula I, Ia, II, or IIa, or a pharmaceutically acceptable salt thereof, Ring B, together with the two carbons to which it is attached, forms a 5-7 membered monocyclic heterocyclyl having 1-3 ring heteroatoms independently selected from N, O, and S.

In some embodiments of the compound of Formula I, Ia, II, or IIa, or a pharmaceutically acceptable salt thereof, Ring B, together with the two carbons to which it is attached, forms a 5-9 membered fused or bridged bicyclic heterocyclyl, wherein the 5-9 membered fused or bridged bicyclic heterocyclyl has 1-3 ring heteroatoms independently selected from N, O, and S and is optionally substituted with 1-5 $R^{16}$ groups. In some embodiments of the compound of Formula I, Ia, II, or IIa, or a pharmaceutically acceptable salt thereof, Ring B, together with the two carbons to which it is attached, forms a 5-9 membered fused or bridged bicyclic heterocyclyl, wherein the 5-9 membered fused or bridged bicyclic heterocyclyl has 1-3 ring heteroatoms independently selected from N, O, and S and is optionally substituted with 1-5 $R^{16a}$ groups.

In some embodiments of the compound of Formula I, Ia, II, or IIa, or a pharmaceutically acceptable salt thereof, Ring B, together with the two carbons to which it is attached, forms a 5-9 membered fused or bridged bicyclic heterocyclyl, wherein the 5-9 membered fused or bridged bicyclic heterocyclyl has 1-3 ring heteroatoms independently selected from N, O, and S and is substituted with 1-5 $R^{16}$ groups. In some embodiments of the compound of Formula I, Ia, II, or IIa, or a pharmaceutically acceptable salt thereof, Ring B, together with the two carbons to which it is attached, forms a 5-9 membered fused or bridged bicyclic heterocyclyl, wherein the 5-9 membered fused or bridged bicyclic heterocyclyl has 1-3 ring heteroatoms independently selected from N, O, and S and is substituted with 1-5 $R^{16a}$ groups. In some embodiments of the compound of Formula I, Ia, II, or IIa, or a pharmaceutically acceptable salt thereof, Ring B, together with the two carbons to which it is attached, forms a 5-9 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, Ring B is cyclohexyl, tetrahydropyranyl, each of which is optionally substituted with 1-5 groups independently selected from oxo, —OH, halogen, —CN, $C_{1-8}$ alkyl, $C_{1-4}$ alkoxy, $C_{3-7}$ monocyclic cycloalkyl, —C(O)NR$^6$R$^6$, —NR$^6$R$^6$, —NR$^6$C(O)R$^8$, and —C(O)R$^8$.

In some embodiments of the compound of Formula I, Ia, II, or IIa, or a pharmaceutically acceptable salt thereof, Ring B is cyclohexyl, tetrahydropyranyl,

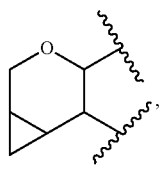

each of which is optionally substituted with 1-4 groups independently selected from oxo, —OH, halogen, —CN, $C_{1-8}$ alkyl, $C_{1-4}$ alkoxy, $C_{3-7}$ monocyclic cycloalkyl, —C(O)NR$^6$R$^6$, —NR$^6$R$^6$, —NR$^6$C(O)R$^8$, and —C(O)R$^8$.

In some embodiments of the compound of Formula I, Ia, II, or IIa, or a pharmaceutically acceptable salt thereof, Ring B is a cyclohexyl,

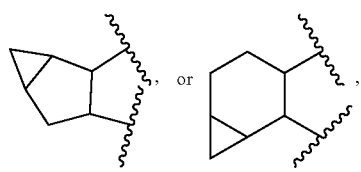 [SMILES: *C1CC2CC2C1* ; *C1CCC2CC2C1*]

each of which is optionally substituted with 1-5 halogens.

In some embodiments of the compound of Formula I, Ia, II, or IIa, or a pharmaceutically acceptable salt thereof, Ring B is a cyclohexyl,

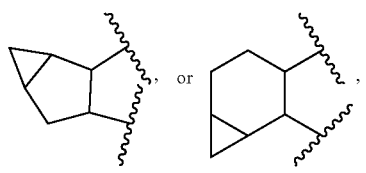 [SMILES: *C1CC2CC2C1* ; *C1CCC2CC2C1*]

each of which is optionally substituted with 1-5 fluoro.

In some embodiments of the compound of Formula I, Ia, II, or IIa, or a pharmaceutically acceptable salt thereof, each $R^{16}$ is independently oxo, —OH, halogen, —CN, $C_{1-8}$ alkyl, $C_{1-4}$ alkoxy, $C_{3-7}$ monocyclic cycloalkyl, —C(O)NR$^6$R$^6$, —NR$^6$R$^6$, —NR$^6$C(O)R$^8$, or —C(O)R$^8$, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy.

In some embodiments of the compound of Formula I, Ia, II, or IIa, or a pharmaceutically acceptable salt thereof, each $R^{16a}$ is independently —OH, halogen, —CN, $C_{1-8}$ alkyl, $C_{1-4}$ alkoxy, and $C_{3-7}$ monocyclic cycloalkyl, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy.

In some embodiments of the compound of Formula I, Ia, II, or IIa, or a pharmaceutically acceptable salt thereof,

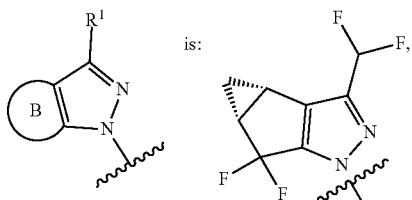

is:

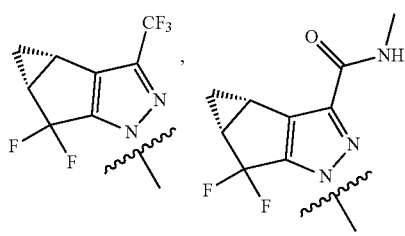

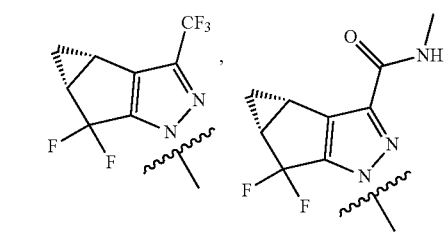

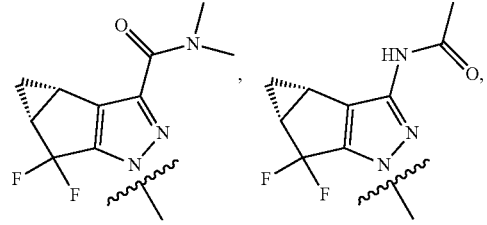

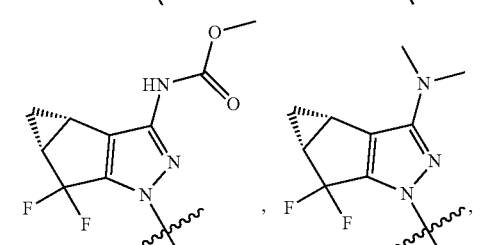

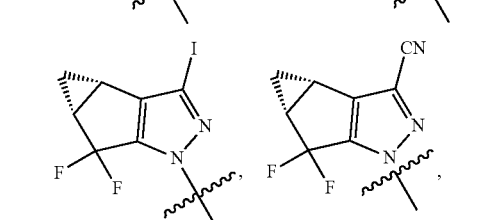

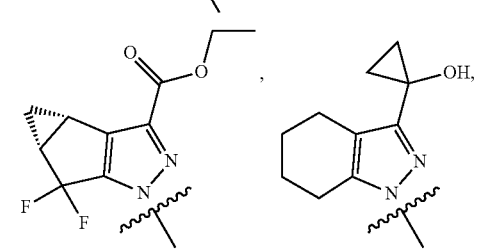

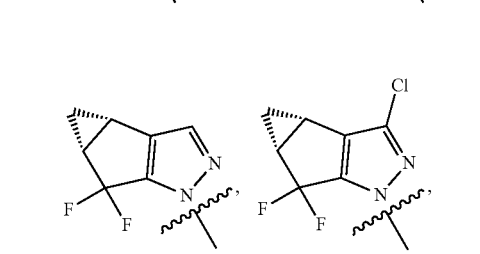

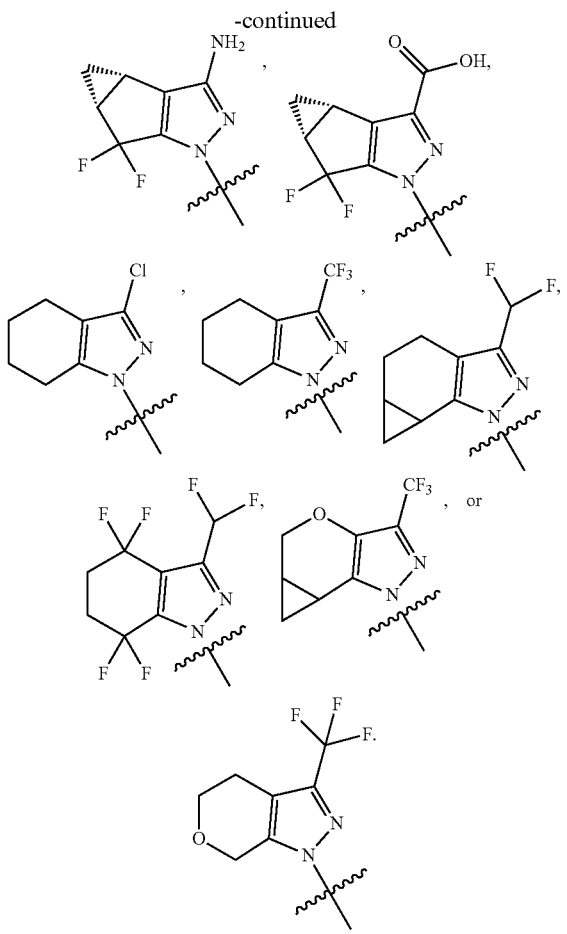

In some embodiments of the compound of Formula I, Ia, II, or IIa, or a pharmaceutically acceptable salt thereof,

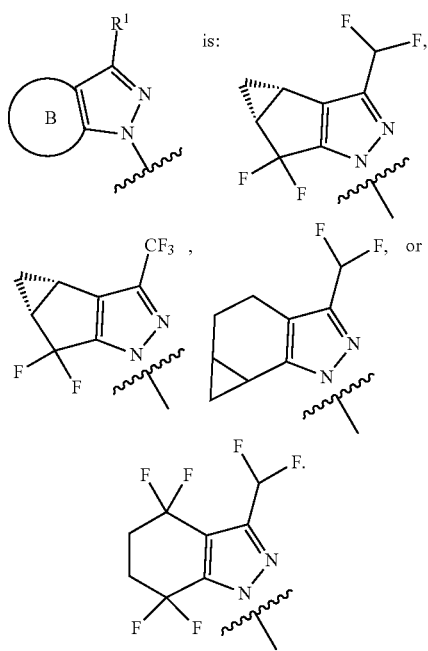

In some embodiments of the compound of Formula I, Ia, II, or IIa, or a pharmaceutically acceptable salt thereof, $R^1$ is H, —CN, halogen, $C_{1-8}$ alkyl, $C_{3-7}$ monocyclic cycloalkyl, —C(O)NR$^6$R$^6$, —NR$^6$R$^6$, —NR$^7$C(O)R$^8$, or —C(O)R$^8$, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is H, —CN, halogen, $C_{1-8}$ alkyl, or $C_{3-7}$ monocyclic cycloalkyl, wherein the $C_{1-8}$ alkyl and $C_{3-7}$ monocyclic cycloalkyl are each optionally substituted with 1-3 groups independently selected from —OH, halogen, —CN, and $C_{1-4}$ alkoxy.

In some embodiments of the compound of Formula I, Ia, II, or IIa, or a pharmaceutically acceptable salt thereof, $R^1$ is H. In some embodiments of the compound of Formula I, Ia, II, or IIa, or a pharmaceutically acceptable salt thereof, $R^1$ is —CN.

In some embodiments of the compound of Formula I, Ia, II, or IIa, or a pharmaceutically acceptable salt thereof, $R^1$ is halogen. In some embodiments of the compound of Formula I, Ia, II, or IIa, or a pharmaceutically acceptable salt thereof, $R^1$ is chloro, fluoro, bromo, or iodo. In some embodiments of the compound of Formula I, Ia, II, or IIa, or a pharmaceutically acceptable salt thereof, $R^1$ is chloro, fluoro, or bromo.

In some embodiments of the compound of Formula I, Ia, II, or IIa, or a pharmaceutically acceptable salt thereof, $R^1$ is $C_{1-8}$ alkyl, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is $C_{1-6}$ alkyl, wherein the $C_{1-6}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is $C_{1-4}$ alkyl, wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is $C_{1-4}$ alkyl, wherein the $C_{1-4}$ alkyl is optionally substituted with 1-3 halogens.

In some embodiments of the compound of Formula I, Ia, II, or IIa, or a pharmaceutically acceptable salt thereof, $R^1$ is $C_{1-8}$ alkyl, wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is $C_{1-6}$ alkyl, wherein the $C_{1-6}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is $C_{1-4}$ alkyl, wherein the $C_{1-4}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $R^1$ is $C_{1-4}$ alkyl, wherein the $C_{1-4}$ alkyl is substituted with 1-3 halogens. In some embodiments of the compound of Formula I, Ia, II, or IIa, or a pharmaceutically acceptable salt thereof, $R^1$ is $C_{1-3}$ alkyl, wherein the $C_{1-3}$ alkyl is substituted with 1-3 halogens. In some embodiments of the compound of Formula I, Ia, II, or IIa, or a pharmaceutically acceptable salt thereof, $R^1$ is $C_{1-3}$ alkyl, wherein the $C_{1-3}$ alkyl is substituted with 1-3 fluoro. In some embodiments of the compound of Formula I, Ia, II, or IIa, or a pharmaceutically acceptable salt thereof, $R^1$ is methyl substituted with 1-3 fluoro. In some embodiments of the compound of Formula I, Ia, II, or IIa, or a pharmaceutically acceptable salt thereof, $R^1$ is ethyl substituted with 1-3 fluoro. In some embodiments of the compound of Formula I, Ia, II, or IIa, or a pharmaceutically acceptable salt thereof, $R^1$ is —CHF$_2$ or —CF$_3$.

In some embodiments of the compound of Formula I, Ia, II, or IIa, or a pharmaceutically acceptable salt thereof, $R^1$ is C$_{1-8}$ alkyl. In some embodiments of the compound of Formula I, Ia, II, or IIa, or a pharmaceutically acceptable salt thereof, $R^1$ is C$_{1-6}$ alkyl. In some embodiments of the compound of Formula I, Ia, II, or IIa, or a pharmaceutically acceptable salt thereof, $R^1$ is C$_{1-4}$ alkyl.

In some embodiments of the compound of Formula I, Ia, II, or IIa, or a pharmaceutically acceptable salt thereof, $R^1$ is C$_{3-7}$ monocyclic cycloalkyl, wherein the C$_{3-7}$ monocyclic cycloalkyl is optionally substituted with 1-3 groups independently selected from —OH, halogen, —CN, and C$_{1-4}$ alkoxy. In some embodiments of the compound of Formula I, Ia, II, or IIa, or a pharmaceutically acceptable salt thereof, $R^1$ is C$_{3-7}$ monocyclic cycloalkyl, wherein the C$_{3-7}$ monocyclic cycloalkyl is substituted with 1-3 groups independently selected from —OH, halogen, —CN, and C$_{1-4}$ alkoxy. In some embodiments of the compound of Formula I, Ia, II, or IIa, or a pharmaceutically acceptable salt thereof, $R^1$ is C$_{3-7}$ monocyclic cycloalkyl.

In some embodiments of the compound of Formula I, Ia, II, or IIa, or a pharmaceutically acceptable salt thereof, $R^1$ is —C(O)NR$^6$R$^6$. In some embodiments of the compound of Formula I, Ia, II, or IIa, or a pharmaceutically acceptable salt thereof, $R^1$ is —NR$^6$R$^6$. In some embodiments of the compound of Formula I, Ia, II, or IIa, or a pharmaceutically acceptable salt thereof, $R^1$ is —NR$^7$C(O)R$^8$. In some embodiments of the compound of Formula I, Ia, II, or IIa, or a pharmaceutically acceptable salt thereof, $R^1$ is —C(O)R$^8$.

In some embodiments of the compound of Formula I, Ia, II, or IIa, or a pharmaceutically acceptable salt thereof, $R^4$ is a phenyl, 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, or 9-12 membered fused tricyclic heteroaryl,
  wherein the phenyl, 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, and 9-12 membered fused tricyclic heteroaryl are each optionally substituted with 1-3 R$^{4a}$ groups, and
  wherein the 5-6 membered monocyclic heterocyclyl, 5-6 membered monocyclic heteroaryl, 8-10 membered fused or bridged bicyclic heterocyclyl, 8-10 membered fused bicyclic heteroaryl, 9-12 membered fused or bridged tricyclic heterocyclyl, and 9-12 membered fused tricyclic heteroaryl each have 1-3 ring heteroatoms independently selected from N, O, and S.

In some embodiments of the compound of Formula I, Ia, II, or IIa, or a pharmaceutically acceptable salt thereof, $R^4$ is a phenyl, 8-10 membered fused or bridged bicyclic heterocyclyl, 8-10 membered fused bicyclic heteroaryl, or 9-12 membered fused or bridged tricyclic heterocyclyl,
  wherein the phenyl, 8-10 membered fused or bridged bicyclic heterocyclyl, 8-10 membered fused bicyclic heteroaryl, and 9-12 membered fused or bridged tricyclic heterocyclyl are each optionally substituted with 1-3 R$^{4a}$ groups, and
  wherein the 8-10 membered fused or bridged bicyclic heterocyclyl, 8-10 membered fused bicyclic heteroaryl, and 9-12 membered fused or bridged tricyclic heterocyclyl each have 1-3 ring heteroatoms independently selected from N, O, and S.

In some embodiments of the compound of Formula I, Ia, II, or IIa, or a pharmaceutically acceptable salt thereof, $R^4$ is a phenyl or 9-10 membered fused or bridged bicyclic heterocyclyl, wherein the phenyl and 9-10 membered fused or bridged bicyclic heterocyclyl are each optionally substituted with 1-3 R$^{4a}$ groups and wherein the 9-10 membered fused or bridged bicyclic heterocyclyl has 1-3 ring heteroatoms independently selected from N, O, and S.

In some embodiments of the compound of Formula I, Ia, II, or IIa, or a pharmaceutically acceptable salt thereof, $R^4$ is a phenyl, wherein the phenyl is optionally substituted with 1-3 R$^{4a}$ groups. In some embodiments of the compound of Formula I, Ia, II, or IIa, or a pharmaceutically acceptable salt thereof, $R^4$ is a phenyl, wherein the phenyl is substituted with 1-3 R$^{4a}$ groups. In some embodiments of the compound of Formula I, Ia, II, or IIa, or a pharmaceutically acceptable salt thereof, $R^4$ is a phenyl.

In some embodiments of the compound of Formula I, Ia, II, or IIa, or a pharmaceutically acceptable salt thereof, $R^4$ is a 5-6 membered monocyclic heterocyclyl, wherein the 5-6 membered monocyclic heterocyclyl has 1-3 ring heteroatoms independently selected from N, O, and S and is optionally substituted with 1-3 R$^{4a}$ groups. In some embodiments of the compound of Formula I, Ia, II, or IIa, or a pharmaceutically acceptable salt thereof, $R^4$ is a 5-6 membered monocyclic heterocyclyl, wherein the 5-6 membered monocyclic heterocyclyl has 1-3 ring heteroatoms independently selected from N, O, and S and is substituted with 1-3 R$^{4a}$ groups. In some embodiments of the compound of Formula I, Ia, II, or IIa, or a pharmaceutically acceptable salt thereof, $R^4$ is a 5-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, $R^4$ is a 5-6 membered monocyclic heteroaryl, wherein the 5-6 membered monocyclic heteroaryl has 1-3 ring heteroatoms independently selected from N, O, and S and is optionally substituted with 1-3 R$^{4a}$ groups. In some embodiments of the compound of Formula I, Ia, II, or IIa, or a pharmaceutically acceptable salt thereof, $R^4$ is a 5-6 membered monocyclic heteroaryl, wherein the 5-6 membered monocyclic heteroaryl has 1-3 ring heteroatoms independently selected from N, O, and S and is substituted with 1-3 R$^{4a}$ groups. In some embodiments of the compound of Formula I, Ia, II, or IIa, or a pharmaceutically acceptable salt thereof, $R^4$ is a 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, $R^4$ is a 8-10 membered fused or bridged bicyclic heterocyclyl, wherein the 8-10 membered fused or bridged bicyclic heterocyclyl has 1-3 ring heteroatoms independently selected from N, O, and S and is optionally substituted with 1-3 R$^{4a}$ groups. In some embodiments of the compound of Formula I, Ia, II, or IIa, or a pharmaceutically acceptable salt thereof, $R^4$ is a 8-10 membered fused or bridged bicyclic heterocyclyl, wherein the 8-10 membered fused or bridged bicyclic heterocyclyl has 1-3 ring heteroatoms independently selected from N, O, and S and is substituted with 1-3 R$^{4a}$ groups. In some embodiments of the compound of Formula I, Ia, II, or IIa, or a pharmaceutically acceptable salt thereof, $R^4$ is a 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, $R^4$ is a 9-10 membered fused or bridged bicyclic heterocyclyl, wherein the 9-10 membered fused or bridged bicyclic heterocyclyl has 1-3 ring heteroatoms independently selected from N, O, and S and is optionally substituted with 1-3 $R^{4a}$ groups. In some embodiments of the compound of Formula I, Ia, II, or IIa, or a pharmaceutically acceptable salt thereof, $R^4$ is a 9-10 membered fused or bridged bicyclic heterocyclyl, wherein the 9-10 membered fused or bridged bicyclic heterocyclyl has 1-3 ring heteroatoms independently selected from N, O, and S and is substituted with 1-3 $R^{4a}$ groups. In some embodiments of the compound of Formula I, Ia, II, or IIa, or a pharmaceutically acceptable salt thereof, $R^4$ is a 9-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, $R^4$ is a 8-10 membered fused bicyclic heteroaryl, wherein the 8-10 membered fused bicyclic heteroaryl has 1-3 ring heteroatoms independently selected from N, O, and S and is optionally substituted with 1-3 $R^{4a}$ groups. In some embodiments of the compound of Formula I, Ia, II, or IIa, or a pharmaceutically acceptable salt thereof, $R^4$ is a 8-10 membered fused bicyclic heteroaryl, wherein the 8-10 membered fused bicyclic heteroaryl has 1-3 ring heteroatoms independently selected from N, O, and S and is substituted with 1-3 $R^{4a}$ groups. In some embodiments of the compound of Formula I, Ia, II, or IIa, or a pharmaceutically acceptable salt thereof, $R^4$ is a 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, $R^4$ is a 9-12 membered fused or bridged tricyclic heterocyclyl, wherein the 9-12 membered fused or bridged tricyclic heterocyclyl has 1-3 ring heteroatoms independently selected from N, O, and S and is optionally substituted with 1-3 $R^{4a}$ groups. In some embodiments of the compound of Formula I, Ia, II, or IIa, or a pharmaceutically acceptable salt thereof, $R^4$ is a 9-12 membered fused or bridged tricyclic heterocyclyl, wherein the 9-12 membered fused or bridged tricyclic heterocyclyl has 1-3 ring heteroatoms independently selected from N, O, and S and is substituted with 1-3 $R^{4a}$ groups. In some embodiments of the compound of Formula I, Ia, II, or IIa, or a pharmaceutically acceptable salt thereof, $R^4$ is a 9-12 membered fused or bridged tricyclic heterocyclyl having 1-3 ring heteroatoms independently selected from N, O, and S.

In some embodiments of the compound of Formula I, Ia, II, or IIa, or a pharmaceutically acceptable salt thereof, $R^4$ is a 9-12 membered fused tricyclic heteroaryl, wherein the 9-12 membered fused tricyclic heteroaryl has 1-3 ring heteroatoms independently selected from N, O, and S and is optionally substituted with 1-3 $R^{4a}$ groups. In some embodiments of the compound of Formula I, Ia, II, or IIa, or a pharmaceutically acceptable salt thereof, $R^4$ is a 9-12 membered fused tricyclic heteroaryl, wherein the 9-12 membered fused tricyclic heteroaryl has 1-3 ring heteroatoms independently selected from N, O, and S and is substituted with 1-3 $R^{4a}$ groups. In some embodiments of the compound of Formula I, Ia, II, or IIa, or a pharmaceutically acceptable salt thereof, $R^4$ is a 9-12 membered fused tricyclic heteroaryl having 1-3 ring heteroatoms independently selected from N, O, and S.

In some embodiments of the compound of Formula I, Ia, II, or IIa, or a pharmaceutically acceptable salt thereof, $R^4$ is

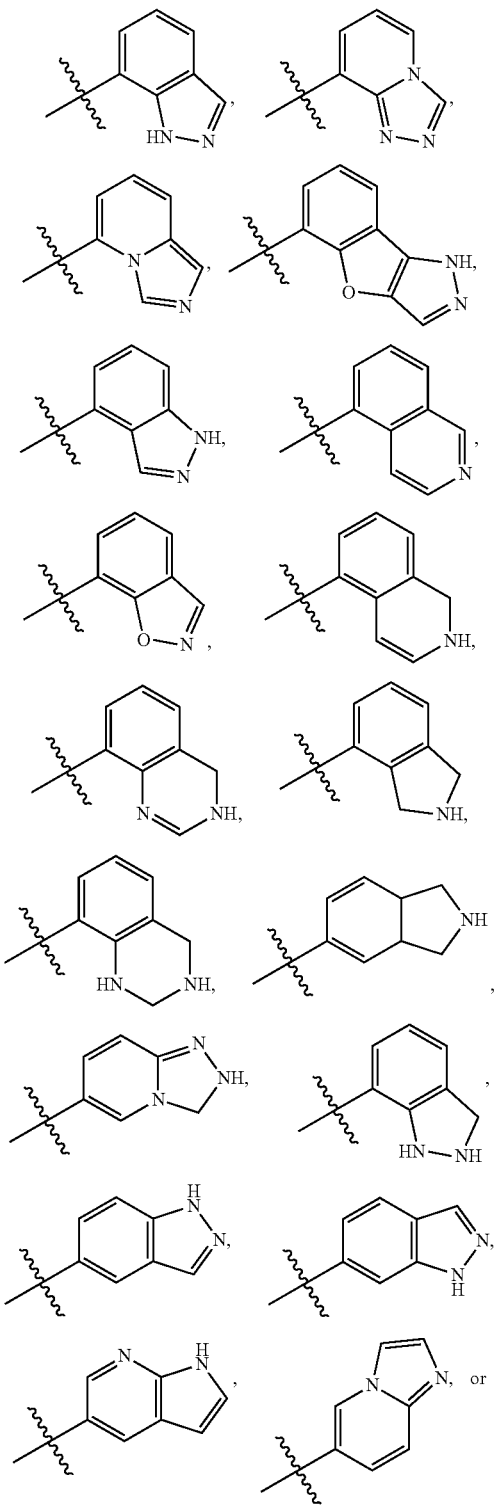

-continued

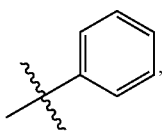

each of which is optionally substituted with 1-3 $R^{4a}$ groups.

In some embodiments of the compound of Formula I, Ia, II, or IIa, or a pharmaceutically acceptable salt thereof, $R^4$ is

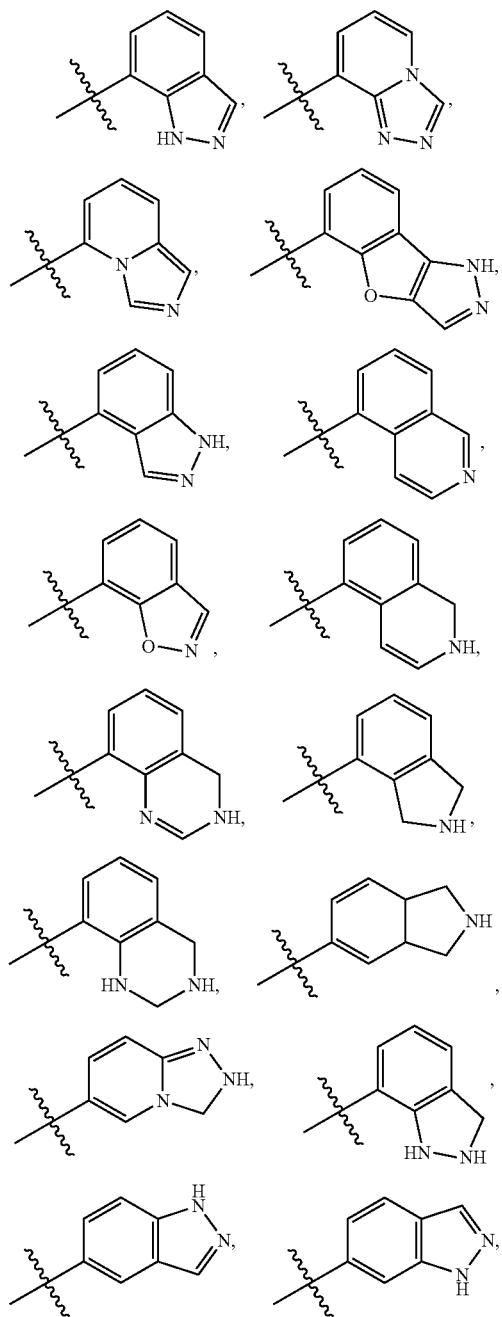

-continued

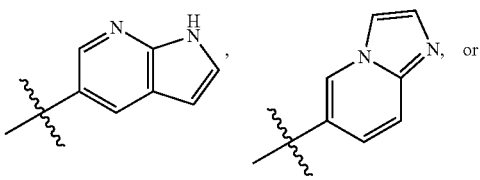

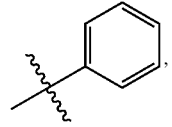

each of which is substituted with 1-3 $R^{4a}$ groups.

In some embodiments of the compound of Formula I, Ia, II, or IIa, or a pharmaceutically acceptable salt thereof, $R^4$ is

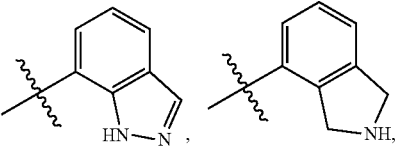

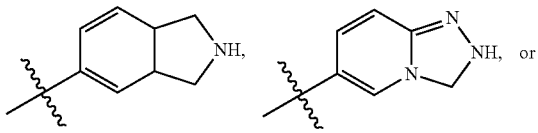

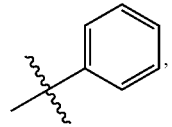

each of which is optionally substituted with 1-3 $R^{4a}$ groups.

In some embodiments of the compound of Formula I, Ia, II, or IIa, or a pharmaceutically acceptable salt thereof, $R^4$ is

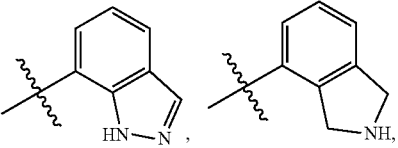

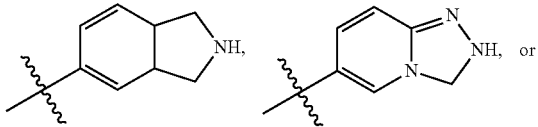

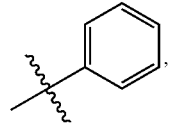

each of which is substituted with 1-3 $R^{4a}$ groups.

In some embodiments of the compound of Formula I, Ia, II, or IIa, or a pharmaceutically acceptable salt thereof, $R^4$ is

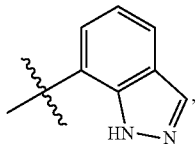 [SMILES: *c1cccc2cn[nH]c12]

which is optionally substituted with 1-3 $R^{4a}$ groups.

In some embodiments of the compound of Formula I, Ia, II, or IIa, or a pharmaceutically acceptable salt thereof, $R^4$ is

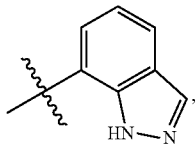 [SMILES: *c1cccc2cn[nH]c12]

which is substituted with 1-3 $R^{4a}$ groups.

In some embodiments of the compound of Formula I, Ia, II, or IIa, or a pharmaceutically acceptable salt thereof, each $R^{4a}$ is independently oxo, —OH, halogen, —CN, $C_{1-8}$ alkyl, $C_{1-8}$ alkoxy, —NR$^6$R$^6$, —NR$^7$S(O)$_2$R$^9$, —NR$^7$S(O)$_2$NR$^6$R$^6$, —NR$^7$C(O)R$^8$, —NR$^7$C(O)R$^{10}$NR$^6$R$^6$, —NR$^7$C(O)NR$^6$R$^6$, or —C(O)NR$^6$R$^6$, wherein the $C_{1-8}$ alkyl is optionally substituted with 1-3 groups independently selected from —OH, halogen, —CN, and $C_{1-4}$ alkoxy; or two $R^{4a}$ of the 1-3 $R^{4a}$ groups are attached to the same carbon and the two $R^{4a}$, together with the carbon to which they are attached, form a $C_{3-7}$ monocyclic cycloalkyl. In some embodiments of the compound of Formula I, Ia, II, or IIa, or a pharmaceutically acceptable salt thereof, each $R^{4a}$ is independently oxo, —OH, halogen, —CN, $C_{1-8}$ alkyl, $C_{1-8}$ alkoxy, —NR$^6$R$^6$, —NR$^7$S(O)$_2$R$^9$, or —C(O)NR$^6$R$^6$, wherein the $C_{1-8}$ alkyl is optionally substituted with 1-3 groups independently selected from —OH, halogen, —CN, and $C_{1-4}$ alkoxy; or two $R^{4a}$ of the 1-3 $R^{4a}$ groups are attached to the same carbon and the two $R^{4a}$, together with the carbon to which they are attached, form a $C_{3-7}$ monocyclic cycloalkyl.

In some embodiments of the compound of Formula I, Ia, II, or IIa, or a pharmaceutically acceptable salt thereof, each $R^{4a}$ is independently oxo, —OH, halogen, —CN, $C_{1-8}$ alkyl, $C_{1-8}$ alkoxy, —NR$^6$R$^6$, —NR$^7$S(O)$_2$R$^9$, —NR$^7$S(O)$_2$NR$^6$R$^6$, —NR$^7$C(O)R$^8$, —NR$^7$C(O)R$^{10}$NR$^6$R$^6$, —NR$^7$C(O)NR$^6$R$^6$, or —C(O)NR$^6$R$^6$, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, each $R^{4a}$ is independently oxo, —OH, halogen, —CN, $C_{1-8}$ alkyl, $C_{1-8}$ alkoxy, —NR$^6$R$^6$, —NR$^7$S(O)$_2$R$^9$, or —C(O)NR$^6$R$^6$, wherein the $C_{1-8}$ alkyl is optionally substituted with 1-3 groups independently selected from —OH, halogen, —CN, and $C_{1-4}$ alkoxy.

In some embodiments of the compound of Formula I, Ia, II, or IIa, or a pharmaceutically acceptable salt thereof, each $R^{4a}$ is independently oxo, halogen, —CN, $C_{1-8}$ alkyl, —NR$^6$R$^6$, —NR$^7$S(O)$_2$R$^9$, or —C(O)NR$^6$R$^6$.

In some embodiments of the compound of Formula I, Ia, II, or IIa, or a pharmaceutically acceptable salt thereof, one or more $R^{4a}$ is oxo. In some embodiments of the compound of Formula I, Ia, II, or IIa, or a pharmaceutically acceptable salt thereof, one $R^{4a}$ is oxo. In some embodiments of the compound of Formula I, Ia, II, or IIa, or a pharmaceutically acceptable salt thereof, one or more $R^{4a}$ is —OH.

In some embodiments of the compound of Formula I, Ia, II, or IIa, or a pharmaceutically acceptable salt thereof, one or more $R^{4a}$ is halogen. In some embodiments of the compound of Formula I, Ia, II, or IIa, or a pharmaceutically acceptable salt thereof, one or more $R^{4a}$ is fluoro or chloro. In some embodiments of the compound of Formula I, Ia, II, or IIa, or a pharmaceutically acceptable salt thereof, one $R^{4a}$ is fluoro. In some embodiments of the compound of Formula I, Ia, II, or IIa, or a pharmaceutically acceptable salt thereof, one $R^{4a}$ is chloro.

In some embodiments of the compound of Formula I, Ia, II, or IIa, or a pharmaceutically acceptable salt thereof, one or more $R^{4a}$ is —CN. In some embodiments of the compound of Formula I, Ia, II, or IIa, or a pharmaceutically acceptable salt thereof, one $R^{4a}$ is —CN.

In some embodiments of the compound of Formula I, Ia, II, or IIa, or a pharmaceutically acceptable salt thereof, one or more $R^{4a}$ is $C_{1-8}$ alkyl, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^{4a}$ is $C_{1-8}$ alkyl, wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^{4a}$ is $C_{1-8}$ alkyl.

In some embodiments of the compound of Formula I, Ia, II, or IIa, or a pharmaceutically acceptable salt thereof, one or more $R^{4a}$ is $C_{1-4}$ alkyl, wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^{4a}$ is $C_{1-4}$ alkyl, wherein the $C_{1-4}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^{4a}$ is $C_{1-4}$ alkyl. In some embodiments of the compound of Formula I, Ia, II, or IIa, or a pharmaceutically acceptable salt thereof, one or more $R^{4a}$ is methyl, ethyl, propyl, or isopropyl. In some embodiments of the compound of Formula I, Ia, II, or IIa, or a pharmaceutically acceptable salt thereof, one or more $R^{4a}$ is methyl.

In some embodiments of the compound of Formula I, Ia, II, or IIa, or a pharmaceutically acceptable salt thereof, one or more $R^{4a}$ is $C_{1-8}$ alkoxy.

In some embodiments of the compound of Formula I, Ia, II, or IIa, or a pharmaceutically acceptable salt thereof, one or more $R^{4a}$ is —NR$^6$R$^6$. In some embodiments of the compound of Formula I, Ia, II, or IIa, or a pharmaceutically acceptable salt thereof, one or more $R^{4a}$ is —NH$_2$. In some embodiments of the compound of Formula I, Ia, II, or IIa, or a pharmaceutically acceptable salt thereof, one $R^{4a}$ is —NH$_2$.

In some embodiments of the compound of Formula I, Ia, II, or IIa, or a pharmaceutically acceptable salt thereof, one or more $R^{4a}$ is —NR$^7$S(O)$_2$R$^9$. In some embodiments of the compound of Formula I, Ia, II, or IIa, or a pharmaceutically acceptable salt thereof, one or more $R^{4a}$ is —NHS(O)$_2$R$^9$. In some embodiments of the compound of Formula I, Ia, II, or IIa, or a pharmaceutically acceptable salt thereof, one $R^{4a}$ is —NHS(O)$_2$R$^9$. In some embodiments of the compound of Formula I, Ia, II, or IIa, or a pharmaceutically acceptable salt thereof, one $R^{4a}$ is —NHS(O)$_2$(C$_{1-4}$ alkyl). In some embodiments of the compound of Formula I, Ia, II, or IIa, or a pharmaceutically acceptable salt thereof, one $R^{4a}$ is —NHS(O)$_2$CH$_3$. In some embodiments of the compound of Formula I, Ia, II, or IIa, or a pharmaceutically acceptable salt thereof, one $R^{4a}$ is —NHS(O)$_2$CH$_2$CH$_3$. In some embodiments of the compound of Formula I, Ia, II, or IIa, or a pharmaceutically acceptable salt thereof, one $R^{4a}$ is —NHS(O)$_2$(C$_{3-8}$ cycloalkyl). In some embodiments of the compound of Formula I, Ia, II, or IIa, or a pharmaceutically acceptable salt thereof, one $R^{4a}$ is —NHS(O)$_2$(cyclopropyl).

In some embodiments of the compound of Formula I, Ia, II, or IIa, or a pharmaceutically acceptable salt thereof, one or more $R^{4a}$ is —NR$^7$S(O)$_2$NR$^6$R$^6$. In some embodiments of the compound of Formula I, Ia, II, or IIa, or a pharmaceutically acceptable salt thereof, one or more $R^{4a}$ is —NR$^7$C(O)R$^8$. In some embodiments of the compound of Formula I, Ia, II, or IIa, or a pharmaceutically acceptable salt thereof, one or more $R^{4a}$ is —NR$^7$C(O)R$^{10}$NR$^6$R$^6$. In some embodiments of the compound of Formula I, Ia, II, or IIa, or a pharmaceutically acceptable salt thereof, one or more $R^{4a}$ is —NR$^7$C(O)NR$^6$R$^6$.

In some embodiments of the compound of Formula I, Ia, II, or IIa, or a pharmaceutically acceptable salt thereof, one or more $R^{4a}$ is —C(O)NR$^6$R$^6$. In some embodiments of the compound of Formula I, Ia, II, or IIa, or a pharmaceutically acceptable salt thereof, one or more $R^{4a}$ is —C(O)NH$_2$. In some embodiments of the compound of Formula I, Ia, II, or IIa, or a pharmaceutically acceptable salt thereof, one $R^{4a}$ is —C(O)NH$_2$.

In some embodiments of the compound of Formula I, Ia, II, or IIa, or a pharmaceutically acceptable salt thereof, two $R^{4a}$ of the 1-3 $R^{4a}$ groups are attached to the same carbon and the two $R^{4a}$, together with the carbon to which they are attached, form a C$_{3-7}$ monocyclic cycloalkyl. In some embodiments of the compound of Formula I, Ia, II, or IIa, or a pharmaceutically acceptable salt thereof, two $R^{4a}$ of the 1-3 $R^{4a}$ groups are attached to the same carbon and the two $R^{4a}$, together with the carbon to which they are attached, form a C$_{3-8}$ monocyclic cycloalkyl. In some embodiments of the compound of Formula I, Ia, II, or IIa, or a pharmaceutically acceptable salt thereof, two $R^{4a}$ of the 1-3 $R^{4a}$ groups are attached to the same carbon and the two $R^{4a}$, together with the carbon to which they are attached, form a cyclopropyl, cyclobutyl, or cyclopentyl. In some embodiments of the compound of Formula I, Ia, II, or IIa, or a pharmaceutically acceptable salt thereof, two $R^{4a}$ of the 1-3 $R^{4a}$ groups are attached to the same carbon and the two $R^{4a}$, together with the carbon to which they are attached, form a cyclopropyl.

In some embodiments of the compound of Formula I, Ia, II, or IIa, or a pharmaceutically acceptable salt thereof, $R^4$ optionally substituted with 1-3 $R^{4a}$ groups is:

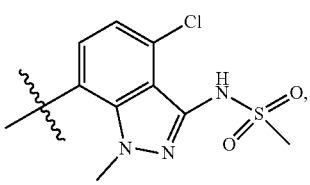

-continued

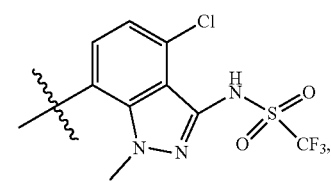

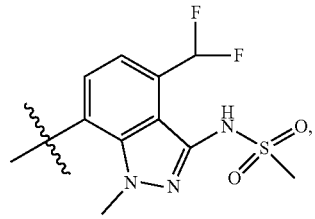

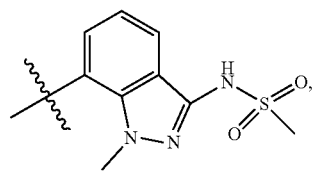

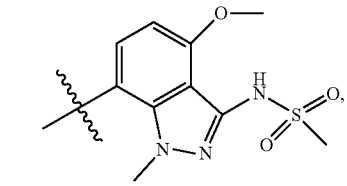

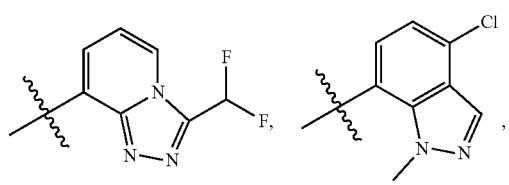

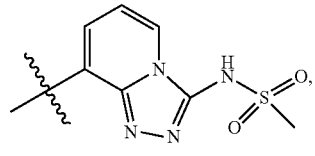

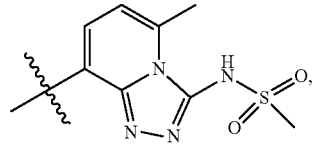

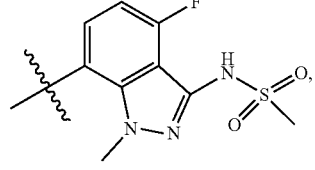

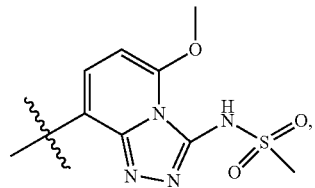

-continued
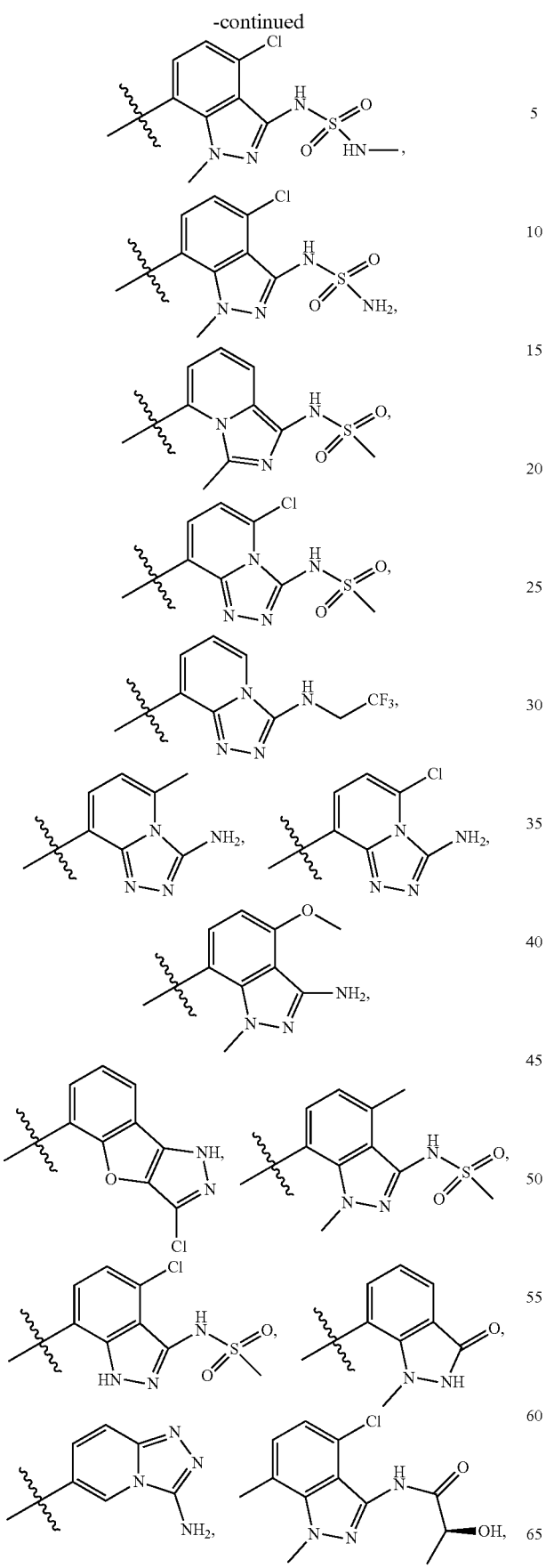
-continued
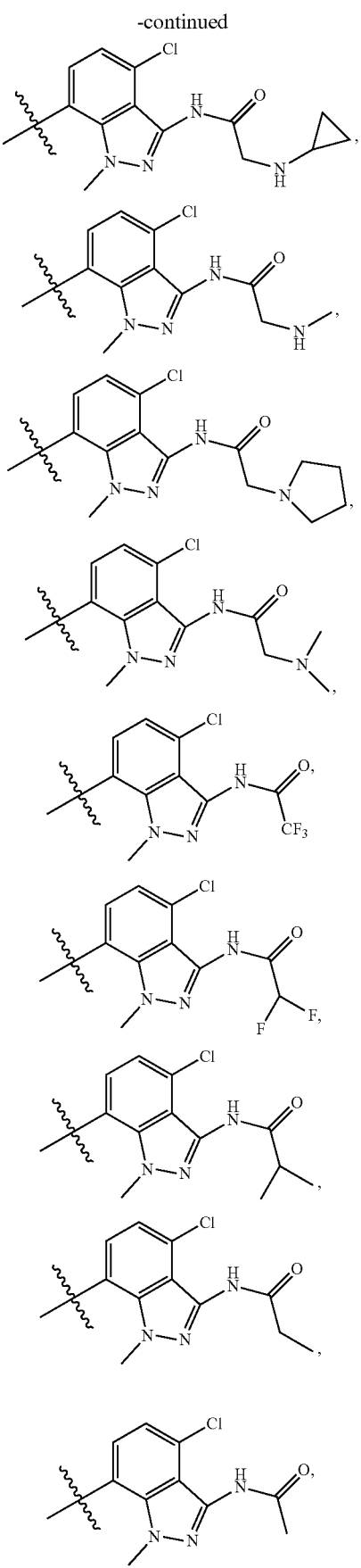

49
-continued
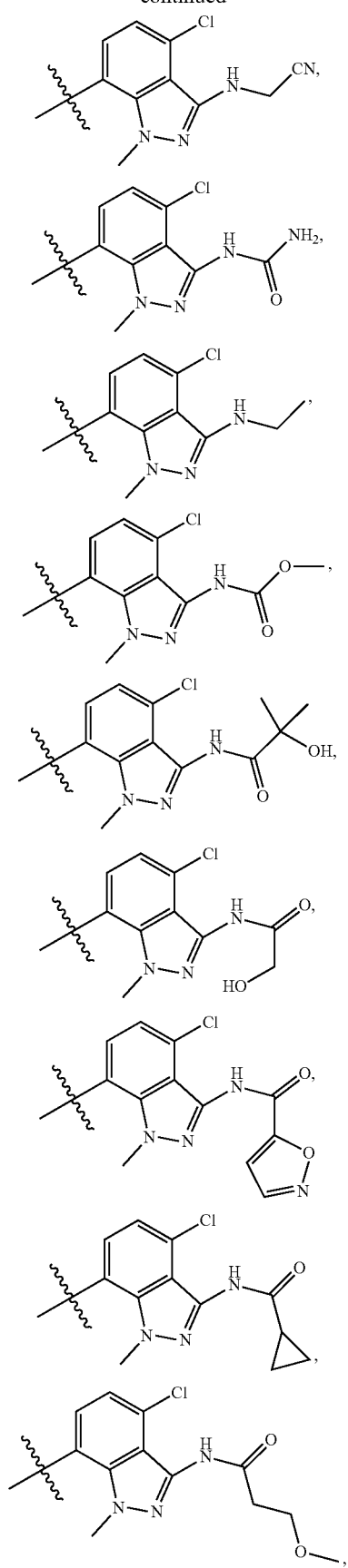
50
-continued
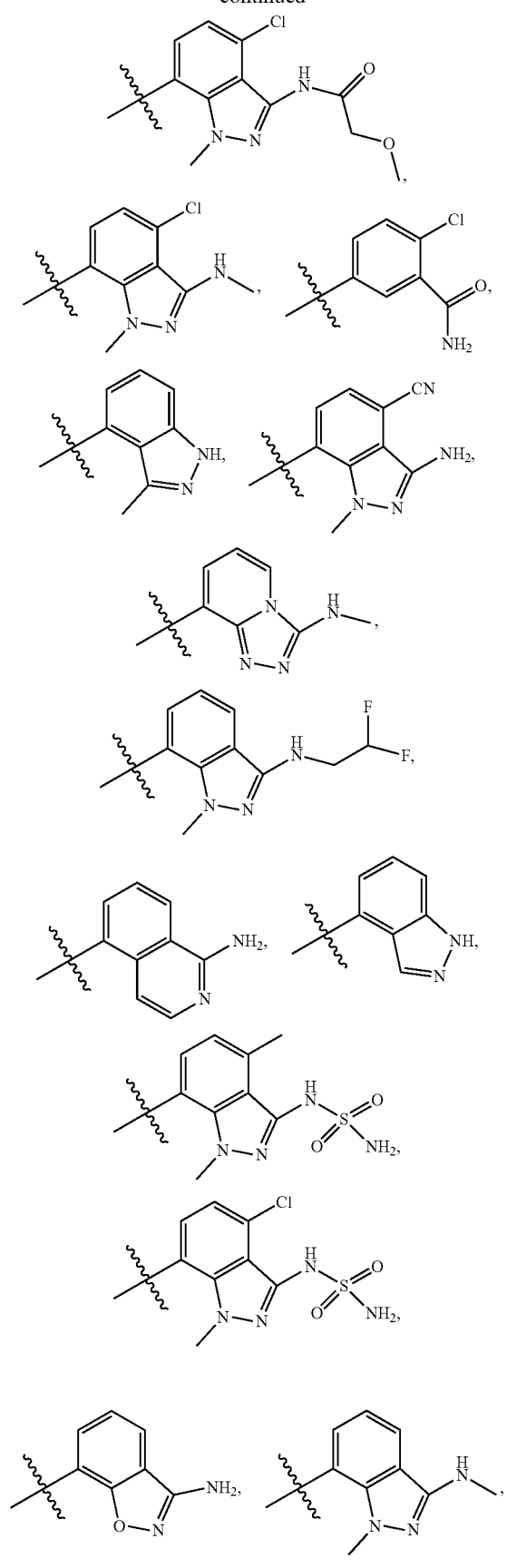

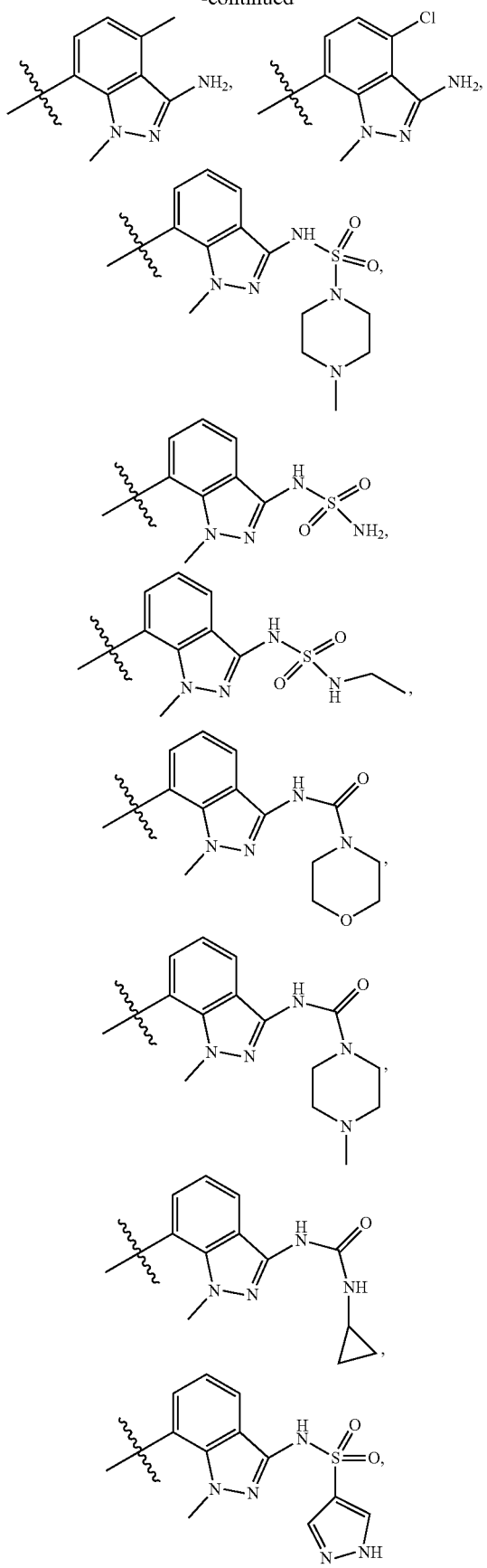
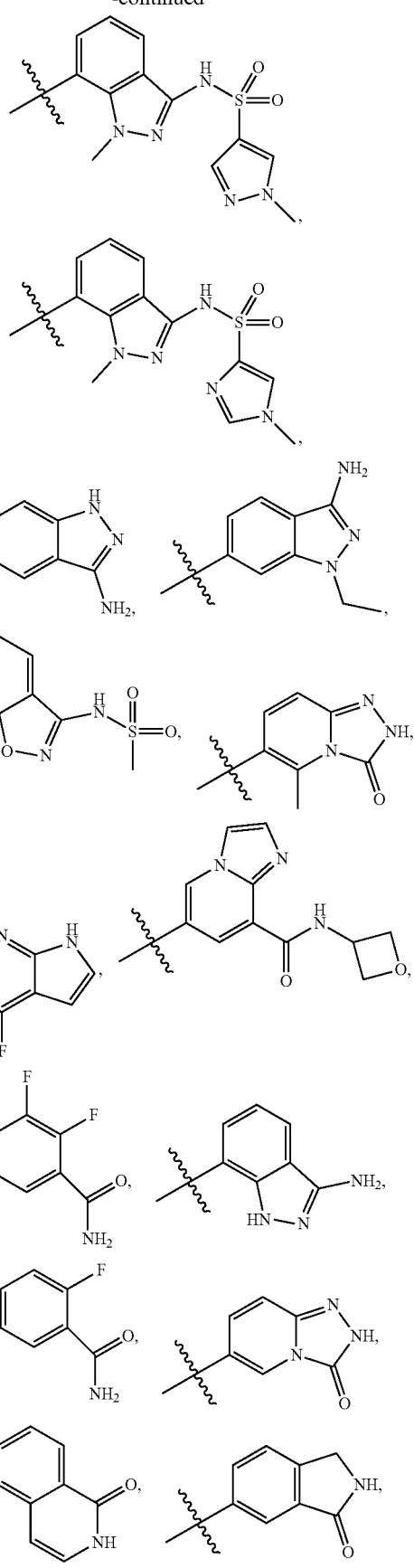

53
-continued
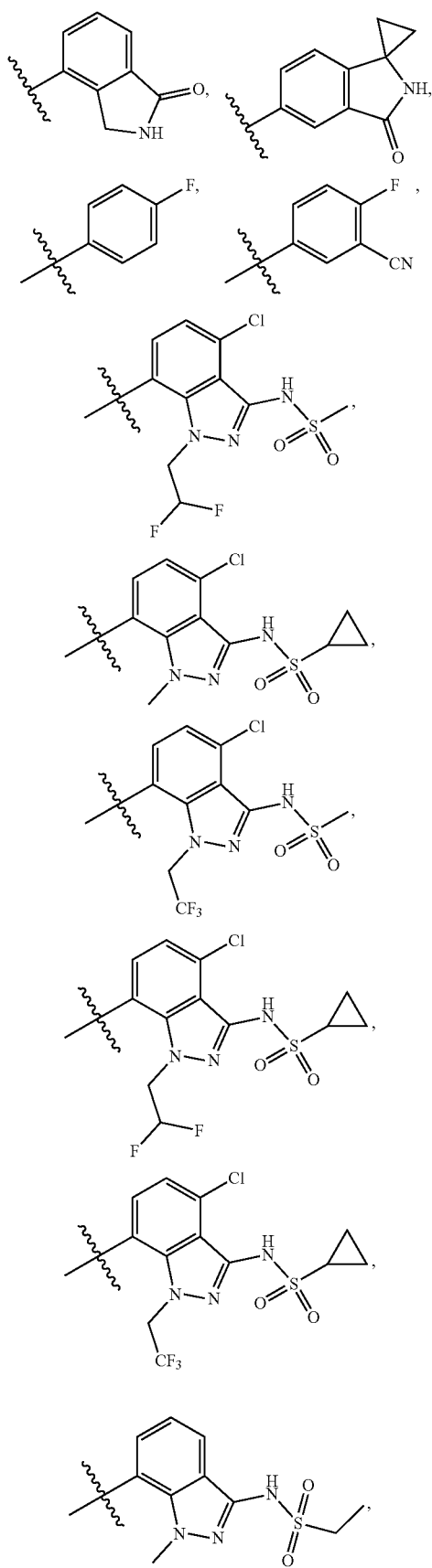
54
-continued
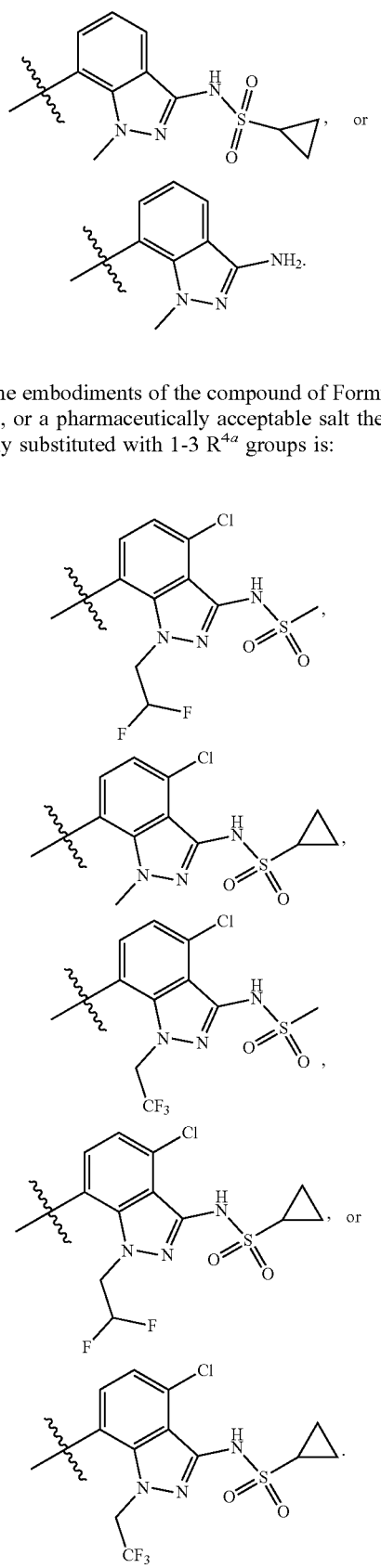
In some embodiments of the compound of Formula I, Ia, II, or IIa, or a pharmaceutically acceptable salt thereof, $R^4$ optionally substituted with 1-3 $R^{4a}$ groups is:

In some embodiments of the compound of Formula I, Ia, II, or IIa, or a pharmaceutically acceptable salt thereof, $R^4$ optionally substituted with 1-3 $R^{4a}$ groups is:

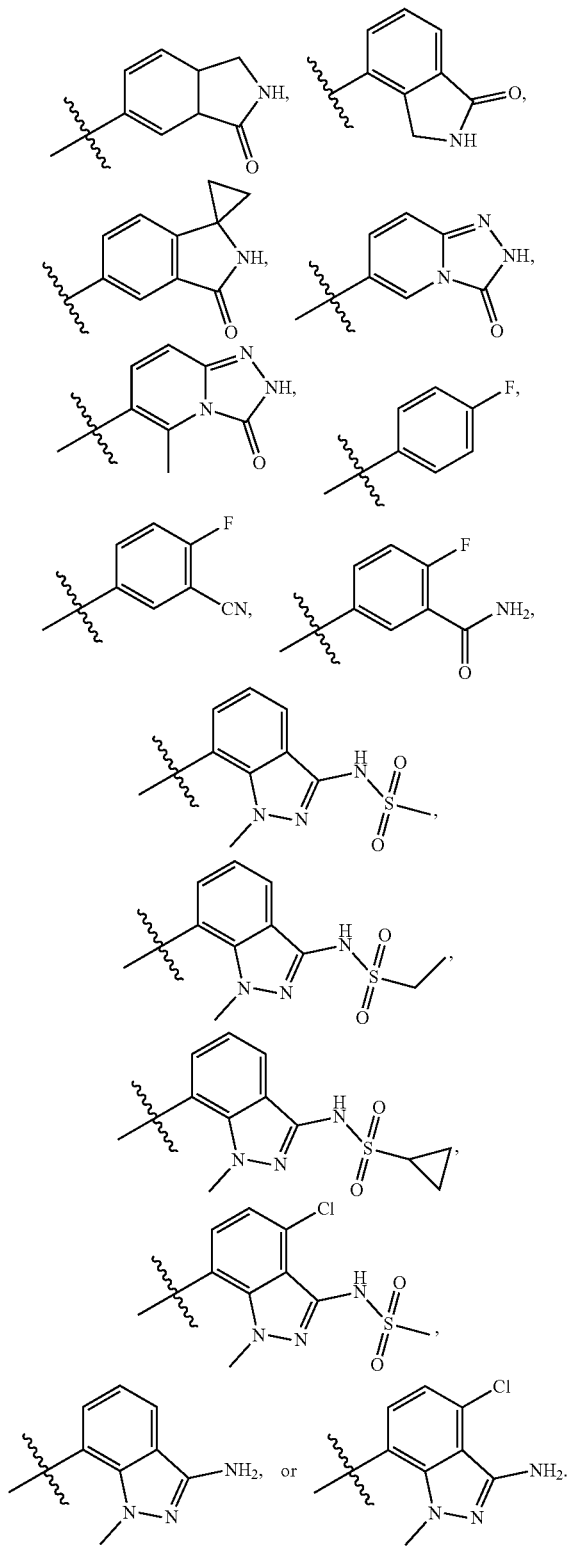

In some embodiments of the compound of Formula I, Ia, II, or IIa, or a pharmaceutically acceptable salt thereof, each $R^6$ is independently H, $C_{1-8}$ alkyl, $C_{3-7}$ monocyclic cycloalkyl, or 4-6 membered monocyclic heterocyclyl having 1-3 ring heteroatoms independently selected from N, O, and S,
  wherein the $C_{1-8}$ alkyl is optionally substituted with 1-3 groups independently selected from —OH, halogen, —CN, and $C_{1-4}$ alkoxy, and
  wherein the $C_{3-7}$ monocyclic cycloalkyl and 4-6 membered monocyclic heterocyclyl having 1-3 ring heteroatoms independently selected from N, O, and S are each optionally substituted with 1-3 groups independently selected from —OH, halogen, —CN, $C_{1-4}$ alkyl, and $C_{1-4}$ alkoxy; or both $R^6$, together with the nitrogen to which they are attached, form a 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, each $R^6$ is independently H, $C_{1-8}$ alkyl, or $C_{3-7}$ monocyclic cycloalkyl,
  wherein the $C_{1-8}$ alkyl is optionally substituted with 1-3 groups independently selected from —OH, halogen, —CN, and $C_{1-4}$ alkoxy, and
  wherein the $C_{3-7}$ monocyclic cycloalkyl is optionally substituted with 1-3 groups independently selected from —OH, halogen, —CN, $C_{1-4}$ alkyl, and $C_{1-4}$ alkoxy.

In some embodiments of the compound of Formula I, Ia, II, or IIa, or a pharmaceutically acceptable salt thereof, each $R^6$ is independently H or $C_{1-4}$ alkyl. In some embodiments of the compound of Formula I, Ia, II, or IIa, or a pharmaceutically acceptable salt thereof, each $R^6$ is independently H or methyl.

In some embodiments of the compound of Formula I, Ia, II, or IIa, or a pharmaceutically acceptable salt thereof, one or more $R^6$ is H.

In some embodiments of the compound of Formula I, Ia, II, or IIa, or a pharmaceutically acceptable salt thereof, one or more $R^6$ is $C_{1-8}$ alkyl, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^6$ is $C_{1-8}$ alkyl, wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^6$ is $C_{1-8}$ alkyl. In some embodiments of the compound of Formula I, Ia, II, or IIa, or a pharmaceutically acceptable salt thereof, one or more $R^6$ is $C_{1-4}$ alkyl. In some embodiments of the compound of Formula I, Ia, II, or IIa, or a pharmaceutically acceptable salt thereof, one or more $R^6$ is methyl.

In some embodiments of the compound of Formula I, Ia, II, or IIa, or a pharmaceutically acceptable salt thereof, one or more $R^6$ is $C_{3-7}$ monocyclic cycloalkyl, wherein the $C_{3-7}$ monocyclic cycloalkyl is optionally substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^6$ is $C_{3-7}$ monocyclic cycloalkyl, wherein the $C_{3-7}$ monocyclic cycloalkyl is substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^6$ is $C_{3-7}$ monocyclic cycloalkyl.

In some embodiments of the compound of Formula I, Ia, II, or IIa, or a pharmaceutically acceptable salt thereof, one or more $R^6$ is 4-6 membered monocyclic heterocyclyl, wherein the 4-6 membered monocyclic heterocyclyl has 1-3 ring heteroatoms independently selected from N, O, and S and is optionally substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^6$ is 4-6 membered monocyclic heterocyclyl, wherein the 4-6 membered monocyclic heterocyclyl has 1-3 ring heteroatoms independently selected from N, O, and S and is substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^6$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, both $R^6$, together with the nitrogen to which they are attached, form a 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, each $R^7$ is independently H or $C_{1-8}$ alkyl which may be the same or different, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, each $R^7$ is independently H or $C_{1-4}$ alkyl which may be the same or different, wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, each $R^7$ is independently H or $C_{1-3}$ alkyl which may be the same or different.

In some embodiments of the compound of Formula I, Ia, II, or IIa, or a pharmaceutically acceptable salt thereof, one or more $R^7$ is H. In some embodiments of the compound of Formula I, Ia, II, or IIa, or a pharmaceutically acceptable salt thereof, one or more $R^7$ is $C_{1-8}$ alkyl which may be the same or different, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^7$ is $C_{1-8}$ alkyl which may be the same or different, wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^7$ is $C_{1-8}$ alkyl which may be the same or different. In some embodiments of the compound of Formula I, Ia, II, or IIa, or a pharmaceutically acceptable salt thereof, one or more $R^7$ is $C_{1-4}$ alkyl which may be the same or different, wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^7$ is $C_{1-4}$ alkyl which may be the same or different, wherein the $C_{1-4}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^7$ is $C_{1-4}$ alkyl which may be the same or different. In some embodiments of the compound of Formula I, Ia, II, or IIa, or a pharmaceutically acceptable salt thereof, one or more $R^7$ is $C_{1-3}$ alkyl which may be the same or different.

In some embodiments of the compound of Formula I, Ia, II, or IIa, or a pharmaceutically acceptable salt thereof, each $R^8$ is independently —OH, $C_{1-8}$ alkyl, $C_{1-8}$ alkoxy, $C_{3-7}$ monocyclic cycloalkyl, 4-6 membered monocyclic heterocyclyl, or 4-6 membered monocyclic heteroaryl,
  wherein the $C_{1-8}$ alkyl and $C_{1-8}$ alkoxy are each optionally substituted with 1-3 groups independently selected from —OH, halogen, —CN, and $C_{1-4}$ alkoxy,
  wherein the $C_{3-7}$ monocyclic cycloalkyl, 4-6 membered monocyclic heterocyclyl, and 4-6 membered monocyclic heteroaryl are each optionally substituted with 1-3 groups independently selected from —OH, halogen, —CN, $C_{1-4}$ alkyl, and $C_{1-4}$ alkoxy, and
  wherein the 4-6 membered monocyclic heterocyclyl and 4-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, each $R^8$ is independently —OH, $C_{1-8}$ alkyl, or $C_{1-8}$ alkoxy.

In some embodiments of the compound of Formula I, Ia, II, or IIa, or a pharmaceutically acceptable salt thereof, one or more $R^8$ is —OH.

In some embodiments of the compound of Formula I, Ia, II, or IIa, or a pharmaceutically acceptable salt thereof, one or more $R^8$ is $C_{1-8}$ alkyl, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-8}$ alkyl, wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-8}$ alkyl. In some embodiments of the compound of Formula I, Ia, II, or IIa, or a pharmaceutically acceptable salt thereof, one or more $R^8$ is $C_{1-4}$ alkyl, wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-4}$ alkyl, wherein the $C_{1-4}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-4}$ alkyl.

In some embodiments of the compound of Formula I, Ia, II, or IIa, or a pharmaceutically acceptable salt thereof, one or more $R^8$ is $C_{1-8}$ alkoxy, wherein the $C_{1-8}$ alkoxy is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-8}$ alkoxy, wherein the $C_{1-8}$ alkoxy is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-8}$ alkoxy.

In some embodiments of the compound of Formula I, Ia, II, or IIa, or a pharmaceutically acceptable salt thereof, one or more $R^8$ is $C_{1-5}$ alkoxy, wherein the $C_{1-5}$ alkoxy is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-8}$ alkoxy, wherein the $C_{1-8}$ alkoxy is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^8$ is $C_{1-5}$ alkoxy.

In some embodiments of the compound of Formula I, Ia, II, or IIa, or a pharmaceutically acceptable salt thereof, one or more $R^8$ is $C_{3-7}$ monocyclic cycloalkyl, wherein the $C_{3-7}$ monocyclic cycloalkyl is optionally substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^8$ is $C_{3-7}$ monocyclic cycloalkyl, wherein the $C_{3-7}$ monocyclic cycloalkyl is substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^8$ is $C_{3-7}$ monocyclic cycloalkyl.

In some embodiments of the compound of Formula I, Ia, II, or IIa, or a pharmaceutically acceptable salt thereof, one or more $R^8$ is 4-6 membered monocyclic heterocyclyl, wherein the 4-6 membered monocyclic heterocyclyl has 1-3 ring heteroatoms independently selected from N, O, and S and is optionally substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^8$ is 4-6 membered monocyclic heterocyclyl, wherein the 4-6 membered monocyclic heterocyclyl has 1-3 ring heteroatoms independently selected from N, O, and S and is substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^8$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, one or more $R^8$ is 4-6 membered monocyclic heteroaryl, wherein the 4-6 membered monocyclic heteroaryl has 1-3 ring heteroatoms independently selected from N, O, and S and is optionally substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^8$ is 4-6 membered monocyclic heteroaryl, wherein the 4-6 membered monocyclic heteroaryl has 1-3 ring heteroatoms independently selected from N, O, and S and is substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one or more $R^8$ is 4-6 membered monocyclic heteroaryl having 1-3 ring heteroatoms independently selected from N, O, and S.

In some embodiments of the compound of Formula I, Ia, II, or IIa, or a pharmaceutically acceptable salt thereof, each $R^9$ is independently $C_{1-8}$ alkyl, $C_{3-7}$ monocyclic cycloalkyl, 4-6 membered monocyclic heterocyclyl, or 5-6 membered monocyclic heteroaryl, wherein the $C_{1-8}$ alkyl is optionally substituted with 1-3 groups independently selected from —OH, halogen, —CN, and $C_{1-4}$ alkoxy, wherein the $C_{3-7}$ monocyclic cycloalkyl, 4-6 membered monocyclic heterocyclyl, and 5-6 membered monocyclic heteroaryl are each optionally substituted with 1-3 groups independently selected from —OH, halogen, —CN, $C_{1-4}$ alkyl, and $C_{1-4}$ alkoxy, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, each $R^9$ is independently $C_{1-8}$ alkyl or $C_{3-7}$ monocyclic cycloalkyl, wherein the $C_{1-8}$ alkyl is optionally substituted with 1-3 groups independently selected from —OH, halogen, —CN, and $C_{1-4}$ alkoxy, and wherein the $C_{3-7}$ monocyclic cycloalkyl is optionally substituted with 1-3 groups independently selected from —OH, halogen, —CN, $C_{1-4}$ alkyl, and $C_{1-4}$ alkoxy.

In some embodiments of the compound of Formula I, Ia, II, or IIa, or a pharmaceutically acceptable salt thereof, each $R^9$ is independently $C_{1-3}$ alkyl or $C_{3-5}$ monocyclic cycloalkyl.

In some embodiments of the compound of Formula I, Ia, II, or IIa, or a pharmaceutically acceptable salt thereof, one or more $R^9$ is $C_{1-8}$ alkyl, wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^9$ is $C_{1-8}$ alkyl, wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^9$ is $C_{1-8}$ alkyl. In some embodiments of the compound of Formula I, Ia, II, or IIa, or a pharmaceutically acceptable salt thereof, one or more $R^9$ is $C_{1-4}$ alkyl, wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^9$ is $C_{1-4}$ alkyl, wherein the $C_{1-4}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, one or more $R^9$ is $C_{1-4}$ alkyl. In some embodiments of the compound of Formula I, Ia, II, or IIa, or a pharmaceutically acceptable salt thereof, one or more $R^9$ is $C_{1-3}$ alkyl. In some embodiments of the compound of Formula I, Ia, II, or IIa, or a pharmaceutically acceptable salt thereof, one or more $R^9$ is methyl, ethyl, propyl, or isopropyl. In some embodiments of the compound of Formula I, Ia, II, or IIa, or a pharmaceutically acceptable salt thereof, one $R^9$ is methyl. In some embodiments of the compound of Formula I, Ia, II, or IIa, or a pharmaceutically acceptable salt thereof, one $R^9$ is ethyl. In some embodiments of the compound of Formula I, Ia, II, or IIa, or a pharmaceutically acceptable salt thereof, one $R^9$ is propyl. In some embodiments of the compound of Formula I, Ia, II, or IIa, or a pharmaceutically acceptable salt thereof, one $R^9$ is isopropyl.

In some embodiments of the compound of Formula I, Ia, II, or IIa, or a pharmaceutically acceptable salt thereof, one or more R⁹ is C₃₋₇ monocyclic cycloalkyl, wherein the C₃₋₇ monocyclic cycloalkyl is optionally substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is C₃₋₇ monocyclic cycloalkyl, wherein the C₃₋₇ monocyclic cycloalkyl is substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is C₃₋₇ monocyclic cycloalkyl. In some embodiments of the compound of Formula I, Ia, II, or IIa, or a pharmaceutically acceptable salt thereof, one or more R⁹ is C₃₋₅ monocyclic cycloalkyl, wherein the C₃₋₅ monocyclic cycloalkyl is optionally substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is C₃₋₅ monocyclic cycloalkyl, wherein the C₃₋₅ monocyclic cycloalkyl is substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is C₃₋₅ monocyclic cycloalkyl. In some embodiments of the compound of Formula I, Ia, II, or IIa, or a pharmaceutically acceptable salt thereof, one R⁹ is cyclopropyl.

In some embodiments of the compound of Formula I, Ia, II, or IIa, or a pharmaceutically acceptable salt thereof, one or more R⁹ is 4-6 membered monocyclic heterocyclyl, wherein the 4-6 membered monocyclic heterocyclyl has 1-3 ring heteroatoms independently selected from N, O, and S and is optionally substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is 4-6 membered monocyclic heterocyclyl, wherein the 4-6 membered monocyclic heterocyclyl has 1-3 ring heteroatoms independently selected from N, O, and S and is substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, one or more R⁹ is 5-6 membered monocyclic heteroaryl, wherein the 5-6 membered monocyclic heteroaryl has 1-3 ring heteroatoms independently selected from N, O, and S and is optionally substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is 5-6 membered monocyclic heteroaryl, wherein the 5-6 membered monocyclic heteroaryl has 1-3 ring heteroatoms independently selected from N, O, and S and is substituted with 1-3 groups independently selected from —OH, halogen, —CN, C₁₋₄ alkyl, and C₁₋₄ alkoxy. In some embodiments of the compound of Formula I, Ia, II, or IIa, or a pharmaceutically acceptable salt thereof, one or more R⁹ is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, each R¹⁰ is C₁₋₄ alkylene, which may be the same or different. In some embodiments of the compound of Formula I, Ia, II, or IIa, or a pharmaceutically acceptable salt thereof, each R¹⁰ is independently methylene, ethylene, propylene, isopropylene, butylene, or isobutylene. In some embodiments of the compound of Formula I, Ia, II, or IIa, or a pharmaceutically acceptable salt thereof, R¹⁰ is —CH(CH₃)₂—.

In some embodiments of the compound of Formula I, Ia, II, or IIa, or a pharmaceutically acceptable salt thereof, Ring A, together with the two carbons to which it is attached, forms a 5-6 membered monocyclic heterocyclyl or 5-6 membered monocyclic heteroaryl, wherein the 5-6 membered monocyclic heterocyclyl and 5-6 membered monocyclic heteroaryl are each substituted with one Z group and each have 1-3 ring heteroatoms independently selected from N, O, and S.

In some embodiments of the compound of Formula I, Ia, II, or IIa, or a pharmaceutically acceptable salt thereof, Ring A, together with the two carbons to which it is attached, forms a 5-6 membered monocyclic heterocyclyl or 5-6 membered monocyclic heteroaryl, wherein the 5-6 membered monocyclic heterocyclyl and 5-6 membered monocyclic heteroaryl are each substituted with one Z group and each have 1-3 ring heteroatoms independently selected from N, O, and S, wherein one or two ring heteroatoms is a nitrogen.

In some embodiments of the compound of Formula I, Ia, II, or IIa, or a pharmaceutically acceptable salt thereof, Ring A, together with the two carbons to which it is attached, forms a 5-6 membered monocyclic heterocyclyl, wherein the 5-6 membered monocyclic heterocyclyl is substituted with one Z group and has 1-3 ring heteroatoms independently selected from N, O, and S. In some embodiments of the compound of Formula I, Ia, II, or IIa, or a pharmaceutically acceptable salt thereof, Ring A, together with the two carbons to which it is attached, forms a 5-6 membered monocyclic heterocyclyl, wherein the 5-6 membered monocyclic heterocyclyl is substituted with one Z group and has 1-3 ring heteroatoms independently selected from N, O, and S, wherein one or two ring heteroatoms is a nitrogen.

In some embodiments of the compound of Formula I, Ia, II, or IIa, or a pharmaceutically acceptable salt thereof, Ring A, together with the two carbons to which it is attached, forms a 5-6 membered monocyclic heteroaryl, wherein 5-6 membered monocyclic heteroaryl is substituted with one Z group and has 1-3 ring heteroatoms independently selected from N, O, and S. In some embodiments of the compound of Formula I, Ia, II, or IIa, or a pharmaceutically acceptable salt thereof, Ring A, together with the two carbons to which it is attached, forms a 5-6 membered monocyclic heteroaryl, wherein 5-6 membered monocyclic heteroaryl is substituted with one Z group and has 1-3 ring heteroatoms independently selected from N, O, and S, wherein one or two ring heteroatoms is a nitrogen.

In some embodiments of the compound of Formula I, Ia, II, or IIa, or a pharmaceutically acceptable salt thereof,

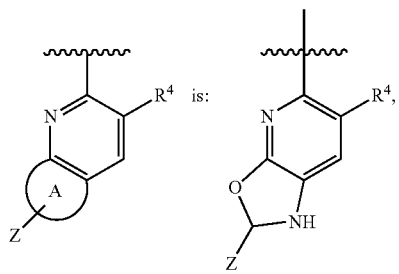

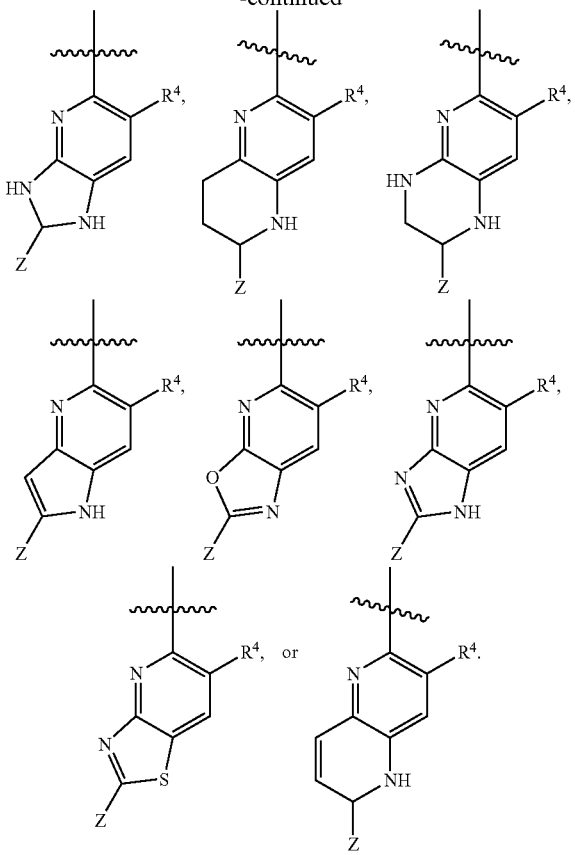

In some embodiments of the compound of Formula I, Ia, II, or IIa, or a pharmaceutically acceptable salt thereof,

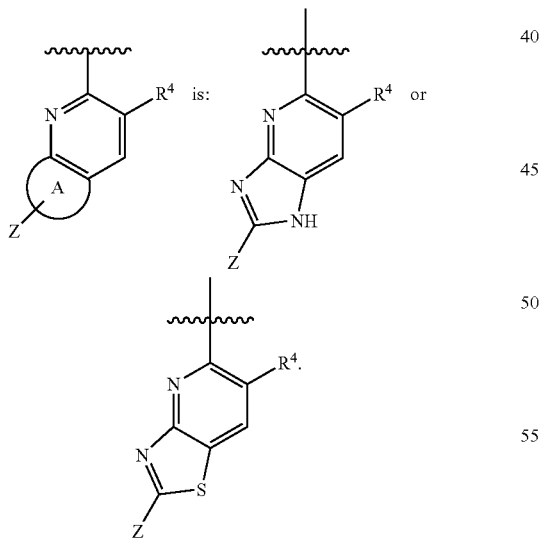

In some embodiments of the compound of Formula I, Ia, II, or IIa, or a pharmaceutically acceptable salt thereof, Z is
i) oxo,
ii) —OH,
iii) —CN,
iv) $C_{1-5}$ alkyl, wherein the $C_{1-5}$ alkyl is substituted with one group selected from —OH and $C_{1-4}$ alkoxy, and wherein the $C_{1-5}$ alkyl is optionally further substituted with 1-2 groups independently selected from —OH, halogen, and —CN,
v) $C_{6-8}$ alkyl, wherein the $C_{6-8}$ alkyl is optionally substituted with 1-3 groups independently selected from —OH, halogen, —CN, and $C_{1-4}$ alkoxy,
vi) —$Z^1$-$Z^2$—$Z^3$—$Z^4$,
wherein $Z^1$ is $C_{2-6}$ alkynylene optionally substituted with 1-3 groups independently selected from —OH, halogen, —CN, and $C_{1-4}$ alkoxy,
wherein $Z^2$ and $Z^3$ are each independently $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, or 7-10 membered spirocyclic heterocyclylene, wherein the $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene each have 1-3 ring heteroatoms independently selected from N, O, and S, and
wherein $Z^4$ is a $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S,
vii) $C_{3-7}$ monocyclic cycloalkyl optionally substituted with 1-3 groups independently selected from —OH, halogen, —CN, $C_{1-4}$ alkyl, and $C_{1-4}$ alkoxy,
viii) —S($C_{1-8}$ alkyl), wherein the $C_{1-8}$ alkyl is optionally substituted with 1-3 groups independently selected from —OH, halogen, —CN, and $C_{1-4}$ alkoxy,
ix) —N$R^{11}R^{12}$, wherein one of $R^{11}$ and $R^{12}$ is H or $C_{1-8}$ alkyl and the other of $R^{11}$ and $R^{12}$ is $C_{1-8}$ alkyl, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl,
   wherein each $C_{1-8}$ alkyl is substituted with 1-3 $R^{17}$ groups,
   wherein the $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and
   wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S,
x) $C_{6-10}$ monocyclic or fused bicyclic aryl optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, —NR$^6$R$^6$, 4-6 membered monocyclic heterocyclyl, and 5-6 membered monocyclic heteroaryl,
   wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, and —NR$^6$R$^6$, and
   wherein the 4-6 membered monocyclic heterocyclyl and 5-6 membered monocyclic heteroaryl each have 1-3 ring heteroatoms independently selected from N, O, and S,
xi) 4-6 membered monocyclic heterocyclyl having 1-3 ring heteroatoms independently selected from N, O, and S and optionally substituted with 1-3 $R^{13}$ groups,
xii) 8-10 membered fused or bridged bicyclic heterocyclyl having 1-3 ring heteroatoms independently selected from N, O, and S and optionally substituted with 1-3 $R^{13}$ groups,
xiii) 5-6 membered monocyclic heteroaryl having 1-3 ring heteroatoms independently selected from N, O, and S and optionally substituted with 1-3 $R^{13}$ groups,
xiv) 8-10 membered fused bicyclic heteroaryl having 1-3 ring heteroatoms independently selected from N, O, and S and optionally substituted with 1-3 $R^{13}$ groups, or
xv) 7-10 membered spirocyclic heterocyclyl having 1-3 ring heteroatoms independently selected from N, O, and S and optionally substituted with 1-3 $R^{13}$ groups.

In some embodiments of the compound of Formula I, Ia, II, or IIa, or a pharmaceutically acceptable salt thereof, Z is
i) oxo,
ii) —OH,
iii) —CN,
iv) $C_{1-5}$ alkyl, wherein the $C_{1-5}$ alkyl is substituted with one group selected from —OH and $C_{1-4}$ alkoxy, and wherein the $C_{1-8}$ alkyl is optionally further substituted with 1-2 groups independently selected from —OH, halogen, and —CN,
v) $C_{6-8}$ alkyl, wherein the $C_{6-8}$ alkyl is optionally substituted with 1-3 groups independently selected from —OH, halogen, —CN, and $C_{1-4}$ alkoxy,
vi) —Z$^1$-Z$^2$—Z$^3$—Z$^4$,
   wherein Z$^1$ is $C_{2-6}$ alkynylene optionally substituted with 1-3 groups independently selected from —OH, halogen, —CN, and $C_{1-4}$ alkoxy,
   wherein Z$^2$ is a $C_{6-10}$ monocyclic or fused bicyclic arylene, 4-6 membered monocyclic heterocyclylene, or 5-6 membered monocyclic heteroarylene, wherein the $C_{6-10}$ monocyclic or fused bicyclic arylene, 4-6 membered monocyclic heterocyclylene, and 5-6 membered monocyclic heteroarylene are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclylene and 5-6 membered monocyclic heteroarylene each have 1-3 ring heteroatoms independently selected from N, O, and S,
   wherein Z$^3$ is a 5-6 membered monocyclic heterocyclylene or 5-6 membered monocyclic heteroarylene,
      wherein the 5-6 membered monocyclic heterocyclylene and 5-6 membered monocyclic heteroarylene are each optionally substituted with 1-3 groups independently selected from —OH, halogen, —CN, $C_{1-4}$ alkyl, $C_{1-4}$ alkoxy, and —C(O)R$^8$, and
      wherein the 4-6 membered monocyclic heterocyclylene and 5-6 membered monocyclic heteroarylene each have 1-3 ring heteroatoms independently selected from N, O, and S, and
   wherein Z$^4$ is a 5-6 membered monocyclic heterocyclyl or 5-6 membered monocyclic heteroaryl,
      wherein the 5-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, and —C(O)R$^8$, and
      wherein the 5-6 membered monocyclic heterocyclyl and 5-6 membered monocyclic heteroaryl each have 1-3 ring heteroatoms independently selected from N, O, and S,
vii) $C_{3-7}$ monocyclic cycloalkyl optionally substituted with 1-3 groups independently selected from —OH, halogen, —CN, $C_{1-4}$ alkyl, and $C_{1-4}$ alkoxy,
viii) —S($C_{1-4}$ alkyl), wherein the $C_{1-4}$ alkyl is optionally substituted with 1-3 groups independently selected from —OH, halogen, —CN, and $C_{1-4}$ alkoxy,
ix) —NR$^{11}$R$^{12}$, wherein one of R$^{11}$ and R$^{12}$ is H or $C_{1-8}$ alkyl and the other of R$^{11}$ and R$^{12}$ is $C_{1-8}$ alkyl, $C_{3-7}$ monocyclic cycloalkyl, 4-6 membered monocyclic heterocyclyl, or 5-6 membered monocyclic heteroaryl,
   wherein each $C_{1-8}$ alkyl is substituted with 1-3 $R^{17a}$ groups,
   wherein the $C_{3-7}$ monocyclic cycloalkyl, 4-6 membered monocyclic heterocyclyl, and 5-6 membered monocyclic heteroaryl are each optionally substituted with 1-3 groups independently selected from oxo, —OH, halogen, —CN, $C_{1-4}$ alkyl, and $C_{1-4}$ alkoxy, and
   wherein the 4-6 membered monocyclic heterocyclyl and 5-6 membered monocyclic heteroaryl each have 1-3 ring heteroatoms independently selected from N, O, and S,
x) $C_{6-10}$ monocyclic or fused bicyclic aryl optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, —NR$^6$R$^6$, 4-6 membered monocyclic heterocyclyl, and 5-6 membered monocyclic heteroaryl, wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, and —NR$^6$R$^6$, and wherein the 4-6 membered monocyclic heterocyclyl and 5-6 membered monocyclic heteroaryl each have 1-3 ring heteroatoms independently selected from N, O, and S, xi) 4-6 membered monocyclic heterocyclyl having 1-3 ring heteroatoms independently selected from N, O, and S and optionally substituted with 1-3 R$^{13}$ groups, xii) 8-10 membered fused or bridged bicyclic heterocyclyl having 1-3 ring heteroatoms independently selected from N, O, and S and optionally substituted with 1-3 R$^{13}$ groups, xiii) 5-6 membered monocyclic heteroaryl having 1-3 ring heteroatoms independently selected from N, O, and S and optionally substituted with 1-3 R$^{13}$ groups, xiv) 8-10 membered fused bicyclic heteroaryl optionally substituted with 1-3 R$^{13}$ groups, or xv) 7-10 membered spirocyclic heterocyclyl having 1-3 ring heteroatoms independently selected from N, O, and S and optionally substituted with 1-3 R$^{13}$ groups.

In some embodiments of the compound of Formula I, Ia, II, or IIa, or a pharmaceutically acceptable salt thereof, Z is oxo.

In some embodiments of the compound of Formula I, Ia, II, or IIa, or a pharmaceutically acceptable salt thereof, Z is —OH or —CN. In some embodiments of the compound of Formula I, Ia, II, or IIa, or a pharmaceutically acceptable salt thereof, Z is —OH. In some embodiments of the compound of Formula I, Ia, II, or IIa, or a pharmaceutically acceptable salt thereof, Z is —CN.

In some embodiments of the compound of Formula I, Ia, II, or IIa, or a pharmaceutically acceptable salt thereof, Z is $C_{1-5}$ alkyl, wherein the $C_{1-5}$ alkyl is substituted with one group selected from —OH and $C_{1-4}$ alkoxy, and wherein the $C_{1-5}$ alkyl is optionally further substituted with 1-2 groups independently selected from —OH, halogen, and —CN. In some embodiments of the compound of Formula I, Ia, II, or IIa, or a pharmaceutically acceptable salt thereof, Z is $C_{1-5}$ alkyl, wherein the $C_{1-5}$ alkyl is substituted with one group selected from —OH and $C_{1-4}$ alkoxy, and wherein the $C_{1-5}$ alkyl is further substituted with 1-2 groups independently selected from —OH, halogen, and —CN. In some embodiments of the compound of Formula I, Ia, II, or IIa, or a pharmaceutically acceptable salt thereof, Z is $C_{1-5}$ alkyl, wherein the $C_{1-8}$ alkyl is substituted with one group independently selected from —OH and $C_{1-4}$ alkoxy. In some embodiments of the compound of Formula I, Ia, II, or IIa, or a pharmaceutically acceptable salt thereof, Z is $C_{1-5}$ alkyl, wherein the $C_{1-5}$ alkyl is substituted with one —OH. In some embodiments of the compound of Formula I, Ia, II, or IIa, or a pharmaceutically acceptable salt thereof, Z is —C(CH$_3$)$_2$OH.

In some embodiments of the compound of Formula I, Ia, II, or IIa, or a pharmaceutically acceptable salt thereof, Z is $C_{6-8}$ alkyl, wherein the $C_{6-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, Z is $C_{6-8}$ alkyl, wherein the $C_{6-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, Z is $C_{6-8}$ alkyl.

In some embodiments of the compound of Formula I, Ia, II, or IIa, or a pharmaceutically acceptable salt thereof, Z is —Z$^1$—Z$^2$-Z$^3$—Z$^4$, wherein Z$^1$ is $C_{2-6}$ alkynylene optionally substituted with 1-3 groups independently selected from —OH, halogen, —CN, and $C_{1-4}$ alkoxy, wherein Z$^2$ and Z$^3$ are each independently $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, or 7-10 membered spirocyclic heterocyclylene, wherein the $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene each have 1-3 ring heteroatoms independently selected from N, O, and S, and wherein Z$^4$ is a $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, Z is —Z$^1$—Z$^2$-Z$^3$—Z$^4$, wherein Z$^1$ is $C_{2-6}$ alkynylene optionally substituted with 1-3 groups independently selected from —OH, halogen, —CN, and $C_{1-4}$ alkoxy, wherein Z$^2$ is a $C_{6-10}$ monocyclic or fused bicyclic arylene, 4-6 membered monocyclic heterocyclylene, or 5-6 membered monocyclic heteroarylene, wherein the $C_{6-10}$ monocyclic or fused bicyclic arylene, 4-6 membered monocyclic heterocyclylene, and 5-6 membered monocyclic heteroarylene are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclylene and 5-6 membered monocyclic heteroarylene each have 1-3 ring heteroatoms independently selected from N, O, and S,
wherein $Z^3$ is a 5-6 membered monocyclic heterocyclylene or 5-6 membered monocyclic heteroarylene,
  wherein the 5-6 membered monocyclic heterocyclylene and 5-6 membered monocyclic heteroarylene are each optionally substituted with 1-3 groups independently selected from —OH, halogen, —CN, $C_{1-4}$ alkyl, $C_{1-4}$ alkoxy, and —C(O)R$^8$, and
  wherein the 4-6 membered monocyclic heterocyclylene and 5-6 membered monocyclic heteroarylene each have 1-3 ring heteroatoms independently selected from N, O, and S, and
wherein $Z^4$ is a 5-6 membered monocyclic heterocyclyl or 5-6 membered monocyclic heteroaryl,
  wherein the 5-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, and —C(O)R$^8$, and
  wherein the 5-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, $Z^1$ is $C_{2-6}$ alkynylene optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $Z^1$ is $C_{2-6}$ alkynylene substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $Z^1$ is $C_{2-6}$ alkynylene. In some embodiments of the compound of Formula I, Ia, II, or IIa, or a pharmaceutically acceptable salt thereof, $Z^1$ is $C_{2-4}$ alkynylene optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $Z^1$ is $C_{2-4}$ alkynylene substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, $Z^1$ is $C_{2-4}$ alkynylene. In some embodiments of the compound of Formula I, Ia, II, or IIa, or a pharmaceutically acceptable salt thereof, $Z^1$ is $C_2$ alkynylene.

In some embodiments of the compound of Formula I, Ia, II, or IIa, or a pharmaceutically acceptable salt thereof, $Z^2$ is $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, or 7-10 membered spirocyclic heterocyclylene, wherein the $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene each have 1-3 ring heteroatoms independently selected from N, O, and S.

In some embodiments of the compound of Formula I, Ia, II, or IIa, or a pharmaceutically acceptable salt thereof, $Z^2$ is $C_{6-10}$ monocyclic or fused bicyclic arylene, 4-6 membered monocyclic heterocyclylene, or 5-6 membered monocyclic heteroarylene, wherein the $C_{6-10}$ monocyclic or fused bicyclic arylene, 4-6 membered monocyclic heterocyclylene, and 5-6 membered monocyclic heteroarylene are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclylene and 5-6 membered monocyclic heteroarylene each have 1-3 ring heteroatoms independently selected from N, O, and S.

In some embodiments of the compound of Formula I, Ia, II, or IIa, or a pharmaceutically acceptable salt thereof, $Z^2$ is $C_{3-7}$ monocyclic cycloalkylene, wherein the $C_{3-7}$ monocyclic cycloalkylene is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^2$ is $C_{3-7}$ monocyclic cycloalkylene, wherein the $C_{3-7}$ monocyclic cycloalkylene is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^2$ is $C_{3-7}$ monocyclic cycloalkylene.

In some embodiments of the compound of Formula I, Ia, II, or IIa, or a pharmaceutically acceptable salt thereof, $Z^2$ is $C_{6-10}$ monocyclic or fused bicyclic arylene, wherein the $C_{6-10}$ monocyclic or fused bicyclic arylene is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^2$ is $C_{6-10}$ monocyclic or fused bicyclic arylene, wherein the $C_{6-10}$ monocyclic or fused bicyclic arylene is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^2$ is $C_{6-10}$ monocyclic or fused bicyclic arylene. In some embodiments of the compound of Formula I, Ia, II, or IIa, or a pharmaceutically acceptable salt thereof, $Z^2$ is phenylene.

In some embodiments of the compound of Formula I, Ia, II, or IIa, or a pharmaceutically acceptable salt thereof, $Z^2$ is 4-6 membered monocyclic heterocyclylene, wherein the 4-6 membered monocyclic heterocyclylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^2$ is 4-6 membered monocyclic heterocyclylene, wherein the 4-6 membered monocyclic heterocyclylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^2$ is 4-6 membered monocyclic heterocyclylene having 1-3 ring heteroatoms independently selected from N, O, and S.

In some embodiments of the compound of Formula I, Ia, II, or IIa, or a pharmaceutically acceptable salt thereof, $Z^2$ is 5-6 membered monocyclic heteroarylene, wherein the 5-6 membered monocyclic heteroarylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 5-6 membered monocyclic heteroarylene, wherein the 5-6 membered monocyclic heteroarylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 5-6 membered monocyclic heteroarylene having 1-3 ring heteroatoms independently selected from N, O, and S.

In some embodiments of the compound of Formula I, Ia, II, or IIa, or a pharmaceutically acceptable salt thereof, $Z^2$ is 8-10 membered fused or bridged bicyclic heterocyclylene, wherein the 8-10 membered fused or bridged bicyclic heterocyclylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 8-10 membered fused or bridged bicyclic heterocyclylene, wherein the 8-10 membered fused or bridged bicyclic heterocyclylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 8-10 membered fused or bridged bicyclic heterocyclylene having 1-3 ring heteroatoms independently selected from N, O, and S.

In some embodiments of the compound of Formula I, Ia, II, or IIa, or a pharmaceutically acceptable salt thereof, $Z^2$ is 8-10 membered fused bicyclic heteroarylene, wherein the 8-10 membered fused bicyclic heteroarylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 8-10 membered fused bicyclic heteroarylene, wherein the 8-10 membered fused bicyclic heteroarylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 8-10 membered fused bicyclic heteroarylene having 1-3 ring heteroatoms independently selected from N, O, and S.

In some embodiments of the compound of Formula I, Ia, II, or IIa, or a pharmaceutically acceptable salt thereof, $Z^2$ is 7-10 membered spirocyclic heterocyclylene, wherein the 7-10 membered spirocyclic heterocyclylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 7-10 membered spirocyclic heterocyclylene, wherein the 7-10 membered spirocyclic heterocyclylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^2$ is 7-10 membered spirocyclic heterocyclylene having 1-3 ring heteroatoms independently selected from N, O, and S.

In some embodiments of the compound of Formula I, Ia, II, or IIa, or a pharmaceutically acceptable salt thereof, $Z^1$ is $C_2$ alkynylene and $Z^2$ is phenylene.

In some embodiments of the compound of Formula I, Ia, II, or IIa, or a pharmaceutically acceptable salt thereof, $Z^3$ is $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, or 7-10 membered spirocyclic heterocyclylene, wherein the $C_{3-7}$ monocyclic cycloalkylene, $C_{6-10}$ monocyclic or fused bicyclic arylene, 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclylene, 5-6 membered monocyclic heteroarylene, 8-10 membered fused or bridged bicyclic heterocyclylene, 8-10 membered fused bicyclic heteroarylene, and 7-10 membered spirocyclic heterocyclylene each have 1-3 ring heteroatoms independently selected from N, O, and S.

In some embodiments of the compound of Formula I, Ia, II, or IIa, or a pharmaceutically acceptable salt thereof, $Z^3$ is 5-6 membered monocyclic heterocyclylene or 5-6 membered monocyclic heteroarylene, wherein the 5-6 membered monocyclic heterocyclylene and 5-6 membered monocyclic heteroarylene are each optionally substituted with 1-3 groups independently selected from —OH, halogen, —CN, $C_{1-4}$ alkyl, $C_{1-4}$ alkoxy, and —C(O)$R^8$, and wherein the 5-6 membered monocyclic heterocyclylene and 5-6 membered monocyclic heteroarylene each have 1-3 ring heteroatoms independently selected from N, O, and S.

In some embodiments of the compound of Formula I, Ia, II, or IIa, or a pharmaceutically acceptable salt thereof, $Z^3$ is $C_{3-7}$ monocyclic cycloalkylene, wherein the $C_{3-7}$ monocyclic cycloalkylene is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^3$ is $C_{3-7}$ monocyclic cycloalkylene, wherein the $C_{3-7}$ monocyclic cycloalkylene is substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^3$ is $C_{3-7}$ monocyclic cycloalkylene.

In some embodiments of the compound of Formula I, Ia, II, or IIa, or a pharmaceutically acceptable salt thereof, $Z^3$ is $C_{6-10}$ monocyclic or fused bicyclic arylene, wherein the $C_{6-10}$ monocyclic or fused bicyclic arylene is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^3$ is $C_{6-10}$ monocyclic or fused bicyclic arylene, wherein the $C_{6-10}$ monocyclic or fused bicyclic arylene is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is $C_{6-10}$ monocyclic or fused bicyclic arylene.

In some embodiments of the compound of Formula I, Ia, II, or IIa, or a pharmaceutically acceptable salt thereof, $Z^3$ is 4-6 membered monocyclic heterocyclylene, wherein the 4-6 membered monocyclic heterocyclylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 4-6 membered monocyclic heterocyclylene, wherein the 4-6 membered monocyclic heterocyclylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 4-6 membered monocyclic heterocyclylene having 1-3 ring heteroatoms independently selected from N, O, and S.

In some embodiments of the compound of Formula I, Ia, II, or IIa, or a pharmaceutically acceptable salt thereof, $Z^3$ is 5-6 membered monocyclic heteroarylene, wherein the 5-6 membered monocyclic heteroarylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 5-6 membered monocyclic heteroarylene, wherein the 5-6 membered monocyclic heteroarylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 5-6 membered monocyclic heteroarylene having 1-3 ring heteroatoms independently selected from N, O, and S. In some embodiments of the compound of Formula I, Ia, II, or IIa, or a pharmaceutically acceptable salt thereof, $Z^3$ is imidazolylene.

In some embodiments of the compound of Formula I, Ia, II, or IIa, or a pharmaceutically acceptable salt thereof, $Z^3$ is 8-10 membered fused or bridged bicyclic heterocyclylene, wherein the 8-10 membered fused or bridged bicyclic heterocyclylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 8-10 membered fused or bridged bicyclic heterocyclylene, wherein the 8-10 membered fused or bridged bicyclic heterocyclylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 8-10 membered fused or bridged bicyclic heterocyclylene having 1-3 ring heteroatoms independently selected from N, O, and S.

In some embodiments of the compound of Formula I, Ia, II, or IIa, or a pharmaceutically acceptable salt thereof, $Z^3$ is 8-10 membered fused bicyclic heteroarylene, wherein the 8-10 membered fused bicyclic heteroarylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 8-10 membered fused bicyclic heteroarylene, wherein the 8-10 membered fused bicyclic heteroarylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 8-10 membered fused bicyclic heteroarylene having 1-3 ring heteroatoms independently selected from N, O, and S.

In some embodiments of the compound of Formula I, Ia, II, or IIa, or a pharmaceutically acceptable salt thereof, $Z^3$ is 7-10 membered spirocyclic heterocyclylene, wherein the 7-10 membered spirocyclic heterocyclylene has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 7-10 membered spirocyclic heterocyclylene, wherein the 7-10 membered spirocyclic heterocyclylene has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^3$ is 7-10 membered spirocyclic heterocyclylene having 1-3 ring heteroatoms independently selected from N, O, and S.

In some embodiments of the compound of Formula I, Ia, II, or IIa, or a pharmaceutically acceptable salt thereof, $Z^4$ is $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein the $C_{3-7}$ monocyclic cycloalkyl, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from —OH, halogen, —CN, $C_{1-4}$ alkyl, $C_{1-4}$ alkoxy, and —C(O)R$^8$, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, $Z^4$ is 5-6 membered monocyclic heterocyclyl or 5-6 membered monocyclic heteroaryl, wherein the 5-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, and —C(O)R$^8$, and wherein the 5-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, $Z^4$ is $C_{3-7}$ monocyclic cycloalkyl, wherein the $C_{3-7}$ monocyclic cycloalkyl is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is $C_{3-7}$ monocyclic cycloalkyl, wherein the $C_{3-7}$ monocyclic cycloalkyl is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is $C_{3-7}$ monocyclic cycloalkyl.

In some embodiments of the compound of Formula I, Ia, II, or IIa, or a pharmaceutically acceptable salt thereof, $Z^4$ is $C_{6-10}$ monocyclic or fused bicyclic aryl, wherein the $C_{6-10}$ monocyclic or fused bicyclic aryl is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is $C_{6-10}$ monocyclic or fused bicyclic aryl, wherein the $C_{6-10}$ monocyclic or fused bicyclic aryl is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is $C_{6-10}$ monocyclic or fused bicyclic aryl.

In some embodiments of the compound of Formula I, Ia, II, or IIa, or a pharmaceutically acceptable salt thereof, $Z^4$ is 4-6 membered monocyclic heterocyclyl, wherein the 4-6 membered monocyclic heterocyclyl has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 4-6 membered monocyclic heterocyclyl, wherein the 4-6 membered monocyclic heterocyclyl has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, $Z^4$ is a 5-6 membered monocyclic heterocyclyl, wherein the 5-6 membered monocyclic heterocyclyl has 1-3 ring heteroatoms independently selected from N, O, and S and is optionally substituted with one group selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is a 5-6 membered monocyclic heterocyclyl, wherein the 5-6 membered monocyclic heterocyclyl has 1-3 ring heteroatoms independently selected from N, O, and S and is substituted with one group selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is a 5-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, $Z^4$ is pyrrolidinyl substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is pyrrolidinyl substituted with one —C(O)R$^8$. In some embodiments of the compound of Formula I, Ia, II, or IIa, or a pharmaceutically acceptable salt thereof, $Z^4$ is pyrrolidinyl.

In some embodiments of the compound of Formula I, Ia, II, or IIa, or a pharmaceutically acceptable salt thereof, $Z^4$ is 5-6 membered monocyclic heteroaryl, wherein the 5-6 membered monocyclic heteroaryl has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 5-6 membered monocyclic heteroaryl, wherein the 5-6 membered monocyclic heteroaryl has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, $Z^4$ is 8-10 membered fused or bridged bicyclic heterocyclyl, wherein the 8-10 membered fused or bridged bicyclic heterocyclyl has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 8-10 membered fused or bridged bicyclic heterocyclyl, wherein the 8-10 membered fused or bridged bicyclic heterocyclyl has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, $Z^4$ is 8-10 membered fused bicyclic heteroaryl, wherein the 8-10 membered fused bicyclic heteroaryl has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 8-10 membered fused bicyclic heteroaryl, wherein the 8-10 membered fused bicyclic heteroaryl has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)R$^8$. In some embodiments of the compound of Formula I, Ia, II, or IIa, or a pharmaceutically acceptable salt thereof, $Z^4$ is 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, $Z^4$ is 7-10 membered spirocyclic heterocyclyl, wherein the 7-10 membered spirocyclic heterocyclyl has 1-3 ring heteroatoms independently selected from N, O, and S and is optionally substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^4$ is 7-10 membered spirocyclic heterocyclyl, wherein the 7-10 membered spirocyclic heterocyclyl has 1-3 ring heteroatoms independently selected from N, O, and S and is substituted with 1-3 groups independently selected from —OH, halogen, —CN, $C_{1-4}$ alkyl, $C_{1-4}$ alkoxy, and —C(O)$R^8$. In some embodiments of the compound of Formula I, Ia, II, or IIa, or a pharmaceutically acceptable salt thereof, $Z^4$ is 7-10 membered spirocyclic heterocyclyl having 1-3 ring heteroatoms independently selected from N, O, and S.

In some embodiments of the compound of Formula I, Ia, II, or IIa, or a pharmaceutically acceptable salt thereof,
  $Z^2$ is $C_{6-10}$ monocyclic or fused bicyclic arylene, 4-6 membered monocyclic heterocyclylene, or 5-6 membered monocyclic heteroarylene, wherein the $C_{6-10}$ monocyclic or fused bicyclic arylene, 4-6 membered monocyclic heterocyclylene, and 5-6 membered monocyclic heteroarylene are each optionally substituted with 1-3 groups independently selected from —OH, halogen, —CN, $C_{1-4}$ alkyl, $C_{1-4}$ alkoxy, and —C(O)$R^8$, and wherein the 4-6 membered monocyclic heterocyclylene and 5-6 membered monocyclic heteroarylene each have 1-3 ring heteroatoms independently selected from N, O, and S, and
  $Z^3$ is a 5-6 membered monocyclic heterocyclylene or 5-6 membered monocyclic heteroarylene,
    wherein the 5-6 membered monocyclic heterocyclylene and 5-6 membered monocyclic heteroarylene are each optionally substituted with 1-3 groups independently selected from —OH, halogen, —CN, $C_{1-4}$ alkyl, $C_{1-4}$ alkoxy, and —C(O)$R^8$, and
    wherein the 5-6 membered monocyclic heterocyclylene and 5-6 membered monocyclic heteroarylene each have 1-3 ring heteroatoms independently selected from N, O, and S.

In some embodiments of the compound of Formula I, Ia, II, or IIa, or a pharmaceutically acceptable salt thereof, Z is $C_{3-7}$ monocyclic cycloalkyl or —S($C_{1-4}$ alkyl), wherein the $C_{3-7}$ monocyclic cycloalkyl and the $C_{1-4}$ alkyl are each optionally substituted with 1-2 groups independently selected from —OH, halogen, —CN, and $C_{1-4}$ alkoxy. In some embodiments of the compound of Formula I, Ia, II, or IIa, or a pharmaceutically acceptable salt thereof, Z is $C_{3-7}$ monocyclic cycloalkyl or —S($C_{1-4}$ alkyl), wherein the $C_{3-7}$ monocyclic cycloalkyl and the $C_{1-4}$ alkyl are each substituted with 1-2 groups independently selected from —OH, halogen, —CN, and $C_{1-4}$ alkoxy. In some embodiments of the compound of Formula I, Ia, II, or IIa, or a pharmaceutically acceptable salt thereof, Z is $C_{3-7}$ monocyclic cycloalkyl or —S($C_{1-4}$ alkyl).

In some embodiments of the compound of Formula I, Ia, II, or IIa, or a pharmaceutically acceptable salt thereof, Z is $C_{3-7}$ monocyclic cycloalkyl, wherein the $C_{3-7}$ monocyclic cycloalkyl is optionally substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, Z is $C_{3-7}$ monocyclic cycloalkyl, wherein the $C_{3-7}$ monocyclic cycloalkyl is substituted with 1-3 groups independently selected from —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, Z is $C_{3-7}$ monocyclic cycloalkyl. In some embodiments of the compound of Formula I, Ia, II, or IIa, or a pharmaceutically acceptable salt thereof, Z is cyclopropyl, cyclobutyl, or cyclopentyl. In some embodiments of the compound of Formula I, Ia, II, or IIa, or a pharmaceutically acceptable salt thereof, Z is cyclopropyl.

In some embodiments of the compound of Formula I, Ia, II, or IIa, or a pharmaceutically acceptable salt thereof, Z is —S($C_{1-8}$ alkyl), wherein the $C_{1-8}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, Z is —S($C_{1-8}$ alkyl), wherein the $C_{1-8}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, Z is —S($C_{1-8}$ alkyl).

In some embodiments of the compound of Formula I, Ia, II, or IIa, or a pharmaceutically acceptable salt thereof, Z is —S($C_{1-4}$ alkyl), wherein the $C_{1-4}$ alkyl is optionally substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, Z is —S($C_{1-4}$ alkyl), wherein the $C_{1-4}$ alkyl is substituted with 1-3 groups independently selected from —OH, halogen, —CN, and $C_{1-4}$ alkoxy. In some embodiments of the compound of Formula I, Ia, II, or IIa, or a pharmaceutically acceptable salt thereof, Z is —S($C_{1-4}$ alkyl). In some embodiments of the compound of Formula I, Ia, II, or IIa, or a pharmaceutically acceptable salt thereof, Z is —S(methyl), —S(ethyl), —S(propyl), or —S(isopropyl). In some embodiments of the compound of Formula I, Ia, II, or IIa, or a pharmaceutically acceptable salt thereof, Z is —S($CH_3$).

In some embodiments of the compound of Formula I, Ia, II, or IIa, or a pharmaceutically acceptable salt thereof, Z is —$NR^{11}R^{12}$, wherein one of $R^{11}$ and $R^{12}$ is H or $C_{1-8}$ alkyl and the other of $R^{11}$ and $R^{12}$ is $C_{1-8}$ alkyl, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl,
    wherein each $C_{1-8}$ alkyl is substituted with 1-3 $R^{17}$ groups,
    wherein the $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and
  wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, Z is —NR¹¹R¹², wherein one of $R^{11}$ and $R^{12}$ is H or $C_{1-8}$ alkyl and the other of $R^{11}$ and $R^{12}$ is $C_{1-8}$ alkyl, $C_{3-7}$ monocyclic cycloalkyl, 4-6 membered monocyclic heterocyclyl, or 5-6 membered monocyclic heteroaryl,
  wherein each $C_{1-8}$ alkyl is substituted with 1-3 $R^{17a}$ groups,
  wherein the $C_{3-7}$ monocyclic cycloalkyl, 4-6 membered monocyclic heterocyclyl, and 5-6 membered monocyclic heteroaryl are each optionally substituted with 1-3 groups independently selected from oxo, —OH, halogen, —CN, $C_{1-4}$ alkyl, and $C_{1-4}$ alkoxy, and
  wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-8}$ alkyl, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl,
  wherein each $C_{1-8}$ alkyl is substituted with 1-3 $R^{17}$ groups,
  wherein the $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and
  wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-8}$ alkyl, wherein the $C_{1-8}$ alkyl is substituted with 1-3 $R^{17}$ groups.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-6}$ alkyl, wherein the $C_{1-6}$ alkyl is substituted with 1-3 $R^{17}$ groups.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-8}$ alkyl, wherein the $C_{1-8}$ alkyl is substituted with 1-3 $R^{17a}$ groups.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-6}$ alkyl, wherein the $C_{1-6}$ alkyl is substituted with 1-3 $R^{17a}$ groups.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-6}$ alkyl, wherein the $C_{1-6}$ alkyl is substituted with 1-3 groups independently selected from —OH, halogen, and —CN.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-6}$ alkyl, wherein the $C_{1-6}$ alkyl is substituted with 1-3 groups independently selected from $C_{1-4}$ alkoxy and —NR⁶R⁶, and wherein the $C_{1-4}$ alkoxy is optionally substituted with one $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is $C_{1-6}$ alkyl, wherein the $C_{1-6}$ alkyl is substituted with one group selected from —OH, methoxy, —OCH₂CH₂OCH₃, or —N($C_{1-3}$ alkyl)₂, wherein each $C_{1-3}$ alkyl may be the same or different.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-6}$ alkyl, wherein the $C_{1-6}$ alkyl is substituted with 1-3 $R^{17a}$ groups.

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{1-6}$ alkyl, wherein the $C_{1-6}$ alkyl is substituted with one group selected from cyclopropyl, morpholinyl, and imidazolyl, wherein the cyclopropyl, morpholinyl, and imidazolyl are each optionally substituted with one group selected from —OH, halogen, and $C_{1-4}$ alkoxy.

In some embodiments of the compound of Formula I, Ia, II, or IIa, or a pharmaceutically acceptable salt thereof, Z is —NR¹¹R¹², wherein —NR¹¹R¹² is

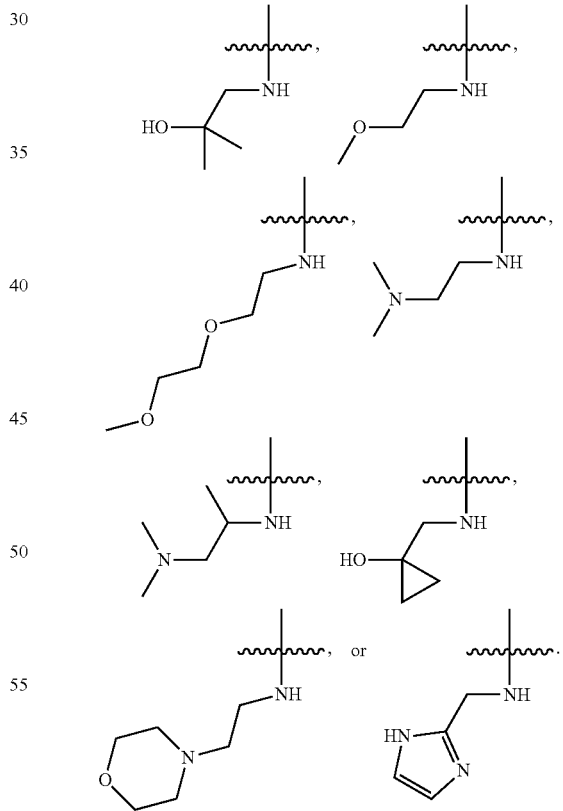

In some embodiments of the compound of Formula I, Ia, II, or IIa, or a pharmaceutically acceptable salt thereof, Z is —NR¹¹R¹², wherein one of $R^{11}$ and $R^{12}$ is H and the other of $R^{11}$ and $R^{12}$ is $C_{3-7}$ monocyclic cycloalkyl, 4-6 membered monocyclic heterocyclyl, or 5-6 membered monocyclic heteroaryl, wherein the $C_{3-7}$ monocyclic cycloalkyl, 4-6 membered monocyclic heterocyclyl, and 5-6 membered monocyclic heteroaryl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is cyclopropyl, oxetanyl, tetrahydrofuranyl, or pyrrolidinyl, each of which is optionally substituted with 1-3 groups independently selected from oxo, —OH, halogen, —CN, $C_{1-4}$ alkyl, and $C_{1-4}$ alkoxy.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is $C_{3-7}$ monocyclic cycloalkyl, 4-6 membered monocyclic heterocyclyl, or 5-6 membered monocyclic heteroaryl, wherein the $C_{3-7}$ monocyclic cycloalkyl, 4-6 membered monocyclic heterocyclyl, and 5-6 membered monocyclic heteroaryl are each substituted with 1-3 groups independently selected from oxo, —OH, halogen, —CN, $C_{1-4}$ alkyl, and $C_{1-4}$ alkoxy, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is cyclopropyl, oxetanyl, tetrahydrofuranyl, or pyrrolidinyl, each of which is substituted with 1-3 groups independently selected from oxo, —OH, halogen, —CN, $C_{1-4}$ alkyl, and $C_{1-4}$ alkoxy.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is $C_{3-7}$ monocyclic cycloalkyl, 4-6 membered monocyclic heterocyclyl, or 5-6 membered monocyclic heteroaryl, wherein the $C_{3-7}$ monocyclic cycloalkyl, 4-6 membered monocyclic heterocyclyl, and 5-6 membered monocyclic heteroaryl are each optionally substituted with 1-3 groups independently selected from oxo and $C_{1-4}$ alkyl, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is $C_{3-7}$ monocyclic cycloalkyl, 4-6 membered monocyclic heterocyclyl, or 5-6 membered monocyclic heteroaryl, wherein the $C_{3-7}$ monocyclic cycloalkyl, 4-6 membered monocyclic heterocyclyl, and 5-6 membered monocyclic heteroaryl are each substituted with 1-3 groups independently selected from oxo and $C_{1-4}$ alkyl, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is $C_{3-7}$ monocyclic cycloalkyl, 4-6 membered monocyclic heterocyclyl, or 5-6 membered monocyclic heteroaryl. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is cyclopropyl, oxetanyl, tetrahydrofuranyl, or pyrrolidinyl.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is $C_{3-7}$ monocyclic cycloalkyl, wherein the $C_{3-7}$ monocyclic cycloalkyl is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is $C_{3-7}$ monocyclic cycloalkyl, wherein the $C_{3-7}$ monocyclic cycloalkyl is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is $C_{3-7}$ monocyclic cycloalkyl.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is cyclopropyl, wherein the cyclopropyl is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is cyclopropyl, wherein the cyclopropyl is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is cyclopropyl.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is 4-6 membered monocyclic heterocyclyl, wherein the 4-6 membered monocyclic heterocyclyl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is 4-6 membered monocyclic heterocyclyl, wherein the 4-6 membered monocyclic heterocyclyl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of R$^{11}$ and R$^{12}$ is H and the other of R$^{11}$ and R$^{12}$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, Z is —NR$^{11}$R$^{12}$, wherein one of R$^{11}$ and R$^{12}$ is H and the other of R$^{11}$ and R$^{12}$ is oxetanyl, tetrahydrofuranyl, or pyrrolidinyl, wherein the oxetanyl, tetrahydrofuranyl, and pyrrolidinyl are each optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is oxetanyl, tetrahydrofuranyl, or pyrrolidinyl, wherein the oxetanyl, tetrahydrofuranyl, and pyrrolidinyl are each substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is oxetanyl, tetrahydrofuranyl, or pyrrolidinyl.

In some embodiments of the compound of Formula I, Ia, II, or IIa, or a pharmaceutically acceptable salt thereof, Z is —$NR^{11}R^{12}$, wherein one of $R^{11}$ and $R^{12}$ is H and the other of $R^{11}$ and $R^{12}$ is 5-6 membered monocyclic heteroaryl, wherein the 5-6 membered monocyclic heteroaryl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 5-6 membered monocyclic heteroaryl, wherein the 5-6 membered monocyclic heteroaryl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein one of $R^{11}$ and $R^{12}$ is H and the other of $R^{11}$ and $R^{12}$ is pyrazolyl, wherein the pyrazolyl is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is pyrazolyl, wherein the pyrazolyl is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is pyrazolyl.

In some embodiments of the compound of Formula I, Ia, II, or IIa, or a pharmaceutically acceptable salt thereof, Z is —$NR^{11}R^{12}$, wherein one of $R^{11}$ and $R^{12}$ is H and the other of $R^{11}$ and $R^{12}$ is 8-10 membered fused or bridged bicyclic heterocyclyl, wherein the 8-10 membered fused or bridged bicyclic heterocyclyl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 8-10 membered fused or bridged bicyclic heterocyclyl, wherein the 8-10 membered fused or bridged bicyclic heterocyclyl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein one of $R^{11}$ and $R^{12}$ is H and the other of $R^{11}$ and $R^{12}$ is 8-10 membered fused bicyclic heteroaryl, wherein the 8-10 membered fused bicyclic heteroaryl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 8-10 membered fused bicyclic heteroaryl, wherein the 8-10 membered fused bicyclic heteroaryl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein one of $R^{11}$ and $R^{12}$ is H and the other of $R^{11}$ and $R^{12}$ is 7-10 membered spirocyclic heterocyclyl, wherein the 7-10 membered spirocyclic heterocyclyl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 7-10 membered spirocyclic heterocyclyl, wherein the 7-10 membered spirocyclic heterocyclyl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is H and the other of $R^{11}$ and $R^{12}$ is 7-10 membered spirocyclic heterocyclyl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein —$NR^{11}R^{12}$ is

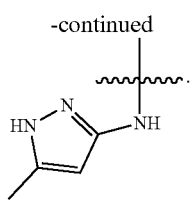

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-8}$ alkyl and the other of $R^{11}$ and $R^{12}$ is $C_{1-8}$ alkyl, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl, wherein each $C_{1-8}$ alkyl is substituted with 1-3 $R^{17}$ groups, wherein the $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-8}$ alkyl and the other of $R^{11}$ and $R^{12}$ is $C_{1-8}$ alkyl, wherein each $C_{1-8}$ alkyl is substituted with 1-3 $R^{17}$ groups.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-6}$ alkyl and the other of $R^{11}$ and $R^{12}$ is $C_{1-6}$ alkyl, wherein each $C_{1-6}$ alkyl is substituted with 1-3 $R^{17}$ groups.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-8}$ alkyl and the other of $R^{11}$ and $R^{12}$ is $C_{1-8}$ alkyl, wherein each $C_{1-8}$ alkyl is substituted with 1-3 $R^{17a}$ groups.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-6}$ alkyl and the other of $R^{11}$ and $R^{12}$ is $C_{1-6}$ alkyl, wherein each $C_{1-6}$ alkyl is substituted with 1-3 $R^{17a}$ groups.

In some embodiments of the compound of Formula I, Ia, II, or IIa, or a pharmaceutically acceptable salt thereof, each $R^{17}$ is independently —OH, halogen, —CN, $C_{1-4}$ alkoxy, $-NR^6R^6$, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl, wherein the $C_{1-4}$ alkoxy, $C_{3-7}$ monocyclic cycloalkyl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, each $R^{17a}$ is independently —OH, halogen, —CN, $C_{1-4}$ alkoxy, $-NR^6R^6$, $C_{3-7}$ monocyclic cycloalkyl, 4-6 membered monocyclic heterocyclyl, and 5-6 membered monocyclic heteroaryl, wherein the $C_{1-4}$ alkoxy, $C_{3-7}$ monocyclic cycloalkyl, 4-6 membered monocyclic heterocyclyl, and 5-6 membered monocyclic heteroaryl are each optionally substituted with 1-3 groups independently selected from oxo, —OH, halogen, —CN, $C_{1-4}$ alkyl, and $C_{1-4}$ alkoxy, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-8}$ alkyl and the other of $R^{11}$ and $R^{12}$ is $C_{3-7}$ monocyclic cycloalkyl, wherein the $C_{3-7}$ monocyclic cycloalkyl is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is $C_{3-7}$ monocyclic cycloalkyl, wherein the $C_{3-7}$ monocyclic cycloalkyl is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is $C_{3-7}$ monocyclic cycloalkyl.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-8}$ alkyl and the other of $R^{11}$ and $R^{12}$ is 4-6 membered monocyclic heterocyclyl, wherein the 4-6 membered monocyclic heterocyclyl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 4-6 membered monocyclic heterocyclyl, wherein the 4-6 membered monocyclic heterocyclyl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, Z is $-NR^{11}R^{12}$, wherein one of $R^{11}$ and $R^{12}$ is $C_{1-8}$ alkyl and the other of $R^{11}$ and $R^{12}$ is 5-6 membered monocyclic heteroaryl, wherein the 5-6 membered monocyclic heteroaryl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 5-6 membered monocyclic heteroaryl, wherein the 5-6 membered monocyclic heteroaryl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein one of $R^{11}$ and $R^{12}$ is $C_{1-8}$ alkyl and the other of $R^{11}$ and $R^{12}$ is 8-10 membered fused or bridged bicyclic heterocyclyl, wherein the 8-10 membered fused or bridged bicyclic heterocyclyl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 8-10 membered fused or bridged bicyclic heterocyclyl, wherein the 8-10 membered fused or bridged bicyclic heterocyclyl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein one of $R^{11}$ and $R^{12}$ is $C_{1-8}$ alkyl and the other of $R^{11}$ and $R^{12}$ is 8-10 membered fused bicyclic heteroaryl, wherein the 8-10 membered fused bicyclic heteroaryl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 8-10 membered fused bicyclic heteroaryl, wherein the 8-10 membered fused bicyclic heteroaryl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, Z is —$NR^{11}R^{12}$, wherein one of $R^{11}$ and $R^{12}$ is $C_{1-8}$ alkyl and the other of $R^{11}$ and $R^{12}$ is 7-10 membered spirocyclic heterocyclyl, wherein the 7-10 membered spirocyclic heterocyclyl has 1-3 ring heteroatoms independently selected from N, O, and S and is optionally substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 7-10 membered spirocyclic heterocyclyl, wherein the 7-10 membered spirocyclic heterocyclyl has 1-3 ring heteroatoms independently selected from N, O, and S and is substituted with 1-3 groups independently selected from oxo, —OH, halogen, —CN, $C_{1-4}$ alkyl, and $C_{1-4}$ alkoxy. In some embodiments of the compound of Formula I, Ia, II, or IIa, or a pharmaceutically acceptable salt thereof, one of $R^{11}$ and $R^{12}$ is $C_{1-8}$ alkyl and the other of $R^{11}$ and $R^{12}$ is 7-10 membered spirocyclic heterocyclyl having 1-3 ring heteroatoms independently selected from N, O, and S.

In some embodiments of the compound of Formula I, Ia, II, or IIa, or a pharmaceutically acceptable salt thereof, Z is $C_{6-10}$ monocyclic or fused bicyclic aryl optionally substituted with 1-3 groups independently selected from —OH, halogen, —CN, $C_{1-4}$ alkyl, $C_{1-4}$ alkoxy, —$C(O)NR^6R^6$, —$C(O)R^8$, —$NR^6R^6$, 4-6 membered monocyclic heterocyclyl, and 5-6 membered monocyclic heteroaryl,
  wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —$C(O)NR^6R^6$, —$C(O)R^8$, and —$NR^6R^6$, and
  wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is $C_{6-10}$ monocyclic or fused bicyclic aryl substituted with 1-3 groups independently selected from —OH, halogen, —CN, $C_{1-4}$ alkyl, $C_{1-4}$ alkoxy, —$C(O)NR^6R^6$, —$C(O)R^8$, —$NR^6R^6$, 4-6 membered monocyclic heterocyclyl, and 5-6 membered monocyclic heteroaryl,
  wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —$C(O)NR^6R^6$, —$C(O)R^8$, and —$NR^6R^6$, and
  wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is $C_{6-10}$ monocyclic or fused bicyclic aryl.

In some embodiments of the compound of Formula I, Ia, II, or IIa, or a pharmaceutically acceptable salt thereof, Z is phenyl optionally substituted with 1-3 groups independently selected from —OH, halogen, —CN, $C_{1-4}$ alkyl, $C_{1-4}$ alkoxy, —$C(O)NR^6R^6$, —$C(O)R^8$, —$NR^6R^6$, 4-6 membered monocyclic heterocyclyl, and 5-6 membered monocyclic heteroaryl,
  wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —$C(O)NR^6R^6$, —$C(O)R^8$, and —$NR^6R^6$, and wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is phenyl substituted with 1-3 groups independently selected from —OH, halogen, —CN, $C_{1-4}$ alkyl, $C_{1-4}$ alkoxy, —C(O)NR$^6$R$^6$, —C(O)R$^8$, —NR$^6$R$^6$, 4-6 membered monocyclic heterocyclyl, and 5-6 membered monocyclic heteroaryl,
wherein the 4-6 membered monocyclic heterocyclyl and 5-6 membered monocyclic heteroaryl are each optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, and —NR$^6$R$^6$, and
wherein the 4-6 membered monocyclic heterocyclyl and 5-6 membered monocyclic heteroaryl each have 1-3 ring heteroatoms independently selected from N, O, and S.

In some embodiments of the compound of Formula I, Ia, II, or IIa, or a pharmaceutically acceptable salt thereof, Z is phenyl, wherein the phenyl is optionally substituted with 1-3 groups independently selected from —OH, halogen, —CN, $C_{1-4}$ alkyl, $C_{1-4}$ alkoxy, —C(O)NR$^6$R$^6$, —C(O)R$^8$, 4-6 membered monocyclic heterocyclyl, and 5-6 membered monocyclic heteroaryl, wherein the 4-6 membered monocyclic heterocyclyl and 5-6 membered monocyclic heteroaryl are each optionally substituted with one —C(O)R$^8$ and each have 1-3 ring heteroatoms independently selected from N, O, and S. In some embodiments of the compound of Formula I, Ia, II, or IIa, or a pharmaceutically acceptable salt thereof, Z is phenyl, wherein the phenyl is substituted with 1-3 groups independently selected from —OH, halogen, —CN, $C_{1-4}$ alkyl, $C_{1-4}$ alkoxy, —C(O)NR$^6$R$^6$, —C(O)R$^8$, 4-6 membered monocyclic heterocyclyl, and 5-6 membered monocyclic heteroaryl, wherein the 4-6 membered monocyclic heterocyclyl and 5-6 membered monocyclic heteroaryl are each optionally substituted with one —C(O)R$^8$ and each have 1-3 ring heteroatoms independently selected from N, O, and S.

In some embodiments of the compound of Formula I, Ia, II, or IIa, or a pharmaceutically acceptable salt thereof, Z is phenyl, wherein the phenyl is optionally substituted 1-3 groups independently selected from halogen, —C(O)NR$^6$R$^6$, morpholinyl, or piperazinyl, wherein the morpholinyl and piperazinyl are each optionally substituted with one —C(O)R$^8$. In some embodiments of the compound of Formula I, Ia, II, or IIa, or a pharmaceutically acceptable salt thereof, Z is phenyl, wherein the phenyl is substituted 1-3 groups independently selected from halogen, —C(O)NR$^6$R$^6$, morpholinyl, or piperazinyl, wherein the morpholinyl and piperazinyl are each optionally substituted with one —C(O)R$^8$.

In some embodiments of the compound of Formula I, Ia, II, or IIa, or a pharmaceutically acceptable salt thereof, Z is

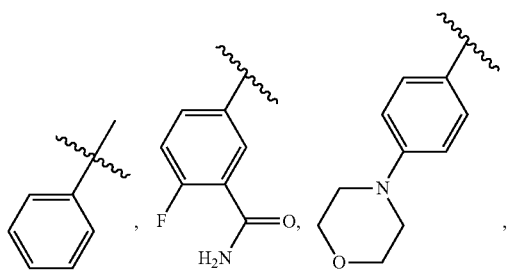

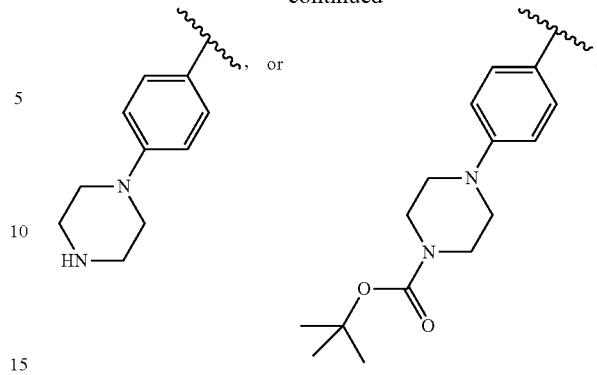

In some embodiments of the compound of Formula I, Ia, II, or IIa, or a pharmaceutically acceptable salt thereof, Z is phenyl.

In some embodiments of the compound of Formula I, Ia, II, or IIa, or a pharmaceutically acceptable salt thereof, Z is 4-6 membered monocyclic heterocyclyl, 8-10 membered fused or bridged bicyclic heterocyclyl, 5-6 membered monocyclic heteroaryl, 8-10 membered fused bicyclic heteroaryl, or 7-10 membered spirocyclic heterocyclyl, wherein the 4-6 membered monocyclic heterocyclyl, 8-10 membered fused or bridged bicyclic heterocyclyl, 5-6 membered monocyclic heteroaryl, 8-10 membered fused bicyclic heteroaryl, and 7-10 membered spirocyclic heterocyclyl are each optionally substituted with 1-3 R$^{13}$ groups and each have 1-3 ring heteroatoms independently selected from N, O, and S.

In some embodiments of the compound of Formula I, Ia, II, or IIa, or a pharmaceutically acceptable salt thereof, Z is 4-6 membered monocyclic heterocyclyl, 8-10 membered fused or bridged bicyclic heterocyclyl, 5-6 membered monocyclic heteroaryl, 8-10 membered fused bicyclic heteroaryl, or 7-10 membered spirocyclic heterocyclyl, wherein the 4-6 membered monocyclic heterocyclyl, 8-10 membered fused or bridged bicyclic heterocyclyl, 5-6 membered monocyclic heteroaryl, 8-10 membered fused bicyclic heteroaryl, and 7-10 membered spirocyclic heterocyclyl are each optionally substituted with 1-3 R$^{13}$ groups and each have 1-3 ring heteroatoms independently selected from N, O, and S, wherein at least one ring heteroatom is a nitrogen.

In some embodiments of the compound of Formula I, Ia, II, or IIa, or a pharmaceutically acceptable salt thereof, Z is 4-6 membered monocyclic heterocyclyl, 8-10 membered fused or bridged bicyclic heterocyclyl, 5-6 membered monocyclic heteroaryl, 8-10 membered fused bicyclic heteroaryl, or 7-10 membered spirocyclic heterocyclyl, wherein the 4-6 membered monocyclic heterocyclyl, 8-10 membered fused or bridged bicyclic heterocyclyl, 5-6 membered monocyclic heteroaryl, 8-10 membered fused bicyclic heteroaryl, and 7-10 membered spirocyclic heterocyclyl are each optionally substituted with 1-2 R$^{13}$ groups and each have 1-3 ring heteroatoms independently selected from N, O, and S.

In some embodiments of the compound of Formula I, Ia, II, or IIa, or a pharmaceutically acceptable salt thereof, Z is 4-6 membered monocyclic heterocyclyl, 8-10 membered fused or bridged bicyclic heterocyclyl, 5-6 membered monocyclic heteroaryl, 8-10 membered fused bicyclic heteroaryl, or 7-10 membered spirocyclic heterocyclyl, wherein the 4-6 membered monocyclic heterocyclyl, 8-10 membered fused or bridged bicyclic heterocyclyl, 5-6 membered monocyclic heteroaryl, 8-10 membered fused bicyclic heteroaryl, and 7-10 membered spirocyclic heterocyclyl are each optionally substituted with 1-2 R$^{13}$ groups and each have 1-3 ring heteroatoms independently selected from N, O, and S, wherein at least one ring heteroatom is a nitrogen.

In some embodiments of the compound of Formula I, Ia, II, or IIa, or a pharmaceutically acceptable salt thereof, Z is azetidinyl, pyrrolidinyl, morpholinyl, piperazinyl, piperidinyl, pyrazolyl, imidazolyl, pyrimidinyl, isoindolinyl, 2-oxa-6-azaspirl[3.3]heptanyl, 2,5-diazabicyclo[2.2.1]heptanyl, 2,6-diazaspiro[3.3]heptanyl, 1,6-diazaspiro[3.3]heptanyl, 2,7-diazaspiro[3.5]nonanyl, 1-oxa-3,8-diazaspiro[4.5]decanyl, or 5,6,7,8-tetrahydro-[1,2,4]triazolo[4,3-a]pyrazinyl, each of which is optionally substituted with 1-3 R$^{13}$ groups.

In some embodiments of the compound of Formula I, Ia, II, or IIa, or a pharmaceutically acceptable salt thereof, Z is azetidinyl, pyrrolidinyl, morpholinyl, piperazinyl, piperidinyl, pyrazolyl, imidazolyl, pyrimidinyl, isoindolinyl, 2-oxa-6-azaspirl[3.3]heptanyl, 2,5-diazabicyclo[2.2.1]heptanyl, 2,6-diazaspiro[3.3]heptanyl, 1,6-diazaspiro[3.3]heptanyl, 2,7-diazaspiro[3.5]nonanyl, 1-oxa-3,8-diazaspiro[4.5]decanyl, or 5,6,7,8-tetrahydro-[1,2,4]triazolo[4,3-a]pyrazinyl, each of which is optionally substituted with 1-2 R$^{13}$ groups.

In some embodiments of the compound of Formula I, Ia, II, or IIa, or a pharmaceutically acceptable salt thereof, Z is azetidinyl, pyrrolidinyl, morpholinyl, piperazinyl, piperidinyl, pyrazolyl, imidazolyl, pyrimidinyl, isoindolinyl, 2-oxa-6-azaspirl[3.3]heptanyl, 2,5-diazabicyclo[2.2.1]heptanyl, 2,6-diazaspiro[3.3]heptanyl, 1,6-diazaspiro[3.3]heptanyl, 2,7-diazaspiro[3.5]nonanyl, 1-oxa-3,8-diazaspiro[4.5]decanyl, or 5,6,7,8-tetrahydro-[1,2,4]triazolo[4,3-a]pyrazinyl, each of which is substituted with 1-3 R$^{13}$ groups.

In some embodiments of the compound of Formula I, Ia, II, or IIa, or a pharmaceutically acceptable salt thereof, Z is azetidinyl, pyrrolidinyl, morpholinyl, piperazinyl, piperidinyl, pyrazolyl, imidazolyl, pyrimidinyl, isoindolinyl, 2-oxa-6-azaspirl[3.3]heptanyl, 2,5-diazabicyclo[2.2.1]heptanyl, 2,6-diazaspiro[3.3]heptanyl, 1,6-diazaspiro[3.3]heptanyl, 2,7-diazaspiro[3.5]nonanyl, 1-oxa-3,8-diazaspiro[4.5]decanyl, or 5,6,7,8-tetrahydro-[1,2,4]triazolo[4,3-a]pyrazinyl, each of which is substituted with 1-2 R$^{13}$ groups.

In some embodiments of the compound of Formula I, Ia, II, or IIa, or a pharmaceutically acceptable salt thereof, Z is azetidinyl, pyrrolidinyl, morpholinyl, piperazinyl, piperidinyl, pyrazolyl, imidazolyl, pyrimidinyl, isoindolinyl, 2-oxa-6-azaspirl[3.3]heptanyl, 2,5-diazabicyclo[2.2.1]heptanyl, 2,6-diazaspiro[3.3]heptanyl, 1,6-diazaspiro[3.3]heptanyl, 2,7-diazaspiro[3.5]nonanyl, 1-oxa-3,8-diazaspiro[4.5]decanyl, or 5,6,7,8-tetrahydro-[1,2,4]triazolo[4,3-a]pyrazinyl.

In some embodiments of the compound of Formula I, Ia, II, or IIa, or a pharmaceutically acceptable salt thereof, Z is 4-6 membered monocyclic heterocyclyl, wherein the 4-6 membered monocyclic heterocyclyl has 1-3 ring heteroatoms independently selected from N, O, and S and is optionally substituted with 1-3 R$^{13}$ groups. In some embodiments of the compound of Formula I, Ia, II, or IIa, or a pharmaceutically acceptable salt thereof, Z is 4-6 membered monocyclic heterocyclyl, wherein the 4-6 membered monocyclic heterocyclyl has 1-3 ring heteroatoms independently selected from N, O, and S and is substituted with 1-3 R$^{13}$ groups. In some embodiments of the compound of Formula I, Ia, II, or IIa, or a pharmaceutically acceptable salt thereof, Z is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, Z is azetidinyl, pyrrolidinyl, morpholinyl, piperazinyl, or piperidinyl, wherein the azetidinyl, pyrrolidinyl, morpholinyl, piperazinyl, and piperidinyl are each optionally substituted with 1-3 R$^{13}$ groups. In some embodiments of the compound of Formula I, Ia, II, or IIa, or a pharmaceutically acceptable salt thereof, Z is azetidinyl, pyrrolidinyl, morpholinyl, piperazinyl, or piperidinyl, wherein the azetidinyl, pyrrolidinyl, morpholinyl, piperazinyl, and piperidinyl are each substituted with 1-3 R$^{13}$ groups. In some embodiments of the compound of Formula I, Ia, II, or IIa, or a pharmaceutically acceptable salt thereof, Z is azetidinyl, pyrrolidinyl, morpholinyl, piperazinyl, or piperidinyl.

In some embodiments of the compound of Formula I, Ia, II, or IIa, or a pharmaceutically acceptable salt thereof, Z is 8-10 membered fused or bridged bicyclic heterocyclyl, wherein the 8-10 membered fused or bridged bicyclic heterocyclyl has 1-3 ring heteroatoms independently selected from N, O, and S and is optionally substituted with 1-3 R$^{13}$ groups. In some embodiments of the compound of Formula I, Ia, II, or IIa, or a pharmaceutically acceptable salt thereof, Z is 8-10 membered fused or bridged bicyclic heterocyclyl, wherein the 8-10 membered fused or bridged bicyclic heterocyclyl has 1-3 ring heteroatoms independently selected from N, O, and S and is substituted with 1-3 R$^{13}$ groups. In some embodiments of the compound of Formula I, Ia, II, or IIa, or a pharmaceutically acceptable salt thereof, Z is 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, Z is 2,5-diazabicyclo[2.2.1]heptanyl, 5,6,7,8-tetrahydro-[1,2,4]triazolo[4,3-a]pyrazinyl, or 2,3-dihydrobenzo[b][1,4]dioxinyl, wherein the 2,5-diazabicyclo[2.2.1]heptanyl, 5,6,7,8-tetrahydro-[1,2,4]triazolo[4,3-a]pyrazinyl, and 2,3-dihydrobenzo[b][1,4]dioxinyl are each optionally substituted with 1-3 R$^{13}$ groups. In some embodiments of the compound of Formula I, Ia, II, or IIa, or a pharmaceutically acceptable salt thereof, Z is 2,5-diazabicyclo[2.2.1]heptanyl, 5,6,7,8-tetrahydro-[1,2,4]triazolo[4,3-a]pyrazinyl, or 2,3-dihydrobenzo[b][1,4]dioxinyl, wherein the 2,5-diazabicyclo[2.2.1]heptanyl, 5,6,7,8-tetrahydro-[1,2,4]triazolo[4,3-a]pyrazinyl, and 2,3-dihydrobenzo[b][1,4]dioxinyl are each substituted with 1-3 R$^{13}$ groups. In some embodiments of the compound of Formula I, Ia, II, or IIa, or a pharmaceutically acceptable salt thereof, Z is 2,5-diazabicyclo[2.2.1]heptanyl, 5,6,7,8-tetrahydro-[1,2,4]triazolo[4,3-a]pyrazinyl, or 2,3-dihydrobenzo[b][1,4]dioxinyl.

In some embodiments of the compound of Formula I, Ia, II, or IIa, or a pharmaceutically acceptable salt thereof, Z is 5-6 membered monocyclic heteroaryl, wherein the 5-6 membered monocyclic heteroaryl has 1-3 ring heteroatoms independently selected from N, O, and S and is optionally substituted with 1-3 R$^{13}$ groups. In some embodiments of the compound of Formula I, Ia, II, or IIa, or a pharmaceutically acceptable salt thereof, Z is 5-6 membered monocyclic heteroaryl, wherein the 5-6 membered monocyclic heteroaryl has 1-3 ring heteroatoms independently selected from N, O, and S and is substituted with 1-3 R$^{13}$ groups. In some embodiments of the compound of Formula I, Ia, II, or IIa, or a pharmaceutically acceptable salt thereof, Z is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, Z is pyrazolyl, imidazolyl, pyrimidinyl, isoindolinyl, pyrazolyl, imidazolyl, or pyrimidinyl, wherein the pyrazolyl, imidazolyl, pyrimidinyl, isoindolinyl, pyrazolyl, imidazolyl, and pyrimidinyl are each optionally substituted with 1-3 R$^{13}$ groups. In some embodiments of the compound of Formula I, Ia, II, or IIa, or a pharmaceutically acceptable salt thereof, Z is pyrazolyl, imidazolyl, pyrimidinyl, isoindolinyl, pyrazolyl, imidazolyl, or pyrimidinyl, wherein the pyrazolyl, imidazolyl, pyrimidinyl, isoindolinyl, pyrazolyl, imidazolyl, and pyrimidinyl are each substituted with 1-3 $R^{13}$ groups. In some embodiments of the compound of Formula I, Ia, II, or IIa, or a pharmaceutically acceptable salt thereof, Z is pyrazolyl, imidazolyl, pyrimidinyl, isoindolinyl, pyrazolyl, imidazolyl, or pyrimidinyl.

In some embodiments of the compound of Formula I, Ia, II, or IIa, or a pharmaceutically acceptable salt thereof, Z is 8-10 membered fused bicyclic heteroaryl, wherein the 8-10 membered fused bicyclic heteroaryl has 1-3 ring heteroatoms independently selected from N, O, and S and is optionally substituted with 1-3 $R^{13}$ groups. In some embodiments of the compound of Formula I, Ia, II, or IIa, or a pharmaceutically acceptable salt thereof, Z is 8-10 membered fused bicyclic heteroaryl, wherein the 8-10 membered fused bicyclic heteroaryl has 1-3 ring heteroatoms independently selected from N, O, and S and is substituted with 1-3 $R^{13}$ groups. In some embodiments of the compound of Formula I, Ia, II, or IIa, or a pharmaceutically acceptable salt thereof, Z is 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, Z is isoindolinyl or 1H-benzo[d]imidazolyl, wherein the isoindolinyl and 1H-benzo[d]imidazolyl are each optionally substituted with 1-3 $R^{13}$ groups. In some embodiments of the compound of Formula I, Ia, II, or IIa, or a pharmaceutically acceptable salt thereof, Z is isoindolinyl or 1H-benzo[d]imidazolyl, wherein the isoindolinyl and 1H-benzo[d]imidazolyl are each substituted with 1-3 $R^{13}$ groups. In some embodiments of the compound of Formula I, Ia, II, or IIa, or a pharmaceutically acceptable salt thereof, Z is isoindolinyl or 1H-benzo[d]imidazolyl.

In some embodiments of the compound of Formula I, Ia, II, or IIa, or a pharmaceutically acceptable salt thereof, Z is 7-10 membered spirocyclic heterocyclyl, wherein the 7-10 membered spirocyclic heterocyclyl has 1-3 ring heteroatoms independently selected from N, O, and S and is optionally substituted with 1-3 $R^{13}$ groups. In some embodiments of the compound of Formula I, Ia, II, or IIa, or a pharmaceutically acceptable salt thereof, Z is 7-10 membered spirocyclic heterocyclyl, wherein the 7-10 membered spirocyclic heterocyclyl has 1-3 ring heteroatoms independently selected from N, O, and S and is substituted with 1-3 $R^{13}$ groups. In some embodiments of the compound of Formula I, Ia, II, or IIa, or a pharmaceutically acceptable salt thereof, Z is 7-10 membered spirocyclic heterocyclyl having 1-3 ring heteroatoms independently selected from N, O, and S.

In some embodiments of the compound of Formula I, Ia, II, or IIa, or a pharmaceutically acceptable salt thereof, Z is 2-oxa-6-azaspiro[3.3]heptanyl, 2,6-diazaspiro[3.3]heptanyl, 1,6-diazaspiro[3.3]heptanyl, 2,7-diazaspiro[3.5]nonanyl, or 1-oxa-3,8-diazaspiro[4.5]decanyl, wherein the 2-oxa-6-azaspiro[3.3]heptanyl, 2,6-diazaspiro[3.3]heptanyl, 1,6-diazaspiro[3.3]heptanyl, 2,7-diazaspiro[3.5]nonanyl, and 1-oxa-3,8-diazaspiro[4.5]decanyl are each optionally substituted with 1-3 $R^{13}$ groups. In some embodiments of the compound of Formula I, Ia, II, or IIa, or a pharmaceutically acceptable salt thereof, Z is 2-oxa-6-azaspiro[3.3]heptanyl, 2,6-diazaspiro[3.3]heptanyl, 1,6-diazaspiro[3.3]heptanyl, 2,7-diazaspiro[3.5]nonanyl, or 1-oxa-3,8-diazaspiro[4.5]decanyl, wherein the 2-oxa-6-azaspiro[3.3]heptanyl, 2,6-diazaspiro[3.3]heptanyl, 1,6-diazaspiro[3.3]heptanyl, 2,7-diazaspiro[3.5]nonanyl, and 1-oxa-3,8-diazaspiro[4.5]decanyl are each substituted with 1-3 $R^{13}$ groups. In some embodiments of the compound of Formula I, Ia, II, or IIa, or a pharmaceutically acceptable salt thereof, Z is 2-oxa-6-azaspiro[3.3]heptanyl, 2,6-diazaspiro[3.3]heptanyl, 1,6-diazaspiro[3.3]heptanyl, 2,7-diazaspiro[3.5]nonanyl, or 1-oxa-3,8-diazaspiro[4.5]decanyl.

In some embodiments of the compound of Formula I, Ia, II, or IIa, or a pharmaceutically acceptable salt thereof, Z is

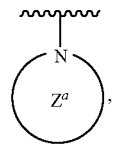

wherein
Ring $Z^a$ is a 4-6 membered monocyclic heterocyclyl, 8-10 membered fused or bridged bicyclic heterocyclyl, 5-6 membered monocyclic heteroaryl, 8-10 membered fused bicyclic heteroaryl, or 7-10 membered spirocyclic heterocyclyl, wherein the 4-6 membered monocyclic heterocyclyl, 8-10 membered fused or bridged bicyclic heterocyclyl, 5-6 membered monocyclic heteroaryl, 8-10 membered fused bicyclic heteroaryl, and 7-10 membered spirocyclic heterocyclyl each have one ring heteroatom that is nitrogen and each optionally have 1-2 additional ring heteroatoms independently selected from N, O, and S, and
Ring $Z^a$ is optionally substituted with 1-3 $R^{13}$ groups.

In some embodiments of the compound of Formula I, Ia, II, or IIa, or a pharmaceutically acceptable salt thereof, Z is

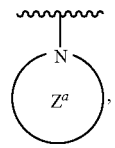

wherein
Ring $Z^a$ is a 4-6 membered monocyclic heterocyclyl, 8-10 membered fused or bridged bicyclic heterocyclyl, 5-6 membered monocyclic heteroaryl, 8-10 membered fused bicyclic heteroaryl, or 7-10 membered spirocyclic heterocyclyl, wherein the 4-6 membered monocyclic heterocyclyl, 8-10 membered fused or bridged bicyclic heterocyclyl, 5-6 membered monocyclic heteroaryl, 8-10 membered fused bicyclic heteroaryl, and 7-10 membered spirocyclic heterocyclyl each have one ring heteroatom that is nitrogen and each optionally have 1-2 aring heteroatoms independently selected from N, O, and S, and
Ring $Z^a$ is optionally substituted with 1-2 $R^{13}$ groups.

In some embodiments of the compound of Formula I, Ia, II, or IIa, or a pharmaceutically acceptable salt thereof, Ring $Z^a$ is each of which is optionally substituted with 1-3 $R^{13}$ groups.

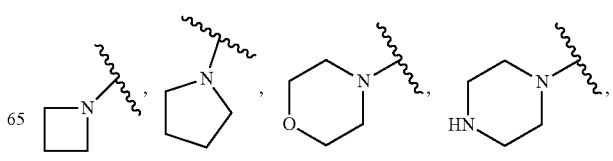

-continued

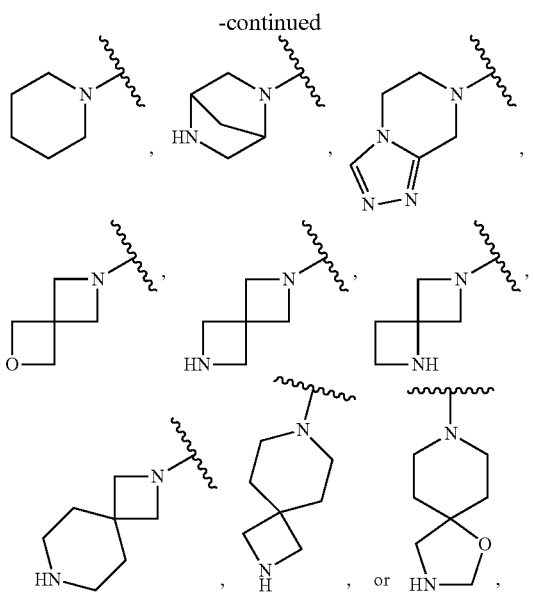

In some embodiments of the compound of Formula I, Ia, II, or IIa, or a pharmaceutically acceptable salt thereof, Ring $Z^a$ is

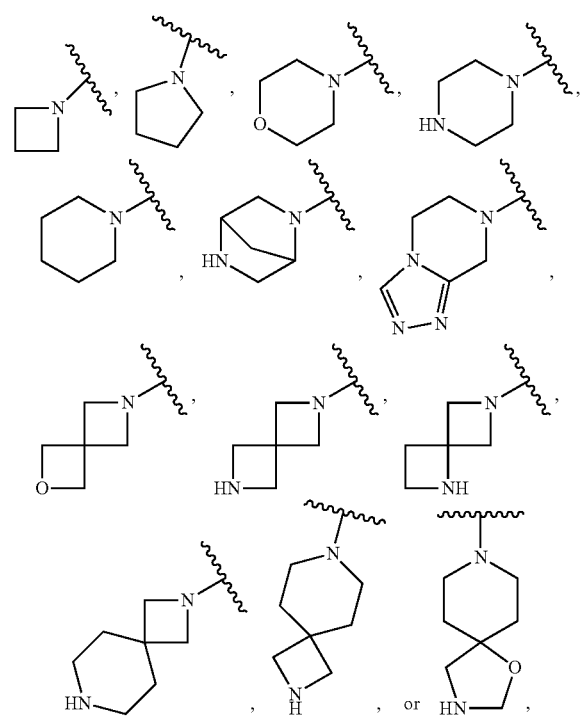

each of which is optionally substituted with 1-2 $R^{13}$ groups.

In some embodiments of the compound of Formula I, Ia, II, or IIa, or a pharmaceutically acceptable salt thereof, each $R^{13}$ is independently oxo, —OH, halogen, —CN, $C_{1-4}$ alkyl, $C_{1-4}$ alkoxy, —$NR^6R^6$, —$C(O)R^{10}NR^6R^6$, —$C(O)NR^6R^6$, —$C(O)R^8$, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl,
wherein the $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with 1-3 $R^{14}$ groups, and
wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, each $R^{13}$ is independently oxo, —OH, halogen, —CN, $C_{1-4}$ alkyl, $C_{1-4}$ alkoxy, —$NR^6R^6$, —$C(O)R^{10}NR^6R^6$, —$C(O)NR^6R^6$, —$C(O)R^8$, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, or 8-10 membered fused bicyclic heteroaryl,
wherein the $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, and 8-10 membered fused bicyclic heteroaryl are each optionally substituted with 1-3 $R^{14}$ groups, and
wherein the 4-6 membered monocyclic heterocyclyl, 5-6 membered monocyclic heteroaryl, 8-10 membered fused or bridged bicyclic heterocyclyl, and 8-10 membered fused bicyclic heteroaryl each have 1-3 ring heteroatoms independently selected from N, O, and S.

In some embodiments of the compound of Formula I, Ia, II, or IIa, or a pharmaceutically acceptable salt thereof, each $R^{13}$ is independently oxo, —OH, halogen, —CN, $C_{1-4}$ alkyl, $C_{1-4}$ alkoxy, —$NR^6R^6$, —$C(O)R^{10}NR^6R^6$, —$C(O)NR^6R^6$, —$C(O)R^8$, $C_{6-10}$ monocyclic or fused bicyclic aryl, 4-6 membered monocyclic heterocyclyl, 5-6 membered monocyclic heteroaryl, 8-10 membered fused or bridged bicyclic heterocyclyl, or 8-10 membered fused bicyclic heteroaryl, wherein the $C_{6-10}$ monocyclic or fused bicyclic aryl is optionally substituted with 1-3 $R^{14}$ groups and wherein the 4-6 membered monocyclic heterocyclyl, 5-6 membered monocyclic heteroaryl, 8-10 membered fused or bridged bicyclic heterocyclyl, and 8-10 membered fused bicyclic heteroaryl each have 1-3 ring heteroatoms independently selected from N, O, and S.

In some embodiments of the compound of Formula I, Ia, II, or IIa, or a pharmaceutically acceptable salt thereof, each $R^{13}$ is independently oxo, —OH, halogen, methyl, ethyl, isopropyl, —$NR^6R^6$, —$C(O)R^{10}NR^6R^6$, —$C(O)NR^6R^6$, —$C(O)R^8$, phenyl, oxetanyl, 2,3-dihydrobenzo[b][1,4]dioxinyl, pyridinyl, pyrimidinyl, or 1H-benzo[d]imidazolyl, wherein the phenyl is optionally substituted with one $R^{14}$ group.

In some embodiments of the compound of Formula I, Ia, II, or IIa, or a pharmaceutically acceptable salt thereof, one or more $R^{13}$ is oxo. In some embodiments of the compound of Formula I, Ia, II, or IIa, or a pharmaceutically acceptable salt thereof, one or more $R^{13}$ is —OH. In some embodiments of the compound of Formula I, Ia, II, or IIa, or a pharmaceutically acceptable salt thereof, one or more $R^{13}$ is halogen. In some embodiments of the compound of Formula I, Ia, II, or IIa, or a pharmaceutically acceptable salt thereof, one or more $R^{13}$ is —CN. In some embodiments of the compound of Formula I, Ia, II, or IIa, or a pharmaceutically acceptable salt thereof, one or more $R^{13}$ is $C_{1-4}$ alkyl. In some embodiments of the compound of Formula I, Ia, II, or IIa, or a pharmaceutically acceptable salt thereof, one or more $R^{13}$ is $C_{1-4}$ alkoxy. In some embodiments of the compound of Formula I, Ia, II, or IIa, or a pharmaceutically acceptable salt thereof, one or more $R^{13}$ is —$NR^6R^6$. In some embodiments of the compound of Formula I, Ia, II, or IIa, or a pharmaceutically acceptable salt thereof, one or more $R^{13}$ is —$C(O)R^{10}NR^6R^6$. In some embodiments of the compound of Formula I, Ia, II, or IIa, or a pharmaceutically acceptable salt thereof, one or more $R^{13}$ is —$C(O)NR^6R^6$. In some embodiments of the compound of Formula I, Ia, II, or IIa, or a pharmaceutically acceptable salt thereof, one or more $R^{13}$ is —$C(O)R^8$.

In some embodiments of the compound of Formula I, Ia, II, or IIa, or a pharmaceutically acceptable salt thereof, one or more $R^{13}$ is $C_{6-10}$ monocyclic or fused bicyclic aryl, wherein the $C_{6-10}$ monocyclic or fused bicyclic aryl is optionally substituted with 1-3 $R^{14}$ groups. In some embodiments of the compound of Formula I, Ia, II, or IIa, or a pharmaceutically acceptable salt thereof, one or more $R^{13}$ is $C_{6-10}$ monocyclic or fused bicyclic aryl, wherein the $C_{6-10}$ monocyclic or fused bicyclic aryl is substituted with 1-3 $R^{14}$ groups. In some embodiments of the compound of Formula I, Ia, II, or IIa, or a pharmaceutically acceptable salt thereof, one or more $R^{13}$ is $C_{6-10}$ monocyclic or fused bicyclic aryl.

In some embodiments of the compound of Formula I, Ia, II, or IIa, or a pharmaceutically acceptable salt thereof, one or more $R^{13}$ is 4-6 membered monocyclic heterocyclyl, wherein the 4-6 membered monocyclic heterocyclyl has 1-3 ring heteroatoms independently selected from N, O, and S and is optionally substituted with 1-3 $R^{14}$ groups. In some embodiments of the compound of Formula I, Ia, II, or IIa, or a pharmaceutically acceptable salt thereof, one or more $R^{13}$ is 4-6 membered monocyclic heterocyclyl, wherein the 4-6 membered monocyclic heterocyclyl has 1-3 ring heteroatoms independently selected from N, O, and S and is substituted with 1-3 $R^{14}$ groups. In some embodiments of the compound of Formula I, Ia, II, or IIa, or a pharmaceutically acceptable salt thereof, one or more $R^{13}$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, one or more $R^{13}$ is 5-6 membered monocyclic heteroaryl, wherein the 5-6 membered monocyclic heteroaryl has 1-3 ring heteroatoms independently selected from N, O, and S and is optionally substituted with 1-3 $R^{14}$ groups. In some embodiments of the compound of Formula I, Ia, II, or IIa, or a pharmaceutically acceptable salt thereof, one or more $R^{13}$ is 5-6 membered monocyclic heteroaryl, wherein the 5-6 membered monocyclic heteroaryl has 1-3 ring heteroatoms independently selected from N, O, and S and is substituted with 1-3 $R^{14}$ groups. In some embodiments of the compound of Formula I, Ia, II, or IIa, or a pharmaceutically acceptable salt thereof, one or more $R^{13}$ is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, one or more $R^{13}$ is 8-10 membered fused or bridged bicyclic heterocyclyl, wherein the 8-10 membered fused or bridged bicyclic heterocyclyl has 1-3 ring heteroatoms independently selected from N, O, and S and is optionally substituted with 1-3 $R^{14}$ groups. In some embodiments of the compound of Formula I, Ia, II, or IIa, or a pharmaceutically acceptable salt thereof, one or more $R^{13}$ is 8-10 membered fused or bridged bicyclic heterocyclyl, wherein the 8-10 membered fused or bridged bicyclic heterocyclyl has 1-3 ring heteroatoms independently selected from N, O, and S and is substituted with 1-3 $R^{14}$ groups. In some embodiments of the compound of Formula I, Ia, II, or IIa, or a pharmaceutically acceptable salt thereof, one or more $R^{13}$ is 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, one or more $R^{13}$ is 8-10 membered fused bicyclic heteroaryl, wherein the 8-10 membered fused bicyclic heteroaryl has 1-3 ring heteroatoms independently selected from N, O, and S and is optionally substituted with 1-3 $R^{14}$ groups. In some embodiments of the compound of Formula I, Ia, II, or IIa, or a pharmaceutically acceptable salt thereof, one or more $R^{13}$ is 8-10 membered fused bicyclic heteroaryl, wherein the 8-10 membered fused bicyclic heteroaryl has 1-3 ring heteroatoms independently selected from N, O, and S and is substituted with 1-3 $R^{14}$ groups. In some embodiments of the compound of Formula I, Ia, II, or IIa, or a pharmaceutically acceptable salt thereof, one or more $R^{13}$ is 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, one or more $R^{13}$ is 7-10 membered spirocyclic heterocyclyl, wherein the 7-10 membered spirocyclic heterocyclyl has 1-3 ring heteroatoms independently selected from N, O, and S and is optionally substituted with 1-3 $R^{14}$ groups. In some embodiments of the compound of Formula I, Ia, II, or IIa, or a pharmaceutically acceptable salt thereof, one or more $R^{13}$ is 7-10 membered spirocyclic heterocyclyl, wherein the 7-10 membered spirocyclic heterocyclyl has 1-3 ring heteroatoms independently selected from N, O, and S and is substituted with 1-3 $R^{14}$ groups. In some embodiments of the compound of Formula I, Ia, II, or IIa, or a pharmaceutically acceptable salt thereof, one or more $R^{13}$ is 7-10 membered spirocyclic heterocyclyl having 1-3 ring heteroatoms independently selected from N, O, and S.

In some embodiments of the compound of Formula I, Ia, II, or IIa, or a pharmaceutically acceptable salt thereof, each $R^{14}$ is independently halogen, $C_{1-4}$ alkyl, —$C(O)R^8$, 4-6 membered monocyclic heterocyclyl, 5-6 membered monocyclic heteroaryl, 8-10 membered fused or bridged bicyclic heterocyclyl, 8-10 membered fused bicyclic heteroaryl, or 7-10 membered spirocyclic heterocyclyl,
  wherein the $C_{1-4}$ alkyl is optionally substituted with 1-3 groups independently selected from —OH, halogen, CN, and $C_{1-4}$ alkoxy, and
  wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl are each optionally substituted with $C_{1-3}$ alkyl, wherein the $C_{1-3}$ alkyl is optionally substituted with —$OR^{10}Si(R^{15})_3$;
  wherein the 4-6 membered monocyclic heterocyclyl, 5-6 membered monocyclic heteroaryl, 8-10 membered fused or bridged bicyclic heterocyclyl, 8-10 membered fused bicyclic heteroaryl, and 7-10 membered spirocyclic heterocyclyl each have 1-3 ring heteroatoms independently selected from N, O, and S.

In some embodiments of the compound of Formula I, Ia, II, or IIa, or a pharmaceutically acceptable salt thereof, each $R^{14}$ is independently halogen, $C_{1-4}$ alkyl, —C(O)$R^8$, or 5-6 membered monocyclic heteroaryl having 1-3 ring heteroatoms independently selected from N, O, and S, wherein the $C_{1-4}$ alkyl is optionally substituted with 1-3 groups independently selected from —OH, halogen, CN, and $C_{1-4}$ alkoxy, and wherein 5-6 membered monocyclic heteroaryl having 1-3 ring heteroatoms independently selected from N, O, and S is optionally substituted with $C_{1-3}$ alkyl, wherein the $C_{1-3}$ alkyl is optionally substituted with —OR$^{10}$Si(R$^{15}$)$_3$.

In some embodiments of the compound of Formula I, Ia, II, or IIa, or a pharmaceutically acceptable salt thereof, each $R^{14}$ is independently halogen, $C_{1-4}$ alkyl, or 5-6 membered monocyclic heteroaryl, wherein the $C_{1-4}$ alkyl is optionally substituted with 1-3 halogens, and wherein the 5-6 membered heteroaryl is optionally substituted with —CH$_2$OCH$_2$CH$_2$Si(CH$_3$)$_3$ and has 1-3 ring heteroatoms independently selected from N, O, and S.

In some embodiments of the compound of Formula I, Ia, II, or IIa, or a pharmaceutically acceptable salt thereof, each $R^{14}$ is independently halogen, $C_{1-4}$ alkyl, or imidazolyl, wherein the $C_{1-4}$ alkyl is optionally substituted with 1-3 halogens, and wherein the imidazolyl is optionally substituted with —CH$_2$OCH$_2$CH$_2$Si(CH$_3$)$_3$.

In some embodiments of the compound of Formula I, Ia, II, or IIa, or a pharmaceutically acceptable salt thereof, one or more $R^{14}$ is halogen. In some embodiments of the compound of Formula I, Ia, II, or IIa, or a pharmaceutically acceptable salt thereof, one or more $R^{14}$ is —C(O)$R^8$.

In some embodiments of the compound of Formula I, Ia, II, or IIa, or a pharmaceutically acceptable salt thereof, one or more $R^{14}$ is $C_{1-4}$ alkyl, wherein the $C_{1-4}$ alkyl is optionally substituted with 1-3 groups independently selected from —OH, halogen, CN, and $C_{1-4}$ alkoxy. In some embodiments of the compound of Formula I, Ia, II, or IIa, or a pharmaceutically acceptable salt thereof, one or more $R^{14}$ is $C_{1-4}$ alkyl, wherein the $C_{1-4}$ alkyl is substituted with 1-3 groups independently selected from —OH, halogen, CN, and $C_{1-4}$ alkoxy.

In some embodiments of the compound of Formula I, Ia, II, or IIa, or a pharmaceutically acceptable salt thereof, one or more $R^{14}$ is $C_{1-4}$ alkyl, wherein the $C_{1-4}$ alkyl is optionally substituted with 1-3 halogens. In some embodiments of the compound of Formula I, Ia, II, or IIa, or a pharmaceutically acceptable salt thereof, one or more $R^{14}$ is $C_{1-4}$ alkyl, wherein the $C_{1-4}$ alkyl is substituted with 1-3 halogens.

In some embodiments of the compound of Formula I, Ia, II, or IIa, or a pharmaceutically acceptable salt thereof, one or more $R^{14}$ is $C_{1-4}$ alkyl.

In some embodiments of the compound of Formula I, Ia, II, or IIa, or a pharmaceutically acceptable salt thereof, one or more $R^{14}$ is 4-6 membered monocyclic heterocyclyl, wherein the 4-6 membered monocyclic heterocyclyl has 1-3 ring heteroatoms independently selected from N, O, and S and is optionally substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 4-6 membered monocyclic heterocyclyl, wherein the 4-6 membered monocyclic heterocyclyl has 1-3 ring heteroatoms independently selected from N, O, and S and is substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 4-6 membered monocyclic heterocyclyl having 1-3 ring heteroatoms independently selected from N, O, and S.

In some embodiments of the compound of Formula I, Ia, II, or IIa, or a pharmaceutically acceptable salt thereof, one or more $R^{14}$ is 5-6 membered monocyclic heteroaryl, wherein the 5-6 membered monocyclic heteroaryl has 1-3 ring heteroatoms independently selected from N, O, and S and is optionally substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 5-6 membered monocyclic heteroaryl, wherein the 5-6 membered monocyclic heteroaryl has 1-3 ring heteroatoms independently selected from N, O, and S and is substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 5-6 membered monocyclic heteroaryl having 1-3 ring heteroatoms independently selected from N, O, and S.

In some embodiments of the compound of Formula I, Ia, II, or IIa, or a pharmaceutically acceptable salt thereof, one or more $R^{14}$ is imidazolyl, wherein the imidazolyl is optionally substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is imidazolyl, wherein the imidazolyl is substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is imidazolyl, wherein the imidazolyl is optionally substituted with —CH$_2$OCH$_2$CH$_2$Si(CH$_3$)$_3$. In some embodiments of the compound of Formula I, Ia, II, or IIa, or a pharmaceutically acceptable salt thereof, one or more $R^{14}$ is imidazolyl.

In some embodiments of the compound of Formula I, Ia, II, or IIa, or a pharmaceutically acceptable salt thereof, one or more $R^{14}$ is 8-10 membered fused or bridged bicyclic heterocyclyl, wherein the 8-10 membered fused or bridged bicyclic heterocyclyl has 1-3 ring heteroatoms independently selected from N, O, and S and is optionally substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 8-10 membered fused or bridged bicyclic heterocyclyl, wherein the 8-10 membered fused or bridged bicyclic heterocyclyl has 1-3 ring heteroatoms independently selected from N, O, and S and is substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 8-10 membered fused or bridged bicyclic heterocyclyl having 1-3 ring heteroatoms independently selected from N, O, and S.

In some embodiments of the compound of Formula I, Ia, II, or IIa, or a pharmaceutically acceptable salt thereof, one or more $R^{14}$ is 8-10 membered fused bicyclic heteroaryl, wherein the 8-10 membered fused bicyclic heteroaryl has 1-3 ring heteroatoms independently selected from N, O, and S and is optionally substituted with $C_{1-3}$ alkyl, wherein the $C_{1-3}$ alkyl is optionally substituted with —OR$^{10}$Si(R$^{15}$)$_3$. In some embodiments of the compound of Formula I, Ia, II, or IIa, or a pharmaceutically acceptable salt thereof, one or more $R^{14}$ is 8-10 membered fused bicyclic heteroaryl, wherein the 8-10 membered fused bicyclic heteroaryl has 1-3 ring heteroatoms independently selected from N, O, and S and is substituted with $C_{1-3}$ alkyl, wherein the $C_{1-3}$ alkyl is optionally substituted with —$OR^{10}Si(R^{15})_3$. In some embodiments of the compound of Formula I, Ia, II, or IIa, or a pharmaceutically acceptable salt thereof, one or more $R^{14}$ is 8-10 membered fused bicyclic heteroaryl having 1-3 ring heteroatoms independently selected from N, O, and S.

In some embodiments of the compound of Formula I, Ia, II, or IIa, or a pharmaceutically acceptable salt thereof, one or more $R^{14}$ is 7-10 membered spirocyclic heterocyclyl, wherein the 7-10 membered spirocyclic heterocyclyl has 1-3 ring heteroatoms independently selected from N, O, and S and is optionally substituted with $C_{1-3}$ alkyl, wherein the $C_{1-3}$ alkyl is optionally substituted with —$OR^{10}Si(R^{15})_3$. In some embodiments of the compound of Formula I, Ia, II, or IIa, or a pharmaceutically acceptable salt thereof, one or more $R^{14}$ is 7-10 membered spirocyclic heterocyclyl, wherein the 7-10 membered spirocyclic heterocyclyl has 1-3 ring heteroatoms independently selected from N, O, and S and is substituted with $C_{1-3}$ alkyl, wherein the $C_{1-3}$ alkyl is optionally substituted with —$OR^{10}Si(R^{15})_3$. In some embodiments of the compound of Formula I, Ia, II, or IIa, or a pharmaceutically acceptable salt thereof, one or more $R^{14}$ is 7-10 membered spirocyclic heterocyclyl having 1-3 ring heteroatoms independently selected from N, O, and S.

In some embodiments of the compound of Formula I, Ia, II, or IIa, or a pharmaceutically acceptable salt thereof, each $R^{15}$ is independently $C_{1-3}$ alkyl, which may be the same or different. In some embodiments of the compound of Formula I, Ia, II, or IIa, or a pharmaceutically acceptable salt thereof, one or more $R^{15}$ is methyl. In some embodiments of the compound of Formula I, Ia, II, or IIa, or a pharmaceutically acceptable salt thereof, one or more $R^{15}$ is ethyl. In some embodiments of the compound of Formula I, Ia, II, or IIa, or a pharmaceutically acceptable salt thereof, one or more $R^{15}$ is propyl. In some embodiments of the compound of Formula I, Ia, II, or IIa, or a pharmaceutically acceptable salt thereof, one or more $R^{15}$ is isopropyl.

In some embodiments of the compound of Formula I, Ia, II, or IIa, the compound is selected from the group consisting of:

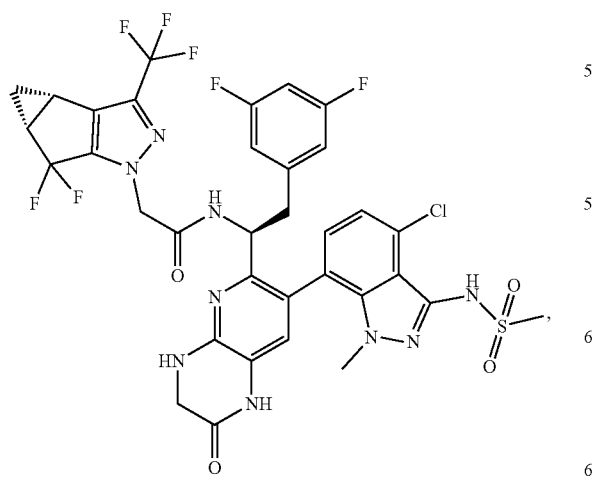

-continued

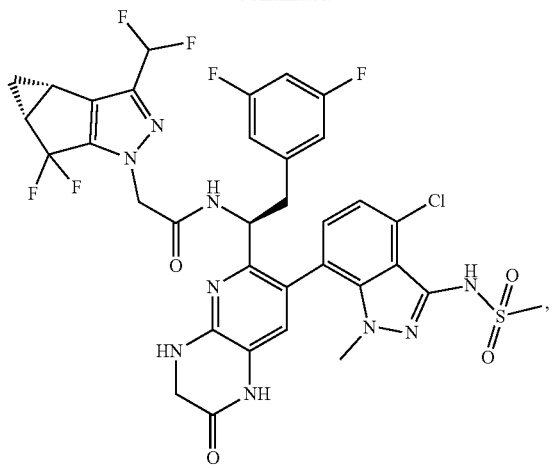

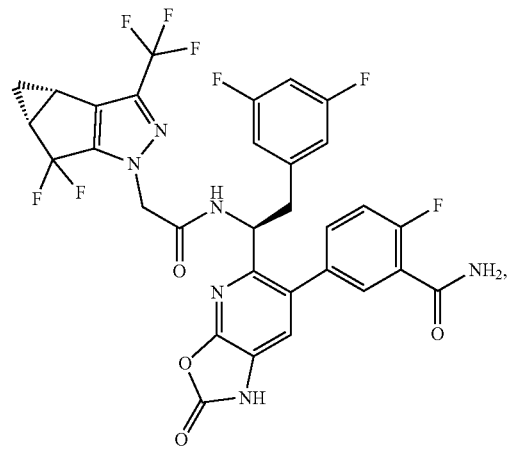

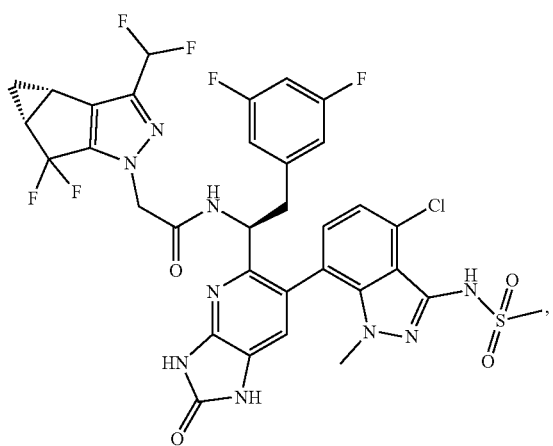

103
-continued
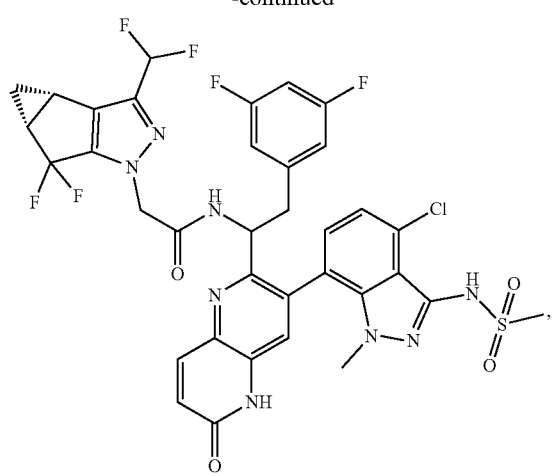
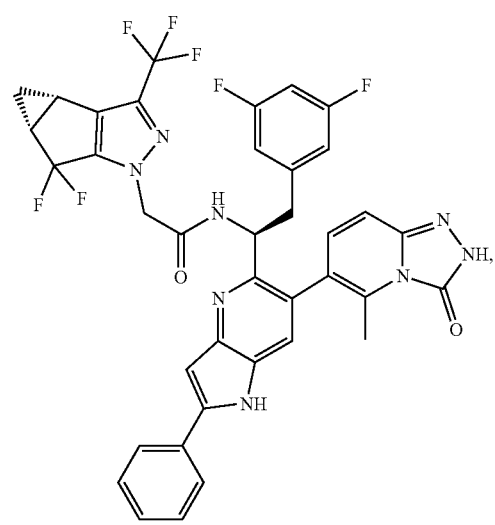
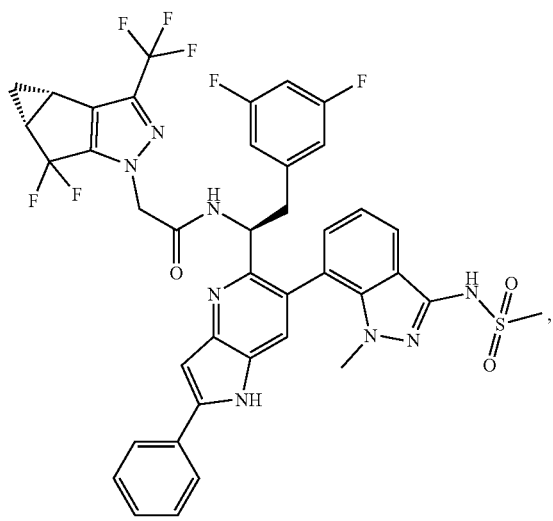
104
-continued
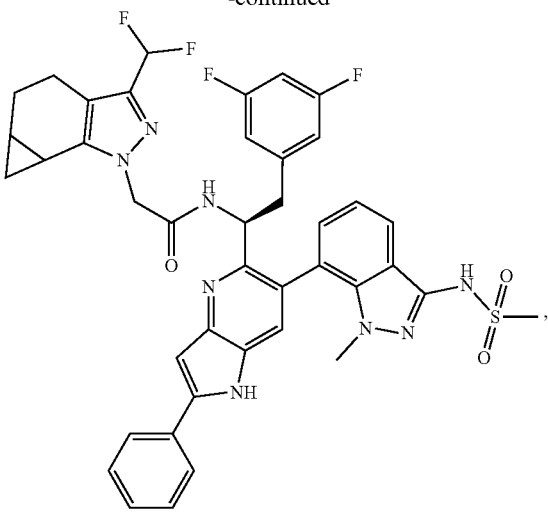
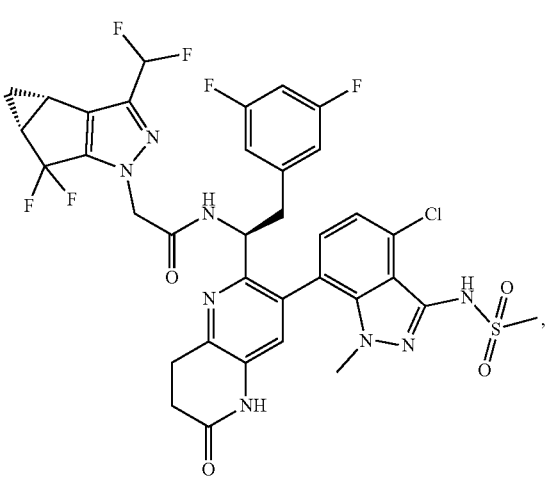
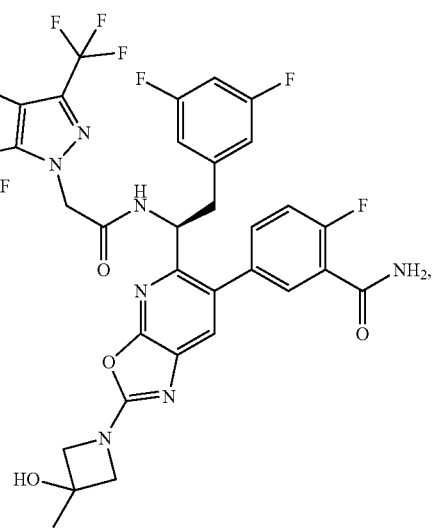

105
-continued
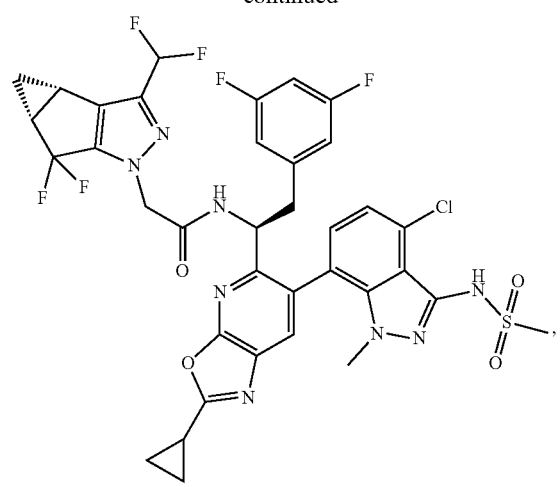
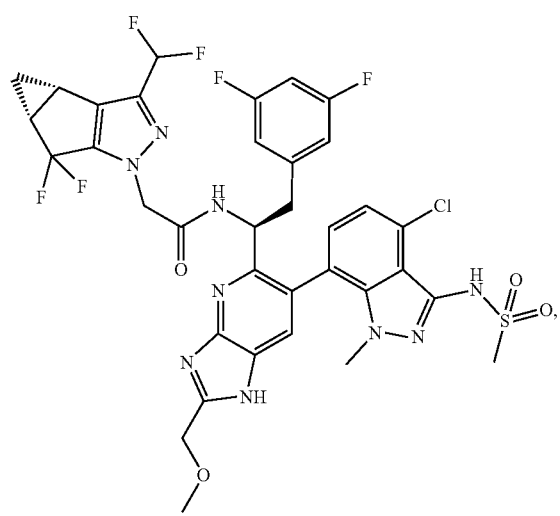
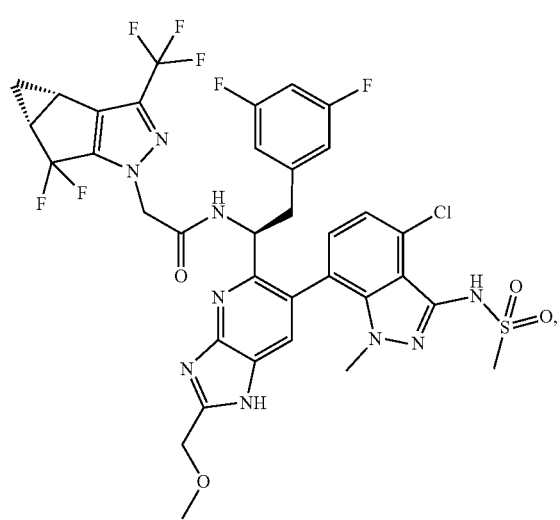
106
-continued
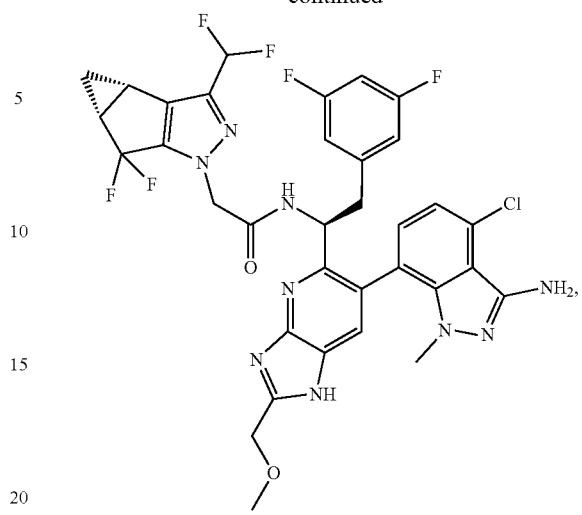
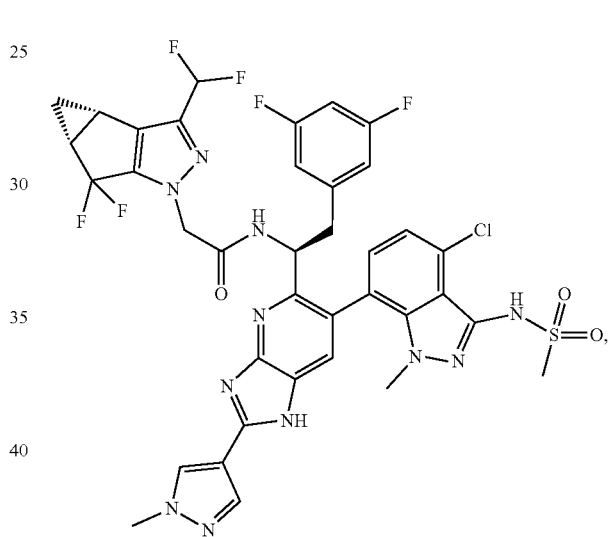
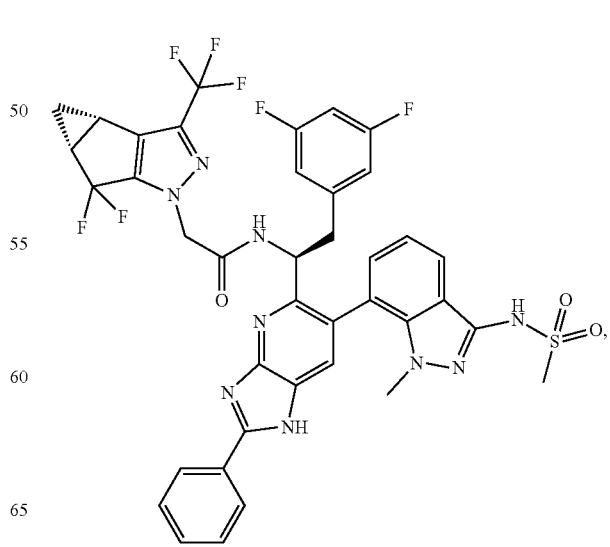

107
-continued
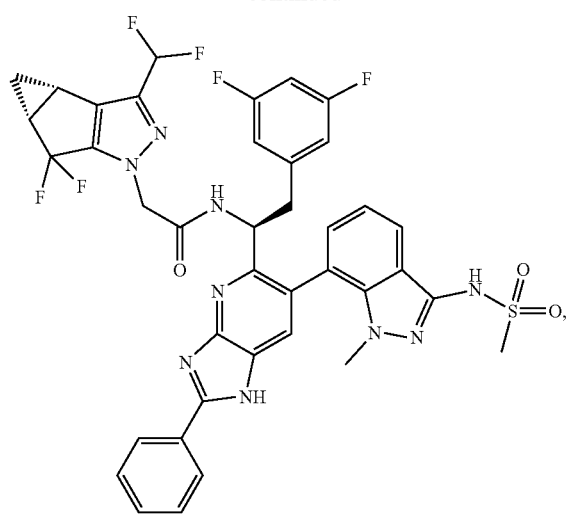
108
-continued
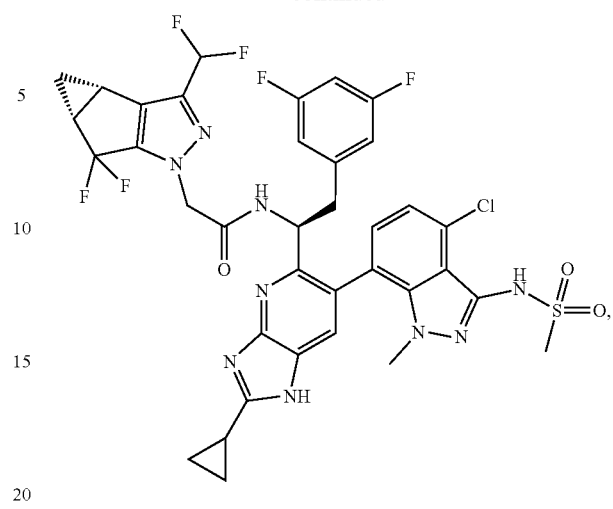
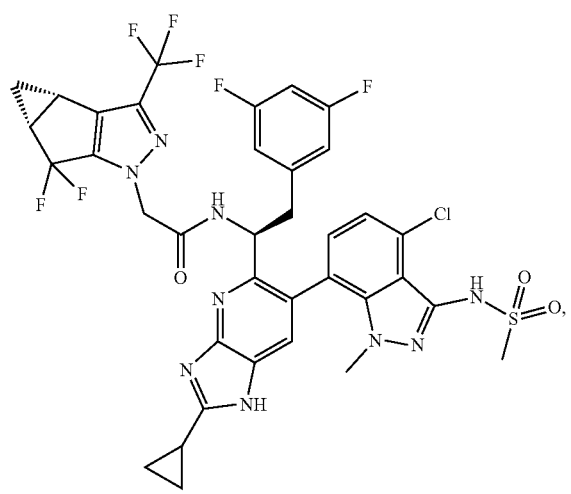
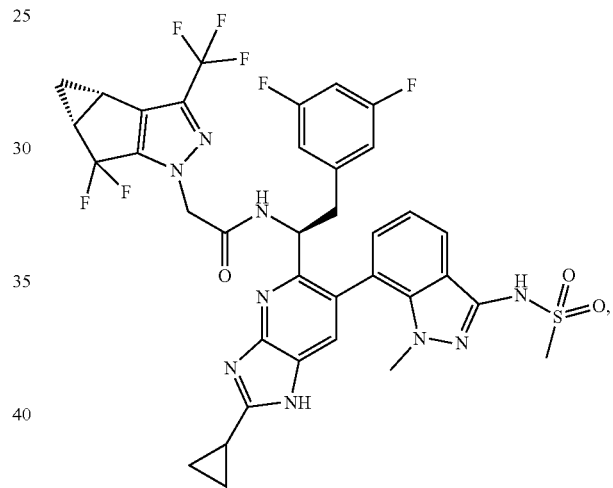
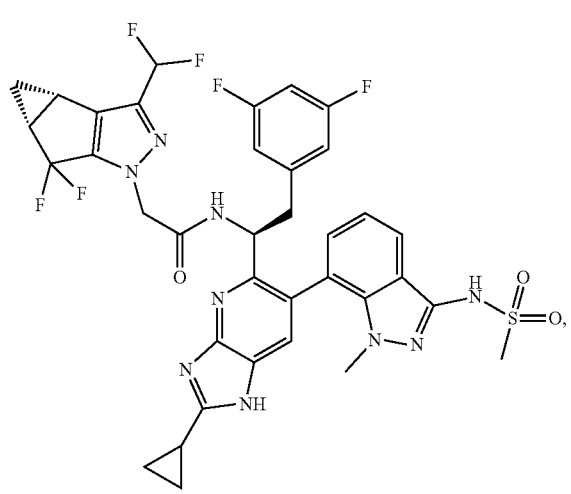
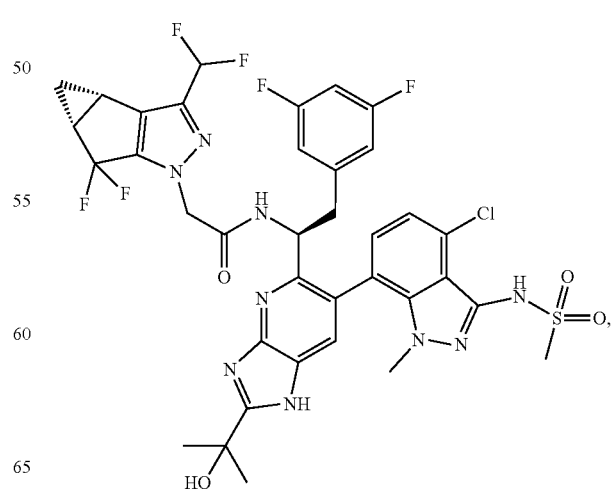

109
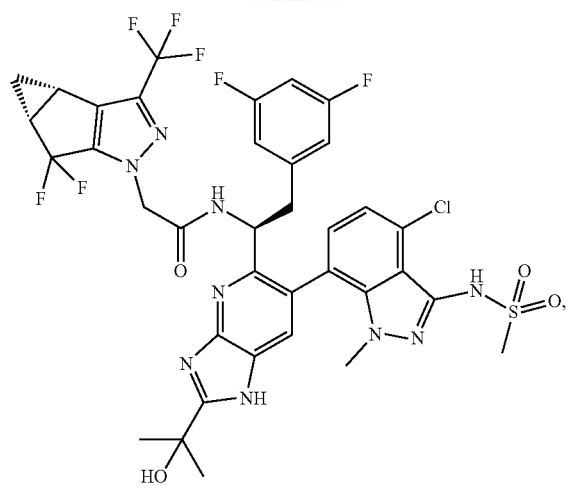
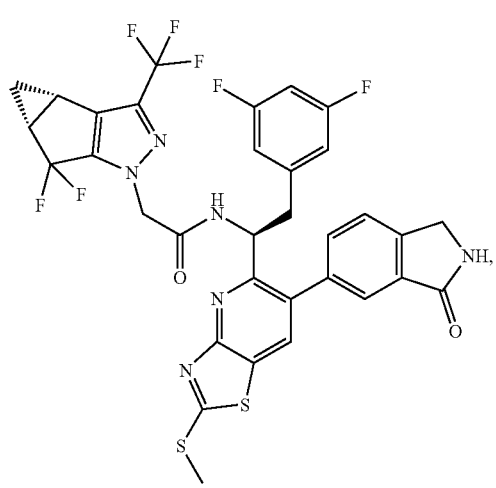
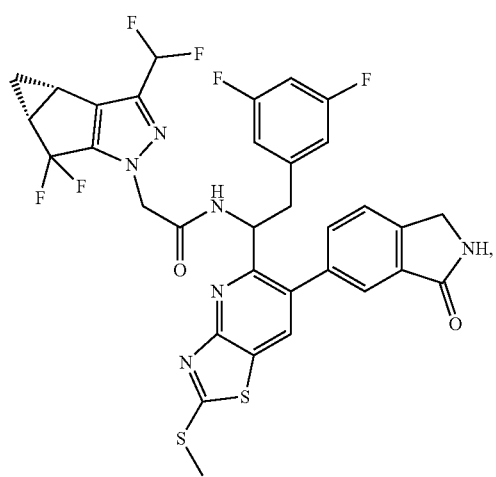
110
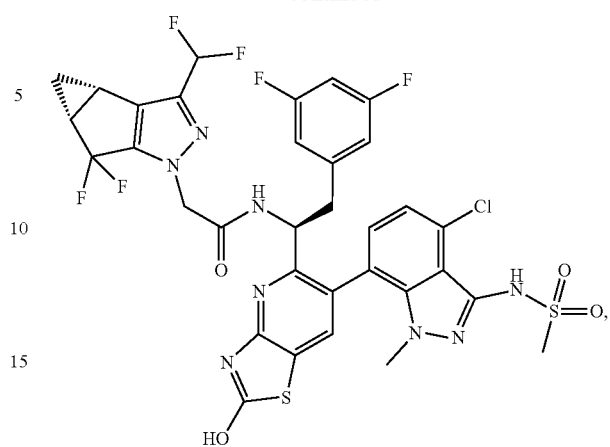
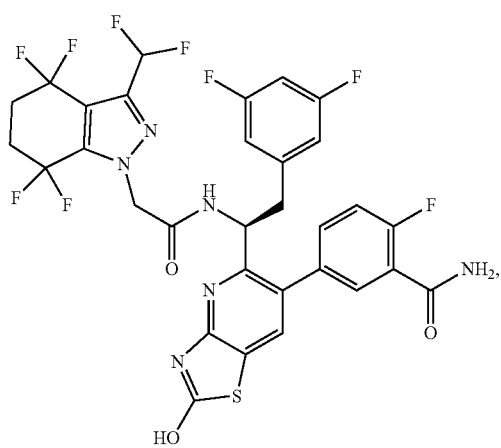

111
-continued
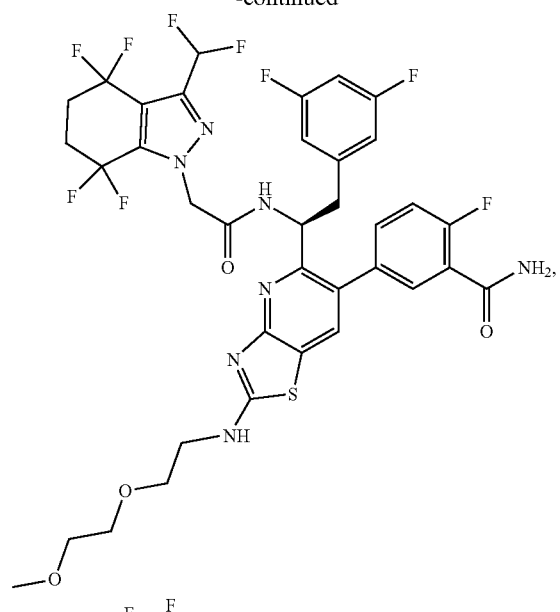
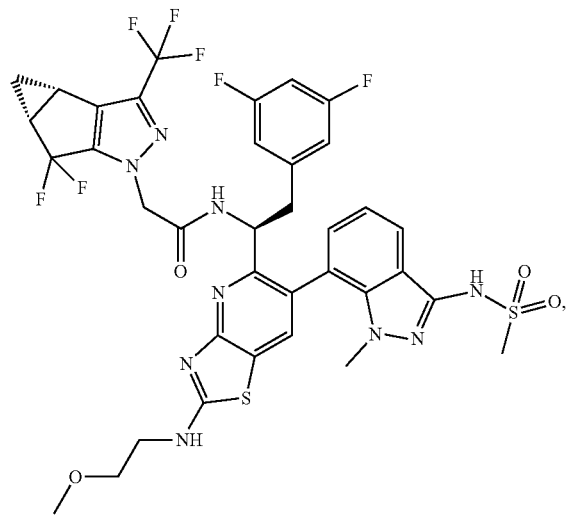
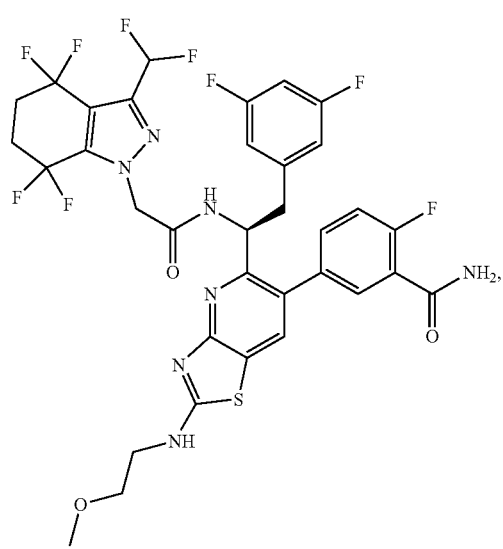
112
-continued
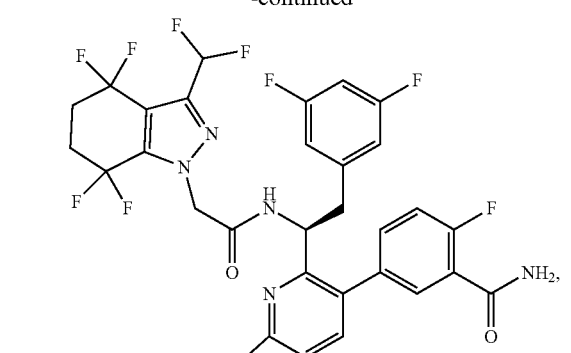
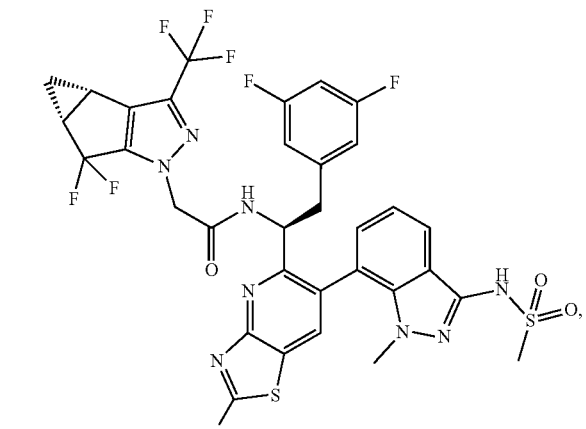
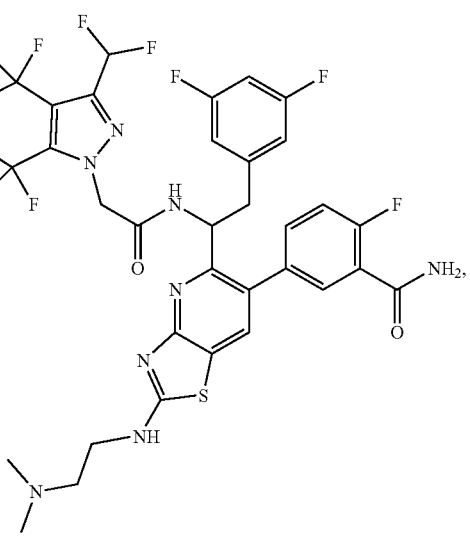

113
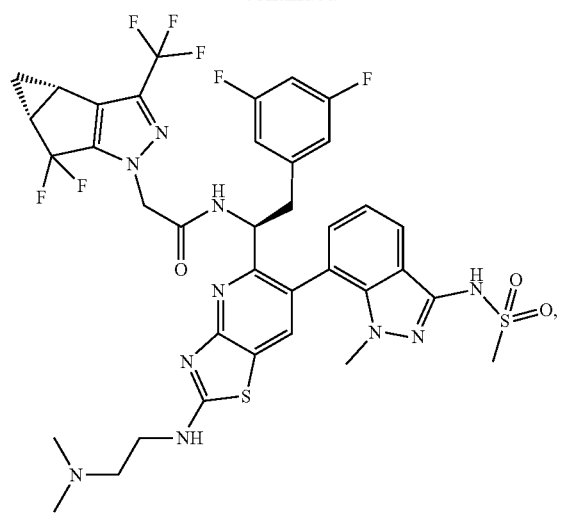
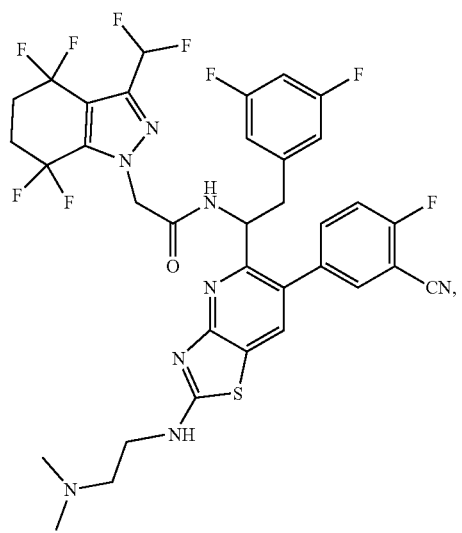
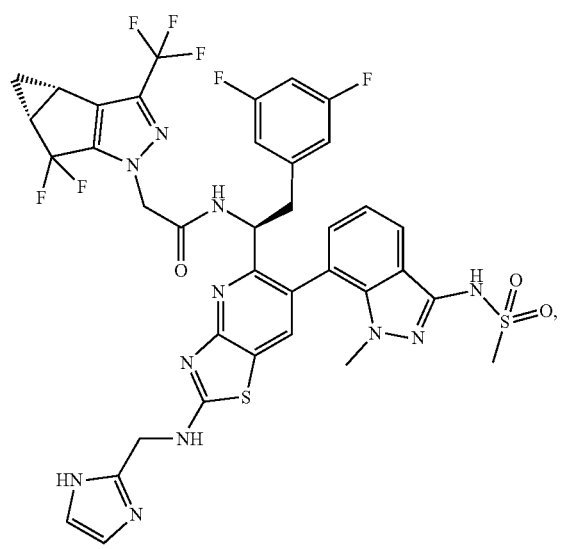
114
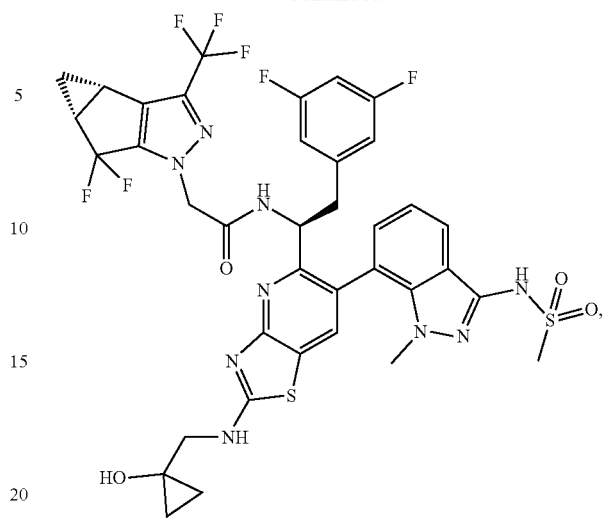
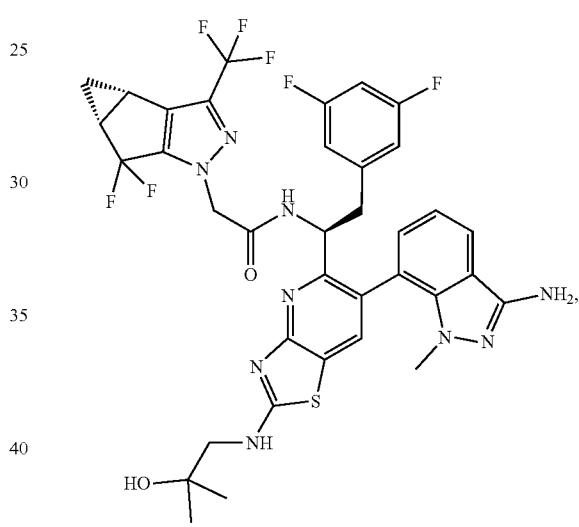
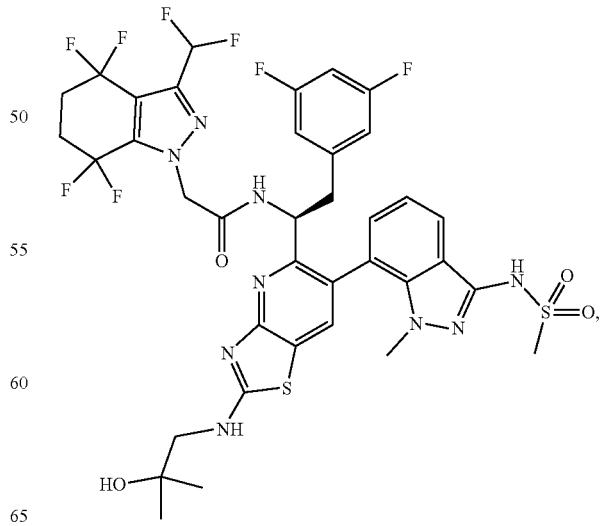

115
-continued
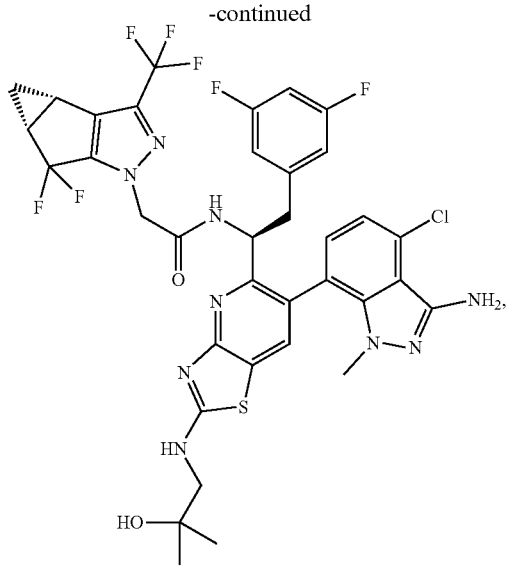
116
-continued
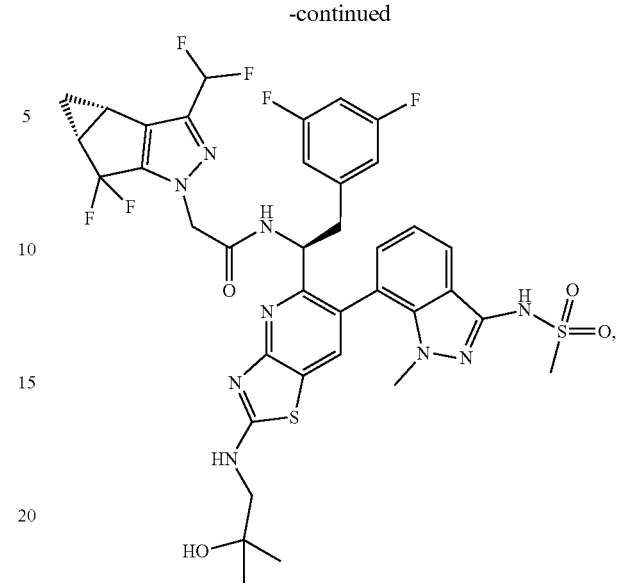
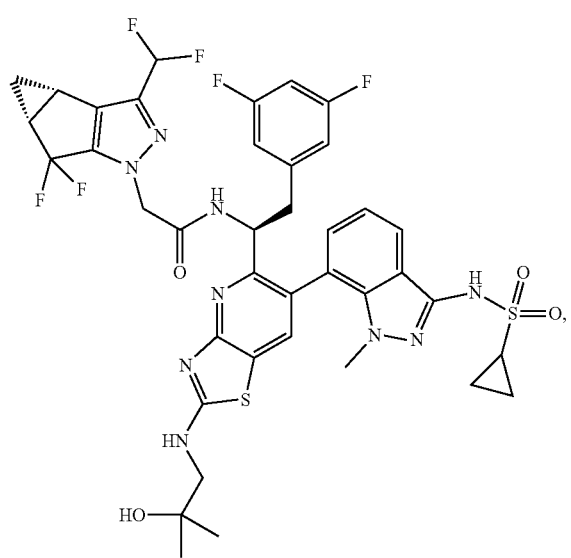
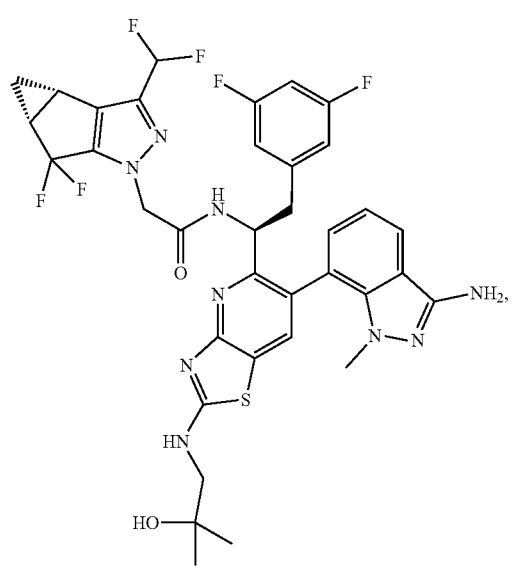
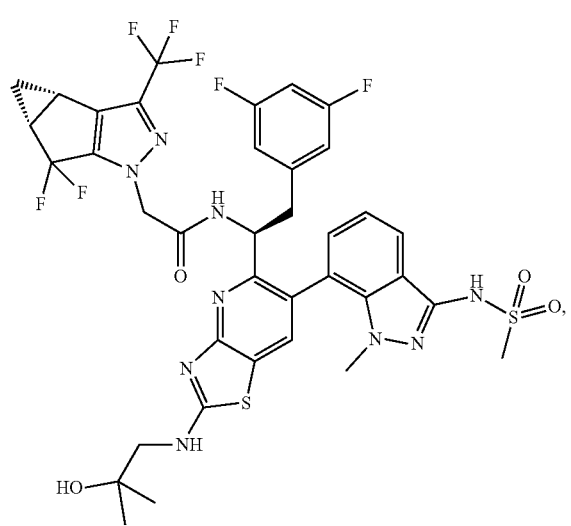
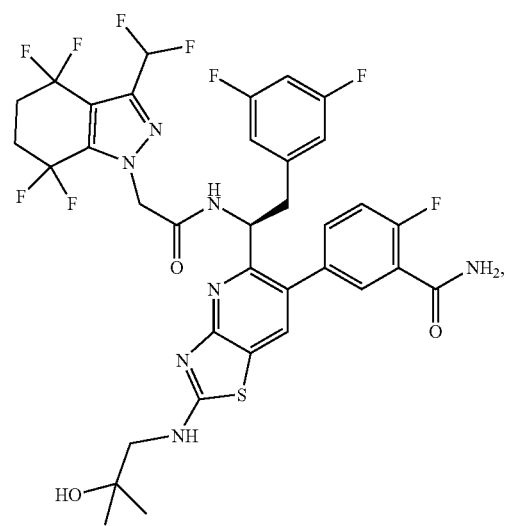

117
-continued
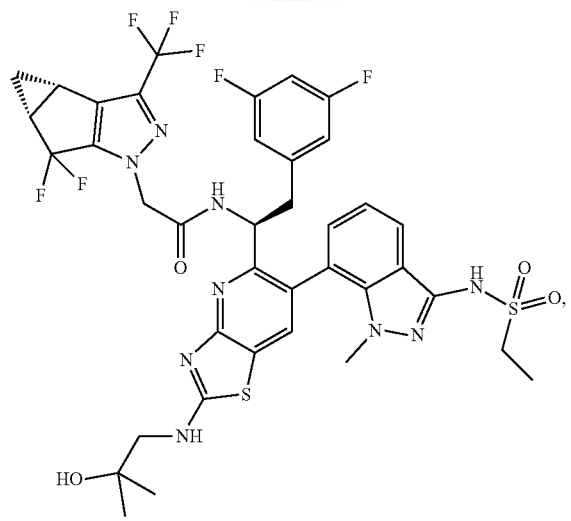
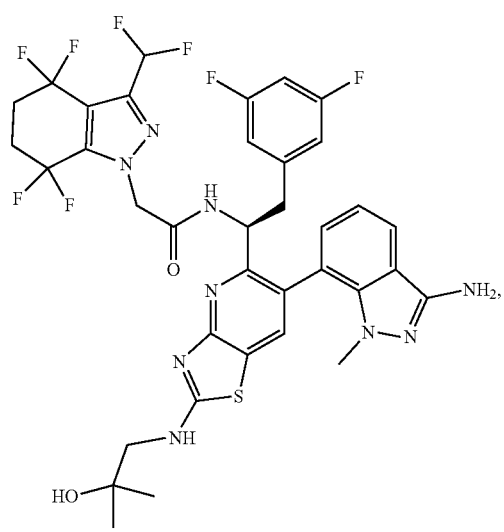
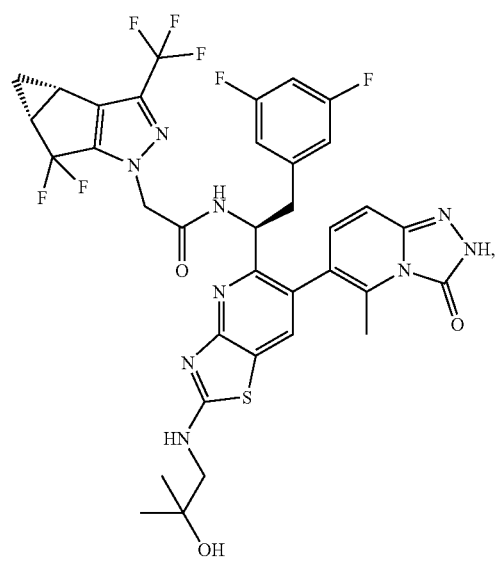
118
-continued
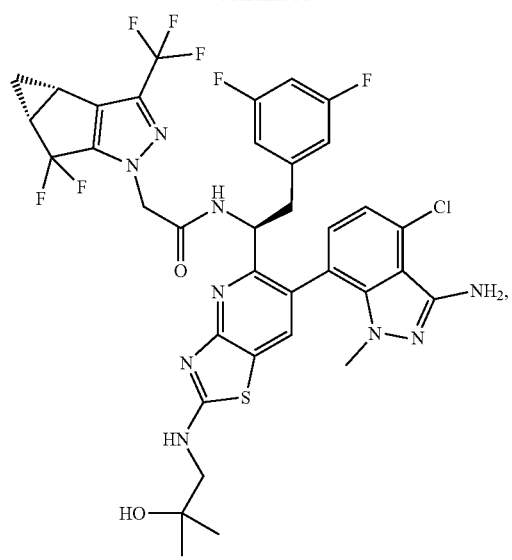
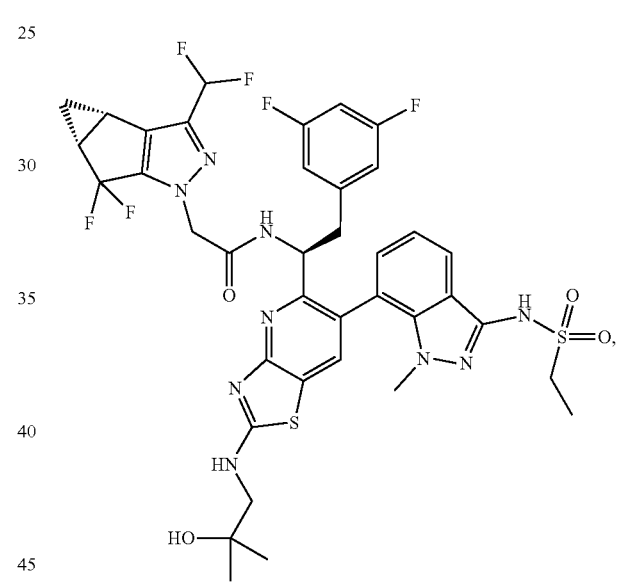
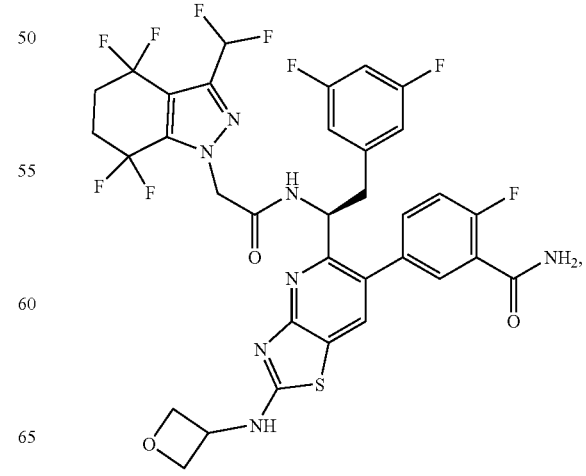

119
-continued
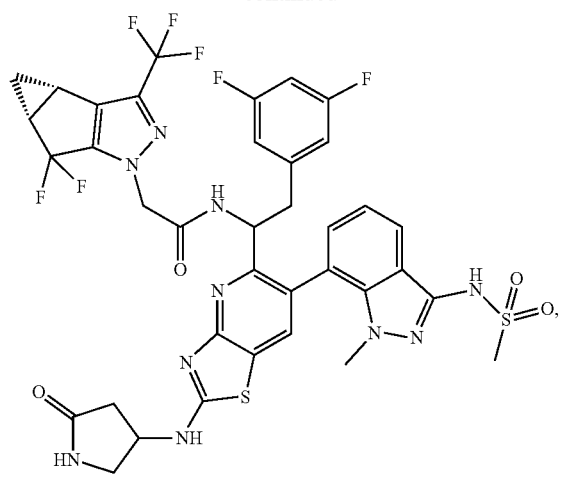
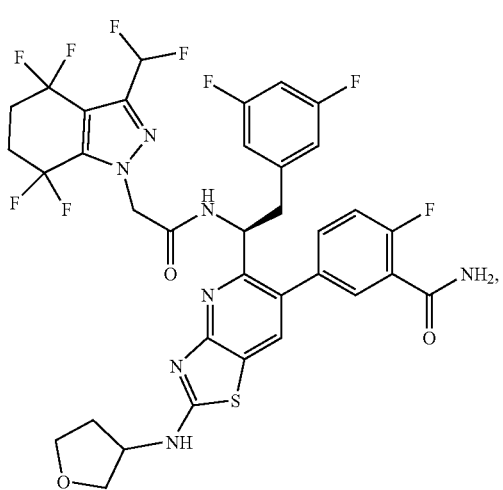
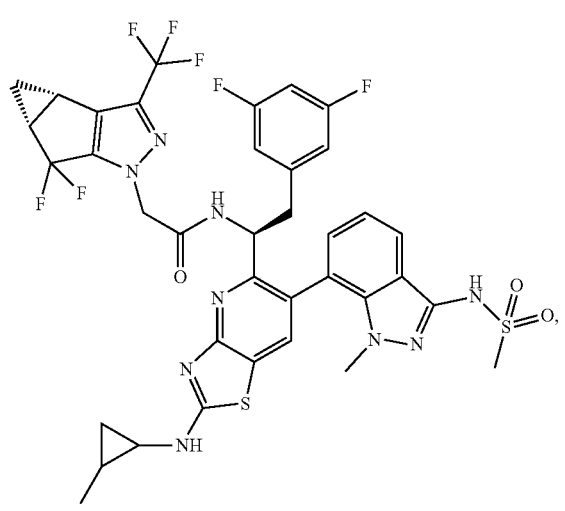
120
-continued
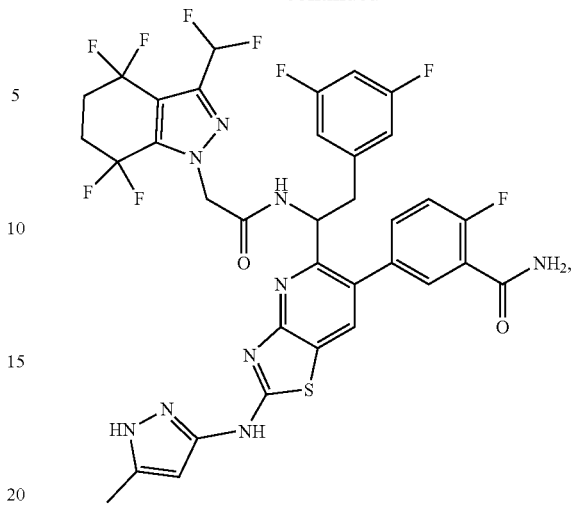
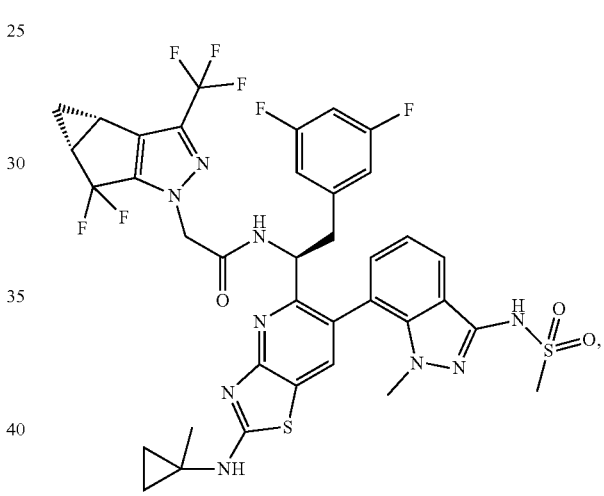
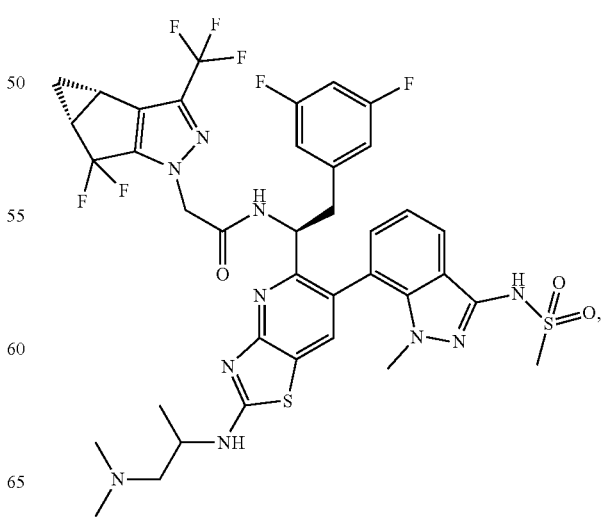

121
-continued
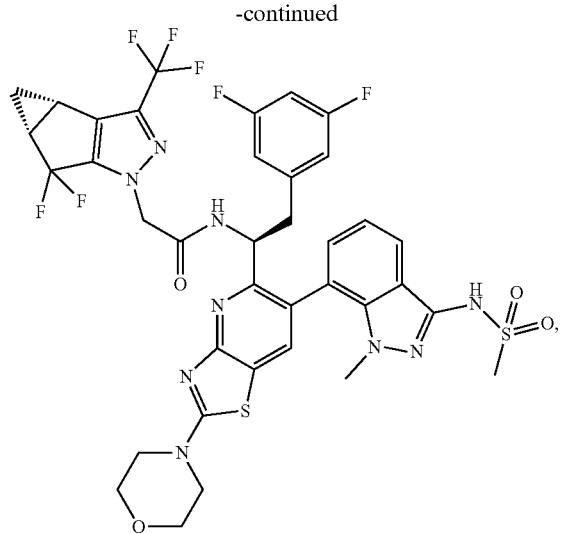
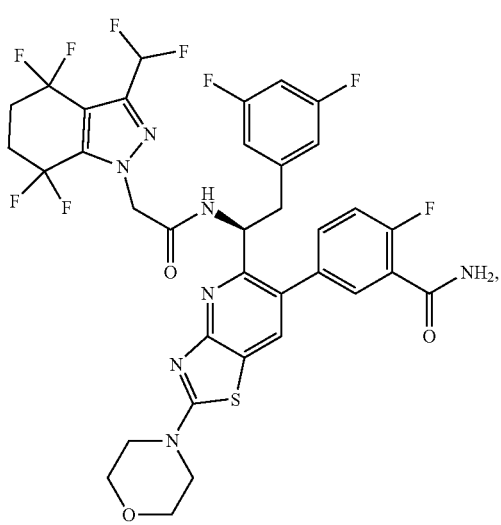
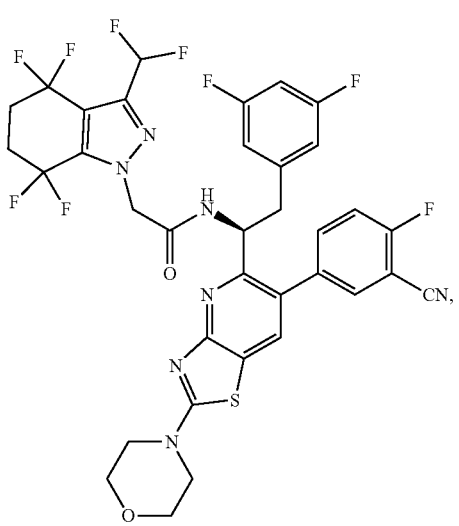
122
-continued
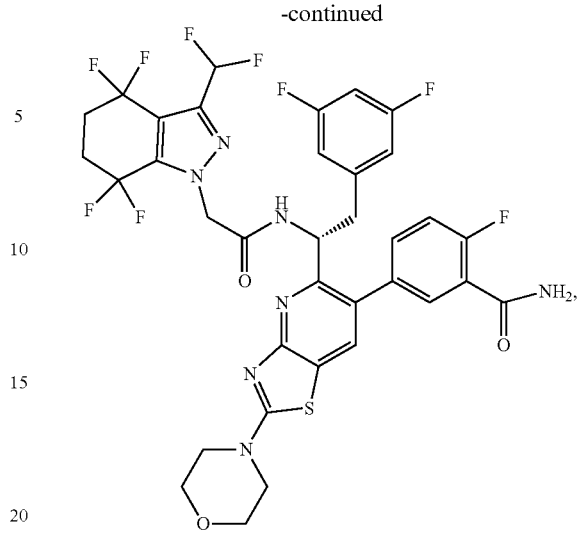
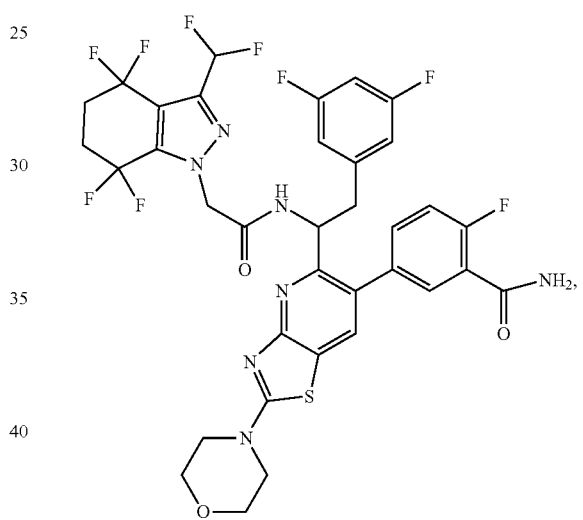
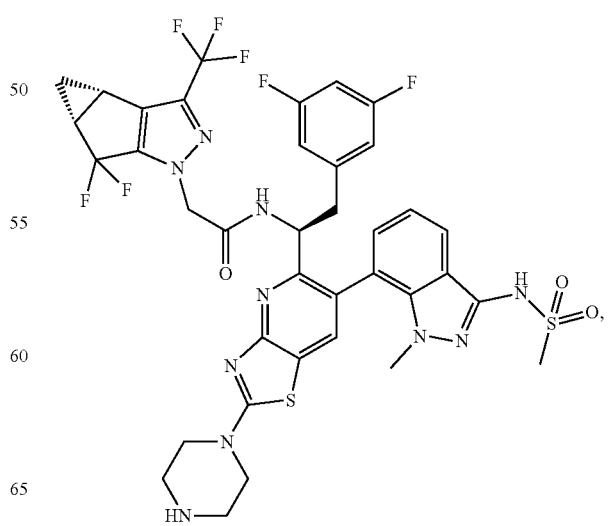

123
-continued
124
-continued
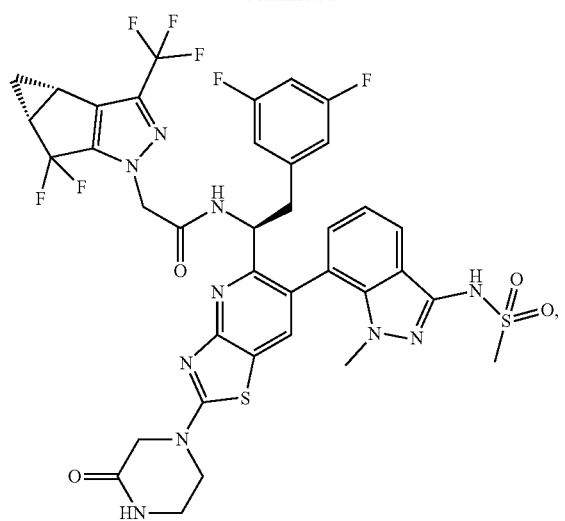
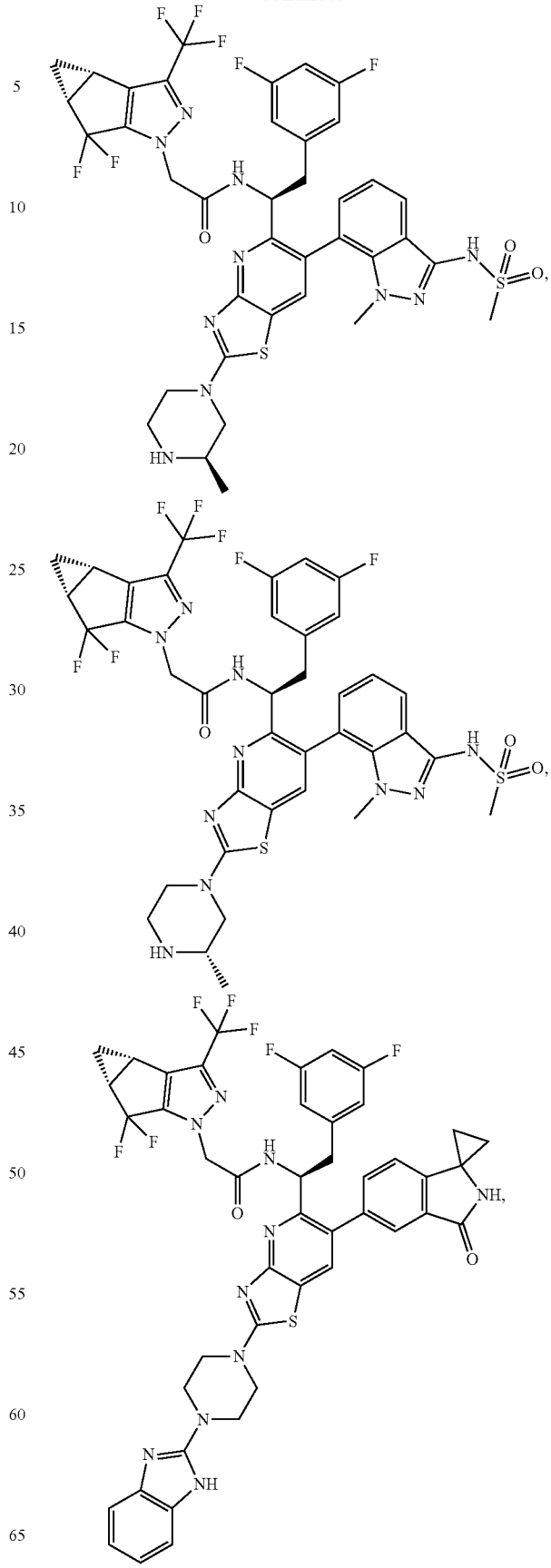

125
-continued
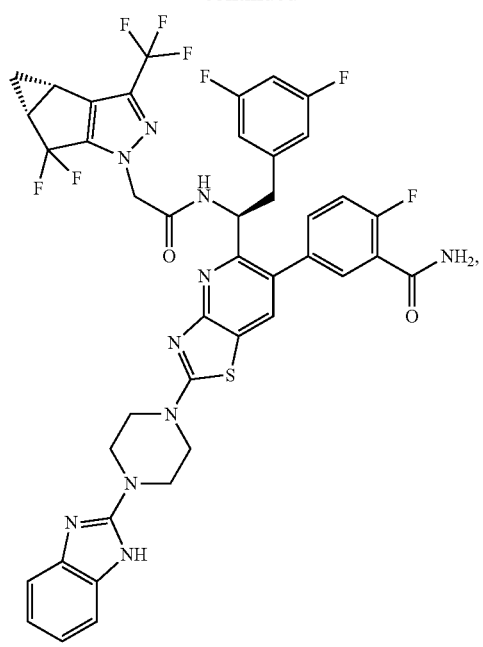
126
-continued
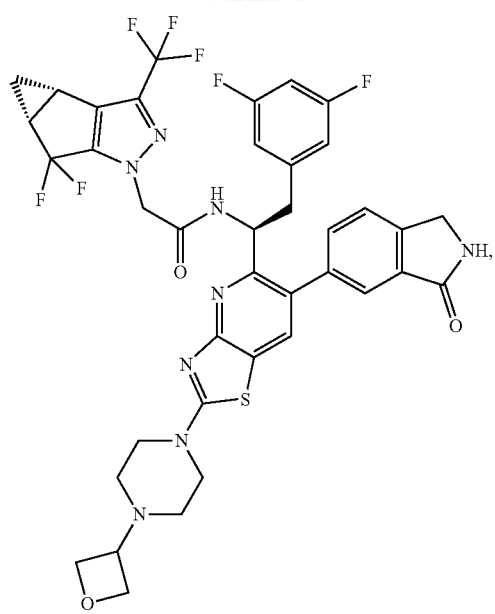
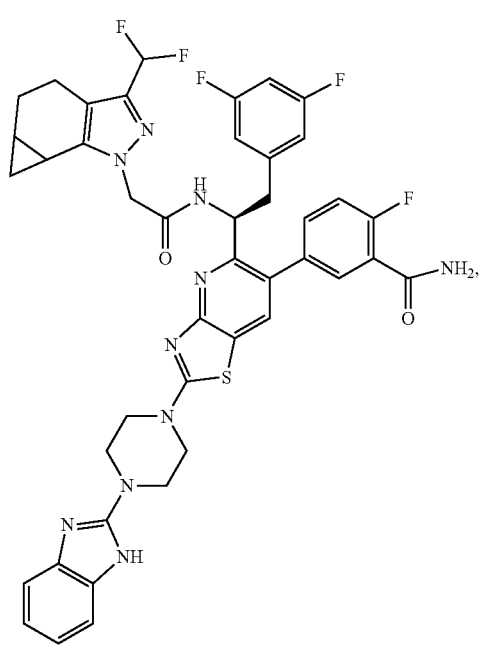
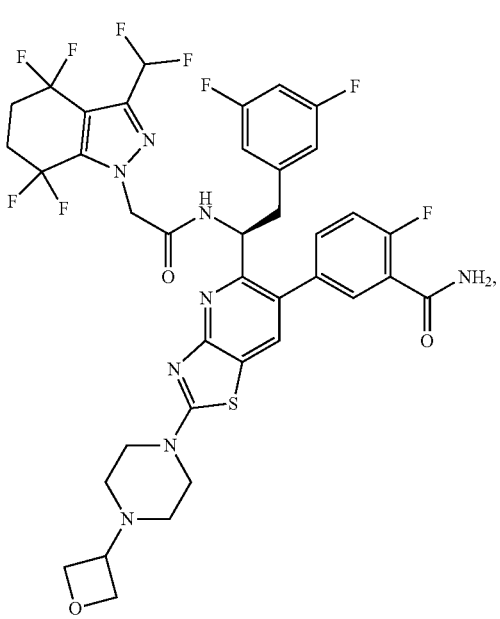

127
-continued
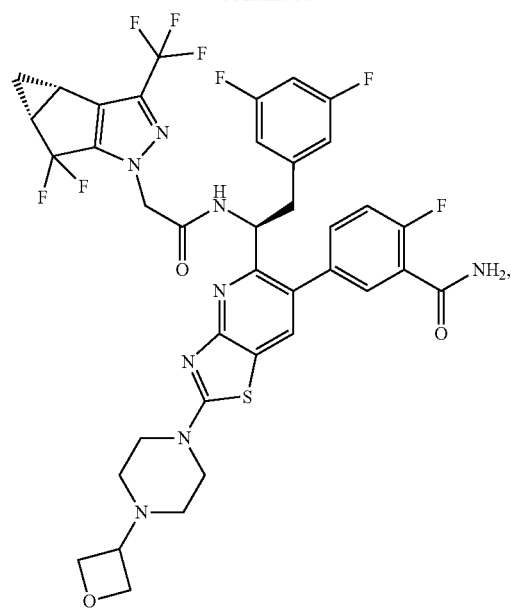
128
-continued
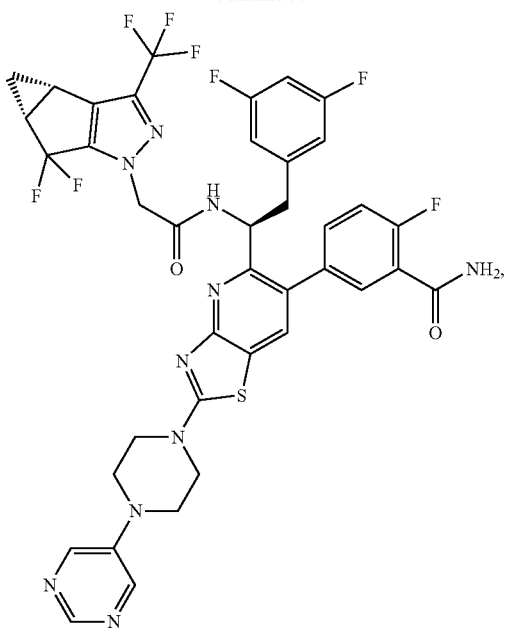
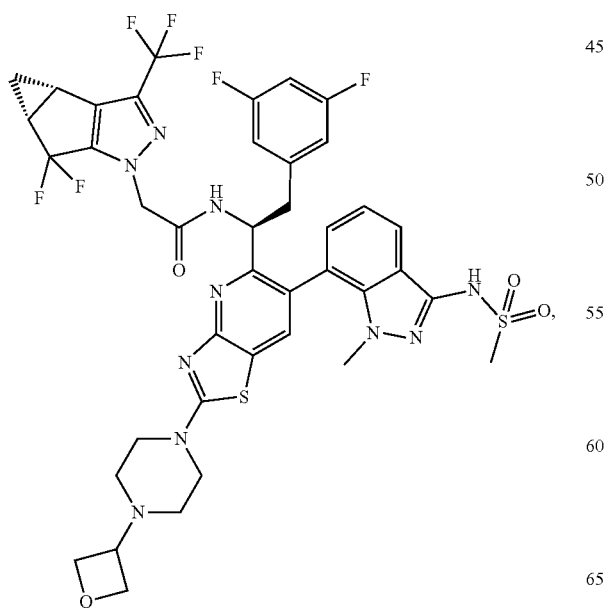
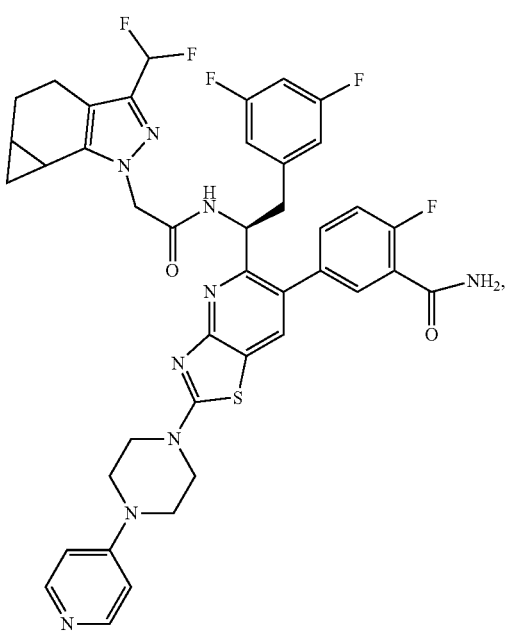

129
-continued
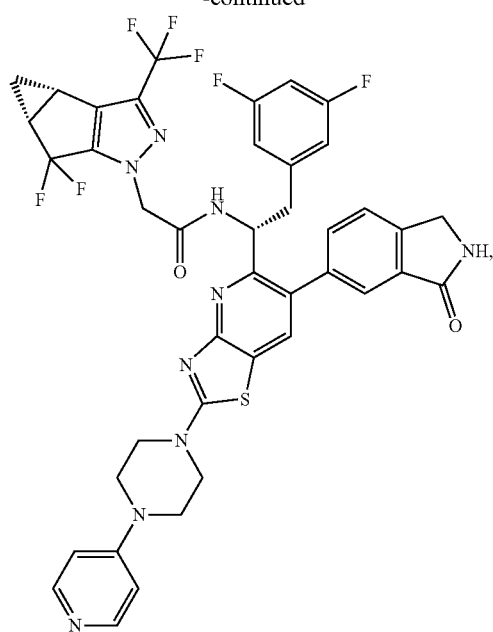
130
-continued
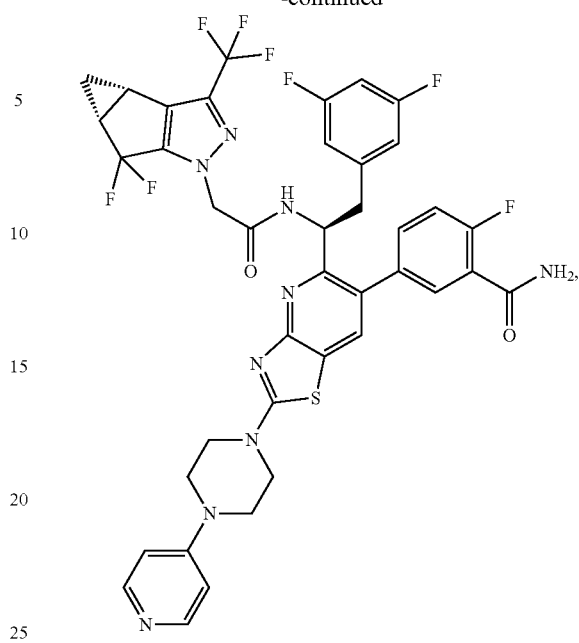
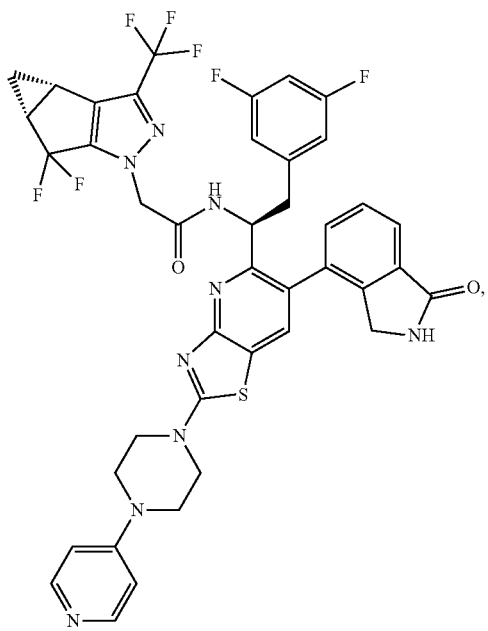
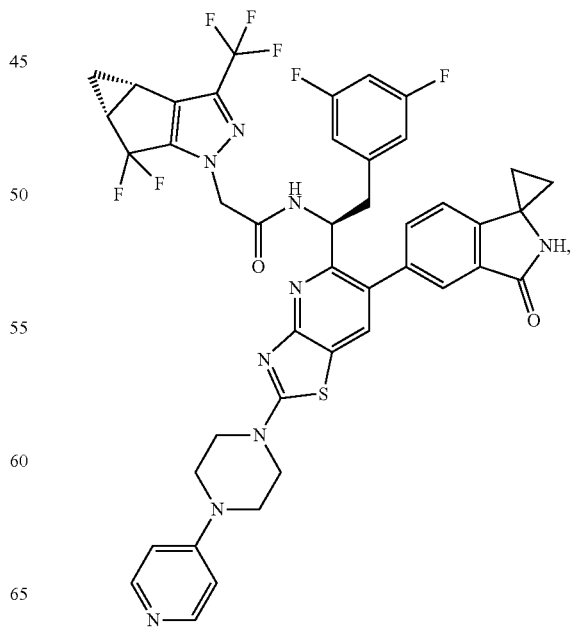

131
-continued
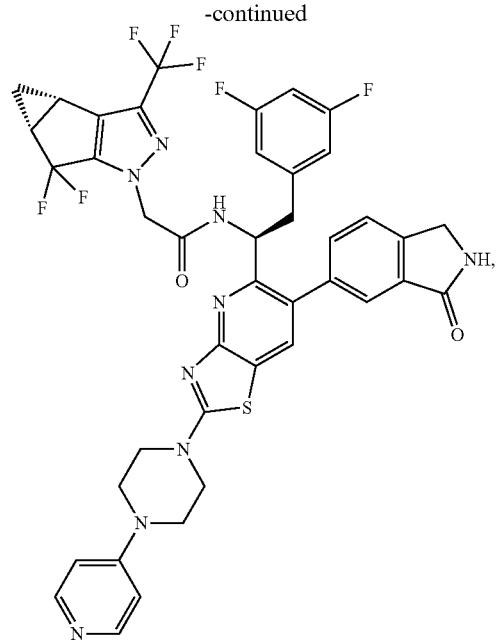
132
-continued
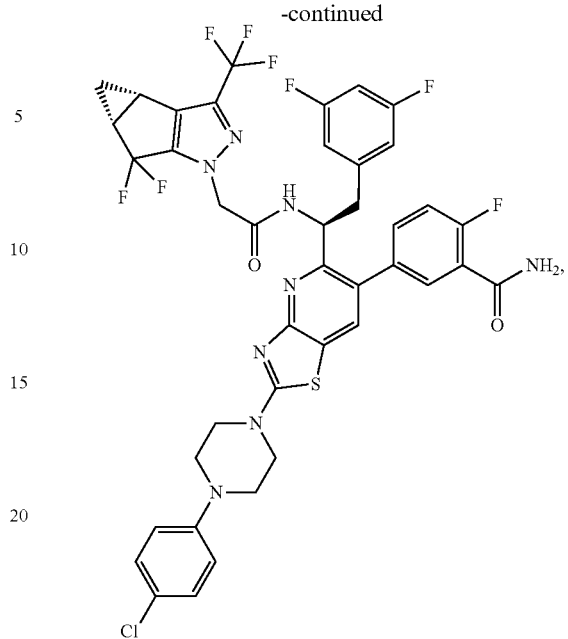
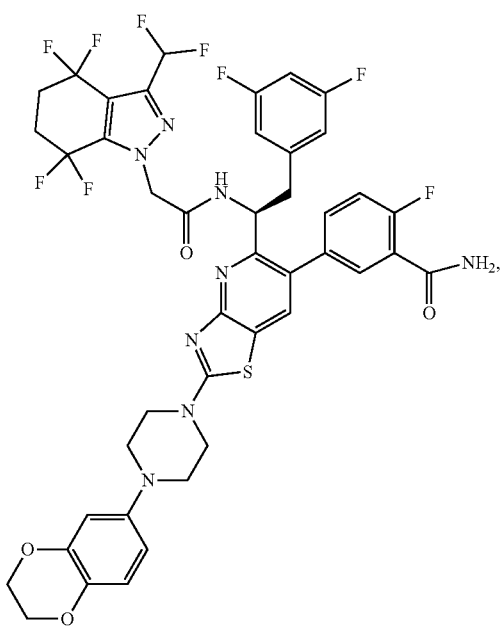
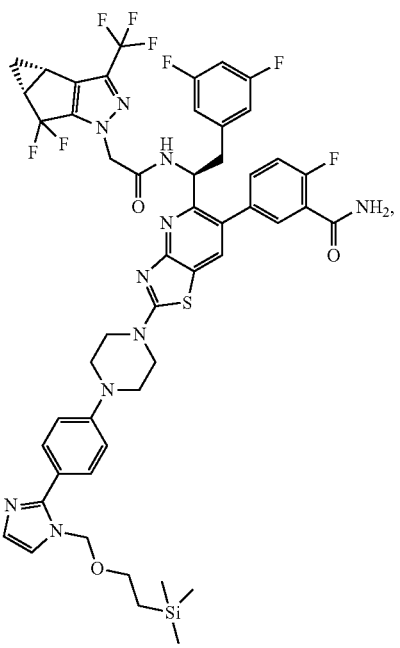

133
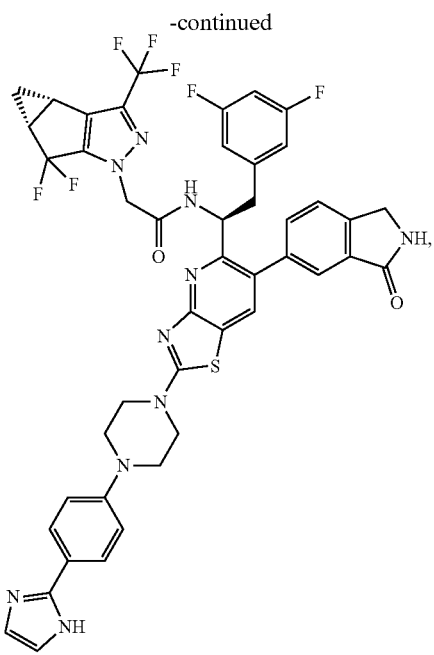
134
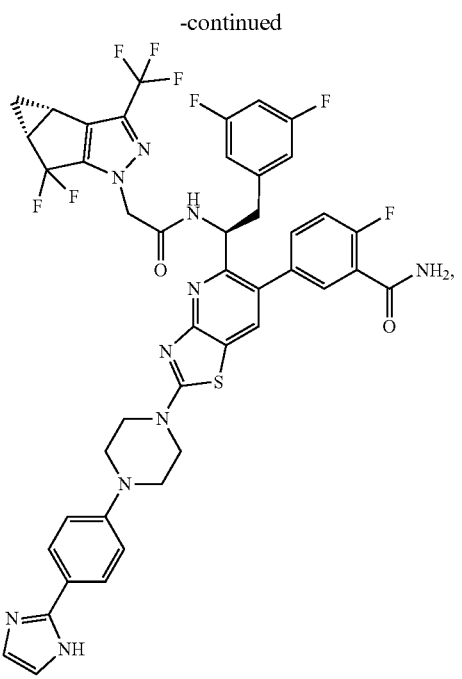
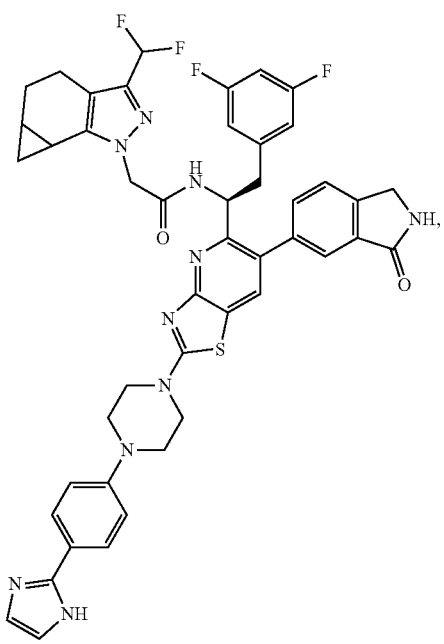
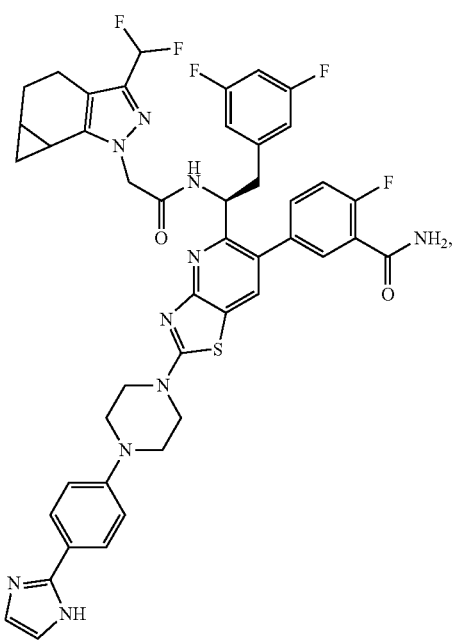

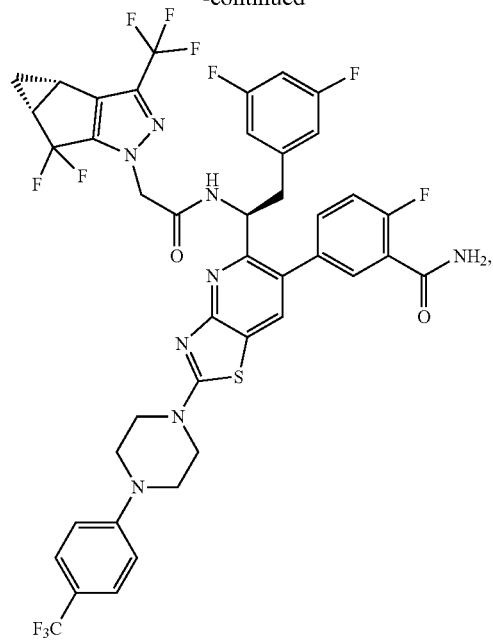
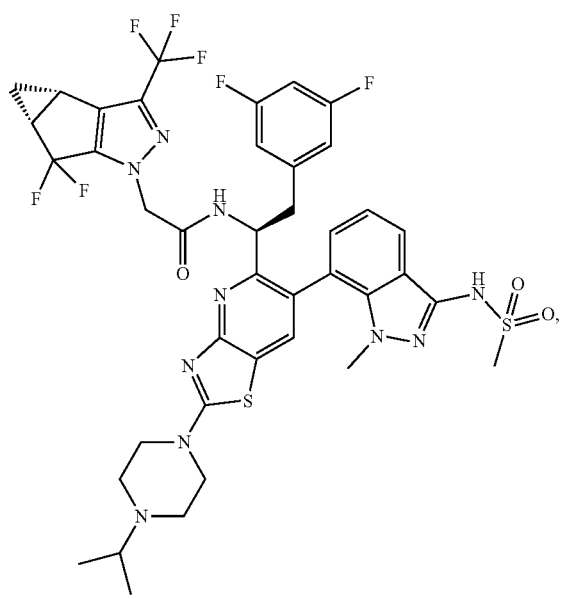
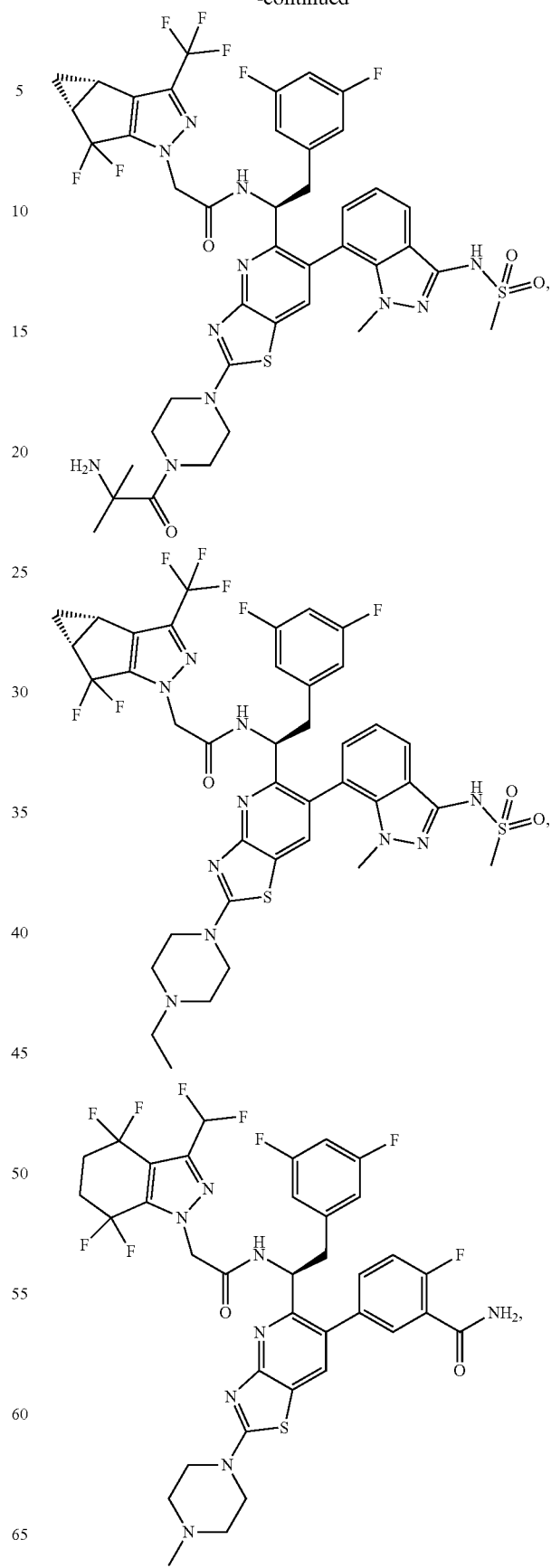

137
-continued
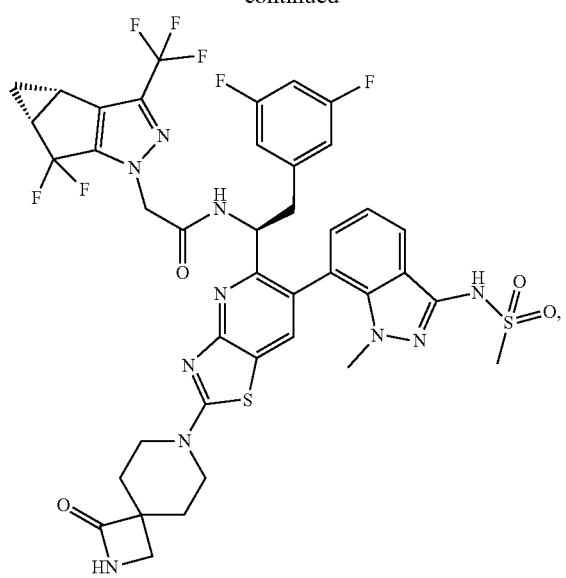
138
-continued
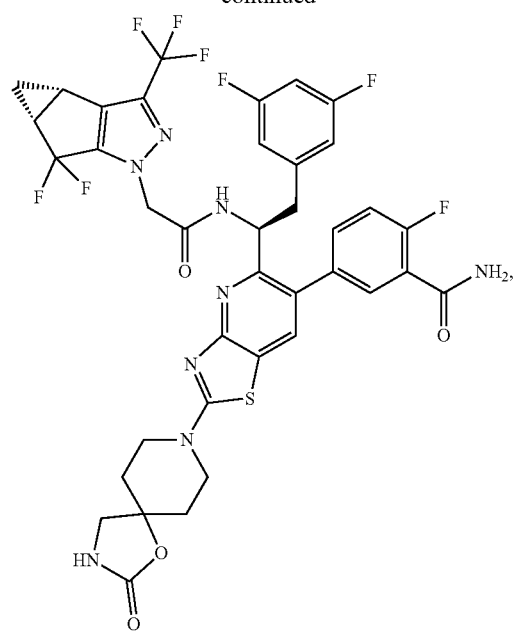
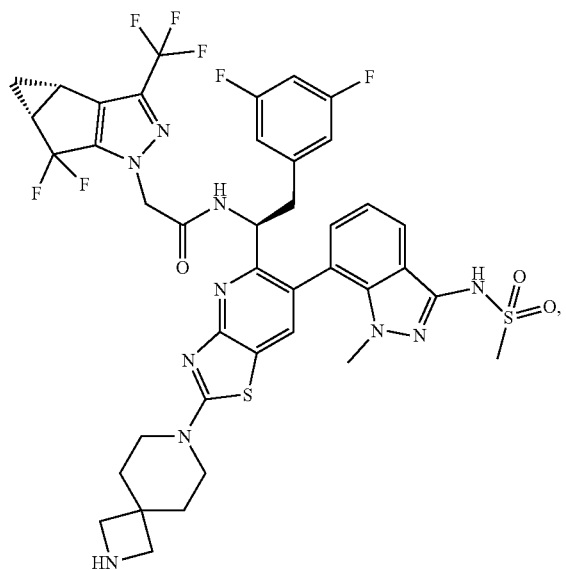
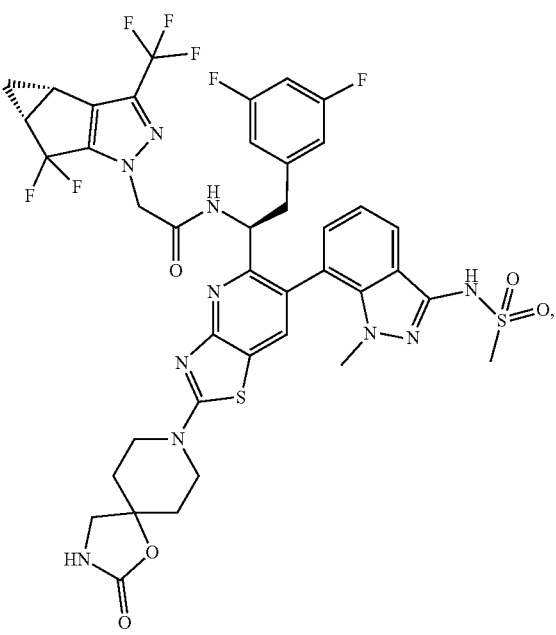

139
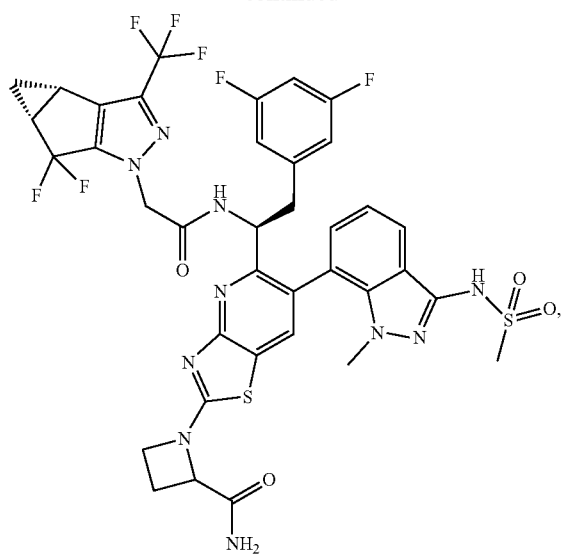
140
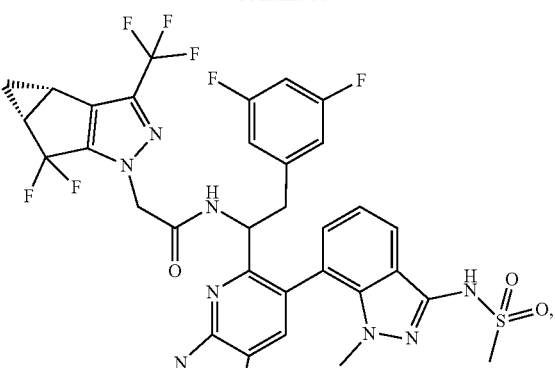

141
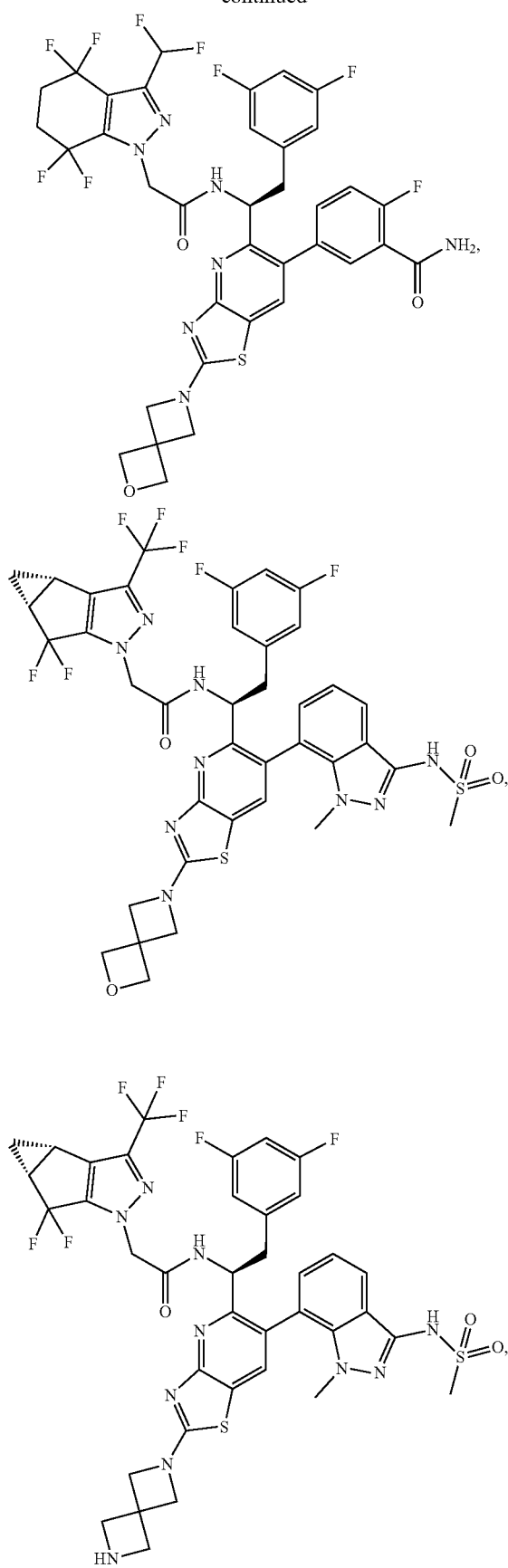
142
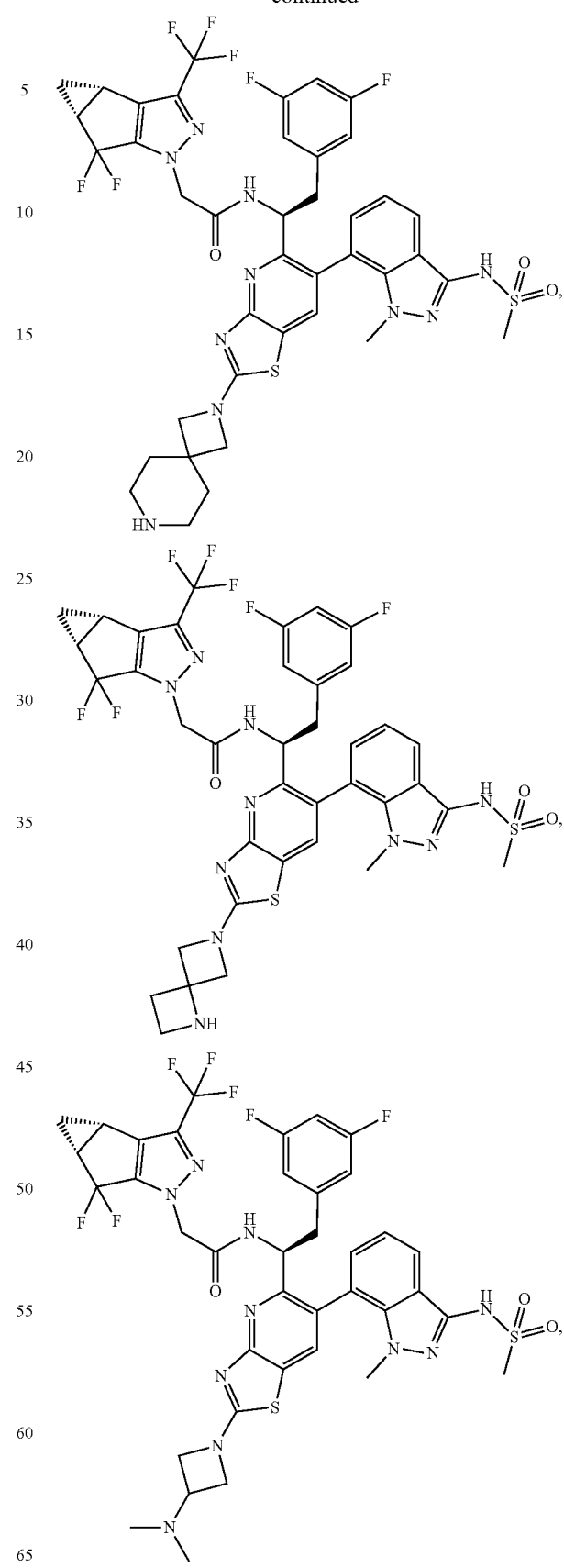

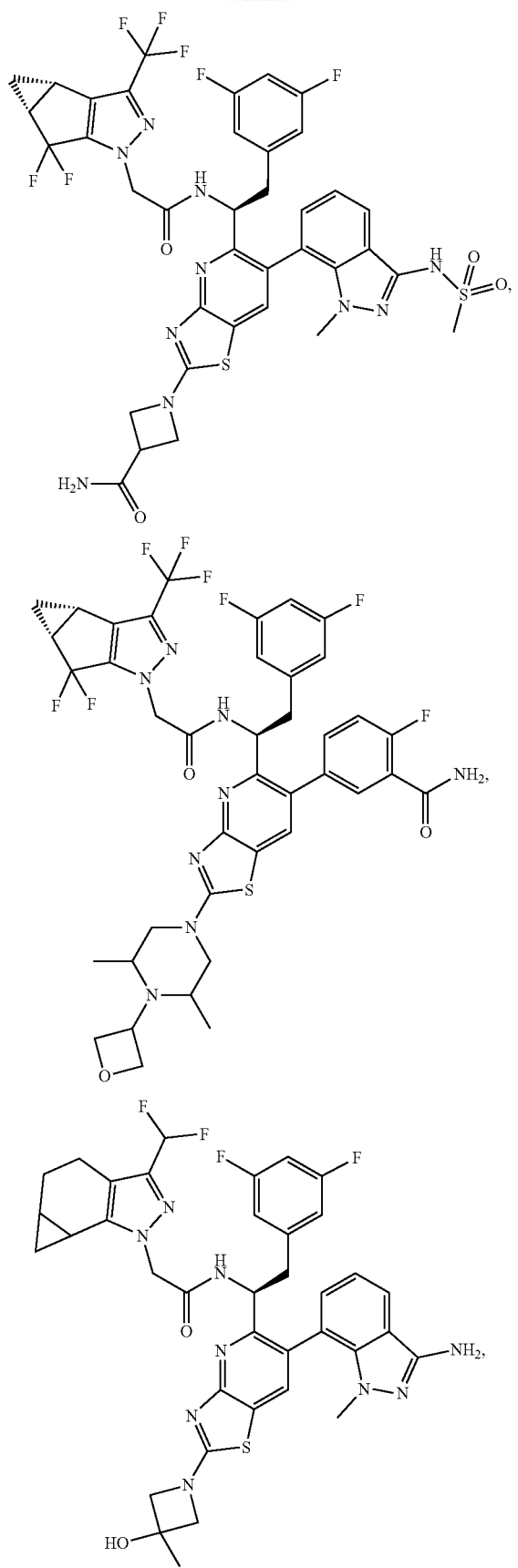
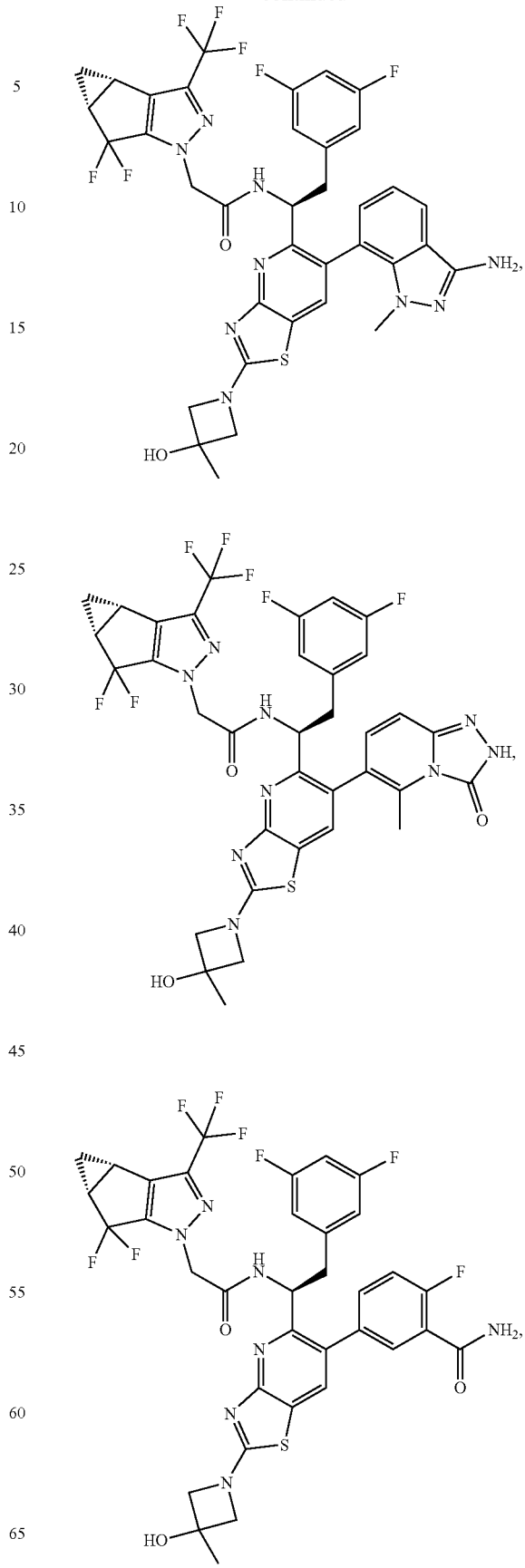

145
-continued
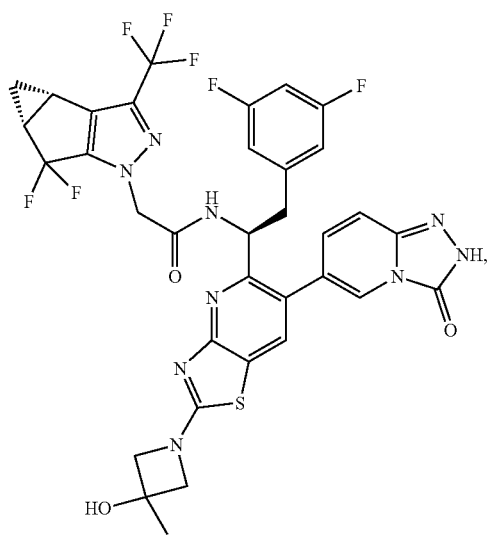
146
-continued
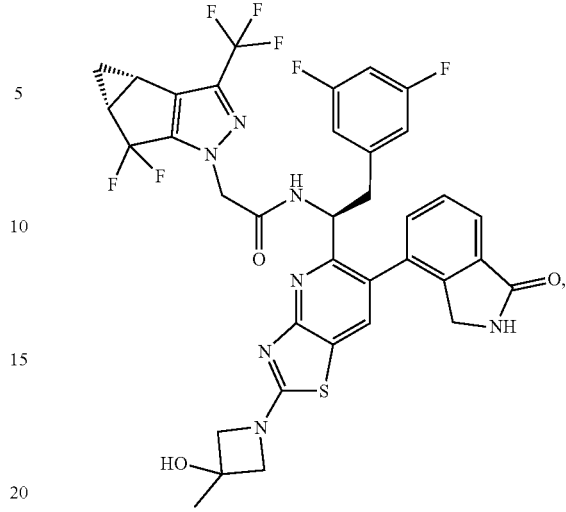
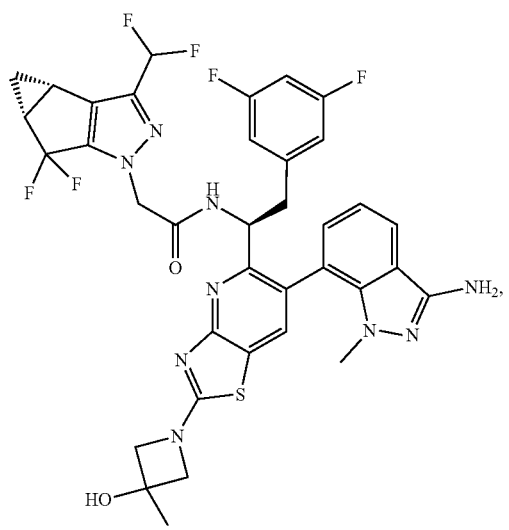
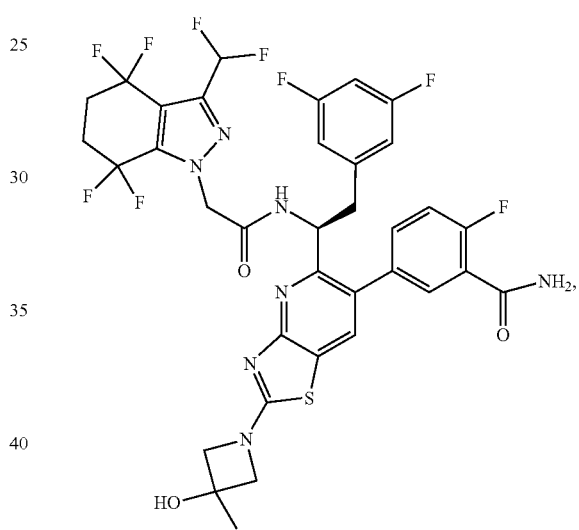
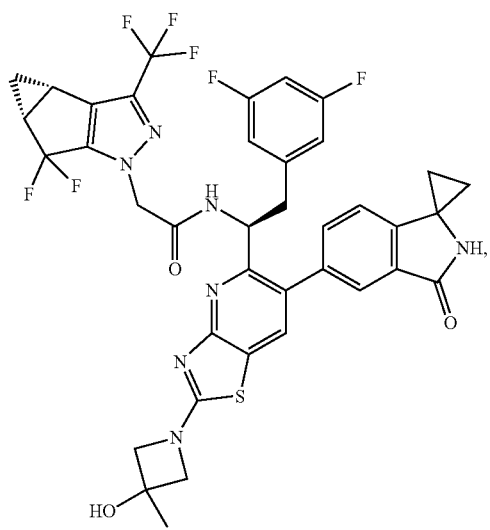
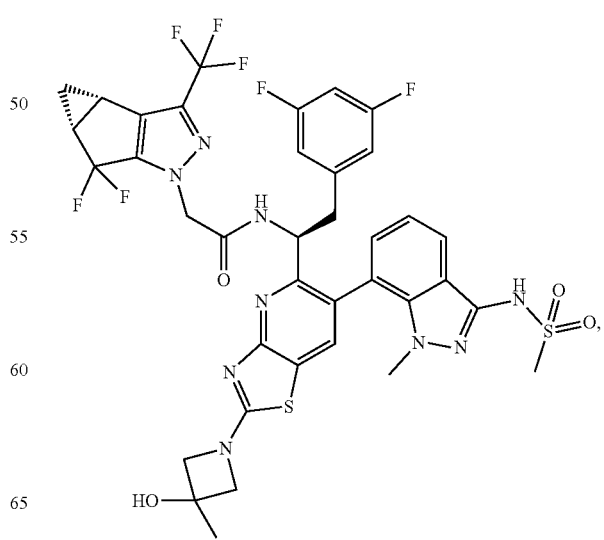

147
-continued
148
-continued
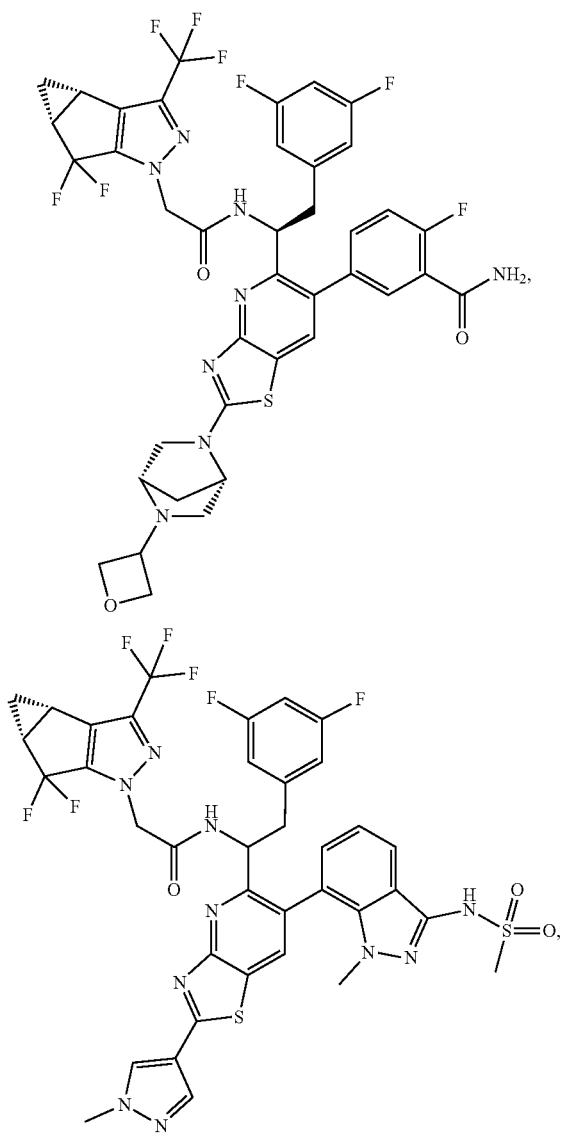
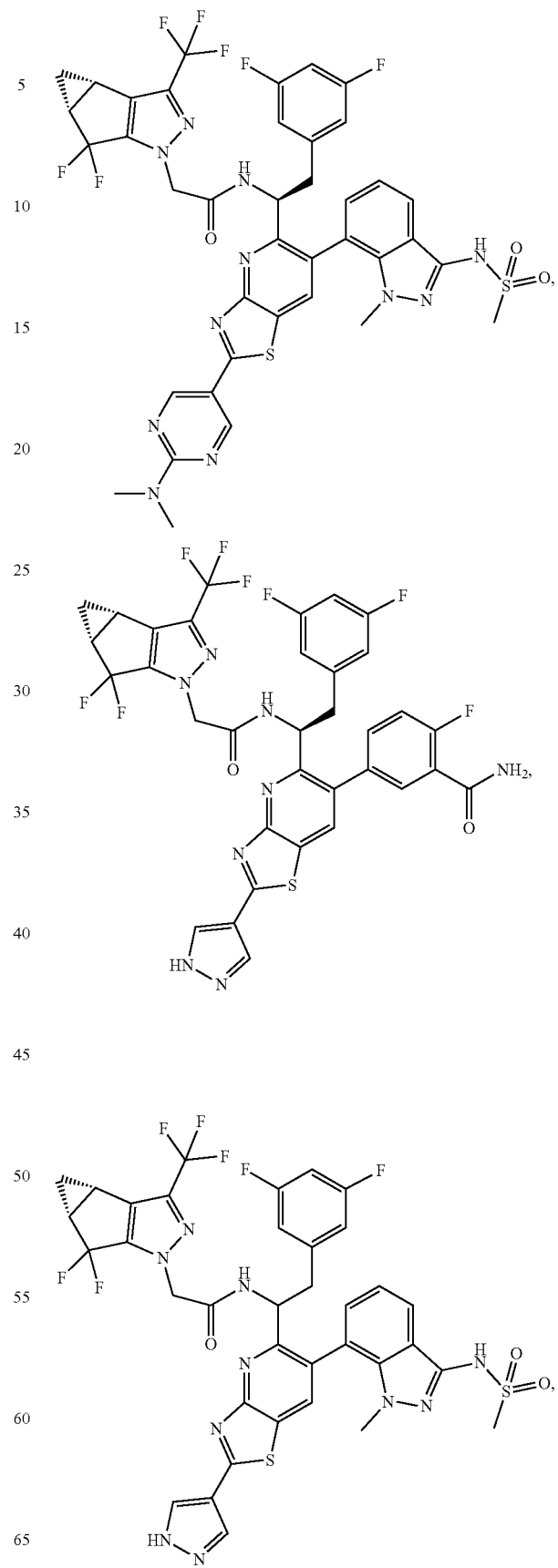

149
-continued
150
-continued
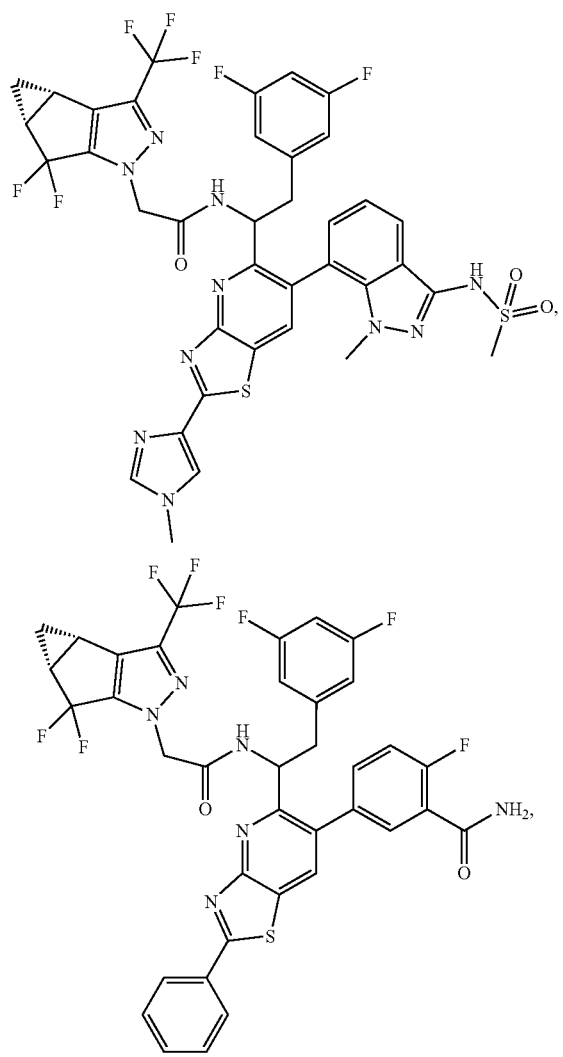
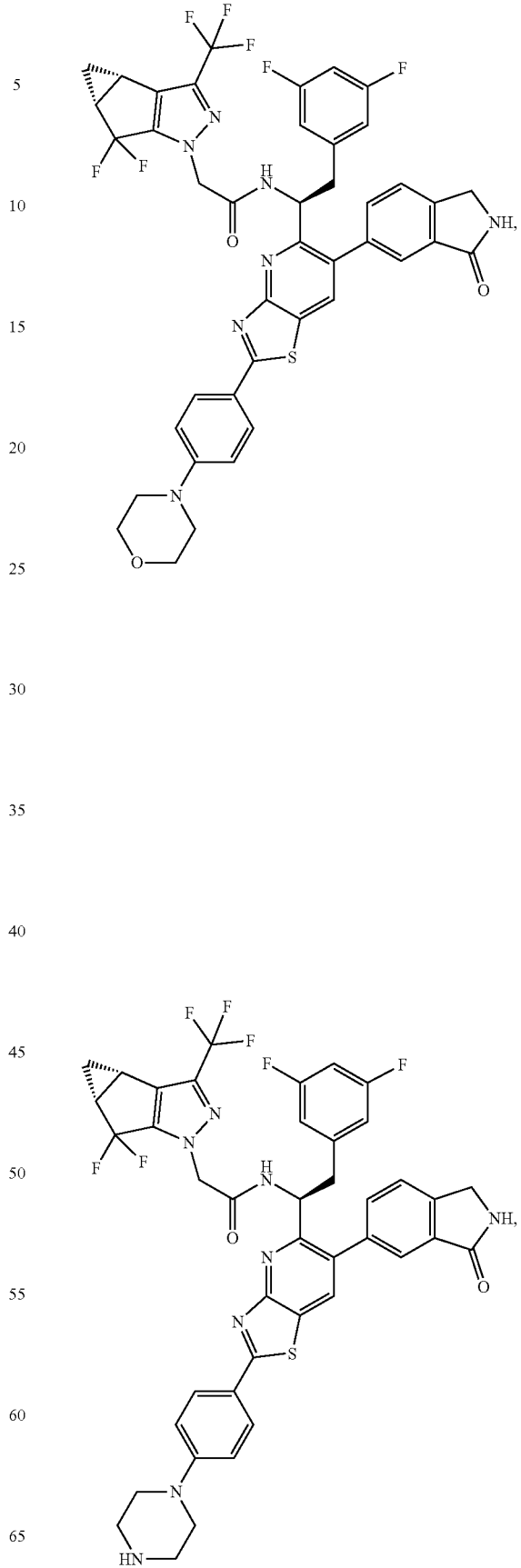

151
-continued
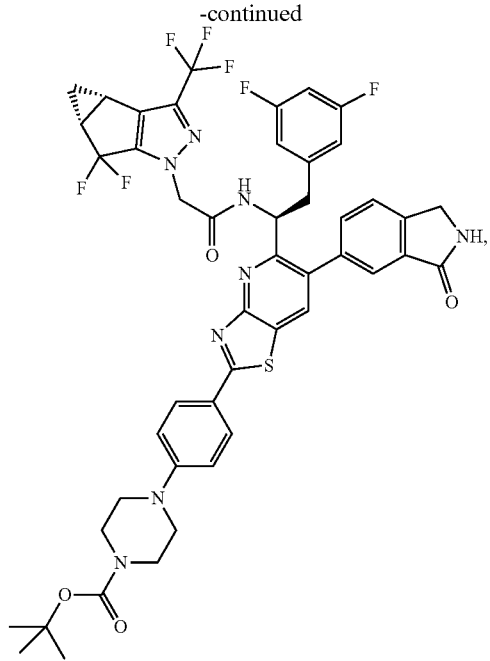
152
-continued
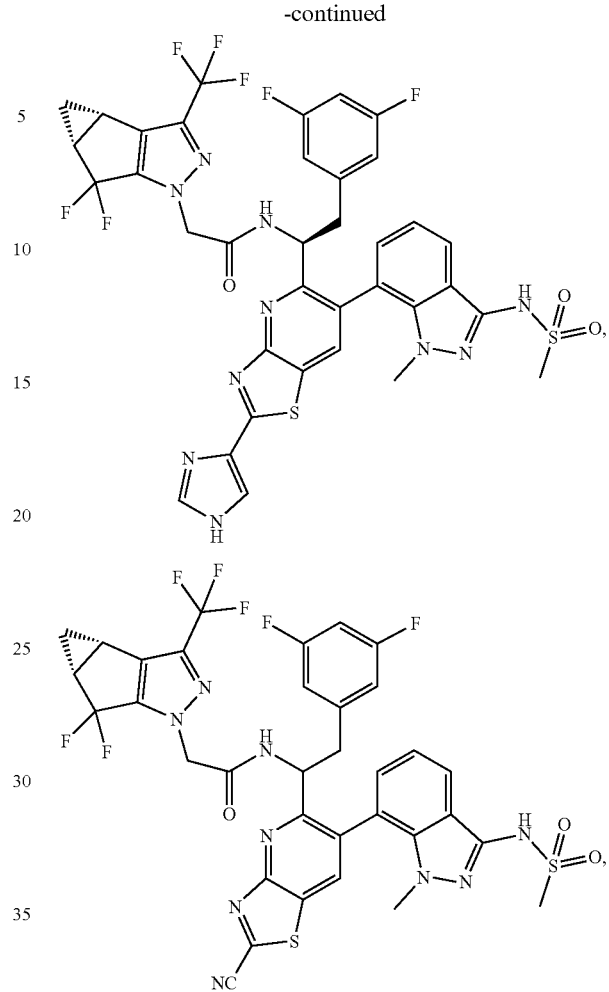
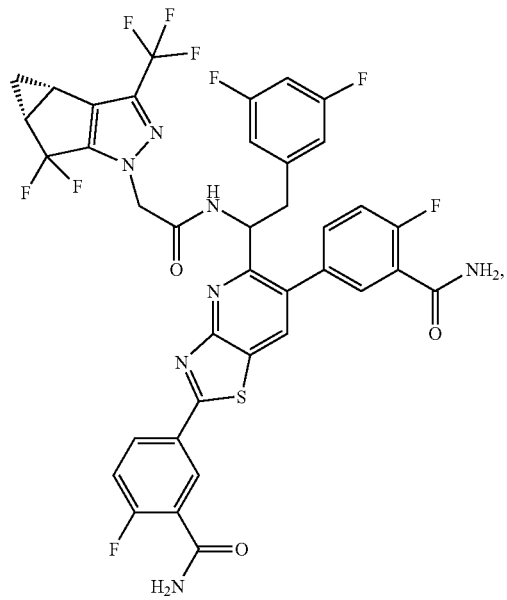

-continued
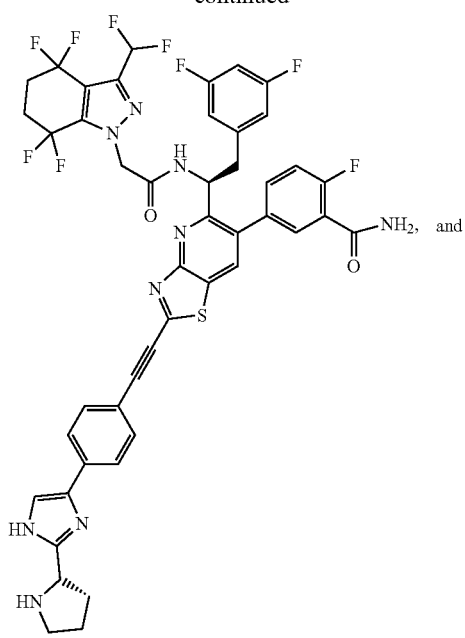
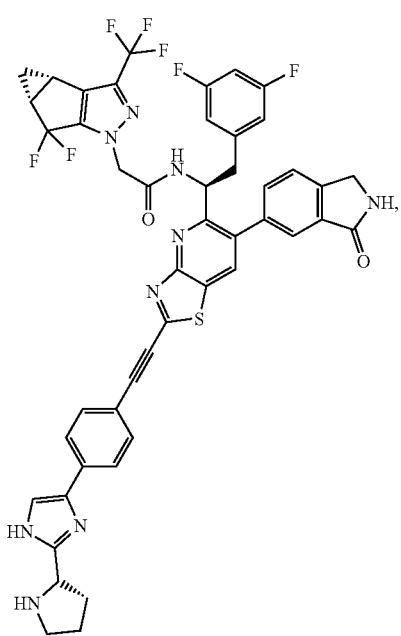
or a pharmaceutically acceptable salt thereof.
In one aspect, provided herein are compounds having the structures:
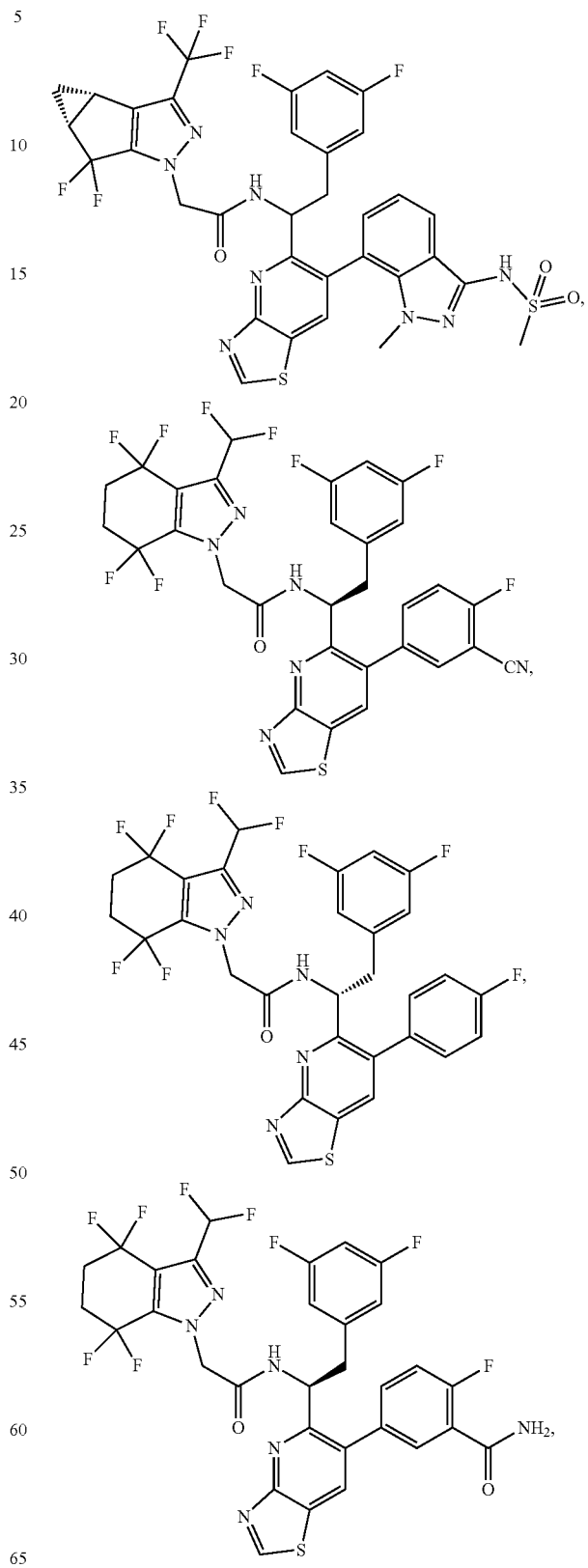

155
-continued
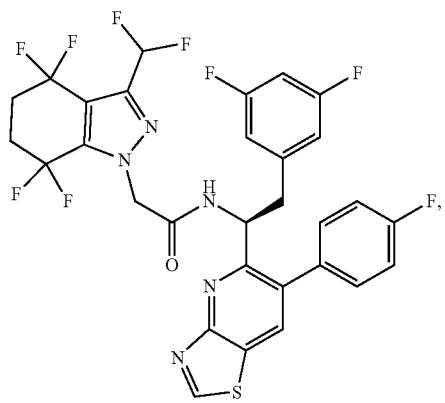
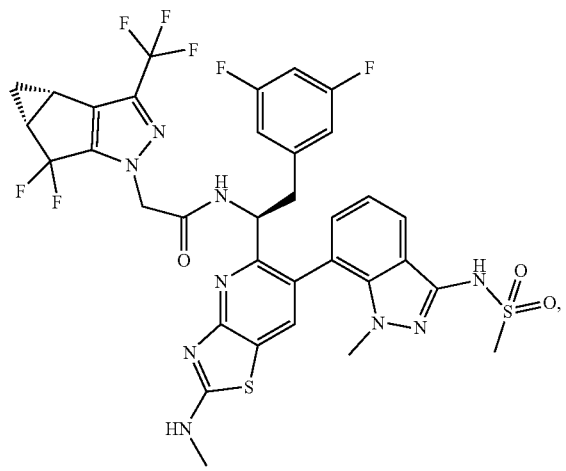
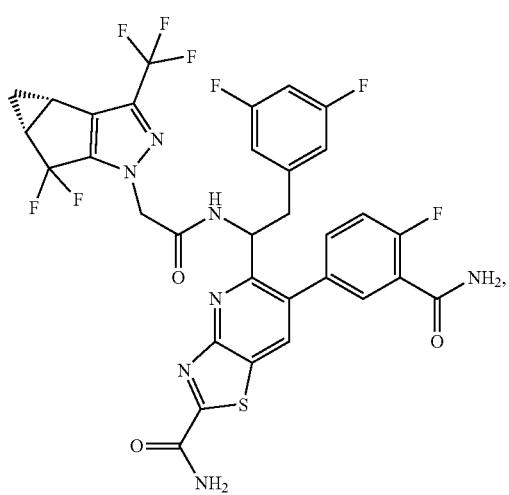
156
-continued
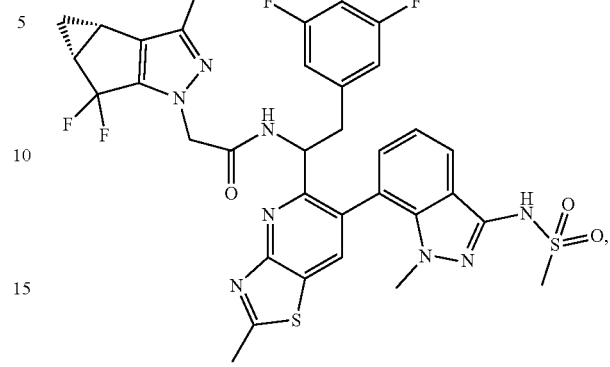
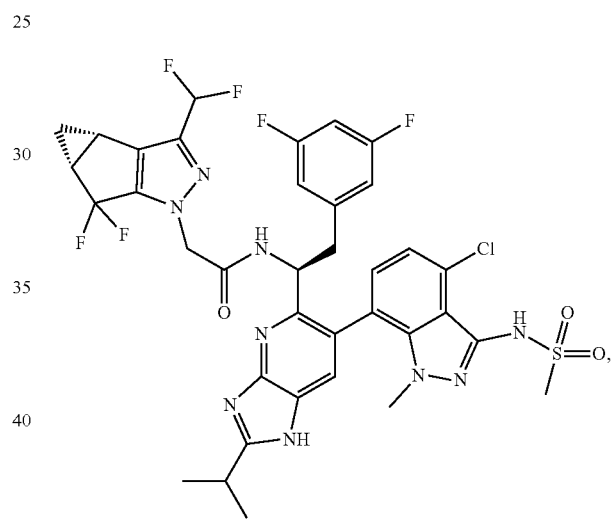
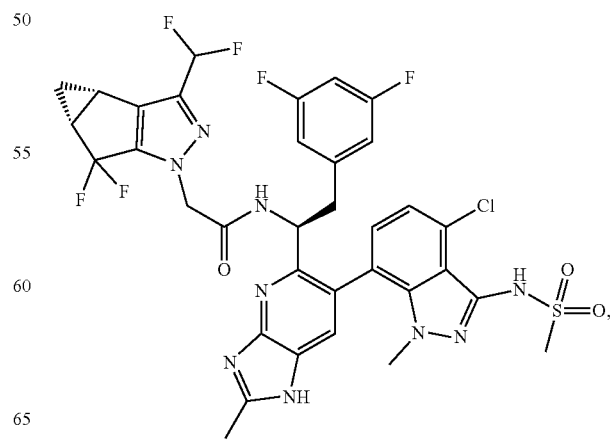

157
-continued

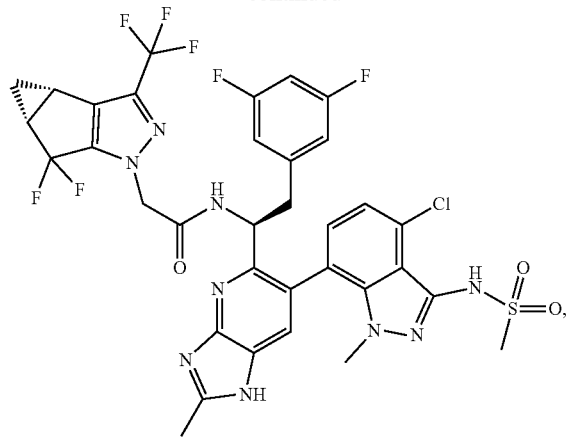

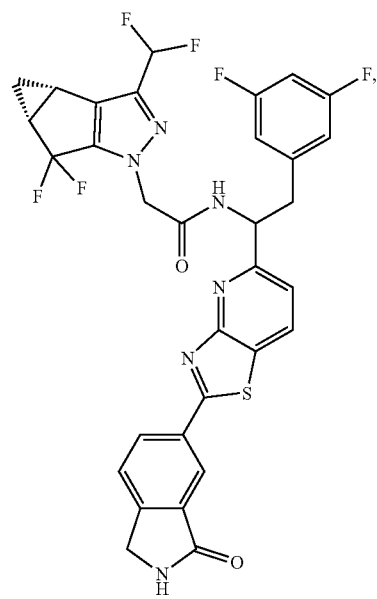

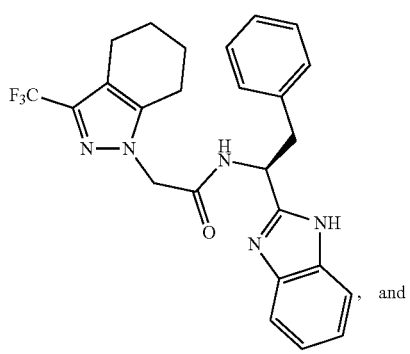
, and

158
-continued

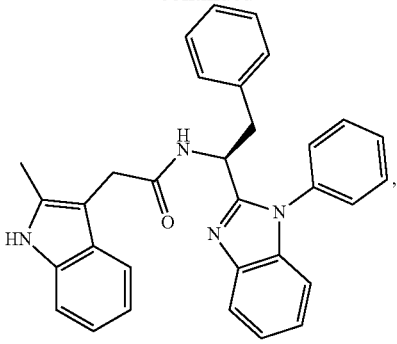 [SMILES: Cc1[nH]c2ccccc2c1CC(=O)N[C@@H](Cc1ccccc1)c1nc2ccccc2n1-c1ccccc1]

or a pharmaceutically acceptable salt thereof.

III. Compositions and Kits

Compounds provided herein are usually administered in the form of pharmaceutical compositions. Thus, provided herein are also pharmaceutical compositions that comprise one or more of the compounds provided herein or pharmaceutically acceptable salts, isomer, or a mixture thereof and one or more pharmaceutically acceptable vehicles selected from carriers, adjuvants and excipients. The compounds provided herein may be the sole active ingredient or one of the active ingredients of the pharmaceutical compositions. Suitable pharmaceutically acceptable vehicles may include, for example, inert solid diluents and fillers, diluents, including sterile aqueous solution and various organic solvents, permeation enhancers, solubilizers and adjuvants. Such compositions are prepared in a manner well known in the pharmaceutical art. See, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.).

In one aspect, provided herein are pharmaceutical compositions comprising a compound provided herein (i.e., a compound of Formula I, Ia, II, or IIa), or a pharmaceutically acceptable salt thereof, and a pharmaceutically acceptable excipient or carrier. In some embodiments, the pharmaceutical compositions comprise a therapeutically effective amount of a compound provided herein, or a pharmaceutically acceptable salt thereof, and a pharmaceutically acceptable excipient or carrier.

In some embodiments, the pharmaceutical compositions provided herein further comprise one or more (i.e., one, two, three, four; one or two; one to three; or one to four) additional therapeutic agents, or a pharmaceutically acceptable salt thereof. In some embodiments, the pharmaceutical compositions further comprise a therapeutically effective amount of the one or more (i.e., one, two, three, four; one or two; one to three; or one to four) additional therapeutic agents, or a pharmaceutically acceptable salt thereof.

In some embodiments, the one or more additional therapeutic agents include agents that are therapeutic for HIV infection. In some embodiments, the one or more additional therapeutic agents is selected from the group consisting of: islatravir, bictegravir or a pharmaceutically acceptable salt thereof, abacavir sulfate, tenofovir, tenofovir disoproxil, tenofovir disoproxil fumarate, tenofovir disoproxil hemifumarate, tenofovir alafenamide, tenofovir alafenamide hemifumarate, emtricitabine, and lamivudine, or a pharmaceutically acceptable salt of any of the foregoing, or any combinations thereof.

The pharmaceutical compositions may be administered in either single or multiple doses. The pharmaceutical compositions may be administered by various methods including, for example, rectal, buccal, intranasal and transdermal routes. In some embodiments, the pharmaceutical compositions may be administered by intra-arterial injection, intravenously, intraperitoneally, parenterally, intramuscularly, subcutaneously, orally, topically, or as an inhalant.

One mode for administration is parenteral, for example, by injection. The forms in which the pharmaceutical compositions described herein may be incorporated for administration by injection include, for example, aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. In some embodiments, the compounds and pharmaceutical compositions disclosed herein are administered by subcutaneous injection.

The pharmaceutical compositions of the present disclosure may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

In some embodiments, the sterile injectable preparation disclosed herein may also be a sterile injectable solution or suspension prepared from a reconstituted lyophilized powder in a non-toxic parenterally acceptable diluent or solvent, such as a solution in 1,3-butane-diol. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. In certain embodiments the suspension is a microsuspension. In certain embodiments the suspension is a nanosuspension.

In some embodiments, formulations suitable for parenteral administration (e.g., intramuscular (IM) and subcutaneous (SC) administration) will include one or more excipients. Excipients should be compatible with the other ingredients of the formulation and physiologically innocuous to the recipient thereof. Examples of suitable excipients are well known to the person skilled in the art of parenteral formulation and may be found e.g., in Handbook of Pharmaceutical Excipients (eds. Rowe, Sheskey & Quinn), 6th edition 2009.

Examples of solubilizing excipients in a parenteral formulation (e.g., an SC or IM formulation) include, but are not limited to, polysorbates (such as polysorbate 20 or 80) and poloxamers (such as poloxamer 338, 188, or 207). In some embodiments, disclosed herein is a parenteral administration (e.g., an SC or IM formulation) that comprises a compound of Formula I, Ia, II, or IIb, or a pharmaceutical salt thereof, and a poloxamer, in particular poloxamer 338. In some embodiments, the amount of poloxamer (e.g., poloxamer 388) in a parenteral administration disclosed herein is less than about 5%, such as less than about 3%, about 2%, about 1%, or about 0.5%.

Examples of solubilizing excipients in a parenteral formulation (e.g., an SC or IM formulation) include, but are not limited to, polysorbates (such as polysorbate 20 or 80), poloxamers (such as poloxamer 338, 188, or 207). In some embodiments, disclosed herein is a parenteral administration (e.g., an SC or IM formulation) that comprises a compound of Formula I, Ia, II, or IIb, or a pharmaceutical salt thereof, and a poloxamer.

In some embodiments, the compounds and pharmaceutical compositions disclosed herein are administered with implants.

Oral administration may be another route for administration of the compounds provided herein. Administration may be via, for example, capsule or enteric coated tablets. In making the pharmaceutical compositions that include at least one compound provided herein or pharmaceutically acceptable salts, isomer, or a mixture thereof, the active ingredient (such as a compound provided herein) is usually diluted by an excipient and/or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the pharmaceutical compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose or any combinations thereof. The pharmaceutical compositions can additionally include lubricating agents such as talc, magnesium stearate, and mineral oil; wetting agents; emulsifying and suspending agents; preserving agents such as methyl and propylhydroxy-benzoates; sweetening agents; and flavoring agents; or any combinations thereof.

The pharmaceutical compositions that include at least one compound described herein or pharmaceutically acceptable salts, isomer, or a mixture thereof can be formulated so as to provide quick, sustained or delayed release of the active ingredient (such as a compound provided herein) after administration to the subject by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds provided herein in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

For preparing solid compositions such as tablets, the principal active ingredient may be mixed with a pharmaceutical excipient to form a solid preformulation composition containing a homogeneous mixture of a compound described herein or pharmaceutically acceptable salts, isomer, or a mixture thereof. When referring to these preformulation compositions as homogeneous, the active ingredient may be dispersed evenly throughout the composition so that the composition may be readily subdivided into equally effective unit dosage forms such as tablets, pills and capsules.

The tablets or pills of the compounds described herein may be coated or otherwise compounded to provide a dosage form affording the advantage of prolonged action, or to protect from the acid conditions of the stomach. For example, the tablet or pill can include an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with materials such as shellac, cetyl alcohol, and cellulose acetate.

Pharmaceutical compositions for inhalation or insufflation may include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. In other embodiments, compositions in pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In one aspect, provided herein are kits that comprise a compound provided herein, (i.e., a compound of Formula I, Ia, II, or IIa), or a pharmaceutically acceptable salt, stereoisomer, prodrug, or solvate thereof, and suitable packaging. In some embodiments, the kit further comprises instructions for use. In some embodiments, the kit comprises a compound provided herein (i.e., a compound of Formula I, Ia, II, or IIa), or a pharmaceutically acceptable salt, stereoisomer, prodrug, or solvate thereof, and a label and/or instructions for use of the compounds in the treatment of the indications, including the diseases or conditions, described herein.

In some embodiments, the kits further comprise one or more (i.e., one, two, three, four; one or two; one to three; or one to four) additional therapeutic agents, or a pharmaceutically acceptable salt thereof.

In one aspect, provided herein are articles of manufacture that comprise a compound described herein or pharmaceutically acceptable salts, isomer, or a mixture thereof in a suitable container. In some embodiments, the container may be a vial, jar, ampoule, preloaded syringe, or intravenous bag.

IV. Methods

The methods provided herein may be applied to cell populations in vivo or ex vivo. "In vivo" means within a living individual, as within an animal or human. In this context, the methods provided herein may be used therapeutically in an individual. "Ex vivo" means outside of a living individual. Examples of ex vivo cell populations include in vitro cell cultures and biological samples including fluid or tissue samples obtained from individuals. Such samples may be obtained by methods well known in the art. Exemplary biological fluid samples include blood, cerebrospinal fluid, urine, and saliva. Exemplary tissue samples include tumors and biopsies thereof. In this context, the present disclosure may be used for a variety of purposes, including therapeutic and experimental purposes. For example, the present disclosure may be used ex vivo to determine the optimal schedule and/or dosing of administration of a HIV capsid inhibitor as disclosed herein for a given cell type, individual, and other parameters. Information gleaned from such use may be used for experimental purposes or in the clinic to set protocols for in vivo treatment. Other ex vivo uses for which the present disclosure may be suited are described below or will become apparent to those skilled in the art. The selected compounds may be further characterized to examine the safety or tolerance dosage in human or non-human subjects. Such properties may be examined using commonly known methods to those skilled in the art.

In one aspect, the present disclosure provides methods of treating or preventing a human immunodeficiency virus (HIV) infection in a subject in need thereof, comprising administering to the subject a therapeutically effective amount of a compound provided herein (i.e., a compound of Formula I, Ia, II, or IIa), or a pharmaceutically acceptable salt thereof, or a pharmaceutical composition provided herein.

In some embodiments, the methods provided herein further comprise administering a therapeutically effective amount of one or more additional therapeutic agents, or a pharmaceutically acceptable salt thereof.

In some embodiments, the one or more additional therapeutic agents is selected from the group consisting of combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the one or more additional therapeutic agents is selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the one or more additional therapeutic agents is selected from the group consisting of islatravir, bictegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the one or more additional therapeutic agents is selected from the group consisting of islatravir, bictegravir, tenofovir alafenamide, tenofovir alafenamide fumarate and tenofovir alafenamide hemifumarate, or a pharmaceutically acceptable salt of any of the foregoing, or any combinations thereof.

In some embodiments, the one or more additional therapeutic agents is selected from the group consisting of islatravir, dolutegravir, cabotegravir, bictegravir, tenofovir disoproxil, tenofovir disoproxil hemifumarate, and tenofovir disoproxil fumarate, or a pharmaceutically acceptable salt of any of the foregoing, or any combinations thereof.

In some embodiments, the one or more additional therapeutic agents is bictegravir, or a pharmaceutically acceptable salt of each thereof.

In some embodiments, the one or more additional therapeutic agents is selected from the group consisting of emtricitabine and lamivudine, or a pharmaceutically acceptable salt of each thereof.

In some embodiments, the one or more additional therapeutic agents is emtricitabine or a pharmaceutically acceptable salt thereof.

In some embodiments, the methods provided herein comprise administering a therapeutically effective amount of a compound provided herein (i.e., a compound of Formula I, Ia, II, or IIa), or a pharmaceutically acceptable salt thereof. In some embodiments, the methods described herein comprise administering a therapeutically effective amount of a pharmaceutical composition provided herein.

In one aspect, provided herein is a compound disclosed herein (i.e., a compound of Formula I, Ia, II, or IIa), or a pharmaceutically acceptable salt thereof, for use in therapy.

In one aspect, provided herein is a compound disclosed herein (i.e., a compound of Formula I, Ia, II, or IIa), or a pharmaceutically acceptable salt thereof, for use in a method of treating or preventing a human immunodeficiency virus (HIV) infection in a subject in need thereof, comprising administering to the subject a therapeutically effective amount of a compound provided herein (i.e., a compound of Formula I, Ia, II, or IIa), or a pharmaceutically acceptable salt thereof, or a pharmaceutical composition provided herein.

In some embodiments, the above uses further comprise administering a therapeutically effective amount of one or more additional therapeutic agents, or a pharmaceutically acceptable salt thereof.

In some embodiments, the above uses further comprise administering one or more additional therapeutic agents selected from the group consisting of: combination drugs for HIV, other drugs for treating HIV, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, and HIV vaccines, or a pharmaceutically acceptable salt of any of the foregoing, or any combinations thereof.

In some embodiments, the above uses further comprise administering one or more additional therapeutic agents selected from the group consisting of HIV protease inhibiting compounds, HIV non-nucleoside inhibitors of reverse transcriptase, HIV non-nucleotide inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, pharmacokinetic enhancers, and other drugs for treating HIV, or a pharmaceutically acceptable salt of any of the foregoing, or any combinations thereof.

In some embodiments, the above uses further comprise administering one or more additional therapeutic agents selected from the group consisting of islatravir, bictegravir, dolutegravir, cabotegravir, abacavir sulfate, tenofovir, tenofovir disoproxil, tenofovir disoproxil fumarate, tenofovir disoproxil hemifumarate, tenofovir alafenamide, and tenofovir alafenamide hemifumarate, or a pharmaceutically acceptable salt of any of the foregoing, or any combinations thereof.

In some embodiments, the above uses further comprise administering one or more additional therapeutic agents selected from the group consisting of islatravir, bictegravir, dolutegravir, cabotegravir, tenofovir alafenamide, tenofovir alafenamide fumarate and tenofovir alafenamide hemifumarate, or a pharmaceutically acceptable salt of any of the foregoing, or any combinations thereof.

In some embodiments, the above uses further comprise administering one or more additional therapeutic agents selected from the group consisting of islatravir, bictegravir, dolutegravir, cabotegravir, tenofovir disoproxil, tenofovir disoproxil hemifumarate, and tenofovir disoproxil fumarate, or a pharmaceutically acceptable salt of any of the foregoing, or any combinations thereof.

In some embodiments, the above uses further comprise administering one or more additional therapeutic agents selected from the group consisting of emtricitabine and lamivudine, or a pharmaceutically acceptable salt of each thereof.

In some embodiments, the above uses further comprise administering emtricitabine or a pharmaceutically acceptable salt thereof.

In some embodiments, the uses described herein comprise administering a therapeutically effective amount of a compound provided herein (i.e., a compound of Formula I, Ia, II, or IIa), or a pharmaceutically acceptable salt thereof.

V. Administration

The compounds of the present disclosure (also referred to herein as the active ingredients), can be administered by any route appropriate to the condition to be treated. Suitable routes include oral, rectal, nasal, topical (including buccal and sublingual), transdermal, vaginal and parenteral (including subcutaneous, intramuscular, intravenous, intradermal, intrathecal and epidural), and the like. It will be appreciated that the preferred route may vary with, for example, the condition of the recipient. An advantage of certain compounds disclosed herein is that they are orally bioavailable and can be dosed orally.

A compound of the present disclosure may be administered to an individual in accordance with an effective dosing regimen for a desired period of time or duration, such as at least about one month, at least about 2 months, at least about 3 months, at least about 6 months, or at least about 12 months or longer. In some embodiments, the compound is administered on a daily or intermittent schedule for the duration of the individual's life.

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, Ia, II, or IIa, or a pharmaceutically acceptable salt or pharmaceutically acceptable tautomer thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 μg to about 30 mg per day, or from about 30 μg to about 300 μg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I, Ia, II, or IIa are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound provided herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1 mg and 1,000 mg, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, or 1000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of the compound of the present disclosure will be determined by the needs of the individual patient and can be, for example, once per day or twice, or more times, per day. Administration of the compound continues for as long as necessary to treat the HBV infection, HIV infection, cancer, hyper-proliferative disease, or any other indication described herein. For example, a compound can be administered to a human being infected with HIV for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VI. Combination Therapy

In some embodiments, a compound of the present disclosure, or a pharmaceutically acceptable salt thereof, is combined with one, two, three, four or more additional therapeutic agents. In some embodiments, a compound of the present disclosure, or a pharmaceutically acceptable salt thereof, is combined with two additional therapeutic agents. In some embodiments, a compound of the present disclosure, or a pharmaceutically acceptable salt thereof, is combined with three additional therapeutic agents. In some embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In some embodiments, when a compound of the present disclosure is combined with one or more additional therapeutic agents as described herein, the components of the composition are administered as a simultaneous or sequential regimen. When administered sequentially, the combination may be administered in two or more administrations.

In some embodiments, a compound of the present disclosure is combined with one or more additional therapeutic agents in a unitary dosage form for simultaneous administration to a patient, for example as a solid dosage form for oral administration.

In some embodiments, a compound of the present disclosure is co-administered with one or more additional therapeutic agents.

Co-administration includes administration of unit dosages of the compounds disclosed herein before or after administration of unit dosages of one or more additional therapeutic agents. The compounds disclosed herein may be administered within seconds, minutes, or hours of the administration of one or more additional therapeutic agents. For example, in some embodiments, a unit dose of a compound disclosed herein is administered first, followed within seconds or minutes by administration of a unit dose of one or more additional therapeutic agents. Alternatively, in other embodiments, a unit dose of one or more additional therapeutic agents is administered first, followed by administration of a unit dose of a compound disclosed herein within seconds or minutes. In some embodiments, a unit dose of a compound disclosed herein is administered first, followed, after a period of hours (i.e., 1-12 hours), by administration of a unit dose of one or more additional therapeutic agents. In other embodiments, a unit dose of one or more additional therapeutic agents is administered first, followed, after a period of hours (i.e., 1-12 hours), by administration of a unit dose of a compound disclosed herein.

In some embodiments, a compound of Formula I, Ia, II, or IIa is formulated as a tablet, which may optionally contain one or more other compounds useful for treating the disease being treated. In certain embodiments, the tablet can contain another active ingredient for treating a HIV infection. In some embodiments, such tablets are suitable for once daily dosing.

Also provided herein are methods of treatment in which a compound of Formula I, Ia, II, or IIa, or a tautomer or pharmaceutically acceptable salt thereof, is given to a patient in combination with one or more additional therapeutic agents or therapy. In some embodiments, the total daily dosage of a compound of Formula I, Ia, II, or IIa, or a tautomer, or a pharmaceutically acceptable salt thereof, may be about 300 mg/day administered in a single dose for a human subject.

HIV Combination Therapy

In certain embodiments, a method for treating or preventing an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (i.e., one, two, three; one or two; or one to three) additional therapeutic agents. In one embodiment, a method for treating an HIV infection in a human or animal having or at risk of having the infection is provided, comprising administering to the human or animal a therapeutically effective amount of a compound disclosed herein, or a pharmaceutically acceptable salt thereof, in combination with a therapeutically effective amount of one or more (i.e., one, two, three; one or two; or one to three) additional therapeutic agents.

In one embodiment, pharmaceutical compositions comprising a compound disclosed herein, or a pharmaceutically acceptable salt thereof, in combination with one or more (i.e., one, two, three; one or two; or one to three) additional therapeutic agents, and a pharmaceutically acceptable carrier, diluent, or excipient are provided.

In certain embodiments, the present disclosure provides a method for treating an HIV infection, comprising administering to a patient in need thereof a therapeutically effective amount of a compound disclosed herein, or a pharmaceutically acceptable salt thereof, in combination with a therapeutically effective amount of one or more additional therapeutic agents which are suitable for treating an HIV infection.

In certain embodiments, the compounds disclosed herein are formulated as a tablet, which may optionally contain one or more other compounds useful for treating HIV. In certain embodiments, the tablet can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, or any combinations thereof.

In certain embodiments, such tablets are suitable for once daily dosing.

In some embodiments, the additional therapeutic agent may be an anti-HIV agent. In some embodiments, the additional therapeutic agent is selected from the group consisting of HIV combination drugs, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T cell receptors, TCR-T), latency reversing agents, compounds that target the HIV capsid (including capsid inhibitors), immune-based therapies, phosphatidylinositol 3-kinase (PI3K) inhibitors, alpha-4/beta-7 antagonists, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, HIV vif gene modulators, Vif dimerization antagonists, HIV-1 viral infectivity factor inhibitors, TAT protein inhibitors, HIV-1 Nef modulators, Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, pharmacokinetic enhancers, HIV gene therapy, HIV vaccines, and other HIV therapeutic agents, or any combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, or any combinations thereof.

HIV Combination Drugs

Examples of combination drugs include ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; Vacc-4x and romidepsin; and APH-0812, or any combinations thereof.

HIV Protease Inhibitors

Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, and TMC-310911.

HIV Reverse Transcriptase Inhibitors

Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, AIC-292, KM-023, PC-1005, and VM-1500.

Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, GS-9131, GS-9148, MK-8504 and KP-1461.

HIV Integrase Inhibitors

Examples of HIV integrase inhibitors include elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169 and cabotegravir.

Examples of HIV non-catalytic site, or allosteric, integrase inhibitors (NCINI) include CX-05045, CX-05168, and CX-14442.

HIV Entry Inhibitors

Examples of HIV entry (fusion) inhibitors include cenicriviroc, CCR5 inhibitors, gp41 inhibitors, CD4 attachment inhibitors, gp120 inhibitors, and CXCR4 inhibitors.

Examples of CCR5 inhibitors include aplaviroc, vicriviroc, maraviroc, cenicriviroc, PRO-140, adaptavir (RAP-101), nifeviroc (TD-0232), anti-GP120/CD4 or CCR5 bispecific antibodies, B-07, MB-66, polypeptide C25P, TD-0680, and vMIP (Haimipu).

Examples of gp41 inhibitors include albuvirtide, enfuvirtide, BMS-986197, enfuvirtide biobetter, enfuvirtide biosimilar, HIV-1 fusion inhibitors (P26-Bapc), ITV-1, ITV-2, ITV-3, ITV-4, PIE-12 trimer and sifuvirtide.

Examples of CD4 attachment inhibitors include ibalizumab and CADA analogs.

Examples of gp120 inhibitors include Radha-108 (receptol) 3B3-PE38, BanLec, bentonite-based nanomedicine, fostemsavir tromethamine, IQP-0831, and BMS-663068.

Examples of CXCR4 inhibitors include plerixafor, ALT-1188, N15 peptide, and vMIP (Haimipu).

HIV Maturation Inhibitors

Examples of HIV maturation inhibitors include BMS-955176 and GSK-2838232.

Latency Reversing Agents

Examples of latency reversing agents include histone deacetylase (HDAC) inhibitors, proteasome inhibitors such as velcade, protein kinase C (PKC) activators, Smyd2 inhibitors, BET-bromodomain 4 (BRD4) inhibitors, ionomycin, PMA, SAHA (suberanilohydroxamic acid, or suberoyl, anilide, and hydroxamic acid), AM-0015, ALT-803, NIZ-985, NKTR-255, IL-15 modulating antibodies, JQ1, disulfiram, amphotericin B, and ubiquitin inhibitors such as largazole analogs, GSK-343, GSK3beta inhibitors, SMAC mimetics, and Gal9.

Examples of HDAC inhibitors include romidepsin, vorinostat, and panobinostat.

Examples of PKC activators include indolactam, prostratin, ingenol B, and DAG-lactones.

Examples of GSK3 beta inhibitors include tideglusib, LY2090314, CHIR99021, and AZD1080.

Examples of SMAC mimetics include birinapant, AZD5582, LCL161, and AT406.

Capsid Inhibitors

Examples of capsid inhibitors include capsid polymerization inhibitors or capsid disrupting compounds, HIV nucleocapsid p7 (NCp7) inhibitors such as azodicarbonamide, HIV p24 capsid protein inhibitors, AVI-621, AVI-101, AVI-201, AVI-301, and AVI-CAN1-15 series.

Immune-Based Therapies

Examples of immune-based therapies include toll-like receptors modulators such as TLR1, TLR2, TLR3, TLR4, TLR5, TLR6, TLR7, TLR8, TLR9, TLR10, TLR11, TLR12, and TLR13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; rintatolimod, polymer polyethyleneimine (PEI); gepon; rintatolimod; IL-12; WF-10; VGV-1; MOR-22; BMS-936559; CYT-107; interleukin-15/Fc fusion protein; normferon; peginterferon alfa-2a; peginterferon alfa-2b; recombinant interleukin-15; RPI-MN; GS-9620; STING modulators; RIG-I modulators; NOD2 modulators; and IR-103.

Examples of TLR8 modulators include motolimod, resiquimod, 3M-051, 3M-052, MCT-465, IMO-4200, VTX-763, VTX-1463 and those disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 9,670,205 (Gilead Sciences Inc.), US20160289229 (Gilead Sciences Inc.), U.S. patent application Ser. No. 15/692,161 (Gilead Sciences Inc.), and U.S. patent application Ser. No. 15/692,093 (Gilead Sciences Inc.).

Phosphatidylinositol 3-Kinase (PI3K) Inhibitors

Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

Examples of Integrin alpha-4/beta-7 antagonists include PTG-100, TRK-170, abrilumab, etrolizumab, carotegrast methyl, and vedolizumab.

HIV Antibodies, Bispecific Antibodies, and "Antibody-Like" Therapeutic Proteins

Examples of HIV antibodies, bispecific antibodies, and "antibody-like" therapeutic proteins include DARTs®, DUOBODIES®, BITES®, XmAbs®, TandAbs®, Fab derivatives, bnABs (broadly neutralizing HIV-1 antibodies), BMS-936559, TMB-360, and those targeting HIV gp120 or gp41, antibody-Recruiting Molecules targeting HIV, anti-CD63 monoclonal antibodies, anti-GB virus C antibodies, anti-GP120/CD4, CCR5 bispecific antibodies, anti-nef single domain antibodies, anti-Rev antibody, camelid derived anti-CD18 antibodies, camelid-derived anti-ICAM-1 antibodies, DCVax-001, gp140 targeted antibodies, gp41-based HIV therapeutic antibodies, human recombinant mAbs (PGT-121), ibalizumab, Immuglo, and MB-66.

Further examples include bavituximab, UB-421, C2F5, 2G12, C4E10, C2F5+C2G12+C4E10, 8ANC195, 3BNC117, 3BNC60, 10-1074, PGT145, PGT121, PGT-151, PGT-133, MDX010 (ipilimumab), DH511, N6, VRC01 PGDM1400, A32, 7B2, 10E8, 10E8v4, CAP256-VRC26.25, DRVIA7, VRC-07-523, VRC-HIVMAB080-00-AB, VRC-HIVMAB060-00-AB, MGD-014 and VRC07.

Additional examples of HIV bispecific antibodies include MGD014.

Pharmacokinetic Enhancers

Examples of pharmacokinetic enhancers include cobicistat and ritonavir.

HIV Vaccines

Examples of HIV vaccines include peptide vaccines, recombinant subunit protein vaccines, live vector vaccines, DNA vaccines, CD4-derived peptide vaccines, vaccine combinations, rgp120 (AIDSVAX), ALVAC HIV (vCP1521)/AIDSVAX B/E (gp120) (RV144), monomeric gp120 HIV-1 subtype C vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), Pennvax-G, Pennvax-GP, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), gp140[delta]V2.TV1+MF-59, rVSVIN HIV-1 gag vaccine, SeV-Gag vaccine, AT-20, DNK-4, ad35-Grin/ENV, TBC-M4, HIVAX, HIVAX-2, NYVAC-HIV-PT1, NYVAC-HIV-PT4, DNA-HIV-PT123, rAAV1-PG9DP, GOVX-B11, GOVX-B21, TVI-HIV-1, Ad-4 (Ad4-env Clade C+Ad4-mGag), EN41-UGR7C, EN41-FPA2, PreVaxTat, AE-H, MYM-V101, CombiHIVvac, ADVAX, MYM-V201, MVA-CMDR, DNA-Ad5 gag/pol/nef/nev (HVTN505), MVATG-17401, ETV-01, CDX-1401, rcAD26.MOS1.HIV-Env, Ad26.Mod.HIV vaccine, AGS-004, AVX-101, AVX-201, PEP-6409, SAV-001, ThV-01, TL-01, TUTI-16, VGX-3300, IHV-001, and virus-like particle vaccines such as pseudovirion vaccine, CombiVICH-vac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI.

Additional HIV Therapeutic Agents

Examples of additional HIV therapeutic agents include the compounds disclosed in WO 2004/096286 (Gilead Sciences), WO 2006/015261 (Gilead Sciences), WO 2006/110157 (Gilead Sciences), WO 2012/003497 (Gilead Sciences), WO 2012/003498 (Gilead Sciences), WO 2012/145728 (Gilead Sciences), WO 2013/006738 (Gilead Sciences), WO 2013/159064 (Gilead Sciences), WO 2014/100323 (Gilead Sciences), US 2013/0165489 (University of Pennsylvania), US 2014/0221378 (Japan Tobacco), US 2014/0221380 (Japan Tobacco), WO 2009/062285 (Boehringer Ingelheim), WO 2010/130034 (Boehringer Ingelheim), WO 2013/006792 (Pharma Resources), US 20140221356 (Gilead Sciences), US 20100143301 (Gilead Sciences) and WO 2013/091096 (Boehringer Ingelheim).

Examples of other drugs for treating HIV include acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, ABX-464, AG-1105, APH-0812, BIT-225, CYT-107, HGTV-43, HPH-116, HS-10234, IMO-3100, IND-02, MK-1376, MK-8507, MK-8591, NOV-205, PA-1050040 (PA-040), PGN-007, SCY-635, SB-9200, SCB-719, TR-452, TEV-90110, TEV-90112, TEV-90111, TEV-90113, RN-18, Immuglo, and VIR-576.

Gene Therapy and Cell Therapy

Gene therapy and cell therapy include the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; and genetic approaches to modify cellular activity to further alter endogenous immune responsiveness against the infection.

Examples of dendritic cell therapy include AGS-004.

Gene Editors

Examples of gene editing systems include a CRISPR/Cas9 system, a zinc finger nuclease system, a TALEN system, a homing endonucleases system, and a meganuclease system.

Examples of HIV targeting CRISPR/Cas9 systems include EBT101.

CAR-T Cell Therapy

CAR-T cell therapy includes a population of immune effector cells engineered to express a chimeric antigen receptor (CAR), wherein the CAR comprises an HIV antigen-binding domain. The HIV antigens include an HIV envelope protein or a portion thereof, gp120 or a portion thereof, a CD4 binding site on gp120, the CD4-induced binding site on gp120, N glycan on gp120, the V2 of gp120, and the membrane proximal region on gp41. In some embodiments, the immune effector cell is a T cell or an NK cell. In some embodiments, the T cell is a CD4+ T cell, a CD8+ T cell, or a combination thereof.

Examples of HIV CAR-T cell therapy include VC-CAR-T.

TCR-T Cell Therapy

TCR-T cell therapy includes T cells engineered to target HIV derived peptides present on the surface of virus-infected cells.

It will be appreciated by one of skill in the art that the additional therapeutic agents listed above may be included in more than one of the classes listed above. The particular classes are not intended to limit the functionality of those compounds listed in those classes.

In a specific embodiment, a compound disclosed herein, or a pharmaceutically acceptable salt thereof, is combined with an HIV nucleoside or nucleotide inhibitor of reverse transcriptase and an HIV non-nucleoside inhibitor of reverse transcriptase. In another specific embodiment, a compound disclosed herein, or a pharmaceutically acceptable salt thereof, is combined with an HIV nucleoside or nucleotide inhibitor of reverse transcriptase, and an HIV protease inhibiting compound. In an additional embodiment, a compound disclosed herein, or a pharmaceutically acceptable salt thereof, is combined with an HIV nucleoside or nucleotide inhibitor of reverse transcriptase, an HIV non-nucleoside inhibitor of reverse transcriptase, and a pharmacokinetic enhancer. In certain embodiments, a compound disclosed herein, or a pharmaceutically acceptable salt thereof, is combined with at least one HIV nucleoside inhibitor of reverse transcriptase, an integrase inhibitor, and a pharmacokinetic enhancer. In another embodiment, a compound disclosed herein, or a pharmaceutically acceptable salt thereof, is combined with two HIV nucleoside or nucleotide inhibitors of reverse transcriptase.

In a particular embodiment, a compound disclosed herein, or a pharmaceutically acceptable salt thereof, is combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY® (bictegravir, emtricitabine, tenofovir alafenamide); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In a particular embodiment, a compound disclosed herein, or a pharmaceutically acceptable salt thereof, is combined with abacavir sulfate, tenofovir, tenofovir disoproxil, tenofovir disoproxil fumarate, tenofovir disoproxil hemifumarate, tenofovir alafenamide, tenofovir alafenamide hemifumarate, or bictegravir.

In a particular embodiment, a compound disclosed herein, or a pharmaceutically acceptable salt thereof, is combined with tenofovir, tenofovir disoproxil, tenofovir disoproxil fumarate, tenofovir alafenamide, tenofovir alafenamide hemifumarate, or bictegravir.

In a particular embodiment, a compound disclosed herein, or a pharmaceutically acceptable salt thereof, is combined with a first additional therapeutic agent selected from the group consisting of abacavir sulfate, tenofovir, tenofovir disoproxil, tenofovir disoproxil fumarate, tenofovir alafenamide, tenofovir alafenamide hemifumarate, and bictegravir and a second additional therapeutic agent selected from the group consisting of emtricitabine and lamivudine.

In a particular embodiment, a compound disclosed herein, or a pharmaceutically acceptable salt thereof, is combined with a first additional therapeutic agent selected from the group consisting of tenofovir, tenofovir disoproxil, tenofovir disoproxil fumarate, tenofovir alafenamide, tenofovir alafenamide hemifumarate, and bictegravir and a second additional therapeutic agent, wherein the second additional therapeutic agent is emtricitabine.

A compound as disclosed herein may be combined with one or more additional therapeutic agents in any dosage amount of the compound (e.g., from 1 mg to 500 mg of compound).

In certain embodiments, a compound disclosed herein, or a pharmaceutically acceptable salt thereof, is combined with 5-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 10 mg tenofovir alafenamide fumarate, tenofovir alafenamide hemifumarate, or tenofovir alafenamide, and 200 mg emtricitabine. In certain embodiments, a compound disclosed herein, or a pharmaceutically acceptable salt thereof, is combined with 25 mg tenofovir alafenamide fumarate, tenofovir alafenamide hemifumarate, or tenofovir alafenamide, and 200 mg emtricitabine. A compound as disclosed herein (i.e., a compound of Formula I, II, or IIA) may be combined with the agents provided herein in any dosage amount of the compound (i.e., from 1 mg to 500 mg of compound) as if each combination of dosages were specifically and individually listed.

In certain embodiments, a compound disclosed herein, or a pharmaceutically acceptable salt thereof, is combined with 200-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, a compound disclosed herein, or a pharmaceutically acceptable salt thereof, is combined with 300 mg tenofovir disoproxil fumarate, tenofovir disoproxil hemifumarate, or tenofovir disoproxil, and 200 mg emtricitabine. A compound as disclosed herein (i.e., a compound of Formula I, II, or IIa) may be combined with the agents provided herein in any dosage amount of the compound (i.e., from 1 mg to 500 mg of compound) as if each combination of dosages were specifically and individually listed.

VII. Compound Preparation

Some embodiments of the present disclosure are directed to processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," $4^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in the schemes below, and the particular examples that follow.

List of Abbreviations and Acronyms
ACN Acetonitrile
AcOH Acetic acid
$Al_2O_3$ Alumina
aq Aqueous
Boc tert-Butyl carbonate
$Boc_2O$ di-tert-Butyl dicarbonate
BnOH Benzyl alcohol
Brine Water saturated with sodium chloride
t-BuOK Potassium tert-butoxide
° C. Degrees Celsius
CDI Carbonyl-1,1'-diimidazole
$Cs_2CO_3$ Cesium carbonate
$CH_2Cl_2$ Dichloromethane
$CH_3CN$ Acetonitrile
COMU (1-Cyano-2-ethoxy-2-oxoethylidenaminooxy)dimethylamino-morpholino-carbenium hexafluorophosphate
$Cs_2CO_3$ Cesium carbonate
CuBr Copper(I) bromide
CuI Copper(I) iodide
$Cu_2O$ Copper(I) oxide
$CuSO_4$ Copper(II) sulfate
DCC Dicyclohexylcarbodiimide DCM dichloromethane
DME 1,2-dimethoxymethane
DMF N,N-dimethylformamide
DIBAL-H Diisobutylaluminum hydride
DIEA N, N-Diisopropylethylamine
DIPEA N, N-Diisopropylethylamine
DMSO Dimethylsulfoxide
DMSO-$d_6$ Deuterated dimethylsulfoxide
d Doublet
dd Doublet of doublets
ddd Doublet of doublet of doublets
dq Doublet of quadruplets
dt Doublet of triplets
EA Ethyl Acetate
EDC 1-Ethyl-3-(3-dimethylaminopropyl)carbodiimide
eq Equivalents
Et Ethyl
$Et_3N$ Trimethylamine
$Et_2O$ Diethyl ether
EtOAc Ethyl Acetate
EtOH Ethanol
g Gram
H Hydrogen
$H_2$ Molecular hydrogen
HATU 1-[Bis(dimethylamino)methylene]-1H-1,2,3-triazolo[4,5-b]pyridinium 3-oxide hexafluorophosphate
HCl Hydrogen Chloride or Hydrochloric Acid
Hex n-Hexane
$H_2O$ Water
$H_2O_2$ Hydrogen peroxide
HOBt Hydroxybenzotriazole
HPLC High Pressure Liquid Chromatography
Hz Hertz
$iPr_2NEt$ Diisopropylethylamine
$K_2CO_3$ potassium carbonate
LiCl Lithium Chloride
m Multiplet
M Molar
mCPBA Meta-chloroperoxybenzoic acid
Me Methyl
MeCN Acetonitrile
MHz Megahertz
$MgSO_4$ Magnesium Sulfate
MeOH Methanol
Methanol-$d_4$ Deuterated methanol
min Minutes
mg Milligram
mL Milliliter
mmol Millimole
MS Mass Spectrometry
m/z Mass-to-charge ratio
N Normal
NaCl Sodium Chloride
$NaHCO_3$ Sodium Hydrogen Carbonate or Sodium Bicarbonate
NaOH Sodium Hydroxide
NaOMe Sodium Methoxide
$Na_2SO_4$ Sodium Sulfate
NBS N-bromosuccinimide
$NH_4Cl$ Ammonium Chloride
n-Hex n-Hexane
$NH_4OH$ Ammonium hydroxide
NMM N-methylmorpholine
NMR Nuclear magnetic resonance
Pd/C Palladium on carbon
$PdCl_2[P(cy)_3]_4$ Dichlorobis(tricyclohexylphosphine)palladium(II)
$Pd_2(dba)_3$ bis-Palladium(0)-tris-dibenzylidene acetone
$Pd(OAc)_2$ Palladium(II) acetate
$Pd(dppf)Cl_2$ [1,1'-Bis(diphenylphosphino)ferrocene]dichloropalladium(II)
$Pd_2(PPh_3)_2Cl_2$ Palladium(II) bis-triphenylphosphine dichloride complex
$Pd(PPh_3)_4$ Palladium(0) tetrakis-triphenylphosphine
Ph Phenyl
P(o-Tol)$_3$ Tris(o-tolyl)phosphine
$PPh_3$ Triphenylphosphine
q Quadruplet
$Rh(PPh_3)_3Cl$ Rhodium(I) tris-triphenylphosphine chloride complex
rt Room temperature
r.t. Room temperature
RT Room temperature
s Singlet
t Triplet
TEA Triethylamine
TFA Trifluoroacetic acid
TFAA Trifluoroacetic anhydride
THF Tetrahydrofuran
TLC Thin layer chromatography
TMS Trimethylsilyl
tt Triplet of triplets
wt. Weight
Xantphos 2-Dicyclohexylphosphino-2',4',6'-triisopropyl-1,1'-biphenyl
$^1$H Proton
° C. Degrees Celsius
δ NMR chemical shift in parts per million General Synthetic Schemes General Reaction Schemes I-V are provided as further embodiments of the present disclosure and illustrate general methods which were used to prepare certain compounds of the present disclosure and which can be used to prepare additional compounds of the present disclosure. Each of the variables (e.g. $R^1$, $R^2$, $R^3$, $R^4$) of the compounds disclosed in General Reaction Schemes I-V are as defined herein.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure.

Typical embodiments of compounds disclosed herein may be synthesized using the general reaction schemes described below. It will be apparent to a skilled artisan given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments disclosed in the present disclosure, inspection of the structure of the compound to be synthesized will provide the identity of each substituent group. The identity of the final product will generally render apparent the identity of the necessary starting materials by a simple process of inspection, given the examples herein.

The terms "solvent", "inert organic solvent", or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, and the like). Unless specified to the contrary, the solvents used in the reactions of the present disclosure are inert organic solvents, and the reactions are carried out under an inert gas, preferably nitrogen or argon.

General Reaction Scheme I

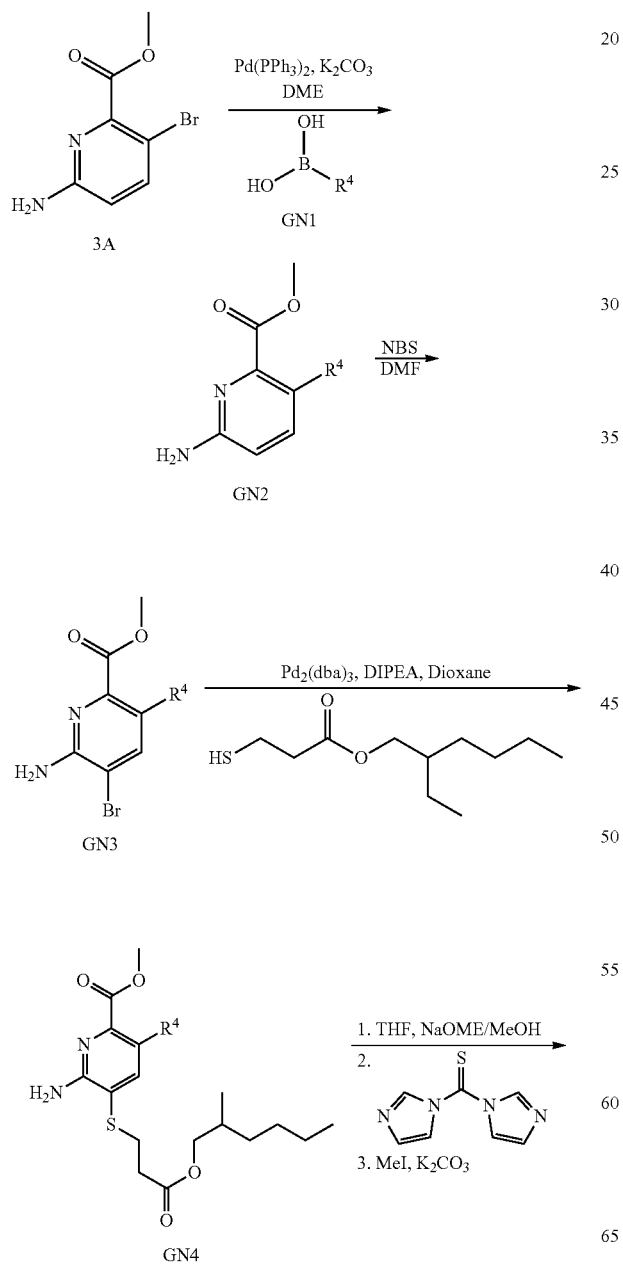

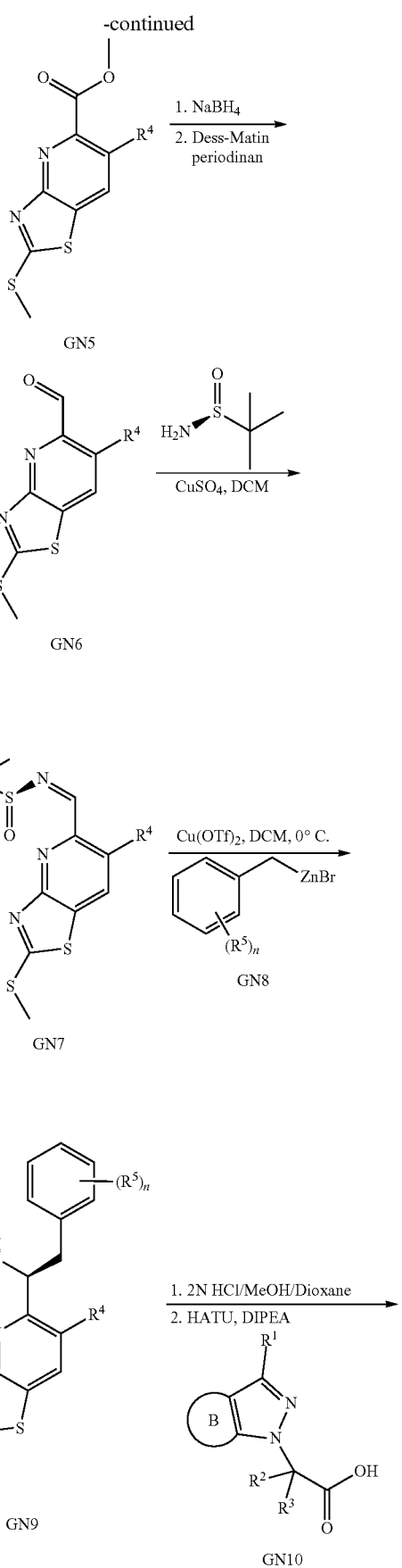

General Reaction Scheme II

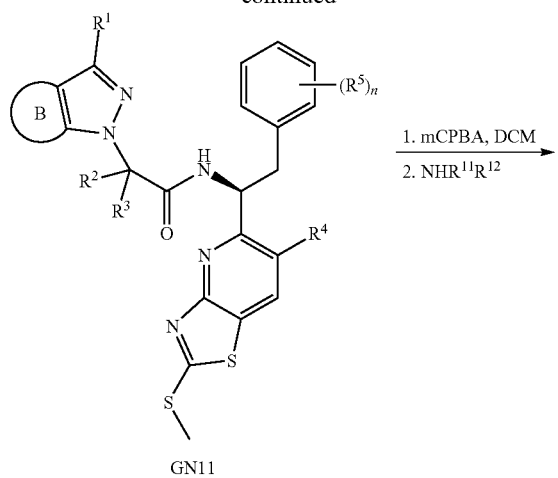

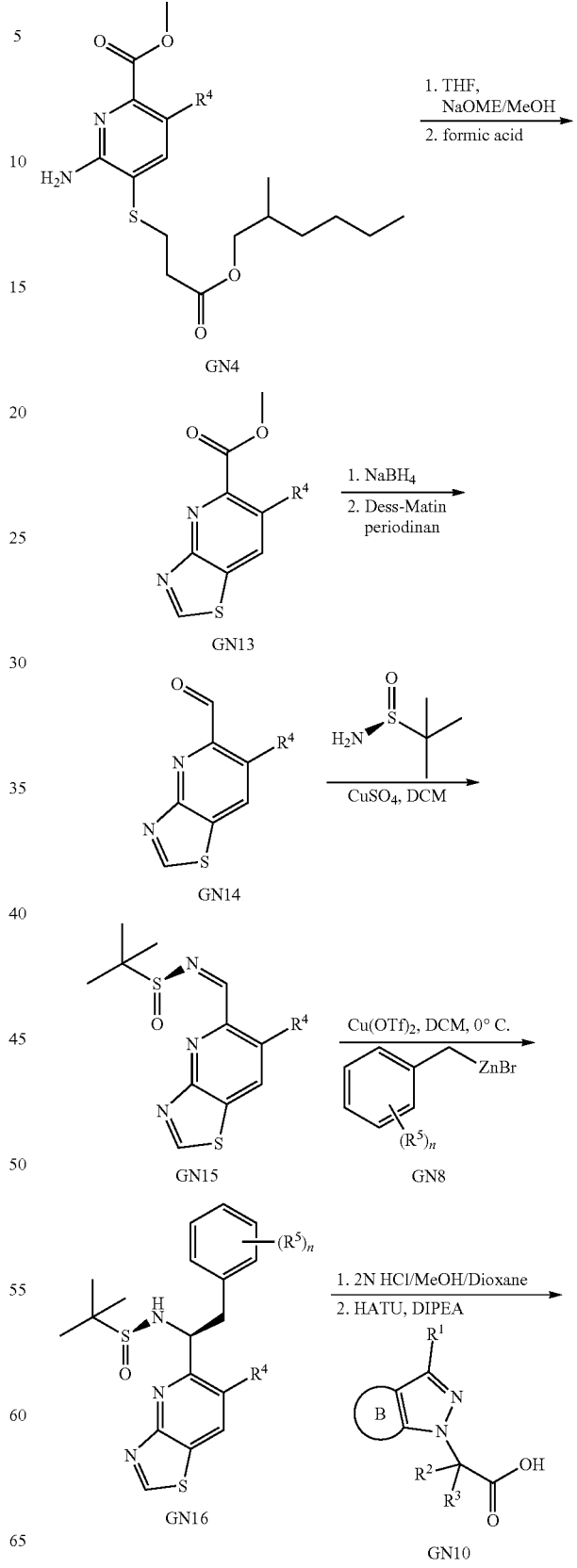

General Reaction Scheme 1 depicts methods to prepare compounds GN12, a subset of Formula 1. Compound 3A may undergo a palladium-catalyzed cross coupling with aryl boronic acid GN1 to form GN2. GN2 can be halogenated by an electrophilic halogen source such as NBS to generate GN3. GN3 can then be converted to thiazolopyridine GN5 by the three-step process depicted. Ester GN5 can be converted aldehyde GN6 by a two-step reduction/oxidation sequence. The aldehyde is converted to N-tert-butanesulfinyl aldimine GN7 by condensation with tert-butanesulfinamide. By treatment with a benzyl zinc reagent GN8 and a Cu(II) catalyst, GN7 is converted to GN9. Under acidic conditions, GN9 is converted to the free amine, which undergoes HATU-mediated coupling with GN10 to provide GN11. The sulfide of GN11 is oxidized with an oxidizing agent such as mCPBA, then displaced with a primary or secondary amine to yield GN12.

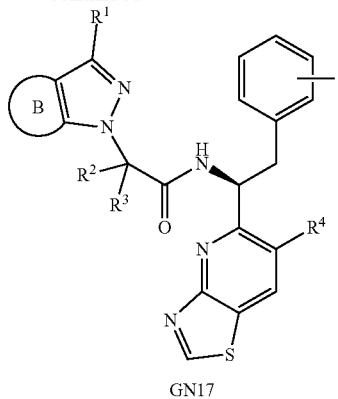

GN17

General Reaction Scheme 2 depicts methods to prepare compounds GN17, a subset of Formula 1. GN4 can be converted to thiazolopyridine GN15 by the two-step process depicted. Ester GN1 can be converted aldehyde G14 by a two-step reduction/oxidation sequence. The aldehyde is converted to N-tert-butanesulfinyl aldimine GN15 by condensation with tert-butanesulfinamide. By treatment with a benzyl zinc reagent GN8 and a Cu(II) catalyst, GN15 is converted to GN16. Under acidic conditions, GN16 is converted to the free amine, which undergoes HATU-mediated coupling with GN10 to provide GN7.

General Reaction Scheme III

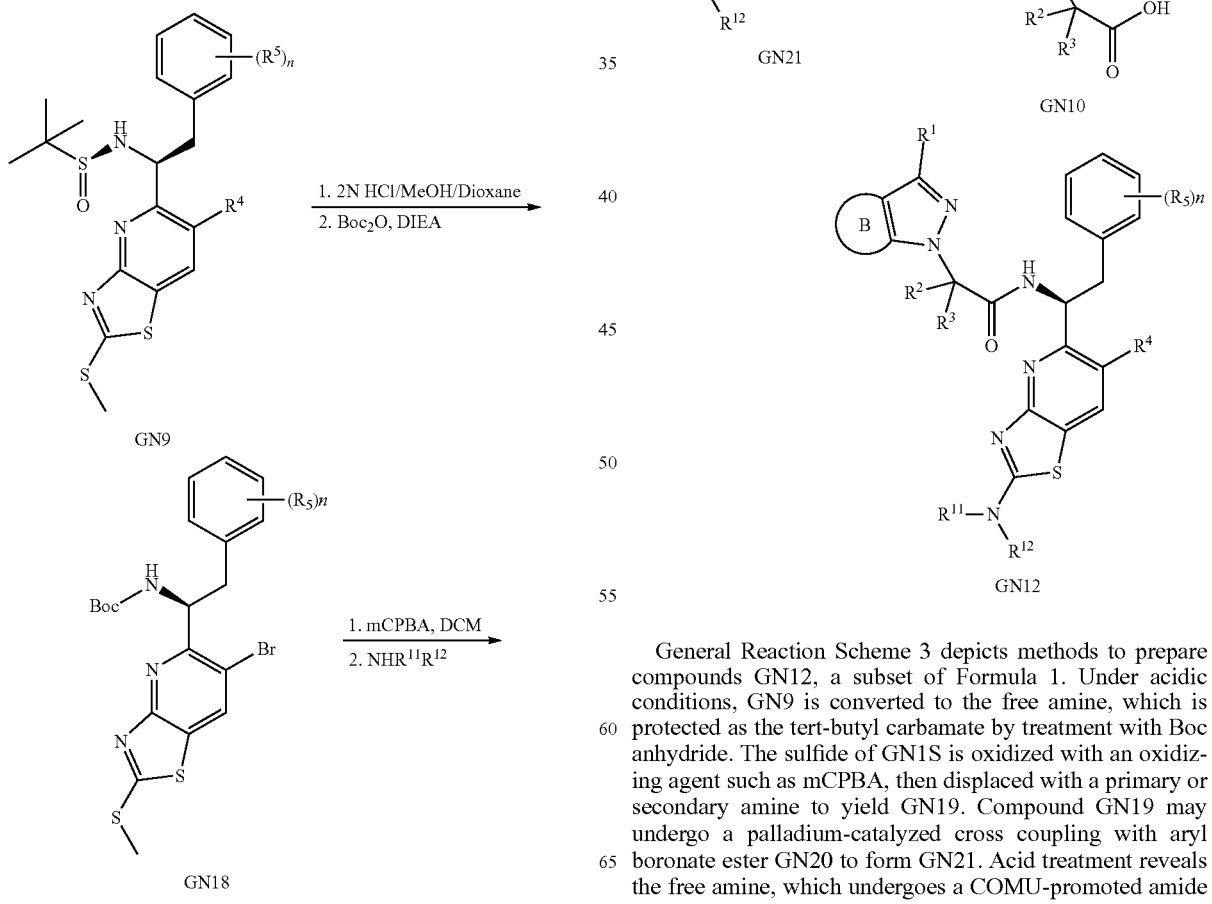

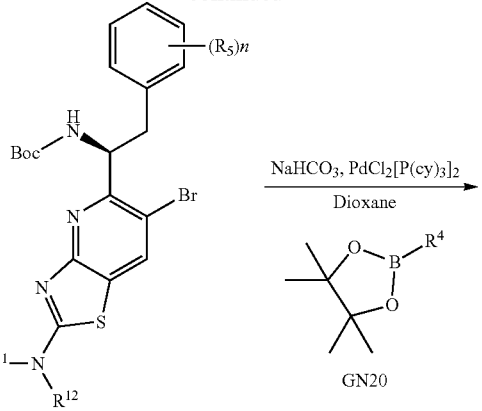

General Reaction Scheme 3 depicts methods to prepare compounds GN12, a subset of Formula 1. Under acidic conditions, GN9 is converted to the free amine, which is protected as the tert-butyl carbamate by treatment with Boc anhydride. The sulfide of GN1S is oxidized with an oxidizing agent such as mCPBA, then displaced with a primary or secondary amine to yield GN19. Compound GN19 may undergo a palladium-catalyzed cross coupling with aryl boronate ester GN20 to form GN21. Acid treatment reveals the free amine, which undergoes a COMU-promoted amide coupling to provide GN12.

General Reaction Scheme IV

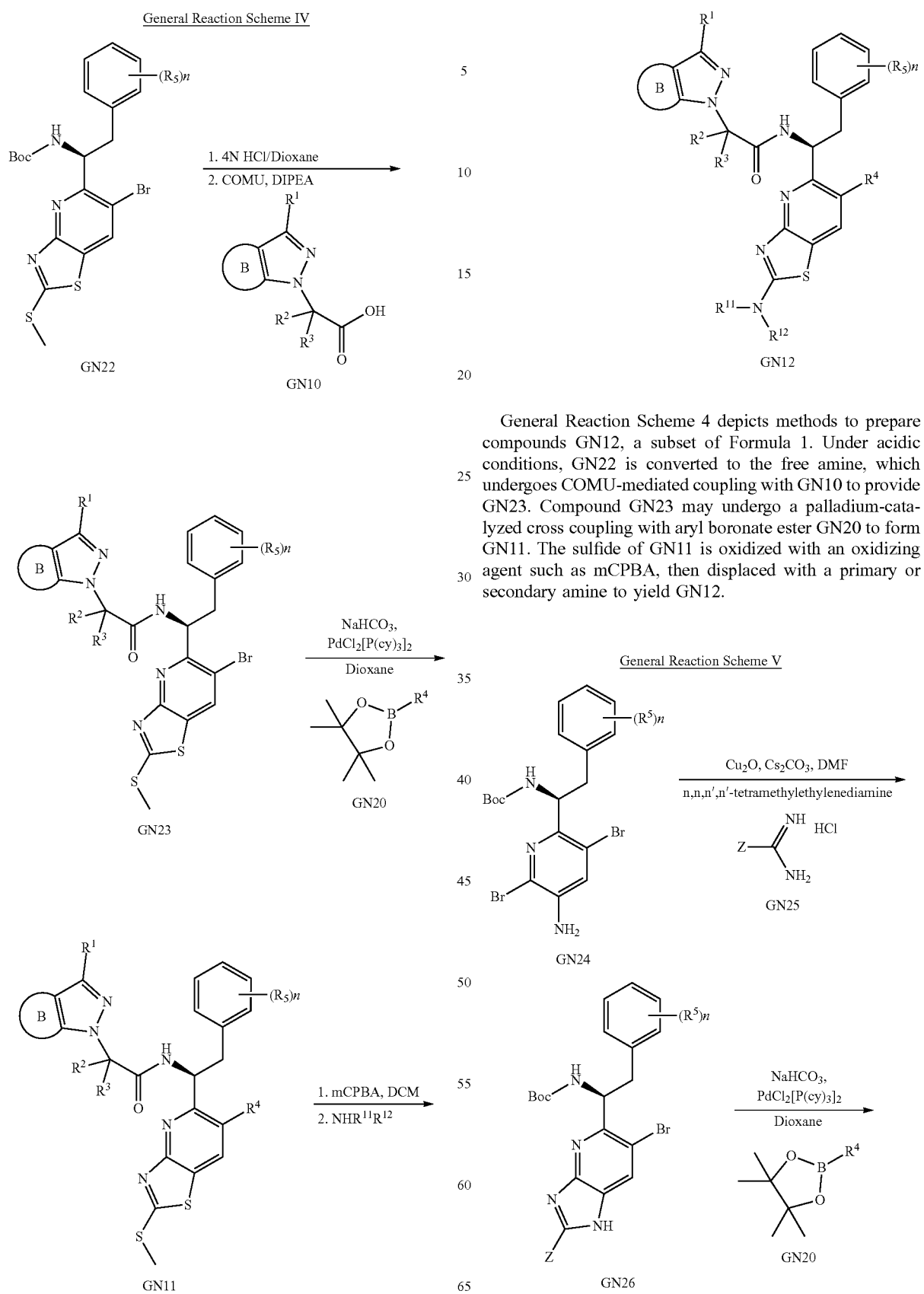

General Reaction Scheme 4 depicts methods to prepare compounds GN12, a subset of Formula 1. Under acidic conditions, GN22 is converted to the free amine, which undergoes COMU-mediated coupling with GN10 to provide GN23. Compound GN23 may undergo a palladium-catalyzed cross coupling with aryl boronate ester GN20 to form GN11. The sulfide of GN11 is oxidized with an oxidizing agent such as mCPBA, then displaced with a primary or secondary amine to yield GN12.

General Reaction Scheme V

-continued

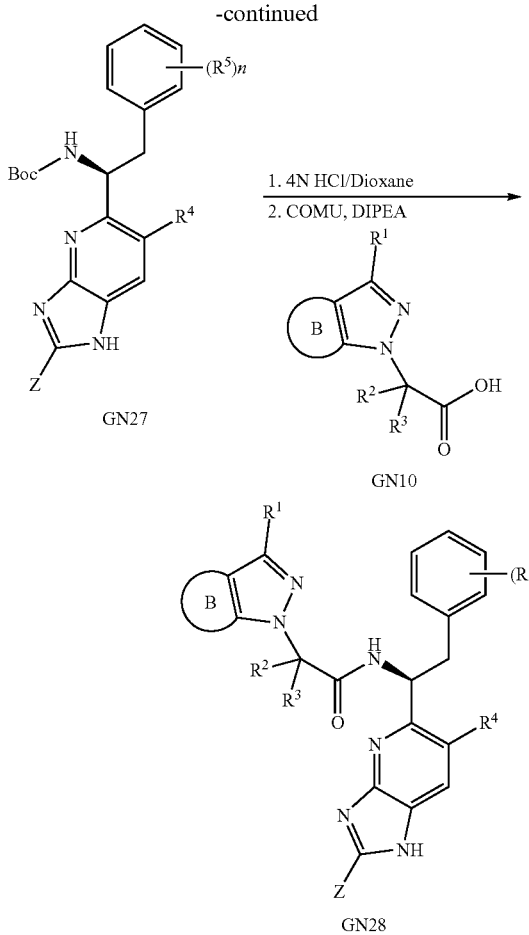

General Reaction Scheme 5 depicts methods to prepare compounds GN28, a subset of Formula 1. Dibromide GN24 is converted into azabenzimidazole GN26 in a copper-promoted condensation with amidine GN25. Compound GN25 may undergo a palladium-catalyzed cross coupling with aryl boronate ester GN20 to form GN27. Under acidic conditions, GN27 is converted to the free amine, which undergoes COMU-mediated coupling with GN10 to provide GN28.

VIII. Examples

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Example 1

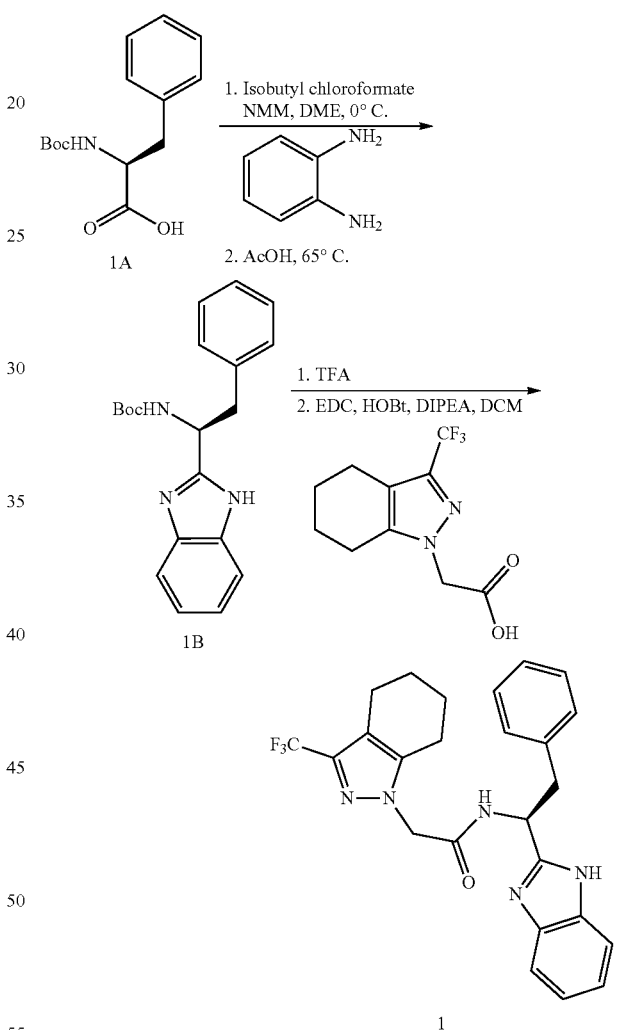

Synthesis of (S)-tert-butyl (1-(1H-benzo[d]imidazol-2-yl)-2-phenylethyl)carbamate (1B): To a solution of (S)-2-((tert-butoxycarbonyl)amino)-3-phenylpropanoic acid (440 mg, 1.66 mmol) and 4-methylmorpholine (0.24 mL, 2.2 mmol) in DME (1.5 mL) at 0° C., isobutyl chloroformate (0.26 mL, 2 mmol) was added to the solution slowly. After 30 minutes, benzene-1,2-diamine (180 mg, 1.66 mmol) was added to the mixture. The reaction was stirred for 2 hours. The reaction was diluted with EtOAc (100 mL) and washed with water (50 mL) and brine (50 mL). The organic layer was separated and was concentrated to dryness in vacuo.

The crude product was dissolved in acetic acid (3 mL) and heated at 65° C. for 1 hour. The solvent was removed and the reaction mixture was purified on preparative reverse phase HPLC using 20-80% B over 20 min. (A=0.10% TFA/H2O; B=0.10% TFA/Acetonitrile) to provide Compound 1B. MS (m/z) 338 [M+H]+.

Synthesis of (S)—N-(1-(1H-benzo[d]imidazol-2-yl)-2-phenylethyl)-2-(3-(trifluoromethyl)-4,5,6,7-tetrahydro-1H-indazol-1-yl)acetamide (1): A solution of Compound 1B (310 mg, 0.92 mmol) in TFA (2 mL) was stirred for 1 hour. The solvent was removed and concentrated to dryness in vacuo. The TFA salt of crude product was dissolved in DCM (3 mL), DIEA (0.35 mL, 2 mmol), 1-hydroxybenzotriazole (89 mg, 0.65 mmol) and N-(3-dimethylaminopropyl)-N'-ethylcarbodiimide hydrochloride (126 mg, 0.65 mmol) were added to the mixture. The reaction was stirred for overnight. The reaction was diluted with EtOAc (100 mL) and washed with water (50 mL) and brine (50 mL). The organic layer was separated and was concentrated to dryness in vacuo. The residue was purified by flash column chromatography to afford Compound 1. MS (m/z) 468 [M+H]+. $^1$H NMR (400 MHz, DMSO-$d_6$) δ 12.32 (s, 1H), 8.96 (d, 1H), 7.64-7.35 (m, 2H), 7.29-7.05 (m, 7H), 5.37-5.19 (m, 1H), 4.90-4.58 (m, 2H), 3.42 (dd, 1H), 3.07 (dd, 1H), 2.43-2.03 (m, 2H), 1.59 (s, 4H).

Example 2

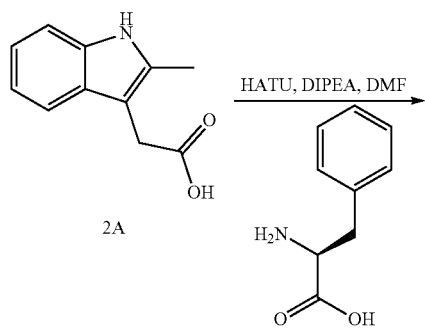

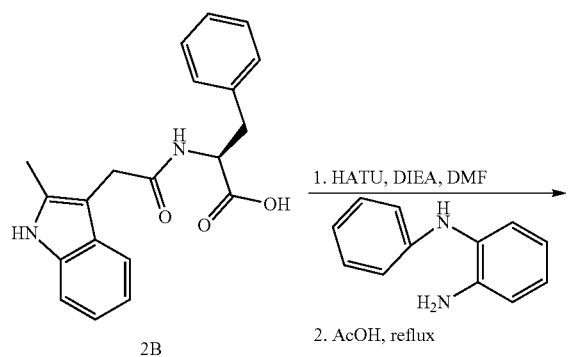

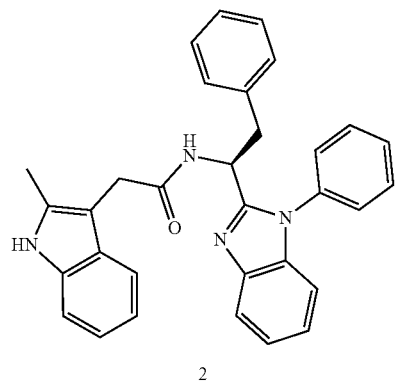

2

Synthesis of (S)-2-(2-(2-methyl-1H-indol-3-yl)acetamido)-3-phenylpropanoic acid (2B): To a solution of 2-(2-methyl-1H-indol-3-yl)acetic acid (3.56 g, 18.83 mmol), diisopropylethylamine (8.2 mL, 47 mmol) and HATU (7.52 g, 19.8 mmol) in DMF (50 mL), L-Phenylalanine (3.27 g, 19.8 mmol) was added to the solution after 10 minutes. The reaction was stirred at room temperature for overnight. The reaction was acidified at pH~4. The reaction was extracted with EtOAc (100 mL three time). The organic layer was separated and was concentrated. The crude product was used without further purification. MS (m/z) 337 [M+H]+.

Synthesis of (S)-2-(2-methyl-1H-indol-3-yl)-N-(2-phenyl-1-(1-phenyl-1H-benzo[d]imidazol-2-yl)ethyl)acetamide (2): To a solution of 2B (1.064 g, 3.16 mmol), diisopropylethylamine (0.83 mL, 4.74 mmol) and HATU (1.44 g, 3.78 mmol) in DMF (5 mL), N1-phenylbenzene-1,2-diamine (757 mg, 4.1 mmol) was added to the solution. The reaction was stirred at room temperature for overnight. The reaction was diluted with EtOAc (100 mL) and washed with water (50 mL) and brine (50 mL). The organic layer was separated and was concentrated to dryness in vacuo. The crude product was dissolved in acetic acid (20 mL) and heated at 65° C. for 2.5 hour. The solvent was removed and the reaction mixture was purified on preparative reverse phase HPLC using 20-80% B over 20 min. (A=0.1% TFA/H$_2$O; B=0.1% TFA/Acetonitrile) to provide Compound 2. MS (m/z) 485 [M+H]+. $^1$H NMR (400 MHz, DMSO-$d_6$) δ 10.68 (s, 1H), 8.92 (d, 1H), 7.79 (d, 1H), 7.61-7.41 (m, 3H), 7.41-7.20 (m, 3H), 7.20-6.99 (m, 5H), 6.96-6.72 (m, 4H), 4.98 (q, 1H), 3.39 (d, 2H), 3.25-3.03 (m, 2H), 2.21 (s, 3H).

Example 3

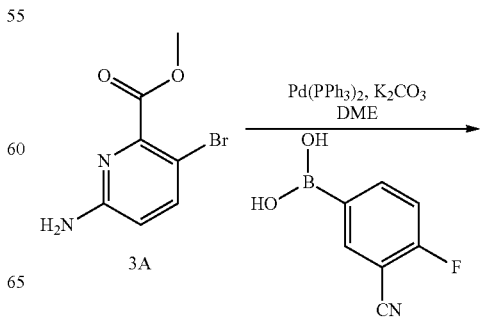

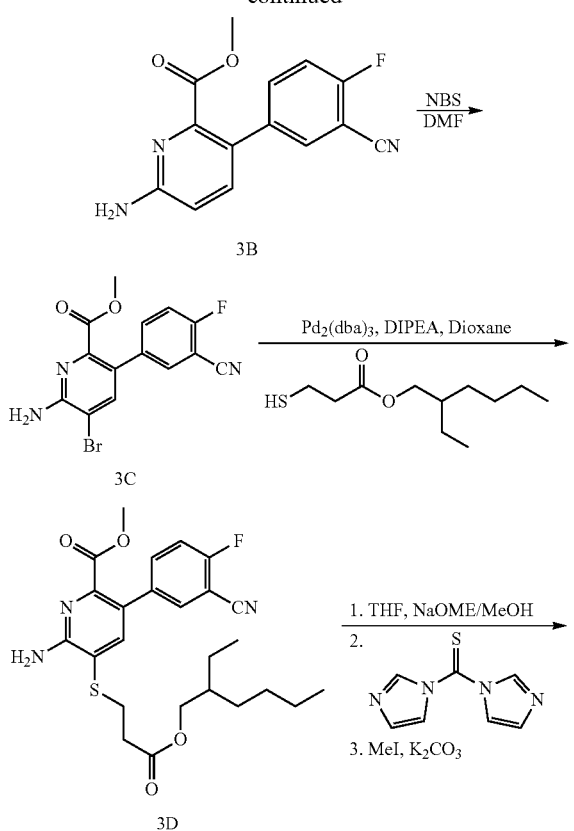
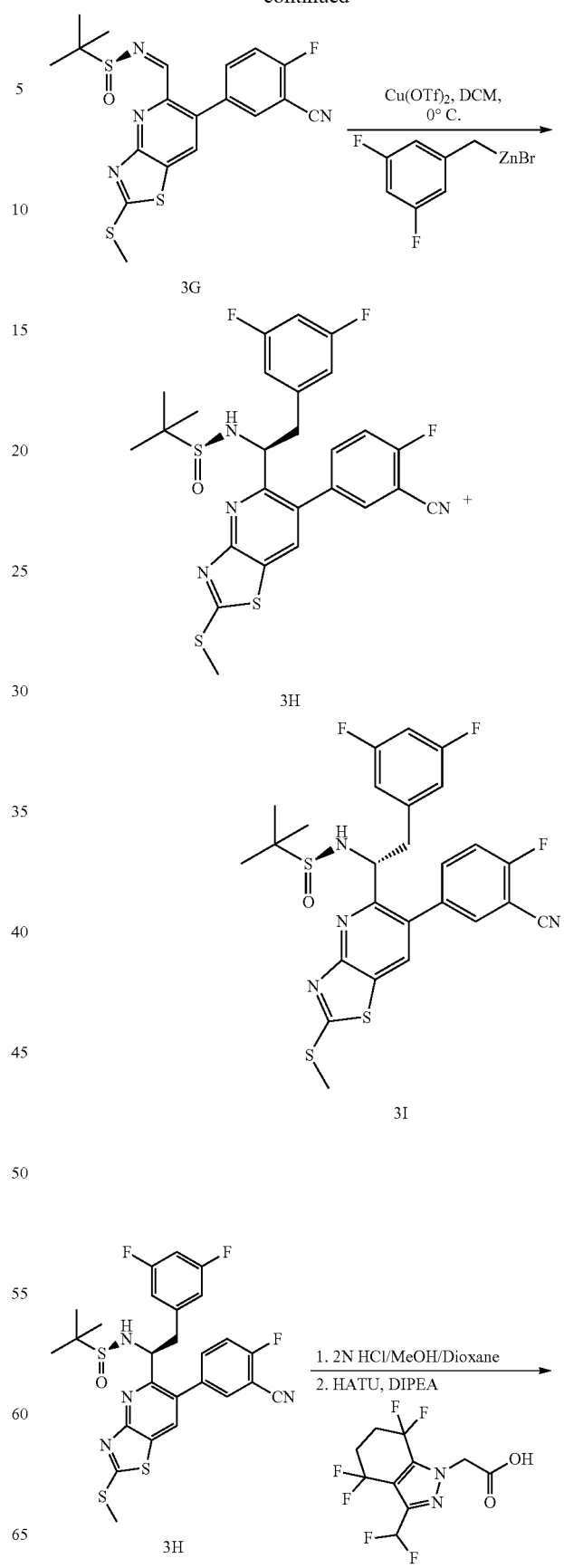

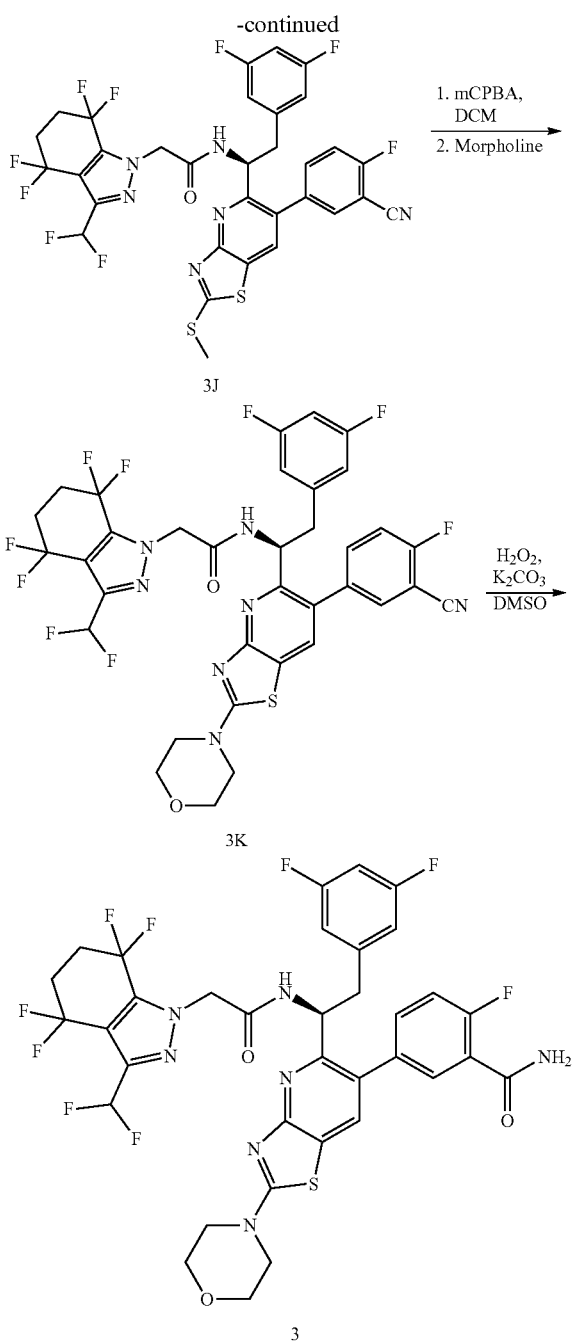

Synthesis of methyl 6-amino-3-(3-cyano-4-fluorophenyl) picolinate (3B): Methyl 6-amino-3-bromopicolinate (3 g, 13 mmol) and (3-cyano-4-fluorophenyl)boronic acid (2.5 g, 15 mmol) were dissolved in 1,2-dimethoxyethane. 1N aq. $K_2CO_3$ (26 mL, 26 mmol) was added and the reaction was degassed by evacuation and purged with $N_2$ (3×). $Pd(PPh_3)_2Cl_2$ (456 mg, 0.65 mmol) was added and the reaction was degassed again. The reaction was heated at 80° C. overnight. The cooled reaction mixture was filtered through celite and washed with EtOAc. The filtrate was partitioned between EtOAc and $H_2O$. The aqueous layer was extracted 2× with EtOAc. The combined organic layers were washed with brine, dried over $MgSO_4$, filtered and concentrated. The residue was purified by flash column using EtOAc/hex. The pure fractions were combined, concentrated, and dried on high vacuum for 3 hrs to provide 3B. MS (m/z) 272 [M+H]+.

Synthesis of methyl 6-amino-5-bromo-3-(3-cyano-4-fluorophenyl)picolinate (3C): To a solution of 3B (1.1 g, 4 mmol) in DMF (6 mL), N-Bromosuccinimide (0.72 g, 4 mmol) was added. After 1 hour, the mixture was diluted with EtOAc (50 mL) and washed with brine and water. The organic layer was separated and was concentrated to dryness in vacuo. The residue was purified by flash column chromatography to afford 3C. MS (m/z) 350 [M+H]+.

Synthesis of methyl 6-amino-3-(3-cyano-4-fluorophenyl)-5-((3-((2-ethylhexyl)oxy)-3-oxopropyl)thio)picolinate (3D): To a round bottom flask were added 3C (4.26 g, 12.2 mmol), i-$Pr_2NEt$ (4.25 ml, 24.4 mmol) and 1,4-dioxane (60 mL). The mixture was evacuated and backfilled with nitrogen (3 cycles). Catalyst $Pd_2(dba)_3$ (559 mg, 0.61 mmol), Xantphos (706 mg, 1.22 mmol) and 2-ethylhexyl 3-mercaptopropionate (2.8 mL, 12.2 mmol) were added and then the batch was degassed twice more. The reaction was gently refluxed for 6 hours and then allowed to cool to room temperature after checking consumption of starting material by TLC analysis. The mixture was filtered through glass paper filter and washed with EtOAc. The filtrate was concentrated to dryness. The residue was purified by flash column chromatography (50% EtOAc/Hexanes) to afford 3D. MS (m/z) 488 [M+H]+.

Synthesis of Methyl 6-(3-cyano-4-fluorophenyl)-2-(methylthio)thiazolo[4,5-b]pyridine-5-carboxylate (3E): To a solution of 3D (5.9 g, 13.1 mmol) in tetrahydrofuran (65 mL), 20% NaOMe (26.2 mmol) in MeOH was added and stirred for 1 h at r.t. The reaction was acidified to pH 5 to 7 by 1N HCl and extracted with EtOAc 5 times. The organic layer was separated and was concentrated to dryness in vacuo. The crude product was dissolved in 65 mL of tetrahydrofuran. 1,1'-Thiocarbonyldiimidazole (3.47 g, 19.5 mmol) was added to the mixture and refluxed for 2 hours. The solvent was removed and the residue was dissolved in EtOAc (100 mL) and washed with water (50 mL) and brine (50 mL). The organic layer was concentrated and dried in vacuo. The crude compound was dissolved in DMF (8 mL), and potassium carbonate (2 g, 14.3 mmol) and iodomethane (1 mL, 16 mmol) were added to the solution. Then the solution was stirred for 16 hours. The reaction was diluted with EtOAc (100 mL) and washed with water (50 mL) and brine (50 mL). The organic layer was separated and was concentrated to dryness in vacuo. The residue was purified by flash column chromatography (30% EtOAc/Hexanes) to afford 3E. MS (m/z) 360 [M+H]+.

Synthesis of 2-fluoro-5-(5-formyl-2-(methylthio)thiazolo[4,5-b]pyridin-6-yl)benzonitrile (3F): To a solution of compound 3E (3.7 g, 10.27 mmol) in $CH_2Cl_2$/MeOH (1:1, 30 mL), sodium borohydride (2 g, 51.14 mmol) was added. Saturated $NH_4Cl$ solution (100 mL) and water (100 mL) were added slowly to the resulting mixture, which was then extracted with EtOAc (50 mL three times). The combined organic layers were dried over $MgSO_4$ and concentrated. The crude product was dissolved in DCM (10 mL), and Dess-Martin periodinane (1.4 g, 3.3 mmol) was added to the solution. Then the mixture was stirred for 2 hour and filtered. The filtrate was washed with $NaHCO_3$ (aq). The organic layer was separated and was concentrated to dryness in vacuo to afford 3F, which was used without further purification. MS (m/z) 330 [M+H]+.

Synthesis of (S)—N-((6-(3-cyano-4-fluorophenyl)-2-(methylthio)thiazolo[4,5-b]pyridin-5-yl)methylene)-2-methylpropane-2-sulfinamide (3G): To a suspension of copper(II) sulfate (anhydrous 1.06 g, 6.6 mmol) was added a solution of compound 3E (1.09 g, 3.3 mmol) and (S)-2-methylpropane-2-sulfinamide (400 mg, 3.3 mmol) in DCM (10 ml). The suspension was stirred overnight at room temperature. The reaction was filtered and washed with DCM (3×20 ml). The filtrate was concentrated. The crude product was purified by flash column (50% EtOAc/Hexanes) to afford 3G. MS (m/z) 433 [M+H]$^+$.

Synthesis of (S)—N—((S)-1-(6-(3-cyano-4-fluorophenyl)-2-(methylthio)thiazolo[4,5-b]pyridin-5-yl)-2-(3,5-difluorophenyl)ethyl)-2-methylpropane-2-sulfinamide (3H) and (S)—N—((R)-1-(6-(3-cyano-4-fluorophenyl)-2-(methylthio)thiazolo[4,5-b]pyridin-5-yl)-2-(3,5-difluorophenyl)ethyl)-2-methylpropane-2-sulfinamide (3I): To a solution of compound 3G (0.8 g, 1.85 mmol) and copper(II) trifluoromethanesulfonate (33.5 mg, 0.093 mmol) in DCM (5 mL), (3,5-difluorobenzyl)zinc bromide (0.5 M in tetrahydrofuran, 6 ml, 3 mmol) was added dropwise at 0° C. The reaction was stirred for 2 hours. Ammonium chloride (aq, 50 ml) was added to the reaction and the mixture was allowed to warm to r.t. The mixture was extracted with EtOAc (2×30 ml). The organic layer was dried over Na$_2$SO$_4$, filtered and concentrated. The reaction mixture was purified on preparative reverse phase HPLC using 20-80% B over 20 min. (A=0.1% TFA/H2O; B=0.1% TFA/Acetonitrile). The pure fractions as determined by LC/MS were combined and lyophilized to provide 3H and 3I. MS (m/z) 561 [M+H]$^+$.

Synthesis of (S)—N-(1-(6-(3-cyano-4-fluorophenyl)-2-(methylthio)thiazolo[4,5-b]pyridin-5-yl)-2-(3,5-difluorophenyl)ethyl)-2-(3-(difluoromethyl)-4,4,7,7-tetrafluoro-4,5,6,7-tetrahydro-1H-indazol-1-yl)acetamide (3J): A solution of 3H (400 mg, 0.72 mmol) in 2N hydrochloride (2 mL of Methanol/2 mL of Dioxane) was stirred for 30 minutes. The solvent was removed and dried in vacuo. To a solution of crude product, 2-(3-(difluoromethyl)-4,4,7,7-tetrafluoro-4,5,6,7-tetrahydro-1H-indazol-1-yl)acetic acid (prepared according to WO2013006738, 220 mg, 0.73 mmol) and HATU (278 mg, 0.73 mmol) dissolved in DMF (3 mL), diisopropylethylamine (0.4 mL, 2.16 mmol) was added. The reaction was stirred at room temperature for 90 min. The reaction mixture was purified on preparative reverse phase HPLC using 20-80% B over 20 min. (A=0.10% TFA/H2O; B=0.10% TFA/Acetonitrile). The pure fractions as determined by LC/MS were combined and lyophilized to provide 3J. MS (m/z) 741 [M+H]$^+$.

Synthesis of (S)—N-(1-(6-(3-cyano-4-fluorophenyl)-2-morpholinothiazolo[4,5-b]pyridin-5-yl)-2-(3,5-difluorophenyl)ethyl)-2-(3-(difluoromethyl)-4,4,7,7-tetrafluoro-4,5,6,7-tetrahydro-1H-indazol-1-yl)acetamide (3K): To a solution of 3J (20 mg, 0.027 mmol) in DCM (1 mL), 3-Chloroperoxybenzoic acid (77% purity, 11 mg, 0.055 mmol) was added. The reaction was stirred for 1 hour and morpholine (0.047 mL, 0.54 mmol) was added to the mixture. After 1 hour, the reaction was diluted with EtOAc (20 mL) and washed with NaHCO$_3$ (aq). The organic layer was separated and was concentrated to dryness in vacuo. The reaction mixture was purified on preparative reverse phase HPLC using 20-80% B over 20 min. (A=0.10% TFA/H2O; B=0.10% TFA/Acetonitrile). The pure fractions as determined by LC/MS were combined and lyophilized to provide 3K. MS (m/z) 780 [M+H]$^+$.

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-morpholinothiazolo[4,5-b]pyridin-6-yl)-2-fluorobenzamide (3): To a suspension of 3K (20 mg, 0.026 mmol) and potassium carbonate (35.4 mg, 0.26 mmol) in DMSO (1 mL), 0.2 mL of hydrogen peroxide (30 wt. % in H$_2$O) was added. The reaction was stirred for 30 minutes. The mixture was filtered and the filtrate was purified on preparative reverse phase HPLC using 20-80% B over 20 min. (A=0.1% TFA/H2O; B=0.1% TFA/Acetonitrile). The pure fractions as determined by LC/MS were combined and lyophilized to provide Compound 3. MS (m/z) 798 [M+H]$^+$. $^1$H NMR (400 MHz, Methanol-d$_4$) δ 7.93 (s, 1H), 7.45-7.25 (m, 2H), 7.20 (dd, 1H), 6.95-6.61 (m, 2H), 6.41-6.27 (m, 2H), 5.32 (dd, 1H), 3.89-3.71 (m, 7H), 3.09 (q, 2H), 2.60-2.40 (m, 4H).

Example 4

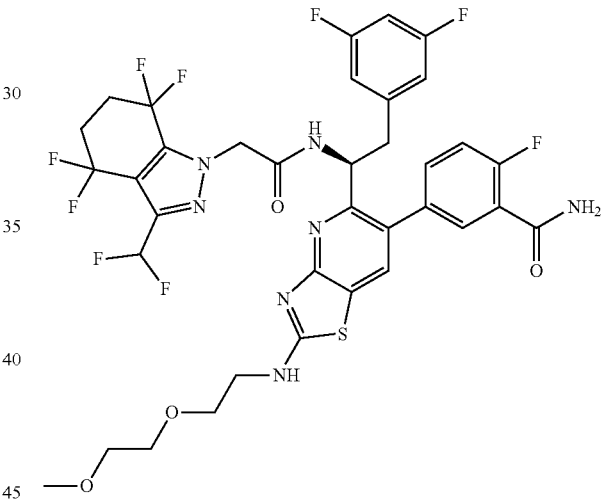

4

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-(2-methoxyethoxy)ethyl)amino)thiazolo[4,5-b]pyridin-6-yl)-2-fluorobenzamide (4): Compound 4 was prepared according to the method presented for the synthesis of Example 3 utilizing 3I and substituting 2-(2-methoxyethoxy)ethanamine for morpholine to provide the desired compound. MS (m/z) 830 [M+H]$^+$. $^1$H NMR (400 MHz, Methanol-d$_4$) δ 7.82 (s, 1H), 7.46-7.24 (m, 2H), 7.24-7.13 (m, 1H), 6.95-6.62 (m, 3H), 6.43-6.30 (m, 2H), 5.31 (dd, 1H), 3.76 (s, 4H), 3.71-3.62 (m, 2H), 3.62-3.53 (m, 2H), 3.36 (s, 3H), 3.16-3.03 (m, 2H), 2.50 (dd, 5H).

Example 5

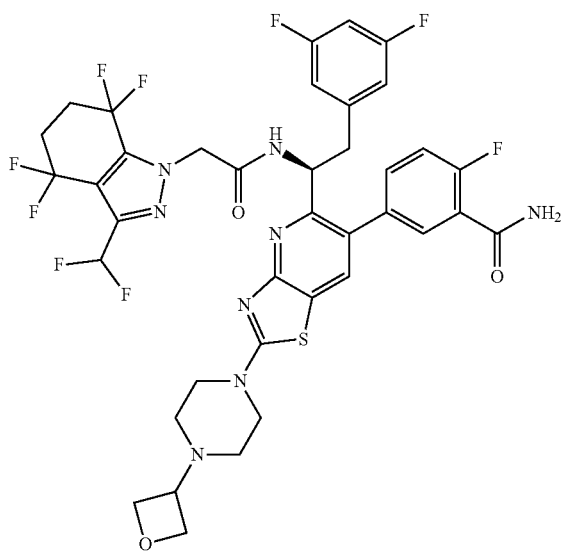

5

Synthesis of (S)-5-(5-1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(4-(oxetan-3-yl)piperazin-1-yl)thiazolo[4,5-b]pyridin-6-yl)-2-fluorobenzamide (5): Compound 5 was prepared according to the method presented for the synthesis of Example 3 utilizing 3I and substituting 1-(oxetan-3-yl)piperazine for morpholine to provide the desired compound. MS (m/z) 853 [M+H]⁺. ¹H NMR (400 MHz, Methanol-d₄) δ 7.90 (s, 1H), 7.35 (s, 2H), 7.23-7.15 (m, 1H), 6.95-6.63 (m, 2H), 6.36-6.26 (m, 2H), 5.32 (d, 1H), 5.05 (s, 2H), 4.78 (d, 2H), 4.20 (s, 1H), 3.99 (s, 4H), 3.11 (d, 6H), 2.51 (d, 4H).

Example 6

6

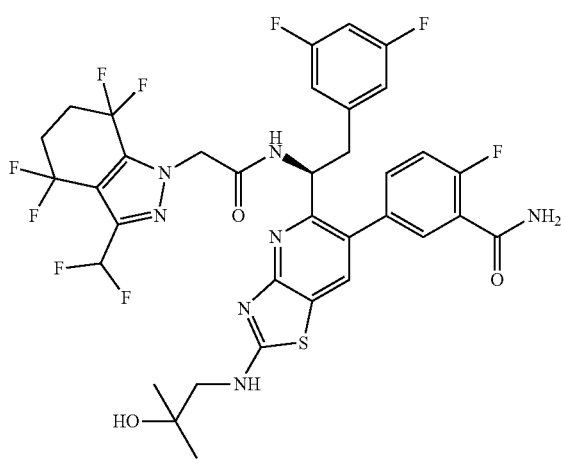

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-hydroxy-2-methylpropyl)amino)thiazolo[4,5-b]pyridin-6-yl)-2-fluorobenzamide (6): Compound 6 was prepared according to the method presented for the synthesis of Example 3 utilizing 3I and substituting 1-amino-2-methylpropan-2-ol for morpholine to provide the desired compound. MS (m/z) 800 [M+H]⁺. ¹H NMR (400 MHz, Methanol-d4) δ 7.80 (s, 1H), 7.38 (d, J=7.0 Hz, 1H), 7.29 (s, 1H), 7.22-7.11 (m, 1H), 6.96-6.54 (m, 2H), 6.36 (d, J=7.3 Hz, 2H), 5.37-5.25 (m, 1H), 5.06 (s, 2H), 3.59 (s, 2H), 3.19-2.93 (m, 2H), 2.60-2.39 (m, 4H), 1.30 (d, J=1.9 Hz, 6H).

Example 7

7

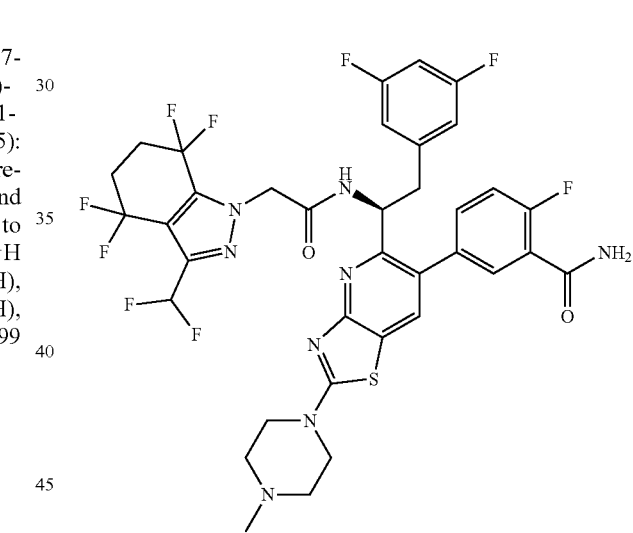

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(4-methylpiperazin-1-yl)thiazolo[4,5-b]pyridin-6-yl)-2-fluorobenzamide (7): Compound 7 was prepared according to the method presented for the synthesis of Example 3 utilizing 3I and substituting 1-methylpiperazine for morpholine to provide the desired compound. MS (m/z) 811 [M+H]⁺. ¹H NMR (400 MHz, Methanol-d₄) δ 7.92 (s, 1H), 7.41-7.15 (m, 3H), 6.96-6.65 (m, 2H), 6.35-6.25 (m, 2H), 5.34 (s, 1H), 3.46 (s, 4H), 3.01 (s, 6H), 2.52 (s, 4H).

Example 8

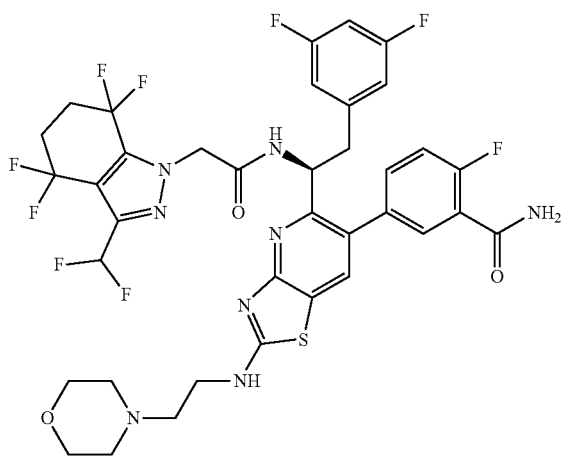

8

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-morpholinoethyl)amino)thiazolo[4,5-b]pyridin-6-yl)-2-fluorobenzamide (8): Compound 8 was prepared according to the method presented for the synthesis of Example 3 utilizing 3I and substituting 2-morpholinoethanamine for morpholine to provide the desired compound. MS (m/z) 841 [M+H]$^+$. $^1$H NMR (400 MHz, Methanol-d$_4$) δ 7.84 (s, 1H), 7.36 (s, 2H), 7.19 (dd, 1H), 6.95-6.65 (m, 2H), 6.32 (d, 2H), 5.31 (t, 1H), 5.05 (d, 2H), 4.23-4.00 (m, 4H), 3.98 (t, 2H), 3.54 (t, 2H), 3.22-2.98 (m, 4H), 2.51 (d, 4H).

Example 9

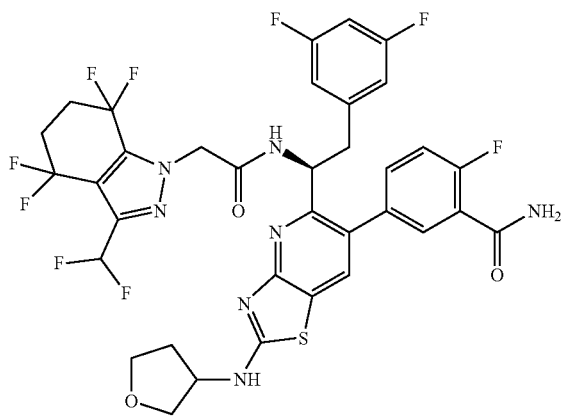

9

Synthesis of 5-(5-((S)-1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((tetrahydrofuran-3-yl)amino)thiazolo[4,5-b]pyridin-6-yl)-2-fluorobenzamide (9): Compound 9 was prepared according to the method presented for the synthesis of Example 3 utilizing 3I and substituting tetrahydrofuran-3-amine for morpholine to provide the desired compound. MS (m/z) 798 [M+H]$^+$. $^1$H NMR (400 MHz, DMSO-d$_6$) δ 9.09 (d, 1H), 8.79 (d, 1H), 7.92 (s, 1H), 7.63 (d, 2H), 7.52-7.41 (m, 1H), 7.41-7.23 (m, 2H), 7.17-6.87 (m, 2H), 6.64-6.54 (m, 2H), 5.15-5.06 (m, 1H), 4.94 (d, 2H), 3.90-3.81 (m, 2H), 3.78-3.67 (m, 2H), 3.02 (t, 2H), 2.25 (dd, 2H), 1.93 (s, 2H).

Example 10

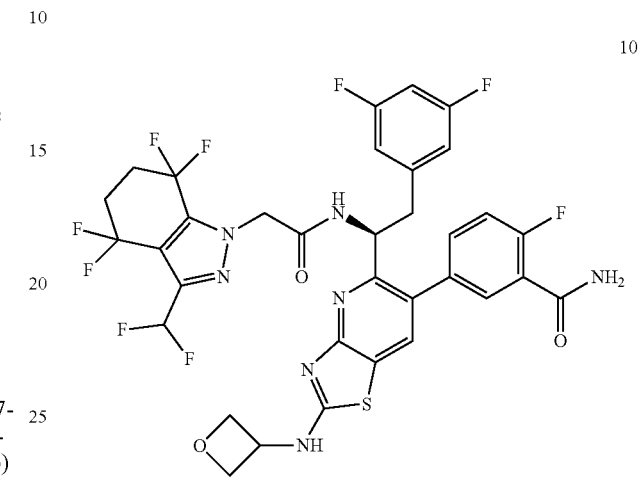

10

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(oxetan-3-ylamino)thiazolo[4,5-b]pyridin-6-yl)-2-fluorobenzamide (10): Compound 10 was prepared according to the method presented for the synthesis of Example 3 utilizing 3I and substituting oxetan-3-amine for morpholine to provide the desired compound. MS (m/z) 784 [M+H]$^+$. $^1$H NMR (400 MHz, DMSO-d$_6$) δ 9.26 (d, 1H), 9.09 (d, 1H), 7.96 (s, 1H), 7.63 (d, 2H), 7.46 (dd, 1H), 7.41-7.22 (m, 2H), 6.91 (d, 2H), 6.65-6.54 (m, 2H), 5.18-4.82 (m, 7H), 4.56 (q, 2H), 3.01 (t, 2H).

Example 11

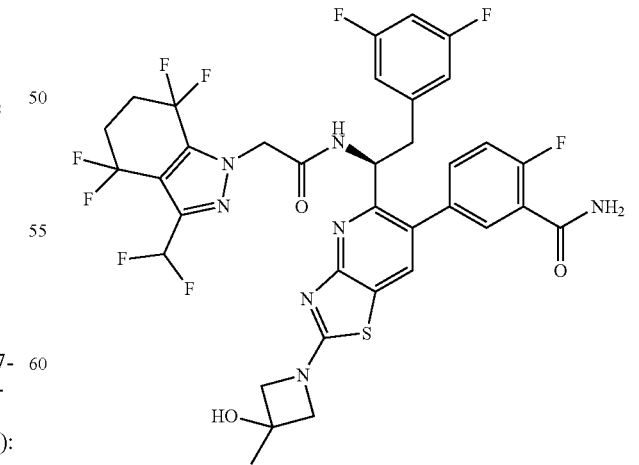

11

Synthesis of (S)-5-(5-(1-(2-(3-(difluoromethyl)-4,4,7,7-tetrafluoro-4,5,6,7-tetrahydro-1H-indazol-1-yl)acetamido)-

2-(3,5-difluorophenyl)ethyl)-2-(3-hydroxy-3-methylazetidin-1-yl)thiazolo[4,5-b]pyridin-6-yl)-2-fluorobenzamide (11): Compound 11 was prepared according to the method presented for the synthesis of Example 3 utilizing 3I and substituting 3-methylazetidin-3-ol for morpholine to provide the desired compound. MS (m/z) 798 [M+H]+. 1H NMR (400 MHz, DMSO-d6) δ 9.03 (d, 1H), 8.02 (s, 1H), 7.63 (d, 2H), 7.43 (dd, 1H), 7.37 (d, 1H), 7.28 (dd, 1H), 6.90 (d, 2H), 6.59-6.50 (m, 2H), 5.17-5.09 (m, 1H), 4.95 (s, 2H), 4.09-4.03 (m, 4H), 3.09-2.95 (m, 2H), 1.47 (s, 3H).

Example 12

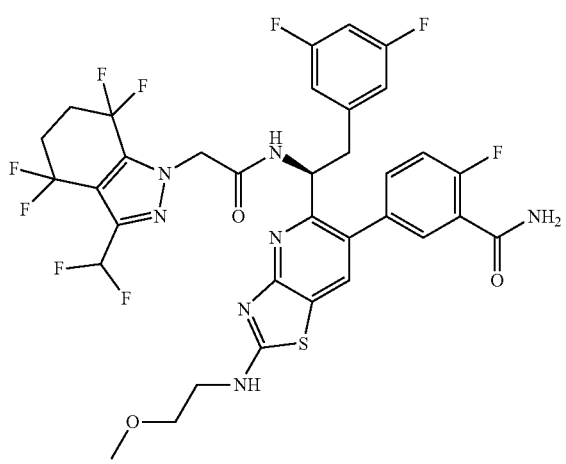

12

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((2-methoxyethyl)amino)thiazolo[4,5-b]pyridin-6-yl)-2-fluorobenzamide (12): Compound 12 was prepared according to the method presented for the synthesis of Example 3 utilizing 3I and substituting 2-methoxyethanamine for morpholine to provide the desired compound. MS (m/z) 786 [M+H]+. 1H NMR (400 MHz, Methanol-d4) δ 7.83 (s, 1H), 7.39 (s, 1H), 7.30 (s, 1H), 7.19 (dd, 1H), 6.67 (d, 2H), 6.36 (d, 2H), 5.31 (t, 1H), 5.07 (s, 2H), 3.75 (t, 2H), 3.67 (t, 2H), 3.41 (s, 3H), 3.19-3.00 (m, 3H), 2.51 (q, 5H).

Example 13

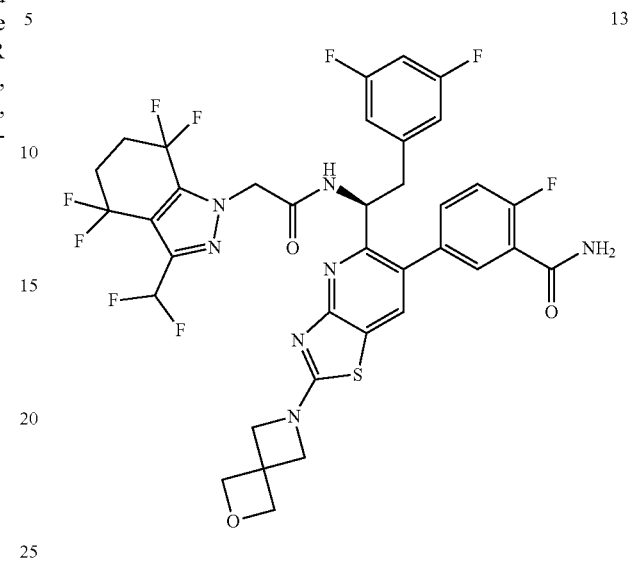

13

Synthesis of (S)-5-(5-(1-(2-(3-(difluoromethyl)-4,4,7,7-tetrafluoro-4,5,6,7-tetrahydro-TH-indazol-1-yl)acetamido)-2-(3,5-difluorophenyl)ethyl)-2-(2-oxa-6-azaspiro[3.3]heptan-6-yl)thiazolo[4,5-b]pyridin-6-yl)-2-fluorobenzamide (13): Compound 13 was prepared according to the method presented for the synthesis of Example 3 utilizing 3I and substituting 2-oxa-6-azaspiro[3.3]heptane for morpholine to provide desired compound. MS (m/z) 810 [M+H]+. 1H NMR (400 MHz, Methanol-d4) δ 7.85 (s, 1H), 7.35 (d, 1H), 7.23-7.13 (m, 1H), 6.95-6.65 (m, 2H), 6.32 (d, 2H), 5.31 (d, 1H), 5.05 (s, 2H), 4.89 (s, 4H), 4.48 (s, 4H), 3.12 (d, 1H), 3.04 (d, 1H), 2.49 (s, 4H).

Example 14

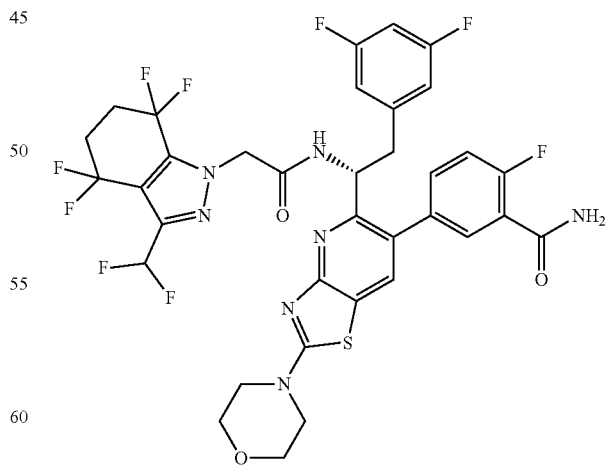

14

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(2-oxa-6-azaspiro[3.3]heptan-6-yl)thiazolo[4,5-b]pyridin-6-yl)-2-fluorobenzamide (14): Compound 14 was prepared according to the method presented for the synthesis of Example 3 substituting 3I for 3H to provide desired compound. MS (m/z) 798 [M+H]$^+$. $^1$H NMR (400 MHz, Methanol-d$_4$) δ 7.88 (s, 1H), 7.42-7.34 (m, 1H), 7.30 (d, 1H), 6.80 (s, 2H), 6.38-6.30 (m, 2H), 5.32 (dd, 1H), 3.85 (t, 4H), 3.75 (dd, 4H), 3.12 (d, 1H), 3.08-3.01 (m, 1H), 2.58-2.43 (m, 4H).

Example 15

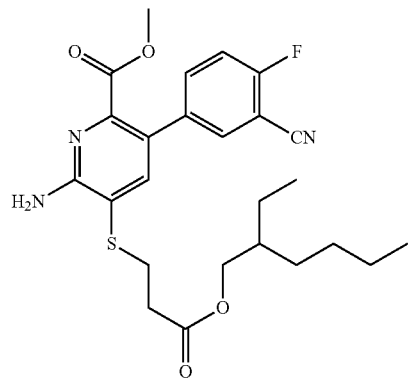

3D

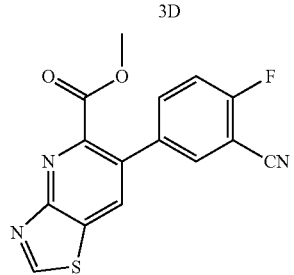

15A

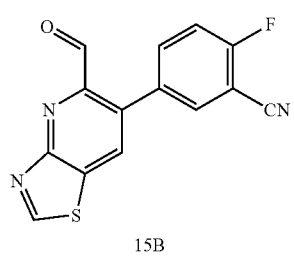

15B

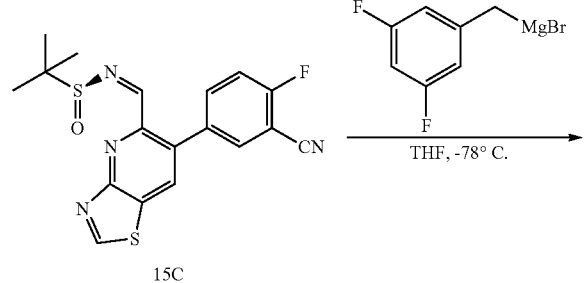

15C

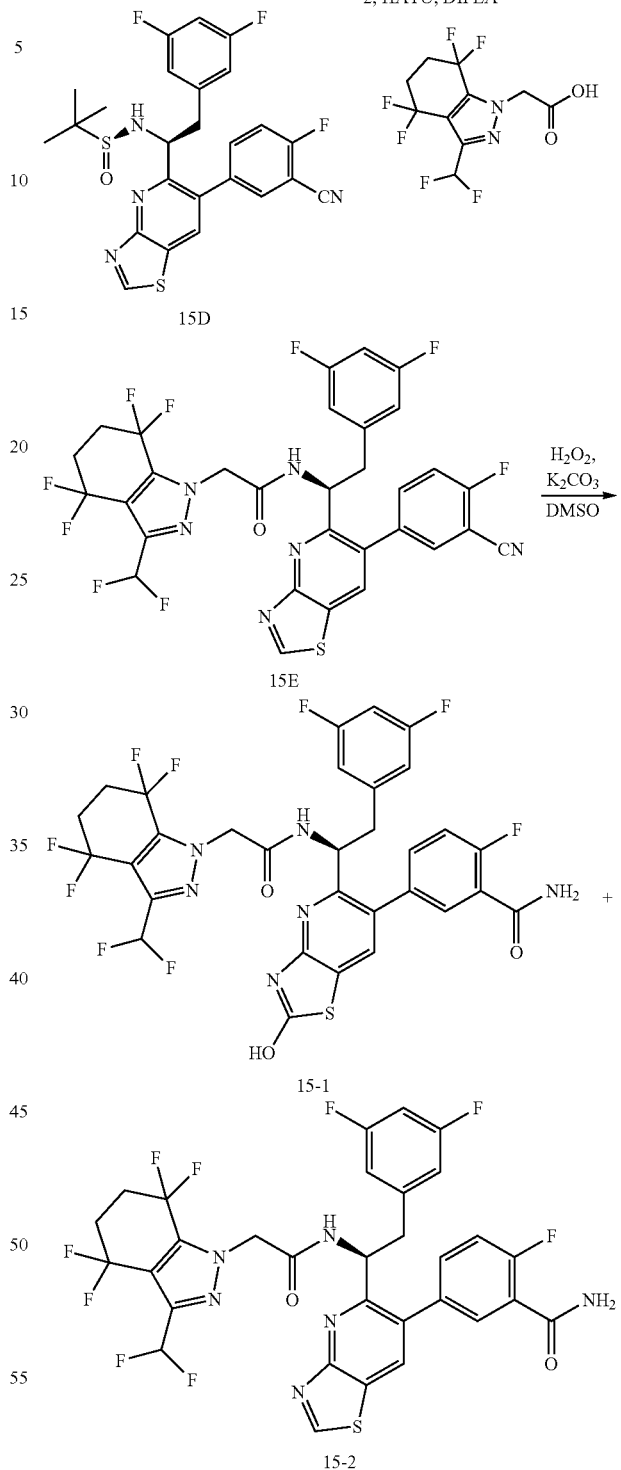

Synthesis of methyl 6-(3-cyano-4-fluorophenyl)thiazolo[4,5-b]pyridine-5-carboxylate (15A): To a solution of 3D (5.64 g, 11.6 mmol) in tetrahydrofuran (61 mL), 20% NaOMe (25 mmol) in MeOH was added and stirred for 1 h at r.t. The reaction was acidified to pH 5 to 7 by 1N HCl and extracted with EtOAc 5 times. The organic layer was separated and was concentrated to dryness in vacuo. A solution of 1 g of crude product in 5 mL of formic acid, was heated at 130° C. for 20 minutes. The solvent was removed and dried in vacuo for overnight. The crude product was used without further purification. MS (m/z) 314 [M+H]+.

Synthesis of 2-fluoro-5-(5-formylthiazolo[4,5-b]pyridin-6-yl)benzonitrile (15B): To a suspension of compound 15A (1 g, 3.2 mmol) in tetrahydrofuran (10 mL), 1 M of diisobutylaluminium hydride in toluene (6.4 mL, 6.4 mmol) was added. Once the reaction was complete, saturated NH₄Cl solution (100 mL) was added slowly, and the resulting mixture was extracted with EtOAc (50 mL twice). The combined organic solvent was dried over MgSO₄ and concentrated to dryness in vacuo. To a solution of crude product in DCM (5 mL), Dess-Martin periodinane (1.0 g, 2.35 mmol) was added. The mixture was stirred for 1 hour, diluted with EtOAc (50 mL), and then washed with NaHCO₃ (aq). The organic layer was separated and was concentrated to dryness in vacuo. MS (m/z) 284 [M+H]+.

Synthesis of (S)—N-((6-(3-cyano-4-fluorophenyl)thiazolo[4,5-b]pyridin-5-yl)methylene)-2-methylpropane-2-sulfinamide (15C): To a suspension of copper(II) sulfate (anhydrous 800 mg, 5 mmol) was added a solution of compound 15B (0.7 g, crude) and (S)-2-methylpropane-2-sulfinamide (333 mg, 2.75 mmol) in DCM (5 ml). The suspension was stirred overnight at room temperature. The reaction was filtered and washed with DCM (3×10 ml). The filtrate was concentrated. The crude product was purified by flash column (50% EtOAc/Hexanes) to afford compound 15C. MS (m/z) 387 [M+H]+.

Synthesis of (S)—N—((S)-1-(6-(3-cyano-4-fluorophenyl)thiazolo[4,5-b]pyridin-5-yl)-2-(3,5-difluorophenyl)ethyl)-2-methylpropane-2-sulfinamide (15D): To a solution of compound 15C (230 mg, 0.6 mmol) in THF (5 ml) at −78° C., (3,5-difluorobenzyl)magnesium bromide (0.25 M in ether, 3.6 ml, 0.9 mmol) was added dropwise. The reaction was stirred for 1 hour at −78° C. Ammonium chloride (aq, 20 ml) was added to the reaction and the mixture was allowed to warm to r.t. The mixture was extracted with EtOAc (2×30 ml). The organic layer was dried over Na₂SO₄, filtered and concentrated. The crude product was purified by flash column (50% EtOAc/Hexanes) to afford compound 15D. (The ratio was 2:1 of two isomers). MS (m/z) 515 [M+H]+.

Synthesis of (S)—N-(1-(6-(3-cyano-4-fluorophenyl)thiazolo[4,5-b]pyridin-5-yl)-2-(3,5-difluorophenyl)ethyl)-2-(3-(difluoromethyl)-4,4,7,7-tetrafluoro-4,5,6,7-tetrahydro-1H-indazol-1-yl)acetamide (15E): Compound 15E was prepared according to the method presented for the synthesis of Example 3 substituting 15D for 3H to provide the desired compound. MS (m/z) 695 [M+H]+. ¹H NMR (400 MHz, Methanol-d₄) δ 9.67 (s, 1H), 8.32 (s, 1H), 7.56 (s, 1H), 7.36 (q, 2H), 6.92-6.65 (m, 2H), 6.34 (qd, 2H), 5.39 (dd, 1H), 5.08 (d, 2H), 3.24-3.07 (m, 2H), 2.58-2.40 (m, 4H).

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-hydroxythiazolo[4,5-b]pyridin-6-yl)-2-fluorobenzamide (15-1) and (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)thiazolo[4,5-b]pyridin-6-yl)-2-fluorobenzamide (15-2): Compounds 15-1 and 15-2 were prepared according to the method presented for the synthesis of Example 3 substituting 15E for 3K to provide Compounds 15-1 and 15-2. Compound 15-1: MS (m/z) 729 [M+H]+. ¹H NMR (400 MHz, Methanol-d₄) δ 7.64 (s, 1H), 7.45-7.37 (m, 1H), 7.32-7.15 (m, 2H), 6.93-6.65 (m, 2H), 6.40 (h, 2H), 5.27 (dd, 1H), 3.14 (dd, 1H), 3.06-3.00 (m, 1H), 2.56-2.44 (m, 4H).

Compound 15-2: MS (m/z) 713 [M+H]+. ¹H NMR (400 MHz, Methanol-d₄) δ 9.58 (s, 1H), 8.28 (s, 1H), 7.37 (d, 2H), 7.18 (dd, 1H), 6.84-6.57 (m, 2H), 6.30 (d, 2H), 5.42 (d, 1H), 4.98 (s, 2H), 3.03 (d, 2H), 2.41 (d, 4H).

Example 16

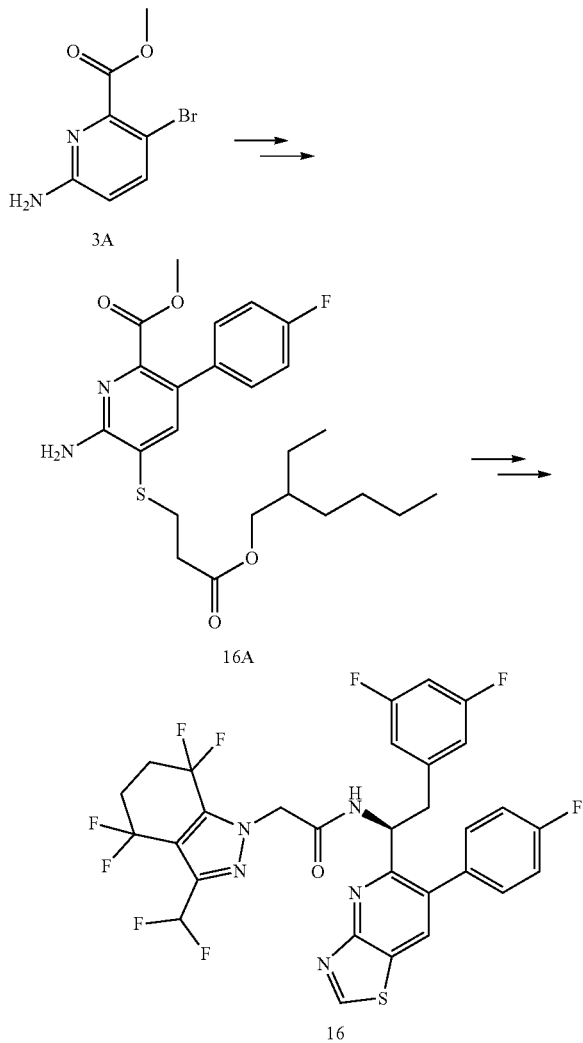

Synthesis of methyl 6-amino-5-((3-((2-ethylhexyl)oxy)-3-oxopropyl)thio)-3-(4-fluorophenyl)picolinate (16A): Compound 16A was prepared according to the method presented for the synthesis of Example 3 utilizing 3A and substituting (4-fluorophenyl)boronic acid for (3-cyano-4-fluorophenyl)boronic acid to provide the desired compound.

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(6-(4-fluorophenyl)thiazolo[4,5-b]pyridin-5-yl)ethyl)acetamide (16): Compound 16 was prepared according to the method presented for the synthesis of Example 15 utilizing 16A in place of 3D to provide the desired compound. MS (m/z) 670 [M+H]+. ¹H NMR (400 MHz, Methanol-d₄) δ 9.64 (s, 1H), 8.33 (s, 1H), 7.25-7.07 (m, 3H), 6.66 (ddd, 2H), 6.41-6.22 (m, 2H), 5.55 (td, 1H), 3.15 (dd, 1H), 3.05 (dd, 1H), 2.66-2.34 (m, 4H).

Example 17

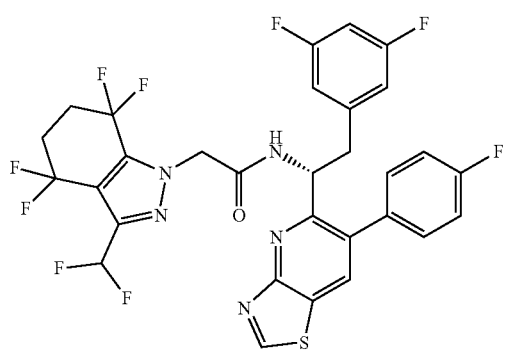

17

Synthesis of (R)-2-(3-(difluoromethyl)-4,4,7,7-tetrafluoro-4,5,6,7-tetrahydro-1H-indazol-1-yl)-N-(2-(3,5-difluorophenyl)-1-(6-(4-fluorophenyl)thiazolo[4,5-b]pyridin-5-yl)ethyl)acetamide (17): Compound 17 was prepared according to the method presented for the synthesis of Example 15 utilizing 16A to provide the desired compound: MS (m/z) 670 [M+H]$^+$. $^1$H NMR (400 MHz, Methanol-d$_4$) δ 9.64 (s, 1H), 9.01 (d, 1H), 8.33 (s, 1H), 7.23-7.12 (m, 3H), 6.92-6.66 (m, 2H), 6.32 (d, 2H), 5.55 (q, 1H), 5.08 (s, 2H), 3.17-3.10 (m, 1H), 3.05 (dd, 1H), 2.48 (t, 4H).

Example 18

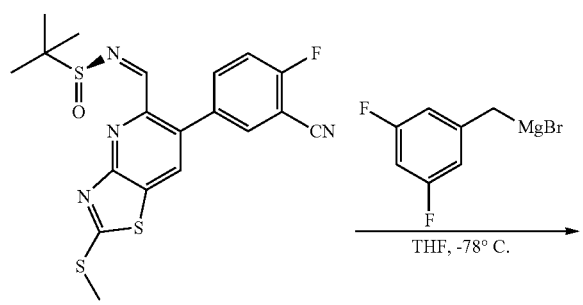

3G

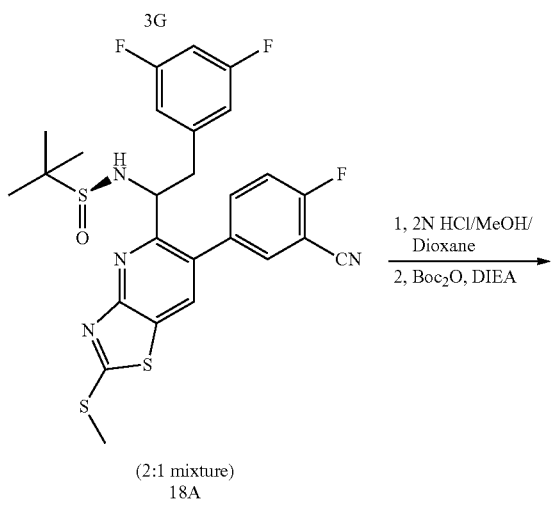

(2:1 mixture)
18A

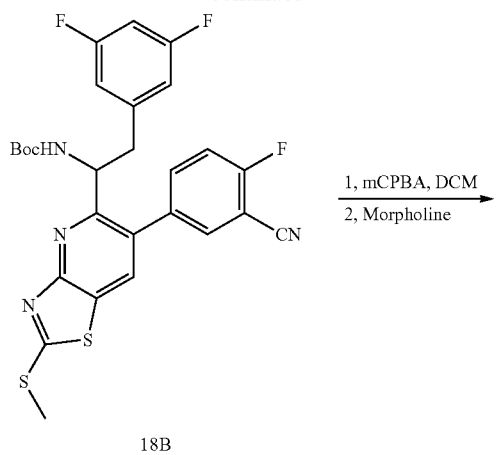

18B

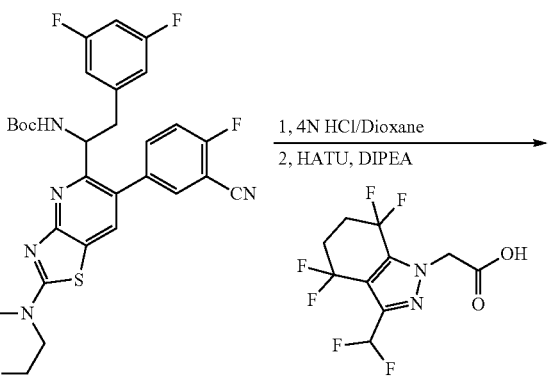

18C

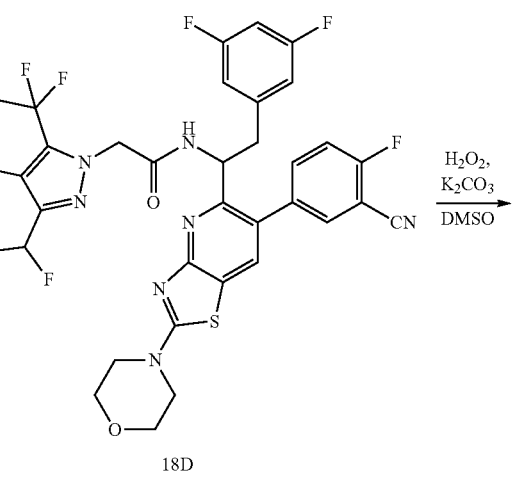

18D

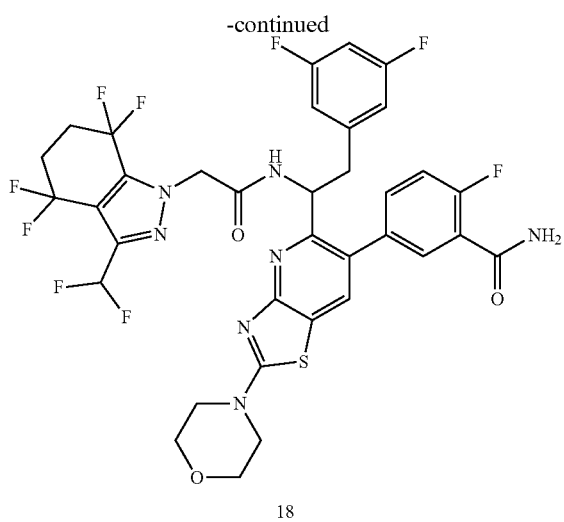

18

Synthesis of (S)—N-(1-(6-(3-cyano-4-fluorophenyl)-2-(methylthio)thiazolo[4,5-b]pyridin-5-yl)-2-(3,5-difluorophenyl)ethyl)-2-methylpropane-2-sulfinamide (18A): To a solution of compound 3G (300 mg, 0.7 mmol) in THF (5 ml) at −78° C., (3,5-difluorobenzyl)magnesium bromide (0.25 M in ether, 4.5 ml, 1.12 mmol) was added dropwise. The reaction was stirred for 1 hour at −78° C. Ammonium chloride (aq, 20 ml) was added to the reaction and the mixture was allowed to warm to r.t. The mixture was extracted with EtOAc (2×30 ml). The organic layer was dried over Na$_2$SO$_4$, filtered and concentrated. The crude product was purified by flash column (50% EtOAc/Hexanes) to afford compound 18A. (The ratio was 2:1 of two isomers). MS (m/z) 515 [M+H]$^+$.

Synthesis of tert-butyl (1-(6-(3-cyano-4-fluorophenyl)-2-(methylthio)thiazolo[4,5-b]pyridin-5-yl)-2-(3,5-difluorophenyl)ethyl)carbamate (18B): A solution of 18A (400 mg, 0.72 mmol) in 2N hydrochloride (2 mL of Methanol/2 mL of Dioxane) was stirred for 30 minutes. The solvent was removed and the mixture was dried in vacuo. The crude product was dissolved in DCM (5 mL), and di-tert-butyl dicarbonate (164 mg, 0.75 mmol) and DIEA (0.32 mL, 1.8 mmol) were added to the solution. The reaction was stirred for 2 hours. The mixture was diluted with EtOAc (50 mL) and washed with brine twice. The organic layer was dried over Na$_2$SO$_4$, filtered and concentrated. The crude product was purified by flash column (40% EtOAc/Hexanes) to afford compound 18B. (The ratio was 2:1 of two isomers). MS (m/z) 557 [M+H]$^+$.

Synthesis of tert-butyl (1-(6-(3-cyano-4-fluorophenyl)-2-morpholinothiazolo[4,5-b]pyridin-5-yl)-2-(3,5-difluorophenyl)ethyl)carbamate (18C): Compound 18C was prepared according to the method presented for the synthesis of Example 3 substituting 18B for 3J to provide compound 18C: MS (m/z) 596 [M+H]$^+$.

Synthesis of N-(1-(6-(3-cyano-4-fluorophenyl)-2-morpholinothiazolo[4,5-b]pyridin-5-yl)-2-(3,5-difluorophenyl)ethyl)-2-(3-(difluoromethyl)-4,4,7,7-tetrafluoro-4,5,6,7-tetrahydro-1H-indazol-1-yl)acetamide (18D): Compound 18D was prepared according to the method presented for the synthesis of Example 3 substituting 18C for 3H and 4N hydrochloride in dioxane for 2N hydrochloride (1 mL of Methanol/1 mL of Dioxane) to provide compound 18D: MS (m/z) 780 [M+H]$^+$. $^1$H NMR (400 MHz, Methanol-d$_4$) δ 7.80 (d, 1H), 7.43 (t, 1H), 7.30 (t, 1H), 7.24-7.13 (m, 1H), 6.98-6.67 (m, 2H), 6.30 (dt, 2H), 5.23 (dd, 1H), 5.08 (s, 2H), 3.84 (dd, 4H), 3.73 (dd, 4H), 3.15-3.03 (m, 2H), 2.60-2.44 (m, 4H).

Synthesis of 5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-morpholinothiazolo[4,5-b]pyridin-6-yl)-2-fluorobenzamide (18): To a suspension of 18D (40 mg, 0.052 mmol) and potassium carbonate (71 mg, 0.52 mmol) in DMSO (1 mL), 0.4 mL of hydrogen peroxide (30 wt. % in H$_2$O) was added. The reaction was stirred for 30 minutes. The mixture was filtered and the filtrate was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide Compound 18. MS (m/z) 798 [M+H]$^+$. $^1$H NMR (400 MHz, Methanol-d$_4$) δ 7.75 (s, 1H), 7.29 (d, 1H), 7.24-7.16 (m, 1H), 7.10 (dd, 1H), 6.86-6.57 (m, 2H), 6.31-6.20 (m, 2H), 5.25 (dd, 1H), 3.76 (dd, 4H), 3.65 (dd, 4H), 3.05 (dd, 1H), 2.99-2.93 (m, 1H), 2.43 (tdd, 4H).

Example 19

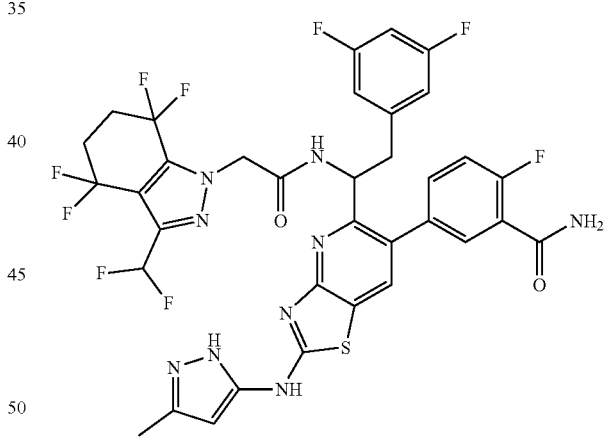

19

Synthesis of 5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((3-methyl-1H-pyrazol-5-yl)amino)thiazolo[4,5-b]pyridin-6-yl)-2-fluorobenzamide (19): Compound 19 was prepared according to the method presented for the synthesis of Example 18 utilizing 18B and substituting 3-methyl-1H-pyrazol-5-amine for morpholine to provide desired compound: MS (m/z) 808 [M+H]$^+$. $^1$H NMR (400 MHz, Methanol-d$_4$) δ 8.82 (s, 1H), 8.15 (s, 1H), 7.47 (s, 1H), 7.24 (dd, 1H), 6.79 (s, 2H), 6.39 (d, 2H), 5.43 (d, 1H), 5.06 (s, 2H), 3.16 (d, 2H), 2.51 (s, 4H), 2.18 (s, 3H).

Example 20

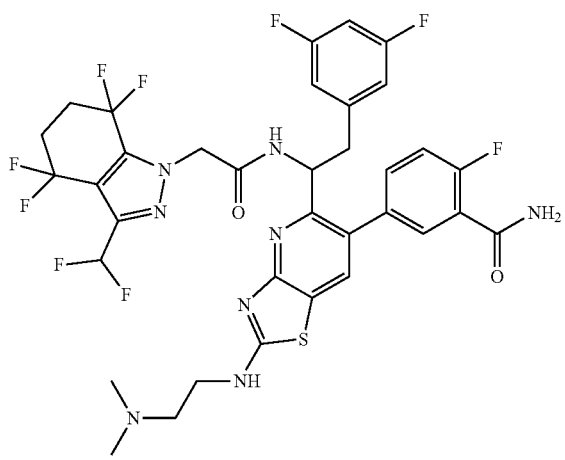

20

Synthesis of 5-(5-(1-(2-(3-(difluoromethyl)-4,4,7,7-tetrafluoro-4,5,6,7-tetrahydro-TH-indazol-1-yl)acetamido)-2-(3,5-difluorophenyl)ethyl)-2-((2-(dimethylamino)ethyl)amino)thiazolo[4,5-b]pyridin-6-yl)-2-fluorobenzamide (20): Compound 20 was prepared according to the method presented for the synthesis of Example 18 utilizing 18B and substituting N1,N1-dimethylethane-1,2-diamine for morpholine to provide desired compound: MS (m/z) 799 MS [M+H]+. ¹H NMR (400 MHz, Methanol-$d_4$) δ 8.75-8.60 (m, 1H), 7.84 (s, 1H), 7.36 (d, 1H), 7.29 (s, 1H), 7.24-7.15 (m, 1H), 6.80 (s, 2H), 6.33 (d, 2H), 5.32 (s, 1H), 5.05 (d, 2H), 3.96 (d, 2H), 3.54 (t, 2H), 3.19-3.06 (m, 2H), 3.04 (s, 3H), 2.51 (d, 3H).

Example 21

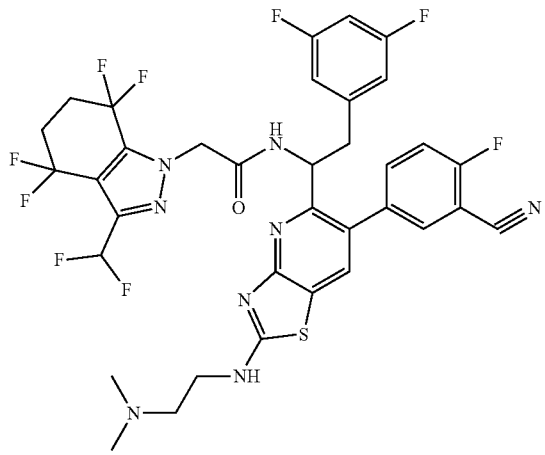

21

Synthesis of N-(1-(6-(3-cyano-4-fluorophenyl)-2-((2-(dimethylamino)ethyl)amino)thiazolo[4,5-b]pyridin-5-yl)-2-(3,5-difluorophenyl)ethyl)-2-(3-(difluoromethyl)-4,4,7,7-tetrafluoro-4,5,6,7-tetrahydro-1H-indazol-1-yl)acetamide (21): Compound 21 was prepared according to the method presented for the synthesis of Example 18 utilizing 18B and substituting N1,N1-dimethylethane-1,2-diamine for morpholine to provide desired compound. MS (m/z) 781 [M+H]+. ¹H NMR (400 MHz, Methanol-$d_4$) δ 7.73 (d, 1H), 7.46-7.37 (m, 1H), 7.31 (q, 1H), 7.17 (d, 1H), 6.94-6.67 (m, 2H), 6.36-6.27 (m, 2H), 5.22 (dd, 1H), 5.08 (s, 2H), 3.70 (q, 2H), 3.19-3.03 (m, 2H), 2.73 (t, 2H), 2.61-2.43 (m, 4H), 2.37 (d, 6H).

Example 22

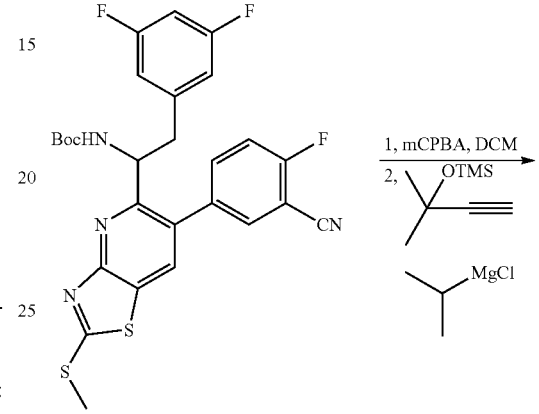

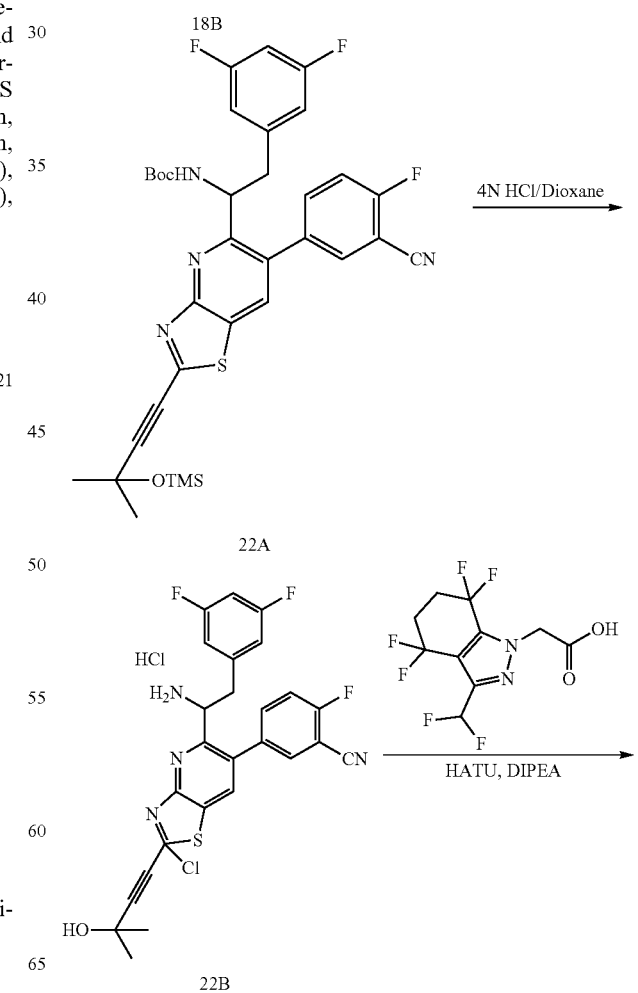

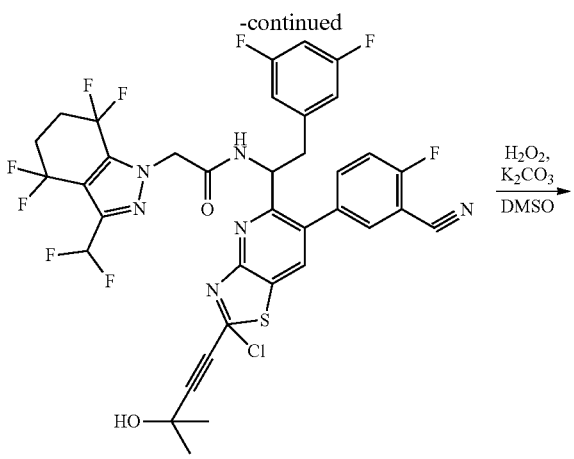

22C

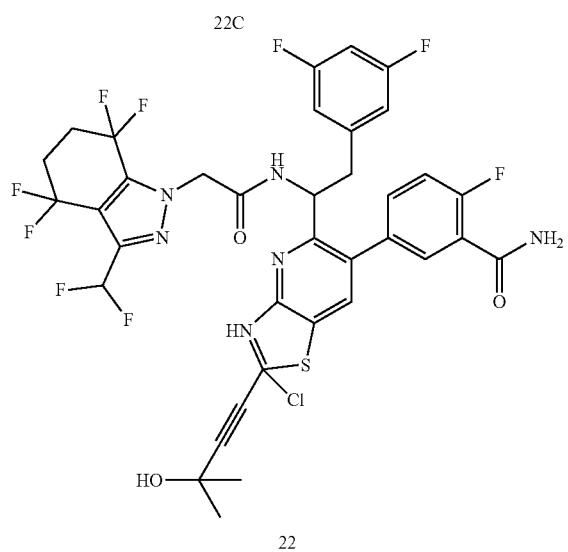

22

Synthesis of tert-butyl (1-(6-(3-cyano-4-fluorophenyl)-2-(3-methyl-3-((trimethylsilyl)oxy)but-1-yn-1-yl)thiazolo[4,5-b]pyridin-5-yl)-2-(3,5-difluorophenyl)ethyl)carbamate (22A): To a solution of 18B (80 mg, 0.144 mmol) in DCM (1 mL), 3-Chloroperoxybenzoic acid (77% purity, 11 mg, 0.055 mmol) was added. The reaction was stirred for 1 hour. The reaction mixture was diluted with EtOAc (20 mL) and washed with NaHCO$_3$ (aq). The organic layer was separated and was concentrated to dryness in vacuo. To a solution of trimethyl((2-methylbut-3-yn-2-yl)oxy)silane (0.112 mL, 0.575 mmol) in tetrahydrofuran (1 mL), 0.29 mL of isopropylmagnesium chloride solution (2.0 M in THF) was added. The mixture was transferred by needle to the crude product of previous reaction and stirred for 10 minutes. Acetic acid (1 mL) was added to the mixture. The reaction was diluted with EtOAc (50 mL) and washed with NaHCO$_3$ (aq). The organic layer was separated and was concentrated to dryness in vacuo. The mixture was filtered and the filtrate was purified on preparatory reverse phase HPLC using 20-80% B over 20 min (A=0.1% TFA/H2O; B=0.10% TFA/Acetonitrile). Pure fractions as determined by LC/MS were combined and lyophilized to provide 22A. MS (m/z) 665 [M+H]$^+$.

Synthesis of 5-(5-(1-amino-2-(3,5-difluorophenyl)ethyl)-2-chloro-2-(3-hydroxy-3-methylbut-1-yn-1-yl)-2,3-dihydrothiazolo[4,5-b]pyridin-6-yl)-2-fluorobenzonitrile hydrochloride (22B): A solution of 22A (30 mg, 0.057 mmol) in 4N HCl in Dioxane was stirred for 30 minutes. The solvent was removed and dried in vacuo. The crude product was used without further purification. MS (m/z) 529 [M+H]$^+$.

Synthesis of 5-(2-chloro-5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(3-hydroxy-3-methylbut-1-yn-1-yl)-2,3-dihydrothiazolo[4,5-b]pyridin-6-yl)-2-fluorobenzamide (22C): To a solution of 22B (crude product from previous step), 2-(3-(difluoromethyl)-4,4,7,7-tetrafluoro-4,5,6,7-tetrahydro-1H-indazol-1-yl)acetic acid (220 mg, 0.73 mmol) and HATU (238 mg, 0.06 mmol) in DMF (3 mL) was added diisopropylethylamine (0.1 mL). The reaction was stirred at room temperature for 90 min. The reaction mixture was purified preparatory reverse phase HPLC using 20-80% B over 20 min (A=0.10% TFA/H2O; B=0.10% TFA/Acetonitrile). The pure fractions as determined by LC/MS were combined and lyophilized to provide 22C. MS (m/z) 813 [M+H]$^+$.

Synthesis of 5-(2-chloro-5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(3-hydroxy-3-methylbut-1-yn-1-yl)-2,3-dihydrothiazolo[4,5-b]pyridin-6-yl)-2-fluorobenzamide (22): Compound 22 was prepared according to the method presented for the synthesis of Example 3 substituting 22C for 3K to provide desired compound: MS (m/z) 831 [M+H]$^+$. $^1$H NMR (400 MHz, DMSO-d$_6$) δ 9.24 (d, 1H), 8.48 (s, 1H), 7.73-7.53 (m, 3H), 7.50 (ddd, 1H), 7.36 (dd, 1H), 6.91 (ddd, 2H), 6.67-6.49 (m, 2H), 5.23 (td, 1H), 4.96 (s, 2H), 3.13-2.99 (m, 2H), 1.46 (s, 6H).

Example 23

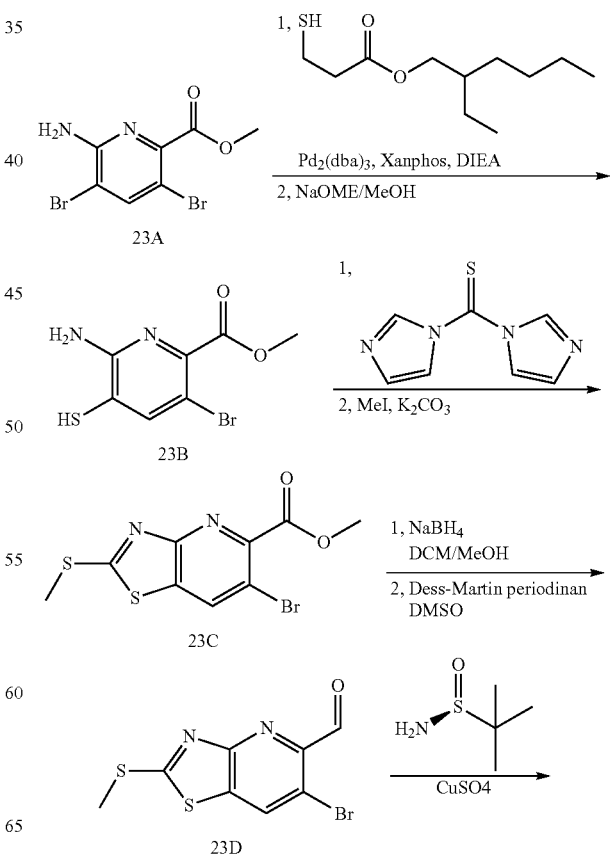

-continued

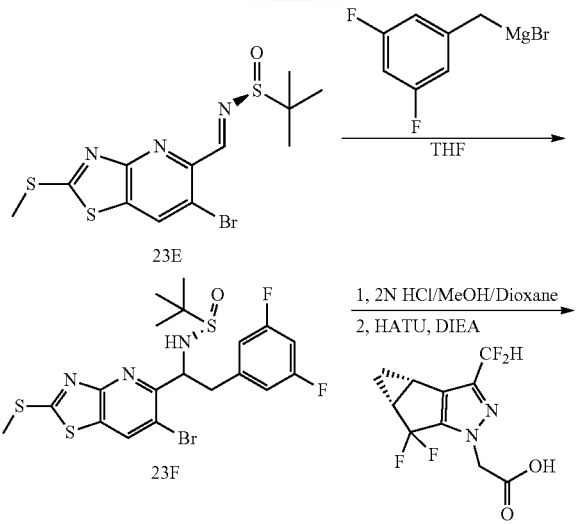

23E

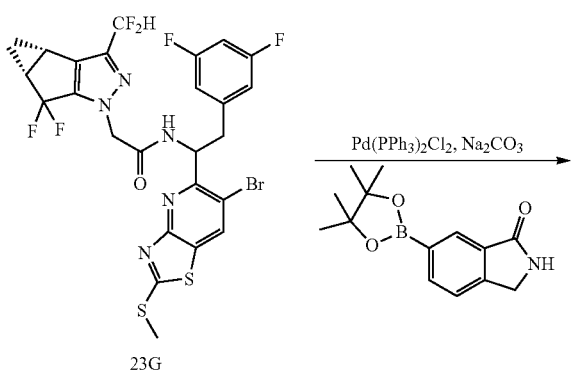

23G

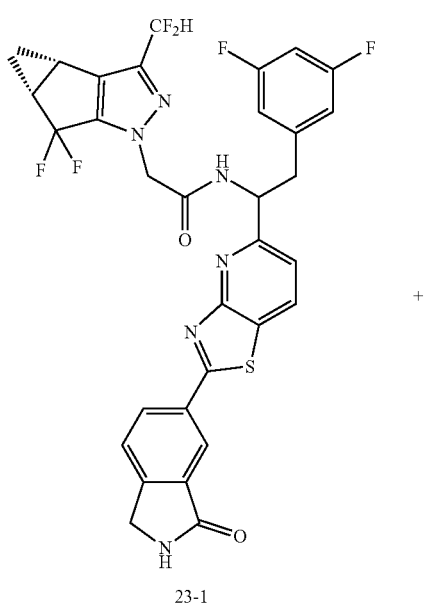

23-1

-continued

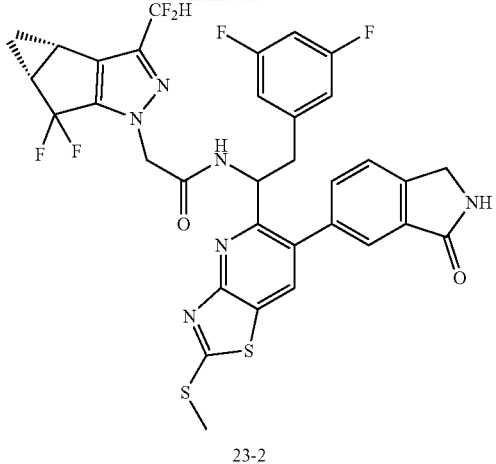

23-2

Synthesis of methyl 6-amino-3-bromo-5-mercaptopicolinate (23B): To a round bottom flask were added methyl 6-amino-3,5-dibromopicolinate (930 mg, 3 mmol), i-Pr$_2$NEt (1.05 ml, 6 mmol), and 1,4-dioxane (15 mL). The mixture was evacuated and backfilled with nitrogen (3 cycles). Catalyst Pd$_2$(dba)$_3$ (138 mg, 0.15 mmol), Xantphos (174 mg, 0.3 mmol) and 2-ethylhexyl 3-mercaptopropionate (0.68 mL, 3 mmol) were added and then the batch was degassed twice more. The reaction was gently refluxed for 12 h and then allowed to cool to room temperature. The mixture was filtered through glass paper filter and washed with EtOAc. The filtrate was concentrated to dryness, and to the residue was added THF (15 mL) and 20% NaOEt in EtOH (6 mmol) then the mixture was aged for 1 h at r.t. The mixture was acidified to pH 5 to 7 with 1N HCl, and extracted with EtOAc 5 times. The organic layer was separated and was concentrated to dryness in vacuo. The residue was purified by flash column chromatography (20% EtOAc/Hexanes) to afford 23B. MS (m/z) 263 [M+H]$^+$.

Synthesis of methyl 6-bromo-2-(methylthio)thiazolo[4,5-b]pyridine-5-carboxylate (23C): To a suspension of compound 23B (603 mg, 2.3 mmol) in THF (10 mL), 1,1'-Thiocarbonyldiimidazole (703 mg, 3.94 mmol) was added. Then the reaction was heated up to reflux for 2 hours. The solvent was removed and the residue was dissolved in EtOAc (50 mL) and washed with water and brine. The organic layer was concentrated and dried in vacuo. The crude compound was dissolved in DMF (8 mL), and potassium carbonate (354 mg, 2.56 mmol) and iodomethane (0.174 mL, 2.79 mmol) were added to the solution. Then the solution was stirred for 5 hours, diluted with EtOAc, and washed with water and brine. The organic layer was separated and concentrated to dryness in vacuo. The residue was purified by flash column chromatography (30% EtOAc/Hexanes) to afford compound 23C. MS (m/z) 319 [M+H]$^+$.

Synthesis of 6-bromo-2-(methylthio)thiazolo[4,5-b]pyridine-5-carbaldehyde 23D: To a solution of compound 23C (1.3 g, 4.1 mmol) in DCM/MeOH (1:1, 20 mL), sodium borohydride (0.93 g, 24.5 mmol) was added. Saturated NH$_4$Cl solution (100 mL) and water (100 mL) was added slowly, and the resulting mixture was extracted with EtOAc. The combined organic layers were dried over MgSO$_4$ and concentrated. Without further purification the crude product (0.8 g, 2.76 mmol) was dissolved in DMSO (10 mL), and Dess-Martin periodinane (1.17 g, 2.76 mmol) was added to the solution. Then the reaction was stirred for 1 hour, diluted with EtOAc (50 mL), and washed with NaHCO$_3$ (aq). The organic layer was separated and was concentrated to dryness in vacuo. The residue was purified by flash column chromatography (20% EtOAc/Hexanes) to afford compound 23D. MS (m/z) 289 [M+H]$^+$.

Synthesis of (S)—N-((6-bromo-2-(methylthio)thiazolo[4,5-b]pyridin-5-yl)methylene)-2-methylpropane-2-sulfinamide (23E): Copper(II) sulfate (anhydrous 672 mg, 4.2 mmol) was added to a solution of compound 23D (600 mg, 1.875 mmol) and (S)-2-methylpropane-2-sulfinamide (250.8 mg, 2.07 mmol) in DCM (5 ml). The suspension was stirred overnight at room temperature. The reaction was filtered and washed with DCM (3×20 ml). The filtrate was concentrated. The crude product was purified by flash column (30% EtOAc/Hexanes) to afford compound 23E. MS (m/z) 392 [M+H]$^+$.

Synthesis of (S)—N-(1-(6-bromo-2-(methylthio)thiazolo[4,5-b]pyridin-5-yl)-2-(3,5-difluorophenyl)ethyl)-2-methylpropane-2-sulfinamide (23F): (3,5-difluorobenzyl)magnesium bromide (0.25 M in ether, 4.5 ml, 1.12 mmol) was added dropwise to a solution of compound 23E (520 mg, 1.0 mmol) in THF (15 ml) at −78° C. The reaction was stirred for 1 hour at −78° C. Ammonium chloride (aq, 10 ml) was added to the reaction and the mixture was allowed to warm to r.t. The mixture was extracted with EtOAc (2×30 ml). The organic layer was dried over Na$_2$SO$_4$, filtered and concentrated. The crude product was purified by flash column (50% EtOAc/Hexanes) to afford compound 23F (2:1 ratio of two isomer). MS (m/z) 520 [M+H]$^+$.

Synthesis of tert-butyl (1-(6-bromo-2-(methylthio)thiazolo[4,5-b]pyridin-5-yl)-2-(3,5-difluorophenyl)ethyl)carbamate (23G): Compound 23G was prepared according to the method presented for the synthesis of Example 15 substituting 23F for 15D and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (prepared according to WO2014110297) for 2-(4,4,7,7-tetrafluoro-3-(trifluoromethyl)-4,5,6,7-tetrahydro-1H-indazol-1-yl)acetic acid to provide compound 23G: MS (m/z) 680 [M+H]$^+$.

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(2-(3-oxoisoindolin-5-yl)thiazolo[4,5-b]pyridin-5-yl)ethyl)acetamide (23-1) and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(2-(methylthio)-6-(3-oxoisoindolin-5-yl)thiazolo[4,5-b]pyridin-5-yl)ethyl)acetamide (23-2): A microwave tube was charged with Compound 23G (58 mg, 0.0875 mmol), 6-(4,4,5,5-tetramethyl-1,3,2-dioxaborolan-2-yl)isoindolin-1-one (26 mg, 0.1 mmol), LiCl (6 mg, 0.15 mmol), Na$_2$CO$_3$ (19 mg, 0.18 mmol), and Pd(PPh$_3$)$_2$Cl$_2$ (5 mg). To the mixture was added 1 mL of DME, 0.2 mL of DMF and 0.2 mL of H$_2$O. The mixture was heated up to 140° C. for 20 min in a Microwave Synthesizer. After being cooled down and filtered through a syringe filter, the reaction mixture was purified on reverse phase HPLC eluting with acetonitrile and water (with 0.1% TFA) to afford 23-1 and 23-2. Compound 23-1: MS (m/z) 669 [M+H]$^+$; $^1$H NMR (400 MHz, Methanol-d$_4$) δ 8.84 (d, 1H), 8.56-8.39 (m, 2H), 7.80 (d, 1H), 7.38 (dd, 1H), 6.88-6.64 (m, 3H), 5.43 (d, 1H), 4.57 (s, 2H), 3.38 (d, 1H), 3.22 (d, 1H), 2.61-2.38 (m, 2H), 1.36 (d, 1H), 1.05 (s, 1H). Compound 23-2: MS (m/z) 715 [M+H]$^+$; $^1$H NMR (400 MHz, Methanol-d$_4$) δ 8.56-8.36 (m, 2H), 7.82-7.70 (m, 1H), 7.37 (dd, 1H), 6.90-6.48 (m, 3H), 5.43 (dt, 1H), 4.53 (d, 2H), 3.38 (ddd, 1H), 3.26-3.16 (m, 1H), 2.44 (ddd, 2H), 1.39-1.29 (m, 1H), 1.05 (dt, 1H).

Example 24

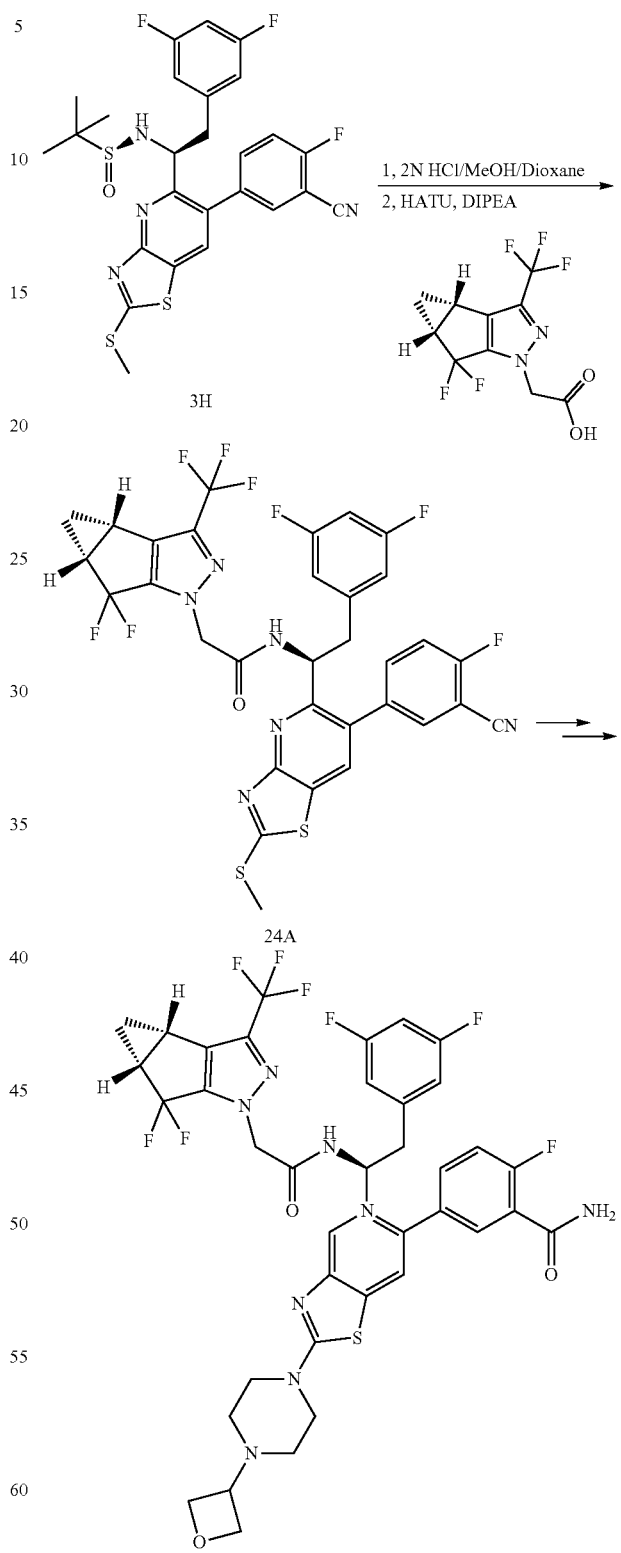

Synthesis of N—((S)-1-(6-(3-cyano-4-fluorophenyl)-2-(methylthio)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (24A): A solution of 3H (400 mg, 0.72 mmol) in 2N hydrochloride (2 mL of Methanol/2 mL of Dioxane), was stirred for 30 minutes. The solvent was removed and dried in vacuo. To a solution of crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (prepared according to WO2014110297, 206 mg, 0.73 mmol) and HATU (278 mg, 0.73 mmol) in DMF (3 mL), diisopropylethylamine (0.4 mL, 2.16 mmol) were added. The reaction was stirred at room temperature for 90 min. The reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide compound 24A. MS (m/z) 721 [M+H]$^+$.

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(4-(oxetan-3-yl)piperazin-1-yl)thiazolo[4,5-b]pyridin-6-yl)-2-fluorobenzamide (24): Compound 24 was prepared according to the method presented for the synthesis of Example 3 substituting 24A for 3J and substituting 1-(oxetan-3-yl)piperazine for morpholine to provide the desired compound. MS (m/z) 833 [M+H]+. $^1$H NMR (400 MHz, Methanol-d4) δ 8.73 (s, OH), 7.89 (s, 1H), 7.32 (s, 2H), 7.24-7.08 (m, 1H), 6.63 (d, J=9.7 Hz, 1H), 6.30 (d, J=7.3 Hz, 2H), 5.34 (d, J=8.0 Hz, 1H), 4.87 (d, J=8.8 Hz, 4H), 4.80-4.68 (m, 2H), 4.18 (s, 1H), 3.99 (s, 4H), 3.24-2.93 (m, 5H), 2.48 (d, J=7.4 Hz, 2H), 1.40 (d, J=6.4 Hz, 1H), 1.12 (s, 1H).

Example 25

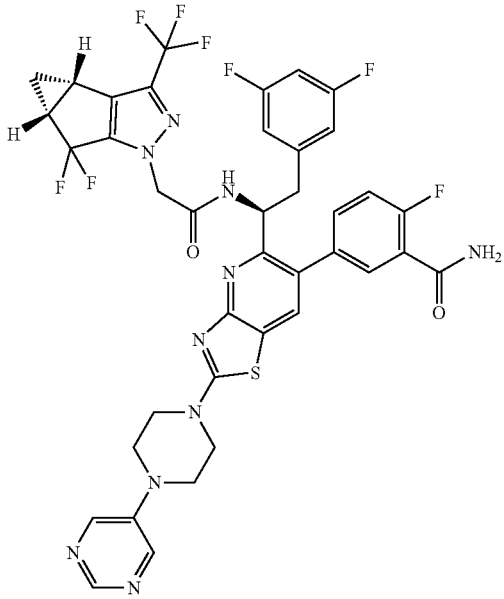

25

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(4-(pyrimidin-5-yl)piperazin-1-yl)thiazolo[4,5-b]pyridin-6-yl)-2-fluorobenzamide (25): Compound 25 was prepared according to the method presented for the synthesis of Example 3 substituting 24A for 3J and substituting 5-(piperazin-1-yl)pyrimidine for morpholine to provide the desired compound. MS (m/z) 855 [M+H]+. $^1$H NMR (400 MHz, Methanol-d4) δ 8.62 (s, 1H), 8.58 (s, 2H), 7.88 (s, 1H), 7.35 (s, 1H), 7.23-7.12 (m, 1H), 6.64 (s, 1H), 6.32 (d, J=7.4 Hz, 2H), 5.37-5.28 (m, 1H), 4.87 (s, 2H), 3.96 (s, 4H), 3.58 (d, J=5.4 Hz, 4H), 3.10 (dd, J=22.6, 7.9 Hz, 2H), 2.71-2.4 (m, 2H) 1.40 (d, J=6.8 Hz, 1H), 1.12 (s, 1H).

Example 26

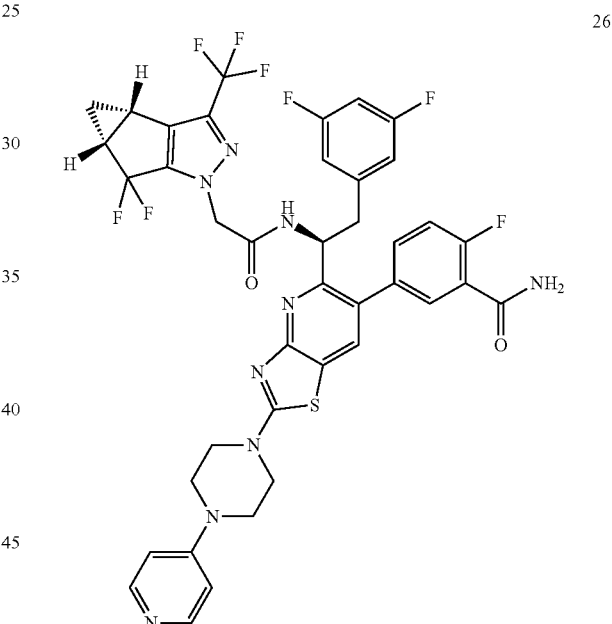

26

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(4-(pyridin-4-yl)piperazin-1-yl)thiazolo[4,5-b]pyridin-6-yl)-2-fluorobenzamide (26): Compound 26 was prepared according to the method presented for the synthesis of Example 3 substituting 24A for 3J and substituting 1-(pyridin-4-yl)piperazine for morpholine to provide the desired compound. MS (m/z) 854 [M+H]+. $^1$H NMR (400 MHz, Methanol-d4) δ 8.20 (d, J=7.1 Hz, 2H), 7.88 (s, 1H), 7.33 (s, 1H), 7.28-7.10 (m, 3H), 6.63 (d, J=9.3 Hz, 1H), 6.31 (d, J=7.5 Hz, 2H), 5.34 (d, J=7.8 Hz, 1H), 4.87 (s, 2H), 4.01 (s, 8H), 3.20-2.98 (m, 1H), 2.64-2.39 (m, 3H), 1.40 (d, J=7.4 Hz, 1H), 1.12 (s, 1H).

Example 27

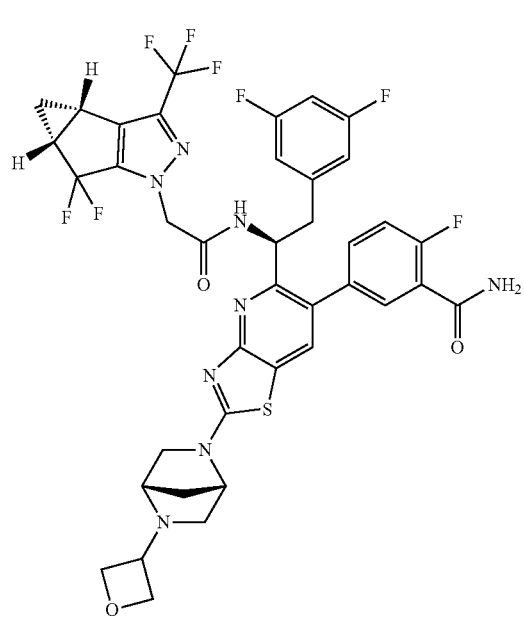

27

Example 28

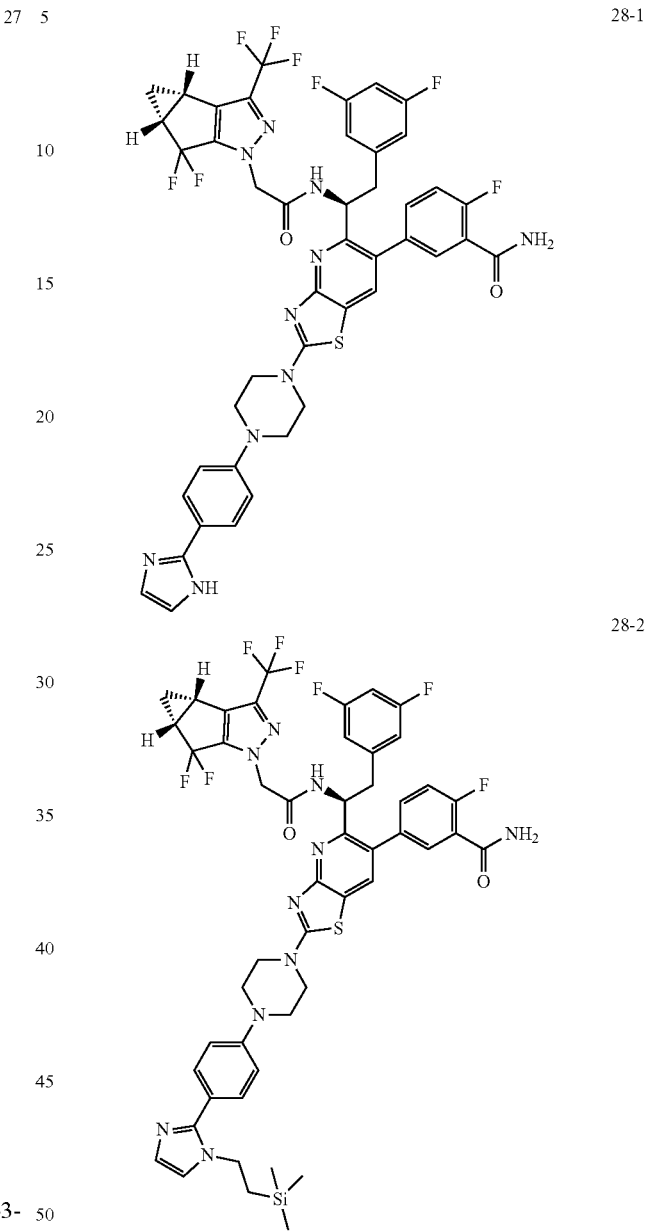

28-1

28-2

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-((1S,4S)-5-(oxetan-3-yl)-2,5-diazabicyclo[2.2.1]heptan-2-yl)thiazolo[4,5-b]pyridin-6-yl)-2-fluorobenzamide (27): Compound 27 was prepared according to the method presented for the synthesis of Example 3 substituting 24A for 3J and substituting (1S,4S)-2-(oxetan-3-yl)-2,5-diazabicyclo[2.2.1]heptane for morpholine to provide desired compound. MS (m/z) 845 [M+H]+. $^1$H NMR (400 MHz, Methanol-d4) δ 7.91 (s, 1H), 7.33 (d, J=7.2 Hz, 2H), 7.25-7.12 (m, 1H), 6.65 (t, J=9.5 Hz, 1H), 6.29 (d, J=7.3 Hz, 2H), 5.33 (t, J=7.6 Hz, 1H), 5.08-4.89 (m, 3H), 4.79-4.68 (m, 1H), 4.64 (d, J=8.3 Hz, 3H), 3.92 (dd, J=27.7, 10.0 Hz, 4H), 3.45 (d, J=11.5 Hz, 1H), 3.18-2.98 (m, 2H), 2.55-2.36 (m, 5H), 1.40 (q, J=7.1 Hz, 1H), 1.11 (s, 1H).

Synthesis of 5-(2-(4-(4-(1H-imidazol-2-yl)phenyl)piperazin-1-yl)-5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)thiazolo[4,5-b]pyridin-6-yl)-2-fluorobenzamide (28-1) and 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(4-(4-(1-(2-(trimethylsilyl)ethyl)-1H-imidazol-2-yl)phenyl)piperazin-1-yl)thiazolo[4,5-b]pyridin-6-yl)-2-fluorobenzamide (28-2): Compounds 28-1 and 28-2 were prepared according to the method presented for the synthesis of Example 3 substituting 24A for 3J and substituting 1-(4-1H-imidazol-2-yl)phenyl)piperazine for morpholine to provide Compound 28-1 and substituting 24A for 3J and substituting 1-(4-(1-(2-(trimethylsilyl)ethyl)-1H-imidazol-2-yl)phenyl)piperazine for morpholine to provide Compound 28-2. Compound 28-1: MS (m/z) 919 [M+H]+; ¹H NMR (400 MHz, Methanol-d4) δ 7.86 (s, 1H), 7.80 (d, J=8.9 Hz, 2H), 7.52 (s, 1H), 7.41-7.26 (m, 3H), 7.20 (dd, J=20.6, 9.2 Hz, 3H), 6.64 (t, J=9.1 Hz, 1H), 6.32 (d, J=7.4 Hz, 2H), 5.41-5.25 (m, 1H), 4.87 (s, 2H), 3.94 (s, 4H), 3.65 (t, J=5.3 Hz, 4H), 3.19-2.99 (m, 2H), 2.60-2.36 (m, 2H), 1.40 (d, J=7.4 Hz, 1H), 1.12 (s, 1H). Compound 28-2: MS (m/z) 1019 [M+H]+; ¹H NMR (400 MHz, Methanol-d4) δ 7.87 (s, 1H), 7.83-7.68 (m, 3H), 7.61 (d, J=2.2 Hz, 1H), 7.41-7.08 (m, 3H), 6.65 (t, J=9.2 Hz, 1H), 6.32 (d, J=7.2 Hz, 2H), 5.53 (s, 2H), 5.44-5.28 (m, 1H), 4.87 (s, 2H), 3.95 (s, 4H), 3.70 (dd, J=15.9, 7.4 Hz, 7H), 3.21-2.98 (m, 2H), 2.61-2.35 (m, 2H), 1.40 (d, J=6.8 Hz, 1H), 1.12 (s, 1H), 1.06-0.87 (m, 2H), 0.00 (s, 9H).

Example 29

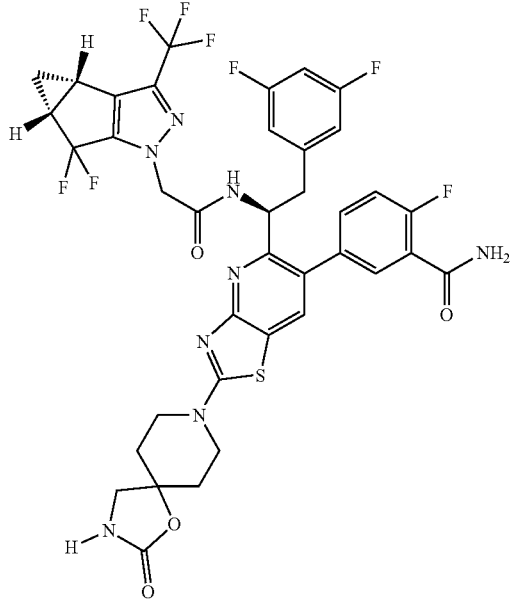

Example 30

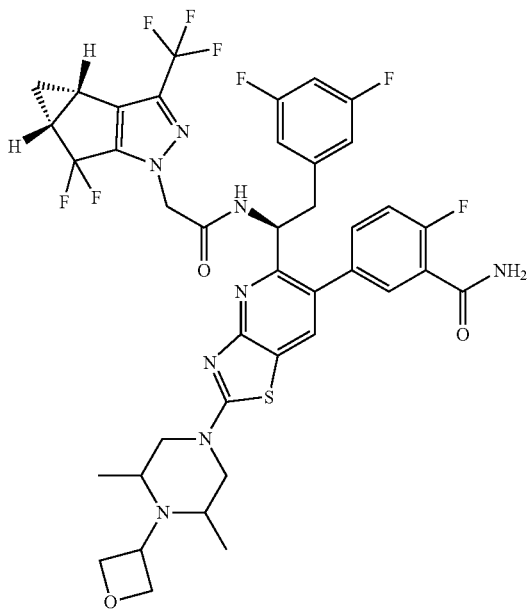

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(2-oxo-1-oxa-3,8-diazaspiro[4.5]decan-8-yl)thiazolo[4,5-b]pyridin-6-yl)-2-fluorobenzamide (29): Compound 29 was prepared according to the method presented for the synthesis of Example 3 substituting 24A for 3J and substituting 1-oxa-3,8-diazaspiro[4.5]decan-2-one for morpholine to provide the desired compound. MS (m/z) 847 [M+H]+. ¹H NMR (400 MHz, Methanol-d4) δ 7.87 (s, 1H), 7.41-7.24 (m, 2H), 7.25-7.05 (m, 1H), 6.65 (t, J=9.3 Hz, 1H), 6.32 (d, J=7.4 Hz, 2H), 5.38-5.26 (m, 1H), 4.87 (s, 2H), 4.10 (s, 2H), 3.73 (t, J=12.6 Hz, 2H), 3.44 (s, 2H), 3.19-2.96 (m, 2H), 2.48 (dd, J=8.1, 4.2 Hz, 1H), 2.14 (d, J=13.7 Hz, 2H), 2.02 (t, J=12.5 Hz, 2H), 1.39 (d, J=7.0 Hz, 1H), 1.11 (s, 1H).

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(3,5-dimethyl-4-(oxetan-3-yl)piperazin-1-yl)thiazolo[4,5-b]pyridin-6-yl)-2-fluorobenzamide (30): Compound 30 was prepared according to the method presented for the synthesis of Example 3 substituting 24A for 3J and substituting 2,6-dimethyl-1-(oxetan-3-yl)piperazine for morpholine to provide the desired compound. MS (m/z) 861 [M+H]+. ¹H NMR (400 MHz, Methanol-d4) δ 7.81 (s, 1H), 7.34 (d, J=6.8 Hz, 1H), 7.27 (s, 1H), 7.24-7.09 (m, 1H), 6.62 (d, J=9.6 Hz, 1H), 6.33 (d, J=7.5 Hz, 2H), 5.41-5.28 (m, 1H), 4.86 (s, 2H), 4.76 (d, J=4.1 Hz, 2H), 4.72-4.65 (m, 2H), 4.50 (d, J=5.5 Hz, 1H), 4.28 (t, J=7.1 Hz, 1H), 3.73 (s, 3H), 3.22-3.09 (m, 1H), 3.03 (dd, J=13.8, 6.5 Hz, 3H), 2.47 (dd, J=7.8, 4.1 Hz, 1H), 1.27 (s, 2H), 1.13 (d, J=6.7 Hz, 7H).

Example 31

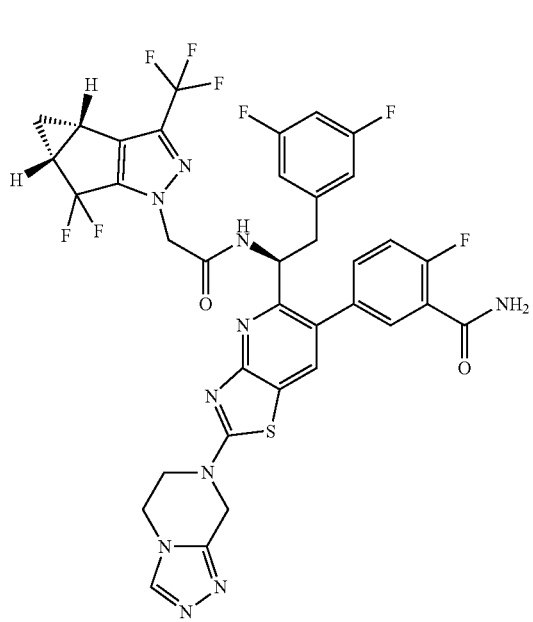

Example 32

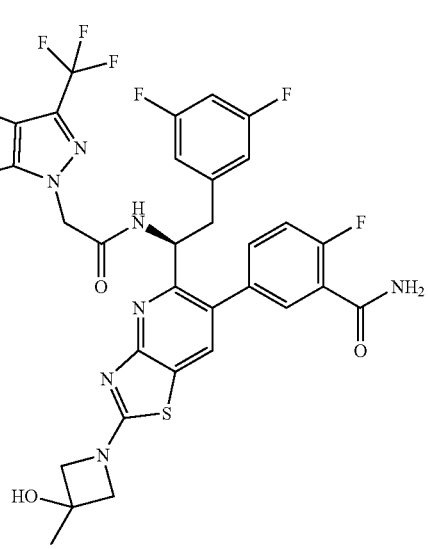

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(5,6-dihydro-[1,2,4]triazolo[4,3-a]pyrazin-7(8H)-yl)thiazolo[4,5-b]pyridin-6-yl)-2-fluorobenzamide (31): Compound 31 was prepared according to the method presented for the synthesis of Example 3 substituting 24A for 3J and substituting 5,6,7,8-tetrahydro-[1,2,4]triazolo[4,3-a]pyrazine for morpholine to provide the desired compound. MS (m/z) 815 [M+H]+. $^1$H NMR (400 MHz, Methanol-d4) δ 8.91 (s, 1H), 7.93 (s, 1H), 7.41-7.25 (m, 2H), 7.25-7.09 (m, 1H), 6.64 (t, J=9.2 Hz, 1H), 6.31 (d, J=7.3 Hz, 2H), 5.34 (t, J=7.4 Hz, 1H), 5.29-5.19 (m, 2H), 4.87 (s, 2H), 4.46 (t, J=5.5 Hz, 2H), 4.27 (d, J=5.6 Hz, 2H), 3.20-2.95 (m, 2H), 2.52-2.41 (m, 2H), 1.40 (q, J=7.1 Hz, 1H), 1.12 (s, 1H).

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(3-hydroxy-3-methylazetidin-1-yl)thiazolo[4,5-b]pyridin-6-yl)-2-fluorobenzamide (32): Compound 32 was prepared according to the method presented for the synthesis of Example 3 substituting 24A for 3J and substituting 3-methylazetidin-3-ol for morpholine to provide the desired compound. MS (m/z) 778 [M+H]+. $^1$H NMR (400 MHz, Methanol-d4) δ 7.86 (s, 1H), 7.34 (d, J=6.6 Hz, 1H), 7.28 (s, 1H), 7.18 (dd, J=10.7, 8.5 Hz, 1H), 6.64 (t, J=9.3 Hz, 1H), 6.32 (d, J=7.2 Hz, 2H), 5.32 (dd, J=8.9, 6.3 Hz, 1H), 4.86 (s, 2H), 4.32-4.12 (m, 4H), 3.14 (dd, J=12.9, 9.0 Hz, 1H), 3.06 (d, J=6.2 Hz, 1H), 2.51-2.41 (m, 2H), 1.59 (s, 3H), 1.39 (q, J=7.4 Hz, 1H), 1.10 (s, 1H).

Example 33

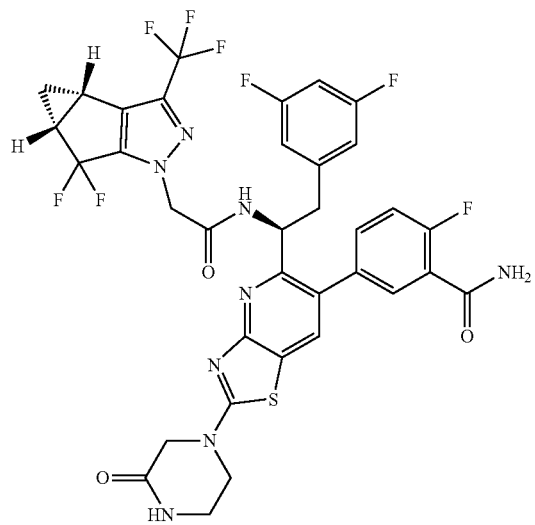

33

Synthesis of 5-(5-((S)-1-(2-(((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(3-oxopiperazin-1-yl)thiazolo[4,5-b]pyridin-6-yl)-2-fluorobenzamide (33): Compound 33 was prepared according to the method presented for the synthesis of Example 3 substituting 24A for 3J and substituting piperazin-2-one for morpholine to provide the desired compound. MS (m/z) 791 [M+H]+. $^1$H NMR (400 MHz, Methanol-d4) δ 7.82 (s, 1H), 7.33-7.18 (m, 2H), 7.11 (dd, J=10.7, 8.5 Hz, 1H), 6.64-6.49 (m, 1H), 6.30-6.18 (m, 2H), 5.26 (dd, J=8.8, 6.2 Hz, 1H), 4.79 (s, 2H), 4.29 (s, 2H), 3.86 (dd, J=6.4, 4.5 Hz, 2H), 3.48 (dd, J=6.3, 4.5 Hz, 2H), 3.06 (dd, J=13.0, 8.8 Hz, 1H), 2.97 (dd, J=12.9, 6.3 Hz, 1H), 2.56 (s, 1H), 2.41 (ddd, J=12.0, 8.0, 4.1 Hz, 1H), 1.32 (q, J=7.1 Hz, 1H), 1.04 (s, 1H).

Example 34

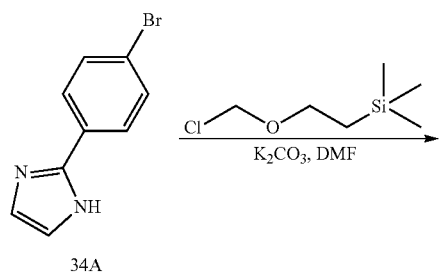

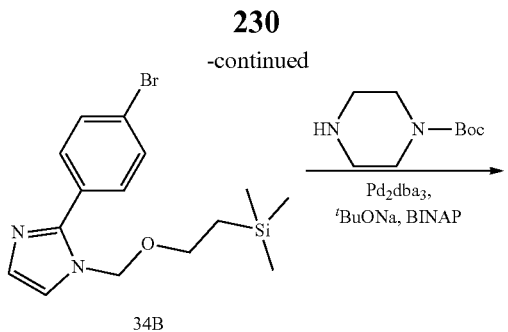

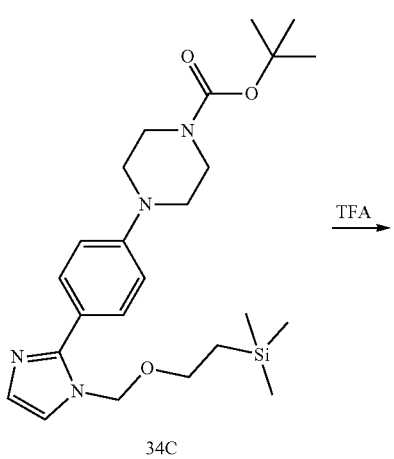

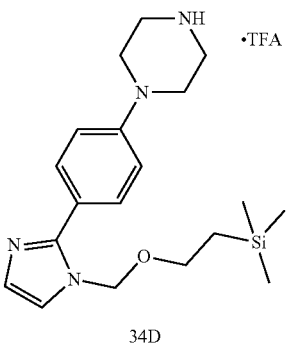

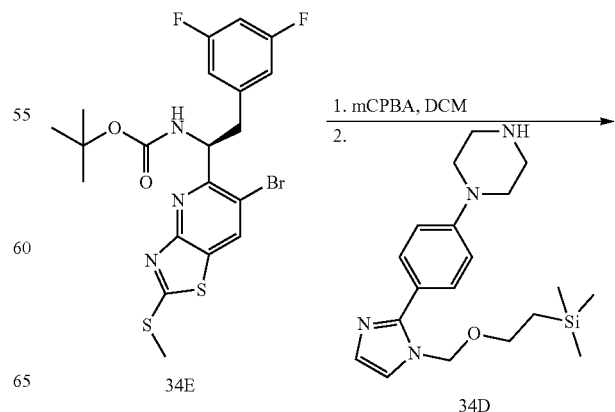

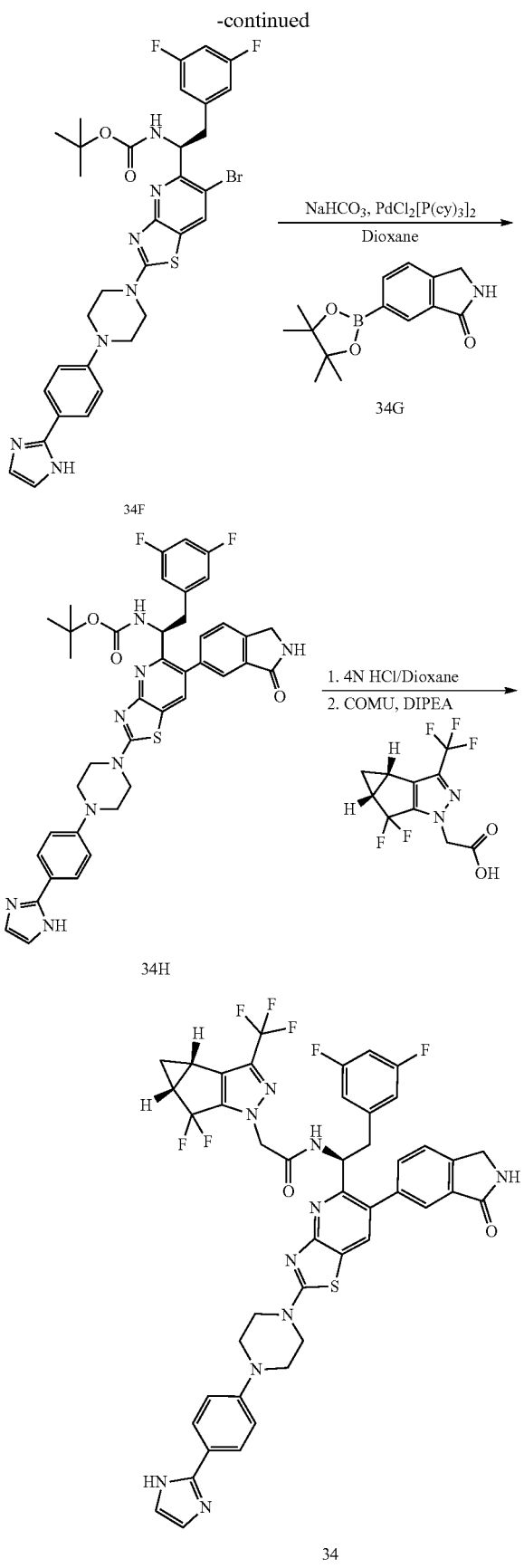

Synthesis of 2-(4-bromophenyl)-1-((2-(trimethylsilyl) ethoxy)methyl)-1H-imidazole (34B): To a solution of 2-(4-bromophenyl)-1H-imidazole in 5 mL of DMF, potassium carbonate (1.25 g, 9.1 mmol) and 2-(trimethylsilyl)ethoxymethyl chloride (1.51 g, 9.1 mmol) were added. The reaction was stirred overnight. The reaction was diluted with EtOAc (100 mL) and washed with water (50 mL) and brine (50 mL). The organic layer was separated and was concentrated to dryness in vacuo to afford compound 34B, which was without further purification. MS (m/z) 353 [M+H]+.

Synthesis of tert-butyl 4-(4-(1-((2-(trimethylsilyl)ethoxy) methyl)-1H-imidazol-2-yl)phenyl)piperazine-1-carboxylate (34C): A solution of tert-butyl piperazine-1-carboxylate (950 mg, 5.1 mmol), 34B (1500 mg, 4.25 mmol), 2,2'-bis (diphenylphosphino)-1,1'-binaphthyl (110 mg, 0.17 mmol), Tris(dibenzylideneacetone) dipalladium (77.8 mg, 0.085 mmol), sodium t-butoxide (571 mg, 5.94 mmol), and toluene (16 mL) was placed in a 100-mL round bottom flask, stirred overnight at reflux in an oil bath, and concentrated under vacuum. Purification via silica gel column (EtOAc/Hexanes (70%)) yielded compound 34C. MS (m/z) 459 [M+H]+.

Synthesis of 1-(4-(1-((2-(trimethylsilyl)ethoxy)methyl)-1H-imidazol-2-yl)phenyl)piperazine 2,2,2-trifluoroacetate (34D): A solution of 34C in 2 mL of trifluoroacetic acid was stirred for 30 minutes. The TFA was removed and the residue was dried under high vacuum to provide compound 34D. MS (m/z) 359 [M+H]+.

Synthesis of tert-butyl (S)-(1-(2-(4-(4-(1H-imidazol-2-yl) phenyl)piperazin-1-yl)-6-bromothiazolo[4,5-b]pyridin-5-yl)-2-(3,5-difluorophenyl)ethyl)carbamate (34F): To a solution of 34E (80 mg, 0.155 mmol) in DCM (6 mL), 3-Chloroperoxybenzoic acid (77% purity, 69.4 mg, 0.31 mmol) was added. The reaction was stirred for 1 hour. 34D (366 mg, 0.78 mmol) and N,N-Diisopropylethylamine (0.81 mL, 4.65 mmol) was added to the mixture. After 6 hours, the reaction was diluted with EtOAc (20 mL) and washed with 10 mL of saturated sodium bicarbonate (aq). The organic layer was separated and was concentrated to dryness in vacuo. The reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide compound 34F. MS (m/z) 696 [M+H]+.

Synthesis of tert-butyl (S)-(1-(2-(4-(4-(1H-imidazol-2-yl) phenyl)piperazin-1-yl)-6-(3-oxoisoindolin-5-yl)thiazolo[4,5-b]pyridin-5-yl)-2-(3,5-difluorophenyl)ethyl)carbamate (34H): To a suspension of 34F (20 mg, 0.029 mmol), 6-(4,4,5,5-tetramethyl-1,3,2-dioxaborolan-2-yl)isoindolin-1-one (11.2 mg, 0.043 mmol), 1 N of sodium bicarbonate (0.086 mL) in 1 mL of dioxane, dichlorobis(tricyclohexylphosphine) palladium(II) (2.12 mg) was added. The reaction was heated at 130° C. by microwave reactor for 10 minutes. The mixture was filtered, and the filtrate was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide compound 34H. MS (m/z) 749 [M+H]+.

Synthesis of N—((S)-1-(2-(4-(4-(1H-imidazol-2-yl)phenyl)piperazin-1-yl)-6-(3-oxoisoindolin-5-yl)thiazolo[4,5-b] pyridin-5-yl)-2-(3,5-difluorophenyl)ethyl)-2-((3bS,4aR)-5, 5-difluoro-3-(trifluoromethyl)-3b,4,4a,5-tetrahydro-1H-cyclopropa[3,4]cyclopenta[1,2-c]pyrazol-1-yl)acetamide (34): A solution of 34H (8 mg, 0.0.011 mmol) in 4 N of hydrochloride in dioxane (2 mL) was stirred for 1 hour. The solvent was removed and dried in vacuo. The crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (3 mg, 0.011 mmol) and (1-Cyano-2-ethoxy-2-oxoethylidenaminooxy)dimethylamino-morpholino-carbenium hexafluorophosphate (4.58 mg, 0.011 mmol) was dissolved in DMF (1 mL) and diisopropylethylamine (0.004 mL, 0.021 mmol) was added to the solution. The reaction was stirred at room temperature for 90 min. The reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide the desired compound. MS (m/z) 913 [M+H]+. $^1$H NMR (400 MHz, Methanol-d4) δ 7.90 (s, 1H), 7.80 (d, J=8.9 Hz, 2H), 7.56 (d, J=7.9 Hz, 1H), 7.52 (s, 2H), 7.45 (s, 1H), 7.31-7.15 (m, 3H), 6.63 (t, J=9.3 Hz, 1H), 6.26 (d, J=7.4 Hz, 2H), 5.47-5.32 (m, 1H), 4.88 (s, 2H), 4.48 (s, 2H), 3.95 (s, 4H), 3.66 (t, J=5.3 Hz, 4H), 3.17-2.99 (m, 2H), 2.52-2.42 (m, 2H), 1.47-1.33 (m, 1H), 1.13 (s, 1H).

Example 35

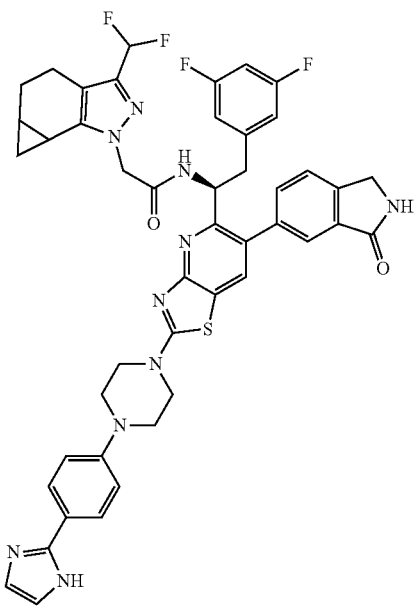

Synthesis of N—((S)-1-(2-(4-(4-(1H-imidazol-2-yl)phenyl)piperazin-1-yl)-6-(3-oxoisoindolin-5-yl)thiazolo[4,5-b]pyridin-5-yl)-2-(3,5-difluorophenyl)ethyl)-2-(3-(difluoromethyl)-5,5a,6,6a-tetrahydrocyclopropa[g]indazol-1(4H)-yl)acetamide (35): Compound 35 was prepared according to the method presented for the synthesis of Example 34 utilizing 34E and substituting 2-(3-(difluoromethyl)-5,5a,6,6a-tetrahydrocyclopropa[g]indazol-1(4H)-yl)acetic acid (prepared according to WO2013006738) for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 873 [M+H]+. $^1$H NMR (400 MHz, Methanol-d4) δ 7.93 (d, J=2.4 Hz, 1H), 7.80 (d, J=9.0 Hz, 2H), 7.59 (d, J=7.9 Hz, 1H), 7.52 (s, 2H), 7.35 (s, 1H), 7.23 (d, J=9.0 Hz, 2H), 6.81-6.42 (m, 2H), 6.30 (t, J=7.2 Hz, 2H), 5.40 (t, J=7.0 Hz, 1H), 4.96-4.85 (m, 3H), 4.49 (s, 2H), 3.96 (s, 4H), 3.65 (t, J=5.2 Hz, 4H), 3.14-2.91 (m, 2H), 2.68 (s, 1H), 2.2-2.14 (m, 1H), 1.77 (dd, J=28.6, 24.2 Hz, 2H), 1.57 (s, 1H), 1.04-0.81 (m, 1H), 0.64 (d, J=26.6 Hz, 1H).

Example 36

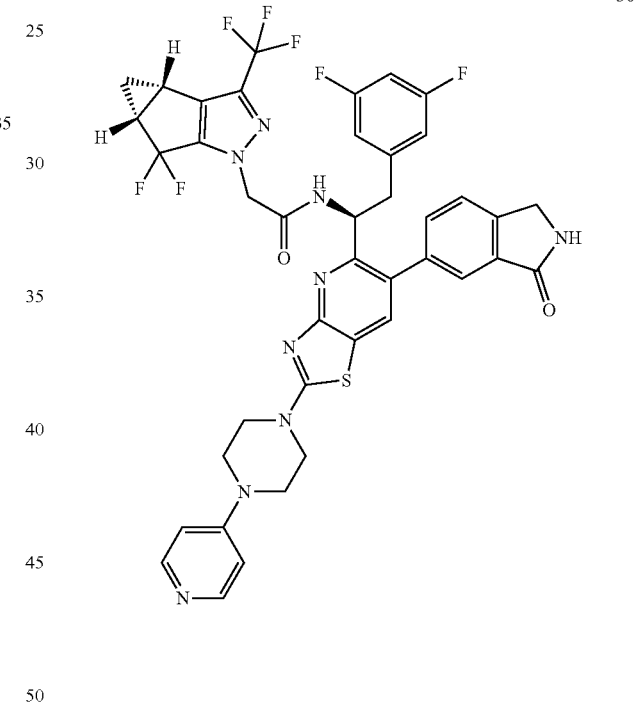

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-oxoisoindolin-5-yl)-2-(4-(pyridin-4-yl)piperazin-1-yl)thiazolo[4,5-b]pyridin-5-yl)ethyl)acetamide (36): Compound 36 was prepared according to the method presented for the synthesis of Example 34 utilizing 34E and substituting 1-(pyridin-4-yl)piperazine for 34D to provide the desired compound. MS (m/z) 848 [M+H]+. $^1$H NMR (400 MHz, Methanol-d4) δ 8.20 (d, J=7.3 Hz, 2H), 7.92 (s, 1H), 7.56 (d, J=7.8 Hz, 1H), 7.46 (s, 1H), 7.24 (d, J=7.6 Hz, 3H), 6.63 (t, J=9.2 Hz, 1H), 6.25 (d, J=7.4 Hz, 2H), 5.38 (dd, J=8.7, 6.1 Hz, 1H), 4.88 (s, 2H), 4.48 (s, 2H), 4.02 (s, 8H), 3.18-2.95 (m, 2H), 2.59-2.33 (m, 2H), 1.40 (q, J=7.2 Hz, 1H), 1.13 (s, 1H).

Example 37

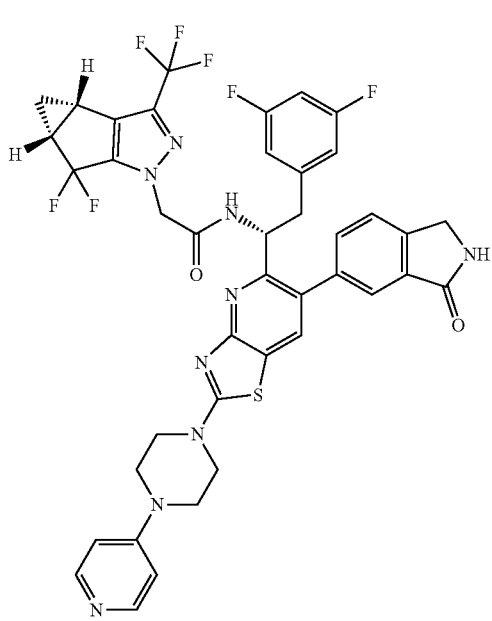

37

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((R)-2-(3,5-difluorophenyl)-1-(6-(3-oxoisoindolin-5-yl)-2-(4-(pyridin-4-yl)piperazin-1-yl)thiazolo[4,5-b]pyridin-5-yl)ethyl)acetamide (37): Compound 37 was prepared according to the method presented for the synthesis of Example 34 utilizing 34E and substituting tert-butyl (R)-(1-(6-bromo-2-(methylthio)thiazolo[4,5-b]pyridin-5-yl)-2-(3,5-difluorophenyl)ethyl)carbamate for 34E and substituting 1-(pyridin-4-yl)piperazine for 34D to provide the desired compound. MS (m/z) 848 [M+H]+. ¹H NMR (400 MHz, Methanol-d4) δ 8.20 (d, J=7.3 Hz, 2H), 7.93 (s, 1H), 7.57 (d, J=7.8 Hz, 1H), 7.46 (d, J=7.9 Hz, 1H), 7.36-7.21 (m, 3H), 6.63 (t, J=9.2 Hz, 1H), 6.25 (d, J=7.5 Hz, 2H), 5.48-5.33 (m, 1H), 4.87 (s, 2H), 4.49 (s, 2H), 4.02 (s, 8H), 3.12-2.95 (m, 2H), 2.51-2.41 (m, 2H), 1.38 (q, J=7.3 Hz, 1H), 1.10 (s, 1H).

Example 38

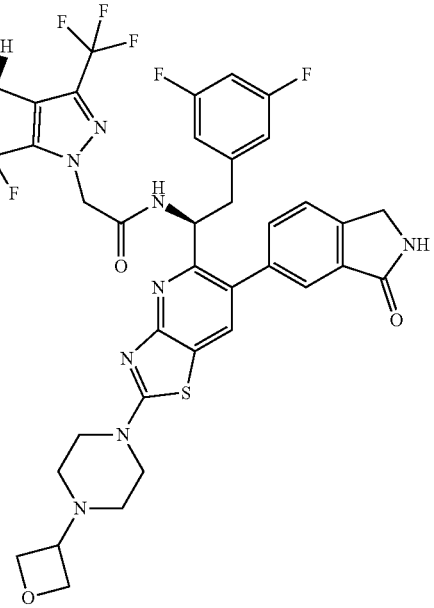

38

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(4-(oxetan-3-yl)piperazin-1-yl)-6-(3-oxoisoindolin-5-yl)thiazolo[4,5-b]pyridin-5-yl)ethyl)acetamide (38): Compound 38 was prepared according to the method presented for the synthesis of Example 34 utilizing 34E and substituting 1-(oxetan-3-yl)piperazine for 34D to provide the desired compound. MS (m/z) 827 [M+H]+. ¹H NMR (400 MHz, Methanol-d4) δ 7.95 (s, 1H), 7.55 (d, J=7.8 Hz, 1H), 7.45 (d, J=8.0 Hz, 1H), 7.27 (s, 1H), 6.62 (tt, J=9.2, 2.3 Hz, 1H), 6.33-6.16 (m, 2H), 5.39 (dd, J=8.5, 6.3 Hz, 1H), 4.88 (d, J=3.3 Hz, 4H), 4.56-4.37 (m, 3H), 4.09 (q, J=5.4 Hz, 4H), 3.42 (t, J=5.3 Hz, 4H), 3.29 (p, J=1.6 Hz, 2H), 3.15-2.96 (m, 2H), 2.60 (s, OH), 2.51-2.41 (m, 2H), 1.50-1.32 (m, 1H), 1.12 (qt, J=4.1, 3.0, 2.2 Hz, 1H).

Example 39

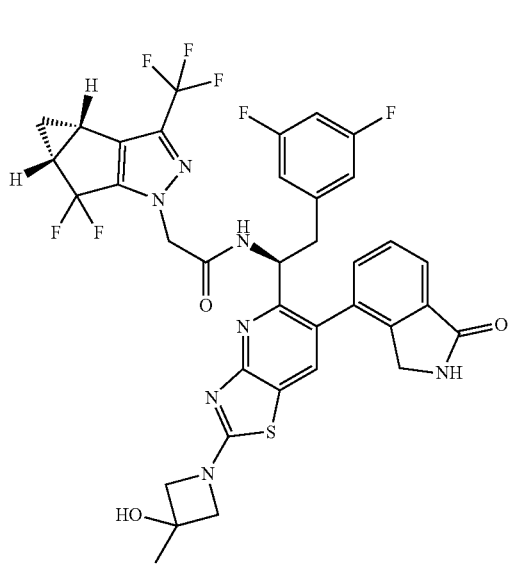

39

Example 40

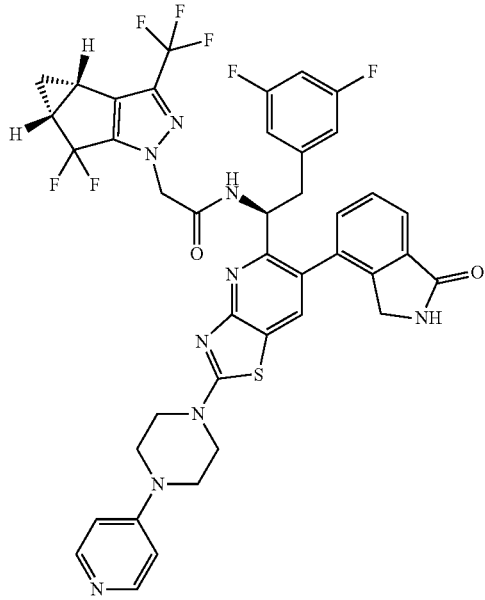

40

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-hydroxy-3-methylazetidin-1-yl)-6-(1-oxoisoindolin-4-yl)thiazolo[4,5-b]pyridin-5-yl)ethyl)acetamide (39): Compound 39 was prepared according to the method presented for the synthesis of Example 34 utilizing 34E and substituting 3-methylazetidin-3-ol for 34D and substituting 2,3-Dihydro-1H-isoindol-1-one-4-boronic acid pinacol ester for 34G to provide the desired compound. MS (m/z) 772 [M+H]+. $^1$H NMR (400 MHz, Methanol-d4) δ 7.84 (d, J=33.6 Hz, 1H), 7.73 (t, J=8.9 Hz, 1H), 7.54-7.29 (m, 1H), 6.59 (dd, J=64.5, 8.9 Hz, 2H), 6.23 (dd, J=43.6, 7.5 Hz, 2H), 5.21 (d, J=6.0 Hz, 1H), 4.83 (d, J=5.0 Hz, 2H), 4.20-3.98 (m, 6H), 3.08 (dd, J=22.6, 11.7 Hz, 1H), 2.40 (s, 2H), 1.52 (s, 3H), 1.41-1.21 (m, 2H), 1.03 (d, J=30.9 Hz, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-oxoisoindolin-4-yl)-2-(4-(pyridin-4-yl)piperazin-1-yl)thiazolo[4,5-b]pyridin-5-yl)ethyl)acetamide (40): Compound 40 was prepared according to the method presented for the synthesis of Example 34 utilizing 34E and substituting 1-(pyridin-4-yl)piperazine for 34D and substituting 2,3-Dihydro-TH-isoindol-1-one-4-boronic acid pinacol ester for 34G to provide the desired compound. MS (m/z) 848 [M+H]+. $^1$H NMR (400 MHz, Methanol-d4) δ 8.21 (d, J=7.3 Hz, 2H), 7.98 (d, J=33.5 Hz, 1H), 7.82 (t, J=9.2 Hz, 1H), 7.70-7.37 (m, 2H), 7.24 (d, J=7.5 Hz, 2H), 6.86-6.51 (m, 1H), 6.31 (dd, J=45.1, 7.6 Hz, 2H), 5.14 (d, J=139.3 Hz, 1H), 4.91 (s, 1H), 4.81 (s, 1H), 4.19 (dd, J=40.3, 20.2 Hz, 1H), 4.02 (s, 8H), 3.33 (s, 1H), 3.23-3.08 (m, 1H), 3.00 (dt, J=12.4, 6.3 Hz, 1H), 2.48 (s, 2H), 1.51-1.32 (m, 1H), 1.11 (d, J=29.1 Hz, 1H).

Example 41

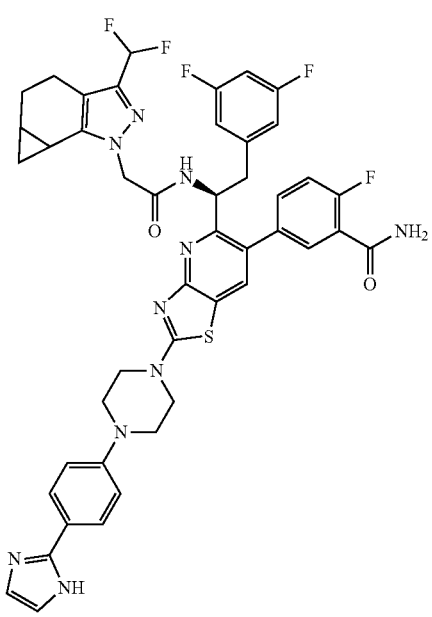

Example 42

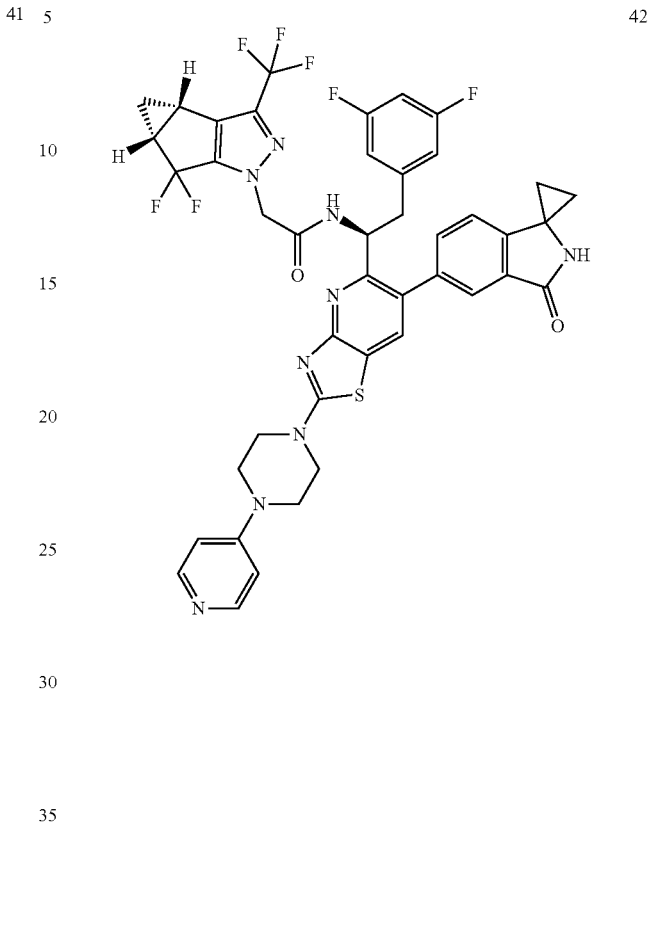

Synthesis of 5-(2-(4-(4-(1H-imidazol-2-yl)phenyl)piperazin-1-yl)-5-(((1S)-1-(2-(3-(difluoromethyl)-5,5a,6,6a-tetrahydrocyclopropa[g]indazol-1(4H)-yl)acetamido)-2-(3,5-difluorophenyl)ethyl)thiazolo[4,5-b]pyridin-6-yl)-2-fluorobenzamide (41): Compound 41 was prepared according to the method presented for the synthesis of Example 34 utilizing 34E and substituting (3-Carbamoyl-4-fluoro-phenyl)boronic acid for 34G and substituting 2-(3-(difluoromethyl)-5,5a,6,6a-tetrahydrocyclopropa[g]indazol-1(4H)-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 879 [M+H]+. $^1$H NMR (400 MHz, Methanol-d4) δ 7.88 (d, J=1.5 Hz, 1H), 7.80 (d, J=8.9 Hz, 2H), 7.52 (s, 2H), 7.43 (s, 1H), 7.33 (s, 1H), 7.23 (d, J=9.1 Hz, 3H), 6.83-6.41 (m, 2H), 6.36 (t, J=7.8 Hz, 2H), 5.41-5.28 (m, 1H), 4.88 (s, 2H), 4.03-3.85 (m, 4H), 3.65 (t, J=5.3 Hz, 4H), 3.33 (s, 1H), 3.08 (dd, J=19.7, 7.3 Hz, 1H), 2.69 (d, J=12.3 Hz, 1H), 2.21-2.01 (m, 2H), 1.82-1.52 (m, 3H), 1.05-0.51 (m, 2H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3'-oxospiro[cyclopropane-1,1'-isoindolin]-5'-yl)-2-(4-(pyridin-4-yl)piperazin-1-yl)thiazolo[4,5-b]pyridin-5-yl)ethyl)acetamide (42): Compound 42 was prepared according to the method presented for the synthesis of Example 34 utilizing 34E and substituting 1-(pyridin-4-yl)piperazine for 34D and substituting 5'-(4,4,5,5-Tetramethyl-1,3,2-dioxaborolan-2-yl)spiro[cyclopropane-1,1'-iso indolin]-3'-one (prepared according to WO2014134566) for 34G to provide the desired compound. MS (m/z) 874 [M+H]+. $^1$H NMR (400 MHz, Methanol-d4) δ 8.20 (d, J=7.2 Hz, 2H), 7.92 (s, 1H), 7.41 (s, 1H), 7.23 (dt, J=16.4, 8.0 Hz, 4H), 6.63 (t, J=9.2 Hz, 1H), 6.24 (d, J=7.3 Hz, 2H), 5.47-5.27 (m, 1H), 4.88 (s, 2H), 4.02 (s, 8H), 3.20-2.89 (m, 2H), 2.47 (dd, J=8.1, 4.2 Hz, 1H), 1.73-1.45 (m, 4H), 1.40 (q, J=7.2 Hz, 1H), 1.13 (s, 1H).

Example 43

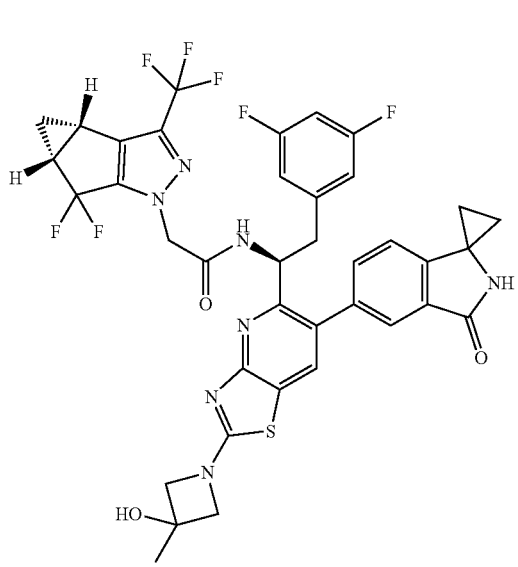

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-hydroxy-3-methylazetidin-1-yl)-6-(3'-oxospiro[cyclopropane-1,1'-isoindolin]-5'-yl)thiazolo[4,5-b]pyridin-5-yl)ethyl)acetamide (43): Compound 43 was prepared according to the method presented for the synthesis of Example 34 utilizing 34E and substituting 3-methylazetidin-3-ol for 34D and substituting 5'-(4,4,5,5-Tetramethyl-1,3,2-dioxaborolan-2-yl)spiro[cyclopropane-1,1'-iso indolin]-3'-one for 34G to provide the desired compound. MS (m/z) 798 [M+H]+. ¹H NMR (400 MHz, Methanol-d4) δ 7.91 (s, 1H), 7.40 (s, 1H), 7.28 (s, 1H), 7.20 (d, J=7.9 Hz, 1H), 6.73-6.50 (m, 1H), 6.26 (d, J=7.4 Hz, 2H), 5.48-5.30 (m, 1H), 4.87 (s, 2H), 4.30-4.05 (m, 4H), 3.15-2.92 (m, 2H), 2.48 (dt, J=12.6, 3.4 Hz, 2H), 1.68-1.45 (m, 7H), 1.39 (q, J=7.1 Hz, 1H), 1.11 (s, 1H).

Example 44

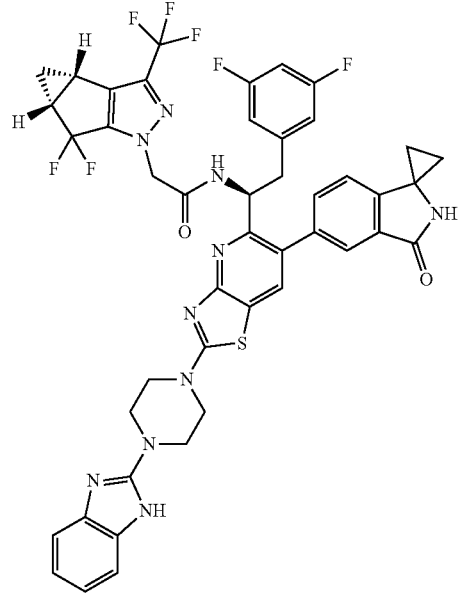

Synthesis of N—((S)-1-(2-(4-(1H-benzo[d]imidazol-2-yl)piperazin-1-yl)-6-(3' oxospiro[cyclopropane-1,1'-isoindolin]-5'-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (44): Compound 44 was prepared according to the method presented for the synthesis of Example 34 utilizing 34E and substituting 2-piperazin-1-yl-1H-benzoimidazole for 34D and substituting 5'-(4,4,5,5-Tetramethyl-1,3,2-dioxaborolan-2-yl)spiro[cyclopropane-1,1'-iso indolin]-3'-one for 34G to provide the desired compound. MS (m/z) 913 [M+H]+. ¹H NMR (400 MHz, Methanol-d4) δ 7.93 (s, 1H), 7.46-7.41 (m, 3H), 7.35 (dd, J=6.0, 3.2 Hz, 2H), 7.27 (s, 1H), 7.25-7.14 (m, 1H), 6.63 (t, J=9.2 Hz, 1H), 6.24 (d, J=7.4 Hz, 2H), 5.45-5.30 (m, 1H), 4.88 (s, 2H), 4.07 (d, J=4.5 Hz, 4H), 3.94 (t, J=5.2 Hz, 4H), 3.12-2.91 (m, 2H), 2.52-2.42 (m, 2H), 1.68-1.46 (m, 4H), 1.46-1.27 (in, TH), 1.13 (s, TH).

Example 45

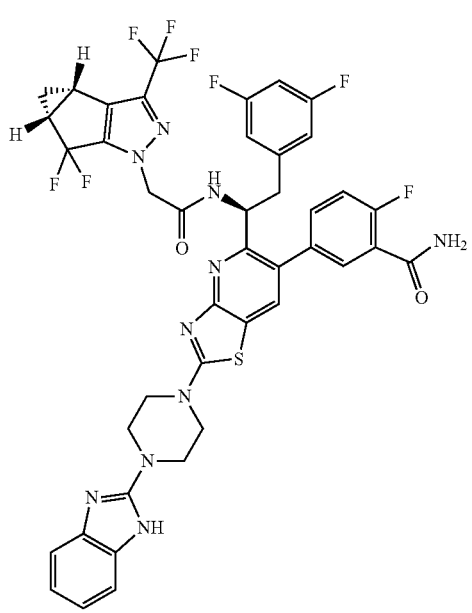

Example 46

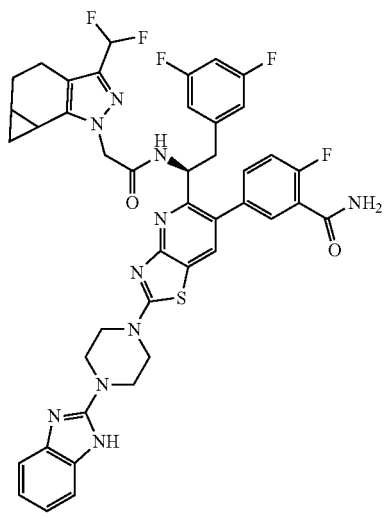

Synthesis of 5-(2-(4-(1H-benzo[d]imidazol-2-yl)piperazin-1-yl)-5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)thiazolo[4,5-b]pyridin-6-yl)-2-fluorobenzamide (45): Compound 45 was prepared according to the method presented for the synthesis of Example 34 utilizing 34E and substituting 2-piperazin-1-yl-1H-benzoimidazole for 34D and substituting (3-Carbamoyl-4-fluoro-phenyl)boronic acid for 34G to provide the desired compound. MS (m/z) 893 [M+H]+. $^1$H NMR (400 MHz, Methanol-d4) δ 7.89 (s, 1H), 7.44 (dd, J=6.0, 3.2 Hz, 3H), 7.41-7.31 (m, 3H), 7.25-7.10 (m, 1H), 6.64 (t, J=9.2 Hz, 1H), 6.31 (d, J=7.2 Hz, 2H), 5.45-5.23 (m, 1H), 4.87 (s, 3H), 4.07 (d, J=4.6 Hz, 4H), 3.93 (t, J=5.2 Hz, 4H), 3.24-2.90 (m, 2H), 2.72-2.25 (m, 2H), 1.44-1.31 (m, 1H), 1.12 (s, 1H).

Synthesis of 5-(2-(4-(1H-benzo[d]imidazol-2-yl)piperazin-1-yl)-5-((1S)-1-(2-(3-(difluoromethyl)-5,5a,6,6a-tetrahydrocyclopropa[g]indazol-1(4H)-yl)acetamido)-2-(3,5-difluorophenyl)ethyl)thiazolo[4,5-b]pyridin-6-yl)-2-fluorobenzamide (46): Compound 46 was prepared according to the method presented for the synthesis of Example 34 utilizing 34E and substituting 2-piperazin-1-yl-1H-benzoimidazole for 34D, substituting (3-Carbamoyl-4-fluoro-phenyl)boronic acid for 34G and substituting 2-(3-(difluoromethyl)-5,5a,6,6a-tetrahydrocyclopropa[g]indazol-1(4H)-yl)acetic acid for 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetic acid to provide the desired compound. MS (m/z) 853 [M+H]+. $^1$H NMR (400 MHz, Methanol-d4) δ 7.91 (d, J=0.8 Hz, 1H), 7.46-7.41 (m, 3H), 7.38-7.28 (m, 3H), 7.22 (t, J=10.1 Hz, 1H), 6.62 (td, J=54.6, 7.3 Hz, 1H), 6.34 (t, J=7.8 Hz, 2H), 5.45-5.21 (m, 1H), 4.87 (d, J=7.7 Hz, 2H), 4.06 (d, J=5.6 Hz, 4H), 3.93 (t, J=5.3 Hz, 4H), 3.20-2.94 (m, 2H), 2.33-1.89 (m, 3H), 1.99-1.46 (m, 2H), 1.04-0.82 (m, 1H), 0.63 (dd, J=31.5, 5.0 Hz, 1H).

Example 47

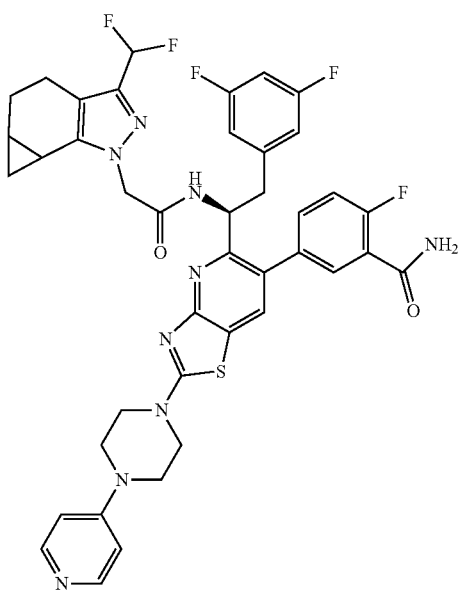

47

Example 48

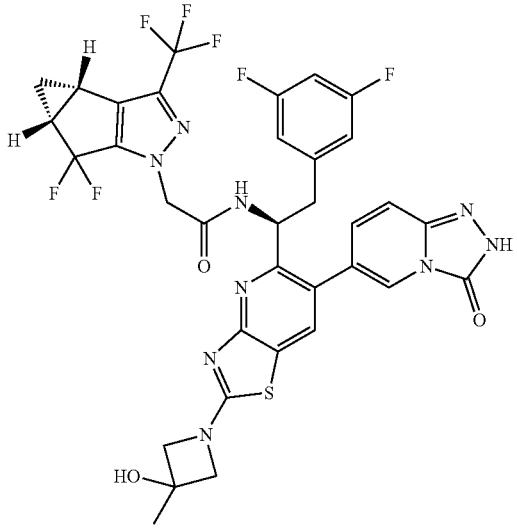

48

Synthesis of 5-(2-(4-(1H-benzo[d]imidazol-2-yl)piperazin-1-yl)-5-((1S)-1-(2-(3-(difluoromethyl)-5,5a,6,6a-tetrahydrocyclopropa[g]indazol-1(4H)-yl)acetamido)-2-(3,5-difluorophenyl)ethyl)thiazolo[4,5-b]pyridin-6-yl)-2-fluorobenzamide (47): Compound 47 was prepared according to the method presented for the synthesis of Example 34 utilizing 34E and substituting 1-(pyridin-4-yl)piperazine for 34D, substituting (3-Carbamoyl-4-fluorophenyl)boronic acid for 34G and substituting 2-(3-(difluoromethyl)-5,5a,6,6a-tetrahydrocyclopropa[g]indazol-1(4H)-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 814 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-hydroxy-3-methylazetidin-1-yl)-6-(3-oxo-2,3-dihydro-[1,2,4]triazolo[4,3-a]pyridin-6-yl)thiazolo[4,5-b]pyridin-5-yl)ethyl)acetamide (48): Compound 48 was prepared according to the method presented for the synthesis of Example 34 utilizing 34E and substituting 3-methylazetidin-3-ol for 34D and substituting 6-(4,4,5,5-tetramethyl-1,3,2-dioxaborolan-2-yl)-[1,2,4]triazolo[4,3-a]pyridin-3(2H)-one for 34G to provide the desired compound. MS (m/z) 774 [M+H]+. $^1$H NMR (400 MHz, Methanol-d4) δ 7.87 (s, 1H), 7.12 (d, J=10.4 Hz, 3H), 6.67 (t, J=9.3 Hz, 1H), 6.38 (d, J=7.4 Hz, 2H), 5.31 (t, J=7.3 Hz, 1H), 4.96-4.85 (m, 3H), 4.18 (q, J=9.2 Hz, 4H), 3.13 (d, J=7.6 Hz, 2H), 2.66-2.33 (m, 2H), 1.59 (s, 3H), 1.39 (d, J=6.7 Hz, 1H), 1.12 (s, 1H).

Example 49

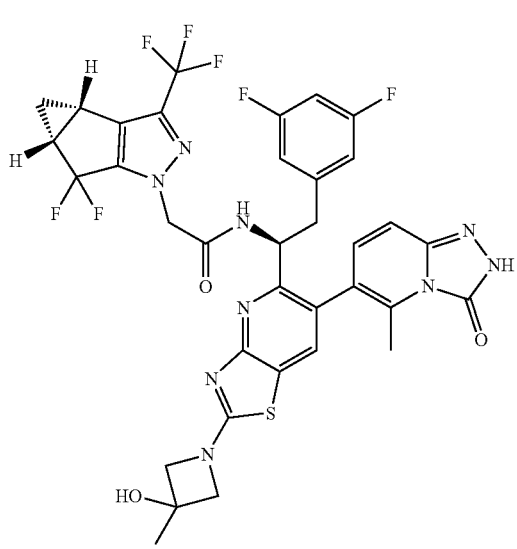

Example 50

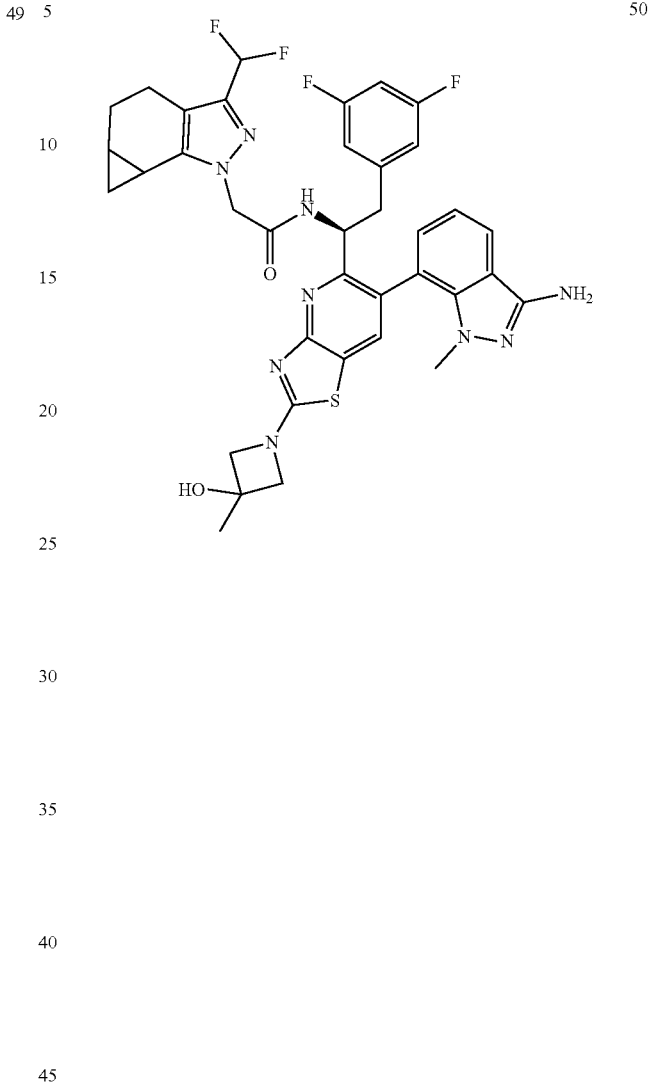

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-hydroxy-3-methylazetidin-1-yl)-6-(5-methyl-3-oxo-2,3-dihydro-[1,2,4]triazolo[4,3-a]pyridin-6-yl)thiazolo[4,5-b]pyridin-5-yl)ethyl)acetamide (49): Compound 49 was prepared according to the method presented for the synthesis of Example 34 utilizing 34E and substituting 3-methylazetidin-3-ol for 34D and substituting 5-methyl-6-(4,4,5,5-tetramethyl-1,3,2-dioxaborolan-2-yl)-[1,2,4]triazolo[4,3-a]pyridin-3(2H)-one for 34G to provide desired compound. MS (m/z) 788 [M+H]+. $^1$H NMR (400 MHz, Methanol-d4) δ 7.82 (d, J=13.2 Hz, 1H), 6.88 (s, 1H), 6.84-6.42 (m, 3H), 5.95 (d, J=9.6 Hz, 1H), 5.17 (ddd, J=21.0, 9.1, 5.7 Hz, 1H), 4.83 (d, J=1.8 Hz, 2H), 4.18 (q, J=9.6, 7.8 Hz, 4H), 3.53-3.32 (m, 1H), 3.16-3.01 (m, 1H), 2.58-2.42 (m, 2H), 2.24 (d, J=117.5 Hz, 3H), 1.59 (d, J=1.5 Hz, 3H), 1.39 (p, J=7.7 Hz, 1H), 1.18-1.00 (m, 1H).

Synthesis of N—((S)-1-(6-(3-amino-1-methyl-1H-indazol-7-yl)-2-(3-hydroxy-3-methylazetidin-1-yl)thiazolo[4,5-b]pyridin-5-yl)-2-(3,5-difluorophenyl)ethyl)-2-(3-(difluoromethyl)-5,5a,6,6a-tetrahydrocyclopropa[g]indazol-1(4H)-yl)acetamide (50): Compound 50 was prepared according to the method presented for the synthesis of Example 34 utilizing 34E and substituting 3-methylazetidin-3-ol for 34D, substituting 1-methyl-7-(4,4,5,5-tetramethyl-1,3,2-dioxaborolan-2-yl)-1H-indazol-3-amine for 34G and substituting 2-(3-(difluoromethyl)-5,5a,6,6a-tetrahydrocyclopropa[g]indazol-1(4H)-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 746 [M+H]+. $^1$H NMR (400 MHz, Methanol-d4) δ 8.00 (d, J=13.4 Hz, 1H), 7.82 (q, J=9.5, 8.4 Hz, 1H), 7.40-7.02 (m, 1H), 6.81-6.22 (m, 4H), 5.11 (dt, J=79.5, 7.3 Hz, 1H), 4.82-4.69 (m, 2H), 4.21 (q, J=10.5, 9.7 Hz, 4H), 3.14 (dd, J=10.6, 2.9 Hz, 3H), 3.03-2.60 (m, 3H), 2.29-2.00 (m, 2H), 1.75-1.51 (m, 5H), 0.91 (d, J=6.0 Hz, 1H), 0.64 (s, 1H).

Example 51

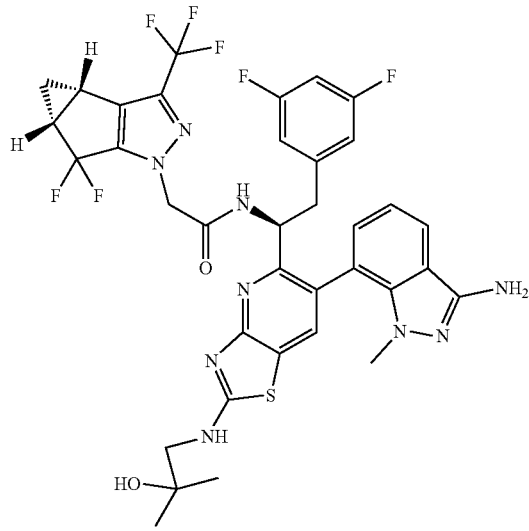

Example 52

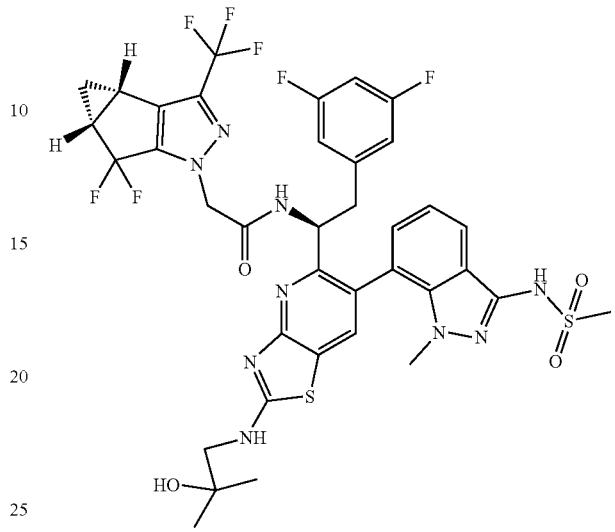

Synthesis of N—((S)-1-(6-(3-amino-1-methyl-1H-indazol-7-yl)-2-((2-hydroxy-2-methylpropyl)amino)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (51): Compound 51 was prepared according to the method presented for the synthesis of Example 34 utilizing 34E and substituting 1-amino-2-methylpropan-2-ol for 34D, and substituting 1-methyl-7-(4,4,5,5-tetramethyl-1,3,2-dioxaborolan-2-yl)-1H-indazol-3-amine for 34G to provide desired compound. MS (m/z) 788 [M+H]+. $^1$H NMR (400 MHz, Methanol-d4) δ 7.99-7.72 (m, 2H), 7.37-7.01 (m, 1H), 6.86-6.57 (m, 2H), 6.55-6.26 (m, 2H), 5.22-4.91 (m, 2H), 4.82-4.73 (m, 1H), 3.72-3.52 (m, 2H), 3.24-2.92 (m, 4H), 2.83 (s, 1H), 2.51 (dddd, J=17.4, 12.5, 8.6, 4.1 Hz, 2H), 1.51-1.35 (m, 1H), 1.32 (d, J=2.1 Hz, 6H), 1.21-1.00 (m, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-((2-hydroxy-2-methylpropyl)amino)-6-(1-methyl-3-(methylsulfonamido)-1H-indazol-7-yl)thiazolo[4,5-b]pyridin-5-yl)ethyl)acetamide (52): Compound 52 was prepared according to the method presented for the synthesis of Example 34 utilizing 34E and substituting 1-amino-2-methylpropan-2-ol for 34D, and substituting N-(1-methyl-7-(4,4,5,5-tetramethyl-1,3,2-dioxaborolan-2-yl)-1H-indazol-3-yl)methanesulfonamide (prepared according to WO2014110297) for 34G to provide the desired compound. MS (m/z) 866 [M+H]+. $^1$H NMR (400 MHz, Methanol-d4) δ 7.92 (d, J=19.2 Hz, 1H), 7.80 (ddd, J=8.1, 4.0, 1.1 Hz, 1H), 7.30-6.97 (m, 1H), 6.85-6.54 (m, 1H), 6.58-6.27 (m, 3H), 5.30-4.90 (m, 1H), 4.80 (d, J=4.2 Hz, 1H), 3.85-3.45 (m, 2H), 3.37 (s, 3H), 3.22-3.14 (m, 2H), 3.14-2.88 (m, 4H), 2.62-2.35 (m, 2H), 1.41 (dq, J=14.2, 7.1 Hz, 1H), 1.33 (d, J=1.9 Hz, 6H), 1.11 (d, J=22.8 Hz, 1H).

Example 53

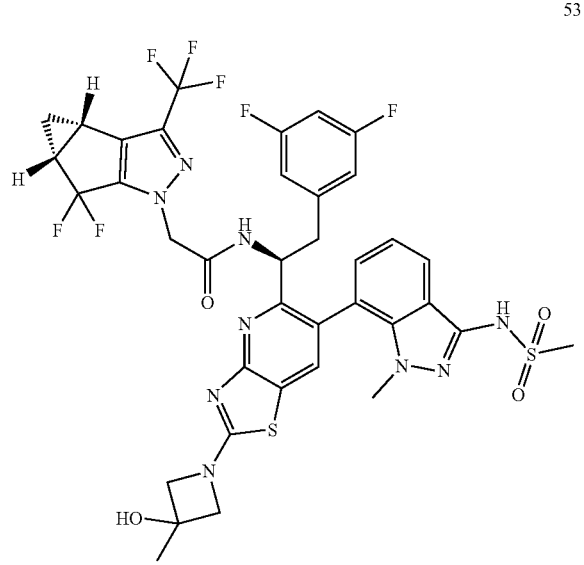 [SMILES: Cn1nc(NS(C)(=O)=O)c2cccc(-c3cc4sc(N5CC(C)(O)C5)nc4nc3[C@H](Cc3cc(F)cc(F)c3)NC(=O)Cn3nc(C(F)(F)F)c4c3C(F)(F)[C@@H]3C[C@H]43)c21]

53

Example 54

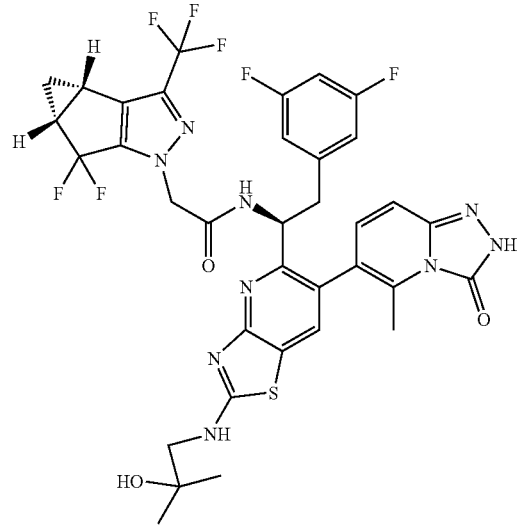

54

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-hydroxy-3-methylazetidin-1-yl)-6-(1-methyl-3-(methylsulfonamido)-1H-indazol-7-yl)thiazolo[4,5-b]pyridin-5-yl)ethyl)acetamide (53): Compound 53 was prepared according to the method presented for the synthesis of Example 34 utilizing 34E and substituting 3-methylazetidin-3-ol for 34D, and substituting N-(1-methyl-7-(4,4,5,5-tetramethyl-1,3,2-dioxaborolan-2-yl)-1H-indazol-3-yl)methanesulfonamide for 34G to provide the desired compound. MS (m/z) 864 [M+H]+. $^1$H NMR (400 MHz, Methanol-d4) δ 8.01 (d, J=17.8 Hz, 1H), 7.81 (ddd, J=8.2, 5.4, 1.1 Hz, 1H), 7.31-7.12 (m, 1H), 7.06 (dd, J=8.2, 7.0 Hz, 1H), 6.82-6.56 (m, 1H), 6.52-6.23 (m, 3H), 5.27-4.93 (m, 1H), 4.82-4.74 (m, 1H), 4.35-4.11 (m, 4H), 3.34 (s, 2H), 3.15 (d, J=20.0 Hz, 4H), 3.06-2.87 (m, 2H), 2.63-2.27 (m, 2H), 1.62 (d, J=1.6 Hz, 3H), 1.55-1.34 (m, 1H), 1.17-1.01 (m, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-((2-hydroxy-2-methylpropyl)amino)-6-(5-methyl-3-oxo-2,3-dihydro-[1,2,4]triazolo[4,3-a]pyridin-6-yl)thiazolo[4,5-b]pyridin-5-yl)ethyl)acetamide (54): Compound 54 was prepared according to the method presented for the synthesis of Example 34 utilizing 34E and substituting 1-amino-2-methylpropan-2-ol for 34D and substituting 5-methyl-6-(4,4,5,5-tetramethyl-1,3,2-dioxaborolan-2-yl)-[1,2,4]triazolo[4,3-a]pyridin-3(2H)-one for 34G to provide desired compound. MS (m/z) 790 [M+H]+. $^1$H NMR (400 MHz, Methanol-d4) δ 7.73 (d, J=12.4 Hz, 1H), 6.88 (d, J=2.0 Hz, 1H), 6.83-6.42 (m, 3H), 5.97 (d, J=9.6 Hz, 1H), 5.29-5.07 (m, 1H), 4.85 (s, 2H), 3.73-3.47 (m, 2H), 3.18-3.00 (m, 1H), 2.49 (ddd, J=12.2, 8.0, 4.1 Hz, 1H), 2.27 (d, J=118.1 Hz, 3H), 1.31 (t, J=2.3 Hz, 8H), 1.01 (dd, J=99.4, 9.2 Hz, 2H).

Example 55

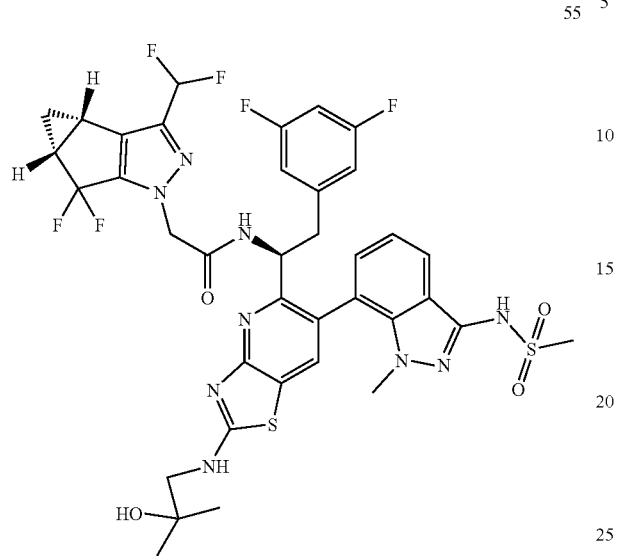

Example 56

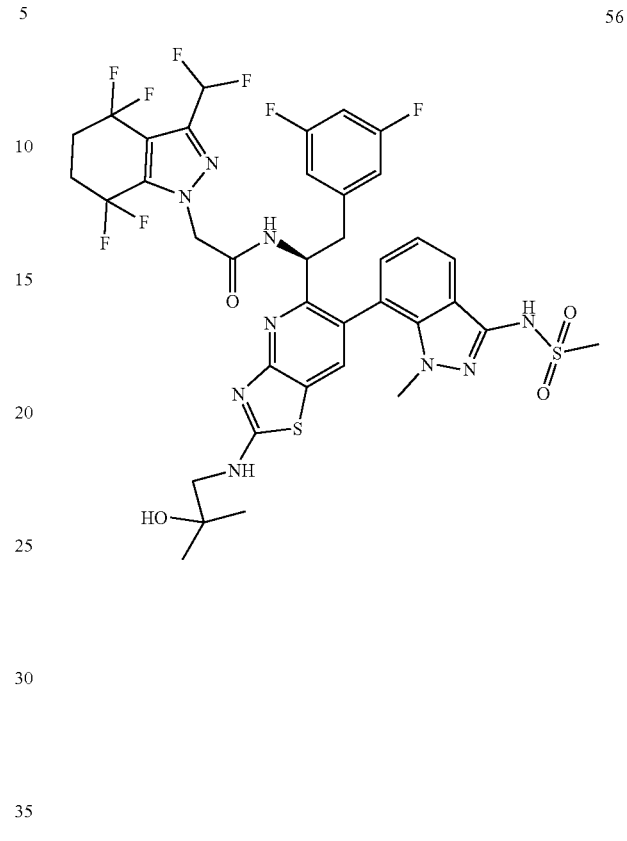

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(2-((2-hydroxy-2-methylpropyl)amino)-6-(1-methyl-3-(methylsulfonamido)-1H-indazol-7-yl)thiazolo[4,5-b]pyridin-5-yl)ethyl)acetamide (55): Compound 55 was prepared according to the method presented for the synthesis of Example 34 utilizing 34E and substituting 1-amino-2-methylpropan-2-ol for 34D, substituting N-(1-methyl-7-(4,4,5,5-tetramethyl-1,3,2-dioxaborolan-2-yl)-1H-indazol-3-yl)methanesulfonamide for 34G and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide desired compound. MS (m/z) 848 [M+H]+. $^1$H NMR (400 MHz, Methanol-d4) δ 7.95 (d, J=22.6 Hz, 1H), 7.82 (dd, J=8.2, 1.1 Hz, 1H), 7.07 (dd, J=8.2, 7.0 Hz, 1H), 6.90-6.67 (m, 1H), 6.67-6.47 (m, 1H), 6.37 (dd, J=15.9, 7.5 Hz, 2H), 5.30-4.90 (m, 1H), 4.79-4.66 (m, 2H), 3.83-3.48 (m, 2H), 3.37 (s, 2H), 3.15 (d, J=22.0 Hz, 4H), 3.07-2.80 (m, 2H), 2.44 (ddd, J=11.2, 7.8, 3.9 Hz, 2H), 1.49-1.26 (m, 7H), 1.06 (d, J=21.6 Hz, 1H).

Synthesis of (S)-2-(3-(difluoromethyl)-4,4,7,7-tetrafluoro-4,5,6,7-tetrahydro-1H-indazol-1-yl)-N-(2-(3,5-difluorophenyl)-1-(2-((2-hydroxy-2-methylpropyl)amino)-6-(1-methyl-3-(methylsulfonamido)-1H-indazol-7-yl)thiazolo[4,5-b]pyridin-5-yl)ethyl)acetamide (56): Compound 56 was prepared according to the method presented for the synthesis of Example 34 utilizing 34E and substituting 1-amino-2-methylpropan-2-ol for 34D, substituting N-(1-methyl-7-(4,4,5,5-tetramethyl-1,3,2-dioxaborolan-2-yl)-1H-indazol-3-yl)methanesulfonamide for 34G and substituting 2-(3-(difluoromethyl)-4,4,7,7-tetrafluoro-4,5,6,7-tetrahydro-1H-indazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 886 [M+H]+. $^1$H NMR (400 MHz, Methanol-d4) δ 7.96 (d, J=20.6 Hz, 1H), 7.82 (dd, J=8.2, 1.0 Hz, 1H), 7.40-7.03 (m, 1H), 7.01-6.48 (m, 3H), 6.37 (ddd, J=12.8, 8.3, 2.2 Hz, 2H), 5.35-4.91 (m, 3H), 3.73-3.51 (m, 2H), 3.39 (s, 2H), 3.26-3.12 (m, 3H), 3.09 (s, 2H), 3.06-2.86 (m, 2H), 2.51 (p, J=11.2, 9.8 Hz, 4H), 1.33 (t, J=1.5 Hz, 6H).

Example 57

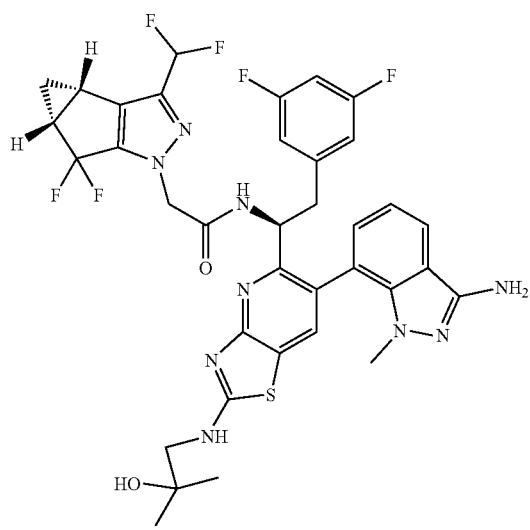

Example 58

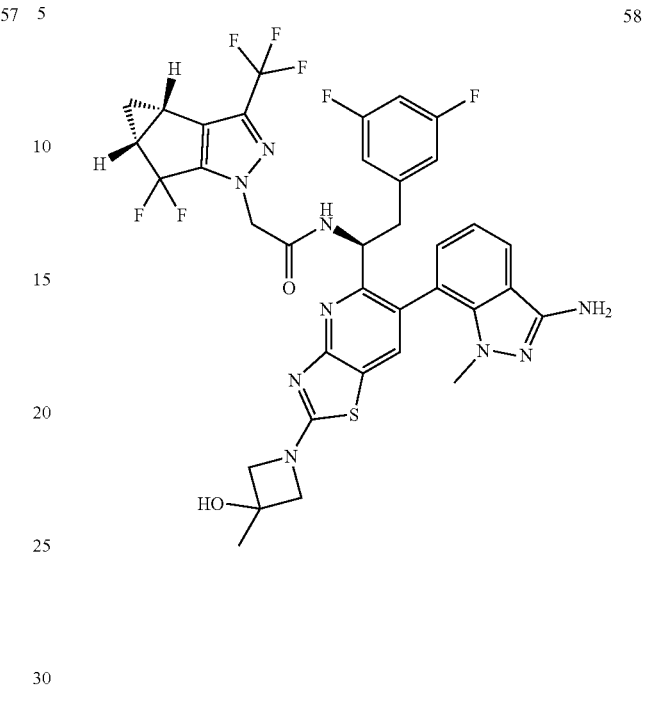

Synthesis of N—((S)-1-(6-(3-amino-1-methyl-1H-indazol-7-yl)-2-((2-hydroxy-2-methylpropyl)amino)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (57): Compound 57 was prepared according to the method presented for the synthesis of Example 34 utilizing 34E and substituting 1-amino-2-methylpropan-2-ol for 34D, substituting 1-methyl-7-(4,4,5,5-tetramethyl-1,3,2-dioxaborolan-2-yl)-1H-indazol-3-amine for 34G and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 770 [M+H]+. $^1$H NMR (400 MHz, Methanol-d4) δ 7.98-7.72 (m, 2H), 7.41-7.08 (m, 1H), 6.90-6.53 (m, 3H), 6.51-6.17 (m, 2H), 5.18-4.92 (m, 1H), 4.75 (d, J=3.8 Hz, 2H), 3.77-3.45 (m, 2H), 3.25-2.77 (m, 5H), 2.44 (ddd, J=11.2, 7.8, 4.0 Hz, 2H), 1.42-1.34 (m, 1H), 1.33 (d, J=2.1 Hz, 6H), 1.15-0.96 (m, 1H).

Synthesis of N—((S)-1-(6-(3-amino-1-methyl-1H-indazol-7-yl)-2-(3-hydroxy-3-methylazetidin-1-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (58): Compound 58 was prepared according to the method presented for the synthesis of Example 34 utilizing 34E and substituting 3-methylazetidin-3-ol for 34D, and substituting 1-methyl-7-(4,4,5,5-tetramethyl-1,3,2-dioxaborolan-2-yl)-1H-indazol-3-amine for 34G to provide the desired compound. MS (m/z) 786 [M+H]+. $^1$H NMR (400 MHz, Methanol-d4) δ 8.00 (d, J=14.0 Hz, 1H), 7.93-7.78 (m, 1H), 7.28 (dd, J=50.2, 7.4 Hz, 1H), 7.21-7.10 (m, 1H), 6.81-6.67 (m, 1H), 6.67-6.41 (m, 1H), 6.41-6.25 (m, 1H), 5.23-4.97 (m, 1H), 4.80 (dd, J=6.0, 2.3 Hz, 2H), 4.30-4.12 (m, 4H), 3.24-2.74 (m, 5H), 2.50 (ddt, J=17.8, 8.2, 4.2 Hz, 2H), 1.61 (d, J=1.7 Hz, 3H), 1.40 (dd, J=14.3, 7.5 Hz, 1H), 1.21-1.01 (m, 1H).

Example 59

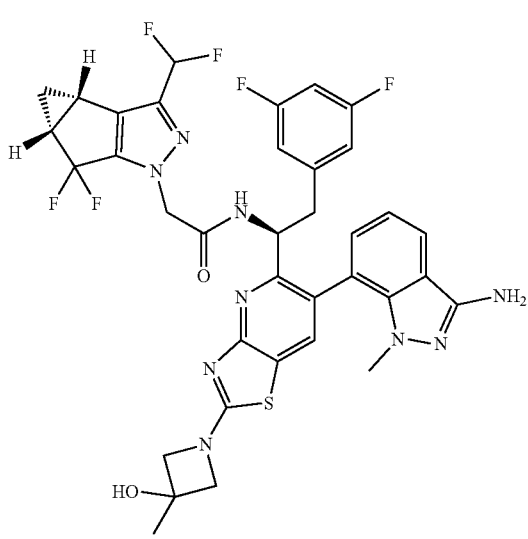

Example 60

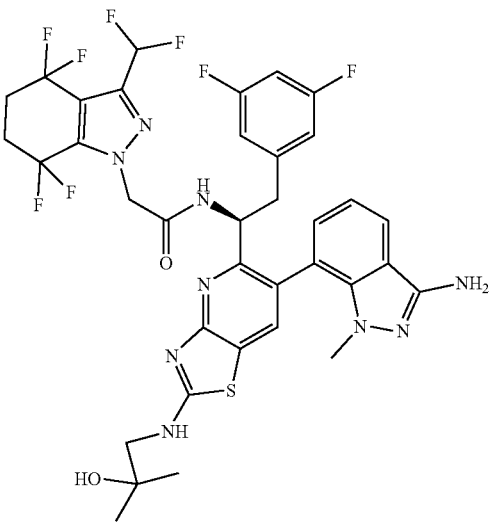

Synthesis of N—((S)-1-(6-(3-amino-1-methyl-1H-indazol-7-yl)-2-(3-hydroxy-3-methylazetidin-1-yl)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (59): Compound 59 was prepared according to the method presented for the synthesis of Example 34 utilizing 34E and substituting 3-methylazetidin-3-ol for 34D, substituting 1-methyl-7-(4,4,5,5-tetramethyl-1,3,2-dioxaborolan-2-yl)-1H-indazol-3-amine for 34G and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 768 [M+H]+. $^1$H NMR (400 MHz, Methanol-d4) δ 8.00 (d, J=13.6 Hz, 1H), 7.85 (ddd, J=15.0, 8.3, 1.1 Hz, 1H), 7.40-7.04 (m, 2H), 6.90-6.51 (m, 2H), 6.51-6.21 (m, 2H), 5.23-4.95 (m, 1H), 4.77-4.72 (m, 2H), 4.33-4.15 (m, 4H), 3.23-2.76 (m, 5H), 2.44 (ddd, J=11.3, 7.8, 4.0 Hz, 2H), 1.61 (d, J=1.7 Hz, 3H), 1.38 (dd, J=10.3, 4.4 Hz, 1H), 1.06 (d, J=17.9 Hz, 1H).

Synthesis of (S)—N-(1-(6-(3-amino-1-methyl-1H-indazol-7-yl)-2-((2-hydroxy-2-methylpropyl)amino)thiazolo[4,5-b]pyridin-5-yl)-2-(3,5-difluorophenyl)ethyl)-2-(3-(difluoromethyl)-4,4,7,7-tetrafluoro-4,5,6,7-tetrahydro-1H-indazol-1-yl)acetamide (60): Compound 60 was prepared according to the method presented for the synthesis of Example 34 utilizing 34E and substituting 1-amino-2-methylpropan-2-ol for 34D, substituting 1-methyl-7-(4,4,5,5-tetramethyl-1,3,2-dioxaborolan-2-yl)-1H-indazol-3-amine for 34G and substituting 2-(3-(difluoromethyl)-4,4,7,7-tetrafluoro-4,5,6,7-tetrahydro-1H-indazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 808 [M+H]+. $^1$H NMR (400 MHz, Methanol-d4) δ 7.87 (d, J=16.4 Hz, 1H), 7.71 (ddd, J=8.2, 7.2, 1.1 Hz, 1H), 7.23-6.87 (m, 1H), 6.85-6.53 (m, 2H), 6.53-6.22 (m, 3H), 5.27-4.92 (m, 3H), 3.68-3.46 (m, 2H), 3.33 (d, J=12.3 Hz, 2H), 3.27-3.08 (m, 3H), 3.04-2.82 (m, 2H), 2.68-2.36 (m, 3H), 1.32 (d, J=1.7 Hz, 6H).

Example 61

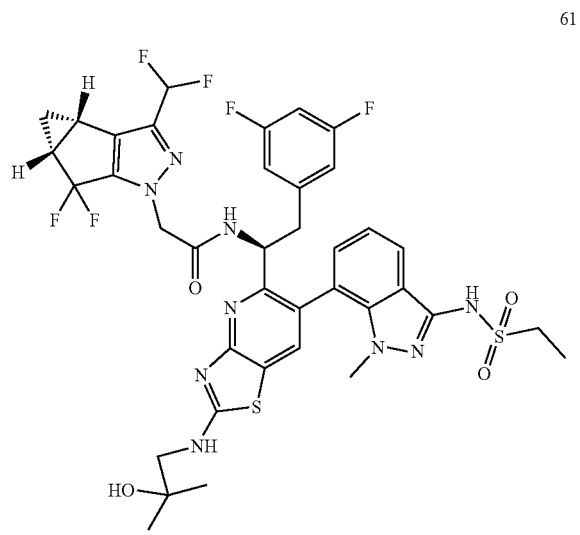 [SMILES: CCS(=O)(=O)Nc1nn(C)c2c(-c3cc4sc(NCC(C)(C)O)nc4nc3[C@H](Cc3cc(F)cc(F)c3)NC(=O)Cn3nc(C(F)F)c4c3C(F)(F)[C@@H]3C[C@H]43)cccc12]

Example 62

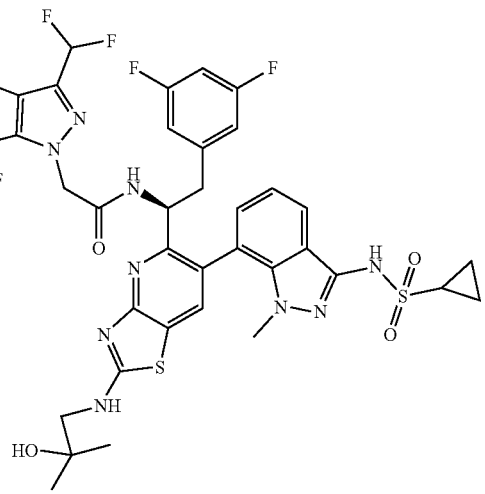

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(3-(ethylsulfonamido)-1-methyl-1H-indazol-7-yl)-2-((2-hydroxy-2-methylpropyl)amino)thiazolo[4,5-b]pyridin-5-yl)ethyl)acetamide (61): Compound 61 was prepared according to the method presented for the synthesis of Example 34 utilizing 34E and substituting 1-amino-2-methylpropan-2-ol for 34D, substituting N-(1-methyl-7-(4,4,5,5-tetramethyl-1,3,2-dioxaborolan-2-yl)-1H-indazol-3-yl)ethanesulfonamide for 34G and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 862 [M+H]+. $^1$H NMR (400 MHz, Methanol-d4) δ 7.98 (d, J=25.5 Hz, 1H), 7.84 (dd, J=8.3, 1.0 Hz, 1H), 7.38-6.45 (m, 4H), 6.45-6.29 (m, 2H), 5.30-4.91 (m, 1H), 4.80-4.61 (m, 2H), 3.71-3.53 (m, 2H), 3.36 (s, 3H), 3.27-2.89 (m, 4H), 2.44 (ddd, J=11.2, 8.0, 4.1 Hz, 2H), 1.45-1.26 (m, 10H), 1.06 (d, J=20.2 Hz, 1H).

Synthesis of N—((S)-1-(6-(3-(cyclopropanesulfonamido)-1-methyl-1H-indazol-7-yl)-2-((2-hydroxy-2-methylpropyl)amino)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (62): Compound 62 was prepared according to the method presented for the synthesis of Example 34 utilizing 34E and substituting 1-amino-2-methylpropan-2-ol for 34D, substituting N-(1-methyl-7-(4,4,5,5-tetramethyl-1,3,2-dioxaborolan-2-yl)-1H-indazol-3-yl)cyclopropanesulfonamide for 34G and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 874 [M+H]+. $^1$H NMR (400 MHz, Methanol-d4) δ 7.98 (d, J=22.4 Hz, 1H), 7.86 (dt, J=8.2, 1.3 Hz, 1H), 7.33-7.00 (m, 1H), 6.90-6.46 (m, 3H), 6.44-6.28 (m, 2H), 5.29-4.88 (m, 1H), 4.79-4.64 (m, 2H), 3.81-3.46 (m, 3H), 3.37 (s, 2H), 3.24-2.86 (m, 2H), 2.84-2.61 (m, 1H), 2.43 (ddd, J=11.3, 7.7, 4.0 Hz, 2H), 1.33 (d, J=1.7 Hz, 8H), 1.17-0.84 (i, 4H).

Example 63

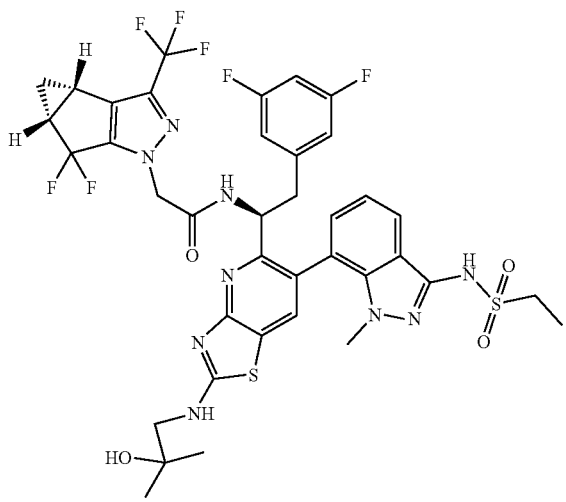

63

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-(ethylsulfonamido)-1-methyl-1H-indazol-7-yl)-2-((2-hydroxy-2-methylpropyl)amino)thiazolo[4,5-b]pyridin-5-yl)ethyl)acetamide (63): Compound 63 was prepared according to the method presented for the synthesis of Example 34 utilizing 34E and substituting 1-amino-2-methylpropan-2-ol for 34D, and substituting N-(1-methyl-7-(4,4,5,5-tetramethyl-1,3,2-dioxaborolan-2-yl)-1H-indazol-3-yl)ethanesulfonamide for 34G to provide the desired compound. MS (m/z) 880 [M+H]+. $^1$H NMR (400 MHz, Methanol-d4) δ 7.95 (d, J=22.9 Hz, 1H), 7.83 (ddd, J=8.2, 3.1, 1.1 Hz, 1H), 7.34-6.96 (m, 1H), 6.82-6.57 (m, 1H), 6.57-6.28 (m, 3H), 5.32-4.91 (m, 1H), 4.81-4.74 (m, 2H), 3.73-3.50 (m, 2H), 3.36 (s, 2H), 3.26-2.81 (m, 3H), 2.65-2.27 (m, 2H), 1.54-1.28 (m, 10H), 1.17-1.03 (m, 1H).

Example 64

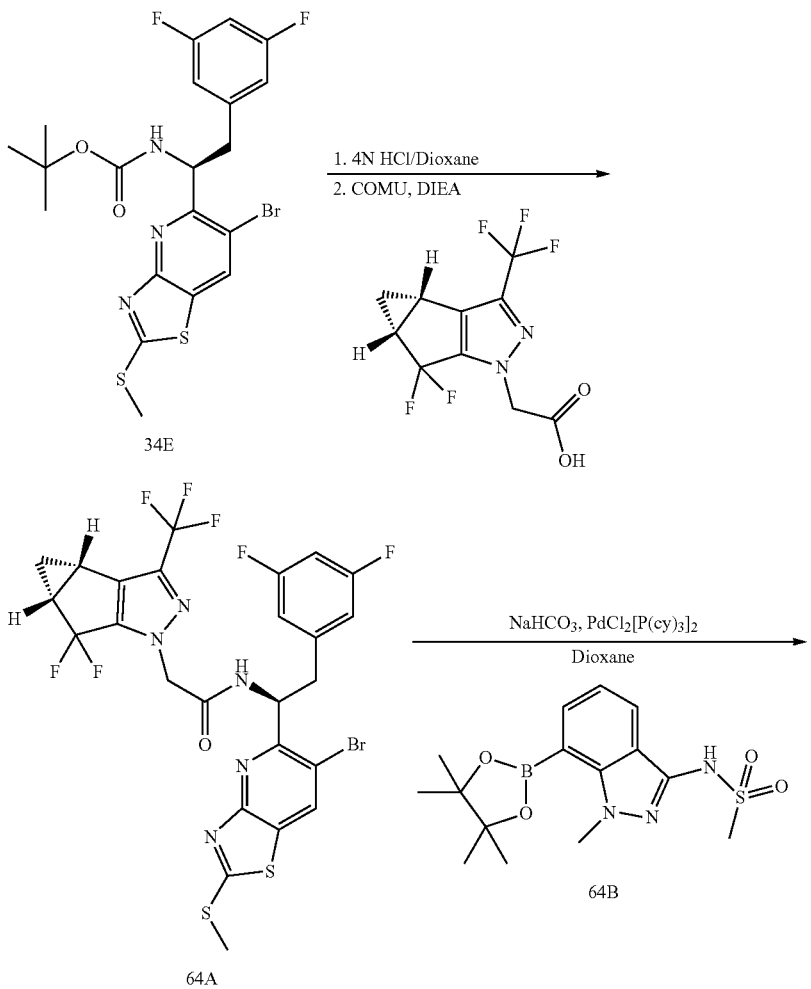

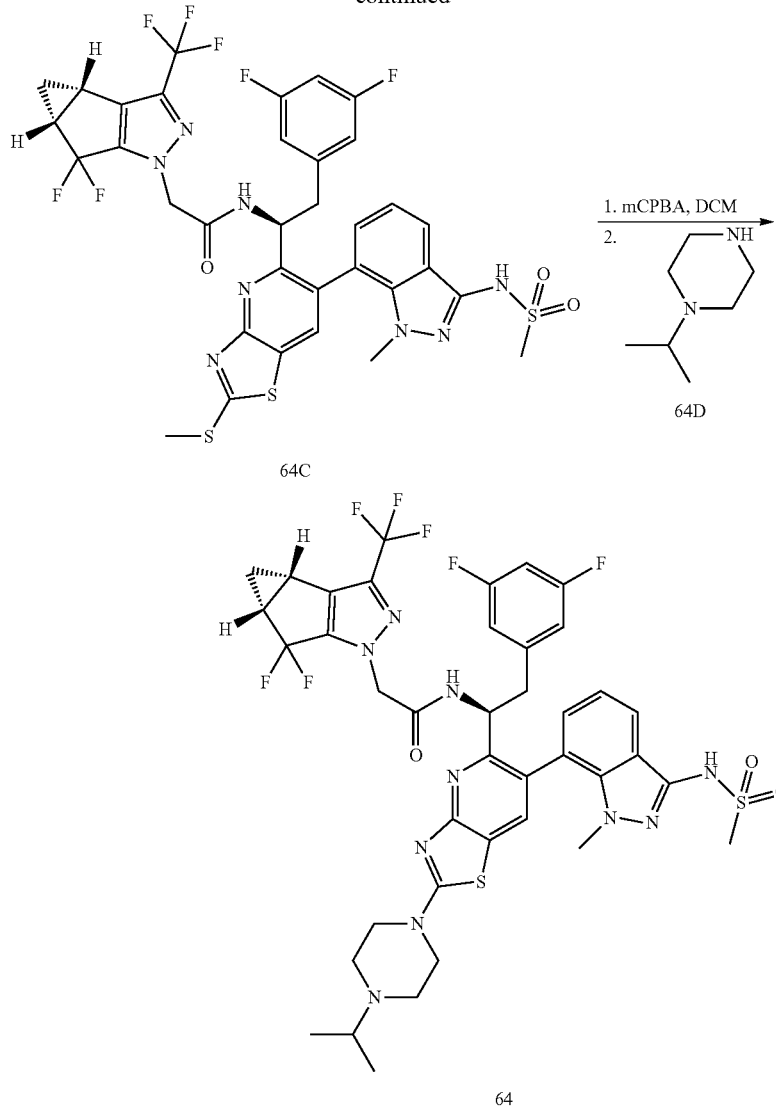

Synthesis of N—((S)-1-(6-bromo-2-(methylthio)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (64A): A solution of 34E (4 g, 7.77 mmol) in 4 N of hydrochloride in dioxane (20 mL) was stirred for 1 hour. The solvent was removed and dried in vacuo. The crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (2.19 g, 7.77 mmol), and (1-Cyano-2-ethoxy-2-oxoethylidenaminooxy)dimethylamino-morpholino-carbenium hexafluorophosphate (3.33 g, 7.77 mmol) were dissolved in DMF (20 mL), and diisopropylethylamine (2.7 mL, 15.4 mmol) was added to the solution. The reaction was stirred at room temperature for 90 min. The mixture was dissolved in 100 mL of EtOAc, and washed with 50 mL of saturated sodium bicarbonate (aq) and 50 mL of brine. The organic layer was dried with sodium sulfate. The solvent was filtered, and the filtrate was concentrated to dryness. The residue was purified by flash column chromatography by 30% EtOAc/Hexanes to afford compound 64A. MS (m/z) 680 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(methylthio)thiazolo[4,5-b]pyridin-5-yl)ethyl)acetamide (64C): To a suspension of 64A (800 mg, 1.18 mmol)), 64B (496 mg, 1.41 mmol, prepared as described in WO2014/134566A2), 1 N of sodium bicarbonate (3.53 mL) in 14 mL of dioxane, dichlorobis(tricyclohexylphosphine)palladium (II) (130 mg, 0.18 mmol) was added. The reaction was heated at 145° C. by microwave reactor for 20 minutes. The mixture was dissolved in 50 mL of EtOAc, and washed with 25 mL of saturated sodium bicarbonate (aq), and 25 mL of brine. The organic layer was dried with sodium sulfate. The solvent was filtered, and the filtrate was concentrated to dryness. The residue was purified by flash column chromatography by 40% EtOAc/Hexanes to afford compound 64C. MS (m/z) 825 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-

(4-isopropylpiperazin-1-yl)-6-(1-methyl-3-(methylsulfonamido)-1H-indazol-7-yl)thiazolo[4,5-b]pyridin-5-yl)ethyl)acetamide (64): To a solution of 64C (30 mg, 0.036 mmol) in DCM (3 mL), 3-Chloroperoxybenzoic acid (77% purity, 16.3 mg, 0.073 mmol) was added. The reaction was stirred for 1 hour. 64D (46.6 mg, 0.36 mmol) and N,N-Diisopropylethylamine (0.19 mL, 1.1 mmol) were added to the mixture. After 2 hours, the reaction was diluted with EtOAc (20 mL), and washed with 10 mL of saturated sodium bicarbonate (aq). The organic layer was separated, and concentrated to dryness in vacuo. The reaction mixture was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide the desired compound. MS (m/z) 905 [M+H]+. $^1$H NMR (400 MHz, Methanol-d4) δ 8.08 (d, J=14.8 Hz, 1H), 7.82 (ddd, J=8.1, 6.0, 1.0 Hz, 1H), 7.32-6.98 (m, 1H), 6.84-6.26 (m, 4H), 5.37-4.94 (m, 1H), 4.83-4.73 (m, 2H), 3.94-3.38 (m, 8H), 3.33 (s, 3H), 3.23-2.86 (m, 6H), 2.49 (ddd, J=16.8, 8.2, 4.3 Hz, 2H), 1.44 (d, J=6.6 Hz, 7H), 1.18-1.04 (m, 1H).

Example 65

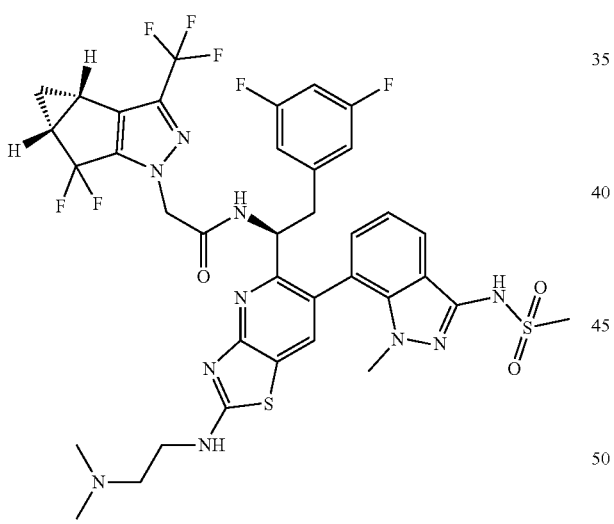

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-((2-(dimethylamino)ethyl)amino)-6-(1-methyl-3-(methylsulfonamido)-1H-indazol-7-yl)thiazolo[4,5-b]pyridin-5-yl)ethyl)acetamide (65): Compound 65 was prepared according to the method presented for the synthesis of Example 64 utilizing 34E and substituting N1,N1-dimethylethane-1,2-diamine for 64D to provide the desired compound. MS (m/z) 865 [M+H]+. $^1$H NMR (400 MHz, Methanol-d4) δ 8.57 (dd, J=24.2, 8.2 Hz, 1H), 8.01 (d, J=13.7 Hz, 1H), 7.87-7.75 (m, 1H), 7.38-6.98 (m, 1H), 6.81-6.54 (m, 1H), 6.55-6.21 (m, 3H), 5.32-4.93 (m, 1H), 4.79 (d, J=8.5 Hz, 2H), 3.99 (q, J=6.8, 6.4 Hz, 2H), 3.57 (t, J=5.8 Hz, 2H), 3.25-2.86 (m, 13H), 2.68-2.37 (m, 3H), 1.41 (dt, J=13.8, 6.8 Hz, 1H), 1.08 (s, 1H).

Example 66

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(4-(dimethylamino)piperidin-1-yl)-6-(1-methyl-3-(methylsulfonamido)-1H-indazol-7-yl)thiazolo[4,5-b]pyridin-5-yl)ethyl)acetamide (66): Compound 66 was prepared according to the method presented for the synthesis of Example 64 utilizing 34E and substituting N,N-dimethylpiperidin-4-amine for 64D to provide the desired compound. MS (m/z) 905 [M+H]+. $^1$H NMR (400 MHz, Methanol-d4) δ 8.57 (d, J=8.8 Hz, 1H), 8.02 (d, J=14.9 Hz, 1H), 7.93-7.74 (m, 1H), 7.31-6.93 (m, 1H), 6.81-6.22 (m, 3H), 5.32-4.89 (m, 1H), 4.79 (d, J=2.8 Hz, 2H), 4.48 (t, J=14.8 Hz, 2H), 3.67-3.33 (m, 5H), 3.21-2.80 (m, 12H), 2.59-2.36 (m, 2H), 2.29 (d, J=12.3 Hz, 2H), 2.05-1.76 (m, 2H), 1.41 (p, J=7.2, 6.7 Hz, 1H), 1.10 (s, 1H).

Example 67

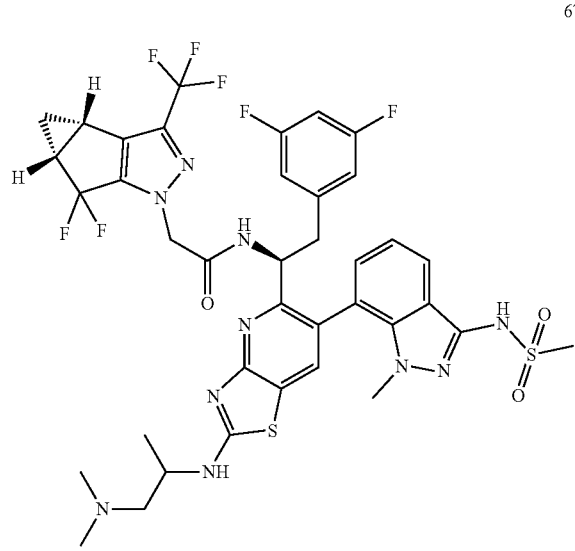 [SMILES: CN(C)CCNc1nc2nc([C@H](Cc3cc(F)cc(F)c3)NC(=O)Cn3nc(C(F)(F)F)c4c3C(F)(F)[C@@H]3C[C@H]43)c(-c3cccc4c(NS(C)(=O)=O)nn(C)c34)cc2s1]

Example 68

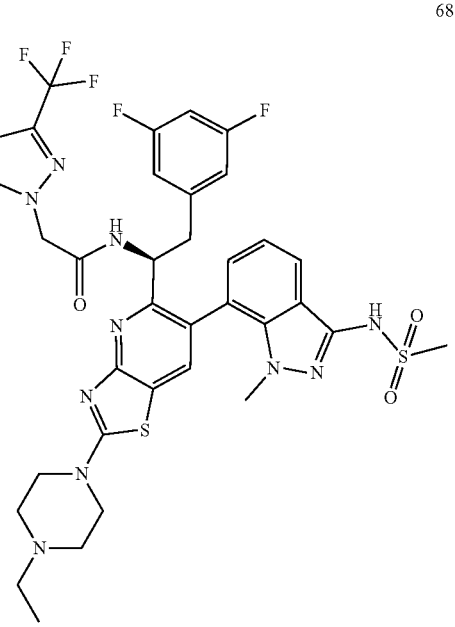

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-((1S)-2-(3,5-difluorophenyl)-1-(2-((1-(dimethylamino)propan-2-yl)amino)-6-(1-methyl-3-(methylsulfonamido)-1H-indazol-7-yl)thiazolo[4,5-b]pyridin-5-yl)ethyl)acetamide (67): Compound 67 was prepared according to the method presented for the synthesis of Example 64 utilizing 34E and substituting N1,N1-dimethylpropane-1,2-diamine for 64D to provide the desired compound. MS (m/z) 879 [M+H]+. $^1$H NMR (400 MHz, Methanol-d4) δ 8.08-7.97 (m, 1H), 7.82 (dt, J=8.5, 4.4 Hz, 1H), 7.34-6.96 (m, 1H), 6.81-6.24 (m, 4H), 5.37-4.94 (m, 1H), 4.82-4.62 (m, 2H), 3.54-3.32 (m, 4H), 3.21-3.08 (m, 7H), 3.08-2.90 (m, 6H), 2.48 (s, 2H), 1.60-1.30 (m, 4H), 1.10 (d, J=22.1 Hz, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(4-ethylpiperazin-1-yl)-6-(1-methyl-3-(methylsulfonamido)-1H-indazol-7-yl)thiazolo[4,5-b]pyridin-5-yl)ethyl)acetamide (68): Compound 68 was prepared according to the method presented for the synthesis of Example 64 utilizing 34E and substituting 1-ethylpiperazine for 64D to provide the desired compound. MS (m/z) 891 [M+H]+. $^1$H NMR (400 MHz, Methanol-d4) δ 8.08 (d, J=15.0 Hz, 1H), 7.82 (ddd, J=8.2, 5.8, 1.1 Hz, 1H), 7.12 (ddd, J=39.9, 8.2, 7.0 Hz, 1H), 6.79-6.56 (m, 1H), 6.54-6.25 (m, 3H), 5.33-4.92 (m, 1H), 4.83-4.76 (m, 2H), 3.50 (d, J=15.5 Hz, 7H), 3.34 (dd, J=7.5, 1.7 Hz, 5H), 3.15 (d, J=19.1 Hz, 4H), 3.05-2.88 (m, 2H), 2.49 (ddd, J=16.8, 8.2, 4.3 Hz, 2H), 1.43 (t, J=7.3 Hz, 4H), 1.21-1.04 (m, 1H).

Example 69

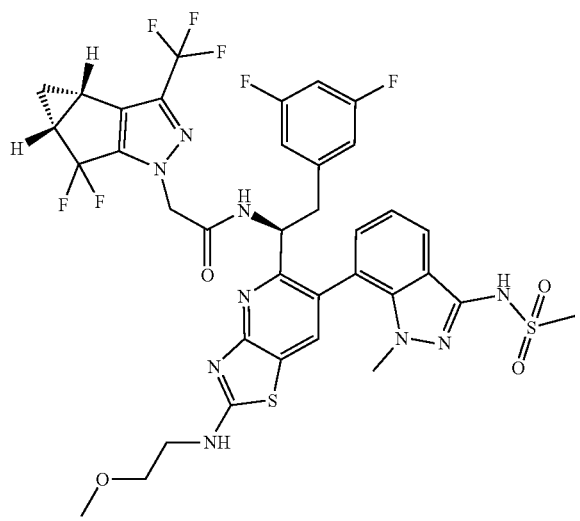

Example 70

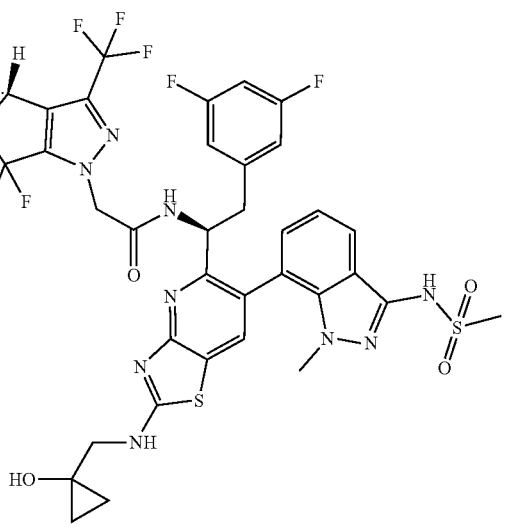

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-((2-methoxyethyl)amino)-6-(1-methyl-3-(methylsulfonamido)-1H-indazol-7-yl)thiazolo[4,5-b]pyridin-5-yl)ethyl)acetamide (69): Compound 69 was prepared according to the method presented for the synthesis of Example 64 utilizing 34E and substituting 2-methoxyethan-1-amine for 64D to provide the desired compound. MS (m/z) 852 [M+H]+. $^1$H NMR (400 MHz, Methanol-d4) δ 7.95 (d, J=22.3 Hz, 1H), 7.81 (ddd, J=8.2, 2.9, 1.1 Hz, 1H), 7.12 (ddd, J=43.6, 8.2, 7.1 Hz, 1H), 6.80-6.54 (m, 1H), 6.53-6.26 (m, 3H), 5.32-4.91 (m, 1H), 4.83-4.70 (m, 2H), 3.87-3.72 (m, 2H), 3.69 (td, J=4.7, 1.2 Hz, 2H), 3.49-3.33 (m, 5H), 3.25-2.85 (m, 6H), 2.49 (ddd, J=17.3, 8.3, 4.3 Hz, 2H), 1.49-1.30 (m, 2H), 1.08 (s, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(((1-hydroxycyclopropyl)methyl)amino)-6-(1-methyl-3-(methylsulfonamido)-1H-indazol-7-yl)thiazolo[4,5-b]pyridin-5-yl)ethyl)acetamide (70): Compound 70 was prepared according to the method presented for the synthesis of Example 64 utilizing 34E and substituting 1-(aminomethyl)cyclopropan-1-ol for 64D to provide the desired compound. MS (m/z) 864 [M+H]+. $^1$H NMR (400 MHz, Methanol-d4) δ 7.94 (d, J=21.2 Hz, 1H), 7.81 (dd, J=8.2, 1.0 Hz, 1H), 7.19-6.96 (m, 1H), 6.73 (t, J=9.1 Hz, 1H), 6.58-6.28 (m, 3H), 5.29-4.91 (m, 1H), 4.79 (d, J=3.5 Hz, 2H), 3.75 (s, 2H), 3.37 (s, 3H), 3.15 (d, J=19.6 Hz, 4H), 3.07-2.87 (m, 2H), 2.54-2.33 (m, 2H), 1.47-1.27 (m, 1H), 1.11 (d, J=24.2 Hz, 1H), 0.90-0.73 (m, 4H).

Example 71

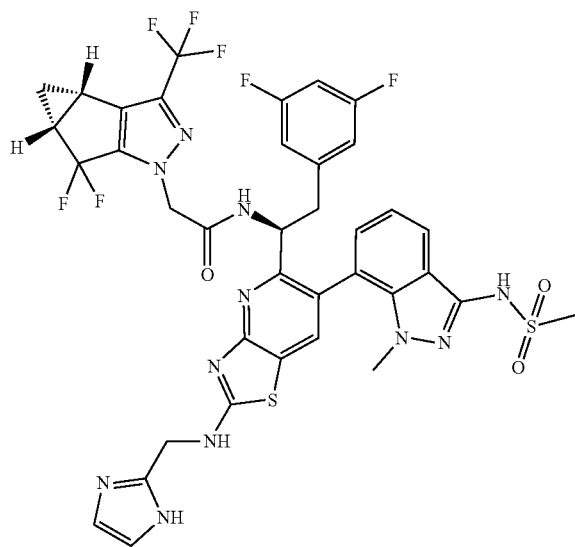

Example 72

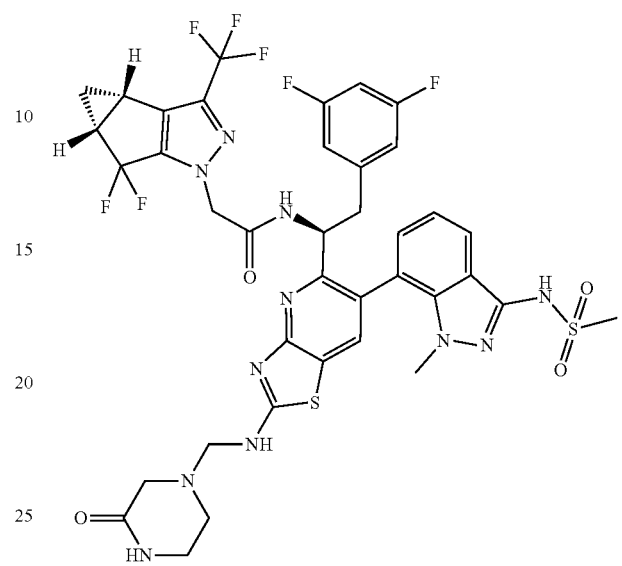

Synthesis of N—((S)-1-(2-(((1H-imidazol-2-yl)methyl)amino)-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (71): Compound 71 was prepared according to the method presented for the synthesis of Example 64 utilizing 34E and substituting (1H-imidazol-2-yl)methanamine for 64D to provide the desired compound. MS (m/z) 874 [M+H]+. $^1$H NMR (400 MHz, Methanol-d4) δ 8.04 (d, J=12.5 Hz, 1H), 7.94-7.68 (m, 1H), 7.56 (d, J=0.6 Hz, 2H), 7.19-6.98 (m, 1H), 6.81-6.54 (m, 1H), 6.51-6.21 (m, 3H), 5.33-4.94 (m, 3H), 4.79-4.64 (m, 2H), 3.32 (s, 2H), 3.20-2.86 (m, 5H), 2.59-2.30 (m, 2H), 1.54-1.25 (m, 3H), 1.10 (d, J=24.7 Hz, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(3-oxopiperazin-1-yl)thiazolo[4,5-b]pyridin-5-yl)ethyl)acetamide (72): Compound 72 was prepared according to the method presented for the synthesis of Example 64 utilizing 34E and substituting piperazin-2-one for 64D to provide the desired compound. MS (m/z) 877 [M+H]+. $^1$H NMR (400 MHz, Methanol-d4) δ 8.06 (d, J=16.5 Hz, 1H), 7.82 (dd, J=8.2, 1.1 Hz, 1H), 7.20-6.95 (m, 1H), 6.83-6.56 (m, 1H), 6.55-6.27 (m, 3H), 5.32-4.89 (m, 1H), 4.80 (d, J=5.2 Hz, 2H), 4.40 (s, 2H), 3.98 (t, J=5.4 Hz, 2H), 3.58 (t, J=5.4 Hz, 2H), 3.34 (s, 2H), 3.23-2.87 (m, 6H), 2.48 (td, J=8.2, 4.0 Hz, 2H), 1.40 (q, J=7.0 Hz, 1H), 1.11 (s, 1H).

Example 73

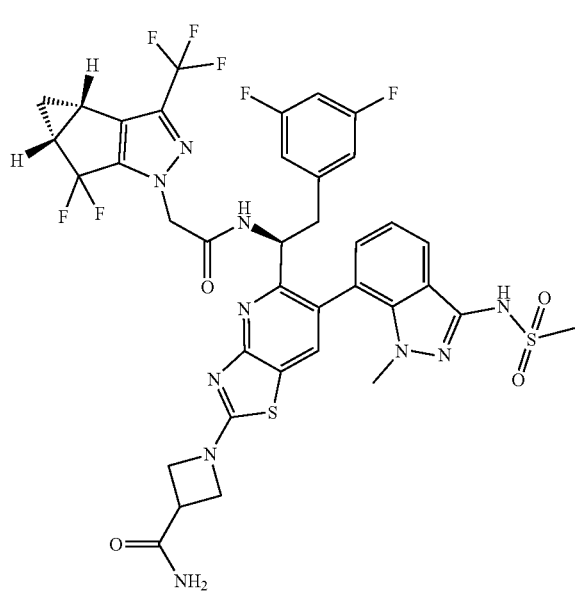

Example 74

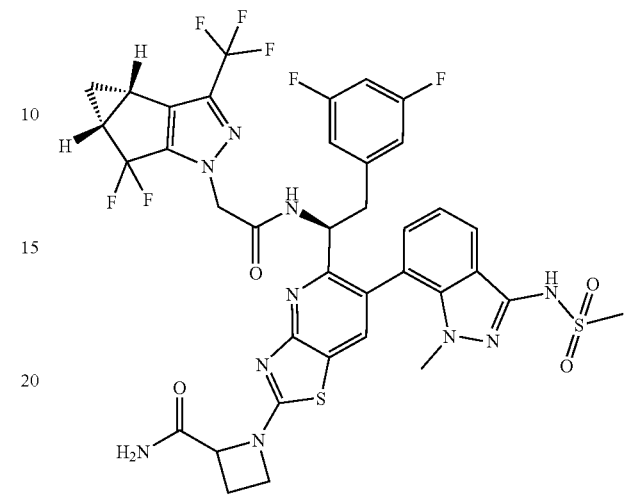

Synthesis of 1-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(1-methyl-3-(methylsulfonamido)-1H-indazol-7-yl)thiazolo[4,5-b]pyridin-2-yl)azetidine-3-carboxamide (73): Compound 73 was prepared according to the method presented for the synthesis of Example 64 utilizing 34E and substituting azetidine-3-carboxamide for 64D to provide the desired compound. MS (m/z) 877 [M+H]+. $^1$H NMR (400 MHz, Methanol-d4) δ 8.01 (d, J=15.6 Hz, 1H), 7.89-7.75 (m, 1H), 7.19-6.97 (m, 1H), 6.73 (d, J=9.2 Hz, 1H), 6.54-6.15 (m, 3H), 5.28-4.93 (m, 1H), 4.79 (d, J=3.9 Hz, 2H), 4.57-4.34 (m, 4H), 3.77 (ddd, J=8.7, 5.9, 2.8 Hz, 1H), 3.34 (s, 2H), 3.22-2.85 (m, 6H), 2.60-2.35 (m, 2H), 1.40 (dt, J=14.3, 7.6 Hz, 1H), 1.11 (d, J=25.0 Hz, 1H).

Synthesis of 1-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(1-methyl-3-(methylsulfonamido)-1H-indazol-7-yl)thiazolo[4,5-b]pyridin-2-yl)azetidine-2-carboxamide (74): Compound 74 was prepared according to the method presented for the synthesis of Example 64 utilizing 34E and substituting azetidine-2-carboxamide for 64D to provide the desired compound. MS (m/z) 877 [M+H]+. $^1$H NMR (400 MHz, Methanol-d4) δ 8.11-7.95 (m, 1H), 7.82 (dt, J=8.3, 1.2 Hz, 1H), 7.20-6.94 (m, 1H), 6.77-6.54 (m, 1H), 6.54-6.23 (m, 3H), 5.37-4.91 (m, 2H), 4.79 (t, J=3.1 Hz, 2H), 4.31 (dt, J=24.2, 9.0 Hz, 2H), 3.36-3.32 (m, 3H), 3.14 (d, J=20.1 Hz, 4H), 3.04-2.84 (m, 2H), 2.72-2.39 (m, 3H), 1.40 (p, J=7.4 Hz, 1H), 1.27-1.00 (m, 1H).

Example 75

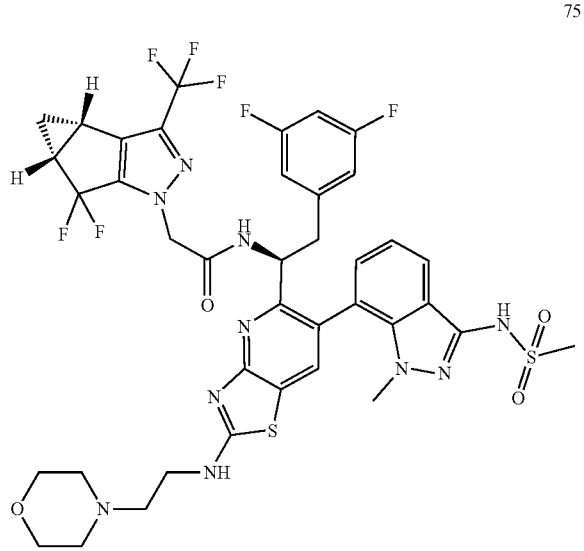 [SMILES: Cn1nc(NS(C)(=O)=O)c2cccc(-c3cc4sc(NCCN5CCOCC5)nc4nc3[C@H](Cc3cc(F)cc(F)c3)NC(=O)Cn3nc(C(F)(F)F)c4c3C(F)(F)[C@@H]3C[C@H]43)c21]

75

Example 76

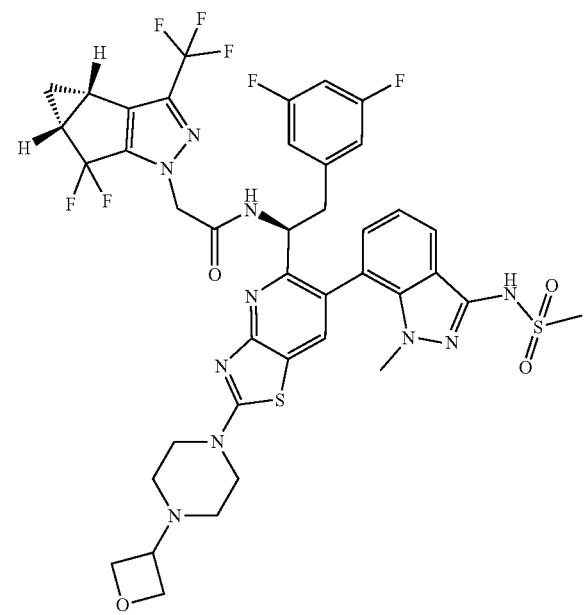

76

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-((2-morpholinoethyl)amino)thiazolo[4,5-b]pyridin-5-yl)ethyl)acetamide (75): Compound 75 was prepared according to the method presented for the synthesis of Example 64 utilizing 34E and substituting 2-morpholinoethan-1-amine for 64D to provide the desired compound. MS (m/z) 907 [M+H]+. $^1$H NMR (400 MHz, Methanol-d4) δ 8.02 (d, J=13.0 Hz, 1H), 7.91-7.76 (m, 1H), 7.23-7.00 (m, 1H), 6.69 (dt, J=44.6, 9.2 Hz, 1H), 6.56-6.26 (m, 3H), 5.35-4.91 (m, 1H), 4.79 (d, J=16.0 Hz, 2H), 4.33-3.84 (m, 6H), 3.84-3.45 (m, 6H), 3.35 (s, 2H), 3.24-2.83 (m, 6H), 2.68-2.36 (m, 2H), 1.52-1.24 (m, 2H), 1.23-0.96 (m, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(4-(oxetan-3-yl)piperazin-1-yl)thiazolo[4,5-b]pyridin-5-yl)ethyl)acetamide (76): Compound 76 was prepared according to the method presented for the synthesis of Example 64 utilizing 34E and substituting 1-(oxetan-3-yl)piperazine for 64D to provide the desired compound. MS (m/z) 919 [M+H]+. $^1$H NMR (400 MHz, Methanol-d4) δ 8.06 (d, J=15.2 Hz, 1H), 7.94-7.78 (m, 1H), 7.12 (dt, J=40.1, 7.6 Hz, 1H), 6.80-6.55 (m, 1H), 6.55-6.11 (m, 3H), 4.98 (t, J=7.1 Hz, 1H), 4.88 (d, J=7.4 Hz, 2H), 4.82-4.72 (m, 4H), 4.15 (t, J=6.3 Hz, 1H), 4.01 (s, 4H), 3.33 (s, 3H), 3.23-2.83 (m, 7H), 2.67-2.37 (m, 2H), 1.40 (p, J=7.1, 6.7 Hz, 1H), 1.10 (s, 1H).

Example 77

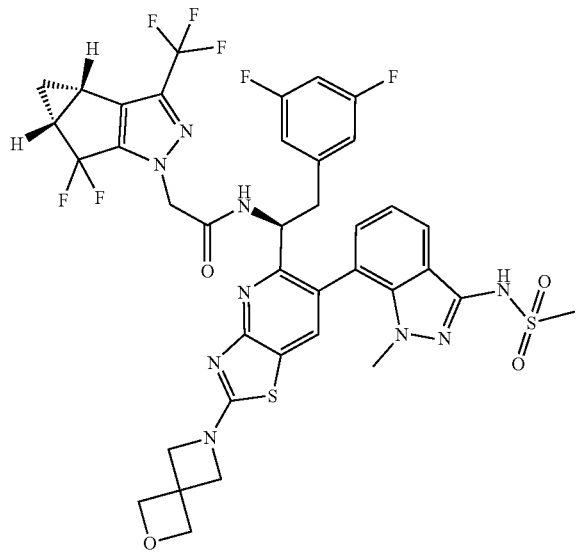

Example 78

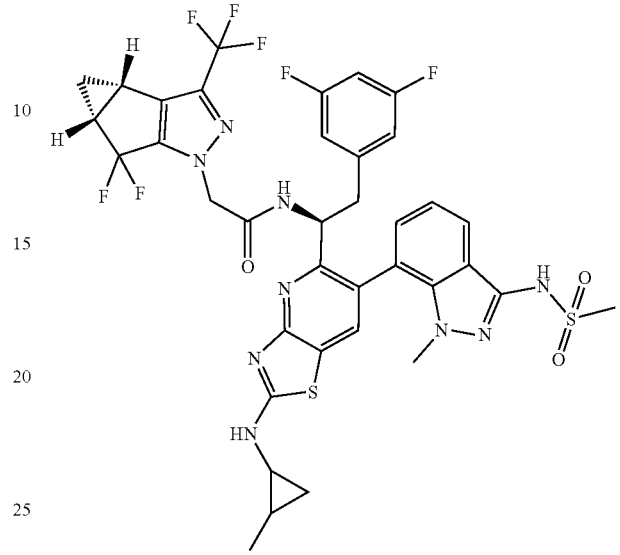

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(2-oxa-6-azaspiro[3.3]heptan-6-yl)thiazolo[4,5-b]pyridin-5-yl)ethyl)acetamide (77): Compound 77 was prepared according to the method presented for the synthesis of Example 64 utilizing 34E and substituting 2-oxa-6-azaspiro[3.3]heptane for 64D to provide the desired compound. MS (m/z) 876 [M+H]+. $^1$H NMR (400 MHz, Methanol-d4) δ 8.00-7.73 (m, 2H), 7.06 (dd, J=8.2, 7.0 Hz, 1H), 6.85-6.54 (m, 1H), 6.51-6.17 (m, 3H), 5.28-4.88 (m, 4H), 4.82-4.66 (m, 3H), 4.51 (s, 3H), 4.30-4.07 (m, 1H), 3.33 (d, J=4.1 Hz, 3H), 3.25-2.81 (m, 6H), 2.46 (dd, J=8.1, 4.1 Hz, 2H), 1.39 (d, J=7.0 Hz, 1H), 1.11 (d, J=24.2 Hz, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-((1S)-2-(3,5-difluorophenyl)-1-(6-(1-methyl-3-(methylsulfonamido)-1H-indazol-7-yl)-2-((2-methylcyclopropyl)amino)thiazolo[4,5-b]pyridin-5-yl)ethyl)acetamide (78): Compound 78 was prepared according to the method presented for the synthesis of Example 64 utilizing 34E and substituting 2-methylcyclopropan-1-amine for 64D to provide the desired compound. MS (m/z) 848 [M+H]+. $^1$H NMR (400 MHz, Methanol-d4) δ 8.07-7.93 (m, 1H), 7.82 (dt, J=8.3, 1.0 Hz, 1H), 7.18-7.01 (m, 1H), 6.76-6.55 (m, 1H), 6.54-6.31 (m, 3H), 5.34-4.90 (m, 1H), 4.82-4.69 (m, 2H), 4.14-3.44 (m, 1H), 3.35 (s, 3H), 3.25-2.90 (m, 6H), 2.59-2.36 (m, 2H), 1.52-1.25 (m, 1H), 1.28-1.03 (m, 4H), 0.97 (dt, J=8.9, 4.6 Hz, 1H), 0.75 (q, J=6.0 Hz, 1H).

Example 79

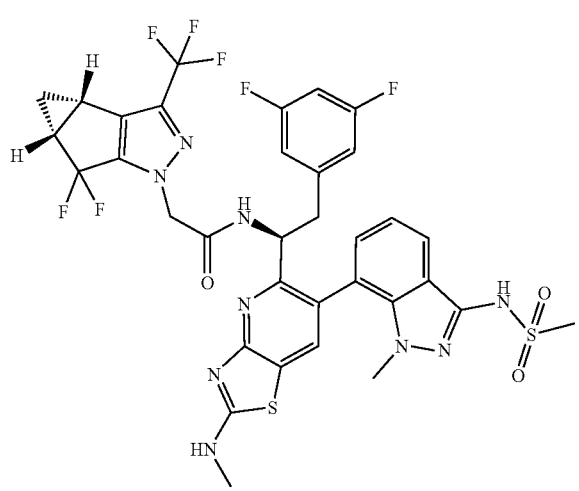

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(methylamino)thiazolo[4,5-b]pyridin-5-yl)ethyl)acetamide (79): Compound 79 was prepared according to the method presented for the synthesis of Example 64 utilizing 34E and substituting methanamine for 64D to provide desired compound. MS (m/z) 808 [M+H]+. $^1$H NMR (400 MHz, Methanol-d4) δ 7.94 (d, J=19.3 Hz, 1H), 7.19-6.99 (m, 1H), 6.88-6.55 (m, 1H), 6.56-6.21 (m, 3H), 5.31-4.90 (m, 1H), 4.77 (d, J=16.4 Hz, 1H), 3.36 (s, 2H), 3.25-2.79 (m, 10H), 2.49 (ddd, J=17.6, 8.7, 4.5 Hz, 2H), 1.41 (dq, J=14.2, 7.1 Hz, 1H), 1.30-1.01 (m, 1H).

Example 80

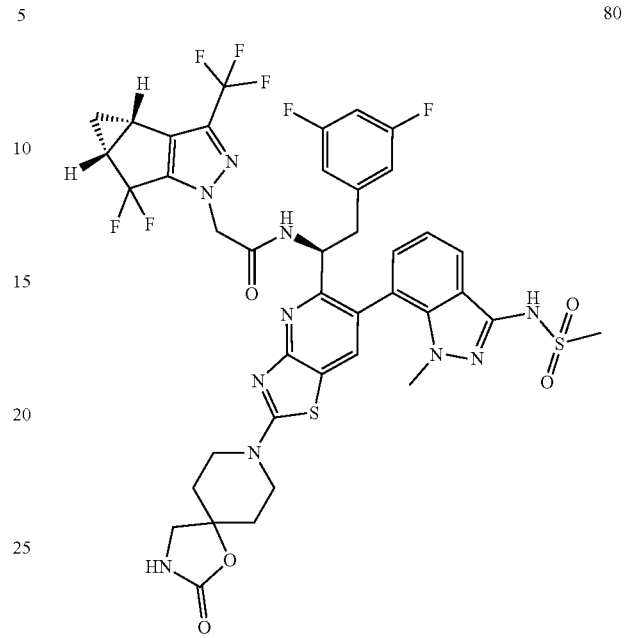

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(2-oxo-1-oxa-3,8-diazaspiro[4.5]decan-8-yl)thiazolo[4,5-b]pyridin-5-yl)ethyl)acetamide (80): Compound 80 was prepared according to the method presented for the synthesis of Example 64 utilizing 34E and substituting 1-oxa-3,8-diazaspiro[4.5]decan-2-one for 64D to provide the desired compound. MS (m/z) 933 [M+H]+. $^1$H NMR (400 MHz, Methanol-d4) δ 8.00 (d, J=18.8 Hz, 1H), 7.92-7.77 (m, 1H), 7.21-6.95 (m, 1H), 6.67 (dt, J=47.9, 9.0 Hz, 1H), 6.53-6.19 (m, 3H), 5.30-4.90 (m, 1H), 4.80 (d, J=4.5 Hz, 2H), 4.10 (d, J=20.7 Hz, 2H), 3.76 (t, J=12.3 Hz, 2H), 3.46 (s, 2H), 3.35 (s, 3H), 3.23-2.83 (m, 6H), 2.65-2.34 (m, 2H), 2.16 (d, J=13.8 Hz, 2H), 2.09-1.84 (m, 2H), 1.47-1.26 (m, 1H), 1.12 (d, J=18.1 Hz, 1H).

Example 81

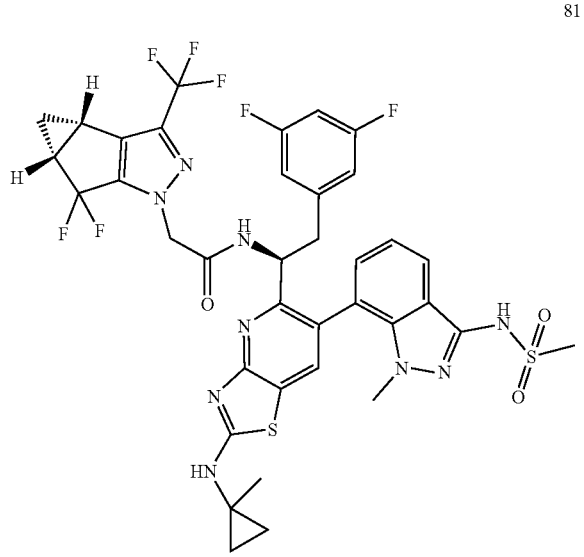 [SMILES: Cn1nc(NS(C)(=O)=O)c2cccc(-c3cc4sc(NC5(C)CC5)nc4nc3[C@H](Cc3cc(F)cc(F)c3)NC(=O)Cn3nc(C(F)(F)F)c4c3C(F)(F)[C@@H]3C[C@H]43)c21]

Example 82

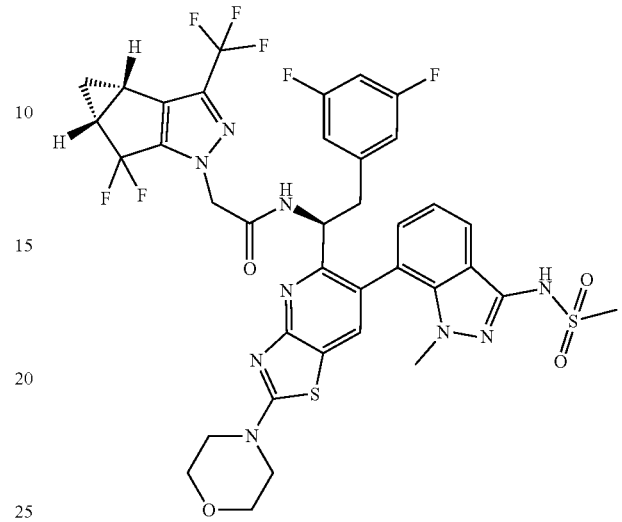

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-((1-methylcyclopropyl)amino)thiazolo[4,5-b]pyridin-5-yl)ethyl)acetamide (81): Compound 81 was prepared according to the method presented for the synthesis of Example 64 utilizing 34E and substituting 1-methylcyclopropan-1-amine for 64D to provide the desired compound. MS (m/z) 848 [M+H]+. $^1$H NMR (400 MHz, Methanol-d4) δ 8.02 (d, J=23.3 Hz, 1H), 7.92-7.72 (m, 1H), 7.21-6.87 (m, 1H), 6.83-6.53 (m, 1H), 6.52-6.23 (m, 3H), 5.33-4.91 (m, 1H), 4.83-4.73 (m, 2H), 3.36 (s, 3H), 3.25-3.05 (m, 4H), 3.05-2.85 (m, 2H), 2.63-2.34 (m, 2H), 1.55 (d, J=2.5 Hz, 3H), 1.39 (q, J=7.2 Hz, 1H), 1.13-0.93 (m, 3H), 0.91-0.76 (m, 2H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-morpholinothiazolo[4,5-b]pyridin-5-yl)ethyl)acetamide (82): Compound 82 was prepared according to the method presented for the synthesis of Example 64 utilizing 34E and substituting morpholine for 64D to provide desired compound. MS (m/z) 864 [M+H]+. $^1$H NMR (400 MHz, Methanol-d4) δ 8.04 (d, J=21.7 Hz, 1H), 7.88-7.72 (m, 1H), 7.21-6.98 (m, 1H), 6.86-6.57 (m, 1H), 6.57-6.24 (m, 3H), 5.35-4.88 (m, 1H), 4.82-4.68 (m, 2H), 3.88 (t, J=4.6 Hz, 4H), 3.79 (d, J=4.8 Hz, 4H), 3.35 (s, 2H), 3.15 (d, J=19.9 Hz, 4H), 3.07-2.84 (m, 2H), 2.48 (ddd, J=12.3, 8.1, 4.1 Hz, 2H), 1.40 (p, J=6.7 Hz, 1H), 1.12 (d, J=19.0 Hz, 1H).

Example 83

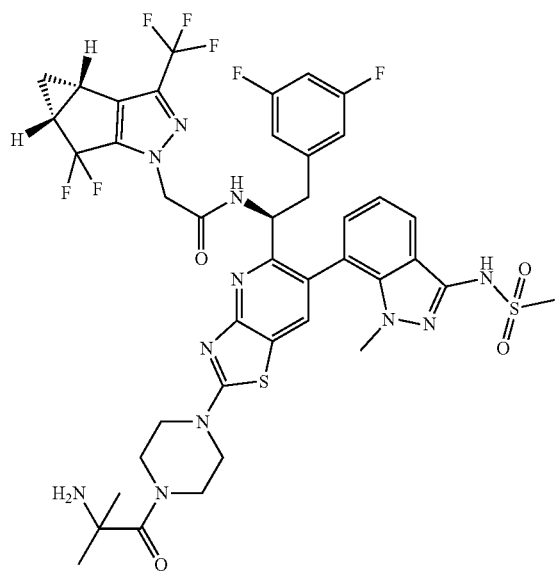

Example 84

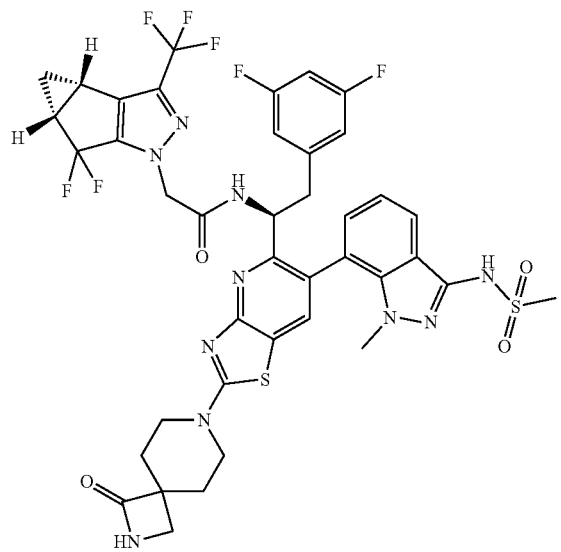

Synthesis of N—((S)-1-(2-(4-(2-amino-2-methylpropanoyl)piperazin-1-yl)-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (83): Compound 83 was prepared according to the method presented for the synthesis of Example 64 utilizing 34E and substituting 2-amino-2-methyl-1-(piperazin-1-yl)propan-1-one for 64D to provide the desired compound. MS (m/z) 948 [M+H]+. $^1$H NMR (400 MHz, Methanol-d4) δ 8.04 (d, J=15.1 Hz, 1H), 7.87-7.72 (m, 1H), 7.12 (dt, J=40.8, 7.7 Hz, 1H), 6.80-6.56 (m, 1H), 6.53-6.22 (m, 3H), 5.30-4.90 (m, 1H), 4.83-4.76 (m, 2H), 3.92 (d, J=4.7 Hz, 4H), 3.87 (s, 4H), 3.34 (s, 2H), 3.15 (d, J=19.0 Hz, 4H), 3.06-2.84 (m, 2H), 2.59-2.33 (m, 2H), 1.74 (s, 6H), 1.40 (q, J=7.0 Hz, 1H), 1.12 (d, J=19.5 Hz, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(1-oxo-2,7-diazaspiro[3.5]nonan-7-yl)thiazolo[4,5-b]pyridin-5-yl)ethyl)acetamide (84): Compound 84 was prepared according to the method presented for the synthesis of Example 64 utilizing 34E and substituting 2,7-diazaspiro[3.5]nonan-1-one for 64D to provide the desired compound. MS (m/z) 917 [M+H]+. $^1$H NMR (400 MHz, Methanol-d4) δ 7.99 (d, J=16.8 Hz, 1H), 7.89-7.72 (m, 1H), 7.19-6.98 (m, 1H), 6.84-6.54 (m, 1H), 6.54-6.20 (m, 3H), 5.30-4.89 (m, 1H), 4.82-4.70 (m, 2H), 4.09 (s, 2H), 3.78 (t, J=10.0 Hz, 2H), 3.35 (s, 3H), 3.15 (d, J=19.1 Hz, 5H), 3.05-2.83 (m, 2H), 2.48 (ddd, J=12.3, 8.4, 4.6 Hz, 2H), 2.20-2.07 (m, 2H), 2.07-1.94 (m, 2H), 1.40 (p, J=7.0 Hz, 1H), 1.10 (s, 1H).

Example 85

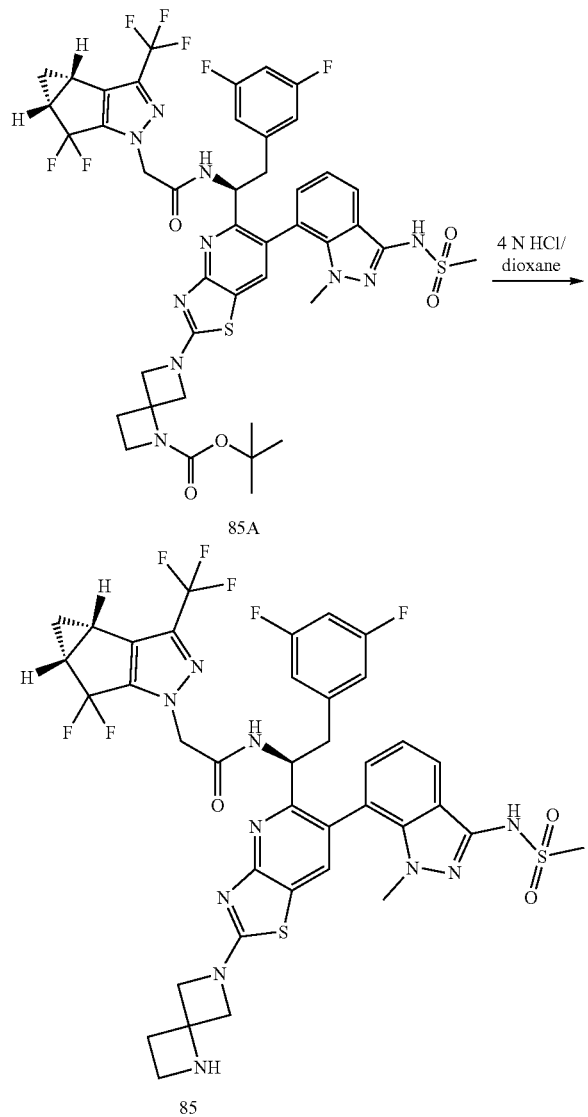

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(1,6-diazaspiro[3.3]heptan-6-yl)thiazolo[4,5-b]pyridin-5-yl)ethyl)acetamide (85): Compound 85A was prepared according to the method presented for the synthesis of Example 64 utilizing 34E and substituting tert-butyl 1,6-diazaspiro[3.3]heptane-1-carboxylate for 64D. Compound 85A was dissolved in 1 mL of 4 N HCl in dioxane. After 1 hour, the solvent was removed and the residue was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide the desired compound. MS (m/z) 875 [M+H]+. $^1$H NMR (400 MHz, Methanol-d4) δ 8.06 (d, J=14.1 Hz, 1H), 7.82 (td, J=7.3, 6.6, 0.9 Hz, 1H), 7.11 (dt, J=38.4, 7.7 Hz, 1H), 6.67 (dt, J=44.4, 9.1 Hz, 1H), 6.54-6.23 (m, 3H), 5.32-4.93 (m, 1H), 4.80 (dd, J=13.0, 2.2 Hz, 4H), 4.73-4.58 (m, 2H), 4.02 (t, J=8.4 Hz, 2H), 3.76-3.41 (m, 1H), 3.15 (d, J=19.6 Hz, 4H), 3.07-2.84 (m, 4H), 2.63-2.28 (m, 2H), 1.40 (p, J=7.2 Hz, 1H), 1.11 (d, J=23.9 Hz, 1H).

Example 86

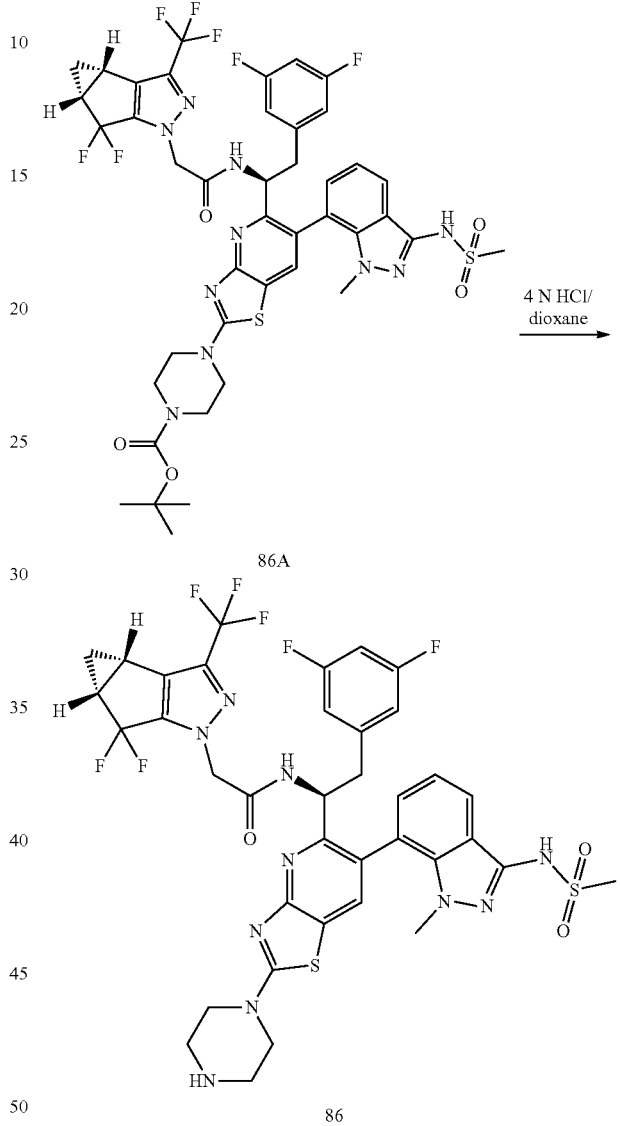

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(piperazin-1-yl)thiazolo[4,5-b]pyridin-5-yl)ethyl)acetamide (86): Compound 86A was prepared according to the method presented for the synthesis of Example 64 utilizing 34E and substituting tert-butyl piperazine-1-carboxylate for 64D. Compound 86A was dissolved in 1 mL of 4 N HCl in dioxane. After 1 hour, the solvent was removed and the residue was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide the desired compound. MS (m/z) 863 [M+H]+. $^1$H NMR (400 MHz, Methanol-d4) δ 8.08 (d, J=14.3 Hz, 1H), 7.82 (dd, J=7.5, 6.4 Hz, 1H), 7.12 (dt, J=40.3, 7.7 Hz, 1H), 6.68 (dt, J=46.7, 9.3 Hz, 1H), 6.54-6.25 (m, 3H), 5.00 (q, J=7.6 Hz, 1H), 4.79 (d, J=2.5 Hz, 2H), 4.18-3.90 (m, 4H), 3.48 (t, J=5.3 Hz, 5H), 3.33 (s, 3H), 3.15 (d, J=19.1 Hz, 4H), 3.09-2.82 (m, 2H), 2.60-2.31 (m, 2H), 1.41 (p, J=7.2, 6.7 Hz, 1H), 1.12 (d, J=18.7 Hz, 1H).

Example 87

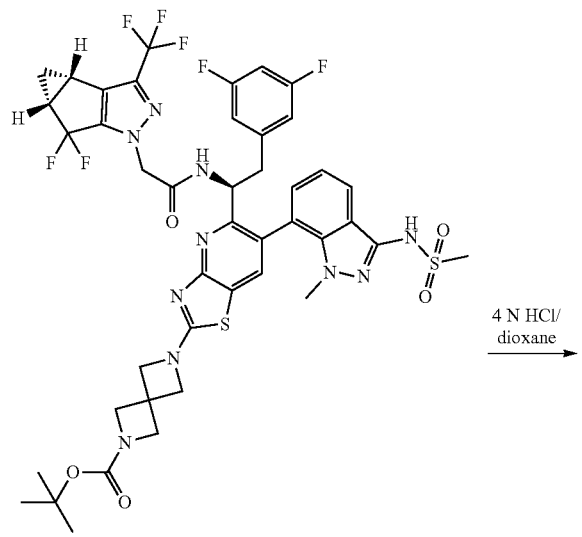

87A

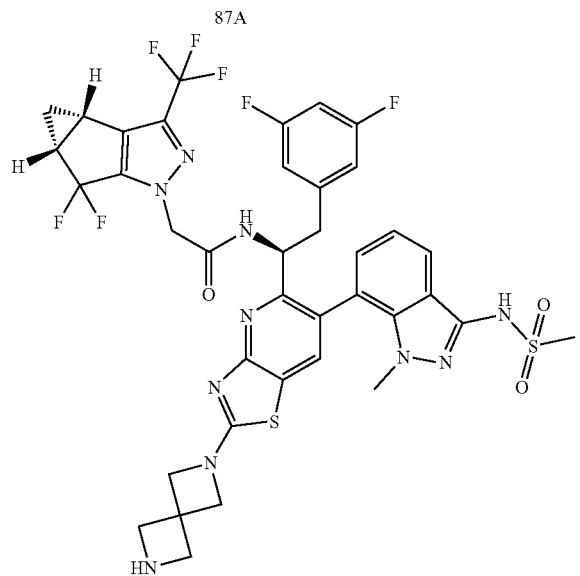

87

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(2,6-diazaspiro[3.3]heptan-2-yl)thiazolo[4,5-b]pyridin-5-yl)ethyl)acetamide (87): Compound 87A was prepared according to the method presented for the synthesis of Example 64 utilizing 34E and substituting tert-butyl 2,6-diazaspiro[3.3]heptane-2-carboxylate for 64D. Compound 87A was dissolved in 1 mL of 4 N HCl in dioxane. After 1 hour, the solvent was removed and the residue was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide the desired compound. MS (m/z) 875 [M+H]+. $^1$H NMR (400 MHz, Methanol-d4) δ 8.02 (d, J=14.6 Hz, 1H), 7.81 (dd, J=7.8, 6.6 Hz, 1H), 7.11 (dt, J=39.4, 7.7 Hz, 1H), 6.67 (dt, J=45.1, 9.4 Hz, 1H), 6.52-6.20 (m, 3H), 5.33-4.91 (m, 1H), 4.82-4.71 (m, 2H), 4.54 (s, 4H), 4.39 (s, 4H), 3.32 (s, 2H), 3.15 (d, J=19.4 Hz, 4H), 3.02-2.71 (m, 2H), 2.46 (td, J=11.9, 10.7, 6.6 Hz, 2H), 1.54-1.19 (m, 1H), 1.10 (d, J=24.3 Hz, 1H).

Example 88

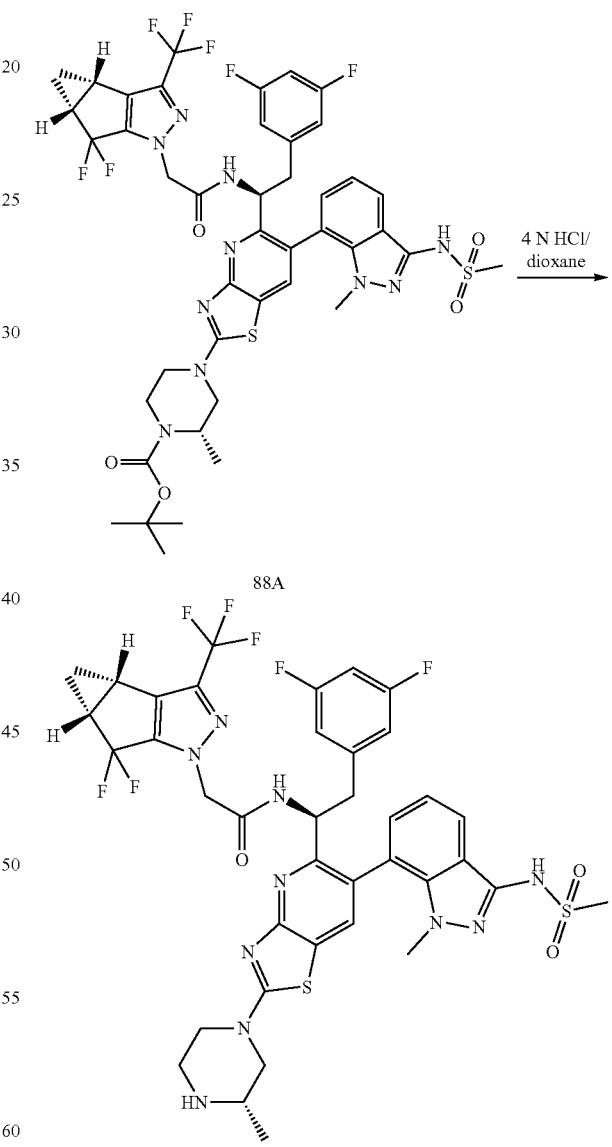

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-((S)-

3-methylpiperazin-1-yl)thiazolo[4,5-b]pyridin-5-yl)ethyl) acetamide (88): Compound 88A was prepared according to the method presented for the synthesis of Example 64 utilizing 34E and substituting tert-butyl (S)-2-methylpiperazine-1-carboxylate for 64D. Compound 88A was dissolved in 1 mL of 4 N HCl in dioxane. After 1 hour, the solvent was removed and the residue was purified on preparatory reverse phase HPLC using 20-80%₀B over 20 min. (A=0.1% TFA/H2O; B=0.1% TFA/Acetonitrile). The pure fractions as determined by LC/MS were combined and lyophilized to provide the desired compound. MS (m/z) 877 [M+H]+. ¹H NMR (400 MHz, Methanol-d4) δ 8.08 (d, J=13.9 Hz, 1H), 7.89-7.75 (m, 1H), 7.12 (dt, J=39.8, 7.7 Hz, 1H), 6.84-6.53 (m, 1H), 6.52-6.20 (m, 3H), 5.35-4.94 (m, 1H), 4.83-4.75 (m, 2H), 4.40 (d, J=14.0 Hz, 2H), 3.63 (t, J=11.1 Hz, 2H), 3.44 (dd, J=14.4, 10.8 Hz, 2H), 3.33 (s, 3H), 3.15 (d, J=19.1 Hz, 4H), 3.08-2.82 (m, 2H), 2.61-2.33 (m, 2H), 1.56-1.29 (m, 4H), 1.10 (s, 1H).

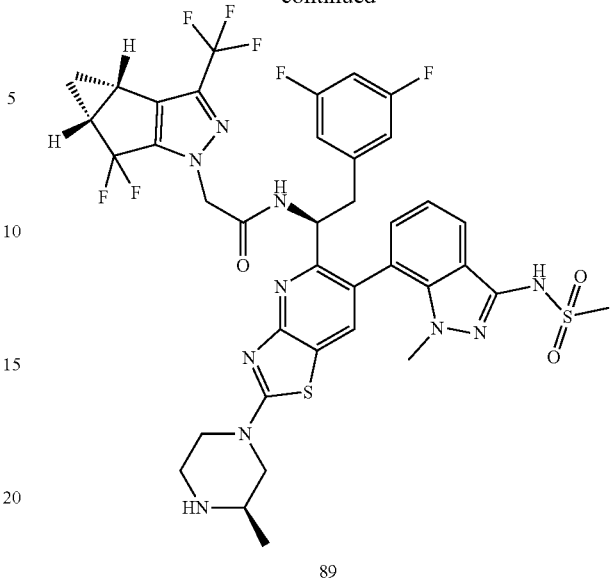

89

Example 89

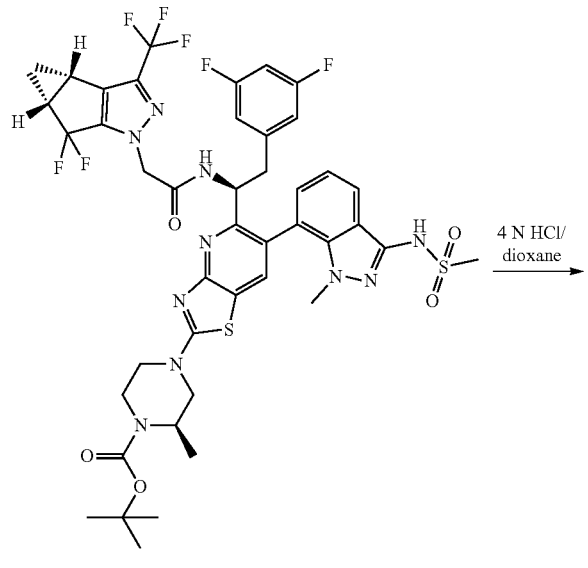

89A

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-((R)-3-methylpiperazin-1-yl)thiazolo[4,5-b]pyridin-5-yl)ethyl) acetamide (89): Compound 89A was prepared according to the method presented for the synthesis of Example 64 utilizing 34E and substituting tert-butyl (R)-2-methylpiperazine-1-carboxylate for 64D. Compound 89A was dissolved in 1 mL of 4 N HCl in dioxane. After 1 hour, the solvent was removed and the residue was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide the desired compound. MS (m/z) 877 [M+H]+. ¹H NMR (400 MHz, Methanol-d4) δ 8.08 (d, J=14.0 Hz, 1H), 7.82 (dd, J=7.7, 6.5 Hz, 1H), 7.12 (dt, J=39.7, 7.7 Hz, 1H), 6.82-6.57 (m, 1H), 6.54-6.23 (m, 3H), 5.00 (q, J=7.3 Hz, 1H), 4.83-4.72 (m, 2H), 4.40 (d, J=14.1 Hz, 2H), 3.63 (t, J=11.4 Hz, 3H), 3.52-3.37 (m, 2H), 3.33 (s, 2H), 3.15 (d, J=19.0 Hz, 4H), 3.09-2.84 (m, 2H), 2.61-2.36 (m, 2H), 1.53-1.31 (m, 4H), 1.12 (d, J=18.4 Hz, 1H).

Example 90

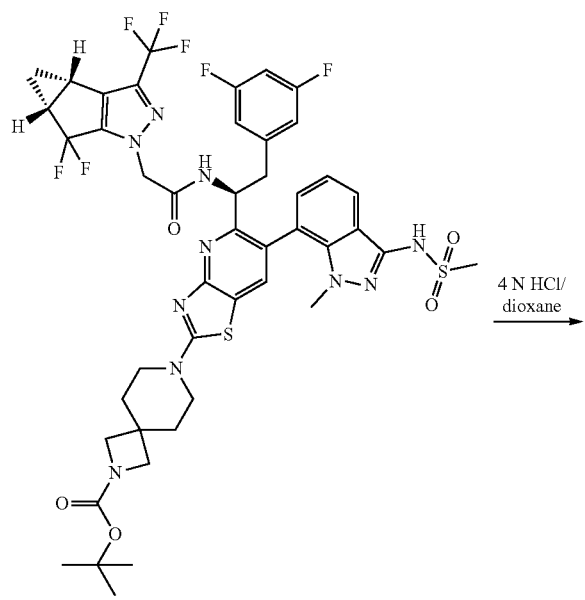

90A

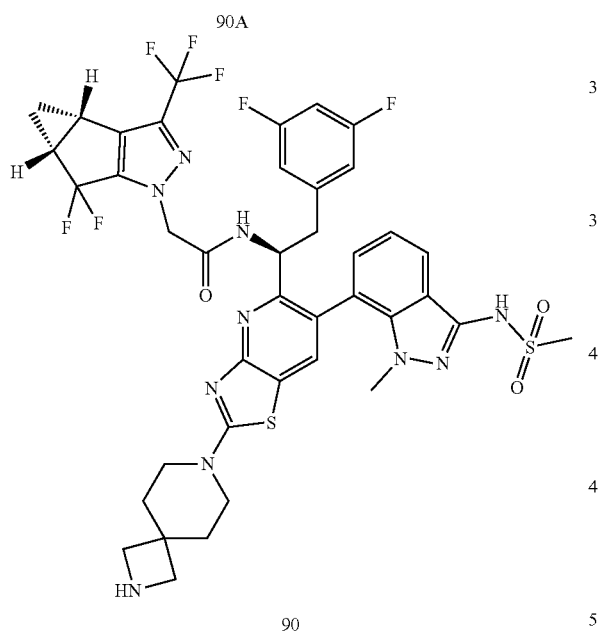

90

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(2,7-diazaspiro[3.5]nonan-7-yl)thiazolo[4,5-b]pyridin-5-yl)ethyl)acetamide (90): Compound 90A was prepared according to the method presented for the synthesis of Example 64 utilizing 34E and substituting tert-butyl 2,7-diazaspiro[3.5]nonane-2-carboxylate for 64D. Compound 90A was dissolved in 1 mL of 4 N HCl in dioxane. After 1 hour, the solvent was removed and the residue was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide desired compound. MS (m/z) 903 [M+H]+. $^1$H NMR (400 MHz, Methanol-d4) δ 7.99 (d, J=15.4 Hz, 1H), 7.88-7.74 (m, 1H), 7.22-6.98 (m, 1H), 6.67 (dt, J=48.1, 9.3 Hz, 1H), 6.53-6.25 (m, 3H), 5.33-4.91 (m, 1H), 4.83-4.76 (m, 2H), 3.98 (s, 4H), 3.79 (d, J=6.2 Hz, 4H), 3.33 (s, 2H), 3.15 (d, J=19.1 Hz, 4H), 3.05-2.87 (m, 2H), 2.48 (ddd, J=12.2, 7.2, 3.4 Hz, 2H), 2.09 (t, J=5.7 Hz, 4H), 1.41 (dq, J=13.8, 6.9 Hz, 1H), 1.10 (s, 1H).

Example 91

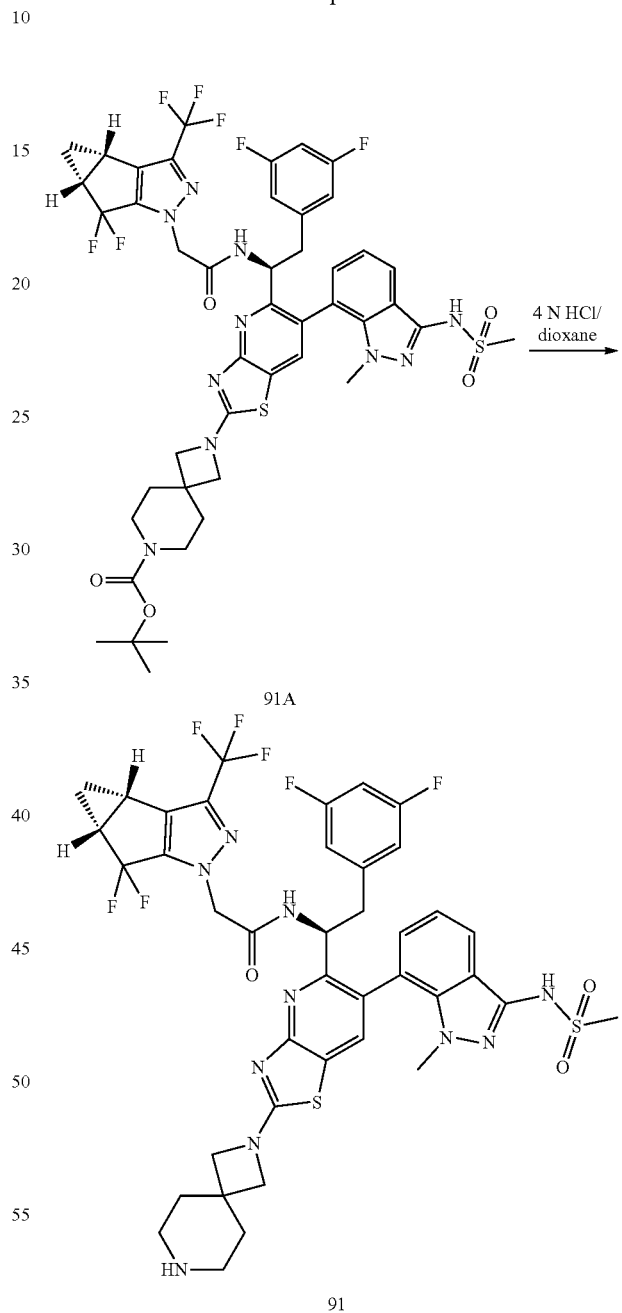

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(2,7-diazaspiro[3.5]nonan-2-yl)thiazolo[4,5-b]pyridin-5-yl)ethyl)acetamide (91): Compound 91A was prepared according to the method presented for the synthesis of Example 64 utilizing 34E and substituting tert-butyl 2,7-diazaspiro[3.5]nonane-7-carboxylate for 64D. Compound 91A was dissolved in 1 mL of 4 N HCl in dioxane. After 1 hour, the solvent was removed and the residue was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide the desired compound. MS (m/z) 903 [M+H]+. $^1$H NMR (400 MHz, Methanol-d4) δ 8.01 (d, J=14.8 Hz, 1H), 7.85-7.73 (m, 1H), 7.19-6.93 (m, 1H), 6.78-6.55 (m, 1H), 6.55-6.22 (m, 3H), 4.98 (d, J=7.2 Hz, 1H), 4.80 (d, J=14.9 Hz, 3H), 4.15 (d, J=4.6 Hz, 4H), 3.33 (s, 2H), 3.26 (t, J=5.6 Hz, 3H), 3.15 (d, J=19.1 Hz, 4H), 3.04-2.85 (m, 2H), 2.59-2.37 (m, 2H), 2.18 (s, 4H), 1.40 (dt, J=14.2, 7.3 Hz, 1H), 1.11 (d, J=23.0 Hz, 1H).

Example 92

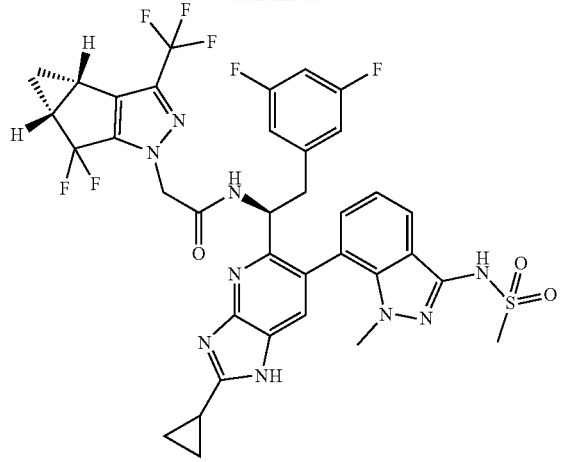

92

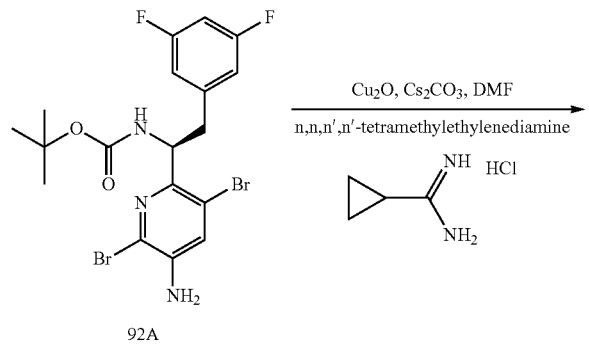

92A

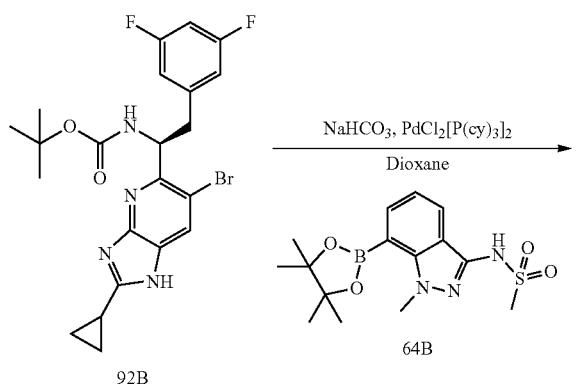

92B

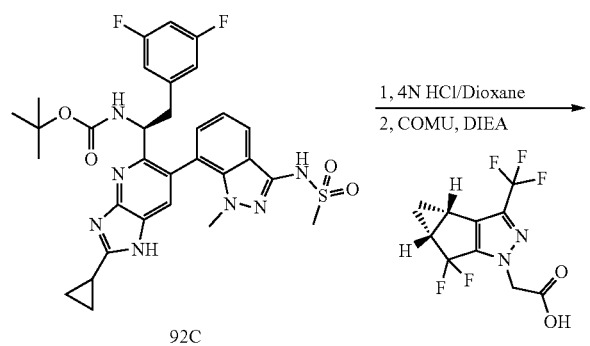

92C

Synthesis of tert-butyl (S)-(1-(6-bromo-2-cyclopropyl-1H-imidazo[4,5-b]pyridin-5-yl)-2-(3,5-difluorophenyl)ethyl)carbamate (92B): A flask was charged with 92A (300 mg, 0.59 mmol, prepared as described in WO2014/134566A2), copper(I) oxide (12.7 mg, 0.09 mmol), Cs$_2$CO$_3$ (771 mg, 2.37 mmol), and cyclopropanecarboximidamide hydrochloride (143 mg, 1.18 mmol) in 1.5 mL DMF under nitrogen atmosphere. The mixture was stirred at room temperature and n,n,n',n'-tetramethylethylenediamine (0.027 mL, 0.18 mmol) was added via syringe. The reaction mixture was then stirred in a preheated oil bath at 140° C. for 2 h, and then cooled to room temperature. The mixture was filtered, and the filtrate was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide compound 92B. MS (m/z) 493 [M+H]+.

Synthesis of tert-butyl (S)-(1-(2-cyclopropyl-6-(1-methyl-3-(methylsulfonamido)-1H-indazol-7-yl)-1H-imidazo[4,5-b]pyridin-5-yl)-2-(3,5-difluorophenyl)ethyl)carbamate (92C): To a suspension of 92B (50 mg, 0.1 mmol)), 64B (53.4 mg, 0.15 mmol), 1 N of sodium bicarbonate (0.3 mL, 0.3 mmol) in 1 mL of dioxane, dichlorobis(tricyclohexylphosphine)palladium(II) (11.1 mg, 0.015 mmol) was added. The reaction was heated at 150° C. by microwave reactor for 15 minutes. The mixture was filtered, and the filtrate was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide compound 92C. MS (m/z) 638 [M+H]+.

Synthesis of N—((S)-1-(2-cyclopropyl-6-(1-methyl-3-(methylsulfonamido)-1H-indazol-7-yl)-1H-imidazo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (92): A solution of 92C (30 mg, 0.047 mmol) in 4 N of hydrochloride in dioxane (2 mL) was stirred for 1 hour. The solvent was removed and dried in vacuo. The crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (13.3 mg, 0.047 mmol) and (1-Cyano-2-ethoxy-2-oxoethylidenaminooxy)dimethylamino-morpholino-carbenium hexafluorophosphate (20.1 mg, 0.047 mmol) was dissolved in DMF (1 mL) and diisopropylethylamine (0.016 mL, 0.094 mmol) was added to the solution. The reaction was stirred at room temperature for 15 mins. The reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide the desired compound. MS (m/z) 802 [M+H]+. ¹H NMR (400 MHz, Methanol-d4) δ 8.76 (d, J=8.4 Hz, 1H), 7.92-7.72 (m, 2H), 7.34-6.93 (m, 1H), 6.81-6.51 (m, 2H), 6.36 (dd, J=35.7, 7.2 Hz, 2H), 5.35-4.96 (m, 1H), 4.77 (d, J=9.2 Hz, 2H), 3.27 (s, 2H), 3.15 (d, J=21.1 Hz, 4H), 2.99 (ddd, J=26.2, 13.3, 6.6 Hz, 1H), 2.87 (s, 1H), 2.62-2.29 (m, 3H), 1.61-1.32 (m, 5H), 1.23-0.90 (m, 1H).

Example 93

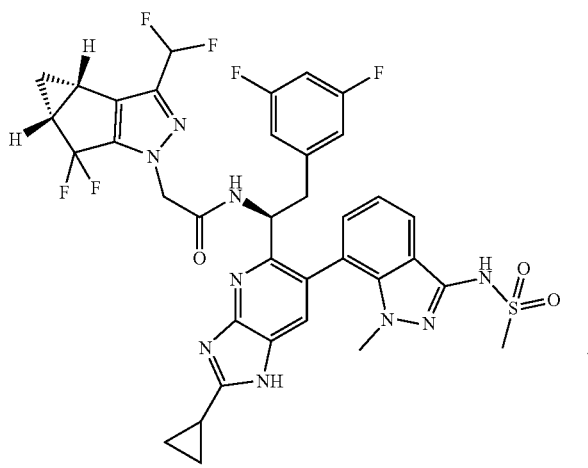

Example 94

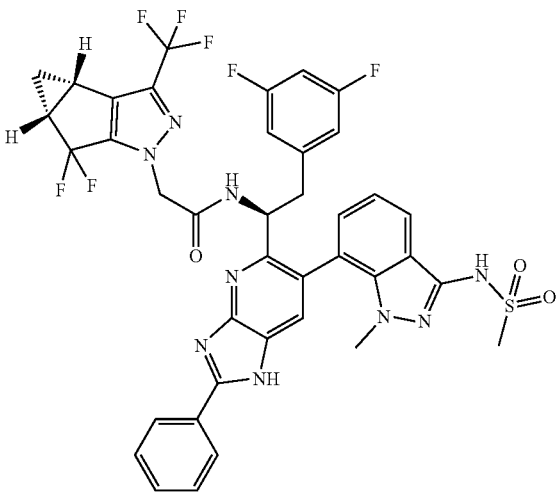

Synthesis of N—((S)-1-(2-cyclopropyl-6-(1-methyl-3-(methylsulfonamido)-1H-indazol-7-yl)-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (93): Compound 93 was prepared according to the method presented for the synthesis of Example 92 utilizing 92A and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 784 [M+H]+. ¹H NMR (400 MHz, Methanol-d4) δ 7.94-7.69 (m, 2H), 7.32-7.03 (m, 2H), 6.81-6.56 (m, 2H), 6.36 (dd, J=35.4, 7.4 Hz, 2H), 5.34-4.96 (m, 1H), 4.77 (d, J=9.2 Hz, 2H), 3.29-3.09 (m, 7H), 2.87 (s, 1H), 2.70-2.25 (m, 2H), 1.57-1.27 (m, 6H), 1.08 (d, J=26.9 Hz, 1H).

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-phenyl-1H-imidazo[4,5-b]pyridin-5-yl)ethyl)acetamide (94): Compound 94 was prepared according to the method presented for the synthesis of Example 92 utilizing 92A and substituting benzimidamide hydrochloride for cyclopropanecarboximidamide hydrochloride to provide the desired compound. MS (m/z) 838 [M+H]+. ¹H NMR (400 MHz, Methanol-d4) δ 8.27-8.13 (m, 2H), 8.04-7.77 (m, 2H), 7.67 (dd, J=4.8, 2.0 Hz, 3H), 7.16 (ddd, J=28.8, 8.2, 7.0 Hz, 1H), 6.81-6.57 (m, 2H), 6.40 (dd, J=47.5, 7.2 Hz, 2H), 5.41-4.99 (m, 1H), 4.80 (d, J=5.6 Hz, 2H), 3.32 (s, 3H), 3.16 (d, J=19.9 Hz, 3H), 3.07-2.72 (m, 2H), 2.60-2.37 (m, 2H), 1.53-1.32 (m, 1H), 1.09 (d, J=26.0 Hz, 1H).

Example 95

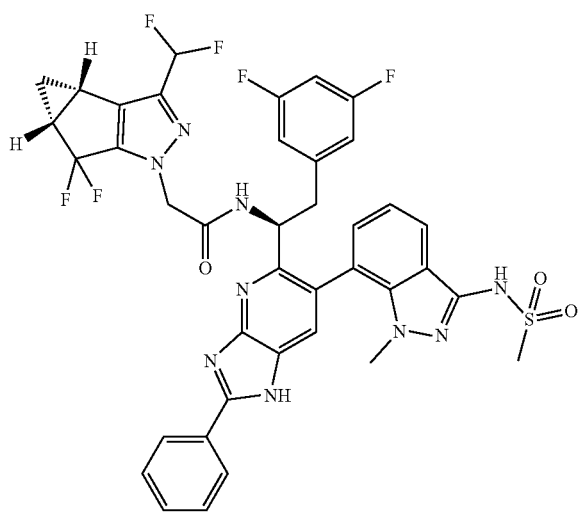

Example 96

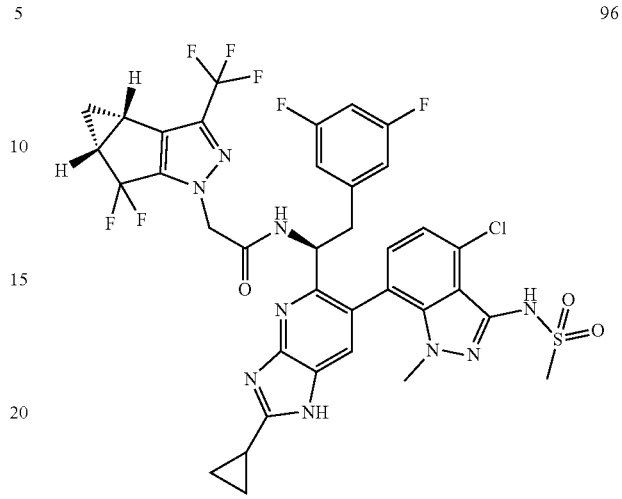

Synthesis of N—((S)-1-(6-(4-chloro-1-methyl-3-(methylsulfonamido)-1H-indazol-7-yl)-2-cyclopropyl-1H-imidazo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (96): Compound 96 was prepared according to the method presented for the synthesis of Example 92 utilizing 92A and substituting N-(4-chloro-1-methyl-7-(4,4,5,5-tetramethyl-1,3,2-dioxaborolan-2-yl)-1H-indazol-3-yl)methanesulfonamide for 64B to provide the desired compound. MS (m/z) 836 [M+H]+. $^1$H NMR (400 MHz, Methanol-d4) δ 7.67 (d, J=16.0 Hz, 1H), 7.18-6.98 (m, 1H), 6.81-6.54 (m, 1H), 6.54-6.24 (m, 3H), 4.99 (dd, J=7.8, 6.6 Hz, 1H), 4.79 (d, J=4.5 Hz, 2H), 3.25 (d, J=3.7 Hz, 3H), 3.23 (s, 3H), 3.00 (td, J=12.9, 12.1, 5.9 Hz, 1H), 2.80 (s, 1H), 2.47 (ddt, J=16.6, 12.4, 6.8 Hz, 2H), 2.26 (tt, J=7.9, 5.5 Hz, 1H), 1.50-1.26 (m, 5H), 1.10 (d, J=23.6 Hz, 1H).

Example 97

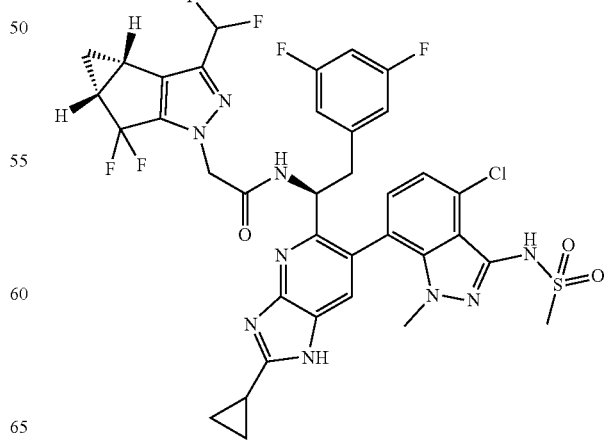

Synthesis of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-phenyl-1H-imidazo[4,5-b]pyridin-5-yl)ethyl)acetamide (95): Compound 95 was prepared according to the method presented for the synthesis of Example 92 utilizing 92A and substituting benzimidamide hydrochloride for cyclopropanecarboximidamide hydrochloride and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 820 [M+H]+. $^1$H NMR (400 MHz, Methanol-d4) δ 8.26-8.15 (m, 2H), 8.06-7.78 (m, 2H), 7.75-7.59 (m, 3H), 7.16 (dt, J=30.3, 7.7 Hz, 1H), 6.95-6.50 (m, 3H), 6.50-6.24 (m, 2H), 5.35-4.98 (m, 1H), 4.74 (d, J=9.5 Hz, 2H), 3.32 (s, 3H), 3.26-3.06 (m, 4H), 3.06-2.85 (m, 1H), 2.43 (ddd, J=11.2, 7.9, 4.0 Hz, 2H), 1.36 (q, J=7.0 Hz, 1H), 1.01 (s, 1H).

Synthesis of N—((S)-1-(6-(4-chloro-1-methyl-3-(methylsulfonamido)-1H-indazol-7-yl)-2-cyclopropyl-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (97): Compound 97 was prepared according to the method presented for the synthesis of Example 92 utilizing 92A and substituting N-(4-chloro-1-methyl-7-(4,4,5,5-tetramethyl-1,3,2-dioxaborolan-2-yl)-1H-indazol-3-yl)methanesulfonamide for 64B and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetic acid to provide the desired compound. MS (m/z) 818 [M+H]+. $^1$H NMR (400 MHz, Methanol-d4) δ 7.67 (d, J=14.8 Hz, 1H), 7.23-7.00 (m, 1H), 6.89-6.51 (m, 2H), 6.51-6.20 (m, 3H), 4.98 (dd, J=7.8, 6.6 Hz, 1H), 4.73 (d, J=9.0 Hz, 2H), 3.25 (d, J=2.3 Hz, 3H), 3.22 (s, 3H), 3.10-2.85 (m, 1H), 2.81 (s, 1H), 2.45 (dtd, J=14.6, 7.7, 7.1, 3.9 Hz, 2H), 2.34-2.13 (m, 1H), 1.44-1.20 (m, 5H), 1.14-0.96 (m, 1H).

Example 98

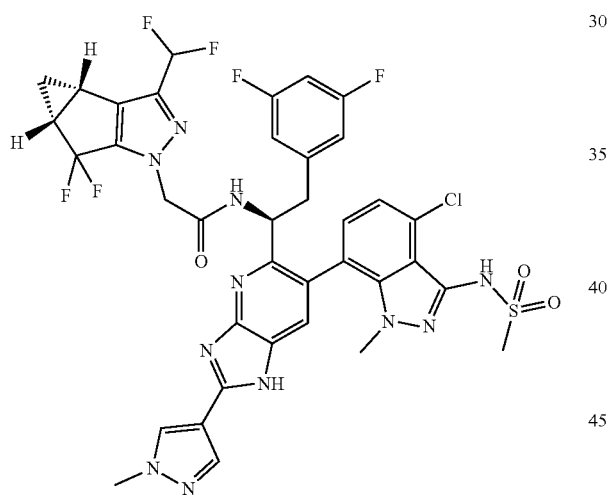

98

Synthesis of N—((S)-1-(6-(4-chloro-1-methyl-3-(methylsulfonamido)-1H-indazol-7-yl)-2-(1-methyl-1H-pyrazol-4-yl)-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (98): Compound 98 was prepared according to the method presented for the synthesis of Example 92 utilizing 92A and substituting 1-methyl-1H-pyrazole-4-carboximidamide hydrochloride for cyclopropanecarboximidamide hydrochloride, substituting N-(4-chloro-1-methyl-7-(4,4,5,5-tetramethyl-1,3,2-dioxaborolan-2-yl)-1H-indazol-3-yl)methanesulfonamide for 64B, and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetic acid to provide the desired compound. MS (m/z) 858 [M+H]+. $^1$H NMR (400 MHz, Methanol-d4) δ 8.34 (d, J=2.9 Hz, 1H), 8.17 (dd, J=2.6, 0.8 Hz, 1H), 7.77 (d, J=15.3 Hz, 1H), 7.22-7.01 (m, 1H), 6.92-6.28 (m, 5H), 5.30-4.98 (m, 1H), 4.74 (d, J=9.7 Hz, 2H), 4.03 (d, J=1.6 Hz, 3H), 3.34 (s, 1H), 3.23 (s, 3H), 3.02 (dd, J=13.1, 6.7 Hz, 1H), 2.84 (s, 1H), 2.44 (ddd, J=11.3, 7.8, 4.0 Hz, 2H), 1.48-1.24 (m, 2H), 1.02 (s, 1H), 0.88 (d, J=11.9 Hz, 1H).

Example 99

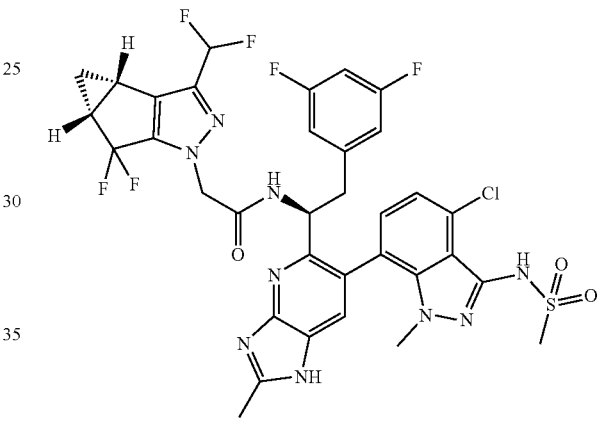

99

Synthesis of N—((S)-1-(6-(4-chloro-1-methyl-3-(methylsulfonamido)-1H-indazol-7-yl)-2-methyl-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (99): Compound 99 was prepared according to the method presented for the synthesis of Example 92 utilizing 92A and substituting acetimidamide hydrochloride for cyclopropanecarboximidamide hydrochloride, substituting N-(4-chloro-1-methyl-7-(4,4,5,5-tetramethyl-1,3,2-dioxaborolan-2-yl)-1H-indazol-3-yl)methanesulfonamide for 64B, and 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 792 [M+H]+. $^1$H NMR (400 MHz, Methanol-d4) δ 7.75 (d, J=15.2 Hz, 1H), 7.24-6.94 (m, 1H), 6.91-6.50 (m, 2H), 6.50-6.23 (m, 3H), 5.09 (ddd, J=62.9, 8.6, 6.1 Hz, 1H), 4.73 (d, J=7.8 Hz, 2H), 3.25 (d, J=2.7 Hz, 3H), 3.22 (s, 3H), 3.00 (td, J=12.9, 11.8, 6.0 Hz, 1H), 2.81 (s, 1H), 2.69 (d, J=4.2 Hz, 3H), 2.45 (tdd, J=11.2, 8.0, 4.1 Hz, 2H), 1.49-1.29 (m, 1H), 1.12-0.93 (m, 1H).

Example 100

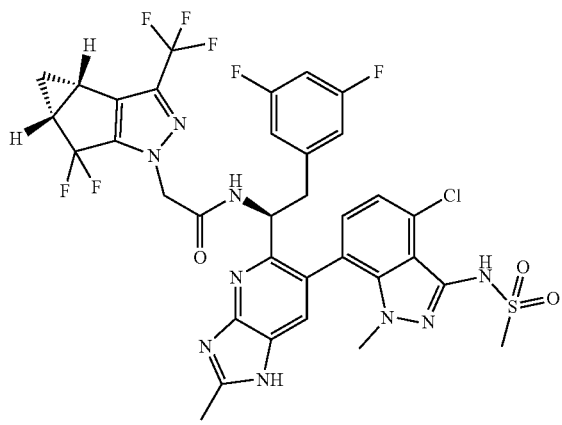

100

Synthesis of N—((S)-1-(6-(4-chloro-1-methyl-3-(methylsulfonamido)-1H-indazol-7-yl)-2-methyl-1H-imidazo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (100): Compound 100 was prepared according to the method presented for the synthesis of Example 92 utilizing 92A and substituting acetimidamide hydrochloride for cyclopropanecarboximidamide hydrochloride, and substituting N-(4-chloro-1-methyl-7-(4,4,5,5-tetramethyl-1,3,2-dioxaborolan-2-yl)-1H-indazol-3-yl)methanesulfonamide for 64B to provide the desired compound. MS (m/z) 810 [M+H]+. $^1$H NMR (400 MHz, Methanol-d4) δ 7.75 (d, J=15.9 Hz, 1H), 7.17-6.95 (m, 1H), 6.77-6.57 (m, 1H), 6.53-6.29 (m, 3H), 5.08 (ddd, J=58.3, 8.6, 6.0 Hz, 1H), 4.79 (dd, J=4.8, 1.1 Hz, 2H), 3.26-3.12 (m, 6H), 3.01 (td, J=13.0, 12.3, 6.1 Hz, 1H), 2.79 (s, 1H), 2.69 (d, J=4.3 Hz, 3H), 2.48 (ddd, J=12.3, 8.1, 4.5 Hz, 1H), 1.52-1.32 (m, 1H), 1.19-0.95 (m, 1H).

Example 101

101

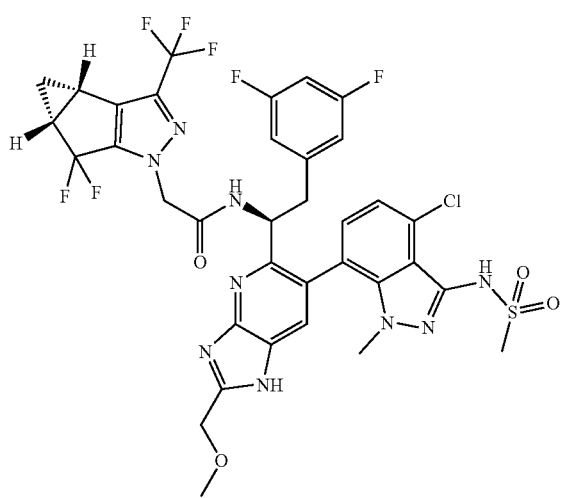 [SMILES: Cn1nc(NS(C)(=O)=O)c2c(Cl)ccc(-c3cc4nc(C5CC5)oc4nc3[C@H](Cc3cc(F)cc(F)c3)NC(=O)Cn3nc(C(F)F)c4c3C(F)(F)[C@@H]3C[C@H]43)c21]

Synthesis of N—((S)-1-(6-(4-chloro-1-methyl-3-(methylsulfonamido)-1H-indazol-7-yl)-2-(methoxymethyl)-1H-imidazo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (101): Compound 101 was prepared according to the method presented for the synthesis of Example 92 utilizing 92A and substituting 2-methoxyacetimidamide hydrochloride for cyclopropanecarboximidamide hydrochloride, and substituting N-(4-chloro-1-methyl-7-(4,4,5,5-tetramethyl-1,3,2-dioxaborolan-2-yl)-1H-indazol-3-yl)methanesulfonamide for 64B to provide the desired compound. MS (m/z) 840 [M+H]+. $^1$H NMR (400 MHz, Methanol-d4) δ 7.92 (d, J=14.2 Hz, 1H), 7.25-7.02 (m, 1H), 6.83-6.57 (m, 1H), 6.55-6.27 (m, 3H), 5.28-4.98 (m, 1H), 4.88 (d, J=3.3 Hz, 2H), 4.79-4.70 (m, 2H), 3.58 (d, J=1.5 Hz, 3H), 3.28-3.20 (m, 6H), 3.13-2.75 (m, 2H), 2.48 (ddd, J=12.1, 7.8, 4.2 Hz, 2H), 1.40 (dt, J=14.2, 7.8 Hz, 1H), 1.18-0.94 (m, 1H).

Example 102

102

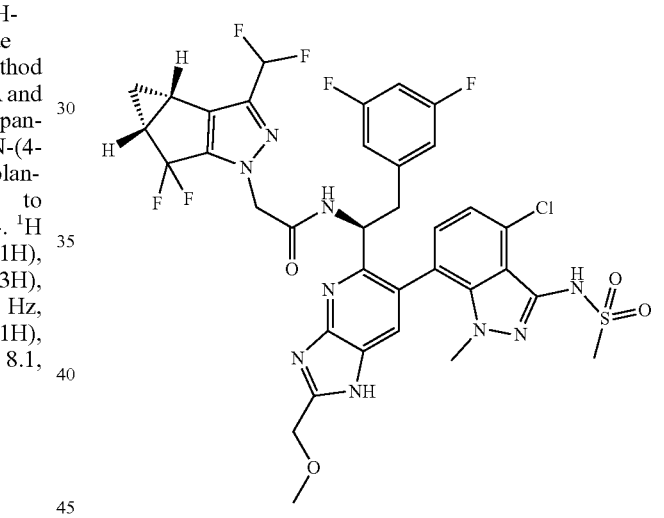

Synthesis of N—((S)-1-(6-(4-chloro-1-methyl-3-(methylsulfonamido)-1H-indazol-7-yl)-2-(methoxymethyl)-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (102): Compound 102 was prepared according to the method presented for the synthesis of Example 92 utilizing 92A and substituting 2-methoxyacetimidamide hydrochloride for cyclopropanecarboximidamide hydrochloride, substituting N-(4-chloro-1-methyl-7-(4,4,5,5-tetramethyl-1,3,2-dioxaborolan-2-yl)-1H-indazol-3-yl)methanesulfonamide for 64B and substituting 2-((3bS,4aR)-3-(difluoromethyl)-5,5-difluoro-3b,4,4a,5-tetrahydro-TH-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetic acid to provide the desired compound. MS (m/z) 822 [M+H]+. $^1$H NMR (400 MHz, Methanol-d4) δ 7.88 (d, J=13.8 Hz, 1H), 7.24-7.01 (m, 1H), 6.94-6.51 (m, 2H), 6.51-6.26 (m, 3H), 5.05 (q, J=7.0 Hz, 1H), 4.85 (s, 2H), 4.72 (d, J=8.3 Hz, 2H), 3.61-3.44 (m, 3H), 3.28-3.17 (m, 7H), 3.14-2.94 (m, 1H), 2.43 (ddd, J=11.2, 7.9, 4.0 Hz, 2H), 1.53-1.16 (m, 1H), 1.04 (d, J=24.2 Hz, 1H).

Example 103

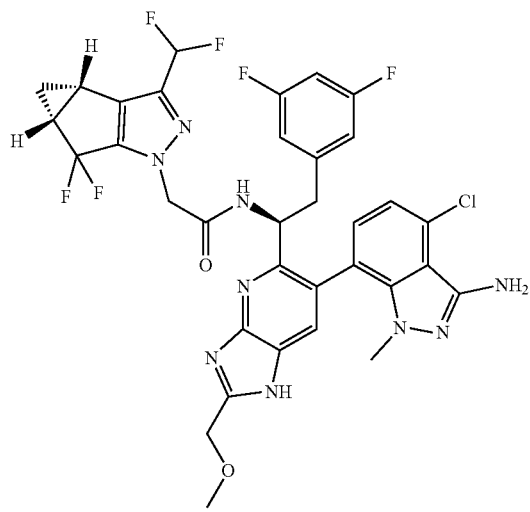

103

Synthesis of N—((S)-1-(6-(3-amino-4-chloro-1-methyl-1H-indazol-7-yl)-2-(methoxymethyl)-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (103): Compound 103 was prepared according to the method presented for the synthesis of Example 92 utilizing 92A and substituting 2-methoxyacetimidamide hydrochloride for cyclopropanecarboximidamide hydrochloride, substituting 4-chloro-1-methyl-7-(4,4,5,5-tetramethyl-1,3,2-dioxaborolan-2-yl)-1H-indazol-3-amine for 64B and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 744 [M+H]+. $^1$H NMR (400 MHz, Methanol-d4) δ 7.89 (d, J=14.3 Hz, 1H), 7.18-6.77 (m, 2H), 6.77-6.41 (m, 3H), 6.35 (d, J=7.2 Hz, 1H), 5.31-5.03 (m, 1H), 4.87 (s, 2H), 4.71 (d, J=1.6 Hz, 2H), 3.57 (s, 4H), 3.25-2.86 (m, 4H), 2.69 (s, 1H), 2.43 (tt, J=7.7, 4.0 Hz, 2H), 1.37 (dt, J=13.5, 6.6 Hz, 1H), 1.04 (d, J=19.4 Hz, 1H).

Example 104

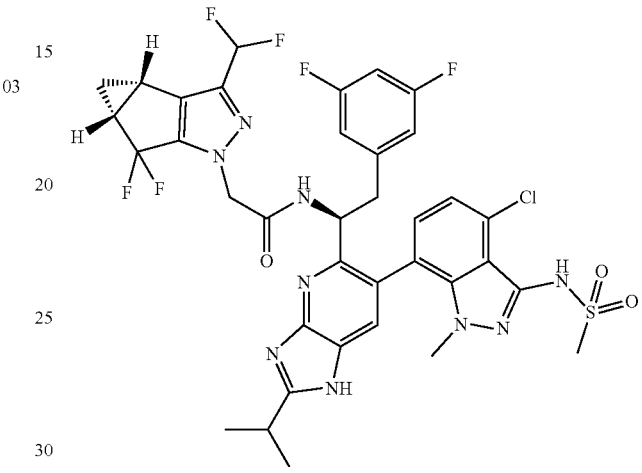

104

Synthesis of N—((S)-1-(6-(4-chloro-1-methyl-3-(methylsulfonamido)-1H-indazol-7-yl)-2-isopropyl-TH-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-TH-cyclopropa[3,4]cyclopenta[1,2-c]pyrazol-1-yl)acetamide (104): Compound 104 was prepared according to the method presented for the synthesis of Example 92 utilizing 92A and substituting isobutyrimidamide hydrochloride for cyclopropanecarboximidamide hydrochloride, substituting N-(4-chloro-1-methyl-7-(4,4,5,5-tetramethyl-1,3,2-dioxaborolan-2-yl)-1H-indazol-3-yl)methanesulfonamide for 64B and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetic acid to provide the desired compound. MS (m/z) 820 [M+H]+. $^1$H NMR (400 MHz, Methanol-d4) δ 7.93 (d, J=15.4 Hz, 1H), 7.14 (dd, J=35.7, 7.3 Hz, 1H), 6.87-6.43 (m, 3H), 6.43-6.29 (m, 1H), 5.30-4.97 (m, 1H), 4.71 (d, J=13.2 Hz, 2H), 3.55-3.37 (m, 1H), 3.34 (s, 1H), 3.28-3.19 (m, 6H), 3.08-2.96 (m, 1H), 2.89-2.82 (m, 1H), 2.69 (s, 1H), 2.44 (ddd, J=11.3, 9.0, 5.0 Hz, 2H), 1.60-1.52 (m, 5H), 1.38 (dq, J=14.1, 7.3 Hz, 1H), 1.11-0.89 (m, 1H).

Example 105

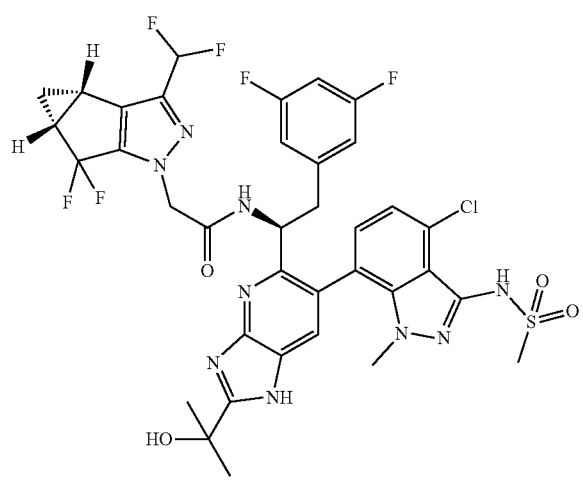 [SMILES: Cn1nc(NS(C)(=O)=O)c2c(Cl)ccc(-c3cc4sc(O)nc4nc3[C@H](Cc3cc(F)cc(F)c3)NC(=O)Cn3nc(C(F)F)c4c3C(F)(F)[C@@H]3C[C@H]43)c21]

Synthesis of N—((S)-1-(6-(4-chloro-1-methyl-3-(methylsulfonamido)-1H-indazol-7-yl)-2-(2-hydroxypropan-2-yl)-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (105): Compound 105 was prepared according to the method presented for the synthesis of Example 92 utilizing 92A and substituting 2-hydroxy-2-methylpropanimidamide hydrochloride for cyclopropanecarboximidamide hydrochloride, substituting N-(4-chloro-1-methyl-7-(4,4,5,5-tetramethyl-1,3,2-dioxaborolan-2-yl)-1H-indazol-3-yl)methanesulfonamide for 64B and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 836 [M+H]+. $^1$H NMR (400 MHz, Methanol-d4) δ 7.94 (d, J=13.7 Hz, 1H), 7.27-6.99 (m, 1H), 6.87-6.53 (m, 2H), 6.53-6.33 (m, 3H), 5.31-5.01 (m, 1H), 4.71 (d, J=13.3 Hz, 2H), 3.26 (d, J=18.6 Hz, 6H), 3.13-2.94 (m, 1H), 2.86 (s, 1H), 2.43 (ddd, J=11.2, 7.8, 4.0 Hz, 2H), 1.78 (d, J=3.2 Hz, 7H), 1.37 (p, J=7.2 Hz, 1H), 1.01 (s, 1H).

Example 106

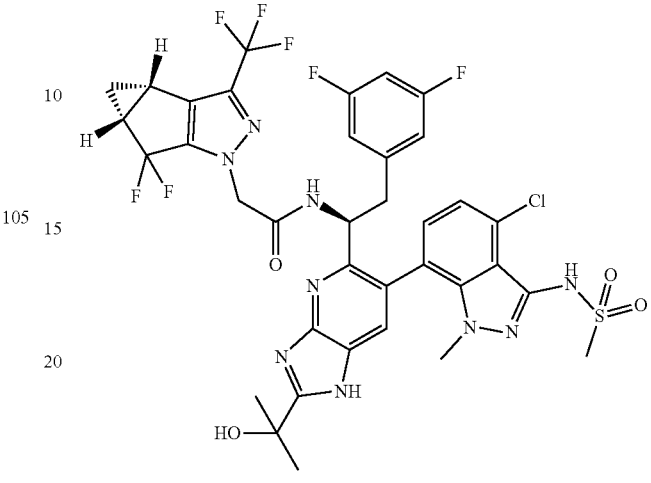

Synthesis of N—((S)-1-(6-(4-chloro-1-methyl-3-(methylsulfonamido)-1H-indazol-7-yl)-2-(2-hydroxypropan-2-yl)-1H-imidazo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (106): Compound 106 was prepared according to the method presented for the synthesis of Example 92 utilizing 92A and substituting 2-hydroxy-2-methylpropanimidamide hydrochloride for cyclopropanecarboximidamide hydrochloride, and substituting N-(4-chloro-1-methyl-7-(4,4,5,5-tetramethyl-1,3,2-dioxaborolan-2-yl)-1H-indazol-3-yl)methanesulfonamide for 64B to provide the desired compound. MS (m/z) 854 [M+H]+. $^1$H NMR (400 MHz, Methanol-d4) δ 7.96 (d, J=13.8 Hz, 1H), 7.13 (dd, J=26.7, 7.6 Hz, 1H), 6.81-6.56 (m, 1H), 6.56-6.26 (m, 3H), 5.31-5.03 (m, 1H), 4.76 (d, J=11.9 Hz, 2H), 3.52-3.32 (m, 1H), 3.25 (d, J=9.5 Hz, 4H), 3.17-2.72 (m, 2H), 2.48 (ddd, J=12.1, 7.9, 4.2 Hz, 2H), 1.78 (d, J=3.3 Hz, 6H), 1.40 (dt, J=14.4, 7.6 Hz, 1H), 1.05 (s, 1H).

Example 107

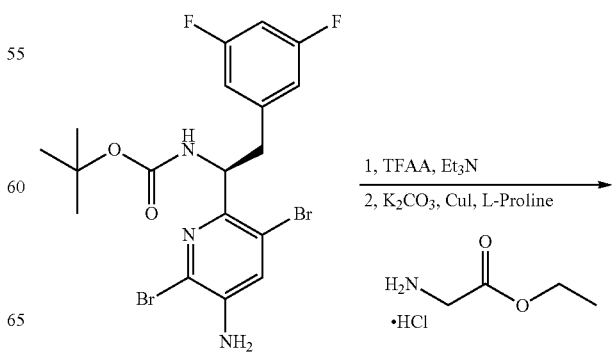

-continued

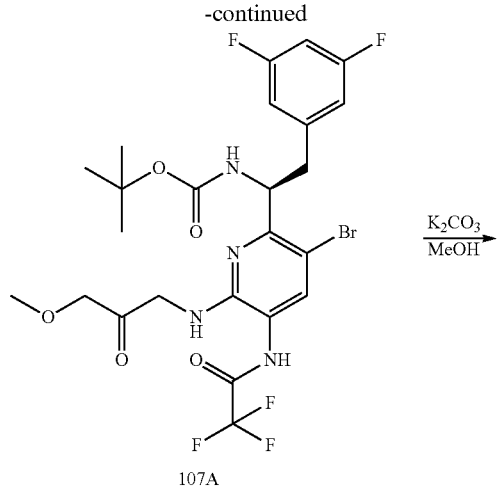

107A

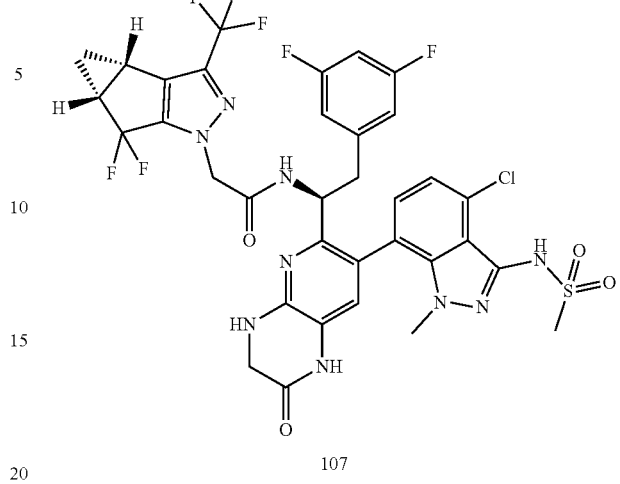

107

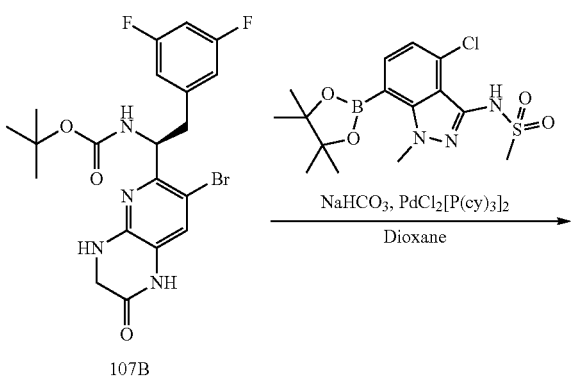

107B

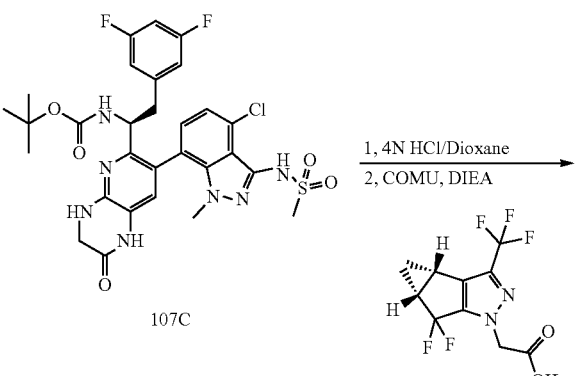

107C

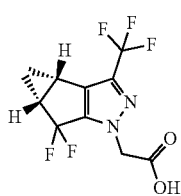

Synthesis of ethyl (S)-(5-bromo-6-(1-((tert-butoxycarbonyl)amino)-2-(3,5-difluorophenyl)ethyl)-3-(2,2,2-trifluoroacetamido)pyridin-2-yl)glycinate (107A): To a solution of 92A (1 g, 1.97 mmol) and triethylamine (0.41 mL, 2.96 mmol) in 10 mL of DCM, trifluoroacetic acid anhydride (0.334 mL, 2.37 mmol) was added. Then the solution was stirred overnight. The reaction was diluted with 50 mL of EtOAc and washed with 20 mL of saturated sodium bicarbonate and brine. The organic layer was dried and concentrated. A flask of crude product, ethylglycinate hydrochloride (338 mg, 2.42 mmol) Cuprous iodide (30.4 mg, 0.16 mmol), L-proline (36.6 mg, 0.32 mmol) and potassium carbonate (660 mg, 4.78 mmol) in 4 mL of DMSO, was degassed by $N_2$. The reaction was heated up to 120° C. for 1 hour, then cooled down, and diluted with EtOAc and washed with brine. The organic layer was concentrated and purified by flash column (20% of EtOAc/Hexane) to get compound 107A. MS (m/z) 625 [M+H]+.

Synthesis of tert-butyl (S)-(1-(7-bromo-2-oxo-1,2,3,4-tetrahydropyrido[2,3-b]pyrazin-6-yl)-2-(3,5-difluorophenyl)ethyl)carbamate (107B): A suspension of 107A (170 mg, 0.27 mmol) and potassium carbonate (376 mg, 2.72 mmol) in 2 mL of methanol and 2 mL of water was heated up to 60° C. for 20 hours. The mixture was filtered, and the filtrate was purified on preparatory reverse phase HPLC using 20-80% B over 20 min. (A=0.1% TFA/H2O; B=0.10% TFA/Acetonitrile). The pure fractions as determined by LC/MS were combined to provide compound 107B. MS (m/z) 483 [M+H]+.

Synthesis of tert-butyl (S)-(1-(7-(4-chloro-1-methyl-3-(methylsulfonamido)-1H-indazol-7-yl)-2-oxo-1,2,3,4-tetrahydropyrido[2,3-b]pyrazin-6-yl)-2-(3,5-difluorophenyl)ethyl)carbamate (107C): To a suspension of 107B (90 mg, 0.19 mmol)), N-(4-chloro-1-methyl-7-(4,4,5,5-tetramethyl-1,3,2-dioxaborolan-2-yl)-1H-indazol-3-yl)methanesulfonamide (101 mg, 0.26 mmol), 1 N of sodium bicarbonate (0.56 mL, 0.56 mmol) in 2 mL of dioxane, dichlorobis(tricyclohexylphosphine)palladium(II) (13.7 mg, 0.019 mmol) was added. The reaction was heated at 150° C. by microwave reactor for 15 minutes. The mixture was filtered and the filtrate was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide compound 107C. MS (m/z) 662 [M+H]+.

309

Synthesis of N—((S)-1-(7-(4-chloro-1-methyl-3-(methylsulfonamido)-1H-indazol-7-yl)-2-oxo-1,2,3,4-tetrahydropyrido[2,3-b]pyrazin-6-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (107): A solution of 107C (32 mg, 0.048 mmol) in 4 N of hydrochloride in dioxane (1.5 mL) was stirred for 1 hour. The solvent was removed and dried in vacuo. The crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (13.6 mg, 0.048 mmol) and (1-Cyano-2-ethoxy-2-oxoethylidenaminooxy)dimethylamino-morpholino-carbenium hexafluorophosphate (20.7 mg, 0.048 mmol) were dissolved in DMF (1 mL) and diisopropylethylamine (0.017 mL, 0.097 mmol) was added to the solution. The reaction was stirred at room temperature for 30 mins. The reaction mixture was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide the desired compound. MS (m/z) 826 [M+H]+. $^1$H NMR (400 MHz, Methanol-d4) δ 7.16-7.01 (m, 1H), 6.94 (dd, J=14.3, 8.5 Hz, 1H), 6.85-6.70 (m, 1H), 6.67-6.33 (m, 3H), 6.15 (d, J=7.6 Hz, 1H), 4.81-4.65 (m, 2H), 4.32-3.98 (m, 2H), 3.56-3.35 (m, 2H), 3.28-3.07 (m, 4H), 3.04 (s, 1H), 3.00-2.84 (m, 2H), 2.63-2.36 (m, 2H), 1.41 (dt, J=14.3, 8.1 Hz, 1H), 1.10 (d, J=29.5 Hz, 1H).

310

Synthesis of N—((S)-1-(7-(4-chloro-1-methyl-3-(methylsulfonamido)-1H-indazol-7-yl)-2-oxo-1,2,3,4-tetrahydropyrido[2,3-b]pyrazin-6-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (108): Compound 108 was prepared according to the method presented for the synthesis of Example 107 utilizing 92A and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z) 808 [M+H]+. $^1$H NMR (400 MHz, Methanol-d4) δ 7.13-6.89 (m, 1H), 6.87-6.52 (m, 3H), 6.42 (d, J=6.7 Hz, 2H), 6.18 (d, J=7.6 Hz, 1H), 4.79-4.61 (m, 3H), 4.34-4.12 (m, 2H), 3.45 (s, 2H), 3.24 (d, J=8.3 Hz, 3H), 3.17-3.00 (m, 2H), 3.01-2.77 (m, 1H), 2.47 (d, J=16.4 Hz, 2H), 1.39 (dq, J=14.1, 7.2 Hz, 1H), 1.06 (d, J=27.8 Hz, 1H).

Example 108

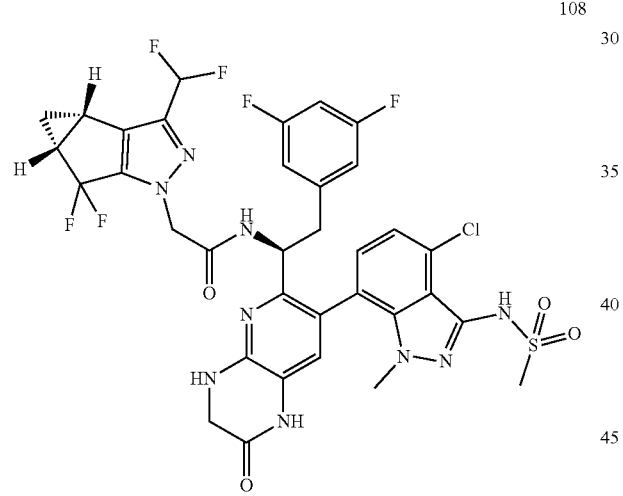

108

Example 109

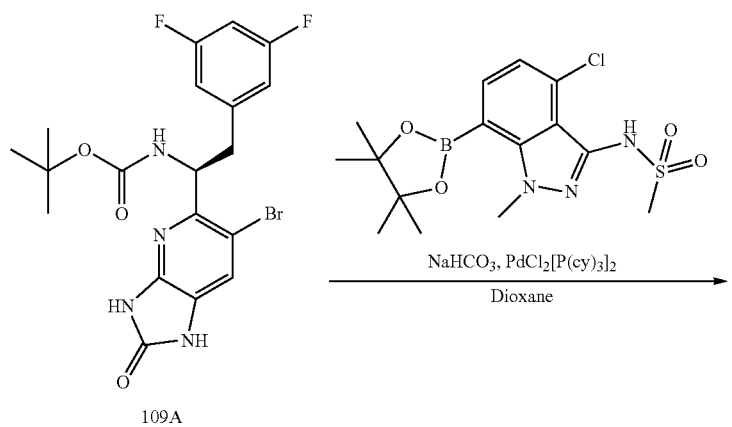

109A

-continued

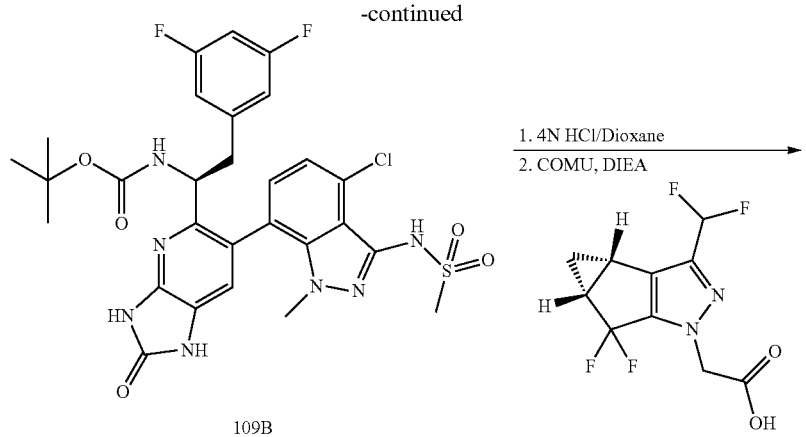

109B

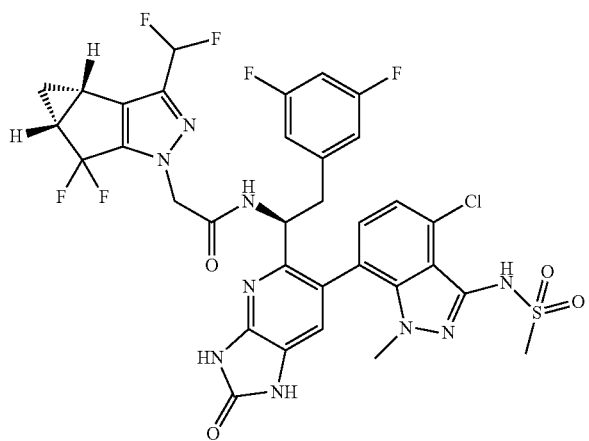

109

Synthesis tert-butyl (S)-(1-(6-(4-chloro-1-methyl-3-(methylsulfonamido)-1H-indazol-7-yl)-2-oxo-2,3-dihydro-1H-imidazo[4,5-b]pyridin-5-yl)-2-(3,5-difluorophenyl)ethyl)carbamate (109B): To a suspension of 109A (32 mg, 0.07 mmol)), N-(4-chloro-1-methyl-7-(4,4,5,5-tetramethyl-1,3,2-dioxaborolan-2-yl)-1H-indazol-3-yl)methanesulfonamide (36.8 mg, 0.1 mmol), 1 N of sodium bicarbonate (0.2 mL, 0.2 mmol) in 1 mL of dioxane, dichlorobis(tricyclohexylphosphine)palladium(II) (5.1 mg, 0.007 mmol) was added. The reaction was heated at 150° C. by microwave reactor for 15 minutes. The mixture was filtered, and the filtrate was purified on preparatory reverse phase HPLC using 20-80% B over 20 min (A=0.1% TFA/H2O; B=0.1% TFA/Acetonitrile). The pure fractions as determined by LC/MS were combined and lyophilized to provide compound 109B. MS (m/z) 648 [M+H]+.

Synthesis of N—((S)-1-(6-(4-chloro-1-methyl-3-(methylsulfonamido)-1H-indazol-7-yl)-2-oxo-2,3-dihydro-1H-imidazo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (109): A solution of 109B (20 mg, 0.031 mmol) in 4 N of hydrochloride in dioxane (1.0 mL) was stirred for 1 hour. The solvent was removed and dried in vacuo. The crude product, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (8.71 mg, 0.031 mmol) and (1-Cyano-2-ethoxy-2-oxoethylidenaminooxy)dimethylamino-morpholino-carbenium hexafluorophosphate (13.2 mg, 0.031 mmol) was dissolved in DMF (1 mL) and diisopropylethylamine (0.011 mL, 0.062 mmol) was added to the solution. The reaction was stirred at room temperature for 30 mins. The reaction mixture was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide the desired compound. MS (m/z) 794 [M+H]+. $^1$H NMR (400 MHz, Methanol-d4) δ 7.14 (s, 1H), 7.01 (d, J=7.6 Hz, 1H), 6.85-6.49 (m, 2H), 6.39 (d, J=7.2 Hz, 2H), 6.29 (d, J=7.5 Hz, 1H), 4.91-4.87 (m, 1H), 4.70 (d, J=3.0 Hz, 2H), 3.35 (s, 3H), 3.23 (s, 3H), 3.05-2.80 (m, 1H), 2.43 (d, J=11.4 Hz, 2H), 1.48-1.26 (m, 2H), 0.94 (d, J=54.7 Hz, 1H).

Example 110

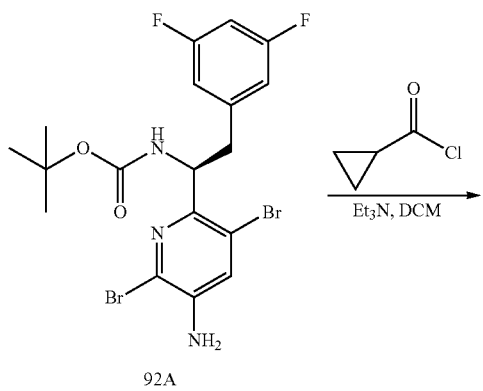

92A

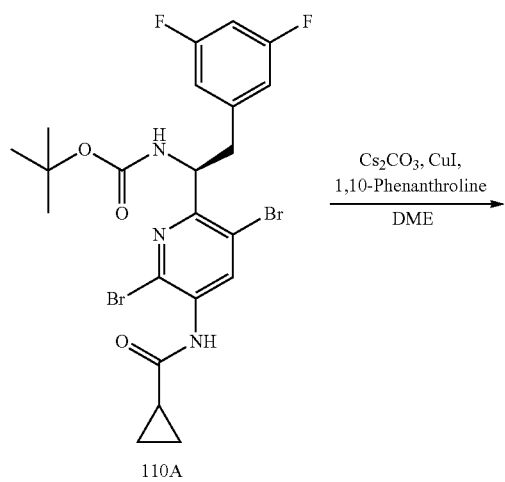

110A

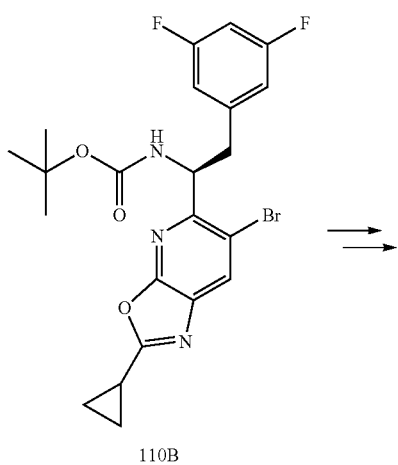

110B

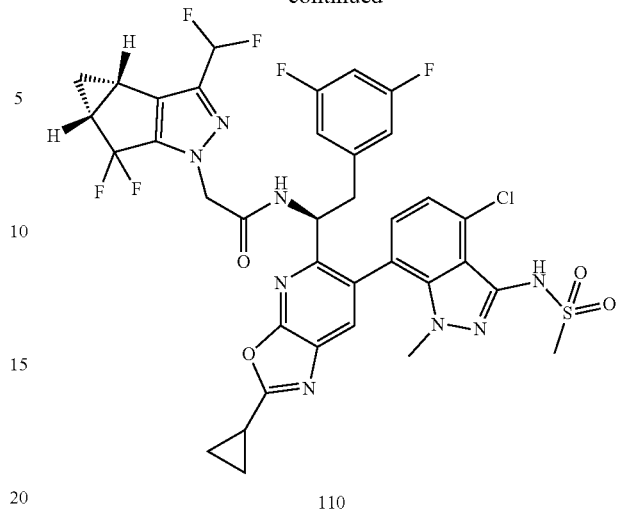

110

Synthesis tert-butyl (S)-(1-(3,6-dibromo-5-(cyclopropanecarboxamido)pyridin-2-yl)-2-(3,5-difluorophenyl)ethyl)carbamate (110A): To a solution of 92A (240 mg, 0.473 mmol) and triethylamine (0.079 mL, 0.568 mmol) in 5 mL of DCM, cyclopropanecarbonyl chloride (0.045 mL, 0.5 mmol) was added slowly. The mixture was filtered and the filtrate was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide compound 110A. MS (m/z) 574 [M+H]+.

Synthesis of tert-butyl (S)-(1-(6-bromo-2-cyclopropyloxazolo[5,4-b]pyridin-5-yl)-2-(3,5-difluorophenyl)ethyl)carbamate (110B): A solution of 110A (180 mg, 0.313 mmol), cesium carbonate (204 mg, 0.626 mmol), cuprous iodide (6 mg, 0.0313 mmol), and 1,10-phenanthroline (11.3 mg, 0.0626 mmol) in 2 mL of DME was heated to reflux overnight. The reaction was filtered and the filtrate was concentrated. The mixture was dissolved in 1 mL of DMF. The reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide compound 110B. MS (m/z) 494 [M+H]+.

Synthesis of N—((S)-1-(6-(4-chloro-1-methyl-3-(methylsulfonamido)-1H-indazol-7-yl)-2-cyclopropyloxazolo[5,4-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (110): Compound 110 was prepared according to the method presented for the synthesis of Example 109 substituting 110B for 109A to provide desired compound. MS (m/z) 819 [M+H]+. $^1$H NMR (400 MHz, Methanol-d4) δ 7.89 (d, J=15.7 Hz, 1H), 7.08 (d, J=7.5 Hz, 1H), 6.92-6.52 (m, 2H), 6.48 (d, J=7.5 Hz, 1H), 6.43-6.30 (m, 2H), 5.29-4.92 (m, 1H), 4.76-4.56 (m, 2H), 3.29-3.11 (m, 8H), 3.09-2.77 (m, 2H), 2.56-2.17 (m, 3H), 1.23 (t, J=7.1 Hz, 2H), 1.10-0.95 (m, 1H), 0.89 (d, J=6.7 Hz, 1H).

Example 111

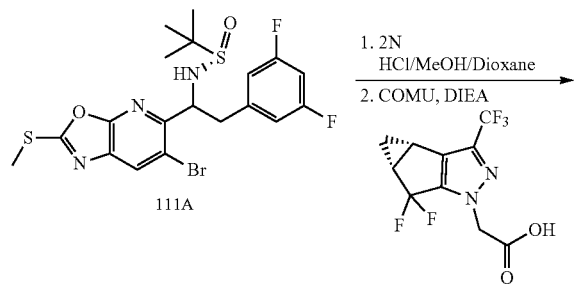

111A

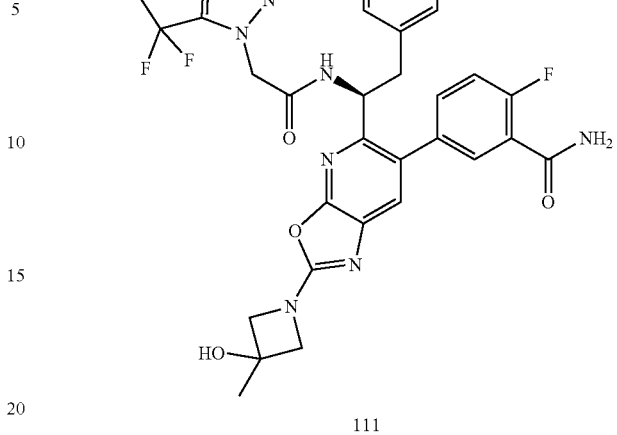

111

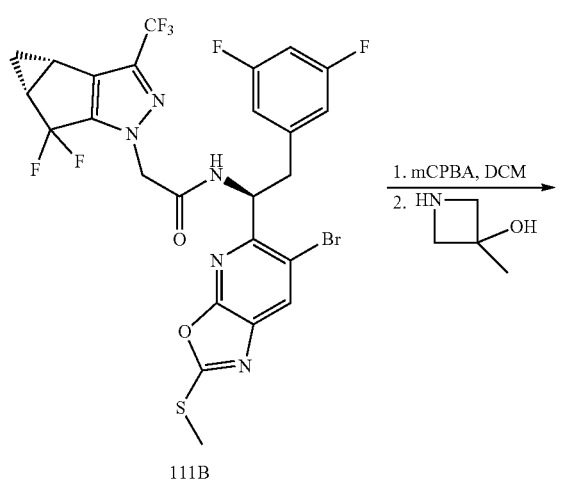

111B

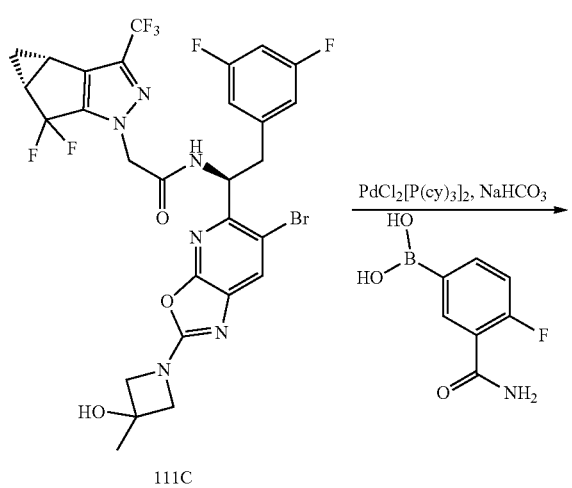

111C

Synthesis of N—((S)-1-(6-bromo-2-(methylthio)oxazolo[5,4-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (111B): A solution of 111A (50 mg, 0.1 mmol) in 1 mL of 4 N of hydrochloride in dioxane and 1 mL of methanol was stirred for 1 hour. The solvent was removed and dried in vacuo. The crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (25.8 mg, 0.092 mmol) and (1-Cyano-2-ethoxy-2-oxoethylidenaminooxy)dimethylamino-morpholino-carbenium hexafluorophosphate (39.2 mg, 0.092 mmol) was dissolved in DMF (1 mL) and diisopropylethylamine (0.032 mL, 0.18 mmol) was added to the solution. The reaction was stirred at room temperature for 30 min. The mixture was dissolved in 10 mL of EtOAc, and washed with 5 mL of saturated sodium bicarbonate (aq) and 5 mL of brine. The organic layer was dried with sodium sulfate. The mixture was filtered and the filtrate was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide compound 111B. MS (m/z) 664 [M+H]+.

Synthesis of N—((S)-1-(6-bromo-2-(3-hydroxy-3-methylazetidin-1-yl)oxazolo[5,4-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (111C): To a solution of 111B (10 mg, 0.015 mmol) in DCM (1 mL), 3-Chloroperoxybenzoic acid (77% purity, 6.75 mg, 0.03 mmol) was added. The reaction was stirred for 1 hour. 3-methylazetidin-3-ol (18.6 mg, 0.15 mmol) and N,N-Diisopropylethylamine (0.08 mL, 0.45 mmol) were added to the mixture. After 2 hours, the reaction was diluted with EtOAc (10 mL) and washed with 5 mL of saturated sodium bicarbonate (aq). The organic layer was separated and was concentrated to dryness in vacuo. The reaction mixture was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide compound 111C. MS (m/z) 703 [M+H]+.

Synthesis of 5-(5-((S)-1-(2-((3bS,4aR)-5,5-difluoro-3-(trifluoromethyl)-3b,4,4a,5-tetrahydro-1H-cyclopropa[3,4]

cyclopenta[1,2-c]pyrazol-1-yl)acetamido)-2-(3,5-difluorophenyl)ethyl)-2-(3-hydroxy-3-methylazetidin-1-yl)oxazolo[5,4-b]pyridin-6-yl)-2-fluorobenzamide (111): To a suspension of 111C (10 mg, 0.014 mmol)), (3-carbamoyl-4-fluorophenyl)boronic acid (3.9 mg, 0.021 mmol), 1 N of sodium bicarbonate (0.043 mL) in 1 mL of dioxane, dichlorobis(tricyclohexylphosphine)palladium(II) (1.1 mg, 0.0014 mmol) was added. The reaction was heated at 130° C. by microwave reactor for 10 minutes. The mixture was filtered and the filtrate was concentrated to dryness. The mixture was dissolved in 1 mL of DMF and the reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide the desired compound. MS (m/z) 762 [M+H]+. $^1$H NMR (400 MHz, Methanol-d4) δ 7.35-7.25 (m, 2H), 7.25-7.15 (m, 2H), 6.64 (d, J=9.8 Hz, 1H), 6.33 (d, J=7.6 Hz, 2H), 5.24 (d, J=6.4 Hz, 1H), 4.21 (d, J=5.1 Hz, 5H), 3.16-2.94 (m, 2H), 2.48 (d, J=8.5 Hz, 2H), 1.57 (s, 4H), 1.39 (d, J=7.3 Hz, 1H), 1.10 (s, 1H).

Example 112

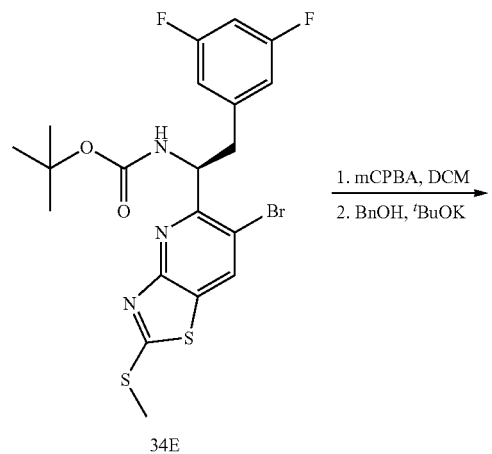

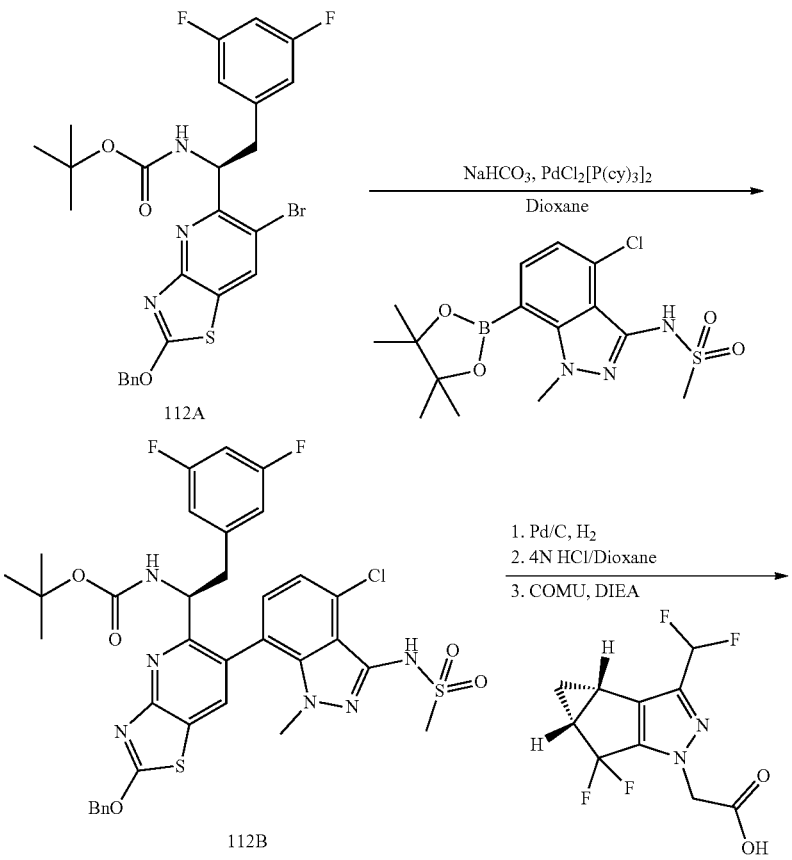

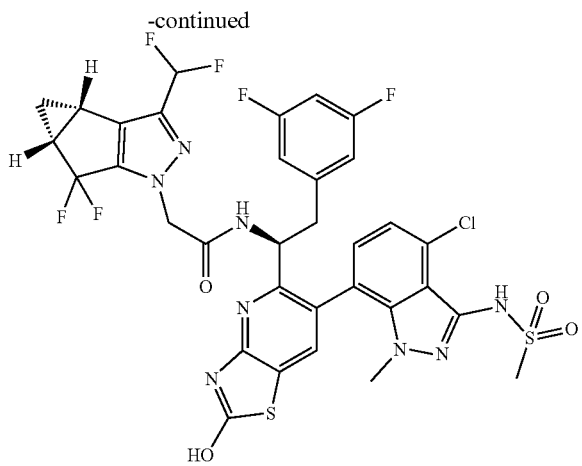

112

Synthesis of tert-butyl (S)-(1-(2-(benzyloxy)-6-bromothiazolo[4,5-b]pyridin-5-yl)-2-(3,5-difluorophenyl)ethyl)carbamate (112A): To a solution of 34E (200 mg, 0.39 mmol) in DCM (3 mL), 3-Chloroperoxybenzoic acid (77% purity, 174 mg, 0.76 mmol) was added. The reaction was stirred for 1 hour. Sodium t-butoxide (112 mg, 1.16 mmol) and phenylmethanol (419 mg, 3.88 mmol) were added to the mixture. After 2 hours, the reaction was diluted with EtOAc (20 mL) and washed with 5 mL of saturated sodium bicarbonate (aq). The organic layer was separated and was concentrated to dryness in vacuo. The reaction mixture was purified on preparatory reverse phase HPLC using 20-80% B over 20 min. (A=0.1% TFA/H2O; B=0.10% TFA/Acetonitrile). The pure fractions as determined by LC/MS were combined and lyophilized to provide compound 112A. MS (m/z) 576 [M+H]+.

Synthesis of tert-butyl (S)-(1-(2-(benzyloxy)-6-(4-chloro-1-methyl-3-(methylsulfonamido)-1H-indazol-7-yl)thiazolo[4,5-b]pyridin-5-yl)-2-(3,5-difluorophenyl)ethyl)carbamate (112B): To a suspension of 112A (50 mg, 0.087 mmol)), N-(4-chloro-1-methyl-7-(4,4,5,5-tetramethyl-1,3,2-dioxaborolan-2-yl)-1H-indazol-3-yl)methanesulfonamide (40.1 mg, 0.1 mmol), 1 N of sodium bicarbonate (0.26 mL) in 1 mL of dioxane, dichlorobis(tricyclohexylphosphine)palladium(II) (9.6 mg, 0.013 mmol) was added. The reaction was heated at 150° C. by microwave reactor for 20 minutes. The mixture was filtered, and the filtrate was concentrated to dryness. The mixture was dissolved in 1 mL of DMF and the reaction mixture was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide compound 112B. MS (m/z) 755 [M+H]+.

Synthesis of N—((S)-1-(6-(4-chloro-1-methyl-3-(methylsulfonamido)-1H-indazol-7-yl)-2-hydroxythiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (112): To a solution of 112B (17 mg, 0.026 mmol) in 2 mL of EtOH, 10 mg of 10% Palladium on carbon was added. Hydrogen balloon was charged to the reaction for 1 hour. The mixture was filtered, and the filtrate was concentrated. The crude product was placed in a flask, 1 mL of 4 N of hydrochloride in dioxane was added, and the reaction was stirred for 1 hour. The solvent was removed and dried in vacuo. The crude product, 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (6.75 mg, 0.026 mmol) and (1-Cyano-2-ethoxy-2-oxoethylidenaminooxy)dimethylamino-morpholino-carbenium hexafluorophosphate (11 mg, 0.026 mmol) were dissolved in DMF (1 mL) and diisopropylethylamine (0.01 mL, 0.05 mmol) was added. The reaction was stirred at room temperature for 30 min. The mixture was filtered, and the filtrate was purified on preparatory reverse phase HPLC using 20-80% B over 20 min. (A=0.10% TFA/H2O; B=0.10% TFA/Acetonitrile). The pure fractions as determined by LC/MS were combined and lyophilized to provide the desired product. MS (m/z) 811 [M+H]+. $^1$H NMR (400 MHz, Methanol-d4) δ 7.81 (d, J=13.7 Hz, 1H), 7.19-6.96 (m, 1H), 6.90-6.52 (m, 2H), 6.43 (ddd, J=19.9, 17.4, 7.5 Hz, 3H), 5.20-4.88 (m, 1H), 4.72 (dd, J=23.4, 2.2 Hz, 2H), 3.39 (s, 2H), 3.26-3.10 (m, 3H), 3.10-2.87 (m, 2H), 2.46 (d, J=15.0 Hz, 2H), 1.44-1.17 (m, 2H), 1.04 (d, J=37.7 Hz, 1H).

Example 113

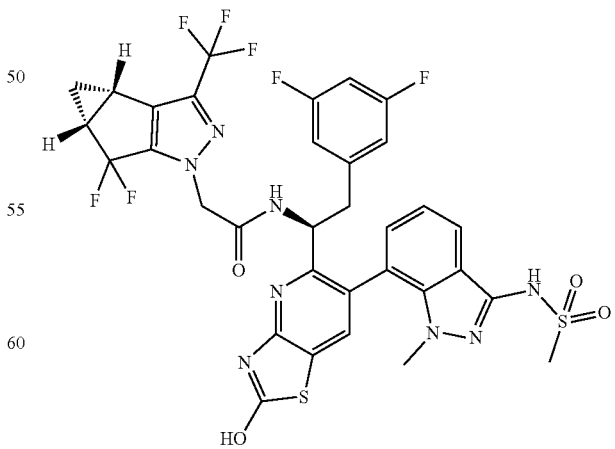

113

Synthesis of 2-((3bS,4aR)-5,5-difluoro-3-(trifluoromethyl)-3b,4,4a,5-tetrahydro-1H-cyclopropa[3,4]cyclopenta

[1,2-c]pyrazol-1-yl)-N—((S)-2-(3,5-difluorophenyl)-1-(2-hydroxy-6-(1-methyl-3-(methylsulfonamido)-1H-indazol-7-yl)thiazolo[4,5-b]pyridin-5-yl)ethyl)acetamide (113): Compound 113 was prepared according to the method presented for the synthesis of Example 112, substituting 64B for N-(4-chloro-1-methyl-7-(4,4,5,5-tetramethyl-1,3,2-dioxaborolan-2-yl)-1H-indazol-3-yl)methanesulfonamide, and substituting 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid for 2-((3bS,4aR)-3-(difluoromethyl)-5,5-difluoro-3b,4,4a,5-tetrahydro-1H-cyclopropa[3,4] cyclopenta[1,2-c]pyrazol-1-yl)acetic acid to provide the desired compound. MS (m/z) 795 [M+H]+. $^1$H NMR (400 MHz, Methanol-d4) δ 7.88-7.63 (m, 2H), 7.11 (ddd, J=32.8, 8.1, 7.0 Hz, 1H), 6.69 (dtt, J=40.7, 9.2, 2.4 Hz, 1H), 6.55-6.25 (m, 3H), 5.20-4.90 (m, 1H), 4.78 (dd, J=19.0, 2.1 Hz, 2H), 3.38 (s, 2H), 3.23-2.82 (m, 6H), 2.64-2.33 (m, 2H), 1.51-1.30 (m, 1H), 1.16-0.98 (m, 1H).

Example 114

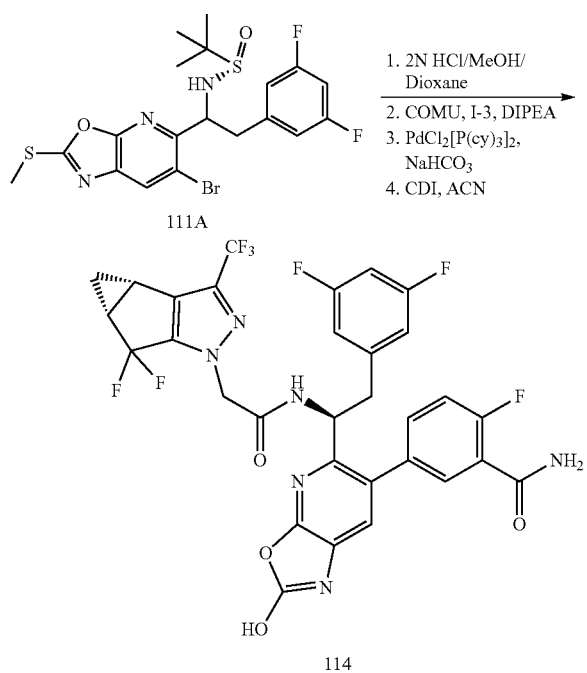

114

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-hydroxyoxazolo[5,4-b]pyridin-6-yl)-2-fluorobenzamide (114): A solution of 111A (50 mg, 0.1 mmol) in 1 mL of 4 N of hydrochloride in dioxane and 1 mL of methanol was stirred for 3 hours. The solvent was removed and dried in vacuo. The crude product, 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (25.8 mg, 0.092 mmol), and (1-Cyano-2-ethoxy-2-oxoethylidenaminooxy) dimethylamino-morpholino-carbenium hexafluorophosphate (39.2 mg, 0.092 mmol) were dissolved in DMF (1 mL) and diisopropylethylamine (0.032 mL, 0.18 mmol) was added. The reaction was stirred at room temperature for 1 hour. The mixture was dissolved in 10 mL of EtOAc, and washed with 5 mL of saturated sodium bicarbonate (aq) and 5 mL of brine. The organic layer was dried with sodium sulfate. The mixture was filtered, and the filtrate was dried and concentrated. The crude product was dissolved in 1 mL of dioxane, (3-carbamoyl-4-fluorophenyl) boronic acid (8.65 mg, 0.047 mmol), 1 N of sodium bicarbonate (0.047 mL), and dichlorobis(tricyclohexylphosphine)palladium(II) (1.16 mg, 0.002 mmol) were added to the mixture. The reaction was heated at 140° C. by microwave reactor for 15 minutes. The mixture was filtered, and the filtrate was concentrated to dryness. The mixture was dissolved in 1 mL of acetonitrile and 1,1'-carbonyldiimidazole (9.73 mg, 0.06 mmol) was added to the solution, which was stirred for 1 hour. The mixture was filtered, and the reaction mixture was purified on preparatory reverse phase HPLC using 20-80% B over 20 min. (A=0.1% TFA/H2O; B=0.1% TFA/Acetonitrile). The pure fractions as determined by LC/MS were combined and lyophilized to provide the desired compound. MS (m/z) 693 [M+H]+. $^1$H NMR (400 MHz, Methanol-d4) δ 8.88 (d, J=8.1 Hz, 1H), 7.34 (s, 1H), 7.22-7.10 (m, 2H), 6.65 (t, J=9.3 Hz, 1H), 6.37 (d, J=6.8 Hz, 2H), 5.37-5.20 (m, 1H), 4.98-4.88 (m, 1H), 3.24 (p, J=1.7 Hz, 1H), 3.15-2.96 (m, 2H), 2.47 (dd, J=8.1, 4.0 Hz, 1H), 1.39 (d, J=6.8 Hz, 1H), 1.10 (s, 1H).

Example 115

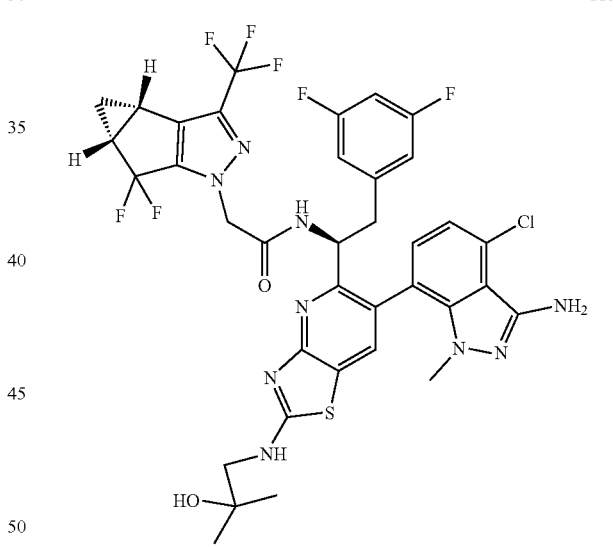

115

Synthesis of N—((S)-1-(6-(3-amino-4-chloro-1-methyl-1H-indazol-7-yl)-2-((2-hydroxy-2-methylpropyl)amino)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (115): Compound 115 was prepared according to the method presented for the synthesis of Example 34 utilizing 34E and substituting 1-amino-2-methylpropan-2-ol for 34D, and substituting 4-chloro-1-methyl-7-(4,4,5,5-tetramethyl-1,3,2-dioxaborolan-2-yl)-1H-indazol-3-amine for 34G to provide desired compound. MS (m/z) 822 [M+H]+. $^1$H NMR (400 MHz, Methanol-d$_4$) δ 7.86 (s, 1H), 6.92 (d, 1H), 6.74 (t, 1H), 6.42-6.27 (m, 3H), 4.92-4.71 (m, 3H), 3.69-3.50 (m, 2H), 3.20 (s, 4H), 3.00 (dt, 1H), 2.56-2.35 (m, 2H), 1.40 (d, 1H), 1.32 (d, 7H), 1.09 (d, 1H).

Example 116

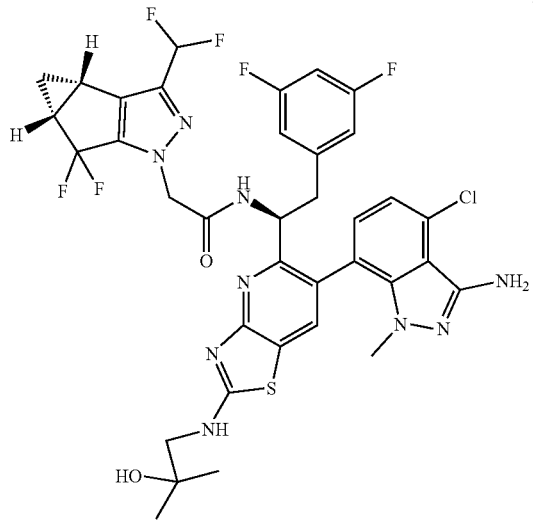

Synthesis of N—((S)-1-(6-(3-amino-4-chloro-1-methyl-1H-indazol-7-yl)-2-((2-hydroxy-2-methylpropyl)amino)thiazolo[4,5-b]pyridin-5-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (116): Compound 116 was prepared according to the method presented for the synthesis of Example 34 utilizing 34E and substituting 1-amino-2-methylpropan-2-ol for 34D, substituting 4-chloro-1-methyl-7-(4,4,5,5-tetramethyl-1,3,2-dioxaborolan-2-yl)-1H-indazol-3-amine for 34G and substituting 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid for 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetic acid to provide desired compound. MS (m/z) 804 [M+H]+. $^1$H NMR (400 MHz, Methanol-$d_4$) δ 7.86 (s, 1H), 7.11-6.98 (m, 1H), 6.92 (d, 1H), 6.79-6.68 (m, 1H), 6.38 (d, 2H), 6.34 (d, 1H), 4.96 (t, 1H), 4.78-4.72 (m, 3H), 3.68-3.56 (m, 3H), 3.19 (s, 3H), 3.17-3.11 (m, 1H), 2.99 (dt, 2H), 2.81 (s, 1H), 2.54-2.40 (m, 2H), 1.32 (d, 6H), 1.07 (d, 1H).

Example 117

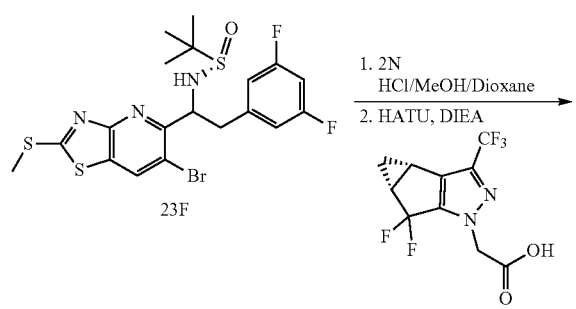

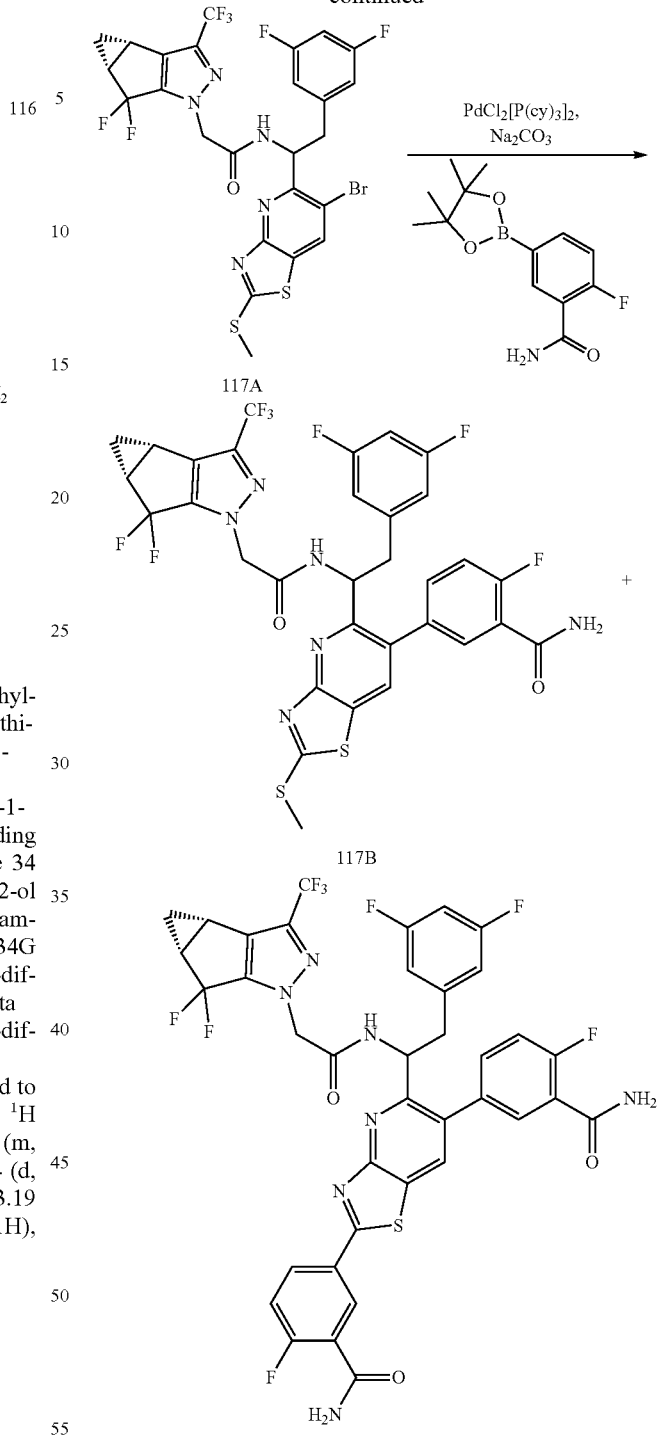

Synthesis of N-(1-(6-bromo-2-(methylthio)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (117A): Compound 117A was prepared in a manner similar to Example 23 using 23F, and using 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid instead of 2-((3bS,4aR)-3-(difluoromethyl)-5,5-difluoro-3b, 4,4a,5-tetrahydro-1H-cyclopropa[3,4]cyclopenta[1,2-c]pyrazol-1-yl)acetic acid to provide compound 117A. MS (m/z): 680.83 [M+H]⁺.

Synthesis of 5,5'-(5-(1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)thiazolo[4,5-b]pyridine-2,6-diyl)bis(2-fluorobenzamide) (117): A microwave tube was charged with N-(1-(6-bromo-2-(methylthio)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (117A, 50 mg, 0.73 mmol), (3-carbamoyl-4-fluorophenyl)boronic acid (20 mg, 0.11 mmol) and PdCl$_2$[P(cy)$_3$]$_2$ (3 mg, 0.004 mmol). To the mixture was added 1.4 mL of 1,4-dioxane and 0.2 mL of sodium bicarbonate aqueous solution (1M). The system was purged with argon and then the microwave tube was sealed and the reaction mixture was heated up to boiling (140° C. bath) for 40 min. After being cooled down, the reaction was partitioned between EtOAc and water. The organic layer was separated and washed with brine, then dried over MgSO$_4$, filtered and concentrated. The residue was purified by reverse phase HPLC eluting with acetonitrile and water (with 0.1% TFA) to afford compound 117B and Compound 117. Compound 117B: (MS (m/z) 738.96 [M+H]⁺). Compound 117: MS (m/z) 829.89 [M+H]⁺. ¹H NMR (400 MHz, Methanol-d$_4$) δ 8.63 (m, 1H), 8.39 (m, 1H), 8.30 (s, 1H), 7.48 (m, 3H), 7.36-7.16 (m, 1H), 6.65 (m, 1H), 6.38 (m, 2H), 5.49 (m, 1H), 4.88 (s, 2H), 3.14 (m, 2H), 2.46 (m, 2H), 1.39 (m, 1H), 1.11 (m, 1H).

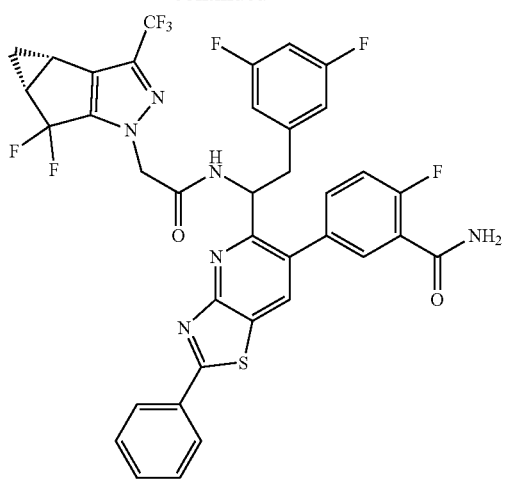

118

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-phenylthiazolo[4,5-b]pyridin-6-yl)-2-fluorobenzamide (118): Compound 118 was prepared in a manner similar to Example 117 using 117B and using phenyl boronic acid instead of (3-carbamoyl-4-fluorophenyl)boronic acid to provide the desired compound. MS (m/z) 768.87 [M+H]⁺. ¹H NMR (400 MHz, Methanol-d$_4$) δ 8.97 (d, J=8.1 Hz, 1H), 8.28 (s, 1H), 8.21 (dd, J=7.9, 1.6 Hz, 2H), 7.62 (m, 3H), 7.44 (m, 2H), 7.25 (m, 1H), 6.65 (m, 1H), 6.38 (m, 2H), 5.48 (m, 1H), 4.86 (s, 2H), 3.23-3.08 (m, 2H), 2.46 (m, 2H), 1.38 (m, 1H), 1.11 (m, 1H).

Example 119

Example 118

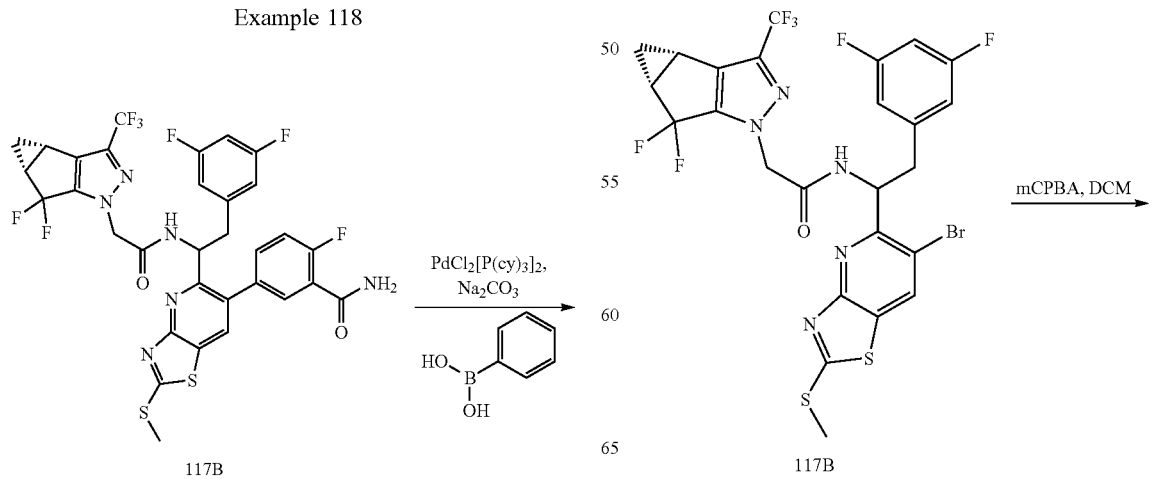

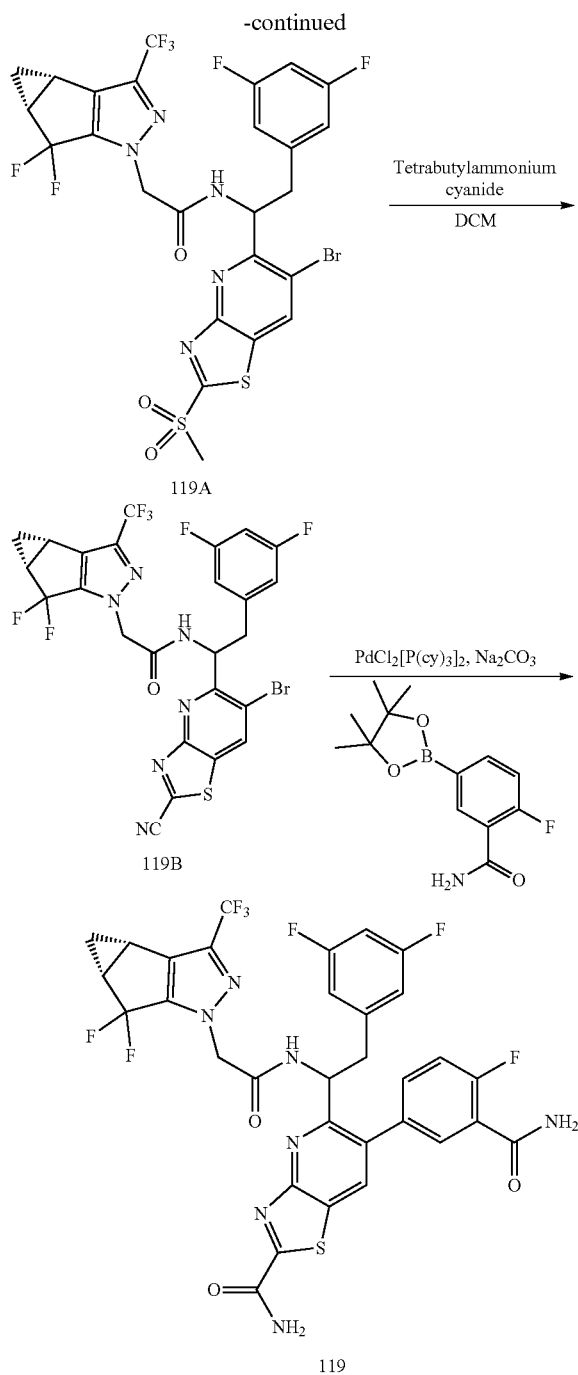

119A

119B

119 ous solution and brine. The organic layer was separated and was concentrated to dryness in vacuo to afford compound 119A. MS (m/z): 713.73 [M+H]+.

Synthesis of N-(1-(6-bromo-2-cyanothiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (119B): To a solution of N-(1-(6-bromo-2-(methylsulfonyl)thiazolo[4,5-b]pyridin-5-yl)-2-(3,5-difluorophenyl)ethyl)-2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)
acetamide (119A, 105 mg, 0.147 mmol) in anhydrous methylene chloride (0.5 mL) was added tetrabutylammonium cyanide (39 mg, 0.147 mmol). The mixture was stirred at room temperature for 1 hour and then diluted with methylene chloride and washed with water. The organic layer was separated, dried over MgSO4, and concentrated to dryness. The residue was purified by silica gel chromatography eluting with EtOAc and hexane to afford compound 119B. MS (m/z): 660.80 [M+H]+.

Synthesis of 6-(3-carbamoyl-4-fluorophenyl)-5-(1-(2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetamido)-2-(3,5-difluorophenyl)ethyl)thiazolo[4,5-b]pyridine-2-carboxamide (119): A microwave tube was charged with N-(1-(6-bromo-2-cyanothiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetamide (119B, 50 mg, 0.076 mmol), (3-carbamoyl-4-fluorophenyl)boronic acid (21 mg, 0.11 mmol) and PdCl2[P(cy)3]2 (3 mg, 0.004 mmol). To the mixture was added 1.4 mL of 1,4-dioxane and 0.2 mL of sodium bicarbonate aqueous solution (1M). The system was purged with argon and then the microwave tube was sealed; and the reaction mixture was heated up at 150° C. in microwave for 15 min. After cooled to room temperature, the reaction was partitioned between EtOAc and water. The organic layer was separated and washed with brine, then dried over MgSO4, filtered and concentrated. The residue was purified by reverse phase HPLC eluting with acetonitrile and water (with 0.1% TFA) to afford Compound 119. MS (m/z) 735.88 [M+H]+. 1H NMR (400 MHz, Methanol-d4) δ 8.98 (d, J=7.9 Hz, 1H), 8.38 (s, 1H), 7.46 (m, 2H), 7.25 (m, 1H), 6.65 (m, 1H), 6.37 (m, 2H), 5.48 (m, 1H), 4.85 (s, 2H), 3.23-3.09 (m, 2H), 2.46 (m, 2H), 1.38 (m, 1H), 1.09 (m, 1H).

Example 120

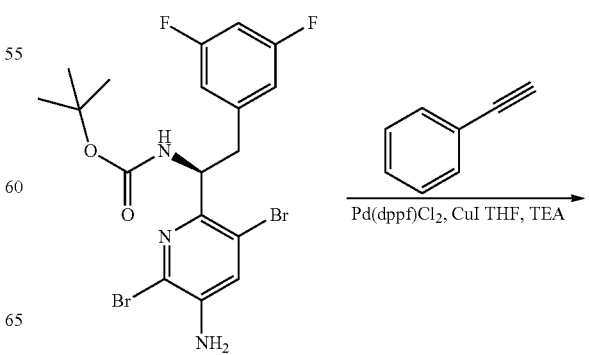

Synthesis of N-(1-(6-bromo-2-(methylsulfonyl)thiazolo[4,5-b]pyridin-5-yl)-2-(3,5-difluorophenyl)ethyl)-2-((3bS, 4aR)-5,5-difluoro-3-(trifluoromethyl)-3b,4,4a,5-tetrahydro-1H-cyclopropa[3,4]cyclopenta[1,2-c]pyrazol-1-yl)
acetamide (119A): To a stirred solution of N-(1-(6-bromo-2-(methylthio)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (117B, 100 mg, 0.147 mmol) in 3 mL of dichloromethane at 0° C. was added meta-chloroperoxybenzoic acid (82 mg, 0.367 mmol). The reaction mixture was allowed to warm to room temperature and was stirred overnight. The mixture was diluted with dichloromethane and washed with saturated NaHCO3 aqueous

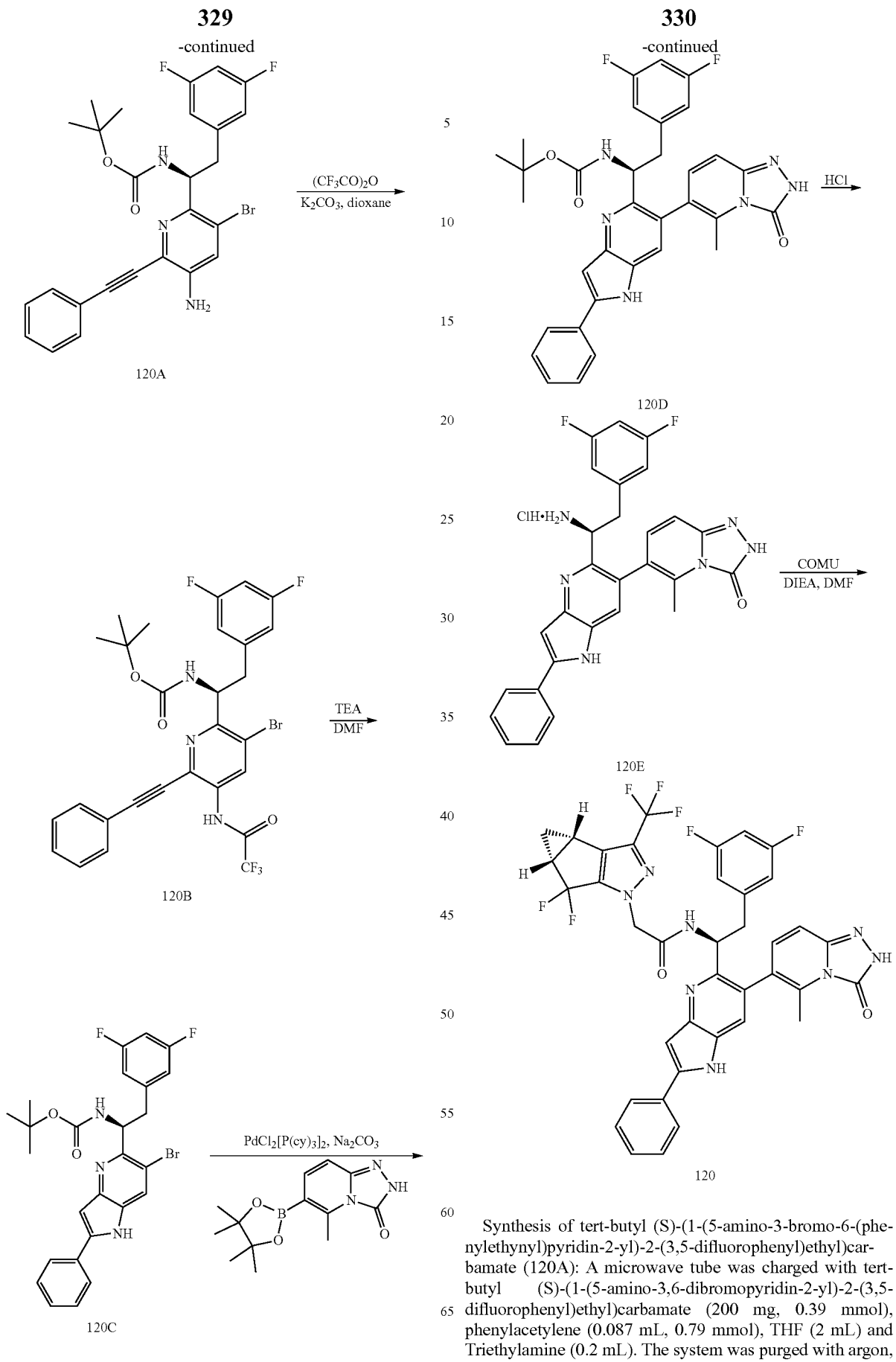
Synthesis of tert-butyl (S)-(1-(5-amino-3-bromo-6-(phenylethynyl)pyridin-2-yl)-2-(3,5-difluorophenyl)ethyl)carbamate (120A): A microwave tube was charged with tert-butyl (S)-(1-(5-amino-3,6-dibromopyridin-2-yl)-2-(3,5-difluorophenyl)ethyl)carbamate (200 mg, 0.39 mmol), phenylacetylene (0.087 mL, 0.79 mmol), THF (2 mL) and Triethylamine (0.2 mL). The system was purged with argon, and then charged with [1,1'-Bis(diphenylphosphino)ferrocene]dichloropalladium(II), complex with dichloromethane (32 mg, 0.039 mmol) and Copper(I) iodide (15 mg, 0.079 mmol). The system was purged with argon again, and the microwave tube was sealed, and the reaction mixture was heated up to 70° C. for 1 hour. After being cooled down, the reaction was diluted with EtOAc, and washed with 50 mL of H$_2$O (with 1 mL of 28% ammonium hydroxide solution) and brine. The organic layer was dried over MgSO$_4$, filtered, concentrated, and purified by silica gel chromatography eluting with EtOAc/hexane to afford compound 120A. MS (m/z) 527.95 [M+H]$^+$.

Synthesis of tert-butyl (S)-(1-(3-bromo-6-(phenylethynyl)-5-(2,2,2-trifluoroacetamido)pyridin-2-yl)-2-(3,5-difluorophenyl)ethyl)carbamate (120B): A solution of tert-butyl (S)-(1-(5-amino-3-bromo-6-(phenylethynyl)pyridin-2-yl)-2-(3,5-difluorophenyl)ethyl)carbamate (120A, 185 mg, 0.35 mmol) in 1,4-dioxane (3 ml) at 0° C. was treated with trifluoroacetic anhydride (0.06 mL, 0.42 mmol) followed by potassium carbonate (62 mg, 0.455 mmol)). The reaction mixture was stirred at room temperature for 5 min, then poured into water and extracted with ethyl acetate. The organic layer was separated, dried over MgSO$_4$, and concentrated in vacuo. The residue was purified by silica gel chromatography eluting with EtOAc/hexane to afford compound 120B. MS (m/z) 625.39 [M+H]$^+$.

Synthesis of tert-butyl (S)-(1-(6-bromo-2-phenyl-1H-pyrrolo[3,2-b]pyridin-5-yl)-2-(3,5-difluorophenyl)ethyl)carbamate (120C): Triethylamine (0.023 mL, 0.167 mmol) was added to a solution of tert-butyl (S)-(1-(3-bromo-6-(phenylethynyl)-5-(2,2,2-trifluoroacetamido)pyridin-2-yl)-2-(3,5-difluorophenyl)ethyl)carbamate (120B, 208 mg, 0.33 mmol) in dry DMF (4 mL), and the reaction was heated for at 100° C. for 20 hours. After cooling the reaction mixture to room temperature, water (20 mL) was added and the mixture was partitioned between EtOAc and 5% LiCl aqueous solution. The organic layer was separated, dried over Na$_2$SO$_4$, filtered and concentrated. The residue was purified by reverse phase HPLC eluted with acetonitrile/water (with 0.1% TFA) to afford compound 120C. MS (m/z) 527.99 [M+H]$^+$.

Synthesis of tert-butyl (S)-(2-(3,5-difluorophenyl)-1-(6-(5-methyl-3-oxo-2,3-dihydro-[1,2,4]triazolo[4,3-a]pyridin-6-yl)-2-phenyl-1H-pyrrolo[3,2-b]pyridin-5-yl)ethyl)carbamate (120D): Compound 120D was prepared in a manner similar to compound 119C, using 120C instead of 119B, and using 5-methyl-6-(4,4,5,5-tetramethyl-1,3,2-dioxaborolan-2-yl)-[1,2,4]triazolo[4,3-a]pyridin-3(2H)-one instead of 2-fluoro-5-(4,4,5,5-tetramethyl-1,3,2-dioxaborolan-2-yl) to provide the desired compound. MS (m/z) 596.91 [M+H]$^+$.

Synthesis of (S)-6-(5-(1-amino-2-(3,5-difluorophenyl)ethyl)-2-phenyl-1H-pyrrolo[3,2-b]pyridin-6-yl)-5-methyl-[1,2,4]triazolo[4,3-a]pyridin-3(2H)-one hydrochloride (120E): Tert-butyl (S)-(2-(3,5-difluorophenyl)-1-(6-(5-methyl-3-oxo-2,3-dihydro-[1,2,4]triazolo[4,3-a]pyridin-6-yl)-2-phenyl-1H-pyrrolo[3,2-b]pyridin-5-yl)ethyl)carbamate (120D, 20 mg, 0.034 mmol) was dissolved in 2 mL of 1,4-dioxane and cooled to 0° C. 1 mL of a solution of HCl (4N) in 1,4-dioxane was added to the reaction, which was then stirred at rt overnight and concentrated to dryness to afford compound 120E. MS (m/z): 496.97 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(5-methyl-3-oxo-2,3-dihydro-[1,2,4]triazolo[4,3-a]pyridin-6-yl)-2-phenyl-1H-pyrrolo[3,2-b]pyridin-5-yl)ethyl) acetamide (120): (S)-6-(5-(1-amino-2-(3,5-difluorophenyl) ethyl)-2-phenyl-1H-pyrrolo[3,2-b]pyridin-6-yl)-5-methyl-[1,2,4]triazolo[4,3-a]pyridin-3(2H)-one hydrochloride (120E, 18 mg, 0.034 mmol) was dissolved in 1 mL of DMF and cooled to 0° C. To the reaction was N,N-diisopropylethylamine (0.061 mL, 0.34 mmol) followed by a solution of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid (9.6 mg, 0.034 mmol) and COMU (14.6 mg, 0.034 mmol) in 1 mL of DMF. After stirring for 5 min, the reaction was partitioned between EtOAc and 5% aq LiCl. The organic layer was separated and dried over Na$_2$SO$_4$, filtered, and concentrated. The residue was dissolved in 1 mL of DMF and 0.1 mL of morpholine and allowed to stand for half hour. Then, the reaction was purified by reverse phase HPLC eluting with acetonitrile and water (with 0.1% TFA) to afford Compound 120. MS (m/z): 761.00 [M+H]$^+$. $^1$H NMR (400 MHz, Acetonitrile-d3) δ 10.80 (s, 1H), 10.14 (s, 1H), 8.18-7.78 (m, 3H), 7.75-7.37 (m, 3H), 7.41-6.32 (m, 6H), 5.64-5.14 (m, 1H), 4.96-4.54 (m, 2H), 3.20 (m, 2H), 2.88-2.07 (m, 5H), 1.38 (m, 1H), 1.04 (m, 1H).

Example 121

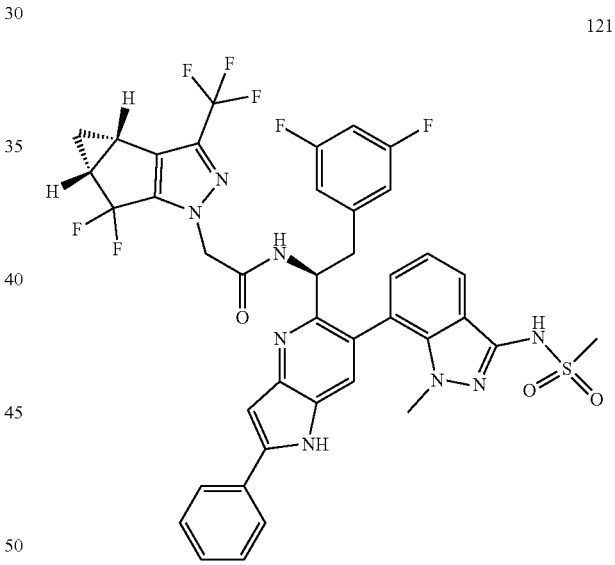

121

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-phenyl-1H-pyrrolo[3,2-b]pyridin-5-yl)ethyl)acetamide (121): Compound 121 was prepared in a manner similar to Example 120 using N-(1-methyl-7-(4,4,5,5-tetramethyl-1,3,2-dioxaborolan-2-yl)-1H-indazol-3-yl)methanesulfonamide instead of 5-methyl-6-(4,4,5,5-tetramethyl-1,3,2-dioxaborolan-2-yl)-[1,2,4]triazolo[4,3-a]pyridin-3(2H)-one to provide the desired compound. MS (m/z): 837.07 [M+H]$^+$. $^1$H NMR (400 MHz, Acetonitrile-d3) δ 11.28 (d, 1H), 9.84 (dd, 1H), 8.42-7.85 (m, 5H), 7.81-7.06 (m, 6H), 6.97-6.03 (m, 3H), 5.67-4.95 (m, 1H), 4.93-4.48 (m, 2H), 3.60-3.03 (m, 8H), 2.63-2.38 (m, 2H), 1.47-1.23 (m, 1H), 1.18-0.88 (m, 1H).

Example 122

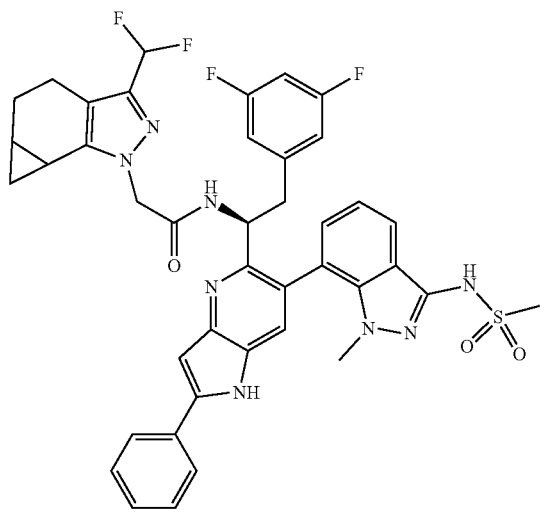

Synthesis of 2-(3-(difluoromethyl)-5,5a,6,6a-tetrahydrocyclopropa[g]indazol-1(4H)-yl)-N—((S)-2-(3,5-difluorophenyl)-1-(6-(1-methyl-3-(methylsulfonamido)-1H-indazol-7-yl)-2-phenyl-1H-pyrrolo[3,2-b]pyridin-5-yl)ethyl) acetamide (122): Compound 122 was prepared in a manner similar to Example 121 using 2-(3-(difluoromethyl)-5,5a,6,6a-tetrahydrocyclopropa[g]indazol-1(4H)-yl)acetic acid instead of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetic acid to provide the desired compound. MS (m/z): 797.05 [M+H]$^+$. $^1$H NMR (400 MHz, Methanol-d4) δ 8.05-7.77 (m, 4H), 7.69-7.41 (m, 4H), 7.39-7.04 (m, 2H), 6.94-6.24 (m, 4H), 5.52-4.99 (m, 1H), 4.88 (s, 2H), 3.49-3.10 (m, 6H), 3.08-2.58 (m, 2H), 2.40-1.22 (m, 6H), 0.92 (m, 1H), 0.59 (m, 1H).

Example 123

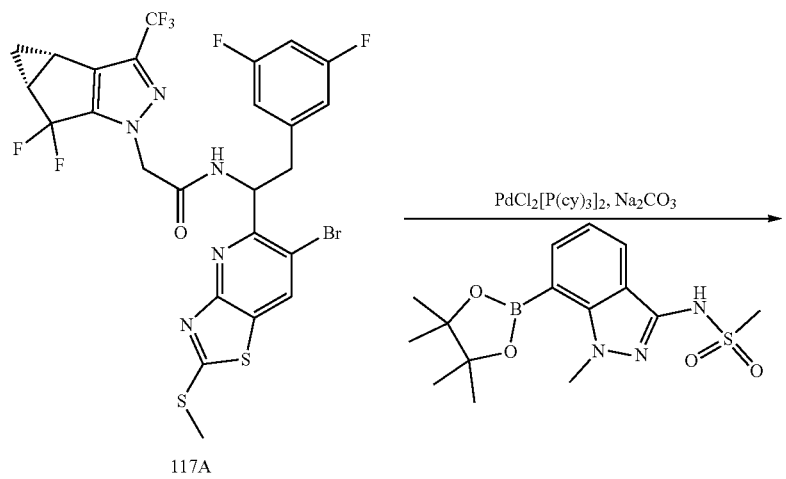

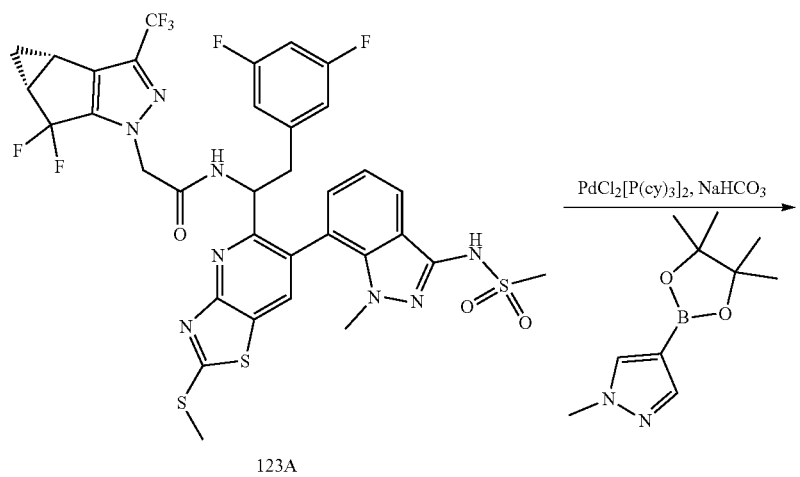

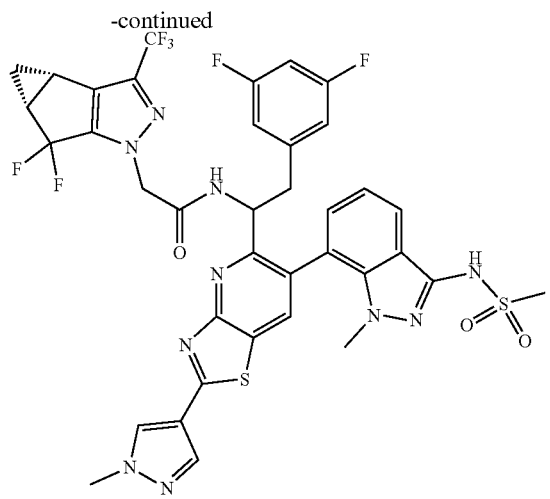

123

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(6-(1-methyl-3-(methylsulfonamido)-1H-indazol-7-yl)-2-(methylthio)thiazolo[4,5-b]pyridin-5-yl)ethyl)acetamide (123A): Compound 123A was prepared in a manner similar to Example 119 using N-(1-methyl-7-(4,4,5,5-tetramethyl-1,3,2-dioxaborolan-2-yl)-1H-indazol-3-yl)methanesulfonamide instead of 2-fluoro-5-(4,4,5,5-tetramethyl-1,3,2-dioxaborolan-2-yl)benzamide to provide the desired compound. MS (m/z): 825.00 [M+H]+.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-(1-methyl-1H-pyrazol-4-yl)-6-(1-methyl-3-(methylsulfonamido)-1H-indazol-7-yl)thiazolo[4,5-b]pyridin-5-yl)ethyl)acetamide (123): Compound 123 was prepared in a manner similar to Example 119 using 1-methyl-4-(4,4,5,5-tetramethyl-1,3,2-dioxaborolan-2-yl)-1H-pyrazole instead of 2-fluoro-5-(4,4,5,5-tetramethyl-1,3,2-dioxaborolan-2-yl)benzamide, and heating to 160° C. for 20 min, instead of 150° C. for 15 min to provide the desired compound. MS (m/z): 858.91 [M+H]+. 1H NMR (400 MHz, Methanol-d4) δ 8.83 (m, 1H), 8.61-7.93 (m, 3H), 7.95-6.96 (m, 2H), 6.83-6.11 (m, 3H), 5.44-4.97 (m, 1H), 4.85 (m, 2H), 4.03 (s, 3H), 3.47-2.77 (m, 8H), 2.62-2.33 (m, 2H), 1.56-0.89 (m, 2H).

Example 124

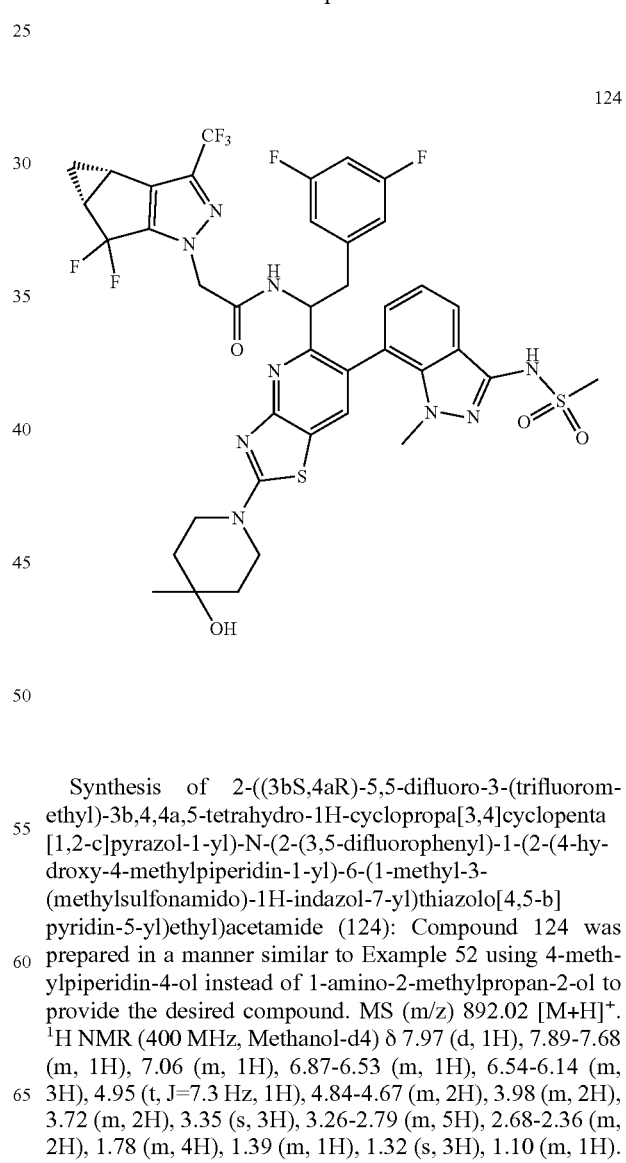

124

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-(4-hydroxy-4-methylpiperidin-1-yl)-6-(1-methyl-3-(methylsulfonamido)-1H-indazol-7-yl)thiazolo[4,5-b]pyridin-5-yl)ethyl)acetamide (124): Compound 124 was prepared in a manner similar to Example 52 using 4-methylpiperidin-4-ol instead of 1-amino-2-methylpropan-2-ol to provide the desired compound. MS (m/z): 892.02 [M+H]+. 1H NMR (400 MHz, Methanol-d4) δ 7.97 (d, 1H), 7.89-7.68 (m, 1H), 7.06 (m, 1H), 6.87-6.53 (m, 1H), 6.54-6.14 (m, 3H), 4.95 (t, J=7.3 Hz, 1H), 4.84-4.67 (m, 2H), 3.98 (m, 2H), 3.72 (m, 2H), 3.35 (s, 3H), 3.26-2.79 (m, 5H), 2.68-2.36 (m, 2H), 1.78 (m, 4H), 1.39 (m, 1H), 1.32 (s, 3H), 1.10 (m, 1H).

Example 125

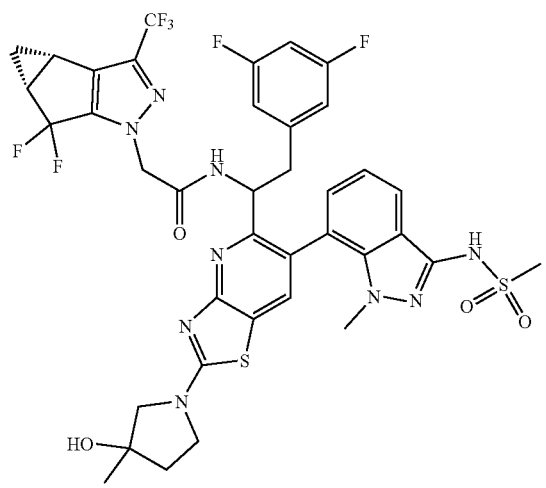

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-(3-hydroxy-3-methylpyrrolidin-1-yl)-6-(1-methyl-3-(methylsulfonamido)-1H-indazol-7-yl)thiazolo[4,5-b]pyridin-5-yl)ethyl)acetamide (125): Compound 125 was prepared in a manner similar to Example 52 using 3-methylpyrrolidin-3-ol instead of 1-amino-2-methylpropan-2-ol to provide the desired compound. MS (m/z) 878.00 [M+H]$^+$.
$^1$H NMR (400 MHz, Methanol-d4) δ 7.99 (d, 1H), 7.88-7.70 (m, 1H), 7.33-6.99 (m, 1H), 6.72 (t, J=9.2 Hz, 1H), 6.52-6.21 (m, 3H), 5.30-4.93 (m, 1H), 4.84 (m, 2H), 4.29-3.45 (m, 4H), 3.42-2.76 (m, 8H), 2.59-2.32 (m, 2H), 2.17 (m, 2H), 1.52 (s, 3H), 1.39 (m, 1H), 1.08 (m, 1H).

Example 126

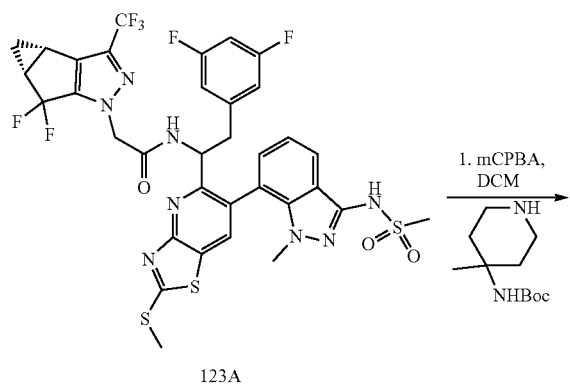

123A

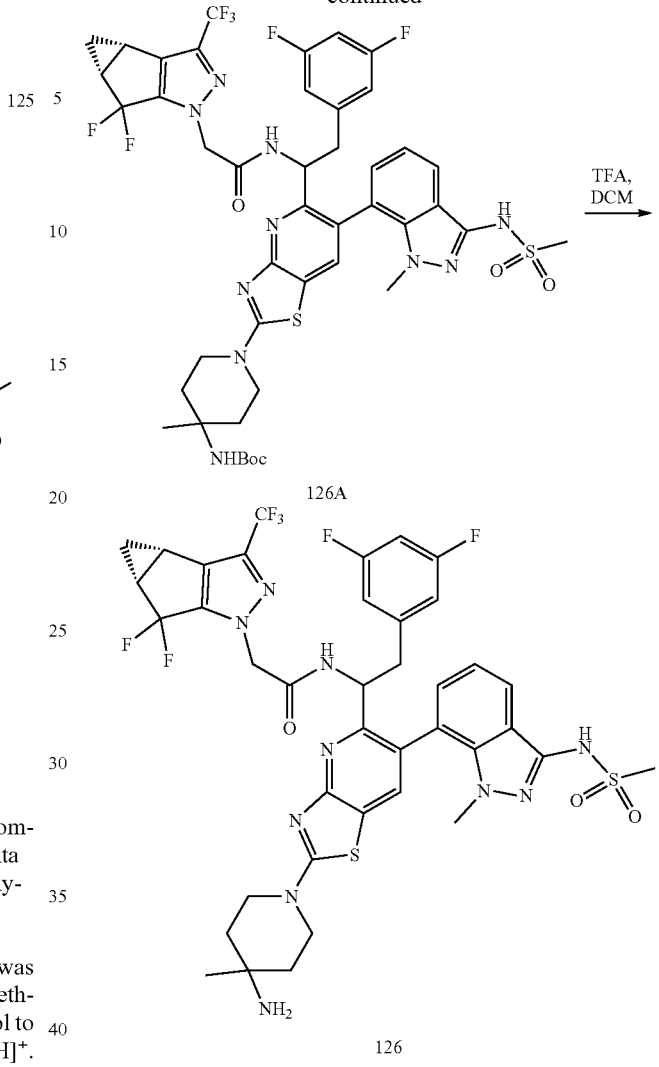

Synthesis of tert-butyl (1-(5-(1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(1-methyl-3-(methylsulfonamido)-1H-indazol-7-yl)thiazolo[4,5-b]pyridin-2-yl)-4-methylpiperidin-4-yl)carbamate (126A): Compound 126A was prepared in a manner similar to Example 52 using tert-butyl (4-methylpiperidin-4-yl)carbamate instead of 1-amino-2-methylpropan-2-ol to provide the desired compound. MS (m/z) 991.28 [M+H]$^+$.

Synthesis of N-(1-(2-(4-amino-4-methylpiperidin-1-yl)-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetamide (126): tert-butyl (1-(5-(1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(1-methyl-3-(methylsulfonamido)-1H-indazol-7-yl)thiazolo[4,5-b]pyridin-2-yl)-4-methylpiperidin-4-yl)carbamate (126A, 7 mg, 0.007 mmol) was dissolved in 1 mL of 20% TFA in methylene chloride and stirred at room temperature for 1.5 hour. The solvent was removed and the residue was dried under high vacuum to afford Compound 126. MS (m/z) 891.09 [M+H]⁺. ¹H NMR (400 MHz, Methanol-d4) δ 8.00 (s, 1H), 7.82 (dd, J=8.1, 1.0 Hz, 1H), 7.06 (dd, J=8.2, 7.0 Hz, 1H), 6.73 (tt, J=9.2, 2.4 Hz, 1H), 6.47 (dd, J=7.0, 1.2 Hz, 1H), 6.45-6.17 (m, 2H), 4.97 (t, J=7.2 Hz, 1H), 4.79 (m, 2H), 4.15 (m, 2H), 3.80-3.54 (m, 2H), 3.34 (s, 3H), 3.13 (m, 4H), 3.08-2.88 (m, 1H), 2.48 (m, 2H), 2.14-1.90 (m, 4H), 1.56 (s, 3H), 1.52-1.32 (m, 1H), 1.22-0.95 (m, 1H).

Example 127

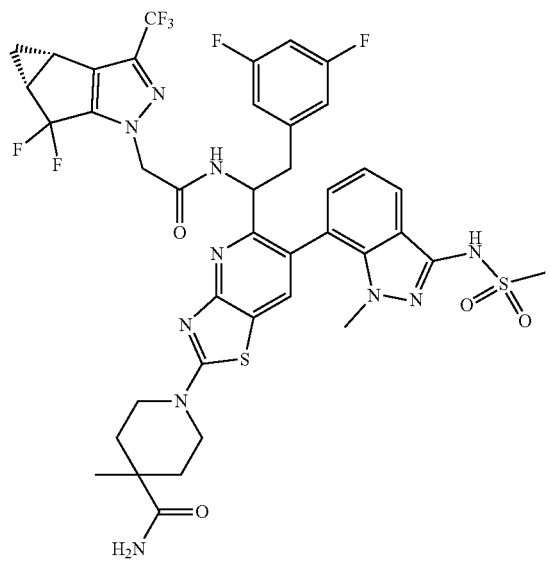

127

Synthesis of 1-(5-(1-(2-((3bS,4aR)-5,5-difluoro-3-(trifluoromethyl)-3b,4,4a,5-tetrahydro-TH-cyclopropa[3,4]cyclopenta[1,2-c]pyrazol-1-yl)acetamido)-2-(3,5-difluorophenyl)ethyl)-6-(1-methyl-3-(methylsulfonamido)-1H-indazol-7-yl)thiazolo[4,5-b]pyridin-2-yl)-4-methylpiperidine-4-carboxamide (127): Compound 127 was prepared in a manner similar to Example 52 using 4-methyl-4-piperidinecarboxamide hydrochloride instead of 1-amino-2-methylpropan-2-ol to provide the desired compound. MS (m/z) 918.97 [M+H]⁺. ¹H NMR (400 MHz, Methanol-d4) δ 7.96 (s, 1H), 7.82 (dd, J=8.1, 1.1 Hz, 1H), 7.06 (dd, J=8.2, 7.0 Hz, 1H), 6.90-6.63 (m, 1H), 6.48 (dd, J=7.0, 1.1 Hz, 1H), 6.44-6.15 (m, 2H), 4.96 (t, J=7.2 Hz, 1H), 4.85 (m, 2H), 4.00 (m, 2H), 3.61 (m, 2H), 3.35 (s, 3H), 3.15 (m, 4H), 3.07-2.91 (m, 1H), 2.47 (m, 2H), 2.26 (m, 2H), 1.68 (m, 2H), 1.47-1.34 (m, 1H), 1.32 (s, 3H), 1.10 (m, 1H).

Example 128

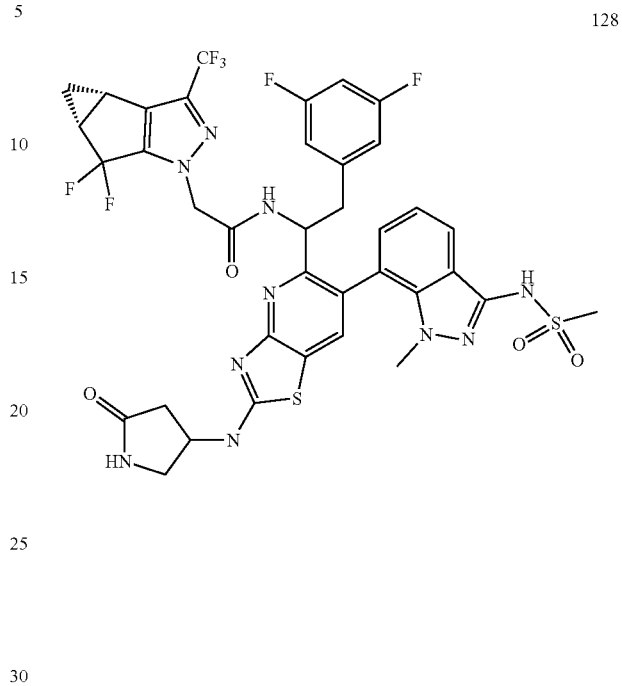

128

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(6-(1-methyl-3-(methylsulfonamido)-1H-indazol-7-yl)-2-((5-oxopyrrolidin-3-yl)amino)thiazolo[4,5-b]pyridin-5-yl)ethyl)acetamide (128): Compound 128 was prepared in a manner similar to Example 52 using 4-aminopyrrolidin-2-one instead of 1-amino-2-methylpropan-2-ol to provide the desired compound. MS (m/z) 876.91[M+H]⁺. ¹H NMR (400 MHz, Methanol-d4) δ 8.09-7.89 (m, 1H), 7.81 (m, 1H), 7.32-6.95 (m, 1H), 6.83-6.56 (m, 1H), 6.57-6.10 (m, 3H), 4.96 (t, J=7.2 Hz, 1H), 4.81 (m, 2H), 4.01-3.80 (m, 1H), 3.61-3.41 (m, 1H), 3.42-3.32 (m, 3H), 3.15 (m, 4H), 3.06-2.84 (m, 3H), 2.46 (m, 3H), 1.50-1.26 (m, 1H), 1.10 (m, 1H).

Example 129

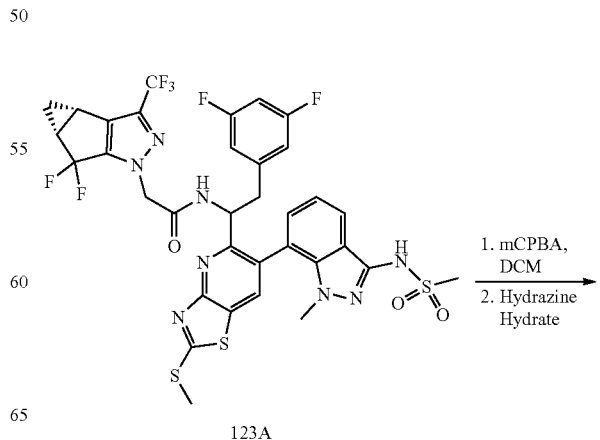

123A

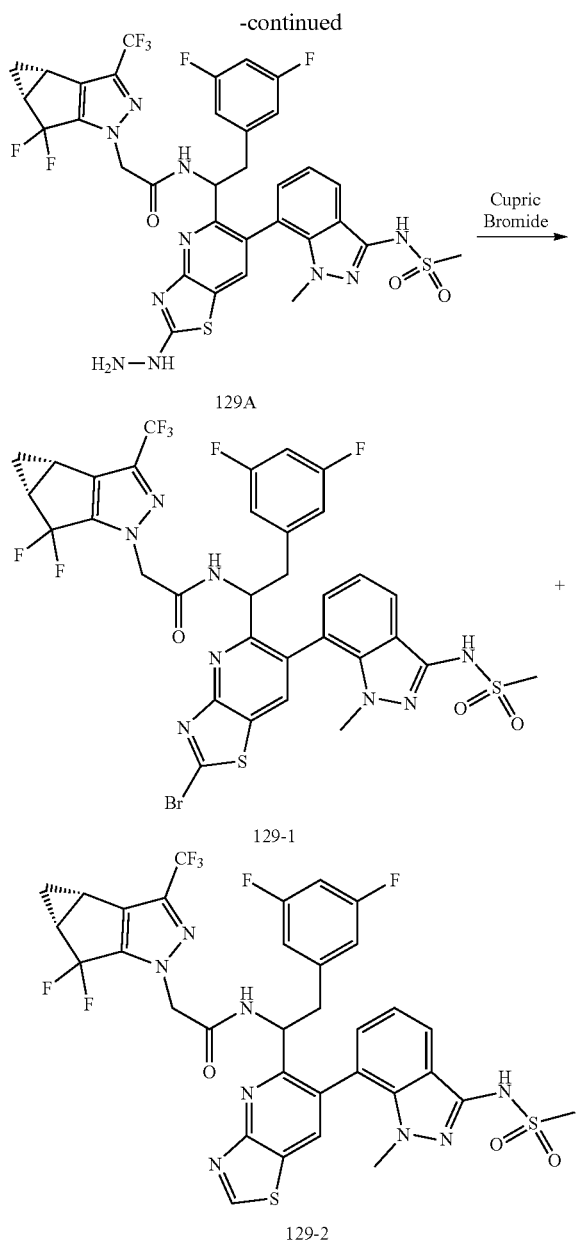

129A 129-1

129-2

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-hydrazinyl-6-(1-methyl-3-(methylsulfonamido)-1H-indazol-7-yl)thiazolo[4,5-b]pyridin-5-yl)ethyl)acetamide (129A): 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(6-(1-methyl-3-(methylsulfonamido)-1H-indazol-7-yl)-2-(methylthio)thiazolo[4,5-b]pyridin-5-yl)ethyl)acetamide (123A, 500 mg, 0.61 mmol) was dissolved in 25 mL of methylene chloride and the solution was cooled to 0° C. To the solution was added 3-Chloroperoxybenzoic acid (77% purity, 204 mg, 0.91 mmol). The reaction mixture was allowed to stir at 0° C. for 1.5 hour and then was diluted with methylene chloride and washed with saturated NaHCO₃ aqueous solution and brine. The organic layer was separated, dried over Na₂SO₄ and concentrated to dryness. To 300 mg of the crude product (0.35 mmol) was added 2 mL of ethanol and the mixture was cooled to 0° C. To the mixture was added 0.2 mL of Hydrazine hydrate dropwise, and the resulting solution was allowed to stir at room temperature for 20 minutes, and the solvent was removed. The residue was suspended in water and filtered. The cake was collected and dried under high vacuum to afford compound 129A. MS (m/z): 808.89[M+H]⁺.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(6-(1-methyl-3-(methylsulfonamido)-1H-indazol-7-yl)thiazolo[4,5-b]pyridin-5-yl)ethyl)acetamide (129-2): Copper(II) bromide (162 mg, 0.73 mmol) was dissolved in a mixture of water (0.3 mL) and glacial acetic acid (0.3 mL). To the mixture was dropwise added a solution of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-hydrazinyl-6-(1-methyl-3-(methylsulfonamido)-1H-indazol-7-yl)thiazolo[4,5-b]pyridin-5-yl)ethyl)acetamide (129A, 196 mg, 0.24 mmol) in 6 mL of glacial acetic acid. The reaction was stirred for 5 min, partitioned between aqueous ammonium hydroxide and ammonium chloride and ethyl acetate. Organic layer was separated, washed with brine, dried over MgSO₄, filtered and concentrated to dryness. The residue was purified by silica gel chromatography eluting with EtOAc/Hexane to afford Compound 129-1 and Compound 129-2, which was purified again on reverse phase-HPLC eluting with ACN/H2O (with 0.1% TFA). Compound 129-1: MS (m/z): 856.78 [M+H]⁺. Compound 129-2: MS (m/z): 778.94 [M+H]⁺. ¹H NMR (400 MHz, Methanol-d4) δ 9.72 (d, J=1.5 Hz, 1H), 8.90 (t, 1H), 8.55 (d, J=9.0 Hz, 1H), 7.98-7.72 (m, 1H), 7.40-7.04 (m, 1H), 6.87-6.51 (m, 2H), 6.50-6.23 (m, 2H), 5.52-5.06 (m, 1H), 4.85 (m, 2H), 3.62-2.81 (m, 8H), 2.65-2.25 (m, 2H), 1.39 (m, 1H), 1.10 (m, 1H).

Example 130

130

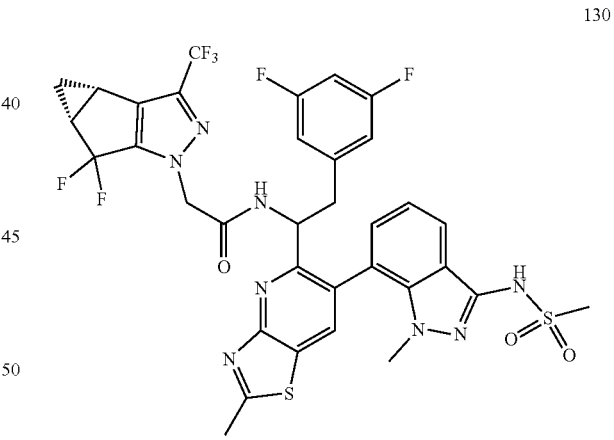

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-methyl-6-(1-methyl-3-(methylsulfonamido)-1H-indazol-7-yl)thiazolo[4,5-b]pyridin-5-yl)ethyl)acetamide (130): A microwave tube was charged with N-(1-(2-bromo-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (129-1, 45 mg, 0.053 mmol), potassium carbonate (22 mg, 0.16 mmol), Trimethylboroxine (0.022 ml, 0.16 mmol) and trans-Dichlorobis(triphenylphosphine)palladium (II) (3.7 mg, 0.005 mmol). To the mixture was added 1 mL of 1,4-dioxane, 0.3 ml of N,N-Dimethylformamide and 0.1 mL of water. The system was purged with argon, and then the microwave tube was sealed and the reaction mixture was heated up to 120° C. in a microwave reactor for 5 min. After cooling to rt, it was partitioned between EtOAc and water. The organic layer was separated, and washed with brine, then dried over MgSO$_4$, filtered, and concentrated. The residue was purified by reverse phase HPLC eluting with acetonitrile and water (0.1% TFA) to afford Compound 130. MS (m/z) 792.92 [M+H]$^+$. $^1$H NMR (400 MHz, Chloroform-d) δ 8.10 (d, 1H), 7.92 (dd, J=8.2, 1.1 Hz, 1H), 7.22-6.90 (m, 1H), 6.79 (m, 1H), 6.69-6.55 (m, 1H), 6.51-6.34 (m, 1H), 6.27-6.02 (m, 2H), 5.12 (t, J=6.9 Hz, 1H), 4.71 (s, 2H), 3.23 (d, 6H), 3.12-2.85 (m, 5H), 2.44 (m, 2H), 1.41 (q, J=7.2 Hz, 1H), 1.34-1.01 (m, 1H).

Example 131

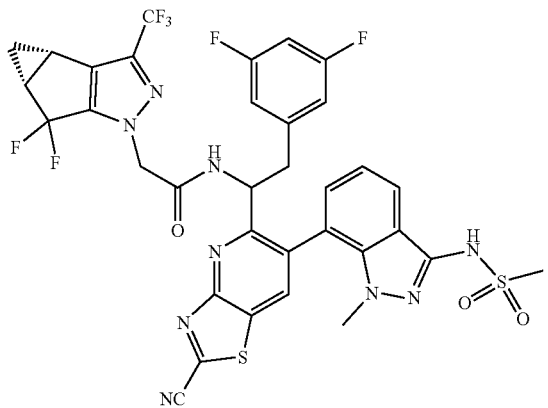

131

Synthesis of N-(1-(2-cyano-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (131): Compound 131 was prepared in a manner similar to Example 119 using 123A instead of 117A to provide the desired compound. MS (m/z): 803.86 [M+H]$^+$. $^1$H NMR (400 MHz, Methanol-d4) δ 8.97 (d, J=8.8 Hz, 1H), 8.65 (s, 1H), 8.10-7.76 (m, 1H), 7.19 (dd, J=8.2, 7.0 Hz, 1H), 6.82 (dd, J=7.1, 1.1 Hz, 1H), 6.78-6.63 (m, 1H), 6.47-6.14 (m, 2H), 5.30-5.10 (m, 1H), 4.83 (m, 2H), 3.28-3.15 (m, 1H), 3.14 (s, 3H), 3.05-2.81 (m, 1H), 2.59-2.35 (m, 2H), 1.38 (q, J=7.1 Hz, 1H), 1.06 (m, 1H).

Example 132

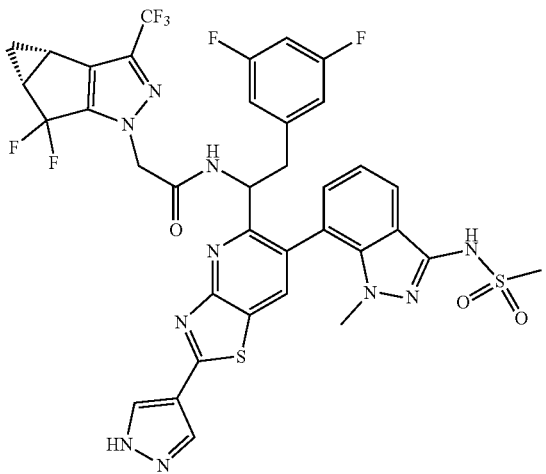

132

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(6-(1-methyl-3-(methylsulfonamido)-1H-indazol-7-yl)-2-(1H-pyrazol-4-yl)thiazolo[4,5-b]pyridin-5-yl)ethyl)acetamide (132): Compound 132 was prepared in a manner similar to Example 123 using 4-(4,4,5,5-tetramethyl-1,3,2-dioxaborolan-2-yl)-1H-pyrazole instead of 1-methyl-4-(4,4,5,5-tetramethyl-1,3,2-dioxaborolan-2-yl)-1H-pyrazole to provide desired compound. MS (m/z): 845.11 [M+H]$^+$. $^1$H NMR (400 MHz, Methanol-d4) δ 8.53-8.22 (m, 3H), 7.99-7.77 (m, 1H), 7.44-7.08 (m, 1H), 6.86-6.53 (m, 2H), 6.39 (dd, J=35.7, 7.5 Hz, 2H), 5.39-5.03 (m, 1H), 4.85 (m, 2H), 3.52-2.84 (m, 8H), 2.67-2.37 (m, 2H), 1.50-1.24 (m, 1H), 1.11 (m, 1H).

Example 133

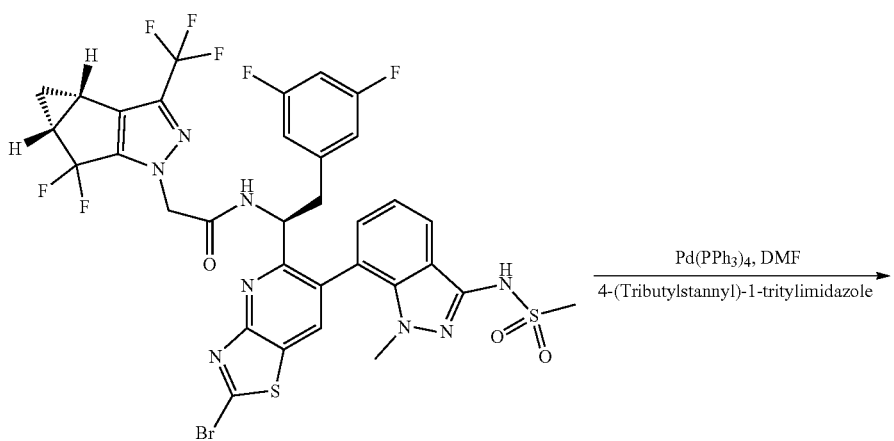

129B

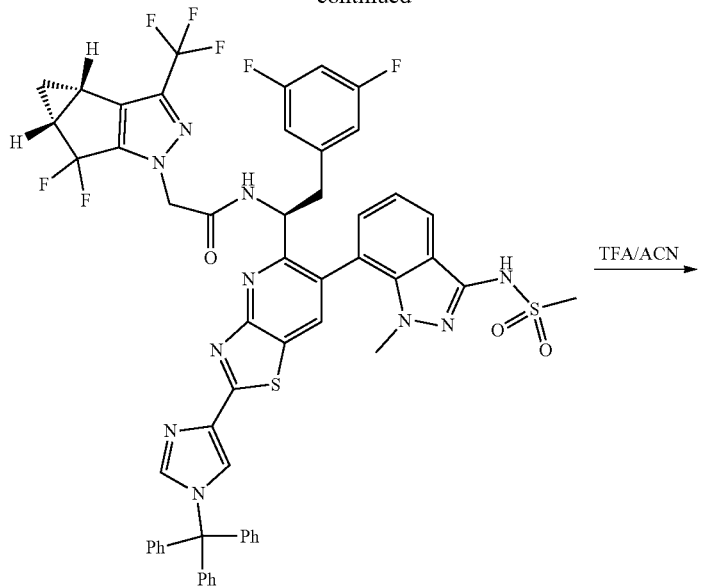

133A

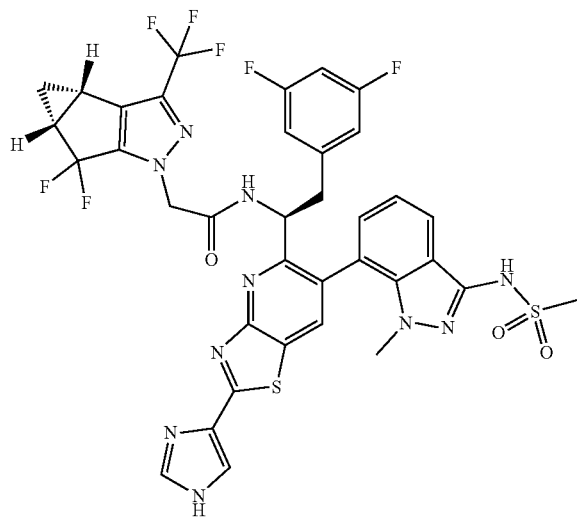

133

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(1-trityl-1H-imidazol-4-yl)thiazolo[4,5-b]pyridin-5-yl)ethyl)acetamide (133A): A microwave tube was charged with N-(1-(2-bromo-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (129-1, 30 mg, 0.035 mmol), 4-(tributylstannyl)-1-tritylimidazole (25 mg, 0.042 mmol) and tetrakis(triphenylphosphine) palladium(0) (1.2 mg, 0.0011 mmol). To the mixture was added 0.3 mL N,N-Dimethylformamide. The system was purged with argon, the microwave tube was sealed, and the reaction mixture was heated up to 100° C. for 4 hours. After cooling to room temperature, the mixture was diluted with 20 mL of saturated NH$_4$Cl, and extracted with three 20-mL portions of EtOAc. The organic extracts were combined, washed with 1 N NaOH, 1M KF aq. solution, dried over Na$_2$SO$_4$, filtered, and concentrated. The residue was purified by reverse phase-HPLC eluting with acetonitrile and water (0.1% TFA) to afford compound 133A. MS (m/z): 1086.73 [M+H]$^+$.

Synthesis of N-(1-(2-(1H-imidazol-4-yl)-6-(1-methyl-3-(methylsulfonamido)-1H-indazol-7-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (133): 2-((3bS,4aR)-5,5-difluoro-3-(trifluoromethyl)-3b,4,4a,5-tetrahydro-TH-cyclopropa[3,4]cyclopenta[1,2-c]pyrazol-1-yl)-N—((S)-2-(3,5-difluorophenyl)-1-(6-(1-methyl-3-(methylsulfonamido)-1H-indazol-7-yl)-2-(1-trityl-TH-imidazol-4-yl)thiazolo[4,5-b]pyridin-5-yl)ethyl)acetamide (133A, 12 mg, 0.011 mmol) was dissolved in 5 mL of 0.1% TFA in acetonitrile, and the resulting solution was stirred at room temperature for 3 hours, and concentrated to dryness. The residue was purified by reverse phase-HPLC eluting with acetonitrile and water (0.1% TFA) to afford Compound 133. MS (m/z): 845.90 [M+H]⁺. ¹H NMR (400 MHz, Methanol-d4) δ 8.83 (d, 1H), 8.45 (d, 1H), 8.18 (dd, 2H), 8.02-7.77 (m, 1H), 7.44-7.04 (m, 1H), 6.84-6.57 (m, 2H), 6.57-6.23 (m, 2H), 5.13 (q, J=7.6 Hz, 1H), 4.85 (m, 2H), 3.55-2.80 (m, 51H), 2.46 (dd, J=7.7, 4.1 Hz, 1H), 1.55-1.26 (m, 1H), 1.07 (s, 1H).

Example 134

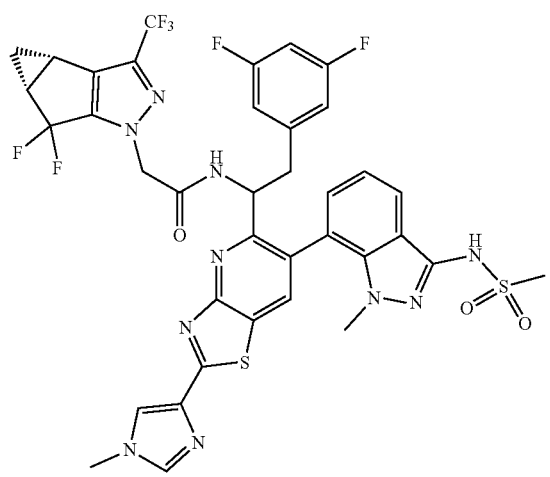

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N-(2-(3,5-difluorophenyl)-1-(2-(1-methyl-1H-imidazol-4-yl)-6-(1-methyl-3-(methylsulfonamido)-1H-indazol-7-yl)thiazolo[4,5-b]pyridin-5-yl)ethyl)acetamide (134): Compound 134 was prepared in a manner similar to Example 133 using 1-methyl-4-(tributylstannyl)-1H-imidazole instead of 4-(tributylstannyl)-1-tritylimidazole to provide the desired compound: MS (m/z): 859.16 [M+H]⁺. ¹H NMR (400 MHz, Methanol-d4) δ 8.81 (d, J=8.6 Hz, 1H), 8.42 (s, 1H), 8.12 (d, J=1.3 Hz, 1H), 8.07-7.97 (m, 1H), 7.88 (dd, J=8.2, 1.0 Hz, 1H), 7.14 (dd, J=8.2, 7.0 Hz, 1H), 6.80-6.58 (m, 2H), 6.44-6.19 (m, 2H), 5.24-4.97 (m, 1H), 4.82-4.73 (m, 2H), 3.92 (s, 3H), 3.33 (s, 3H), 3.27-3.17 (m, 1H), 3.13 (s, 3H), 3.07-2.85 (m, 1H), 2.46 (m, 2H), 1.54-1.25 (m, 1H), 1.20-0.90 (m, 1H).

Example 135

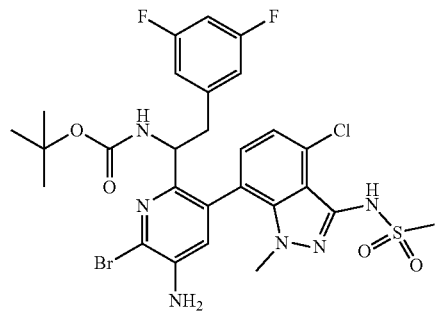

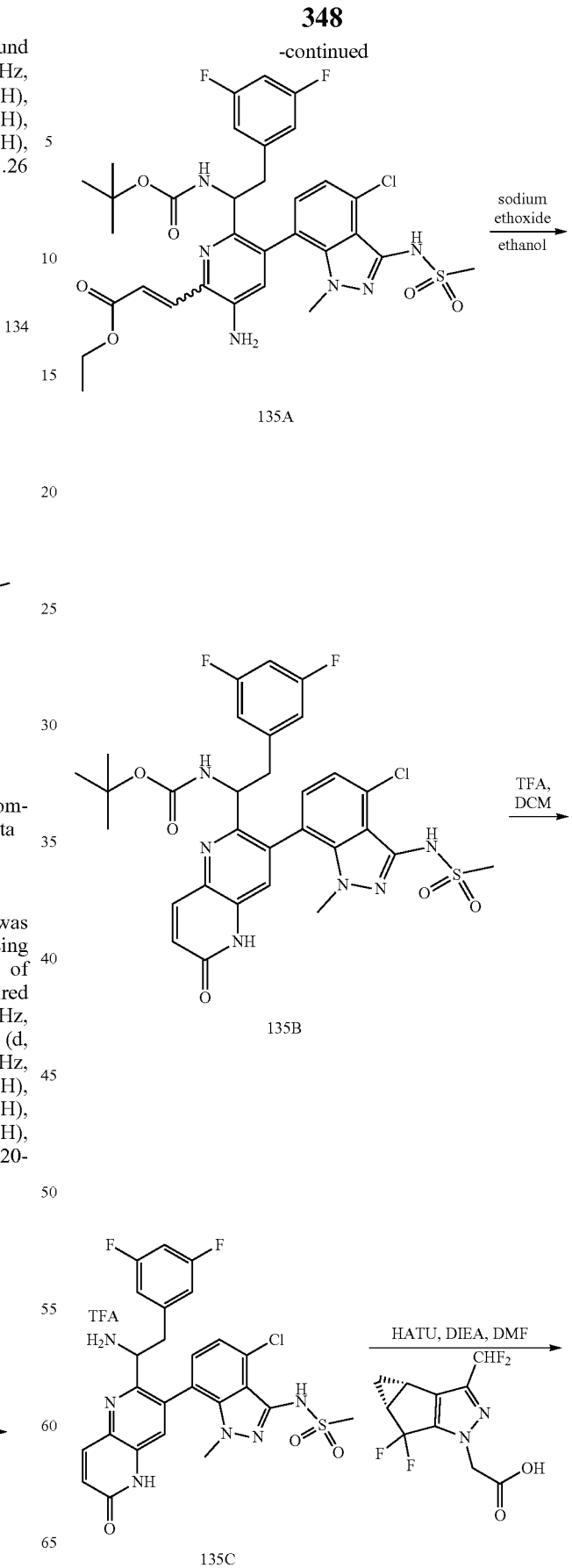

-continued

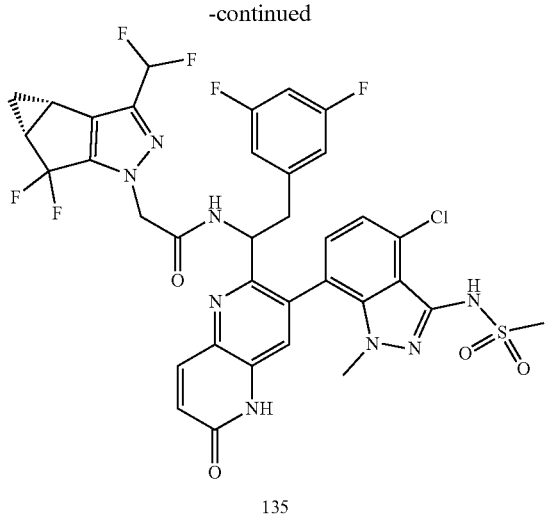

135

Synthesis of ethyl 3-(3-amino-6-(1-((tert-butoxycarbonyl)amino)-2-(3,5-difluorophenyl)ethyl)-5-(4-chloro-1-methyl-3-(methylsulfonamido)-1H-indazol-7-yl)pyridin-2-yl)acrylate (135A): A microwave tube was charged with tert-butyl (1-(5-amino-6-bromo-3-(4-chloro-1-methyl-3-(methylsulfonamido)-1H-indazol-7-yl)pyridin-2-yl)-2-(3,5-difluorophenyl)ethyl)carbamate (prepared according to WO 2014110297, 100 mg, 0.15 mmol), ethyl acrylate (0.048 mL, 0.44 mmol), tri(o-tolyl)phosphine (8.9 mg, 0.029 mmol) and palladium acetate trimer (3.3 mg, 0.015 mmol). To the mixture was added 1.5 mL of acetonitrile and triethylamine (0.122 mL, 0.88 mmol). The system was purged with argon and then the microwave tube was sealed; and the reaction mixture was heated at 140° C. for 1 hour. After cooled to room temperature, the reaction was partitioned between methylene chloride and brine. The organic layer was separated, and washed with brine, then dried over MgSO₄, filtered, and concentrated. The residue was purified by silica gel chromatography eluting with EtOAc/hexane to afford compound 135A. MS (m/z): 705.24 [M+H]⁺.

Synthesis of tert-butyl (1-(3-(4-chloro-1-methyl-3-(methylsulfonamido)-1H-indazol-7-yl)-6-oxo-5,6-dihydro-1,5-naphthyridin-2-yl)-2-(3,5-difluorophenyl)ethyl)carbamate (135B): Ethyl 3-(3-amino-6-(1-((tert-butoxycarbonyl)amino)-2-(3,5-difluorophenyl)ethyl)-5-(4-chloro-1-methyl-3-(methylsulfonamido)-1H-indazol-7-yl)pyridin-2-yl)acrylate (135A, 48 mg, 0.068 mmol) was dissolved in ethanol (10 mL), and to it was added sodium ethoxide solution (0.053 mL, 0.68 mmol, 21% in ethanol). The mixture was heated at 100° C. for 30 min, then cooled to room temperature and more sodium ethoxide solution (0.1 mL, 21% in ethanol) was added. The reaction was heated at 100° C. for another 30 min, cooled to room temperature, and some solvent was removed. The reaction was partitioned between 50% n-butanol/EtOAc and brine. The organic layer was separated, dried over Na₂SO₄, filtered and concentrated. The residue was purified by reverse-HPLC eluting with ACN/water (with 0.1% TFA) to afford compound 135B. MS (m/z): 659.14 [M+H]⁺.

Synthesis of N-(7-(2-(1-amino-2-(3,5-difluorophenyl)ethyl)-6-oxo-5,6-dihydro-1,5-naphthyridin-3-yl)-4-chloro-1-methyl-1H-indazol-3-yl)methanesulfonamide (135C): Tert-butyl (1-(3-(4-chloro-1-methyl-3-(methylsulfonamido)-1H-indazol-7-yl)-6-oxo-5,6-dihydro-1,5-naphthyridin-2-yl)-2-(3,5-difluorophenyl)ethyl)carbamate (135B, 28 mg, 0.043 mmol) was dissolved in 2 mL of methylene chloride, and to it was added 0.3 mL of TFA. The reaction was stirred at room temperature for 1 hour. The solvent was removed to afford compound 135C as a TFA salt. MS (m/z): 559.02 [M+H]⁺.

Synthesis of N-(1-(3-(4-chloro-1-methyl-3-(methylsulfonamido)-1H-indazol-7-yl)-6-oxo-5,6-dihydro-1,5-naphthyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (135): N-(7-(2-(1-amino-2-(3,5-difluorophenyl)ethyl)-6-oxo-5,6-dihydro-1,5-naphthyridin-3-yl)-4-chloro-1-methyl-1H-indazol-3-yl)methanesulfonamide (135C, 28 mg, 0.043 mmol) was dissolved in 0.5 mL of DMF and cooled to 0° C. To the solution was added N,N-diisopropylethylamine (0.027 mL, 0.214 mmol), followed by a solution of 2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetic acid (11.3 mg, 0.043 mmol), and HATU (24.4 mg, 0.064 mmol) in 0.5 mL of DMF. The reaction mixture was stirred at 0° C. for 5 min. To the reaction mixture was added 0.5 mL of ethanol and 0.1 mL of 15% NaOH aqueous solution and the reaction mixture was stirred for 5 min. The reaction mixture was acidified with 5% citric acid, and then extracted with EtOAc. The organic layer was separated, dried over Na₂SO₄, filtered and concentrated. The residue was purified by reverse phase-HPLC eluting with ACN/water to afford Compound 135. MS (m/z): 805.05 [M+H]⁺. ¹H NMR (400 MHz, Methanol-d4) δ 8.68 (m, 1H), 8.20 (m, 1H), 7.60 (m, 1H), 7.21 (q, J=7.7 Hz, 1H), 7.12 (d, J=7.6 Hz, 1H), 6.97 (dd, J=9.8, 0.9 Hz, 1H), 6.89-6.51 (m, 3H), 6.50-6.21 (m, 2H), 5.43-4.93 (m, 1H), 4.81-4.54 (m, 2H), 3.34 (s, 2H), 3.28-2.87 (m, 6H), 2.45 (m, 2H), 1.49-1.27 (m, 1H), 1.16-0.89 (m, 1H).

Example 136

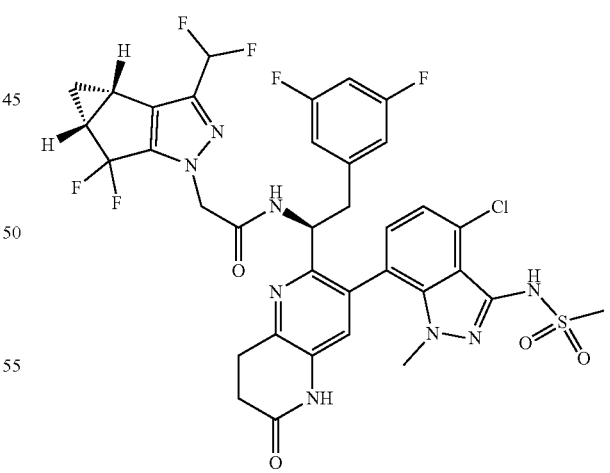

136

Synthesis of N—((S)-1-(3-(4-chloro-1-methyl-3-(methylsulfonamido)-1H-indazol-7-yl)-6-oxo-5,6,7,8-tetrahydro-1,5-naphthyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4]cyclopenta[1,2-c]pyrazol-1-yl)acetamide (136): N-(1-(3-(4-chloro-1-methyl-3-(methylsulfonamido)-1H-indazol-7-yl)-6-oxo-5,6-dihydro- 1,5-naphthyridin-2-yl)-2-(3,5-difluorophenyl)ethyl)-2-((3bS,4aR)-3-(difluoromethyl)-5,5-difluoro-3b,4,4a,5-tetrahydro-1H-cyclopropa[3,4] cyclopenta[1,2-c]pyrazol-1-yl)acetamide (135C, 13 mg, 0.016 mmol) was dissolved in 3 mL of ethyl acetate. The solution was degassed by vacuum and back flushed with argon. To the solution was added Rhodium (2 mg, 5 wt. % on alumina, powder, Degussa type G214 RA/D), then the reaction was placed under vacuum and stirred under a Hydrogen balloon for 1 hour. To the reaction was added 0.1 mL of acetic acid and 5 mg of Rh/Al$_2$O$_3$, and stirred under a hydrogen balloon overnight. After filtration, the solvent was removed, and the residue was purified by reverse phase-HPLC eluting with ACN/H2O (w/0.1% TFA) to afford Compound 136. MS (m/z): 807.16 [M+H]$^+$. $^1$H NMR (400 MHz, Methanol-d4) δ 7.17-6.95 (m, 2H), 6.89-6.48 (m, 2H), 6.48-6.25 (m, 3H), 4.88 (m, 1H), 4.82-4.39 (m, 2H), 3.37 (s, 3H), 3.24 (s, 3H), 3.17-3.02 (m, 1H), 2.94 (m, 1H), 2.81 (m, 2H), 2.46 (m, 2H), 1.39 (q, J=6.8 Hz, 1H), 1.15-0.76 (m, 1H).

Example 137

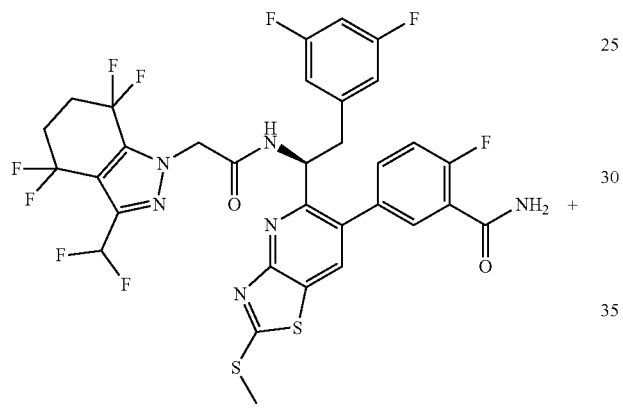

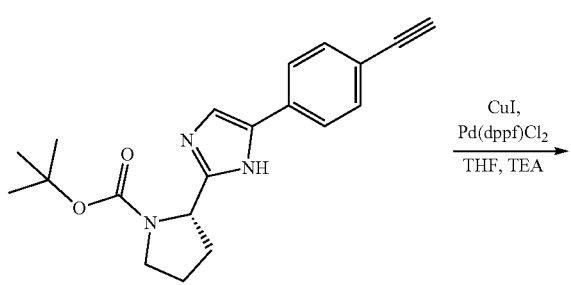

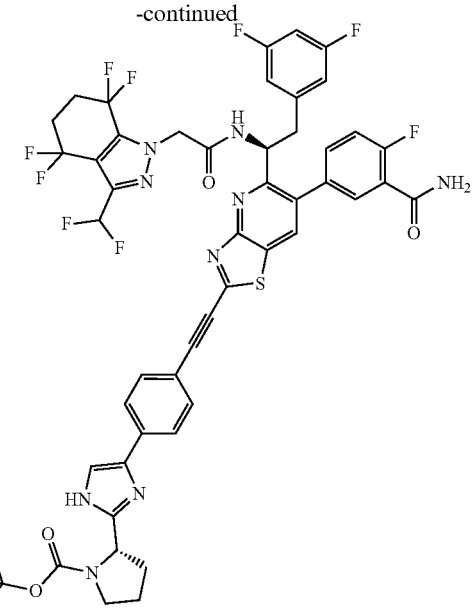

137

Synthesis of tert-butyl (S)-2-(4-(4-((6-(3-carbamoyl-4-fluorophenyl)-5-((S)-1-(2-(3-(difluoromethyl)-4,4,7,7-tetrafluoro-4,5,6,7-tetrahydro-1H-indazol-1-yl)acetamido)-2-(3,5-difluorophenyl)ethyl)thiazolo[4,5-b]pyridin-2-yl)ethynyl)phenyl)-1H-imidazol-2-yl)pyrrolidine-1-carboxylate (137): A microwave tube was charged with (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(methylthio)thiazolo[4,5-b]pyridin-6-yl)-2-fluorobenzamide (44 mg, 0.06 mmol), tert-butyl (S)-2-(5-(4-ethynylphenyl)-1H-imidazol-2-yl)pyrrolidine-1-carboxylate (29.2 mg, 0.087 mmol), cuprous iodide (1.1 mg, 0.006 mmol) and dichloro 1,1'-bis(diphenylphosphino)ferrocene palladium (II) dichloromethane (4.75 mg, 0.006 mmol). To the mixture was added 1 mL of THF and 0.2 mL of triethylamine. The system was purged with argon and then the microwave tube was sealed and the reaction mixture was heated up to 120° C. for 30 min in a microwave. After cooling to room temperature, the reaction was partitioned between EtOAc (100 mL) and water/ammonium hydroxide (30 mL). The organic layer was separated, dried over Na$_2$SO$_4$, and concentrated to dryness. The residue was purified by reverse phase HPLC eluting with acetonitrile and water (with 0.1% TFA) to afford Compound 137. MS (m/z): 1048.30 [M+H]$^+$).

Example 138

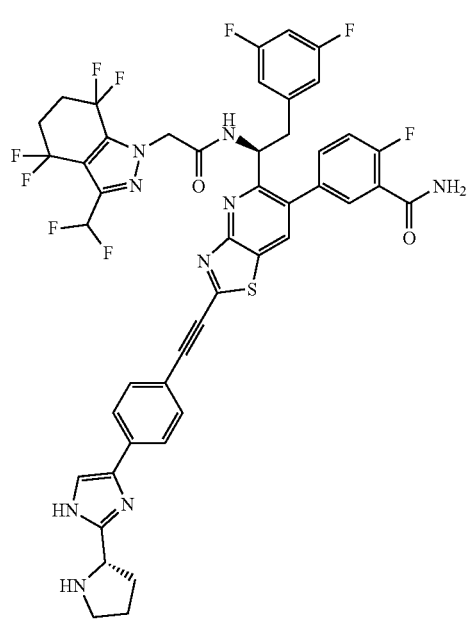

Example 139

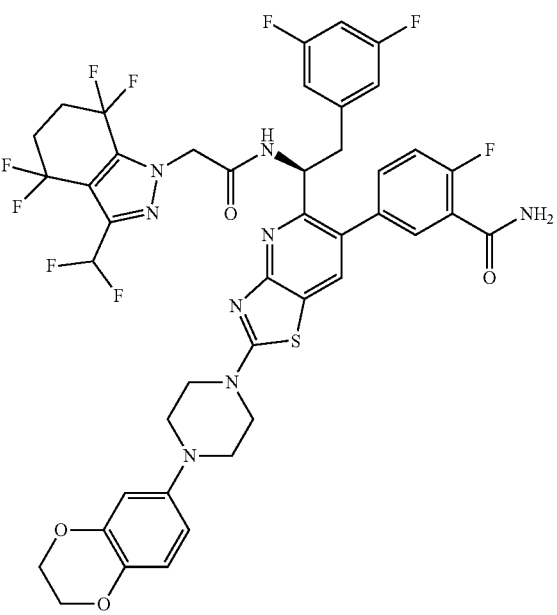

Synthesis of 5-(5-((S)-1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-((4-(2-((S)-pyrrolidin-2-yl)-1H-imidazol-4-yl)phenyl)ethynyl)thiazolo[4,5-b]pyridin-6-yl)-2-fluorobenzamide (138): tert-butyl (S)-2-(4-(4-((6-(3-carbamoyl-4-fluorophenyl)-5-((S)-1-(2-(3-(difluoromethyl)-4,4,7,7-tetrafluoro-4,5,6,7-tetrahydro-1H-indazol-1-yl)acetamido)-2-(3,5-difluorophenyl)ethyl)thiazolo[4,5-b]pyridin-2-yl)ethynyl)phenyl)-1H-imidazol-2-yl)pyrrolidine-1-carboxylate (137, 2.1 mg) was dissolved in 1 mL of DCM and 1 mL of TFA. The reaction mixture was stirred at room temperature for 10 minutes and concentrated to dryness to afford Compound 138. MS (m/z) 948.04 [M+H]$^+$.

Synthesis of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(4-(2,3-dihydrobenzo[b][1,4]dioxin-6-yl)piperazin-1-yl)thiazolo[4,5-b]pyridin-6-yl)-2-fluorobenzamide (139): Compound 139 was prepared in a manner similar to Example 3, using 1-(2,3-dihydrobenzo[b][1,4]dioxin-6-yl)piperazine instead of morpholine. MS (m/z): 931.26 [M+H]$^+$.

Example 140

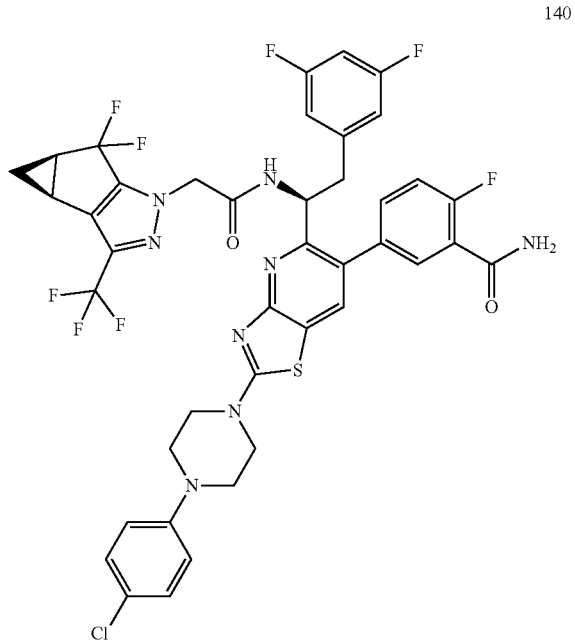 [SMILES: NC(=O)c1cc(-c2cc3sc(N4CCN(c5ccc(Cl)cc5)CC4)nc3nc2[C@H](Cc2cc(F)cc(F)c2)NC(=O)Cn2nc(C(F)(F)F)c3c2C(F)(F)[C@@H]2C[C@H]32)ccc1F]

Example 141

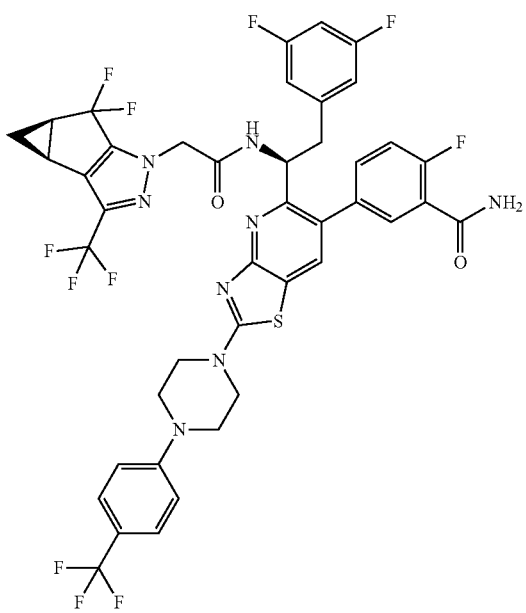

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(4-(4-(trifluoromethyl)phenyl)piperazin-1-yl)thiazolo[4,5-b]pyridin-6-yl)-2-fluorobenzamide (141): Compound 141 was prepared in a manner similar to Example 24 using 1-(4-(trifluoromethyl)phenyl) piperazine instead of 1-(oxetan-3-yl)piperazine to provide the desired compound. MS (m/z): 921.51 [M+H]$^+$.

Example 142

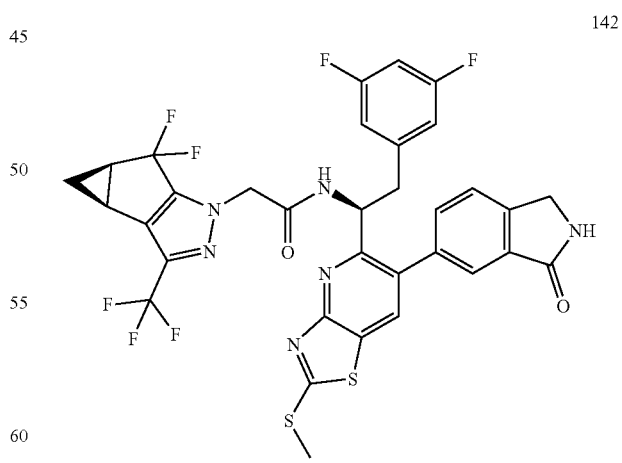

Synthesis of 5-(2-(4-(4-chlorophenyl)piperazin-1-yl)-5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)thiazolo[4,5-b]pyridin-6-yl)-2-fluorobenzamide (140): Compound 140 was prepared in a manner similar to Example 24 using 1-(4-chlorophenyl)piperazine instead of 1-(oxetan-3-yl)piperazine to provide the desired compound. MS (m/z): 887.24 [M+H]$^+$.

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(methylthio)-6-(3-oxoisoindolin-5-yl)thiazolo[4,5-b]pyridin-5-yl)ethyl)acetamide (142): Compound 142 was prepared in a manner similar to Example 117, using 6-(4,4,5,5-tetramethyl-1,3,2-dioxaborolan-2-yl)isoindolin-1-one instead of 2-fluoro-5-(4,4,5,5-tetramethyl-1,3,2-dioxaborolan-2-yl)benzamide to provide the desired compound. MS (m/z): 733.32 [M+H]+.

Example 143

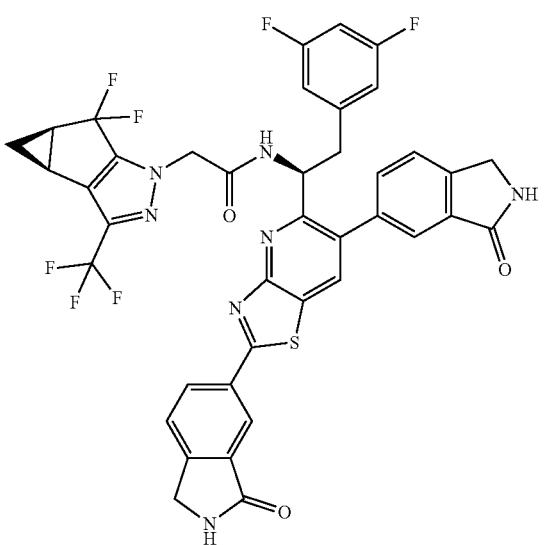

143

Synthesis of N—((S)-1-(2,6-bis(3-oxoisoindolin-5-yl)thiazolo[4,5-b]pyridin-5-yl)-2-(3,5-difluorophenyl)ethyl)-2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamide (143): Compound 143 was prepared in a manner similar to Example 117 using 6-(4,4,5,5-tetramethyl-1,3,2-dioxaborolan-2-yl)isoindolin-1-one instead of 2-fluoro-5-(4,4,5,5-tetramethyl-1,3,2-dioxaborolan-2-yl)benzamide to provide the desired compound. MS (m/z): 817.92 [M+H]+.

Example 144

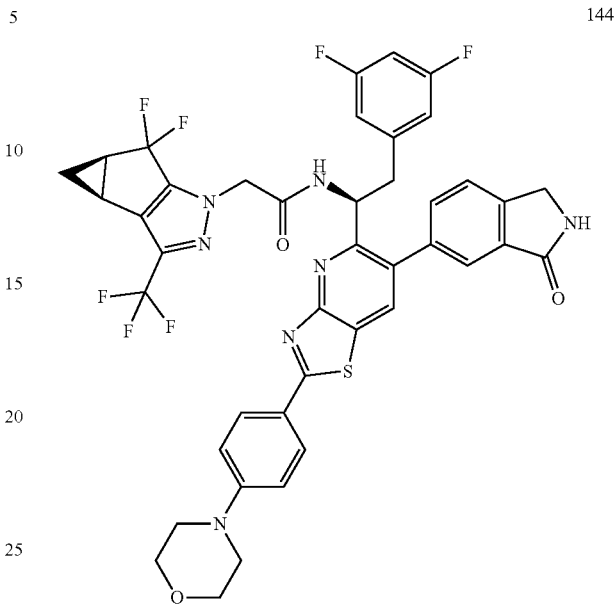

144

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(4-morpholinophenyl)-6-(3-oxoisoindolin-5-yl)thiazolo[4,5-b]pyridin-5-yl)ethyl)acetamide (144): Compound 144 was prepared in a manner similar to Example 118 using Compound 142, and (4-morpholinophenyl)boronic acid instead of (3-carbamoyl-4-fluorophenyl)boronic acid to provide the desired compound. MS (m/z): 848.14 [M+H]+.

Example 145

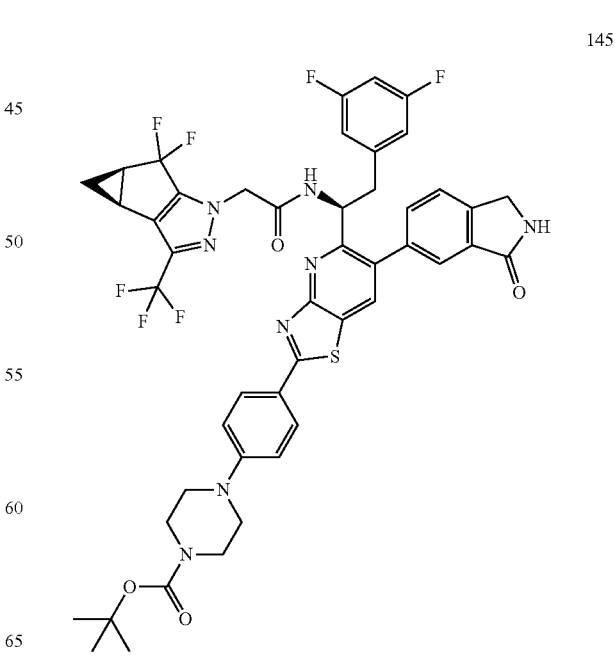

145

Synthesis of tert-butyl 4-(4-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-6-(3-oxoisoindolin-5-yl)thiazolo[4,5-b]pyridin-2-yl)phenyl)piperazine-1-carboxylate (145): Compound 145 was prepared in a manner similar to Example 118 using Compound 142, and tert-butyl 4-(4-(4,4,5,5-tetramethyl-1,3,2-dioxaborolan-2-yl)phenyl)piperazine-1-carboxylate instead of (3-carbamoyl-4-fluorophenyl) boronic acid to provide the desired compound. MS (m/z): 947.12 [M+H]+.

Example 146

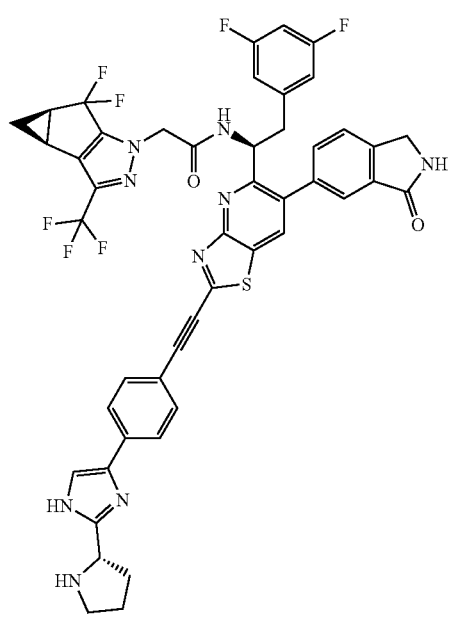

146

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-oxoisoindolin-5-yl)-2-((4-(2-((S)-pyrrolidin-2-yl)-1H-imidazol-4-yl)phenyl)ethynyl)thiazolo[4,5-b]pyridin-5-yl)ethyl)acetamide (146): Compound 146 was prepared in a manner similar to Example 138 using Compound 142 instead of (S)-5-(5-(1-(2-(3-(difluoromethyl)-4,4,7,7-tetrafluoro-4,5,6,7-tetrahydro-1H-indazol-1-yl)acetamido)-2-(3,5-difluorophenyl)ethyl)-2-(methylthio)thiazolo[4,5-b]pyridin-6-yl)-2-fluorobenzamide to provide the desired compound. MS (m/z): 922.93 [M+H]+.

Example 147

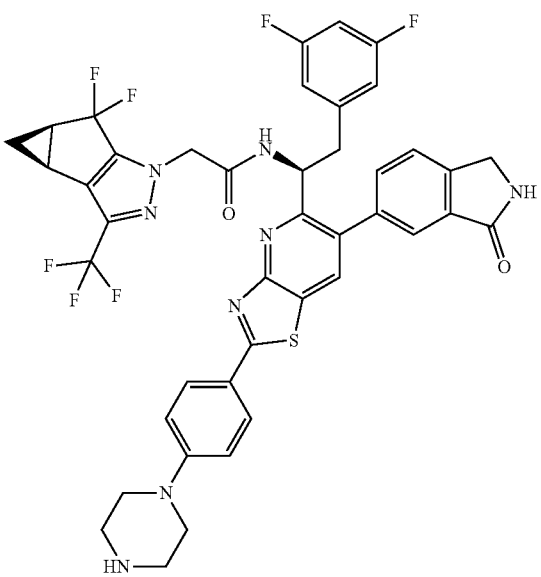

147

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(6-(3-oxoisoindolin-5-yl)-2-(4-(piperazin-1-yl)phenyl)thiazolo[4,5-b]pyridin-5-yl)ethyl)acetamide (147): Compound 147 was prepared in a manner similar to Example 138 using Compound 145 instead of Compound 137 to provide the desired compound. MS (m/z): 847.04 [M+H]+.

Example 148

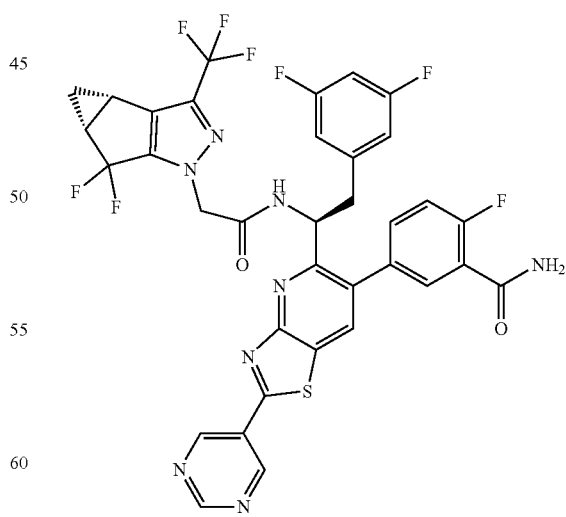

148

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(pyrimidin-5-yl)thiazolo[4,5-b]pyridin-6- yl)-2-fluorobenzamide (148): Compound 148 was prepared in a manner similar to Example 118 using 5-(4,4,5,5-tetramethyl-1,3,2-dioxaborolan-2-yl)pyrimidine instead of phenyl boronic acid to provide the desired compound. MS (m/z): 771.02 [M+H]+. $^1$H NMR (400 MHz, Methanol-d4) δ 9.67 (s, OH), 9.55 (s, 1H), 9.36 (s, 1H), 8.38 (d, J=5.6 Hz, 1H), 7.50 (d, J=7.0 Hz, 1H), 7.36-7.14 (m, 1H), 6.78-6.56 (m, 1H), 6.52-6.27 (m, 2H), 5.53-5.43 (m, 1H), 4.90 (s, 2H), 3.27-2.93 (m, 3H), 2.47 (tt, J=6.7, 3.7 Hz, 2H), 1.40 (q, J=7.2 Hz, 1H), 1.12 (dd, J=6.3, 3.9 Hz, 1H).

Example 149

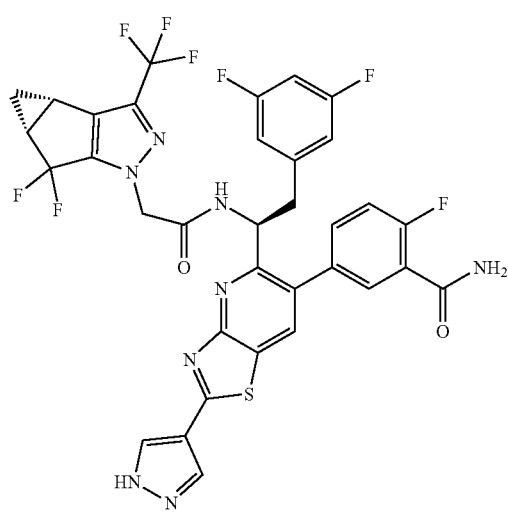

149

Synthesis of 5-(5-((S)-1-(2-((3bS,4aR)-5,5-difluoro-3-(trifluoromethyl)-3b,4,4a,5-tetrahydro-1H-cyclopropa[3,4]cyclopenta[1,2-c]pyrazol-1-yl)acetamido)-2-(3,5-difluorophenyl)ethyl)-2-(1H-pyrazol-4-yl)thiazolo[4,5-b]pyridin-6-yl)-2-fluorobenzamide (149): Compound 149 was prepared in a manner similar to Example 118 using 4-(4,4,5,5-tetramethyl-1,3,2-dioxaborolan-2-yl)-1H-pyrazole instead of phenyl boronic acid to provide the desired compound. MS (m/z): 759.10 [M+H]+. $^1$H NMR (400 MHz, Methanol-d4) δ 8.39 (s, 2H), 8.22 (s, 1H), 7.46 (d, J=6.9 Hz, 1H), 7.40 (s, 1H), 7.25 (dd, J=10.7, 8.5 Hz, 1H), 6.72-6.62 (m, 1H), 6.42-6.35 (m, 2H), 5.46 (t, J=7.5 Hz, 1H), 4.90 (s, 2H), 3.24 (dd, J=13.0, 8.4 Hz, 1H), 3.18-3.08 (m, 1H), 2.55-2.42 (m, 2H), 1.40 (q, J=7.0 Hz, 1H), 1.12 (s, 1H).

Example 150

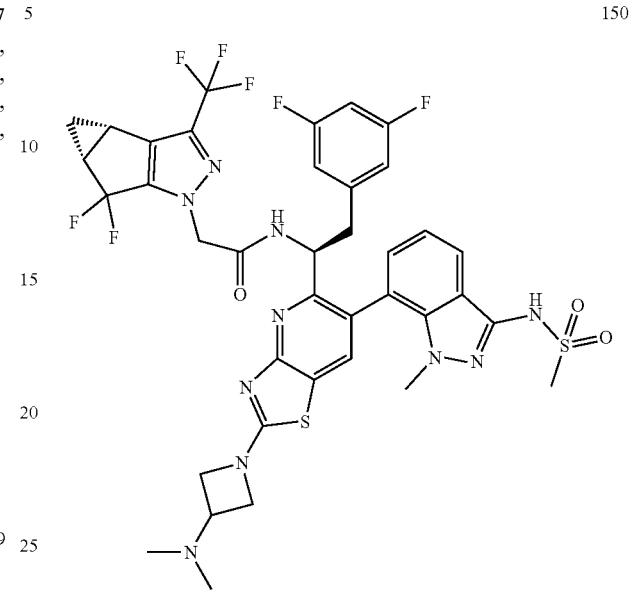

150

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(3-(dimethylamino)azetidin-1-yl)-6-(1-methyl-3-(methylsulfonamido)-1H-indazol-7-yl)thiazolo[4,5-b]pyridin-5-yl)ethyl)acetamide (150): Compound 150 was prepared in a manner similar to Example 3 using N,N-dimethylazetidin-3-amine instead of morpholine to provide the desired compound. MS (m/z): 877.06 [M+H]$^+$.

Example 151

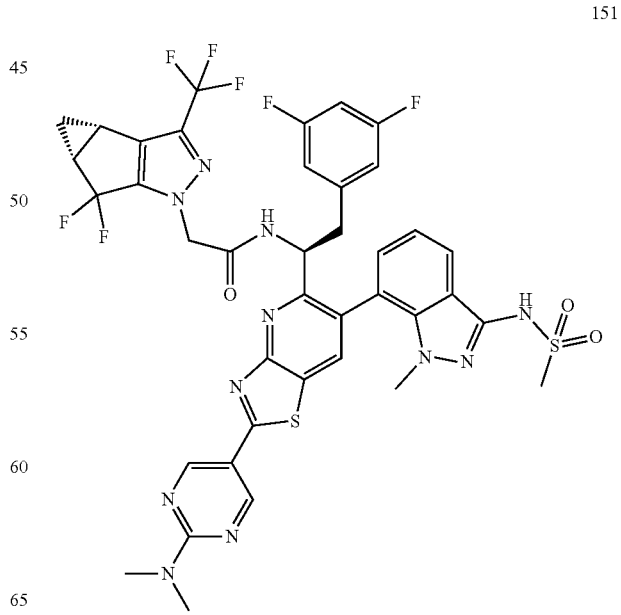

151

Synthesis of 2-((3bS,4aR)-5,5-difluoro-3-(trifluoromethyl)-3b,4,4a,5-tetrahydro-1H-cyclopropa[3,4]cyclopenta[1,2-c]pyrazol-1-yl)-N—((S)-2-(3,5-difluorophenyl)-1-(2-(2-(dimethylamino)pyrimidin-5-yl)-6-(1-methyl-3-(methylsulfonamido)-1H-indazol-7-yl)thiazolo[4,5-b]pyridin-5-yl)ethyl)acetamide (151): Compound 151 was prepared in a similar manner to Example 118 using (2-(dimethylamino)pyrimidin-5-yl)boronic acid instead of (3-carbamoyl-4-fluorophenyl)boronic acid to provide the desired compound. MS (m/z): 900.01 [M+H]$^+$.

Antiviral Assay in MT4 Cells

For the antiviral assay, 40 µL of a concentration required to achieve a final effective 1× test concentration of 3-fold serially diluted compound in culture medium with 10% FBS was added to each well of a 384-well plate (10 concentrations) in quadruplicate. MT-4 cells were next mixed with HIV-IIIb at an m.o.i of 0.003 for 1 hour, after which time 35 µL of virus/cell mixture (2000 cells) was immediately added to each well containing 40 µL of diluted compound. The plates were then incubated at 37° C. for 5 days. After 5 days of incubation, 25 µl of 2× concentrated CellTiter-Glom Reagent (catalog #G7571, Promega Biosciences, Inc., Madison, WI) was added to each well containing MT-4 cells. Cell lysis was carried out by incubating at room temperature for 10 min and then chemiluminescence was read. EC50 values were calculated as the compound concentration that caused a 50% decrease in luminescence signal, a measure of HIV-1 replication and are shown below in Table 1.

TABLE 1

| Compound No. | EC$_{50}$ (nM) |
| --- | --- |
| 1 | 29745.2 |
| 2 | 29702.6 |
| 3K | 1800.8 |
| 3 | 160.5 |
| 4 | 154.1 |
| 5 | 76.9 |
| 6 | 98.6 |
| 7 | 126.9 |
| 8 | 161.7 |
| 9 | 265.5 |
| 10 | 384.2 |
| 11 | 162.0 |
| 12 | 157.9 |
| 13 | 126.0 |
| 14 | 3947.6 |
| 15E | 2635.6 |
| 15-1 | 318.5 |
| 15-2 | 325.7 |
| 16 | 1018.5 |
| 17 | 7993.6 |
| 18 | 253.7 |
| 19 | 1050.2 |
| 20 | 302.6 |
| 21 | 53191.5 |
| 22 | 183.9 |
| 23-1 | 1934.9 |
| 23-2 | 984.3 |
| 24 | 32.7 |
| 25 | 111.2 |
| 26 | 113.5 |
| 27 | 52.3 |
| 28-1 | 300.3 |
| 28-2 | 53191.5 |
| 29 | 121.1 |
| 30 | 47.3 |
| 31 | 466.3 |
| 32 | 60.6 |
| 33 | 88.3 |
| 34 | 97.8 |
| 35 | 31.9 |
| 36 | 28.7 |
| 37 | 1071.1 |

TABLE 1-continued

| Compound No. | EC$_{50}$ (nM) |
| --- | --- |
| 38 | 10.1 |
| 39 | 14.6 |
| 40 | 28.1 |
| 41 | 98.1 |
| 42 | 87.2 |
| 43 | 22.5 |
| 44 | 89.1 |
| 45 | 143.8 |
| 46 | 85.2 |
| 47 | 29.3 |
| 48 | 248.6 |
| 49 | 31.7 |
| 50 | 1.3 |
| 51 | 9.7 |
| 52 | 9.6 |
| 53 | 20.4 |
| 54 | 26.2 |
| 55 | 13.5 |
| 56 | 55.8 |
| 57 | 13.0 |
| 58 | 14.7 |
| 59 | 16.3 |
| 60 | 60.0 |
| 61 | 10.0 |
| 62 | 7.9 |
| 63 | 7.2 |
| 64 | 9.2 |
| 65 | 23.6 |
| 66 | 22.4 |
| 67 | 27.3 |
| 68 | 6.7 |
| 69 | 9.2 |
| 70 | 13.8 |
| 71 | 52.2 |
| 72 | 32.0 |
| 73 | 67.7 |
| 74 | 57.3 |
| 75 | 9.4 |
| 76 | 4.5 |
| 77 | 15.8 |
| 78 | 42.7 |
| 79 | 14.9 |
| 80 | 24.8 |
| 81 | 18.6 |
| 82 | 6.6 |
| 83 | 52.3 |
| 84 | 9.9 |
| 85 | 21.8 |
| 86 | 15.3 |
| 87 | 269.1 |
| 88 | 10.3 |
| 89 | 11.3 |
| 90 | 430.9 |
| 91 | 64.9 |
| 92 | 14.8 |
| 93 | 11.1 |
| 94 | 81.2 |
| 95 | 67.5 |
| 96 | 3.9 |
| 97 | 3.1 |
| 98 | 3.0 |
| 99 | 1.6 |
| 100 | 2.4 |
| 101 | 2.1 |
| 102 | 1.5 |
| 103 | 5.9 |
| 104 | 4.4 |
| 105 | 4.9 |
| 106 | 6.4 |
| 107 | 42.2 |
| 108 | 34.5 |
| 109 | 36.8 |
| 110 | 11.9 |
| 111 | 156.5 |
| 112 | 3.8 |
| 113 | 8.1 |
| 114 | 589.4 |
| 115 | 7.0 |

TABLE 1-continued
| Compound No. | EC$_{50}$ (nM) |
| --- | --- |
| 116 | 3.5 |
| 117 | 93.5 |
| 118 | 302.9 |
| 119 | 72.0 |
| 120 | 294.1 |
| 121 | 79.6 |
| 122 | 12.3 |
| 123 | 8.6 |
| 124 | 13.6 |
| 125 | 17.4 |
| 126 | 33.8 |
| 127 | 31.9 |
| 128 | 341.9 |
| 129 | 16.9 |
| 130 | 6.0 |
| 131 | 28.1 |
| 132 | 43.7 |
| 133 | 43.3 |
| 134 | 10.2 |
| 135 | 18.0 |
| 136 | 4.3 |
| 137 | 408.9 |
| 138 | 112.2 |
| 139 | 545.3 |
| 140 | 1368.7 |
| 141 | 1811.2 |
| 142 | 38.9 |
| 143 | 15.5 |
| 144 | 44.4 |
| 145 | 370.0 |
| 146 | — |
| 147 | 37.0 |
| 148 | 90.4 |
| 149 | 106.5 |
| 150 | 8.0 |
| 151 | 14.1 |
What is claimed is:
1. A compound that is selected from the group consisting of:
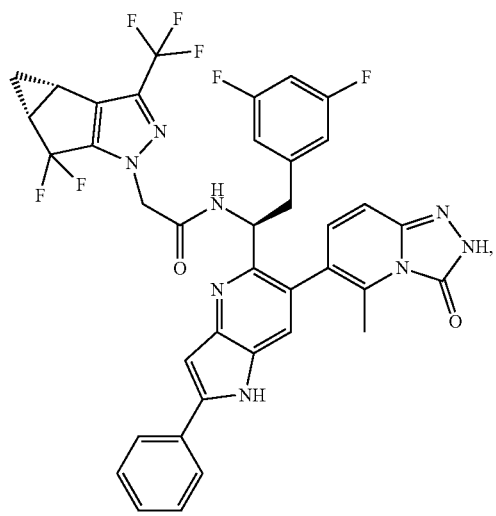
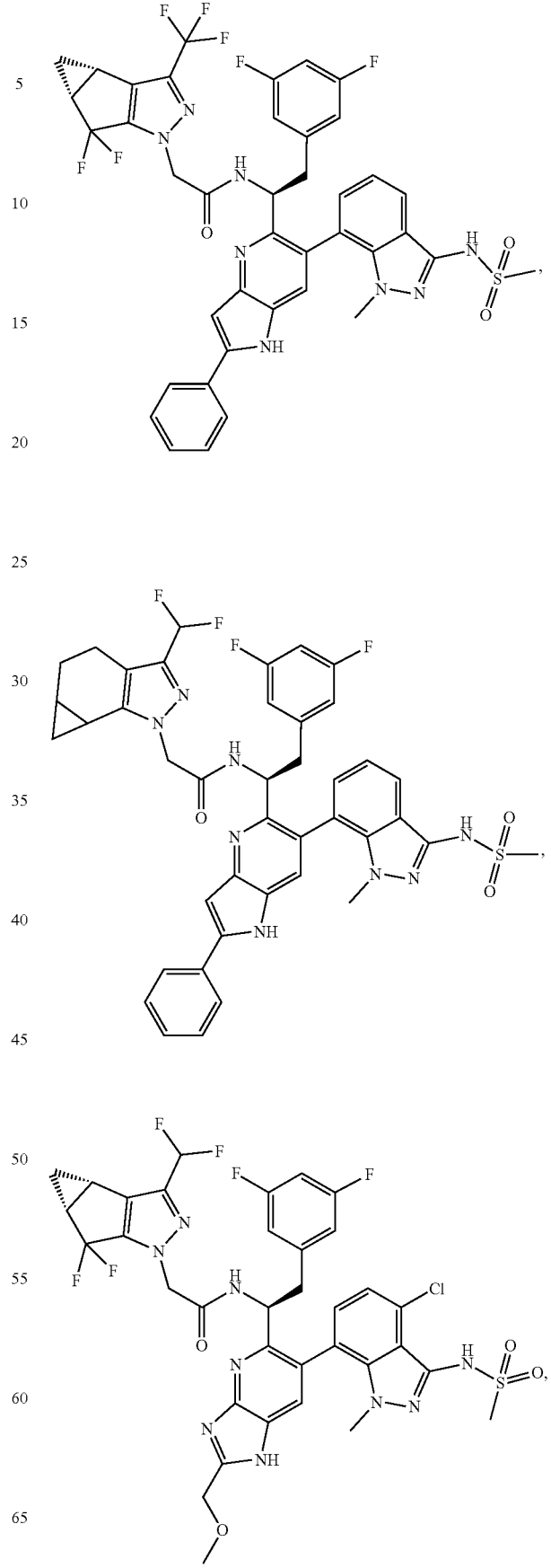

367
-continued
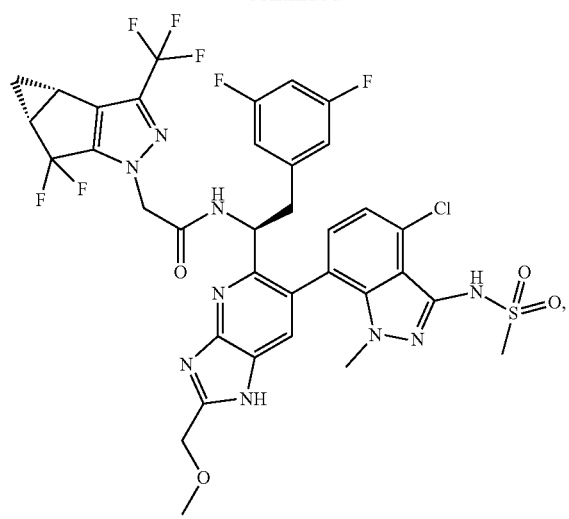
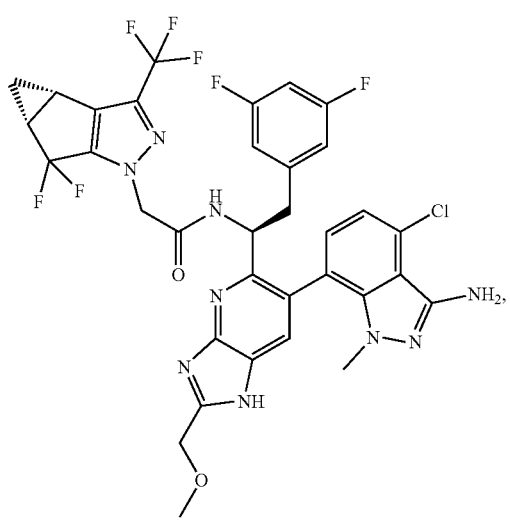
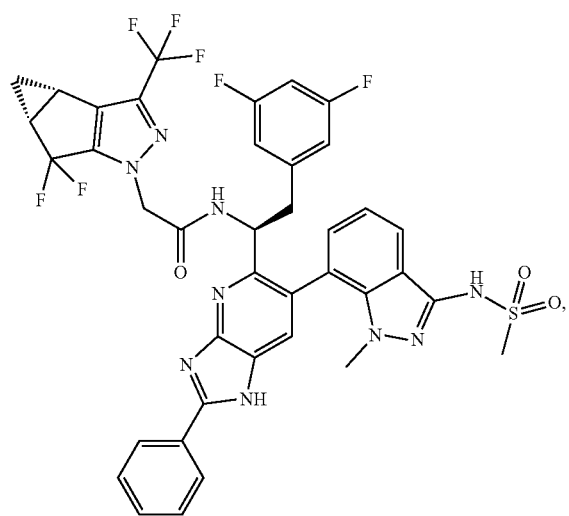
368
-continued
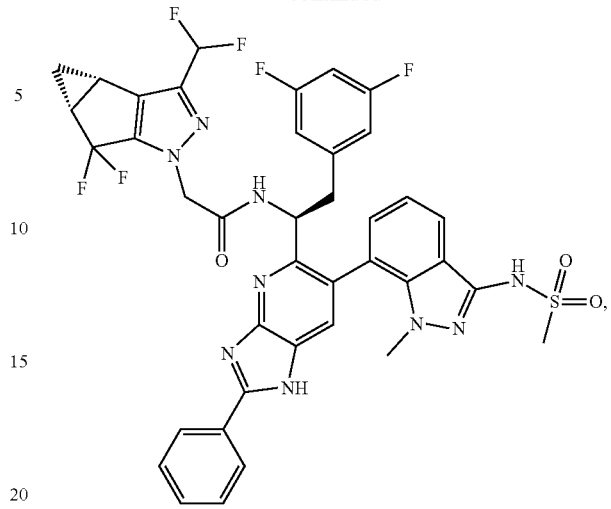
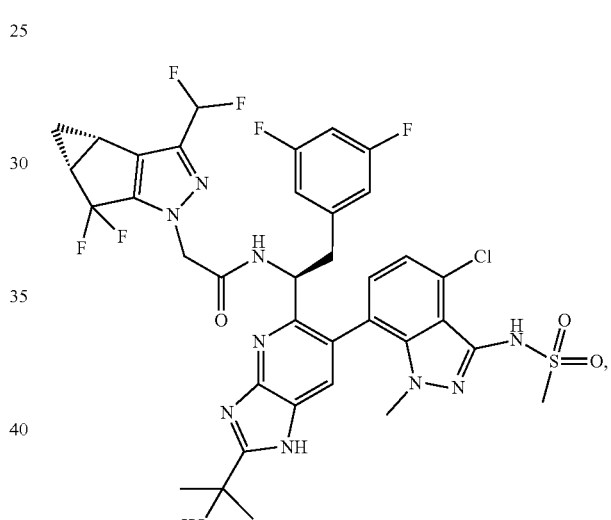
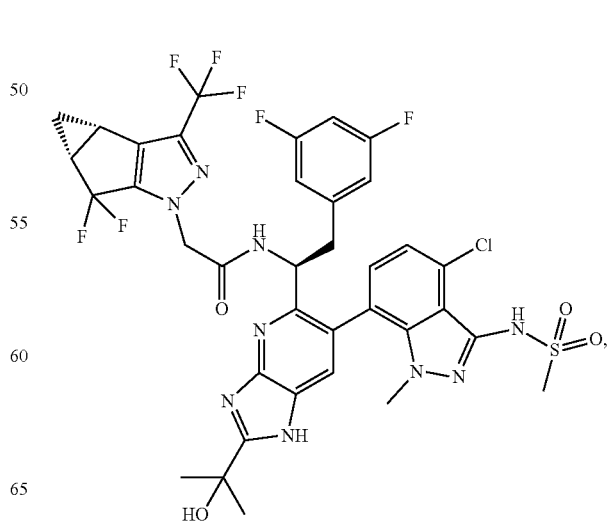

369
-continued
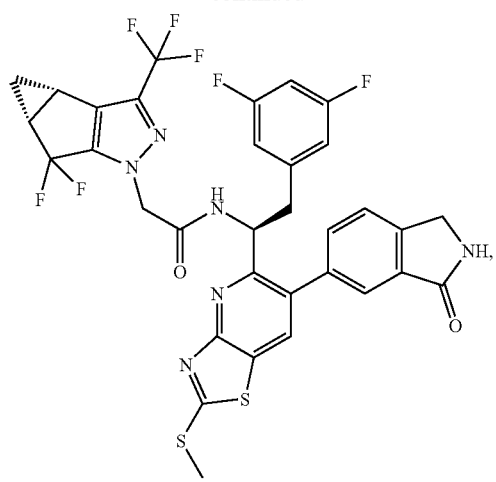
370
-continued
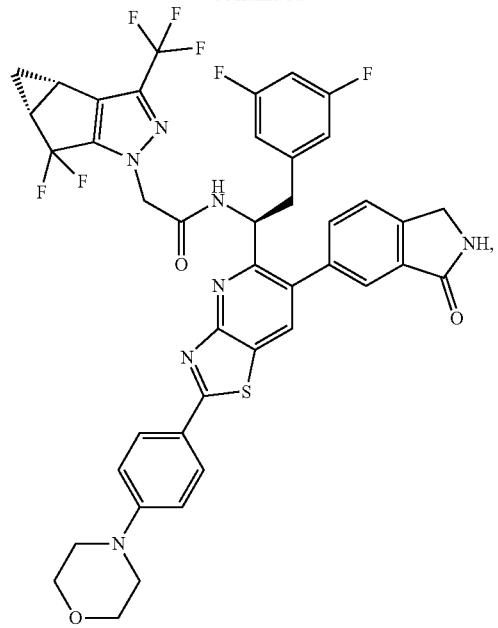
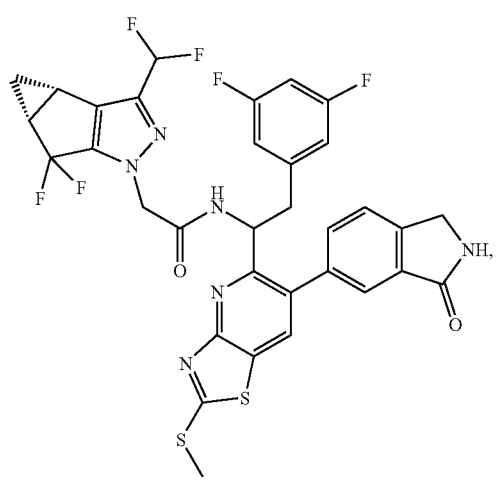
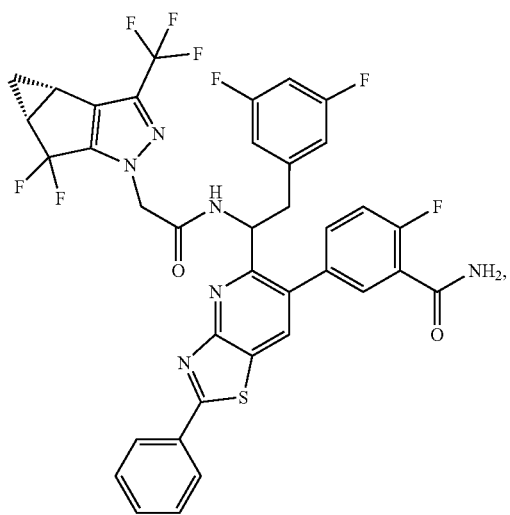
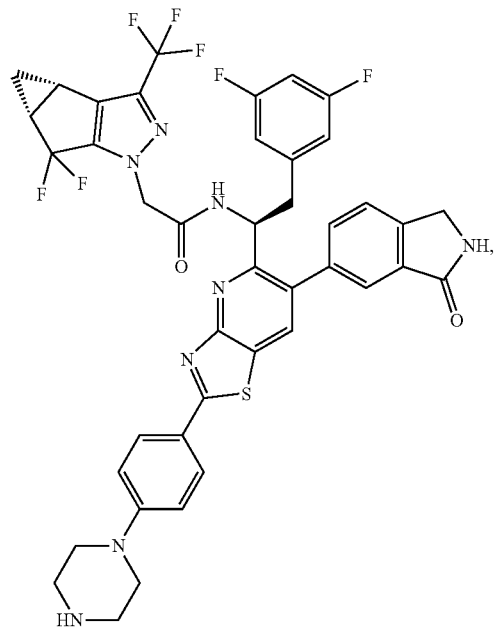

371
-continued
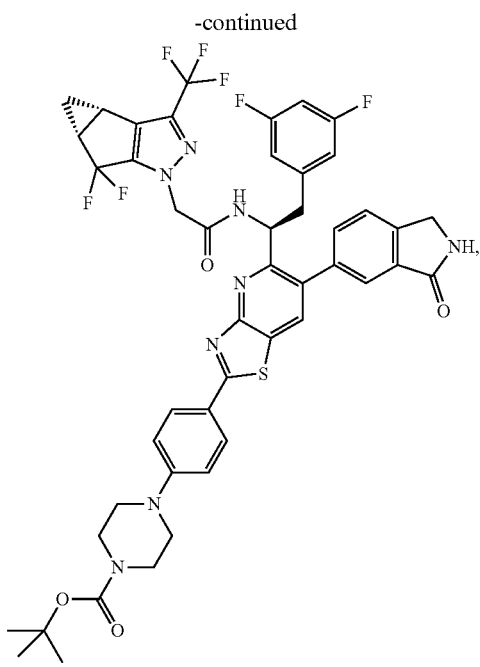
372
-continued
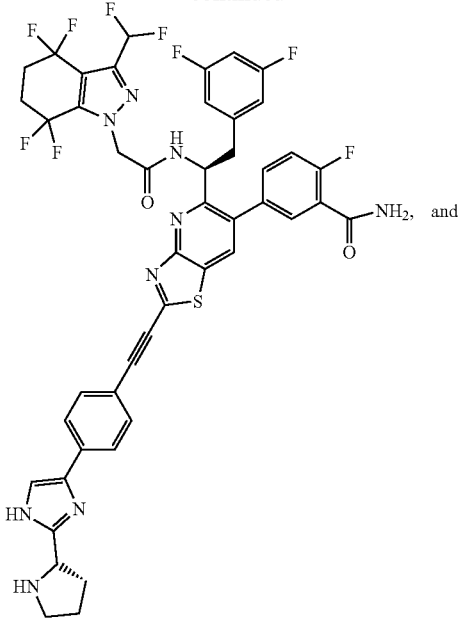
NH₂, and
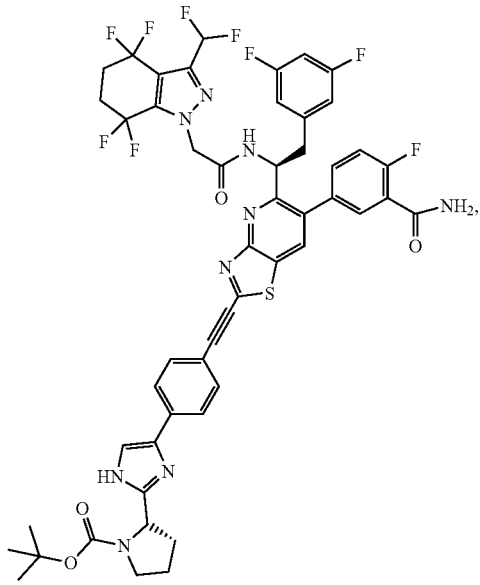
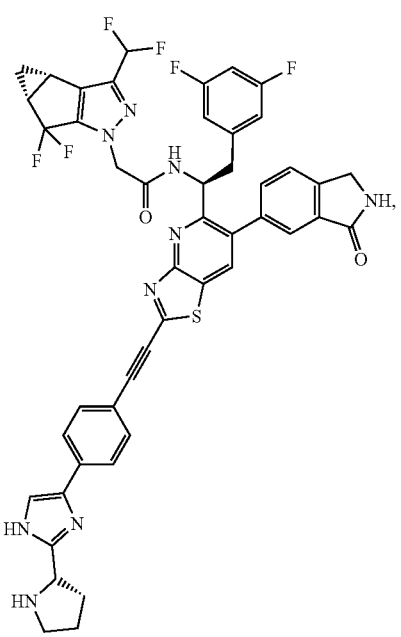
or a pharmaceutically acceptable salt thereof.

2. A compound that is selected from the group consisting of
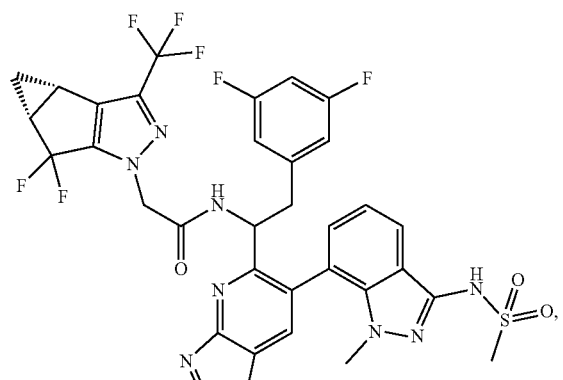
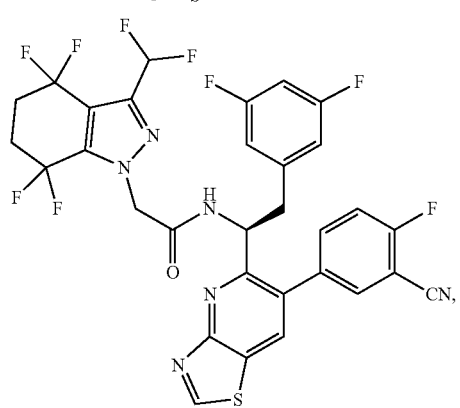
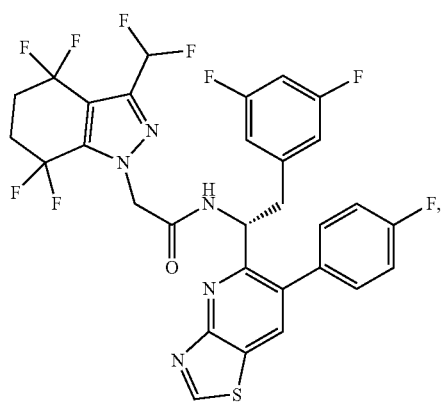
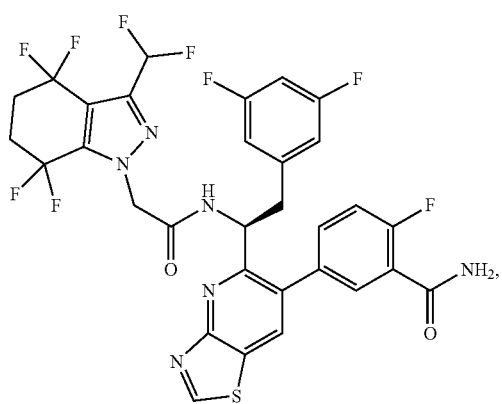
-continued
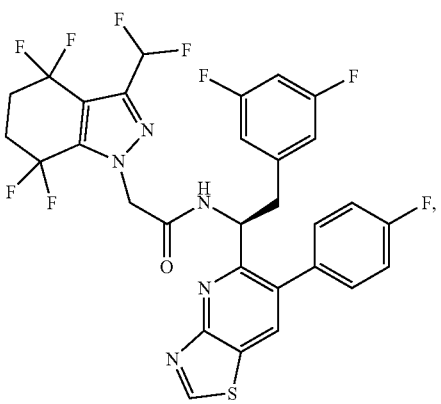
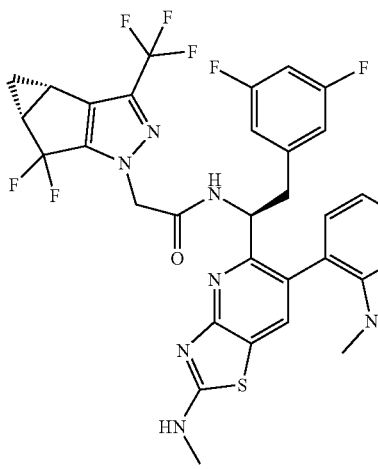
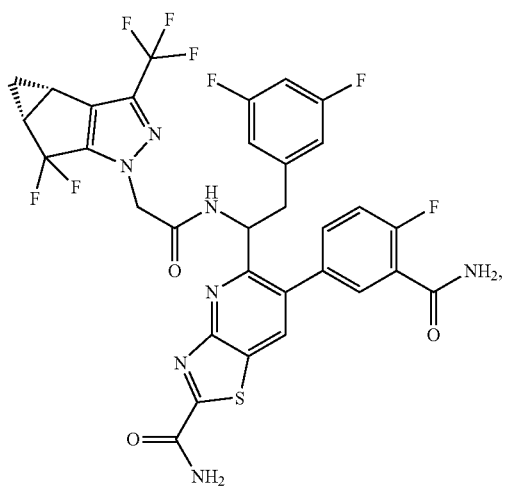

375
-continued
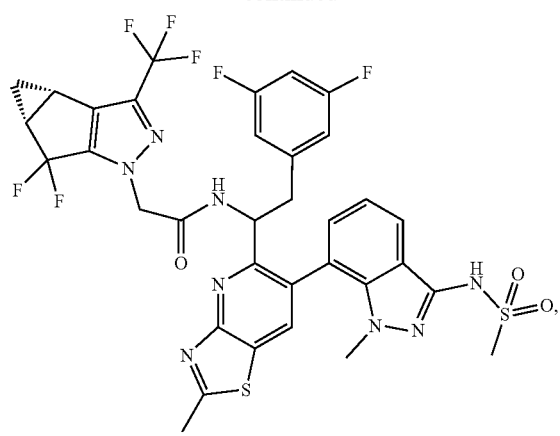
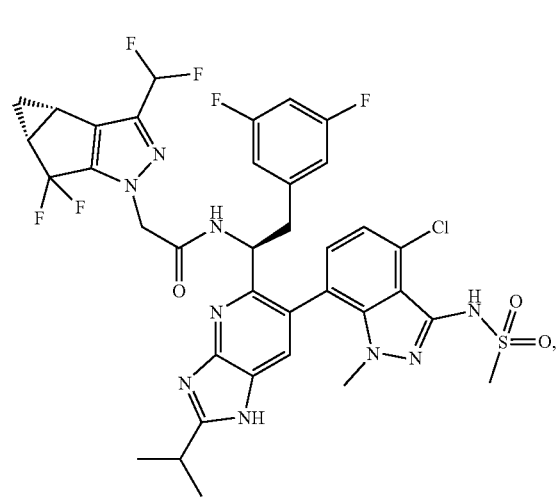
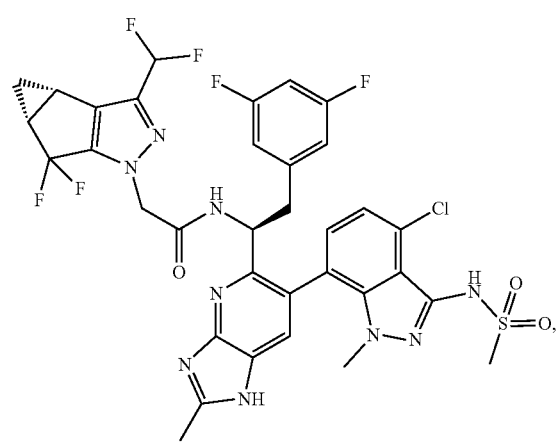
376
-continued
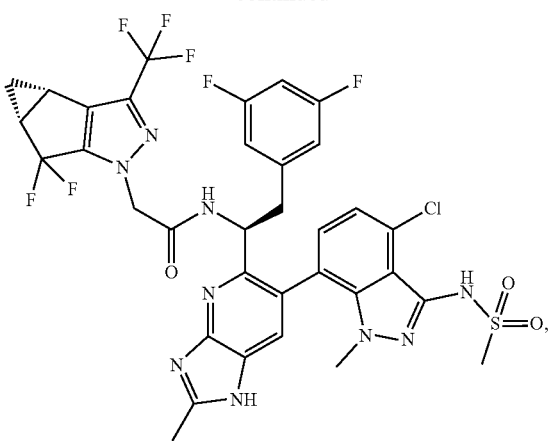
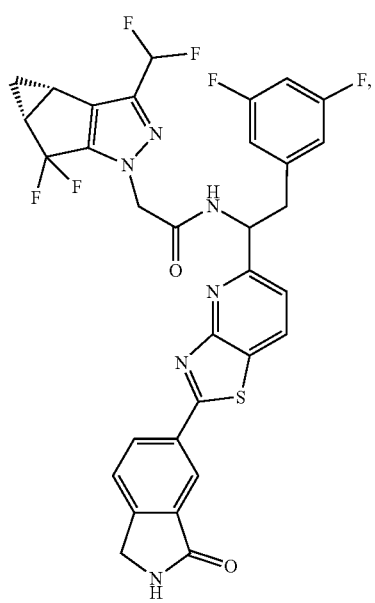
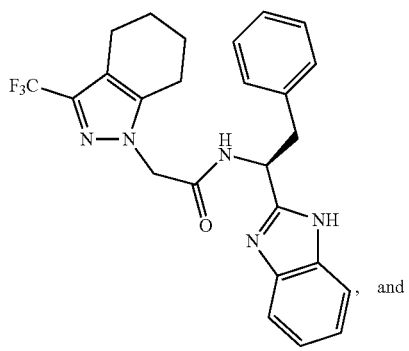
, and -continued

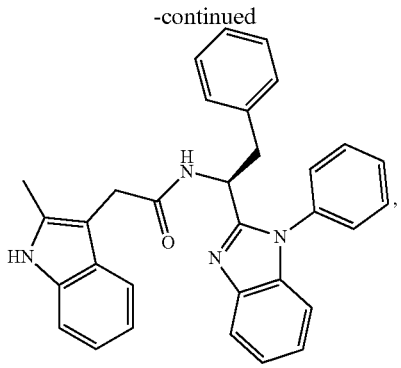

or a pharmaceutically acceptable salt thereof.

3. A pharmaceutical composition comprising a compound of claim 1, or a pharmaceutically acceptable salt thereof, and a pharmaceutically acceptable excipient or carrier.

4. A method of treating or preventing a human immunodeficiency virus (HIV) infection in a subject in need thereof, comprising administering to the subject a therapeutically effective amount of the compound of claim 1, or a pharmaceutically acceptable salt thereof.

5. The method of claim 4, further comprising administering a therapeutically effective amount of one or more additional therapeutic agents, or a pharmaceutically acceptable salt thereof.

6. A pharmaceutical composition comprising a compound of claim 2, or a pharmaceutically acceptable salt thereof, and a pharmaceutically acceptable excipient or carrier.

7. A method of treating or preventing a human immunodeficiency virus (HIV) infection in a subject in need thereof, comprising administering to the subject a therapeutically effective amount of the compound of claim 2, or a pharmaceutically acceptable salt thereof.

8. The method of claim 7, further comprising administering a therapeutically effective amount of one or more additional therapeutic agents, or a pharmaceutically acceptable salt thereof.

* * * * *